(12) United States Patent
Bernett et al.

(10) Patent No.: US 12,239,688 B2
(45) Date of Patent: Mar. 4, 2025

(54) IL-15/IL-15RA HETERODIMERIC Fc FUSION PROTEINS AND USES THEREOF

(71) Applicant: Xencor, Inc., Monrovia, CA (US)

(72) Inventors: Matthew Bernett, Monrovia, CA (US); John Desjarlais, Pasadena, CA (US); Rumana Rashid, Temple City, CA (US); Rajat Varma, Monrovia, CA (US); Christine Bonzon, Los Angeles, CA (US)

(73) Assignee: Xencor, Inc., Pasadena, CA (US)

( * ) Notice: Subject to any disclaimer, the term of this patent is extended or adjusted under 35 U.S.C. 154(b) by 518 days.

(21) Appl. No.: 17/209,047

(22) Filed: Mar. 22, 2021

(65) Prior Publication Data

US 2022/0040264 A1 Feb. 10, 2022

Related U.S. Application Data

(63) Continuation of application No. 16/388,174, filed on Apr. 18, 2019, now abandoned.

(60) Provisional application No. 62/756,800, filed on Nov. 7, 2018, provisional application No. 62/724,396, filed on Aug. 29, 2018, provisional application No. 62/684,143, filed on Jun. 12, 2018, provisional application No. 62/659,563, filed on Apr. 18, 2018.

(51) Int. Cl.
| | |
|---|---|
| *A61K 38/20* | (2006.01) |
| *A61K 38/17* | (2006.01) |
| *A61K 39/395* | (2006.01) |
| *A61P 35/00* | (2006.01) |
| *C07K 14/54* | (2006.01) |
| *C07K 14/715* | (2006.01) |
| *C07K 16/28* | (2006.01) |

(52) U.S. Cl.
CPC ...... *A61K 38/2086* (2013.01); *A61K 38/1793* (2013.01); *A61K 39/3955* (2013.01); *A61P 35/00* (2018.01); *C07K 14/5443* (2013.01); *C07K 14/7155* (2013.01); *C07K 16/2818* (2013.01); *C07K 16/28* (2013.01); *C07K 2317/21* (2013.01); *C07K 2317/24* (2013.01); *C07K 2319/30* (2013.01)

(58) Field of Classification Search
CPC ............ A61K 38/2086; C07K 2319/00; C07K 14/5443; C07K 2319/30
See application file for complete search history.

(56) References Cited

U.S. PATENT DOCUMENTS

| | | | |
|---|---|---|---|
| 5,595,756 A * | 1/1997 | Bally | A61K 9/1272 264/4.1 |
| 5,731,168 A | 3/1998 | Carter et al. | |
| 5,821,333 A | 10/1998 | Carter et al. | |
| 6,013,480 A | 1/2000 | Grabstein et al. | |
| 6,737,056 B1 | 5/2004 | Presta | |
| 7,276,585 B2 | 10/2007 | Lazar et al. | |
| 7,355,008 B2 | 4/2008 | Stavenhagen et al. | |
| 7,632,497 B2 | 12/2009 | Stavenhagen | |
| 7,834,152 B2 | 11/2010 | Strom et al. | |
| 7,858,081 B2 | 12/2010 | Bernard et al. | |
| 7,960,512 B2 | 6/2011 | Stavenhagen et al. | |
| 8,003,774 B2 | 8/2011 | Stavenhagen et al. | |
| 8,124,084 B2 | 2/2012 | LeFrancois et al. | |
| 8,192,737 B2 | 6/2012 | Stavenhagen et al. | |
| 8,216,574 B2 | 7/2012 | Stavenhagen | |
| 8,216,805 B2 | 7/2012 | Carter et al. | |
| 8,309,690 B2 | 11/2012 | Allan et al. | |
| 8,592,562 B2 | 11/2013 | Kannan et al. | |
| 8,629,245 B2 | 1/2014 | Georgiou et al. | |
| 8,679,493 B2 | 3/2014 | Georgiou et al. | |
| 8,742,074 B2 | 6/2014 | Behrens et al. | |
| 8,871,912 B2 | 10/2014 | Davis et al. | |
| 8,940,288 B2 | 1/2015 | LeFrancois et al. | |
| 8,940,289 B2 | 1/2015 | Wong et al. | |
| 8,951,517 B2 | 2/2015 | Stavenhagen et al. | |
| 9,028,815 B2 | 5/2015 | Stavenhagen et al. | |
| 9,150,663 B2 | 10/2015 | Labrijn et al. | |
| 9,308,258 B2 | 4/2016 | Kannan et al. | |
| RE45,992 E | 5/2016 | Behrens et al. | |
| 9,365,630 B2 | 6/2016 | LeFrancois et al. | |
| 9,371,368 B2 | 6/2016 | LeFrancois et al. | |
| 9,464,127 B2 | 10/2016 | Wong et al. | |
| 9,493,533 B2 | 11/2016 | Bernard et al. | |
| 9,505,848 B2 | 11/2016 | Davis et al. | |

(Continued)

FOREIGN PATENT DOCUMENTS

| | | |
|---|---|---|
| AU | 2014377106 | 8/2016 |
| EP | 2724728 | 4/2002 |

(Continued)

OTHER PUBLICATIONS

Heppner et al. Cancer Metastasis Review 2:5-23; 1983 (Year: 1983).*

(Continued)

*Primary Examiner* — Vanessa L. Ford
*Assistant Examiner* — Sandra Carter
(74) *Attorney, Agent, or Firm* — Kelly A. Plummer; Christopher J. Betti; Morgan, Lewis & Bockius, LLP

(57) ABSTRACT

The present invention is directed to novel IL-15/IL-15Rα heterodimeric Fc fusion proteins and uses thereof. The IL-15/IL-15Rα heterodimeric Fc fusion proteins can be administered to a patient to treat cancer. In some cases, the IL-15/IL-15Rα heterodimeric Fc fusion protein is administered in combination with a checkpoint blockage antibody such as a PD-1 antibody.

20 Claims, 330 Drawing Sheets

Specification includes a Sequence Listing.

(56) References Cited

U.S. PATENT DOCUMENTS

| | | |
|---|---|---|
| 9,527,926 B2 | 12/2016 | Ho et al. |
| 9,562,109 B2 | 2/2017 | Von Kreudenstein et al. |
| 9,683,052 B2 | 6/2017 | Blein et al. |
| 9,683,053 B2 | 6/2017 | Blein et al. |
| 9,763,705 B2 | 9/2017 | Faulhaber |
| 9,763,765 B2 | 9/2017 | Horan et al. |
| 9,931,377 B2 | 4/2018 | Pavlakis et al. |
| 9,932,387 B2 | 4/2018 | LeFrancois et al. |
| 9,969,790 B2 | 5/2018 | LeFrancois et al. |
| 10,011,858 B2 | 7/2018 | Igawa et al. |
| 10,138,303 B2 | 11/2018 | Ho et al. |
| 10,350,270 B2 | 7/2019 | McCauley |
| 10,550,185 B2 | 2/2020 | Bernett et al. |
| 2003/0050236 A1 | 3/2003 | Dawson et al. |
| 2006/0257361 A1 | 11/2006 | Watanabe et al. |
| 2006/0263857 A1 | 11/2006 | LeFrancois et al. |
| 2009/0238791 A1 | 9/2009 | Jacques et al. |
| 2010/0267934 A1 | 10/2010 | Van de Winkel et al. |
| 2011/0054151 A1 | 3/2011 | Lazar et al. |
| 2012/0149876 A1 | 6/2012 | Von Kreudenstein et al. |
| 2012/0177595 A1 | 7/2012 | Wong et al. |
| 2013/0039913 A1 | 2/2013 | Labrijn et al. |
| 2013/0131319 A1 | 5/2013 | Igawa et al. |
| 2013/0178605 A1 | 7/2013 | Blein et al. |
| 2014/0134128 A1 | 5/2014 | Wong et al. |
| 2014/0187753 A1 | 7/2014 | Blein et al. |
| 2014/0199294 A1 | 7/2014 | Mimoto et al. |
| 2014/0288275 A1 | 9/2014 | Moore et al. |
| 2014/0335089 A1 | 11/2014 | Igawa et al. |
| 2014/0356381 A1 | 12/2014 | Moore et al. |
| 2014/0363426 A1 | 12/2014 | Moore et al. |
| 2015/0351275 A1 | 12/2015 | Imbimbo et al. |
| 2016/0068584 A1 | 3/2016 | Bechard et al. |
| 2016/0157951 A1 | 6/2016 | Schoenig et al. |
| 2016/0175459 A1 | 6/2016 | Gey et al. |
| 2016/0176969 A1 | 6/2016 | Bernett et al. |
| 2016/0184399 A1 | 6/2016 | Bechard et al. |
| 2016/0318986 A1 | 11/2016 | Morisseau et al. |
| 2016/0333067 A1 | 11/2016 | LeFrancois et al. |
| 2016/0347818 A1 | 12/2016 | LeFrancois et al. |
| 2016/0355608 A1 | 12/2016 | Bernett et al. |
| 2016/0367635 A1 | 12/2016 | Wong et al. |
| 2017/0020963 A1* | 1/2017 | Qu ................... A61K 38/2086 |
| 2017/0056874 A1 | 3/2017 | Bechard et al. |
| 2017/0088597 A1 | 3/2017 | Wong et al. |
| 2017/0145078 A1 | 5/2017 | Davis et al. |
| 2017/0151310 A1 | 6/2017 | Felber et al. |
| 2017/0233497 A1 | 8/2017 | Labrijn et al. |
| 2018/0094077 A1 | 4/2018 | Blein et al. |
| 2018/0118805 A1 | 5/2018 | Bernett et al. |
| 2018/0118828 A1 | 5/2018 | Bernett et al. |
| 2018/0118836 A1 | 5/2018 | Bernett et al. |
| 2018/0194860 A1 | 7/2018 | Von Kreudenstein et al. |
| 2018/0200366 A1 | 7/2018 | Wong et al. |
| 2018/0298079 A1 | 10/2018 | LeFrancois et al. |
| 2018/0312560 A1 | 11/2018 | Morisseau et al. |
| 2019/0016778 A1 | 1/2019 | Bernett et al. |
| 2019/0263877 A1 | 8/2019 | Yeung et al. |
| 2019/0270816 A1 | 9/2019 | Bernett et al. |
| 2019/0359684 A1 | 11/2019 | Bernett et al. |
| 2019/0365861 A1 | 12/2019 | Bernett et al. |
| 2020/0040083 A1 | 2/2020 | Bernett et al. |
| 2020/0247862 A1 | 8/2020 | Bernett et al. |
| 2020/0392235 A1 | 12/2020 | Lu et al. |
| 2021/0047407 A1 | 2/2021 | Christian et al. |
| 2023/0149509 A1 | 5/2023 | Ungewickell et al. |

FOREIGN PATENT DOCUMENTS

| | | |
|---|---|---|
| EP | 0927254 | 6/2005 |
| EP | 3263581 | 1/2008 |
| EP | 1801119 B1 | 6/2009 |
| EP | 1718670 | 7/2011 |
| EP | 1934353 | 10/2011 |
| EP | 2388266 | 4/2014 |
| EP | 2986312 | 2/2016 |
| EP | 3030262 | 6/2016 |
| EP | 3093295 | 11/2016 |
| EP | 3113858 | 1/2017 |
| EP | 2769984 | 8/2017 |
| EP | 3235830 | 10/2017 |
| EP | 3030575 | 7/2018 |
| EP | 2723869 B1 | 2/2019 |
| EP | 3265478 B1 | 9/2019 |
| EP | 3030262 B1 | 10/2019 |
| EP | 1899364 B1 | 2/2020 |
| WO | WO96027011 | 9/1996 |
| WO | WO1997041232 | 11/1997 |
| WO | WO2001010912 A1 | 2/2001 |
| WO | WO2005014642 A2 | 2/2005 |
| WO | WO2005085282 | 9/2005 |
| WO | WO2006063974 | 6/2006 |
| WO | WO2007001677 | 1/2007 |
| WO | WO2007046006 | 4/2007 |
| WO | WO2007084342 | 7/2007 |
| WO | WO2007110205 | 10/2007 |
| WO | WO2007128563 A1 | 11/2007 |
| WO | WO2007147901 | 12/2007 |
| WO | WO2008143794 | 11/2008 |
| WO | WO2009002562 | 12/2008 |
| WO | WO2009036209 | 3/2009 |
| WO | WO2009089004 | 7/2009 |
| WO | WO2010017103 | 2/2010 |
| WO | WO2011005621 | 1/2011 |
| WO | WO2011020047 A1 | 2/2011 |
| WO | WO2011063348 | 5/2011 |
| WO | WO2011143545 | 11/2011 |
| WO | WO2011131746 | 12/2011 |
| WO | WO2012032080 | 3/2012 |
| WO | WO2012040323 A2 | 3/2012 |
| WO | WO2012146628 | 11/2012 |
| WO | WO2012131555 | 12/2012 |
| WO | WO2012175222 | 12/2012 |
| WO | WO2013/055809 | 4/2013 |
| WO | WO2013107791 A1 | 7/2013 |
| WO | WO2014079000 | 5/2014 |
| WO | WO2014/110601 | 7/2014 |
| WO | WO2014145806 | 9/2014 |
| WO | WO2014145907 | 9/2014 |
| WO | WO2014170032 | 10/2014 |
| WO | WO2014207173 | 12/2014 |
| WO | WO2015018528 | 2/2015 |
| WO | WO2015018529 | 2/2015 |
| WO | WO2015103928 | 7/2015 |
| WO | WO2015131994 | 9/2015 |
| WO | WO2015195163 | 12/2015 |
| WO | WO2016004060 | 1/2016 |
| WO | WO2016086186 | 6/2016 |
| WO | WO2016086189 A2 | 6/2016 |
| WO | WO2016086196 A2 | 6/2016 |
| WO | WO2016095642 | 6/2016 |
| WO | WO2016106159 | 6/2016 |
| WO | WO2016141387 | 9/2016 |
| WO | WO2016142314 | 9/2016 |
| WO | WO2016182751 A1 | 11/2016 |
| WO | WO2017055547 A1 | 4/2017 |
| WO | WO2018007919 A1 | 1/2018 |
| WO | WO2018071918 | 4/2018 |
| WO | WO2018071919 | 4/2018 |
| WO | WO2018075989 | 4/2018 |
| WO | WO2018091661 | 5/2018 |
| WO | WO2019006472 | 1/2019 |
| WO | WO2019094637 A1 | 5/2019 |
| WO | WO2019204592 | 10/2019 |
| WO | WO2019204646 A1 | 10/2019 |
| WO | WO2019204665 | 10/2019 |
| WO | WO2020077276 | 4/2020 |
| WO | WO2020132646 | 6/2020 |
| WO | WO2020172631 A2 | 8/2020 |
| WO | WO2020185739 | 9/2020 |
| WO | WO2021072298 A1 | 4/2021 |
| WO | WO2021119429 A1 | 6/2021 |

(56) References Cited

FOREIGN PATENT DOCUMENTS

| WO | WO2021155042 A1 | 8/2021 |
|---|---|---|
| WO | WO2022140701 A1 | 6/2022 |
| WO | WO2023196905 A1 | 10/2023 |

OTHER PUBLICATIONS

Sporn et al. Chemoprevention of Cancer, Carcinogenesis, vol. 21 (2000), 525-530 (Year: 2000).*
Auerbach et al. Cancer and Metastasis Reviews, 2000, 19: 167-172 (Year: 2000).*
Gura T. Science, 1997, 278(5340): 1041-1042 (Year: 1997).*
Jain RK. Scientific American, Jul. 1994,58-65 (Year: 1994).*
Hait. Nature Reviews/Drug Discovery, 2010, 9, pp. 253-254 (Year: 2010).*
Gravanis et al. Chin Clin Oncol, 2014, 3, pp. 1-5 (Year: 2014).*
Beans. PNAS 2018; 115(50): 12539-12543 (Year: 2018).*
Hamanishi et al. PD-1/PD-L1 blockade in cancer treatment: perspectives and issues. Int J Clin Oncol (2016) 21:462-473. (Year: 2016).*
Romee et al., First-in-human phase 1 clinical study of the IL-15 superagonist complex ALT-803 to treat relapse after transplantation., Blood. Jun. 7, 2018;131(23):2515-2527. doi: 10.1182/blood-2017-12-823757. Epub Feb. 20, 2018.
Ding et al., Fusion Proteins of NKG2D/NKG2DL in Cancer Immunotherapy., Int J Mol Sci. Jan. 7, 2018;19(1):177. doi: 10.3390/ijms19010177.
Kosobokova, E.N. at al. Fusion proteins based antibodies cytokines: production, functionality and perspectives applications of oncology, CTM, 2013, vol. 5(4): 102-111.
Bulanova et al., Soluble Interleukin (IL)-15Rα Is Generated by Alternative Splicing or Proteolytic Cleavage and Forms Functional Complexes with IL-15*., Protein Structure and Folding| vol. 282, Issue 18, p. 13167-13179, May 2007.
Burkett et al., IL-15Rα expression on CD8+ T cells is dispensable for T cell memory., 4724-4729, PNAS, Apr. 15, 2003, vol. 100, No. 8.
Carson, William E. III, Braking Bad: Blockade of Inhibitory Pathways Improves Interleukin-15 Therapy., Clin Cancer Res (2010) 16 (24): 5917-5919.
Dubois et al., Natural splicing of exon 2 of human interleukin-15 receptor alpha-chain mRNA results in a shortened form with a distinct pattern of expression., J Biol Chem. Sep. 17, 1999;274(38):26978-84. doi: 10.1074/jbc.274.38.26978.
Giri et al., Identification and cloning of a novel IL-15 binding protein that is structurally related to the alpha chain of the IL-2 receptor., EMBO J. Aug. 1, 1995;14(15):3654-63. doi: 10.1002/j.1460-2075.1995.tb00035.x.
Ruchatz et al., Soluble IL-15 receptor alpha-chain administration prevents murine collagen-induced arthritis: a role for IL-15 in development of antigen-induced immunopathology., J Immunol. Jun. 1, 1998;160(11):5654-60.
U.S. Appl. No. 17/692,755, 2022-0195048, Published, filed Mar. 11, 2022, Jun. 23, 2022.
U.S. Appl. No. 16/718,072, 2020-0123259, Published, filed Dec. 17, 2019, Apr. 23, 2020.
U.S. Appl. No. 16/388,174, 2019-0365861, Abandoned, filed Apr. 18, 2019, Dec. 5, 2019.
U.S. Appl. No. 16/388,811, 2019-0389933, Allowed, filed Apr. 18, 2019, Dec. 26, 2019.
U.S. Appl. No. 17/878,903, Pending, filed Aug. 1, 2022.
U.S. Appl. No. 17/831,197, Pending, filed Jun. 2, 2022.
U.S. Appl. No. 17/366,565, 2022-0073588, Published, filed Jul. 2, 2021, Mar. 10, 2022.
U.S. Appl. No. 17/696,799, 2022-0204624, Published, filed Mar. 16, 2022, Jun. 30, 2022.
U.S. Appl. No. 16/388,646, 2019-0352362, Published, filed Apr. 18, 2019, Nov. 21, 2019.
U.S. Appl. No. 16/388,729, 2019-0359684, Allowed, filed Apr. 18, 2019, Nov. 28, 2019.
U.S. Appl. No. 16/724,118, 2020-0247862, Allowed, filed Dec. 20, 2019, Aug. 6, 2020.
U.S. Appl. No. 17/561,613, 2022-0227867, Published, filed Dec. 23, 2021, Jul. 21, 2022.
Chappel et al, "Identification of a Secondary Fcγ RI Binding Site within a Genetically Engineered Human IgG Actibody," J. Biol. Chem., 268(33):25124-25131 (Nov. 1993).
Chappel et al., "Identification of the Fcγ receptor class I binding site in human IgG through the use of recombinant IgG1/IgG2 hybrid and point-mutated antibodies," PNAS, USA, 88:9036-9040 (Oct. 1991).
Miranda-Carus et al., IL-15 and the initiation of cell contact-dependent synovial fibroblast-T lymphocyte cross-talk in rheumatoid arthritis: effect of methotrexate., 2004 J. Immunol. 13:1463-1476.
Koka et al, Cutting edge: murine dendritic cells require IL-15R alpha to prime NK cells., 2004 J. Immunol. 173:3594-3598.
Matsumoto et al., On-column refolding and characterization of soluble human interleukin-15 receptor alpha-chain produced in *Escherichia coli*., Protein Purification and Expression, 2003 64-71.
Schluns et al., Distinct cell types control lymphoid subset development by means of IL-15 and IL-15 receptor alpha expression., 2004, PNAS 101(5):5616-5621.
Wei et al., The Sushi domain of soluble IL-15 receptor alpha is essential for binding IL-15 and inhibiting inflammatory and allogenic responses in vitro and in vivo., 2001, J. Immunol. 167:277-282.
Han et al., IL-15:IL-15 receptor alpha superagonist complex: high-level co-expression in recombinant mammalian cells, purification and characterization., Cytokine. Dec. 2011;56(3):804-10.
Stone et al., Design and characterization of a protein superagonist of IL-15 fused with IL-15Rα and a high-affinity T cell receptor., Biotechnol Prog. Nov.-Dec. 2012;28(6):1588-97.
Kermer et al., An antibody fusion protein for cancer immunotherapy mimicking IL-15 trans-presentation at the tumor site., Mol Cancer Ther. Jun. 2012;11(6):1279-88.
Kermer et al., Combining Antibody-Directed Presentation of IL-15 and 4-1BBL in a Trifunctional Fusion Protein for Cancer Immunotherapy, Mol Cancer Ther. Jan. 2014;13(1):112-21.
C. Bergamaschi et al, "Intracellular Interaction of Interleukin-15 with Its Receptor during Production Leads to Mutual Stabilization and Increased Bioactivity", 2008, Journal of Biological Chemistry, vol. 283, No. 7, pp. 4189-4199.
Genbank accession No. NM_172174, 1998.
Genbank accession No. NP_002180, Jul. 4, 2020.
S. Dubois et al, "IL-15Rα Recycles and Presents IL-15 In Trans to Neighbouring Cells", Immunity, vol. 17, 537-547.
Y Tagaya et al, "Generation of secretable and non-secretable interleukin-15 isoforms through alternate usage of signal peptides", 1997, Proc. Natl. Acad. Sci. USA, vol. 44, 14444-14449.
Genbank accession No. AF031167.1.
D Anderson et al, "Functional Characterization of the Human IL-15 Receptor α Chain and Close Linkage of IL15RA and IL2RA genes", J. Biol. Chem., vol. 270, No. 50, 29862-29869.
Mortier E et al, "Natural, Proteolytic Release of a Soluble Form of Human IL-15 Receptor α-Chain That Behaves as a Specific, High Affinity IL-15 Antagonist", J. Immunol 2004; 173: 1681-1688.
Matthew J Bernett et al: Abstract 5565: Potency-reduced IL15/IL15R[alpha] heterodimeric Fc-fusions display enhanced in vivo activity through increased exposure 11 , Cancer Research, vol. 78, No. 13(Suppl)., Apr. 18, 2018 (Apr. 18, 2018), pp. 1-2, XP055658295. abstract.
Kowalsky Stacy J et al: "Superagonist IL-15-Armed Oncolytic Virus Elicits Potent Antitumor Immunity and Therapy That Are Enhanced with PD-1 Blockade", Molecular Therapy, Nature Publishing Group, GB, vol. 26, No. 10, Oct. 3, 2018 (Oct. 3, 2018), pp. 2476-2486, XP002794091, ISSN: 1525-0024, DOI: 10.1016/J.YMTHE.2018. 07.013 abstract, figures 5 and 6.
John M Wrangle et al: "ALT-803, an IL-15 superagonist, in combination with nivolumab in patients with metastatic non-small cell lung cancer: a non randomised, open-label, phase lb trial", The

(56) References Cited

OTHER PUBLICATIONS

Lancet Oncology, vol. 19, No. 5, Apr. 5, 2018 (Apr. 5, 2018), pp. 694-704, XP055605963, DOI: 10.1016/S1470-2045(18)30148-7 abstract, figures 2, 3 table 3.
Ha et al., Immunoglobulin Fc Heterodimer Platform Technology: From Design to Applications in Therapeutic Antibodies and Proteins., Front Immunol. 2016; 7: 394. Published online Oct. 6, 2016. doi: 10.3389/fimmu.2016.00394.
Rhode et al., Comparison of the Superagonist Complex, ALT-803, to IL15 as Cancer Immunotherapeutics in Animal Models., Cancer Immunol Res. Jan. 2016;4(1):49-60. doi: 10.1158/2326-6066.CIR-15-0093-T. Epub Oct. 28, 2015.
Steinbacher et al., An Fc-optimized NKG2D-immunoglobulin G Fusion Protein for Induction of Natural Killer Cell Reactivity Against Leukemia., Int J Cancer. Mar. 1, 2015;136(5):1073-84. doi: 10.1002/ijc.29083. Epub Jul. 28, 2014.
Prajapati et al., Functions of NKG2D in CD8 + T Cells: An Opportunity for Immunotherapy., Cell Mol Immunol. May 2018;15(5):470-479. doi: 10.1038/cmi.2017.161. Epub Feb. 5, 2018.
Wells, Additivity of mutational effects in proteins., Biochemistry 1990, 29, 37, 8509-8517.
Bork, Powers and Pitfalls in Sequence Analysis: The 70% Hurdle., Genome Res. 2000. 10: 398-400.
Skolnick et al., From Genes to Protein Structure and Function: Novel Applications of Computational Approaches in the Genomic Era., Trends Biotechnol. Jan. 2000;18(1):34-9.
Doerks et al., Protein annotation: detective work for function prediction., Trends in Genetics, 1998 vol. 14, Issue 6, p. 248-250, Jun. 1, 1998.
Tokuriki et al., Stability effects of mutations and protein evolvability., Current Opinion in Structural Biology 2009, 19: 596-604.
Fabbi et al, Dual Roles of IL-15 in Cancer Biology, Journal of Cytokine Biology, 2016, vol. 1, No. 2, pp. 1-7.
Mathios et al, Therapeutic administration of IL-15 superagonist complex ALT-803 leads to long-term survival and durable antitumor immune response in a murine glioblastoma model., International Journal of Cancer, 2016; vol. 138, pp. 187-194.
Alter et al., Targeted IL-15-based Protein Fusion Complexes as Cancer Immunotherapy Approaches., J Immunological Sci. (2018); 2(1): 15-18.
Bailey et al., New interleukin-15 superagonist (IL-15SA) significantly enhances graft-versus-tumor activity., Oncotarget. Jul. 4, 2017; 8(27): 44366-44378.
Charych et al., NKTR-214, an Engineered Cytokine with Biased IL2 Receptor Binding, Increased Tumor Exposure, and Marked Efficacy in Mouse Tumor Models., Clin Cancer Res; 22(3) Feb. 1, 2016.
Chen et al., A targeted IL-15 fusion protein with potent antitumor activity., (2015) Cancer Biology & Therapy, 16:9, 1415-1421, DOI: 10.1080/15384047.2015.1071739.
Ghasemi et al., Selective targeting of IL-2 to NKG2D bearing cells for improved immunotherapy., Nature Communications vol. 7, Article No. 12878 (2016).
Jochems et al., The multi-functionality of N-809, a novel fusion protein encompassing anti-PD-L1 and the IL-15 superagonist fusion complex., OncoImmunology, 2019, vol. 8, No. 2, e1532764 (15 pages).
Klein et al., Cergutuzumab amunaleukin (CEA-IL2v), a CEAtargeted IL-2 variant-based immunocytokine for combination cancer immunotherapy: Overcoming limitations of aldesleukin and conventional IL-2-based immunocytokines., (2017) OncoImmunology, 6:3, e1277306, DOI: 10.1080/2162402X.2016.1277306.
Olsen et al., Crystal Structure of the Interleukin-15 * Interleukin-15 Receptor α Complex., The Journal of Biological Chemistry vol. 282, No. 51, pp. 37191-37204, Dec. 21, 2007.
Vallera et al., IL15 Trispecific Killer Engagers (TriKE) Make Natural Killer Cells Specific to CD33þ Targets While Also Inducing Persistence, In Vivo Expansion, and Enhanced Function., Clin Cancer Res; 22(14) Jul. 15, 2016.
Xu et al., Efficacy and Mechanism-of-Action of a Novel Superagonist Interleukin-15: Interleukin-15 Receptor α Su/Fc Fusion Complex in Syngeneic Murine Models of Multiple Myeloma., Cancer Res. May 15, 2013;73(10):3075-86.
Zhu et al., Novel Human Interleukin-15 Agonists., The Journal of Immunology; 2009; vol. 183, No. 6; pp. 1-28.
Bernard et al., Identification of an Interleukin-15α Receptor-binding Site on Human Interleukin-15*., The Journal of Biological Chemistry; 2004; vol. 279, No. 23, pp. 24313-24322.
Robinson et al., The potential and promise of IL-15 in immuno-oncogenic therapies, Immunology Letters, vol. 190, 2017, pp. 159-168.
Schmid et al., Design and characterisation of a novel interleukin-15 receptor alpha fusion protein and analysis of interleukin-15 complexation., PLoS One. Jul. 26, 2019;14(7):e0219313.
Genbank accession No. U31628, Dec. 19, 1995.
Muller, Dafne, Targeted cancer immunotherapy, Mimicking physiological trans-presentation of IL-15., Oncoimmunology. Oct. 1, 2012; 1(7): 1213-1214.
Garcin et al. High efficiency cell-specific targeting of cytokine activity. Nat Commun 5, 3016 (2014).
Kaspar et al, The antibody-mediated targeted delivery of interleukin-15 and GM-CSF to the tumor neovasculature inhibits tumor growth and metastasis., Cancer Res. May 15, 2007;67(10):4940-8.
Conlon et al., Redistribution, hyperproliferation, activation of natural killer cells and CD8 T cells, and cytokine production during first-in-human clinical trial of recombinant human interleukin-15 in patients with cancer., J Clin Oncol. Jan. 1, 2015;33(1):74-82.
List et al., Immunocytokines: a review of molecules in clinical development for cancer therapy., Clin Pharmacol. 2013; 5(Suppl 1): 29-45.
Gillies et al., Antibody-targeted interleukin 2 stimulates T-cell killing of autologous tumor cells., PNAS Feb. 15, 1992 89 (4) 1428-1432.
Albertini et al. Phase II trial of hu14.18-IL2 for patients with metastatic melanoma., Cancer Immunol Immunother. Dec. 2012;61(12):2261-71.
Ribas et al., Phase I/II open-label study of the biologic effects of the interleukin-2 immunocytokine EMD 273063 (hu14.18-IL2) in patients with metastatic malignant melanoma., J Transl Med. Jul. 29, 2009;7:68.
Hofmann et al., Generation, selection and preclinical characterization of an Fc-optimized FLT3 antibody for the treatment of myeloid leukemia., Leukemia. Jun. 2012;26(6):1228-37.
Kellner et al., Heterodimeric bispecific antibody-derivatives against CD19 and CD16 induce effective antibody-dependent cellular cytotoxicity against B-lymphoid tumor cells., Cancer Lett. Apr. 28, 2011;303(2):128-39.
Skera, Arne, 'Anticalins': a new class of engineered ligand-binding proteins with antibody-like properties., J Biotechnol. Jun. 2001;74(4):257-75.
Skera, Arne, Engineered protein scaffolds for molecular recognition., J Mol Recognit. Jul.-Aug. 2000;13(4):167-87.
Horton et al. Potent in vitro and in vivo activity of an Fc-engineered anti-CD19 monoclonal antibody against lymphoma and leukemia., Cancer Res, 2008, vol. 68, 8049-8057.
Ortiz-Sánchez et al., Antibody-cytokine fusion proteins: applications in cancer therapy., Expert Opin Biol Ther. May 2008 ; 8(5): 609-632.
Zhu et al., Novel Human Interleukin-15 Agonists., J Immunol Sep. 15, 2009, 183 (6) 3598-3607.
Xia et al., In vivo effect of recombined IL-15/Fc fusion protein on EAU. Sichuan Da Xue Xue Bao Yi Xue Ban. Nov. 2008;39(6) 944-949.
Wu et al., IL-15Rα-IgG1-Fc Enhances IL-2 and IL-15 Anti-tumor Action through NK and CD8+ T Cells Proliferation and Activation., Journal of Molecular Cell Biology, vol. 2, Issue 4, Aug. 2010, pp. 217-222.
Ridgway et al., 'Knobs-into-holes' engineering of antibody CH3 domains for heavy chain heterodimerization., Protein Engineering, Design and Selection, vol. 9, Issue 7, Jul. 1996, pp. 617-621.
Carter P. Bispecific human IgG by design. J Immunol Methods. Feb. 1, 2001;248(1-2):7-15. doi: 10.1016/s0022-1759(00)00339-2. PMID: 11223065.

(56) References Cited

OTHER PUBLICATIONS

Atwell et al., Stable heterodimers from remodeling the domain interface of a homodimer using a phage display library 1.,Journal of Molecular Biology, vol. 270, Issue 1,1997,pp. 26-35, ISSN 0022-2836, https://doi.org/10.1006/jmbi.1997.1116.
Merchant, et al., An efficient route to human bispecific IgG, Nature Biotechnology, 1998, vol. 16, pp. 677-681.
Klein, et al., Progress in overcoming the chain association issue in bispecific heterodimeric IgG antibodies, mAbs, Nov.-Dec. 2012, vol. 4, issue 6, pp. 653-663, doi: 10.4161/mabs.21379, Epub Aug. 27, 2012.
Deshpande et al., (2013), Kinetic analysis of cytokine-mediated receptor assembly using engineered FC heterodimers. Protein Science, 22: 1100-1108. https://doi.org/10.1002/pro.2285.
Dumont et al. Monomeric Fc Fusions. BioDrugs 20, 151-160 (2006). https://doi.org/10.2165/00063030-200620030-00002.
Belladonna et al., (2013) Bioengineering heterodimeric cytokines: turning promiscuous proteins into therapeutic agents, Biotechnology and Genetic Engineering Reviews, 29:2, 149-174, DOI: 10.1080/02648725.2013.801228.
Hinrichs, Christian S., Can interleukin-15 keep its therapeutic promise? Science Translational Medicine Mar. 7, 2018: vol. 10, Issue 431, eaar7532, DOI: 10.1126/scitranslmed.aar7532.
Rubinstein et al., Converting IL-15 to a superagonist by binding to soluble IL-15R{alpha}. Proc Natl Acad Sci U S A. Jun. 13, 2006;103(24):9166-71. doi: 10.1073/pnas.0600240103. Epub Jun. 6, 2006. PMID: 16757567; PMCID: PMC1482584.
Stoklasek et al., Combined IL-15/IL-15Ralpha immunotherapy maximizes IL-15 activity in vivo. J Immunol. Nov. 1, 2006;177(9):6072-80. doi: 10.4049/jimmunol.177.9.6072. PMID: 17056533; PMCID: PMC2847275.
Landolfi NF. A chimeric IL-2/Ig molecule possesses the functional activity of both proteins. J Immunol. Feb. 1, 1991;146(3):915-9. PMID: 1988502.
Zheng et al., Administration of noncytolytic IL-10/Fc in murine models of lipopolysaccharide-induced septic shock and allogeneic islet transplantation., J Immunol May 15, 1995, 154 (10) 5590-5600.
Low, et al., Oral and pulmonary delivery of FSH-Fc fusion proteins via neonatal Fc receptor-mediated transcytosis, Human Reproduction, vol. 20, Issue 7, Jul. 2005, pp. 1805-1813.
Kim et al., Targeting the IL-15 Receptor with an Antagonist IL-15 Mutant/Fcγ2a Protein Blocks Delayed-Type Hypersensitivity., J Immunol Jun. 15, 1998, 160 (12) 5742-5748.
Larrick et al., 2013, Inflammation, Advancing Age and Nutrition. D26 Chapter 28. Trophokines: Novel Therapy for Senescence-Related Fibrosis htto://dx rlo1.ora/10 1016/B978-0-12-397803-5.00028-9.
Mortier et al., Soluble interleukin-15 receptor alpha (IL-15R alpha)-sushi as a selective and potent agonist of IL-15 action through IL-15R beta/gamma. Hyperagonist IL-15 x IL-15R alpha fusion proteins. J Biol Chem. Jan. 20, 2006;281(3):1612-9. doi: 10.1074/jbc.M508624200. Epub Nov. 11, 2005. PMID: 16284400.
Wu J. IL-15 Agonists: The Cancer Cure Cytokine. J Mol Genet Med. Oct. 28, 2013;7:85. doi: 10.4172/1747-0862.1000085. PMID: 24587813; PMCID: PMC3938108.
C. Spiess et al., J. Biol. 288(37):26583-93 (2013), Development of a Human IgG4 Bispecific Antibody for Dual Targeting of Interleukin-4 (IL-4) and Interleukin-13 (IL-13) Cytokines.
Hopp et al. 1988. "A Short Polypeptide Marker Sequence Useful for Recombinant Protein Identification and Purification" Nat. Biotechnol. 6, 1204-1210.
Budagian et al., IL-15/IL-15 receptor biology: a guided tour through an expanding universe., Cytokine Growth Factor Rev. Aug. 2006;17(4):259-8.
Bodnar et al., A biophysical approach to IL-2 and IL-15 receptor function: Localization, conformation and interactions., Immunology Letters 116 (2008) 117-125.

Numerof et al., Cytokines as Potential Therapeutic Targets for Inflammatory Skin Diseases., Springer-Verlag, Berlin Heidelberg 2006.
Dumont, Francis J. (2005) Interleukin-2 family cytokines: potential for therapeutic immmunoregulation, Expert Opinion on Therapeutic Patents, 15:5, 521-554.
Savio et al., IL-15: a relevant cytolcine for lymphoid homeostasis and autoimmune diseases., Biotecnologia Ap/icada 2006;23:87-93.
Lichtenegger et al., Targeting LAG-3 and PD-1 to Enhance T Cell Activation by Antigen-Presenting Cells., Front. Immunol. Feb. 27, 2018; 9: 385; pp. 1-12.
Guo et al., Immunobiology of the IL-15/IL-15Rα complex as an antitumor and antiviral agent., Cytokine Growth Factor Rev. Dec. 2017; 38: 10-21.
Ng et al., Heterodimeric IL15 Treatment Enhances Tumor Infiltration, Persistence, and Effector Functions of Adoptively Transferred Tumor-specific T Cells in the Absence of Lymphodepletion., Clin. Cancer Res. Jun. 2017; 23 (11): 2817-30.
Liang et al., Targeting IFNα to tumor by anti-PD-L1 creates feedforward antitumor responses to overcome checkpoint blockade resistance ., Nat. Commun. Nov. 2, 2018; 9 (1): 4586.
Chen et al., Therapeutic efficacy of an anti-PD-L1 antibody based immunocytokine in a metastatic mouse model of colorectal cancer ., Biochem. Biophys. Res. Commun. Nov. 11, 2016; 480 (2): 160-5.
Kiefer et al., Immunocytokines and bispecific antibodies: two complementary strategies for the selective activation of immune cells at the tumor site., Immunol. Rev. Mar. 2016; 270 (1): 178-92; author manuscript; pp. 1-27.
Sondel et al., Current and Potential Uses of Immunocytokines as Cancer Immunotherapy., Antibodies. 212; 1: 149-71.
Kim et al., IL-15 superagonist/IL-15RαSushi-Fc fusion complex (IL-15SA/IL-15RαSu-Fc; ALT-803) markedly enhances specific subpopulations of NK and memory CD8+ T cells, and mediates potent anti-tumor activity against murine breast and colon carcinomas., Oncotarget. Mar. 29, 2016; 7 (13): 16130-45.
Rogers et al., Molecular characterization of immunoglobulin D in mammals: immunoglobulin heavy constant delta genes in dogs, chimpanzees and four old world monkey species., Immunology. May 2006; 118 (1): 88-100.
Rowley J. et al., Inhibition of tumor growth by NK1. 1+ cells and CD8+ T cells activated by IL-15 through receptor β/common γ signaling in trans, The Journal of Immunology, 2008, V. 181, N. 12, p. 8237-8247, p. 8237.
Shen J. et al., Single variable domain-IgG fusion: a novel recombinant approach to Fc domain-containing bispecific antibodies, Journal of Biological Chemistry, 2006, V. 281, N. 16, p. 10706-10714, p. 10713.
Chen X. et al., Fusion protein linkers: property, design and functionality, Advanced drug delivery reviews, 2013, V. 65, N. 10, p. 1357-1369, the whole text, p. 1365.
Maeda Y. et al., Engineering of functional chimeric protein G-VargulaLuciferase, Analytical biochemistry, 1997, V. 249, N. 2, p. 147-152, the whole text, p. 148, p. 151.
Bessard et al. High antitumor activity of RLI, an interleukin-15 (IL-15)-IL-15 receptor alpha fusion protein, in metastatic melanoma and colorectal cancer. Mol Cancer Ther. 2009;8(9):2736-2745.
Yu et al., "Simultaneous inhibition of two regulatory T-cell subsets enhanced Interleukin-15 efficacy in a prostate tumor model.", Proc Natl Acad Sci USA. 2012;109(16):6187-6192.
Perdreau et al. "Different dynamics of IL-15R activation following IL-15 cis- or trans-presentation." Eur Cytokine Netw. Dec. 2010;21(4):297-307.
Desbois et al. "IL-15 Trans-Signaling with the Superagonist RLI Promotes Effector/Memory CD8+ T Cell Responses and Enhances Antitumor Activity of PD-1 Antagonists.", J Immunol. Jul. 1, 2016;197(1):168-78. doi: 10.4049/jimmunol.1600019. Epub May 23, 2016.
Intlekofer et al., "At the Bench: Preclinical rationale for CTLA-4 and PD-1 blockade as cancer immunotherapy", Journal of Leukocyte Biology, vol. 94, Jul. 2013.
Melero et al.: "Evolving synergistic combinations of targeted immunotherapies to combat cancer", Nature Reviews, Cancer, vol. 15, 2015.

(56) References Cited

OTHER PUBLICATIONS

Waldmann: "The biology of interleukin-2 and interleukin-15: implications for cancer therapy and vaccine design", 2006, Nat Rev Immunol 6(8): 595-601.

Dubois et al., Preassociation of IL-15 with IL-15Rα-IgG1-Fc Enhances Its Activity on Proliferation of NK and CD8+/CD44high T Cells and Its Antitumor Action., J Immunol Feb. 15, 2008, 180 (4) 2099-2106; DOI: https://doi.org/10.4049/jimmunol.180.4.2099.

Alter et al., Targeted IL-15-based Protein Fusion Complexes as Cancer Immunotherapy Approaches., J Immunol Sci. (2018); 2(1): 15-18.

Mazzarella et al., The evolving landscape of 'next-generation' immune checkpoint inhibitors: A review., Eur J Cancer. Aug. 2019; 117:14-31. doi: 10.1016/j.ejca.2019.04.035. Epub Jun. 21, 2019.

Gasser B. et al., Antibody production with yeasts and filamentous fungi: on the road to large scale? Biotechnology letters, 2007, V. 29, N. 2, p. 201-212, p. 208.

An Z., Therapeutic monoclonal antibodies: from bench to clinic, John Wiley And Sons, 2011, 896 p., p. 350.

Burns W. R. et al., A high molecular weight melanoma-associated antigen-specific chimeric antigen receptor redirects lymphocytes to target human melanomas, Cancer research, 2010, V. 70, N. 8, p. 3027-3033, p. 3028.

Colman P. M., Effects of amino acid sequence changes on antibody-antigen interactions, Research in Immunology, 1994, V. 145, N. 1, p. 33-36, c.33.

Safdari Y. et al., Antibody humanization methods—a review and update, Biotechnology and Genetic Engineering Reviews, 2013, V. 29, N. 2, p. 175-186, p. 178, 180.

Teplyakov A. et al., Antibody modeling assessment II. Structures and models, Proteins: Structure, Function, and Bioinformatics, 2014, V. 82, N. 8, p. 1563-1582, the whole text, p. 1582).

Yu et al. Simultaneous blockade of multiple immune system inhibitory checkpoints enhances antitumor activity mediated by interleukin-15 in a murine metastatic colon carcinoma model. Clin Cancer Res. 2010;16(24):6019-6028.

Vincent et al. Tumor targeting of the IL-15 superagonist RLI by an anti-GD2 antibody strongly enhances its antitumor potency. Int J Cancer. 2013;133(3):757-765.

Vincent et al. CS14-6. Development of two IL15 immunocytokines targeting either GD2- or CD20-tumoral bearing cells. Cytokine. 2011;56 (1):102.

Xu et al. The tumor immunosuppressive microenvironment impairs the therapy of anti-HER2/neu antibody. Protein Cell. 2012;3(6):441-449.

Nellis et al., Characterization of recombinant human IL-15 deamidation and its practical elimination through substitution of asparagine 77., Pharm Res. Mar. 2012;29(3):722-38. doi: 10.1007/s11095-011-0597-0. Epub Oct. 19, 2011.

Perez et al., Epitope mapping of 10 monoclonal antibodies against the pig analogue of human membrane cofactor protein (MCP)., Immunology. Apr. 1999;96(4):663-70. doi: 10.1046/j.1365-2567.1999.00732.x.

\* cited by examiner

Figure 2A

Human IL-15 precursor sequence

>sp|P40933 (SEQ ID NO:1)
MRISKPHLRSISIQCYLCLLLNSHFLTEAGIHVFILGCFSAGLPKTEANWVNVISDLKKIEDLIQSMHIDATLYTES
DVHPSCKVTAMKCFLLELQVISLESGDASIHDTVENLIILANNSLSSNGNVTESGCKECEELEEKNIKEFLQSFVHI
VQMFINTS

Human IL-15 mature form sequence

>sp|P40933|49-162 (SEQ ID NO:2)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS

Human IL-15Rα sequence

>sp|Q13261 (SEQ ID NO:3)
MAPRRARGCRTLGLPALLLLLLLRPPATRGITCPPPMSVEHADIWVKSYSLYSRERYICNSGFKRKAGTSSLTECVLNKAT
NVAHWTTPSLKCIRDPALVHQRPAPPSTVTTAGVTPQPESLSPSGKEPAASSPSSNNTAATTAAIVPGSQLMPSKSPST
GTTEISSHESSHGTPSQTTAKNWELTASASHQPPGVYPQGHSDTTVAISTSTVLLCGLSAVSLLACYLKSRQTPPLASVE
MEAMEALPVTWGTSSRDEDLENCSHHL

Human IL-15Rα, extracellular domain

>sp|Q13261|31-205 (SEQ ID NO:4)
ITCPPPMSVEHADIWVKSYSLYSRERYICNSGFKRKAGTSSLTECVLNKATNVAHWTTPSLKCIRDPALVHQRPAPPSTV
TTAGVTPQPESLSPSGKEPAASSPSSNNTAATTAAIVPGSQLMPSKSPSTGTTEISSHESSHGTPSQTTAKNWELTASAS
HQPPGVYPQGHSDTT

Human IL-15Rα, sushi domain

>sp|Q13261|31-95 (SEQ ID NO:5)
ITCPPPMSVEHADIWVKSYSLYSRERYICNSGFKRKAGTSSLTECVLNKATNVAHWTTPSLKCIR

Human IL-15Rß sequence

>sp|P14784 (SEQ ID NO:6)
MAAPALSWRLPLLILLLPLATSWASAAVNGTSQFTCFYNSRANISCVWSQDGALQDTSCQVHAWPDRRRWNQTCELL
PVSQASWACNLILGAPDSQKLTTVDIVTLRVLCREGVRWRVMAIQDFKPFENLRLMAPISLQVVHVETHRCNISWEI
SQASHYFERHLEFEARTLSPGHTWEEAPLLTLKQKQEWICLETLTPDTQYEFQVRVKPLQGEFTTWSPWSQPLAFRT
KPAALGKDTIPWLGHLLVGLSGAFGFIILVYLLINCRNTGPWLKKVLKCNTPDPSKFFSQLSSEHGGDVQKWLSSPF
PSSSFSPGGLAPEISPLEVLERDKVTQLLLQQDKVPEPASLSSNHSLTSCFTNQGYFFFHLPDALEIEACQVYFTYD
PYSEEDPDEGVAGAPTGSSPQPLQPLSGEDDAYCTFPSRDDLLLFSPSLLGGPSPPSTAPGGSGAGEERMPPSLQER
VPRDWDPQPLGPPTPGVPDLVDFQPPPELVLREAGEEVPDAGPREGVSFPWSRPPGQGEFRALNARLPLNTDAYLSL
QELQGQDPTHLV

Figure 2B

Human IL-15Rß, extracellular domain

>sp|P14784|27-240 (SEQ ID NO:7)
AVNGTSQFTCFYNSRANISCVWSQDGALQDTSCQVHAWPDRRRWNQTCELLPVSQASWACNLILGAPDSQKLTTVD
IVTLRVLCREGVRWRVMAIQDFKPFENLRLMAPISLQVVHVETHRCNISWEISQASHYFERHLEFEARTLSPGHTWEEA
PLLTLKQKQEWICLETLTPDTQYEFQVRVKPLQGEFTTWSPWSQPLAFRTKPAALGKDT

Human common gamma chain sequence

>sp|P31785 (SEQ ID NO:8)
MLKPSLPFTSLLFLQLPLLGVGLNTTILTPNGNEDTTADFFLTTMPTDSLSVSTLPLPEVQCFVFNVEYMNCTWNSSSEP
QPTNLTLHYWYKNSDNDKVQKCSHYLFSEEITSGCQLQKKEIHLYQTFVVQLQDPREPRRQATQMLKLQNLVIPWAPE
NLTLHKLSESQLELNWNNRFLNHCLEHLVQYRTDWDHSWTEQSVDYRHKFSLPSVDGQKRYTFRVRSRFNPLCGSAQ
HWSEWSHPIHWGSNTSKENPFLFALEAVVISVGSMGLIISLLCVYFWLERTMPRIPTLKNLEDLVTEYHGNFSAWSGVS
KGLAESLQPDYSERLCLVSEIPPKGGALGEGPGASPCNQHSPYWAPPCYTLKPET

Human common gamma chain, extracellular domain

>sp|P31785|23-262 (SEQ ID NO:9)
LNTTILTPNGNEDTTADFFLTTMPTDSLSVSTLPLPEVQCFVFNVEYMNCTWNSSSEPQPTNLTLHYWYKNSDNDKVQ
KCSHYLFSEEITSGCQLQKKEIHLYQTFVVQLQDPREPRRQATQMLKLQNLVIPWAPENLTLHKLSESQLELNWNNRFL
NHCLEHLVQYRTDWDHSWTEQSVDYRHKFSLPSVDGQKRYTFRVRSRFNPLCGSAQHWSEWSHPIHWGSNTSKENP
FLFALEA

Figure 3A

| Monomer 1 | Monomer 2 |
|---|---|
| F405A | T394F |
| S364D | Y349K |
| S364E | L368K |
| S364E | Y349K |
| S364F | K370G |
| S364H | Y349K |
| S364H | Y349T |
| S364Y | K370G |
| T411K | K370E |
| V397S/F405A | T394F |
| K370R/T411K | K370E/T411E |
| L351E/S364D | Y349K/L351K |
| L351E/S364E | Y349K/L351K |
| L351E/T366D | L351K/T366K |
| P395T/V397S/F405A | T394F |
| S364D/K370G | S364Y/K370R |
| S364D/T394F | Y349K/F405A |
| S364E/F405A | Y349K/T394F |
| S364E/F405S | Y349K/T394Y |
| S364E/T411E | Y349K/D401K |
| S364H/D401K | Y349T/T411E |
| S364H/F405A | Y349T/T394F |
| S364H/T394F | Y349T/F405A |
| Y349C/S364E | Y349K/S354C |
| L351E/S364D/F405A | Y349K/L351K/T394F |
| L351K/S364H/D401K | Y349T/L351E/T411E |
| S364E/T411E/F405A | Y349K/T394F/D401K |
| S364H/D401K/F405A | Y349T/T394F/T411E |
| S364H/F405A/T411E | Y349T/T394F/D401K |

Figure 3B

| Monomer 1 | Monomer 2 |
|---|---|
| K370E/T411D | T411K |
| L368E/K409E | L368K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |
| L368D/K370S | S364K |
| L368D/K370S | S364K/E357L |
| L368D/K370S | S364K/E357Q |
| T411E/K360E/Q362E | D401K |
| K370S | S364K |
| L368E/K370S | S364K/E357Q |
| K370S | S364K/E357Q |
| T411E/K360D | D401K |
| T411E/K360E | D401K |
| T411E/Q362E | D401K |
| T411E/N390D | D401K |
| T411E | D401K/Q347K |
| T411E | D401K/Q347R |
| T411E/K360D/Q362E | D401K |

Figure 3C

| Monomer 1 | Monomer 2 |
|---|---|
| T411E/K360E/N390D | D401K |
| T411E/Q362E/N390D | D401K |
| T411E/Q347R | D401K/K360D |
| T411E/Q347R | D401K/K360E |
| T411E/K360 | D401K/Q347K |
| T411E/K360D | D401K/Q347R |
| T411E/K360E | D401K/Q347K |
| T411E/K360E | D401K/Q347R |
| T411E/S364K | D401K/K370S |
| T411E/K370S | D401K/S364K |
| Q347E | E357Q |
| Q347E | E357Q/Q362K |
| K360D/Q362E | Q347R |
| K360D/Q362E | D401K |
| K360D/Q362E | Q347R/D401K |
| K360E/Q362E | Q347R |
| K360E/Q362E | D401K |
| K360E/Q362E | Q347R/D401K |
| Q362E/N390D | D401K |
| Q347E/K360D | D401N |
| K360D | Q347R/N390K |
| K360D | N390K/D401N |
| K360E | Y349H |
| K370S/Q347E | S364K |
| K370S/E357L | S364K |
| K370S/E357Q | S364K |
| K370S/Q347E/E357L | S364K |
| K370S/Q347E/E357Q | S364K |

Figure 3D

| Monomer 1 | Monomer 2 |
|---|---|
| L368D/K370S/Q347E | S364K |
| L368D/K370S/E357L | S364K |
| L368D/K370S/E357Q | S364K |
| L368D/K370S/Q347E/E357L | S364K |
| L368D/K370S/Q347E/E357Q | S364K |
| L368E/K370S/Q347E | S364K |
| L368E/K370S/E357L | S364K |
| L368E/K370S/E357Q | S364K |
| L368E/K370S/Q347E/E357L | S364K |
| L368E/K370S/Q347E/E357Q | S364K |
| L368D/K370T/Q347E | S364K |
| L368D/K370T/E357L | S364K |
| L368D/K370T/E357Q | S364K |
| L368D/K370T/Q347E/E357L | S364K |
| L368D/K370T/Q347E/E357Q | S364K |
| L368E/K370T/Q347E | S364K |
| L368E/K370T/E357L | S364K |
| L368E/K370T/E357Q | S364K |
| L368E/K370T/Q347E/E357L | S364K |
| L368E/K370T/Q347E/E357Q | S364K |
| T411E/Q362E | D401K/T411K |
| T411E/N390D | D401K/T411K |
| T411E/Q362E | D401R/T411R |
| T411E/N390D | D401R/T411R |
| Y407T | T366Y |
| F405A | T394W |
| T366Y/F405A | T394W/Y407T |
| Y407A | T366W |
| T366S/L368A/Y407V | T366W |
| T366S/L368A/Y407V/Y349C | T366W/S354C |

Figure 3E

| Monomer 1 | Monomer 2 |
|---|---|
| K392D/K409D | E356K/D399K |
| K370D/K392D/K409D | E356K/E357K/D399K |
| K247Q/R355Q/N384S/K392N/V397M/Q419E/K447_ | P217R/P228R/N276K |
| K247Q/R355Q/N384S/K392N/V397M/Q419E/K447_ | N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| K247Q/R355Q/Q419E/K447_ | P217R/P228R/N276K |
| K247Q/R355Q/Q419E/K447_ | N276K |
| K274Q/R355Q/N384S/K392N/V397M/Q419E/K447_ | |
| Q295E/N384D/Q418E/N421D | |
| Q295E/Q418E/N421D | |
| P217R/P228R/N276K | |
| N276K | |
| E269Q/E272Q/E283Q/E357Q | |
| E269Q/E272Q/E283Q | |
| E269Q/E272Q | |
| E269Q/E283Q | |
| E272Q/E283Q | |
| E269Q | |

Figure 4

| Variant constant region | Substitutions |
|---|---|
| pI_ISO(-)-Fc only | K274Q/R355Q/N384S/K392N/V397M/Q419E/K447_ |
| pI_(-)_isosteric A-Fc only | Q295E/N384D/Q418E/N421D |
| pI_(-)_isosteric_B-Fc only | Q295E/Q418E/N421D |
| pI_ISO(+RR)-Fc only | P217R/P228R/N276K |
| pI_ISO(+)-Fc only | N276K |
| pI_(+)_isosteric_A | E269Q/E272Q/E283Q/E357Q |
| pI_(+)_isosteric_B | E269Q/E272Q/E283Q |
| pI_(+)_isosteric_E269Q/E272Q | E269Q/E272Q |
| pI_(+)_isosteric_E269Q/E283Q | E269Q/E283Q |
| pI_(+)_isosteric_E272Q/E283Q | E272Q/E283Q |
| pI_(+)_isosteric_E269Q | E269Q |

Figure 5

Ablation Variants
G236R
S239G
S239K
S239Q
S239R
V266D
S267K
S267R
H268K
E269R
299R
299K
K322A
A327G
A327L
A327N
A327Q
L328E
P329K
A330L
A330S/P331S
I332K
I332R
V266D/A327Q
V266D/P329K
S267R/A327Q
S267R/P329K
G236R/L328R
E233P/L234V/L235A/G236_/S239K
E233P/L234V/L235A/G236_/S267K
E233P/L234V/L235A/G236_/S239K/A327G
E233P/L234V/L235A/G236_/S267K/A327G
E233P/L234V/L235A/G236_
S239K/S267K
267K/P329K

Figure 6A

| IL-15-Fc monomer (-) | IL-15Rα(sushi)-Fc monomer (+) |
|---|---|
| C220S | C220S |
| Heterodimer pI variants L368D/K370S | Heterodimer pI variants S364K/E357Q |
| Isosteric pI substitutions Q295E/N384D/Q418E/N421D | |
| FcKO E233P/L234V/L235A/G236_/S267K | FcKO E233P/L234V/L235A/G236_/S267K |
| ±M428L/N434S | ±M428L/N434S |

Figure 6B

| scIL-15/Rα-Fc monomer (-) | empty-Fc monomer (+) |
|---|---|
| C220S | C220S |
| Heterodimer pI variants L368D/K370S | Heterodimer pI variants S364K/E357Q |
| Isosteric pI substitutions Q295E/N384D/Q418E/N421D | |
| FcKO E233P/L234V/L235A/G236_/S267K | FcKO E233P/L234V/L235A/G236_/S267K |
| ±M428L/N434S | ±M428L/N434S |

Figure 6C

| empty-Fc monomer (-) | IL-15Rα(sushi)-Fc monomer (+) |
|---|---|
| C220S | C220S |
| Heterodimer pI variants L368D/K370S | Heterodimer pI variants S364K/E357Q |
| Isosteric pI substitutions Q295E/N384D/Q418E/N421D | |
| FcKO E233P/L234V/L235A/G236_/S267K | FcKO E233P/L234V/L235A/G236_/S267K |
| ±M428L/N434S | ±M428L/N434S |

Figure 6D

| IL-15Rα(sushi)-Fc Chain 1 | IL-15Rα(sushi)-Fc Chain 2 |
|---|---|
| C220S | C220S |
| FcKO | FcKO |
| E233P/L234V/L235A/G236_/S267K | E233P/L234V/L235A/G236_/S267K |
| ±M428L/N434S | ±M428L/N434S |

Figure 6E

| Fc-IL-15Rα(sushi) (-) | empty-Fc monomer (+) |
|---|---|
| C220S | C220S |
| Heterodimer pI variants L368D/K370S | Heterodimer pI variants S364K/E357Q |
|  | Isosteric pI substitutions P217R/P228R/N276K |
| FcKO | FcKO |
| E233P/L234V/L235A/G236_/S267K | E233P/L234V/L235A/G236_/S267K |
| ±M428L/N434S | ±M428L/N434S |

Figure 7

| Name | Sequence | SEQ ID NO: |
|---|---|---|
| (GGGGS)$_1$ or GGGGS | GGGGS | 27 |
| (GGGGS)$_2$ | GGGGSGGGGS | 28 |
| (GGGGS)$_3$ | GGGGSGGGGSGGGGS | 30 |
| (GGGGS)$_4$ | GGGGSGGGGSGGGGSGGGGS | 29 |
| (GGGGS)$_5$ | GGGGSGGGGSGGGGSGGGGSGGGGS | 32 |
| (GGGGS)$_6$ | GGGGSGGGGSGGGGSGGGGSGGGGSGGGGS | 31 |
| (GGGGS)$_7$ | GGGGSGGGGSGGGGSGGGGSGGGGSGGGGSGGGGS | 35 |
| 30AA-linker | DPALVHQRPAPPGGGGSGGGGSGGGGSGGG | 36 |
| (GKPGS)$_1$ or GKPGS | GKPGS | 37 |
| (GKPGS)$_5$ | GKPGSGKPGSGKPGSGKPGSGKPGS | 34 |
| (GKPGS)$_6$ | GKPGSGKPGSGKPGSGKPGSGKPGSGKPGS | 33 |
| (GGGES)$_1$ or GGGES | GGGES | 38 |

Figure 8A

IL-15/Rα-Fc Backbone 1

>IL-15/Rα-Fc monomer 1 (SEQ ID NO:39)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK >IL-15/Rα-Fc monomer 2 (SEQ ID NO:40)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK IL-15/Rα-Fc Backbone 2

>IL-15/Rα-Fc monomer 1 (SEQ ID NO:41)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVKLTCLVKGFY
PSDIAVEWESNGQPENNYKTTPPVLDSDGSFFLYSKLTVDKSRWQQGNVFSCSVMHEALHNHYTQKSLSLSPGK >IL-15/Rα-Fc monomer 2 (SEQ ID NO:42)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK IL-15/Rα-Fc Backbone 3

>IL-15/Rα-Fc monomer 1 (SEQ ID NO:43)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVKLTCLVKGFY
PSDIAVEWESNGQPENNYKTTPPVLDSDGSFFLYSKLTVDKSRWQQGNVFSCSVMHEALHNHYTQKSLSLSPGK >IL-15/Rα-Fc monomer 2 (SEQ ID NO:44)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCEVSGFYPS
DIAVEWESDGQPENNYKTTPPVLDSDGSFFLYSKLTVDKSRWEQGDVFSCSVMHEALHNHYTQKSLSLSPGK

Figure 8B

IL-15/Rα-Fc Backbone 4

>IL-15/Rα-Fc monomer 1 (SEQ ID NO:45)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVSLTCLVKGFY
PSDIAVEWESNGQPENNYKTTPPVLDSKGSFFLYSKLTVDKSRWQQGNVFSCSVMHEALHNHYTQKSLSLSPGK >IL-15/Rα-Fc monomer 2 (SEQ ID NO:46)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTENEVSLTCLVKGFYPS
DIAVEWESDGQPENNYKTTPPVLDSDGSFFLYSKLEVDKSRWEQGDVFSCSVMHEALHNHYTQKSLSLSPGK IL-15/Rα-Fc Backbone 5

>IL-15/Rα-Fc monomer 1 (SEQ ID NO:47)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSRDQLTKNQVKLTCLVKGFYP
SDIAVEWESNGQPENNYKTTPPVLDSDGSFFLYSKLTVDKSRWQQGNVFSCSVMHEALHNHYTQKSLSLSPGK >IL-15/Rα-Fc monomer 2 (SEQ ID NO:48)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSRDELTKNQVSLTCDVSGFYPS
DIAVEWESDGQPENNYKTTPPVLDSDGSFFLYSKLTVDKSRWEQGDVFSCSVMHEALHNHYTQKSLSLSPGK IL-15/Rα-Fc Backbone 6

>IL-15/Rα-Fc monomer 1 (SEQ ID NO:49)
EPKSSDKTHTCPPCPAPPVAGPSVFLFPPKPKDTLMISRTPEVTCVVVDVKHEDPEVKFNWYVDGVEVHNAKTKPREE
QYASTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK >IL-15/Rα-Fc monomer 2 (SEQ ID NO:50)
EPKSSDKTHTCPPCPAPPVAGPSVFLFPPKPKDTLMISRTPEVTCVVVDVKHEDPEVKFNWYVDGVEVHNAKTKPREEE
YASTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK

Figure 8C

IL-15/Rα-Fc Backbone 7

>IL-15/Rα-Fc monomer 1 (SEQ ID NO:51)
EPKSSDKTHTCPPCPAPPVAGPSVFLFPPKPKDTLMISRTPEVTCVVVDVKHEDPEVKFNWYVDGVEVHNAKTKPREE
QYSSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK >IL-15/Rα-Fc monomer 2 (SEQ ID NO:52)
EPKSSDKTHTCPPCPAPPVAGPSVFLFPPKPKDTLMISRTPEVTCVVVDVKHEDPEVKFNWYVDGVEVHNAKTKPREEE
YSSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK IL-15/Rα-Fc Backbone 8

>IL-15/Rα-Fc monomer 1 (SEQ ID NO:53)
ESKYGPPCPPCPAPEFLGGPSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQEQMTKNQVKLTCLVKGFYPS
DIAVEWESNGQPENNYKTTPPVLDSDGSFFLYSRLTVDKSRWQEGNVFSCSVMHEALHNHYTQKSLSLSLGK >IL-15/Rα-Fc monomer 2 (SEQ ID NO:54)
ESKYGPPCPPCPAPEFLGGPSVFLFPPKPKDTLMISRTPEVTCVVVDVSQEDPEVQFNWYVDGVEVHNAKTKPREEEFN
STYRVVSVLTVLHQDWLNGKEYKCKVSNKGLPSSIEKTISKAKGQPREPQVYTLPPSQEEMTKNQVSLTCDVSGFYPSDI
AVEWESDGQPENNYKTTPPVLDSDGSFFLYSRLTVDKSRWEEGDVFSCSVMHEALHNHYTQKSLSLSLGK IL-15/Rα-Fc Backbone 9

>IL-15/Rα-Fc monomer 1 (SEQ ID NO:55)
ERKCCVECPPCPAPPVAGPSVFLFPPKPKDTLMISRTPEVTCVVVDVSHEDPEVQFNWYVDGVEVHNAKTKPREEQFN
STFRVVSVLTVVHQDWLNGKEYKCKVSNKGLPAPIEKTISKTKGQPREPQVYTLPPSREQMTKNQVKLTCLVKGFYPSDI
AVEWESNGQPENNYKTTPPMLDSDGSFFLYSKLTVDKSRWQQGNVFSCSVMHEALHNHYTQKSLSLSPGK >IL-15/Rα-Fc monomer 2 (SEQ ID NO:56)
ERKCCVECPPCPAPPVAGPSVFLFPPKPKDTLMISRTPEVTCVVVDVSHEDPEVQFNWYVDGVEVHNAKTKPREEEFN
STFRVVSVLTVVHQDWLNGKEYKCKVSNKGLPAPIEKTISKTKGQPREPQVYTLPPSREEMTKNQVSLTCDVSGFYPSDI
AVEWESDGQPENNYKTTPPMLDSDGSFFLYSKLTVDKSRWEQGDVFSCSVMHEALHNHYTQKSLSLSPGK IL-15/Rα-Fc Backbone 10

>IL-15/Rα-Fc monomer 1 (SEQ ID NO:57)
ERKCCVECPPCPAPPVAGPSVFLFPPKPKDTLMISRTPEVTCVVVDVKHEDPEVQFNWYVDGVEVHNAKTKPREEQFN
STFRVVSVLTVVHQDWLNGKEYKCKVSNKGLPAPIEKTISKTKGQPREPQVYTLPPSREQMTKNQVKLTCLVKGFYPSDI
AVEWESNGQPENNYKTTPPMLDSDGSFFLYSKLTVDKSRWQQGNVFSCSVMHEALHNHYTQKSLSLSPGK

Figure 8D

>IL-15/Rα-Fc monomer 2 (SEQ ID NO:58)
ERKCCVECPPCPAPPVAGPSVFLFPPKPKDTLMISRTPEVTCVVVDVKHEDPEVQFNWYVDGVEVHNAKTKPREEEFN
STFRVVSVLTVVHQDWLNGKEYKCKVSNKGLPAPIEKTISKTKGQPREPQVYTLPPSREEMTKNQVSLTCDVSGFYPSDI
AVEWESDGQPENNYKTTPPMLDSDGSFFLYSKLTVDKSRWEQGDVFSCSVMHEALHNHYTQKSLSLSPGK IL-15/Rα-Fc Backbone 11

>IL-15/Rα-Fc monomer 1 (SEQ ID NO:59)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVLHEALHSHYTQKSLSLSPGK >IL-15/Rα-Fc monomer 2 (SEQ ID NO:60)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVLHEALHSHYTQKSLSLSPGK IL-15/Rα-Fc Backbone 12

>IL-15/Rα-Fc monomer 1 (SEQ ID NO:61)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHNHYTQKSLSLSPGK >IL-15/Rα-Fc monomer 2 (SEQ ID NO:62)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHNHYTQKSLSLSPGK IL-15/Rα-Fc Backbone 13

>IL-15/Rα-Fc monomer 1 (SEQ ID NO:63)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK >IL-15/Rα-Fc monomer 2 (SEQ ID NO:64)
ERKSSDKTHTCPRCPAPPVAGPSVFLFPPKPKDTLMISRTPEVTCVVVDVKHEDPEVKFKWYVDGVEVHNAKTKPREEQ
YNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK IL-15/Rα-heteroFc
Example: XENP20818 scIL-15/Rα-Fc
Example: XENP21478 ncIL-15/Rα-Fc
Example: XENP21479

Bivalent ncIL-15/Rα-Fc
Example: XENP21978

Bivalent scIL-15/Rα-Fc

Fc-ncIL-15/Rα
Example: XENP22637

Fc-scIL-15/Rα

Figure 10

>XENP20818 – human IL15-(GGGGS)₁ x human IL15Rα(Sushi)-(GGGGS)₁ Fc heterodimer

Chain 1 - human_IL15_(GGGGS)₁_Fc(216)_IgG1_pI(-)_Isosteric_A_C220S/PVA_/S267K/L368D/K370S (15902) (SEQ ID NO:65)
<u>NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS</u>/<u>GGGGS</u>/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Rα(Sushi)_(GGGGS)₁_Fc(216)_IgG1_C220S/PVA_/S267K/S364K/E357Q (15908)
(SEQ ID NO:66)
<u>ITCPPPMSVEHADIWVKSYSLYSRERYICNSGFKRKAGTSSLTECVLNKATNVAHWTTPSLKCIR</u>/<u>GGGGS</u>/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK >XENP21475 – human IL15 x human IL15Rα(Sushi) Fc heterodimer Chain 1 - human_IL15-Fc(216)_IgG1_pI(-)_Isosteric_A_C220S/PVA_/S267K/L368D/K370S (16479) (SEQ ID NO:67)
<u>NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS</u>/EPKSSDKTHTCPPCPAPPVAGPSVFLFPPKPKDTLMISRTPEVTCVVVD
VKHEDPEVKFNWYVDGVEVHNAKTKPREEEYNSTYRVVSVLTVLHQDWLNGKEYKCKVSNKALPAPIEKTISKAKGQP
REPQVYTLPPSREEMTKNQVSLTCDVSGFYPSDIAVEWESDGQPENNYKTTPPVLDSDGSFFLYSKLTVDKSRWEQGD
VFSCSVMHEALHNHYTQKSLSLSPGK Chain 2 - human_IL15Rα(Sushi)-Fc(216)_IgG1_C220S/PVA_/S267K/S364K/E357Q (16481) (SEQ ID NO:68)
<u>ITCPPPMSVEHADIWVKSYSLYSRERYICNSGFKRKAGTSSLTECVLNKATNVAHWTTPSLKCIR</u>/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREQMTKNQVKLTCLVKGFYPSDIAVEWESNGQP
ENNYKTTPPVLDSDGSFFLYSKLTVDKSRWQQGNVFSCSVMHEALHNHYTQKSLSLSPGK

Figure 11

>XENP21478 – human IL15Rα(Sushi)-(GGGGS)₆-human IL15(single-chain) Fc heterodimer Chain 1 - human_IL15Rα(sushi)_(GGGGS)₆-human_IL15-Fc(216)_IgG1_pI(-)_Isosteric_A_C220S/PVA_/S267K/L368D/K370S (16478) (SEQ ID NO:69)
ITCPPPMSVEHADIWVKSYSLYSRERYICNSGFKRKAGTSSLTECVLNKATNVAHWTTPSLKCIR/<u>GGGGSGGGGSGGG
GSGGGGSGGGGSGGGGS</u>/NWVNVISDLKKIEDLIQSMHIDATLYTESDVHPSCKVTAMKCFLLELQVISLESGDASIHD
TVENLIILANNSLSSNGNVTESGCKECEELEEKNIKEFLQSFVHIVQMFINTS/EPKSSDKTHTCPPCPAPPVAGPSVFLFPP
KPKDTLMISRTPEVTCVVVDVKHEDPEVKFNWYVDGVEVHNAKTKPREEEYNSTYRVVSVLTVLHQDWLNGKEYKCK
VSNKALPAPIEKTISKAKGQPREPQVYTLPPSREEMTKNQVSLTCDVSGFYPSDIAVEWESDGQPENNYKTTPPVLDSD
GSFFLYSKLTVDKSRWEQGDVFSCSVMHEALHNHYTQKSLSLSPGK Chain 2 - empty-Fc(216)_IgG1_C220S/PVA_/S267K/S364K/E357Q (8924) (SEQ ID NO:70)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK

Figure 12A

>XENP21479 – empty-Fc-IL15(non-covalent)-human_IL15Rα(Sushi) Fc heterodimer

Chain 1 - human_IL15_no_tag (16484) (SEQ ID NO:71)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS Chain 2 - empty-Fc(216)_IgG1_pI(-)_Isosteric_A_C220S/PVA_/S267K/L368D/K370S (8793) (SEQ ID NO:72)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK Chain 3 - human_IL15Rα(Sushi)-Fc(216)_IgG1_C220S/PVA_/S267K/S364K/E357Q (16481) (SEQ ID NO:73)
<u>ITCPPPMSVEHADIWVKSYSLYSRERYICNSGFKRKAGTSSLTECVLNKATNVAHWTTPSLKCIR</u>/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREQMTKNQVKLTCLVKGFYPSDIAVEWESNGQP
ENNYKTTPPVLDSDGSFFLYSKLTVDKSRWQQGNVFSCSVMHEALHNHYTQKSLSLSPGK >XENP022366 – empty-Fc-IL15(non-covalent)-human_IL15Ra(sushi)_(GGGGS)1_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15_no_tag (16484) (SEQ ID NO:74)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS Chain 2 - empty-Fc(216)_IgG1_pI(-)_Isosteric_A_C220S/PVA_/S267K/L368D/K370S (8793) (SEQ ID NO:75)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK Chain 3 - human_IL15Ra(Sushi)_(GGGGS)1_Fc(216)_IgG1_C220S/PVA_/S267K/S364K/E357Q (15908) (SEQ ID NO:76)
<u>ITCPPPMSVEHADIWVKSYSLYSRERYICNSGFKRKAGTSSLTECVLNKATNVAHWTTPSLKCIR</u>/<u>GGGGS</u>/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK

Figure 12B

>XENP024348 IL15(non-covalent)-human_IL15Ra(Sushi)_empty-Fc_Fc(216)_IgG1_pI(-
)_Isosteric_A_C220S/PVA_/S267K/L368D/K370S-Fc(216)_IgG1_C220S/PVA_/S267K/S364K/E357Q Chain 1 – IL15 WT (SEQ ID NO:77)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS Chain 2 – human_IL15Ra(Sushi)_Fc(216)_IgG1_pI(-)_Isosteric_A_C220S/PVA_/S267K/L368D/K370S
(SEQ ID NO:78)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEEYNSTYRVVSVLTVLH
QDWLNGKEYKCKVSNKALPAPIEKTISKAKGQPREPQVYTLPPSREEMTKNQVSLTCDVSGFYPSDIAVEWESDGQPE
NNYKTTPPVLDSDGSFFLYSKLTVDKSRWEQGDVFSCSVMHEALHNHYTQKSLSLSPGK Chain 3 – empty_ Fc(216)_IgG1_C220S/PVA_/S267K/S364K/E357Q (SEQ ID NO:79)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK

Figure 13

>XENP021978 – human_IL15(non-covalent)-human_IL15Ra(Sushi)_Fc(216)_IgG1_C220S/PVA_/S267K Chain 1 - human_IL15Ra(Sushi)-Fc(216)_IgG1_C220S/PVA_/S267K (17023) (SEQ ID NO:80)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK Chain 2 - human_IL15_no_tag (16484) (SEQ ID NO:81)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS

Figure 14 human_IL15Ra(sushi)(single-chain)-human_IL15_Fc(216)_IgG1_C220S/PVA_/S267K (SEQ ID NO:82)

ITCPPPMSVEHADIWVKSYSLYSRERYICNSGFKRKAGTSSLTECVLNKATNVAHWTTPSLKCIR/GGGGS/NWVNVISD
LKKIEDLIQSMHIDATLYTESDVHPSCKVTAMKCFLLELQVISLESGDASIHDTVENLIILANNSLSSNGNVTESGCKECEEL
EEKNIKEFLQSFVHIVQMFINTS/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSCSVMH
EALHNHYTQKSLSLSPGK

Figure 15

>XENP022637 – empty-Fc(216)_IgG1_pI(-
)_Isosteric_A_C220S/PVA_/S267K/L368D/K370S_(GGGGS)2_IL15Ra(Sushi)_IL15(non-covalent)_IgG1_ISO(+RR)_C220S/PVA_/S267K/S364K/E357Q Chain 1 - empty-Fc(216)_IgG1_pI(-
)_Isosteric_A_C220S/PVA_/S267K/L368D/K370S_(GGGGS)2_IL15Ra(Sushi) (17603) (SEQ ID NO:83)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK/<u>GGGGS
GGGGS/ITCPPPMSVEHADIWVKSYSLYSRERYICNSGFKRKAGTSSLTECVLNKATNVAHWTTPSLKCIR</u>

Chain 2 - empty-Fc(216)_IgG1_ISO(+RR)_C220S/PVA_/S267K/S364K/E357Q (8927) (SEQ ID NO:84)
ERKSSDKTHTCPRCPAPPVAGPSVFLFPPKPKDTLMISRTPEVTCVVVDVKHEDPEVKFKWYVDGVEVHNAKTKPREEQ
YNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK Chain 3 - human_IL15_no_tag (16484) (SEQ ID NO:85)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS

Figure 16 empty-Fc(216)_IgG1_pI(-)_Isosteric_A_C220S/PVA_/S267K/L368D/K370S_(GGGGS)2_IL15Ra(Sushi)_IL15(single-chain)_IgG1_ISO(+RR)_C220S/PVA_/S267K/S364K/E357Q Chain 1 - empty-Fc(216)_IgG1_pI(-)_Isosteric_A_C220S/PVA_/S267K/L368D/K370S_(GGGGS)2_IL15Ra(Sushi)_IL15(single-chain)
(SEQ ID NO:86)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK/<u>GGGGS
GGGGS</u>/<u>ITCPPPMSVEHADIWVKSYSLYSRERYICNSGFKRKAGTSSLTECVLNKATNVAHWTTPSLKCIR</u>/<u>GGGGS</u>/<u>N
WVNVISDLKKIEDLIQSMHIDATLYTESDVHPSCKVTAMKCFLLELQVISLESGDASIHDTVENLIILANNSLSSNGNVTES
GCKECEELEEKNIKEFLQSFVHIVQMFINTS</u>

Chain 2 - empty-Fc(216)_IgG1_ISO(+RR)_C220S/PVA_/S267K/S364K/E357Q (8927) (SEQ ID NO:87)
ERKSSDKTHTCPRCPAPPVAGPSVFLFPPKPKDTLMISRTPEVTCVVVDVKHEDPEVKFKWYVDGVEVHNAKTKPREEQ
YNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

Figure 17A
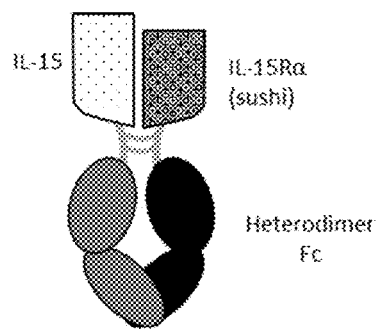
XENP20818
Figure 17B
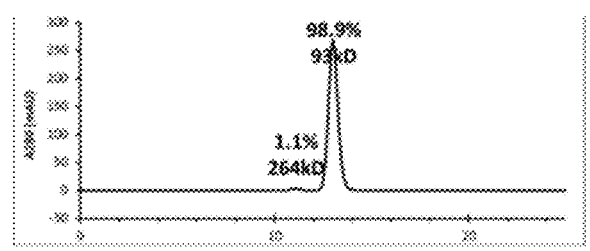
pI(MW) = 6.41 (72.7 kDa)
Protein A yield = 25.7 mg/L
Figure 17C
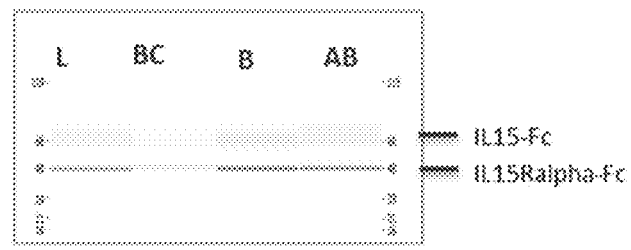
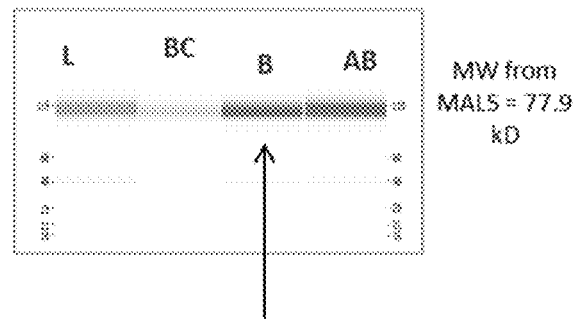
Purified
XENP20818

Octet Red 96 — AHC capture of XENP20818; dip in 200 nM, 40 nM, or 8 nM IL2-Rβ (R&D systems); KD ~ 3 nM

Figure 18A
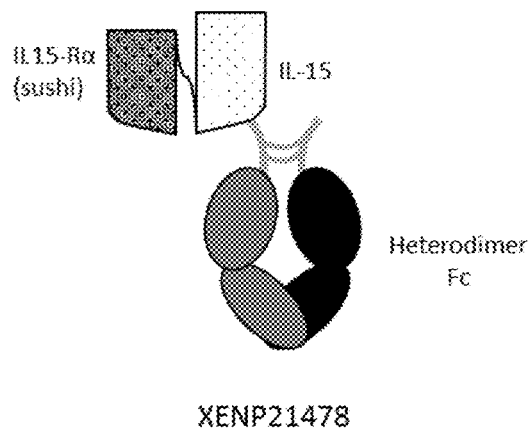
XENP21478
Figure 18B
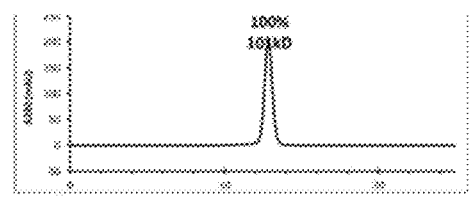
pI(MW) = 6.41 (74.0 kDa)
Protein A yield = 68.1 mg/L
Figure 18C
Reducing
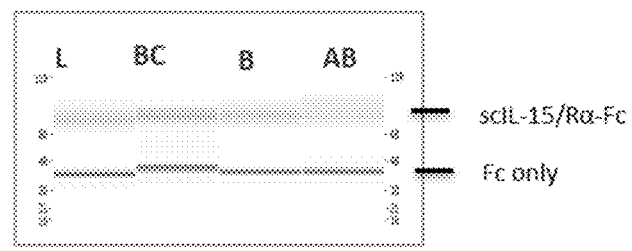
Non Reducing
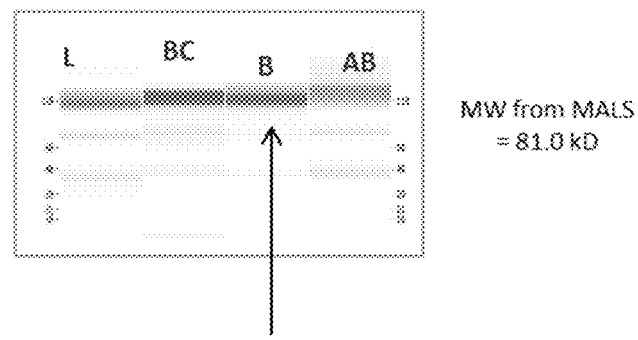

Octet Red 96 – AHC capture of XENP21478; dip in 200 nM, 40 nM, or 8 nM IL2Rβ (R&D systems); KD ~ 3 nM Figure 19A
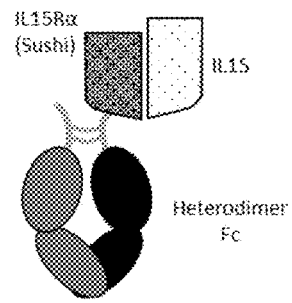
Figure 19B
XENP21479
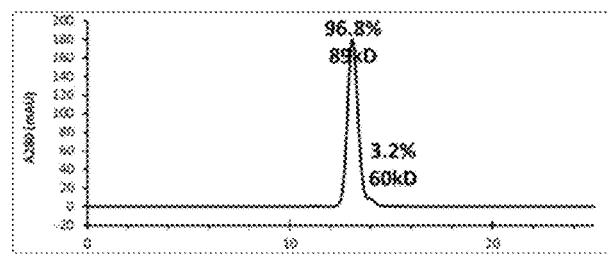
pI(MW) = 6.41 (72.1 kDa)
Protein A yield = 57.1 mg/L
Figure 19C
Reducing
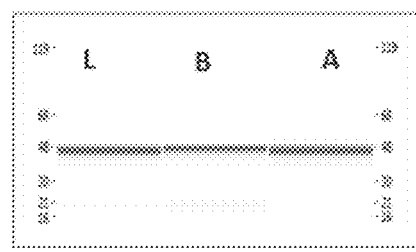
Non Reducing
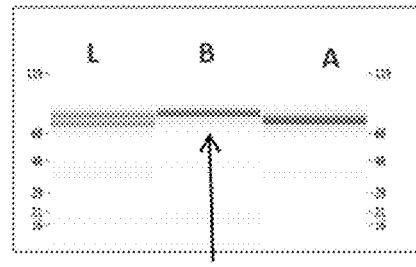
Purified
XENP21479

Octet Red 96 – AHC capture of XENP21479; dip in 200 nM, 40 nM, or 8 nM IL2Rβ (R&D systems); KD ~ 3 nM

DSF TM = 67.5 °C

Figure 27

IL-15Rα(sushi-D96) (SEQ ID NO:88)
ITCPPPMSVEHADIWVKSYSLYSRERYICNSGFKRKAGTSSLTECVLNKATNVAHWTTPSLKCIRD IL-15Rα(sushi-D96/P97) (SEQ ID NO:89)
ITCPPPMSVEHADIWVKSYSLYSRERYICNSGFKRKAGTSSLTECVLNKATNVAHWTTPSLKCIRDP IL-15Rα(sushi-D96/P97/A98) (SEQ ID NO:90)
ITCPPPMSVEHADIWVKSYSLYSRERYICNSGFKRKAGTSSLTECVLNKATNVAHWTTPSLKCIRDPA

Figure 28

IL-15(E87C) (SEQ ID NO:91)
NWVNVISDLKKIEDLIQSMHIDATLYTESDVHPSCKVTAMKCFLLELQVISLESGDASIHDTVENLIILANNSLSSNGNVTE
SGCKCCEELEEKNIKEFLQSFVHIVQMFINTS

IL-15(V49C) (SEQ ID NO:92)
NWVNVISDLKKIEDLIQSMHIDATLYTESDVHPSCKVTAMKCFLLELQCISLESGDASIHDTVENLIILANNSLSSNGNVTE
SGCKECEELEEKNIKEFLQSFVHIVQMFINTS

IL-15(L52C) (SEQ ID NO:93)
NWVNVISDLKKIEDLIQSMHIDATLYTESDVHPSCKVTAMKCFLLELQVISCESGDASIHDTVENLIILANNSLSSNGNVTE
SGCKECEELEEKNIKEFLQSFVHIVQMFINTS

IL-15(E89C) (SEQ ID NO:94)
NWVNVISDLKKIEDLIQSMHIDATLYTESDVHPSCKVTAMKCFLLELQVISLESGDASIHDTVENLIILANNSLSSNGNVTE
SGCKECCELEEKNIKEFLQSFVHIVQMFINTS

IL-15(Q48C) (SEQ ID NO:95)
NWVNVISDLKKIEDLIQSMHIDATLYTESDVHPSCKVTAMKCFLLELCVISLESGDASIHDTVENLIILANNSLSSNGNVTE
SGCKECEELEEKNIKEFLQSFVHIVQMFINTS

IL-15(E53C) (SEQ ID NO:96)
NWVNVISDLKKIEDLIQSMHIDATLYTESDVHPSCKVTAMKCFLLELQVISLCSGDASIHDTVENLIILANNSLSSNGNVTE
SGCKECEELEEKNIKEFLQSFVHIVQMFINTS

IL-15(C42S) (SEQ ID NO:97)
NWVNVISDLKKIEDLIQSMHIDATLYTESDVHPSCKVTAMKSFLLELQVISLESGDASIHDTVENLIILANNSLSSNGNVTE
SGCKECEELEEKNIKEFLQSFVHIVQMFINTS

IL-15(L45C) (SEQ ID NO:98)
NWVNVISDLKKIEDLIQSMHIDATLYTESDVHPSCKVTAMKCFLCELQVISLESGDASIHDTVENLIILANNSLSSNGNVTE
SGCKECEELEEKNIKEFLQSFVHIVQMFINTS

Figure 29

IL-15Rα(sushi-D96/C97) (SEQ ID NO:99)
ITCPPPMSVEHADIWVKSYSLYSRERYICNSGFKRKAGTSSLTECVLNKATNVAHWTTPSLKCIRDC IL-15Rα(sushi-D96/P97/C98) (SEQ ID NO:100)
ITCPPPMSVEHADIWVKSYSLYSRERYICNSGFKRKAGTSSLTECVLNKATNVAHWTTPSLKCIRDPC IL-15Rα(sushi-D96/C97/A98) (SEQ ID NO:101)
ITCPPPMSVEHADIWVKSYSLYSRERYICNSGFKRKAGTSSLTECVLNKATNVAHWTTPSLKCIRDCA IL-15Rα(sushi-S40C) (SEQ ID NO:102)
ITCPPPMSVEHADIWVKSYSLYSRERYICNSGFKRKAGTCSLTECVLNKATNVAHWTTPSLKCIR IL-15Rα(sushi-K34C) (SEQ ID NO:103)
ITCPPPMSVEHADIWVKSYSLYSRERYICNSGFCRKAGTSSLTECVLNKATNVAHWTTPSLKCIR IL-15Rα(sushi-G38C) (SEQ ID NO:104)
ITCPPPMSVEHADIWVKSYSLYSRERYICNSGFKRKACTSSLTECVLNKATNVAHWTTPSLKCIR IL-15Rα(sushi-L42C) (SEQ ID NO:105)
ITCPPPMSVEHADIWVKSYSLYSRERYICNSGFKRKAGTSSCTECVLNKATNVAHWTTPSLKCIR IL-15Rα(sushi-A37C) (SEQ ID NO:106)
ITCPPPMSVEHADIWVKSYSLYSRERYICNSGFKRKCGTSSLTECVLNKATNVAHWTTPSLKCIR ncIL-15/Rα Heterodimer
Example: XENP21996 dsIL-15/Rα Heterodimer
Example: XENP22004 scIL-15/Rα Heterodimer
Example: XENP22049

Figure 31

>XENP021996 - human_IL15(non-covalent)-human_IL15Ra(Sushi)

Chain 1 - human_IL15_no_tag (16484) (SEQ ID NO:107)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS Chain 2 - human_IL15Ra(Sushi) (17033) (SEQ ID NO:108)
ITCPPPMSVEHADIWVKSYSLYSRERYICNSGFKRKAGTSSLTECVLNKATNVAHWTTPSLKCIR

Figure 32

>XENP022004 - human_IL15_E87C-human_IL15Ra(Sushi-D96/C97)

Chain 1 - human_IL15_E87C_no_tag (17074) (SEQ ID NO:109)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS Chain 2 - human_IL15Ra(Sushi-D96/C97) (17051) (SEQ ID NO:110)
ITCPPPMSVEHADIWVKSYSLYSRERYICNSGFKRKAGTSSLTECVLNKATNVAHWTTPSLKCIRDC >XENP022005 - human_IL15_E87C-human_IL15Ra(Sushi-D96/P97/C98)

Chain 1 - human_IL15_E87C_no_tag (17074) (SEQ ID NO:111)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS Chain 2 - human_IL15Ra(Sushi-D96/P97/C98) (17052) (SEQ ID NO:112)
ITCPPPMSVEHADIWVKSYSLYSRERYICNSGFKRKAGTSSLTECVLNKATNVAHWTTPSLKCIRDPC >XENP022006 - human_IL15_E87C-human_IL15Ra(Sushi-D96/C97/A98)

Chain 1 - human_IL15_E87C_no_tag (17074) (SEQ ID NO:113)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS Chain 2 - human_IL15Ra(Sushi-D96/C97/A98) (17053) (SEQ ID NO:114)
ITCPPPMSVEHADIWVKSYSLYSRERYICNSGFKRKAGTSSLTECVLNKATNVAHWTTPSLKCIRDCA >XENP022008 - human_IL15_L52C-human_IL15Ra(Sushi-S40C)

Chain 1 - human_IL15_L52C_no_tag (17072) (SEQ ID NO:115)
NWVNVISDLKKIEDLIQSMHIDATLYTESDVHPSCKVTAMKCFLLELQVISCESGDASIHDTVENLIILANNSLSSNGNVTE
SGCKECEELEEKNIKEFLQSFVHIVQMFINTS Chain 2 - human_IL15Ra(Sushi-S40C) (17057) (SEQ ID NO:116)
ITCPPPMSVEHADIWVKSYSLYSRERYICNSGFKRKAGTCSLTECVLNKATNVAHWTTPSLKCIR >XENP022494 – human_IL15_L45C-human_IL15Ra(Sushi-A37C)

Chain 1 - human_IL15_L45C_no_tag (17069) (SEQ ID NO:117)
NWVNVISDLKKIEDLIQSMHIDATLYTESDVHPSCKVTAMKCFLCELQVISLESGDASIHDTVENLIILANNSLSSNGNVTE
SGCKECEELEEKNIKEFLQSFVHIVQMFINTS Chain 2 - human_IL15Ra(Sushi-A37C) (17055) (SEQ ID NO:118)
ITCPPPMSVEHADIWVKSYSLYSRERYICNSGFKRKCGTSSLTECVLNKATNVAHWTTPSLKCIR

Figure 33

>XENP022049 - human_IL15Ra(sushi)_(GGGGS)6-human_IL15-sc (SEQ ID NO:119)

ITCPPPMSVEHADIWVKSYSLYSRERYICNSGFKRKAGTSSLTECVLNKATNVAHWTTPSLKCIR/<u>GGGGSGGGGSGGG
GSGGGGSGGGGSGGGGS</u>/NWVNVISDLKKIEDLIQSMHIDATLYTESDVHPSCKVTAMKCFLLELQVISLESGDASIHD
TVENLIILANNSLSSNGNVTESGCKECEELEEKNIKEFLQSFVHIVQMFINTS

Figure 38

| XENP | Variant | Yield (mg/ml) | MW (g/mol) | Calculated ΔAffinity | $T_m$ (°C) | IL2Rß Affinity (~nM $K_D$) |
|---|---|---|---|---|---|---|
| 21996 | No Disulfide Control IL-15/Rα | 8.04 | 21079.9 | NA | 70.0 | 6.3 |
| 22001 | No Disulfide Control IL-15/Rα(D96) | 2.45 | 21195.0 | NA | 70.0 | 5.2 |
| 22002 | No Disulfide Control IL-15/Rα(D96/P97) | 2.47 | 21292.1 | NA | 72.0 | 7.4 |
| 22003 | No Disulfide Control IL-15/Rα(D96/P97/A98) | 3.48 | 21363.2 | NA | 72.5 | 5.7 |
| 22004 | IL-15(E87C)/Rα(D96/C97) | 4.58 | 21272.2 | -7.61 | 83.0 | 4.1 |
| 22005 | IL-15(E87C)/Rα(D96/C97/A98) | 8.4 | 21369.3 | NA | 83 (shoulder) | 6.1 |
| 22006 | IL-15(E87C)/Rα(D96/C97/A98) | 3.19 | 21343.2 | -7.61 | 83.0 | 5.1 |
| 22007 | IL-15(V49C)/Rα(S40C) | 1.58 | 21100.0 | 1.22 | 77.0 | 11 |
| 22008 | IL-15(L52C)/Rα(S40C) | 4.56 | 21085.9 | -0.97 | 82.5 | 17 |
| 22009 | IL-15(E89C)/Rα(K34C) | 0.51 | 21028.9 | -0.33 | 70.5 | 7.3 |
| 22010 | IL-15(Q48C)/Rα(G38C) | 0.42 | 21101.0 | 0.91 | 57.5 | 3.8 |
| 22011 | IL-15(E53C)/Rα(L42C) | 3.72 | 21043.9 | 3.73 | 76.0 | 17 |
| 22012 | IL-15(C42S)/Rα(A37C) | 0.44 | 21095.9 | NA | 75.0 | 5.3 |
| 22049 | Single-chain control | 5.77 | 22953.6 | NA | 73.0 | 22 |
| 22493 | IL-15(L45C)/Rα(G38C) | 0.40 | 21116.0 | 0.77 | 71.5 | NA |
| 22494 | IL-15(L45C)/Rα(A37C) | 3.63 | 21101.9 | 0.63 | 82.5 | NA | dsIL-15/Rα-heteroFc
Example: XENP22013 dsIL-15/Rα-Fc
Example: XENP22357

Bivalent dsIL-15/Rα-Fc
Example: XENP22634

Fc-dsIL-15/Rα
Example: XENP22639

Figure 40A

>XENP022013 human_IL15_E87C_(GGGGS)1-human_IL15Ra(Sushi-
D96/C97)_(GGGGS)1_Fc(216)_IgG1_pI(-)_Isosteric_A_C220S/PVA_/S267K/L368D/K370S-
Fc(216)_IgG1_C220S/PVA_/S267K/S364K/E357Q Chain 1 - human_IL15_E87C_(GGGGS)1_Fc(216)_IgG1_pI(-
)_Isosteric_A_C220S/PVA_/S267K/L368D/K370S (SEQ ID NO:120)
NWVNVISDLKKIEDLIQSMHIDATLYTESDVHPSCKVTAMKCFLLELQVISLESGDASIHDTVENLIILANNSLSSNGNVTE
SGCKCCEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Ra(Sushi-D96/C97)_(GGGGS)1_Fc(216)_IgG1_C220S/PVA_/S267K/S364K/E357Q
(SEQ ID NO:121)
ITCPPPMSVEHADIWVKSYSLYSRERYICNSGFKRKAGTSSLTECVLNKATNVAHWTTPSLKCIRDC/GGGGS/EPKSSDK
THTCPPCPAPPVAGPSVFLFPPKPKDTLMISRTPEVTCVVVDVKHEDPEVKFNWYVDGVEVHNAKTKPREEQYNSTYR
VVSVLTVLHQDWLNGKEYKCKVSNKALPAPIEKTISKAKGQPREPQVYTLPPSREQMTKNQVKLTCLVKGFYPSDIAVE
WESNGQPENNYKTTPPVLDSDGSFFLYSKLTVDKSRWQQGNVFSCSVMHEALHNHYTQKSLSLSPGK >XENP022014 human_IL15_E87C_(GGGGS)1-human_IL15Ra(Sushi-
D96/P97/C98)_(GGGGS)1_Fc(216)_IgG1_pI(-)_Isosteric_A_C220S/PVA_/S267K/L368D/K370S-
Fc(216)_IgG1_C220S/PVA_/S267K/S364K/E357Q Chain 1 - human_IL15_E87C_(GGGGS)1_Fc(216)_IgG1_pI(-
)_Isosteric_A_C220S/PVA_/S267K/L368D/K370S (SEQ ID NO:122)
NWVNVISDLKKIEDLIQSMHIDATLYTESDVHPSCKVTAMKCFLLELQVISLESGDASIHDTVENLIILANNSLSSNGNVTE
SGCKCCEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Ra(Sushi-
D96/P97/C98)_(GGGGS)1_Fc(216)_IgG1_C220S/PVA_/S267K/S364K/E357Q (SEQ ID NO:123)
ITCPPPMSVEHADIWVKSYSLYSRERYICNSGFKRKAGTSSLTECVLNKATNVAHWTTPSLKCIRDPC/GGGGS/EPKSSD
KTHTCPPCPAPPVAGPSVFLFPPKPKDTLMISRTPEVTCVVVDVKHEDPEVKFNWYVDGVEVHNAKTKPREEQYNSTY
RVVSVLTVLHQDWLNGKEYKCKVSNKALPAPIEKTISKAKGQPREPQVYTLPPSREQMTKNQVKLTCLVKGFYPSDIAVE
WESNGQPENNYKTTPPVLDSDGSFFLYSKLTVDKSRWQQGNVFSCSVMHEALHNHYTQKSLSLSPGK

Figure 40B

>XENP022015 human_IL15_E87C_(GGGGS)1-human_IL15Ra(Sushi-
D96/C97/A98)_(GGGGS)1_Fc(216)_IgG1_pI(-)_Isosteric_A_C220S/PVA_/S267K/L368D/K370S-
Fc(216)_IgG1_C220S/PVA_/S267K/S364K/E357Q Chain 1 - human_IL15_E87C_(GGGGS)1_Fc(216)_IgG1_pI(-
)_Isosteric_A_C220S/PVA_/S267K/L368D/K370S (SEQ ID NO:124)
NWVNVISDLKKIEDLIQSMHIDATLYTESDVHPSCKVTAMKCFLLELQVISLESGDASIHDTVENLIILANNSLSSNGNVTE
SGCKCCEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Ra(Sushi-
D96/C97/A98)_(GGGGS)1_Fc(216)_IgG1_C220S/PVA_/S267K/S364K/E357Q (SEQ ID NO:125)
ITCPPPMSVEHADIWVKSYSLYSRERYICNSGFKRKAGTSSLTECVLNKATNVAHWTTPSLKCIRDCA/GGGGS/EPKSSD
KTHTCPPCPAPPVAGPSVFLFPPKPKDTLMISRTPEVTCVVVDVKHEDPEVKFNWYVDGVEVHNAKTKPREEQYNSTY
RVVSVLTVLHQDWLNGKEYKCKVSNKALPAPIEKTISKAKGQPREPQVYTLPPSREQMTKNQVKLTCLVKGFYPSDIAVE
WESNGQPENNYKTTPPVLDSDGSFFLYSKLTVDKSRWQQGNVFSCSVMHEALHNHYTQKSLSLSPGK >XENP022017 human_IL15_L52C_(GGGGS)1-human_IL15Ra(Sushi-S40C)_(GGGGS)1_Fc(216)_IgG1_pI(-
)_Isosteric_A_C220S/PVA_/S267K/L368D/K370S-Fc(216)_IgG1_C220S/PVA_/S267K/S364K/E357Q Chain 1 – human_IL15_L52C_(GGGGS)1-_Fc(216)_IgG1_pI(-
)_Isosteric_A_C220S/PVA_/S267K/L368D/K370S (SEQ ID NO:126)
NWVNVISDLKKIEDLIQSMHIDATLYTESDVHPSCKVTAMKCFLLELQVISCESGDASIHDTVENLIILANNSLSSNGNVTE
SGCKECEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 – human_IL15Ra(Sushi-S40C)_(GGGGS)1_Fc(216)_IgG1_C220S/PVA_/S267K/S364K/E357Q
(SEQ ID NO:127)
ITCPPPMSVEHADIWVKSYSLYSRERYICNSGFKRKAGTCSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK

Figure 41A

>XENP022358 – empty-Fc-IL15_E87C-human_IL15Ra(Sushi-D96/P97/C98)_(GGGGS)1_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15_E87C_no_tag (17074) (SEQ ID NO:128)
NWVNVISDLKKIEDLIQSMHIDATLYTESDVHPSCKVTAMKCFLLELQVISLESGDASIHDTVENLIILANNSLSSNGNVTE
SGCKCCEELEEKNIKEFLQSFVHIVQMFINTS Chain 2 - empty-Fc(216)_IgG1_pI(-)_Isosteric_A_C220S/PVA_/S267K/L368D/K370S (8793)
(SEQ ID NO:129)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK Chain 3 - human_IL15Ra(Sushi-D96/P97/C98)_(GGGGS)1_Fc(216)_IgG1_C220S/PVA_/S267K/S364K/E357Q (17039)
(SEQ ID NO:130)
<u>ITCPPPMSVEHADIWVKSYSLYSRERYICNSGFKRKAGTSSLTECVLNKATNVAHWTTPSLKCIRDPC</u>/<u>GGGGS</u>/EPKSSD
KTHTCPPCPAPPVAGPSVFLFPPKPKDTLMISRTPEVTCVVVDVKHEDPEVKFNWYVDGVEVHNAKTKPREEQYNSTY
RVVSVLTVLHQDWLNGKEYKCKVSNKALPAPIEKTISKAKGQPREPQVYTLPPSREQMTKNQVKLTCLVKGFYPSDIAVE
WESNGQPENNYKTTPPVLDSDGSFFLYSKLTVDKSRWQQGNVFSCSVMHEALHNHYTQKSLSLSPGK >XENP022359 – empty-Fc-IL15_E87C-human_IL15Ra(Sushi-D96/C97/A98)_(GGGGS)1_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15_E87C_no_tag (17074) (SEQ ID NO:131)
NWVNVISDLKKIEDLIQSMHIDATLYTESDVHPSCKVTAMKCFLLELQVISLESGDASIHDTVENLIILANNSLSSNGNVTE
SGCKCCEELEEKNIKEFLQSFVHIVQMFINTS Chain 2 - empty-Fc(216)_IgG1_pI(-)_Isosteric_A_C220S/PVA_/S267K/L368D/K370S (8793)
(SEQ ID NO:132)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK Chain 3 - human_IL15Ra(Sushi-D96/C97/A98)_(GGGGS)1_Fc(216)_IgG1_C220S/PVA_/S267K/S364K/E357Q (17040)
(SEQ ID NO:133)
<u>ITCPPPMSVEHADIWVKSYSLYSRERYICNSGFKRKAGTSSLTECVLNKATNVAHWTTPSLKCIRDCA</u>/<u>GGGGS</u>/EPKSSD
KTHTCPPCPAPPVAGPSVFLFPPKPKDTLMISRTPEVTCVVVDVKHEDPEVKFNWYVDGVEVHNAKTKPREEQYNSTY
RVVSVLTVLHQDWLNGKEYKCKVSNKALPAPIEKTISKAKGQPREPQVYTLPPSREQMTKNQVKLTCLVKGFYPSDIAVE
WESNGQPENNYKTTPPVLDSDGSFFLYSKLTVDKSRWQQGNVFSCSVMHEALHNHYTQKSLSLSPGK

Figure 41B

>XENP022361 – empty-Fc-IL15_L52C-human_IL15Ra(Sushi-S40C)_(GGGGS)1_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15_L52C_no_tag (17072) (SEQ ID NO:134)
NWVNVISDLKKIEDLIQSMHIDATLYTESDVHPSCKVTAMKCFLLELQVISCESGDASIHDTVENLIILANNSLSSNGNVTE
SGCKECEELEEKNIKEFLQSFVHIVQMFINTS Chain 2 - empty-Fc(216)_IgG1_pI(-)_Isosteric_A_C220S/PVA_/S267K/L368D/K370S (8793)
(SEQ ID NO:135)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK Chain 3 - human_IL15Ra(Sushi-S40C)_(GGGGS)1_Fc(216)_IgG1_C220S/PVA_/S267K/S364K/E357Q
(17044) (SEQ ID NO:136)
<u>ITCPPPMSVEHADIWVKSYSLYSRERYICNSGFKRKAGTCSLTECVLNKATNVAHWTTPSLKCIR</u>/<u>GGGGS</u>/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREMTKNQVKLTCLVKGFYPSDIAVEWE
SNGQPENNYKTTPPVLDSDGSFFLYSKLTVDKSRWQQGNVFSCSVMHEALHNHYTQKSLSLSPGK >XENP022684 empty-Fc-IL15_E87C-human_IL15Ra(Sushi-D96/C97/A98)_Fc(216)_IgG1_pI(-)_Isosteric_A_C220S/PVA_/S267K/L368D/K370S-Fc(216)_IgG1_C220S/PVA_/S267K/S364K/E357Q Chain 1 – IL15_E87C (SEQ ID NO:137)
NWVNVISDLKKIEDLIQSMHIDATLYTESDVHPSCKVTAMKCFLLELQVISLESGDASIHDTVENLIILANNSLSSNGNVTE
SGCKCCEELEEKNIKEFLQSFVHIVQMFINTS Chain 2 - IL15Ra(Sushi-D96/C97/A98)_Fc(216)_IgG1_pI(-)_Isosteric_A_C220S/PVA_/S267K/L368D/K370S
(SEQ ID NO:138)
<u>ITCPPPMSVEHADIWVKSYSLYSRERYICNSGFKRKAGTSSLTECVLNKATNVAHWTTPSLKCIRDCA</u>/EPKSSDKTHTCP
PCPAPPVAGPSVFLFPPKPKDTLMISRTPEVTCVVVDVKHEDPEVKFNWYVDGVEVHNAKTKPREEQYNSTYRVVSVLT
VLHQDWLNGKEYKCKVSNKALPAPIEKTISKAKGQPREPQVYTLPPSREMTKNQVKLTCLVKGFYPSDIAVEWESNG
QPENNYKTTPPVLDSDGSFFLYSKLTVDKSRWQQGNVFSCSVMHEALHNHYTQKSLSLSPGK

Figure 42

>XENP022634 – human_IL15(E87C)-human_IL15Ra(Sushi-D96/C97)_Fc(216)_IgG1_C220S/PVA_/S267K Chain 1 - human_IL15Ra(Sushi-D96/C97)-Fc(216)_IgG1_C220S/PVA_/S267K (17581) (SEQ ID NO:139)
<u>ITCPPPMSVEHADIWVKSYSLYSRERYICNSGFKRKAGTSSLTECVLNKATNVAHWTTPSLKCIRDC</u>/EPKSSDKTHTCPP
CPAPPVAGPSVFLFPPKPKDTLMISRTPEVTCVVVDVKHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHYTQKSLSLSPGK Chain 2 - human_IL15_E87C_no_tag (17074) (SEQ ID NO:140)
NWVNVISDLKKIEDLIQSMHIDATLYTESDVHPSCKVTAMKCFLLELQVISLESGDASIHDTVENLIILANNSLSSNGNVTE
SGCKCCEELEEKNIKEFLQSFVHIVQMFINTS >XENP022635 – human_IL15(E87C)-human_IL15Ra(Sushi-D96/C97/A98)_Fc(216)_IgG1_C220S/PVA_/S267K Chain 1 - human_IL15Ra(Sushi-D96/C97/A98)-Fc(216)_IgG1_C220S/PVA_/S267K (17582)
(SEQ ID NO:141)
<u>ITCPPPMSVEHADIWVKSYSLYSRERYICNSGFKRKAGTSSLTECVLNKATNVAHWTTPSLKCIRDCA</u>/EPKSSDKTHTCP
PCPAPPVAGPSVFLFPPKPKDTLMISRTPEVTCVVVDVKHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHYTQKSLSLSPGK Chain 2 - human_IL15_E87C_no_tag (17074) (SEQ ID NO:142)
NWVNVISDLKKIEDLIQSMHIDATLYTESDVHPSCKVTAMKCFLLELQVISLESGDASIHDTVENLIILANNSLSSNGNVTE
SGCKCCEELEEKNIKEFLQSFVHIVQMFINTS >XENP022636 – human_IL15(L52C)-human_IL15Ra(Sushi-S40C)_Fc(216)_IgG1_C220S/PVA_/S267K Chain 1 - human_IL15Ra(Sushi-S40C)-Fc(216)_IgG1_C220S/PVA_/S267K (17583) (SEQ ID NO:143)
<u>ITCPPPMSVEHADIWVKSYSLYSRERYICNSGFKRKAGTCSLTECVLNKATNVAHWTTPSLKCIR</u>/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK Chain 2 - human_IL15_L52C_no_tag (17072) (SEQ ID NO:144)
NWVNVISDLKKIEDLIQSMHIDATLYTESDVHPSCKVTAMKCFLLELQVISCESGDASIHDTVENLIILANNSLSSNGNVTE
SGCKECEELEEKNIKEFLQSFVHIVQMFINTS

Figure 43

>XENP022639 – empty-Fc(216)_IgG1_pI(-
)_Isosteric_A_C220S/PVA_/S267K/L368D/K370S_(GGGGS)2_IL15Ra(Sushi-
D96/C97)_IL15(E87C)_IgG1_ISO(+RR)_C220S/PVA_/S267K/S364K/E357Q Chain 1 - empty-Fc(216)_IgG1_pI(-
)_Isosteric_A_C220S/PVA_/S267K/L368D/K370S_(GGGGS)2_IL15Ra(Sushi-D96/C97) (17605)
(SEQ ID NO:145)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK/GGGGS
GGGGS/ITCPPPMSVEHADIWVKSYSLYSRERYICNSGFKRKAGTSSLTECVLNKATNVAHWTTPSLKCIRDC Chain 2 - empty-Fc(216)_IgG1_ISO(+RR)_C220S/PVA_/S267K/S364K/E357Q (8927)
(SEQ ID NO:146)
ERKSSDKTHTCPRCPAPPVAGPSVFLFPPKPKDTLMISRTPEVTCVVVDVKHEDPEVKFKWYVDGVEVHNAKTKPREEQ
YNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK Chain 3 - human_IL15_E87C_no_tag (17074) (SEQ ID NO:147)
NWVNVISDLKKIEDLIQSMHIDATLYTESDVHPSCKVTAMKCFLLELQVISLESGDASIHDTVENLIILANNSLSSNGNVTE
SGCKCCEELEEKNIKEFLQSFVHIVQMFINTS >XENP022640 empty-Fc(216)_IgG1_pI(-
)_Isosteric_A_C220S/PVA_/S267K/L368D/K370S_IgG1_ISO(+RR)_C220S/PVA_/S267K/S364K/E357Q_(GG
GGS)2_IL15Ra(Sushi-D96/C97)_IL15(E87C)

Chain 1 – IL15 (SEQ ID NO:148)
NWVNVISDLKKIEDLIQSMHIDATLYTESDVHPSCKVTAMKCFLLELQVISLESGDASIHDTVENLIILANNSLSSNGNVTE
SGCKCCEELEEKNIKEFLQSFVHIVQMFINTS Chain 2 – empty_Fc(216)_IgG1_pI(-)_Isosteric_A_C220S/PVA_/S267K/L368D/K370S (SEQ ID NO:149)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK

Figure 47A

N1D (SEQ ID NO:150)
DWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS

N4D (SEQ ID NO:151)
NWVDVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS

D8N (SEQ ID NO:152)
NWVNVISNLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS

D30N (SEQ ID NO:153)
NWVNVISDLKKIEDLIQSMHIDATLYTESNVHPSCKVTAMKCFLLELQVISLESGDASIHDTVENLIILANNSLSSNGNVTE
SGCKECEELEEKNIKEFLQSFVHIVQMFINTS

D61N (SEQ ID NO:154)
NWVNVISDLKKIEDLIQSMHIDATLYTESDVHPSCKVTAMKCFLLELQVISLESGDASIHNTVENLIILANNSLSSNGNVTE
SGCKECEELEEKNIKEFLQSFVHIVQMFINTS

E64Q (SEQ ID NO:155)
NWVNVISDLKKIEDLIQSMHIDATLYTESDVHPSCKVTAMKCFLLELQVISLESGDASIHDTVQNLIILANNSLSSNGNVTE
SGCKECEELEEKNIKEFLQSFVHIVQMFINTS

N65D (SEQ ID NO:156)
NWVNVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS

Q108E (SEQ ID NO:157)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVEMFINTS

N1D/D61N (SEQ ID NO:158)
DWVNVISDLKKIEDLIQSMHIDATLYTESDVHPSCKVTAMKCFLLELQVISLESGDASIHNTVENLIILANNSLSSNGNVTE
SGCKECEELEEKNIKEFLQSFVHIVQMFINTS

Figure 47B

N1D/E64Q (SEQ ID NO:159)
DWVNVISDLKKIEDLIQSMHIDATLYTESDVHPSCKVTAMKCFLLELQVISLESGDASIHDTVQNLIILANNSLSSNGNVTE
SGCKECEELEEKNIKEFLQSFVHIVQMFINTS

N4D/D61N (SEQ ID NO:160)
NWVDVISDLKKIEDLIQSMHIDATLYTESDVHPSCKVTAMKCFLLELQVISLESGDASIHNTVENLIILANNSLSSNGNVTE
SGCKECEELEEKNIKEFLQSFVHIVQMFINTS

N4D/E64Q (SEQ ID NO:161)
NWVDVISDLKKIEDLIQSMHIDATLYTESDVHPSCKVTAMKCFLLELQVISLESGDASIHDTVQNLIILANNSLSSNGNVTE
SGCKECEELEEKNIKEFLQSFVHIVQMFINTS

D8N/D61N (SEQ ID NO:162)
NWVNVISNLKKIEDLIQSMHIDATLYTESDVHPSCKVTAMKCFLLELQVISLESGDASIHNTVENLIILANNSLSSNGNVTE
SGCKECEELEEKNIKEFLQSFVHIVQMFINTS

D8N/E64Q (SEQ ID NO:163)
NWVNVISNLKKIEDLIQSMHIDATLYTESDVHPSCKVTAMKCFLLELQVISLESGDASIHDTVQNLIILANNSLSSNGNVT
ESGCKECEELEEKNIKEFLQSFVHIVQMFINTS

D61N/E64Q (SEQ ID NO:164)
NWVNVISDLKKIEDLIQSMHIDATLYTESDVHPSCKVTAMKCFLLELQVISLESGDASIHNTVQNLIILANNSLSSNGNVT
ESGCKECEELEEKNIKEFLQSFVHIVQMFINTS

E64Q/Q108E (SEQ ID NO:165)
NWVNVISDLKKIEDLIQSMHIDATLYTESDVHPSCKVTAMKCFLLELQVISLESGDASIHDTVQNLIILANNSLSSNGNVTE
SGCKECEELEEKNIKEFLQSFVHIVEMFINTS

N1D/N4D/D8N (SEQ ID NO:166)
DWVDVISNLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS

D61N/E64Q/N65D (SEQ ID NO:167)
NWVNVISDLKKIEDLIQSMHIDATLYTESDVHPSCKVTAMKCFLLELQVISLESGDASIHNTVQDLIILANNSLSSNGNVTE
SGCKECEELEEKNIKEFLQSFVHIVQMFINTS

N1D/D61N/E64Q/Q108E (SEQ ID NO:168)
DWVNVISDLKKIEDLIQSMHIDATLYTESDVHPSCKVTAMKCFLLELQVISLESGDASIHNTVQNLIILANNSLSSNGNVTE
SGCKECEELEEKNIKEFLQSFVHIVEMFINTS

N4D/D61N/E64Q/Q108E (SEQ ID NO:169)
NWVDVISDLKKIEDLIQSMHIDATLYTESDVHPSCKVTAMKCFLLELQVISLESGDASIHNTVQNLIILANNSLSSNGNVTE
SGCKECEELEEKNIKEFLQSFVHIVEMFINTS

Figure 47C

N1D/N65D (SEQ ID NO:170)
DWVNVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS

N1D/Q108E (SEQ ID NO:171)
DWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVEMFINTS

N4D/N65D (SEQ ID NO:172)
NWVDVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS

D30N/N65D (SEQ ID NO:173)
NWVNVISDLKKIEDLIQSMHIDATLYTESNVHPSCKVTAMKCFLLELQVISLESGDASIHDTVEDLIILANNSLSSNGNVTE
SGCKECEELEEKNIKEFLQSFVHIVQMFINTS

D30N/Q108E (SEQ ID NO:174)
NWVNVISDLKKIEDLIQSMHIDATLYTESNVHPSCKVTAMKCFLLELQVISLESGDASIHDTVENLIILANNSLSSNGNVTE
SGCKECEELEEKNIKEFLQSFVHIVEMFINTS

N65D/Q108E (SEQ ID NO:175)
NWVNVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVEMFINTS

E64Q/N65D (SEQ ID NO:176)
NWVNVISDLKKIEDLIQSMHIDATLYTESDVHPSCKVTAMKCFLLELQVISLESGDASIHDTVQDLIILANNSLSSNGNVTE
SGCKECEELEEKNIKEFLQSFVHIVQMFINTS

N1D/N4D/N65D (SEQ ID NO:177)
DWVDVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS

D30N/E64Q/N65D (SEQ ID NO:178)
NWVNVISDLKKIEDLIQSMHIDATLYTESNVHPSCKVTAMKCFLLELQVISLESGDASIHDTVQDLIILANNSLSSNGNVTE
SGCKECEELEEKNIKEFLQSFVHIVQMFINTS

N4D/D61N/N65D (SEQ ID NO:179)
NWVDVISDLKKIEDLIQSMHIDATLYTESDVHPSCKVTAMKCFLLELQVISLESGDASIHNTVEDLIILANNSLSSNGNVTE
SGCKECEELEEKNIKEFLQSFVHIVQMFINTS

Figure 48A

>XENP022816 - human_IL15_N4D_(GGGGS)₁-human_IL15Rα(Sushi)_(GGGGS)₁_Fc(216)_IgG1_pI(-)_Isosteric_A_C220S/PVA_/S267K/L368D/K370-Fc(216)_IgG1_C220S/PVA_/S267K/S364K/E357Q Chain 1 - human_IL15_N4D_(GGGGS)₁ (17687) (SEQ ID NO:180)
<u>NWVDVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVQMFINTS</u>/<u>GGGGS</u>/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Rα(Sushi)_(GGGGS)₁_Fc(216)_IgG1_pI(-)_Isosteric_A_C220S/PVA_/S267K/L368D/K370-Fc(216)_IgG1_C220S/PVA_/S267K/S364K/E357Q (15908) (SEQ ID NO:181)
<u>ITCPPPMSVEHADIWVKSYSLYSRERYICNSGFKRKAGTSSLTECVLNKATNVAHWTTPSLKCIR</u>/<u>GGGGS</u>/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK >XENP022819 - human_IL15_D61N_(GGGGS)₁-human_IL15Rα(Sushi)_(GGGGS)₁_Fc(216)_IgG1_pI(-)_Isosteric_A_C220S/PVA_/S267K/L368D/K370-Fc(216)_IgG1_C220S/PVA_/S267K/S364K/E357Q Chain 1 - human_IL15_D61N_(GGGGS)₁ (17690) (SEQ ID NO:182)
<u>NWVNVISDLKKIEDLIQSMHIDATLYTESDVHPSCKVTAMKCFLLELQVISLESGDASIHNTVENLIILANNSLSSNGNVTE
SGCKECEELEEKNIKEFLQSFVHIVQMFINTS</u>/<u>GGGGS</u>/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Rα(Sushi)_(GGGGS)₁_Fc(216)_IgG1_pI(-)_Isosteric_A_C220S/PVA_/S267K/L368D/K370-Fc(216)_IgG1_C220S/PVA_/S267K/S364K/E357Q (15908) (SEQ ID NO:183)
<u>ITCPPPMSVEHADIWVKSYSLYSRERYICNSGFKRKAGTSSLTECVLNKATNVAHWTTPSLKCIR</u>/<u>GGGGS</u>/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK

Figure 48B

>XENP022820 - human_IL15_E64Q_(GGGGS)₁-human_IL15Rα(Sushi)_(GGGGS)₁_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15_E64Q_(GGGGS)₁ (17691) (SEQ ID NO:184)
<u>NWVNVISDLKKIEDLIQSMHIDATLYTESDVHPSCKVTAMKCFLLELQVISLESGDASIHDTVQNLIILANNSLSSNGNVTE
SGCKECEELEEKNIKEFLQSFVHIVQMFINTS</u>/<u>GGGGS</u>/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Rα(Sushi)_(GGGGS)₁_Fc(216)_IgG1_pI(-)_Isosteric_A_C220S/PVA_/S267K/L368D/K370S-Fc(216)_IgG1_C220S/PVA_/S267K/S364K/E357Q (15908) (SEQ ID NO:185)
<u>ITCPPPMSVEHADIWVKSYSLYSRERYICNSGFKRKAGTSSLTECVLNKATNVAHWTTPSLKCIR</u>/<u>GGGGS</u>/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK >XENP022821 - human_IL15_N65D_(GGGGS)₁-human_IL15Rα(Sushi)_(GGGGS)₁_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15_N65D_(GGGGS)₁ (17692) (SEQ ID NO:186)
<u>NWVNVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS</u>/<u>GGGGS</u>/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Rα(Sushi)_(GGGGS)₁_Fc(216)_IgG1_pI(-)_Isosteric_A_C220S/PVA_/S267K/L368D/K370S-Fc(216)_IgG1_C220S/PVA_/S267K/S364K/E357Q (15908) (SEQ ID NO:187)
<u>ITCPPPMSVEHADIWVKSYSLYSRERYICNSGFKRKAGTSSLTECVLNKATNVAHWTTPSLKCIR</u>/<u>GGGGS</u>/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK

Figure 48C

>XENP022822 - human_IL15_Q108E_(GGGGS)₁-human_IL15Rα(Sushi)_(GGGGS)₁_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15_Q108E_(GGGGS)₁ (17693) (SEQ ID NO:188)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVEMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Rα(Sushi)_(GGGGS)₁_Fc(216)_IgG1_pI(-)_Isosteric_A_C220S/PVA_/S267K/L368D/K370S-Fc(216)_IgG1_C220S/PVA_/S267K/S364K/E357Q (15908) (SEQ ID NO:189)
ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK >XENP022829 - human_IL15_D61N/E64Q_(GGGGS)₁-human_IL15Rα(Sushi)_(GGGGS)₁_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15_D61N/E64Q_(GGGGS)₁ (17700) (SEQ ID NO:190)
NWVNVISDLKKIEDLIQSMHIDATLYTESDVHPSCKVTAMKCFLLELQVISLESGDASIHNTVQNLIILANNSLSSNGNVT
ESGCKECEELEEKNIKEFLQSFVHIVQMFINTS/GGGGS/EPKSSDKTHTCPPCPAPPVAGPSVFLFPPKPKDTLMISRTPE
VTCVVVDVKHEDPEVKFNWYVDGVEVHNAKTKPREEEYNSTYRVVSVLTVLHQDWLNGKEYKCKVSNKALPAPIEKTI
SKAKGQPREPQVYTLPPSREEMTKNQVSLTCDVSGFYPSDIAVEWESDGQPENNYKTTPPVLDSDGSFFLYSKLTVDKS
RWEQGDVFSCSVMHEALHNHYTQKSLSLSPGK Chain 2 - human_IL15Rα(Sushi)_(GGGGS)₁_Fc(216)_IgG1_pI(-)_Isosteric_A_C220S/PVA_/S267K/L368D/K370S-Fc(216)_IgG1_C220S/PVA_/S267K/S364K/E357Q (15908) (SEQ ID NO:191)
ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK

Figure 48D

>XENP022834 - human_IL15_N4D/D61N/E64Q/Q108E_(GGGGS)₁-
human_IL15Rα(Sushi)_(GGGGS)₁_Fc(216)_IgG1_pI(-)_Isosteric_A_C220S/PVA_/S267K/L368D/K370S-
Fc(216)_IgG1_C220S/PVA_/S267K/S364K/E357Q Chain 1 - human_IL15_N4D/D61N/E64Q/Q108E_(GGGGS)₁ (17705) (SEQ ID NO:192)
NWVDVISDLKKIEDLIQSMHIDATLYTESDVHPSCKVTAMKCFLLELQVISLESGDASIHNTVQNLIILANNSLSSNGNVTE
SGCKECEELEEKNIKEFLQSFVHIVEMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Rα(Sushi)_(GGGGS)₁_Fc(216)_IgG1_pI(-
)_Isosteric_A_C220S/PVA_/S267K/L368D/K370S-Fc(216)_IgG1_C220S/PVA_/S267K/S364K/E357Q
(15908) (SEQ ID NO:193)
ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK >XENP023554 - human_IL15_N1D/N65D_(GGGGS)1-human_IL15Ra(Sushi)_(GGGGS)1_Fc(216)_IgG1_pI(-
)_Isosteric_A_C220S/PVA_/S267K/L368D/K370S-Fc(216)_IgG1_C220S/PVA_/S267K/S364K/E357Q Chain 1 - human_IL15_N1D/N65D_(GGGGS)1_Fc(216)_IgG1_pI(-
)_Isosteric_A_C220S/PVA_/S267K/L368D/K370S (18783) (SEQ ID NO:194)
DWVNVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Rα(Sushi)_(GGGGS)1_Fc(216)_IgG1_C220S/PVA_/S267K/S364K/E357Q (15908)
(SEQ ID NO:195)
ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK

Figure 48E

>XENP023557 - human_IL15_N4D/N65D_(GGGGS)1-human_IL15Ra(Sushi)_(GGGGS)1_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15_N4D/N65D_(GGGGS)1_Fc(216)_IgG1_pI(-)_Isosteric_A_C220S/PVA_/S267K/L368D/K370S (18786) (SEQ ID NO:196)
NWVDVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Ra(Sushi)_(GGGGS)1_Fc(216)_IgG1_C220S/PVA_/S267K/S364K/E357Q (15908) (SEQ ID NO:197)
ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK >XENP023561 human_IL15_N65D/Q108E_(GGGGS)1-human_IL15Ra(Sushi)_(GGGGS)1_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15_N65D/Q108E_(GGGGS)1_Fc(216)_IgG1_pI(-)_Isosteric_A_C220S/PVA_/S267K/L368D/K370S (SEQ ID NO:198)
NWVNVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVEMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 - human_IL15Ra(Sushi)_(GGGGS)1_Fc(216)_IgG1_C220S/PVA_/S267K/S364K/E357Q (SEQ ID NO:199)
ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK

Figure 48F

>XENP024018 human_IL15(N65D)-human_IL15Ra(Sushi)_Fc(216)_IgG1_pI(-
)_Isosteric_A_C220S/PVA_/S267K/L368D/K370S-Fc(216)_IgG1_C220S/PVA_/S267K/S364K/E357Q Chain 1 - human_IL15(N65D)_Fc(216)_IgG1_pI(-)_Isosteric_A_C220S/PVA_/S267K/L368D/K370S
(SEQ ID NO:200)
NWVNVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS/EPKSSDKTHTCPPCPAPPVAGPSVFLFPPKPKDTLMISRTPEVTCVVVD
VKHEDPEVKFNWYVDGVEVHNAKTKPREEEYNSTYRVVSVLTVLHQDWLNGKEYKCKVSNKALPAPIEKTISKAKGQP
REPQVYTLPPSREEMTKNQVSLTCDVSGFYPSDIAVEWESDGQPENNYKTTPPVLDSDGSFFLYSKLTVDKSRWEQGD
VFSCSVMHEALHNHYTQKSLSLSPGK Chain 2 - human_IL15Ra(Sushi)_Fc(216)_IgG1_C220S/PVA_/S267K/S364K/E357Q
(SEQ ID NO:201)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREQMTKNQVKLTCLVKGFYPSDIAVEWESNGQP
ENNYKTTPPVLDSDGSFFLYSKLTVDKSRWQQGNVFSCSVMHEALHNHYTQKSLSLSPGK >XENP024019 - human_IL15(Q108E)-human_IL15Ra(Sushi)_Fc(216)_IgG1_pI(-
)_Isosteric_A_C220S/PVA_/S267K/L368D/K370S-Fc(216)_IgG1_C220S/PVA_/S267K/S364K/E357Q Chain 1 - human_IL15(Q108E)-human_IL15Ra(Sushi)_Fc(216)_IgG1_pI(-
)_Isosteric_A_C220S/PVA_/S267K/L368D/K370S (19242)
(SEQ ID NO:202)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVEMFINTS/EPKSSDKTHTCPPCPAPPVAGPSVFLFPPKPKDTLMISRTPEVTCVVVD
VKHEDPEVKFNWYVDGVEVHNAKTKPREEEYNSTYRVVSVLTVLHQDWLNGKEYKCKVSNKALPAPIEKTISKAKGQP
REPQVYTLPPSREEMTKNQVSLTCDVSGFYPSDIAVEWESDGQPENNYKTTPPVLDSDGSFFLYSKLTVDKSRWEQGD
VFSCSVMHEALHNHYTQKSLSLSPGK Chain 2 - human_IL15Ra(Sushi)_Fc(216)_IgG1_C220S/PVA_/S267K/S364K/E357Q (16481)
(SEQ ID NO:203)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREQMTKNQVKLTCLVKGFYPSDIAVEWESNGQP
ENNYKTTPPVLDSDGSFFLYSKLTVDKSRWQQGNVFSCSVMHEALHNHYTQKSLSLSPGK

Figure 48G

>XENP024045 human_IL15_D30N/E64Q/N65D_(GGGGS)1-
human_IL15Rα(Sushi)_(GGGGS)1_Fc(216)_IgG1_pI(-)_Isosteric_A_C220S/PVA_/S267K/L368D/K370S-
Fc(216)_IgG1_C220S/PVA_/S267K/S364K/E357Q Chain 1 – human_IL15_D30N/E64Q/N65D_(GGGGS)1_Fc(216)_IgG1_pI(-
)_Isosteric_A_C220S/PVA_/S267K/L368D/K370S (SEQ ID NO:204)
NWVNVISDLKKIEDLIQSMHIDATLYTESNVHPSCKVTAMKCFLLELQVISLESGDASIHDTVQDLIILANNSLSSNGNVTE
SGCKECEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVMHEALHNHYTQKSLSLSPGK Chain 2 – human_IL15Rα(Sushi)_(GGGGS)1_ Fc(216)_IgG1_C220S/PVA_/S267K/S364K/E357Q
(SEQ ID NO:205)
ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVMHEALHNHYTQKSLSLSPGK >XENP024051 human_IL15_N1D/N65D-human_IL15Rα(Sushi)_Fc(216)_IgG1_pI(-
)_Isosteric_A_C220S/PVA_/S267K/L368D/K370S-Fc(216)_IgG1_C220S/PVA_/S267K/S364K/E357Q Chain 1 – human_IL15_N1D/N65D-human_Fc(216)_IgG1_pI(-
)_Isosteric_A_C220S/PVA_/S267K/L368D/K370S (SEQ ID NO:206)
DWVNVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS/EPKSSDKTHTCPPCPAPPVAGPSVFLFPPKPKDTLMISRTPEVTCVVVD
VKHEDPEVKFNWYVDGVEVHNAKTKPREEEYNSTYRVVSVLTVLHQDWLNGKEYKCKVSNKALPAPIEKTISKAKGQP
REPQVYTLPPSREEMTKNQVSLTCDVSGFYPSDIAVEWESDGQPENNYKTTPPVLDSDGSFFLYSKLTVDKSRWEQGD
VFSCSVMHEALHNHYTQKSLSLSPGK Chain 2 – human_IL15Rα(Sushi)_ Fc(216)_IgG1_C220S/PVA_/S267K/S364K/E357Q (SEQ ID NO:207)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREQMTKNQVKLTCLVKGFYPSDIAVEWESNGQP
ENNYKTTPPVLDSDGSFFLYSKLTVDKSRWQQGNVFSCSVMHEALHNHYTQKSLSLSPGK

Figure 48H

>XENP024052_human_IL15_N4D/N65D-human_IL15Rα(Sushi)_Fc(216)_IgG1_pI(-)_Isosteric_A_C220S/PVA_/S267K/L368D/K370S-Fc(216)_IgG1_C220S/PVA_/S267K/S364K/E357Q Chain 1 – human_IL15_N4D/N65D-human_Fc(216)_IgG1_pI(-)_Isosteric_A_C220S/PVA_/S267K/L368D/K370S (SEQ ID NO:208)
NWVDVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS/EPKSSDKTHTCPPCPAPPVAGPSVFLFPPKPKDTLMISRTPEVTCVVVD
VKHEDPEVKFNWYVDGVEVHNAKTKPREEEYNSTYRVVSVLTVLHQDWLNGKEYKCKVSNKALPAPIEKTISKAKGQP
REPQVYTLPPSREEMTKNQVSLTCDVSGFYPSDIAVEWESDGQPENNYKTTPPVLDSDGSFFLYSKLTVDKSRWQQGD
VFSCSVMHEALHNHYTQKSLSLSPGK Chain 2 – human_IL15Rα(Sushi)_Fc(216)_IgG1_C220S/PVA_/S267K/S364K/E357Q (SEQ ID NO:209)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREQMTKNQVKLTCLVKGFYPSDIAVEWESNGQP
ENNYKTTPPVLDSDGSFFLYSKLTVDKSRWQQGNVFSCSVMHEALHNHYTQKSLSLSPGK

Figure 49A

>XENP024015 human_IL15Ra(sushi)_(GGGGS)5-human_IL15(Q108E;single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(GGGGS)5-human_IL15(Q108E;single-chain)_Fc(216)_IgG1_pI(-)_Isosteric_A_C220S/PVA_/S267K/L368D/K370S (SEQ ID NO:210)
ITCPPPMSVEHADIWVKSYSLYSRERYICNSGFKRKAGTSSLTECVLNKATNVAHWTTPSLKCIR/<ins>GGGGSGGGGSGGGGSGGGGSGGGGS</ins>/NWVNVISDLKKIEDLIQSMHIDATLYTESDVHPSCKVTAMKCFLLELQVISLESGDASIHDTVENLII
LANNSLSSNGNVTESGCKECEELEEKNIKEFLQSFVHIVEMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVMHEALHNHYTQKSLSLSPGK Chain 2 – empty_Fc(216)_IgG1_C220S/PVA_/S267K/S364K/E357Q (SEQ ID NO:211)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK >XENP024050 human_IL15Ra(sushi)_(GGGGS)5-human_IL15_N4D/N65D_(single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(GGGGS)5-human_IL15_N4D/N65D_(single-chain)_Fc(216)_IgG1_pI(-)_Isosteric_A_C220S/PVA_/S267K/L368D/K370S (SEQ ID NO:212)
ITCPPPMSVEHADIWVKSYSLYSRERYICNSGFKRKAGTSSLTECVLNKATNVAHWTTPSLKCIR/<ins>GGGGSGGGGSGGGGSGGGGSGGGGS</ins>/NWVDVISDLKKIEDLIQSMHIDATLYTESDVHPSCKVTAMKCFLLELQVISLESGDASIHDTVEDLII
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVMHEALHNHYTQKSLSLSPGK Chain 2 – empty_ Fc(216)_IgG1_C220S/PVA_/S267K/S364K/E357Q (SEQ ID NO:213)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK

Figure 49B

>XENP024475 human_IL15Ra(sushi)_(GGGGS)6-human_IL15(single-chain;Q108E)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(GGGGS)6-human_IL15(single-chain;Q108E)_Fc(216)_IgG1_pI(-)_Isosteric_A_C220S/PVA_/S267K/L368D/K370S (SEQ ID NO:214)
ITCPPPMSVEHADIWVKSYSLYSRERYICNSGFKRKAGTSSLTECVLNKATNVAHWTTPSLKCIR/<u>GGGGSGGGGSGGGGSGGGGSGGGGSGGGGS</u>/NWVNVISDLKKIEDLIQSMHIDATLYTESDVHPSCKVTAMKCFLLELQVISLESGDASIHDTVENLIILANNSLSSNGNVTESGCKECEELEEKNIKEFLQSFVHIVEMFINTS/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVMHEALHNHYTQKSLSLSPGK Chain 2 – empty_ Fc(216)_IgG1_C220S/PVA_/S267K/S364K/E357Q (SEQ ID NO:215)
EPKSSDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP024476 human_IL15Ra(sushi)_(GGGGS)6-human_IL15(single-chain;N4D/N65D)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(GGGGS)6-human_IL15(single-chain;N4D/N65D)_Fc(216)_IgG1_pI(-)_Isosteric_A_C220S/PVA_/S267K/L368D/K370S (SEQ ID NO:216)
ITCPPPMSVEHADIWVKSYSLYSRERYICNSGFKRKAGTSSLTECVLNKATNVAHWTTPSLKCIR/<u>GGGGSGGGGSGGGGSGGGGSGGGGSGGGGS</u>/NWVDVISDLKKIEDLIQSMHIDATLYTESDVHPSCKVTAMKCFLLELQVISLESGDASIHDTVEDLIILANNSLSSNGNVTESGCKECEELEEKNIKEFLQSFVHIVQMFINTS/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVMHEALHNHYTQKSLSLSPGK Chain 2 – empty_ Fc(216)_IgG1_C220S/PVA_/S267K/S364K/E357Q (SEQ ID NO:217)
EPKSSDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK

Figure 49C

>XENP024478 human_IL15Ra(sushi)_(GGGGS)7-human_IL15(single-chain;Q108E)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(GGGGS)7-human_IL15(single-chain;Q108E)_Fc(216)_IgG1_pI(-)_Isosteric_A_C220S/PVA_/S267K/L368D/K370S (SEQ ID NO:218)
ITCPPPMSVEHADIWVKSYSLYSRERYICNSGFKRKAGTSSLTECVLNKATNVAHWTTPSLKCIR/<u>GGGGSGGGGSGGG
GSGGGGSGGGGSGGGGSGGGGS</u>/NWVNVISDLKKIEDLIQSMHIDATLYTESDVHPSCKVTAMKCFLLELQVISLESG
DASIHDTVENLIILANNSLSSNGNVTESGCKECEELEEKNIKEFLQSFVHIVEMFINTS/EPKSSDKTHTCPPCPAPPVAGPS
VFLFPPKPKDTLMISRTPEVTCVVVDVKHEDPEVKFNWYVDGVEVHNAKTKPREEEYNSTYRVVSVLTVLHQDWLNGK
EYKCKVSNKALPAPIEKTISKAKGQPREPQVYTLPPSREEMTKNQVSLTCDVSGFYPSDIAVEWESDGQPENNYKTTPPV
LDSDGSFFLYSKLTVDKSRWEQGDVFSCSVMHEALHNHYTQKSLSLSPGK Chain 2 – empty_ Fc(216)_IgG1_C220S/PVA_/S267K/S364K/E357Q (SEQ ID NO:219)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK >XENP024479 human_IL15Ra(sushi)_(GGGGS)7-human_IL15(single-chain;N4D/N65D)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(GGGGS)7-human_IL15(single-chain;N4D/N65D)_Fc(216)_IgG1_pI(-)_Isosteric_A_C220S/PVA_/S267K/L368D/K370S (SEQ ID NO:220)
ITCPPPMSVEHADIWVKSYSLYSRERYICNSGFKRKAGTSSLTECVLNKATNVAHWTTPSLKCIR/<u>GGGGSGGGGSGGG
GSGGGGSGGGGSGGGGSGGGGS</u>/NWVDVISDLKKIEDLIQSMHIDATLYTESDVHPSCKVTAMKCFLLELQVISLESGD
ASIHDTVEDLIILANNSLSSNGNVTESGCKECEELEEKNIKEFLQSFVHIVQMFINTS/EPKSSDKTHTCPPCPAPPVAGPS
VFLFPPKPKDTLMISRTPEVTCVVVDVKHEDPEVKFNWYVDGVEVHNAKTKPREEEYNSTYRVVSVLTVLHQDWLNGK
EYKCKVSNKALPAPIEKTISKAKGQPREPQVYTLPPSREEMTKNQVSLTCDVSGFYPSDIAVEWESDGQPENNYKTTPPV
LDSDGSFFLYSKLTVDKSRWEQGDVFSCSVMHEALHNHYTQKSLSLSPGK Chain 2 - empty-Fc_Fc(216)_IgG1_C220S/PVA_/S267K/S364K/E357Q (SEQ ID NO:221)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK

Figure 49D

\>XENP024481 human_IL15Ra(sushi)_(30AA_linker_variant)-human_IL15(single-chain;Q108E)-empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 - human_IL15Ra(sushi)_(30AA_linker_variant)-human_IL15(single-chain;Q108E)_Fc(216)_IgG1_pI(-)_Isosteric_A_C220S/PVA_/S267K/L368D/K370S (SEQ ID NO:222)
ITCPPPMSVEHADIWVKSYSLYSRERYICNSGFKRKAGTSSLTECVLNKATNVAHWTTPSLKCIR/<u>DPALVHQRPAPPGG
GGSGGGGSGGGGSGGG</u>/NWVNVISDLKKIEDLIQSMHIDATLYTESDVHPSCKVTAMKCFLLELQVISLESGDASIHDT
VENLIILANNSLSSNGNVTESGCKECEELEEKNIKEFLQSFVHIVEMFINTS/EPKSSDKTHTCPPCPAPPVAGPSVFLFPPK
PKDTLMISRTPEVTCVVVDVKHEDPEVKFNWYVDGVEVHNAKTKPREEEYNSTYRVVSVLTVLHQDWLNGKEYKCKV
SNKALPAPIEKTISKAKGQPREPQVYTLPPSREEMTKNQVSLTCDVSGFYPSDIAVEWESDGQPENNYKTTPPVLDSDGS
FFLYSKLTVDKSRWEQGDVFSCSVMHEALHNHYTQKSLSLSPGK Chain 2 – empty_ Fc(216)_IgG1_C220S/PVA_/S267K/S364K/E357Q (SEQ ID NO:223)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK

Figure 50A

>XENP024349 IL15_Q108E_(non-covalent)-human_IL15Rα(Sushi)_empty-Fc_Fc(216)_IgG1_pI(-)_Isosteric_A_C220S/PVA_/S267K/L368D/K370S-Fc(216)_IgG1_C220S/PVA_/S267K/S364K/E357Q Chain 1 – human_IL15Rα(Sushi)_ Isosteric_A_C220S/PVA_/S267K/L368D/K370S (SEQ ID NO:224)
<u>ITCPPPMSVEHADIWVKSYSLYSRERYICNSGFKRKAGTSSLTECVLNKATNVAHWTTPSLKCIR</u>/EPKSSDKTHTCPPCP
APPVAGPSVFLFPPKPKDTLMISRTPEVTCVVVDVKHEDPEVKFNWYVDGVEVHNAKTKPREEEYNSTYRVVSVLTVLH
QDWLNGKEYKCKVSNKALPAPIEKTISKAKGQPREPQVYTLPPSREEMTKNQVSLTCDVSGFYPSDIAVEWESDGQPE
NNYKTTPPVLDSDGSFFLYSKLTVDKSRWEQGDVFSCSVMHEALHNHYTQKSLSLSPGK Chain 2 – empty- Fc(216)_IgG1_C220S/PVA_/S267K/S364K/E357Q (SEQ ID NO:225)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK

Chain 3 – IL15_Q108E_(non-covalent) (SEQ ID NO:226)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVEMFINTS >XENP024890 IL15_N4D/N65D_(non-covalent)-human_IL15Ra(Sushi)-empty-Fc_IgG1_Fc(216)_IgG1_pI(-)_Isosteric_A_C220S/PVA_/S267K/L368D/K370S-IgG1_PVA_/S267K/S364K/E357Q Chain 1 – IL-15_N4D/N65D (SEQ ID NO:227)
<u>ITCPPPMSVEHADIWVKSYSLYSRERYICNSGFKRKAGTSSLTECVLNKATNVAHWTTPSLKCIR</u>/EPKSSDKTHTCPPCP
APPVAGPSVFLFPPKPKDTLMISRTPEVTCVVVDVKHEDPEVKFNWYVDGVEVHNAKTKPREEEYNSTYRVVSVLTVLH
QDWLNGKEYKCKVSNKALPAPIEKTISKAKGQPREPQVYTLPPSREEMTKNQVSLTCDVSGFYPSDIAVEWESDGQPE
NNYKTTPPVLDSDGSFFLYSKLTVDKSRWEQGDVFSCSVMHEALHNHYTQKSLSLSPGK Chain 2 - human_IL15Ra(Sushi)_Fc(216)_IgG1_pI(-)_Isosteric_A_C220S/PVA_/S267K/L368D/K370S
(SEQ ID NO:228)
<u>ITCPPPMSVEHADIWVKSYSLYSRERYICNSGFKRKAGTSSLTECVLNKATNVAHWTTPSLKCIR</u>/EPKSSDKTHTCPPCP
APPVAGPSVFLFPPKPKDTLMISRTPEVTCVVVDVKHEDPEVKFNWYVDGVEVHNAKTKPREEEYNSTYRVVSVLTVLH
QDWLNGKEYKCKVSNKALPAPIEKTISKAKGQPREPQVYTLPPSREEMTKNQVSLTCDVSGFYPSDIAVEWESDGQPE
NNYKTTPPVLDSDGSFFLYSKLTVDKSRWEQGDVFSCSVMHEALHNHYTQKSLSLSPGK Chain 3 – empty_Fc(216)_ IgG1_PVA_/S267K/S364K/E357Q
(SEQ ID NO:229)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK

Figure 50B

>XENP25138 IL15_D30N/E64Q/N65D_(non-covalent)-empty-Fc_Fc(216)_IgG1_pI(-
)_Isosteric_A_C220S/PVA_/S267K/L368D/K370S-IgG1_PVA_/S267K/S364K/E357Q Chain 1 - IL15_D30N/E64Q/N65D (SEQ ID NO:230)
NWVNVISDLKKIEDLIQSMHIDATLYTESNVHPSCKVTAMKCFLLELQVISLESGDASIHDTVQDLIILANNSLSSNGNVTE
SGCKECEELEEKNIKEFLQSFVHIVQMFINTS Chain 2 - human_IL15Ra(Sushi)_Fc(216)_IgG1_pI(-)_Isosteric_A_C220S/PVA_/S267K/L368D/K370S
(SEQ ID NO:231)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEEYNSTYRVVSVLTVLH
QDWLNGKEYKCKVSNKALPAPIEKTISKAKGQPREPQVYTLPPSREEMTKNQVSLTCDVSGFYPSDIAVEWESDGQPE
NNYKTTPPVLDSDGSFFLYSKLTVDKSRWEQGDVFSCSVMHEALHNHYTQKSLSLSPGK Chain 3 - empty_Fc(216)_ IgG1_PVA_/S267K/S364K/E357Q (SEQ ID NO:232)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVMHEALHNHYTQKSLSLSPGK

Figure 51

>XENP022801 - human_IL15_N65D(non-covalent)-human_IL15Rα(Sushi)

Chain 1 - human_IL15_N65D(non-covalent) (17672) (SEQ ID NO:233)
NWVNVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS Chain 2 - human_IL15Rα(Sushi) (17033) (SEQ ID NO:234)
ITCPPPMSVEHADIWVKSYSLYSRERYICNSGFKRKAGTSSLTECVLNKATNVAHWTTPSLKCIR >XENP022802 - human_IL15_Q108E(non-covalent)-human_IL15Rα(Sushi)

Chain 1 - human_IL15_Q108E(non-covalent) (17673) (SEQ ID NO:235)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVEMFINTS Chain 2 - human_IL15Rα(Sushi) (17033) (SEQ ID NO:236)
ITCPPPMSVEHADIWVKSYSLYSRERYICNSGFKRKAGTSSLTECVLNKATNVAHWTTPSLKCIR

Figure 52

>XENP024342 human_IL15(non-covalent; Q108E)-
human_IL15Rα(Sushi)_Fc(216)_IgG1_C220S/PVA_/S267K Chain 1 – human_IL15Rα(Sushi)_Fc(216)_IgG1_C220S/PVA_/S267K (SEQ ID NO:237)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK Chain 2 –human_IL15(non-covalent; Q108E) (SEQ ID NO:238)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVEMFINTS

Figure 53

>XENP023472 empty-Fc-IL15_N65D/E87C-human_IL15Ra(Sushi-D96/C97)_Fc(216)_IgG1_pI(-
)_Isosteric_A_C220S/PVA_/S267K/L368D/K370S-Fc(216)_IgG1_C220S/PVA_/S267K/S364K/E357Q Chain 1 – empty_ Fc(216)_IgG1_pI(-)_Isosteric_A_C220S/PVA_/S267K/L368D/K370S
(SEQ ID NO:239)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK Chain 2 - IL15_N65D/E87C (SEQ ID NO:240)
NWVNVISDLKKIEDLIQSMHIDATLYTESDVHPSCKVTAMKCFLLELQVISLESGDASIHDTVEDLIILANNSLSSNGNVTE
SGCKCCEELEEKNIKEFLQSFVHIVQMFINTS Chain 3 - IL15Ra(Sushi-D96/C97)_Fc(216)_IgG1_C220S/PVA_/S267K/S364K/E357Q
(SEQ ID NO:241)
ITCPPPMSVEHADIWVKSYSLYSRERYICNSGFKRKAGTSSLTECVLNKATNVAHWTTPSLKCIRDC/EPKSSDKTHTCPP
CPAPPVAGPSVFLFPPKPKDTLMISRTPEVTCVVVDVKHEDPEVKFNWYVDGVEVHNAKTKPREEQYNSTYRVVSVLT
VLHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVMHEALHNHYTQKSLSLSPGK >XENP023473 empty-Fc-IL15_N65D/L52C-human_IL15Ra(Sushi-S40C)_Fc(216)_IgG1_pI(-
)_Isosteric_A_C220S/PVA_/S267K/L368D/K370S-Fc(216)_IgG1_C220S/PVA_/S267K/S364K/E357Q Chain 1 – empty_ Fc(216)_IgG1_pI(-)_Isosteric_A_C220S/PVA_/S267K/L368D/K370S (SEQ ID NO:242)
EPKSSDKTHTCPPCPAPPVAGPSVFLFPPKPKDTLMISRTPEVTCVVVDVKHEDPEVKFNWYVDGVEVHNAKTKPREEE
YNSTYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK Chain 2 - IL15_N65D/L52C (SEQ ID NO:243)
NWVNVISDLKKIEDLIQSMHIDATLYTESDVHPSCKVTAMKCFLLELQVISCESGDASIHDTVEDLIILANNSLSSNGNVTE
SGCKECEELEEKNIKEFLQSFVHIVQMFINTS Chain 3 - IL15Ra(Sushi-S40C)_Fc(216)_IgG1_C220S/PVA_/S267K/S364K/E357Q (SEQ ID NO:244)
ITCPPPMSVEHADIWVKSYSLYSRERYICNSGFKRKAGTCSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREQMTKNQVKLTCLVKGFYPSDIAVEWESNGQP
ENNYKTTPPVLDSDGSFFLYSKLTVDKSRWQQGNVFSCSVMHEALHNHYTQKSLSLSPGK

Figure 55

| XENP | Variant | EC50 pM (NK cells) | Fold reduced (NK cells) | EC50 pM (CD8 T cells) | Fold reduced (CD8 T cells) |
|---|---|---|---|---|---|
| 20818 | WT | 200.6 | | 637.1 | |
| 21478 | single-chain | 848.5 | 4.2 | 4982.0 | 7.8 |
| 22815 | N1D | 281.3 | 1.4 | 1051.0 | 1.6 |
| 22816 | N4D | 321.9 | 1.6 | 1190.0 | 1.9 |
| 22817 | D8N | very weak | very weak | very weak | very weak |
| 22818 | D30N | 376.3 | 1.9 | 1366.0 | 2.1 |
| 22819 | D61N | 5934.0 | 29.6 | 161937.0 | >100 |
| 22820 | E64Q | 877.0 | 4.4 | 2858.0 | 4.5 |
| 22821 | N65D | 2883.0 | 14.4 | 6928.0 | 10.9 |
| 22822 | Q108E | 9777.0 | 48.7 | very weak | >100 |
| 22823 | N1D/D61N | 918.0 | 4.6 | 4225.0 | 6.6 |
| 22824 | N1D/E64Q | 1091.0 | 5.4 | 4228.0 | 6.6 |
| 22825 | N4D/D61N | 309.0 | 1.5 | 1070.0 | 1.7 |
| 22826 | N4D/E64Q | very weak | very weak | very weak | very weak |
| 22827 | D8N/D61N | ND | ND | ND | ND |
| 22828 | D8N/E64Q | 597.7 | 3.0 | 1658.0 | 2.6 |
| 22829 | D61N/E64Q | 458.2 | 2.3 | 2115.0 | 3.3 |
| 22830 | E64Q/Q108E | 436.6 | 2.2 | 1815.0 | 2.8 |
| 22831 | N1D/N4D/D8N | very weak | very weak | very weak | very weak |
| 22832 | D61N/E64Q/N65D | ND | ND | ND | ND |
| 22833 | N1D/D61N/E64Q/Q108E | ND | ND | ND | ND |
| 22834 | N4D/D61N/E64Q/Q108E | very weak | very weak | very weak | very weak |

Figure 59A

NK Cells (CD3-CD16+)

Figure 59B

CD8⁺ T Cells (CD3+CD8+CD45RA-)

Figure 59D

| XENP | EC50 nM (NK cells) | Fold reduced (NK cells) | EC50 nM (CD8 T cells) | Fold reduced (CD8 T cells) | EC50 nM (CD4 T cells) | Fold reduced (CD4 T cells) |
|---|---|---|---|---|---|---|
| 20818 | 0.3223 | 1.0 | 2.701 | 1.0 | 16.467 | 1.0 |
| 21478 | 1.116 | 3.5 | 11.728 | 4.3 | 28.349 | 1.7 |
| 22818 | 0.4205 | 1.3 | 2.829 | 1.0 | 40.676 | 2.5 |
| 22819 | 1.016 | 3.2 | 8.254 | 3.1 | 18.101 | 1.1 |
| 22820 | 0.562 | 1.7 | 3.918 | 1.5 | 10.362 | 0.6 |
| 22821 | 3.14 | 9.7 | 18.706 | 6.9 | 112.823 | 6.9 |
| 22822 | 68.866 | 213.7 | 6439.69 | 2384.2 | 48.738 | 3.0 |
| 22825 | 1.769 | 5.5 | 12.09 | 4.5 | 60.081 | 3.6 |
| 22826 | 1.448 | 4.5 | 9.678 | 3.6 | 22.41 | 1.4 |
| 22829 | 4.839 | 15.0 | 29.638 | 11.0 | 337.571 | 20.5 |
| 22834 | 331.293 | 1027.9 | 4107.897 | 1520.9 | ND | ND |
| IL-15 | 0.05322 | 0.2 | 0.3452 | 0.1 | ND | ND |

Figure 67C

| XENP | EC50 nM (CD8 T cells) | Fold reduced (CD8 T cells) | EC50 nM (CD4 T cells) | Fold reduced (CD4 T cells) |
|---|---|---|---|---|
| 22822 | 19.34 | 25.6 | 61.46 | 53.8 |
| 20818 | 0.7543 | 1.0 | 1.142 | 1.0 |
| 22821 | 5.196 | 6.9 | 8.485 | 7.4 |
| 22829 | 25.27 | 33.5 | 47.11 | 41.3 |
| 22834 | ND | ND | ND | ND |
| 23554 | 21.56 | 28.6 | 44.18 | 38.7 |
| 23555 | 270 | 357.9 | 818.2 | 716.5 |
| 23557 | 34.27 | 45.4 | 78.62 | 68.8 |
| 23559 | 32.91 | 43.6 | 76.03 | 66.6 |
| 24019 | 198.1 | 262.6 | 176.7 | 154.7 |
| 24020 | 15.92 | 21.1 | 30.98 | 27.1 |

Figures 80A-80B respectively depict CD4+ T cell (CD4+CD45RA+) counts on Day 7 (Figure 80A) and Day 11 (Figure 80B) after treatment of NSG mice engrafted with human PBMCs with the indicated IL15/Rα-Fc fusion proteins or control.

Figure 99A

>XENP023343 - human_IL15_N65D_(GGGGS)1-human_IL15Ra(Sushi)_(GGGGS)1_Fc(216)_IgG1_pl(-
)_Isosteric_A_C220S/PVA_/S267K/L368D/K370S/M428L/N434S-
Fc(216)_IgG1_C220S/PVA_/S267K/S364K/E357Q/M428L/N434S Chain 1 - human_IL15_N65D_(GGGGS)1_Fc(216)_IgG1_pl(-
)_Isosteric_A_C220S/PVA_/S267K/L368D/K370S/M428L/N434S (18295) (SEQ ID NO:245)
NWVNVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVLHEALHSHYTQKSLSLSPGK Chain 2 -
human_IL15Ra(Sushi)_(GGGGS)1_Fc(216)_IgG1_C220S/PVA_/S267K/S364K/E357Q/M428L/N434S
(17761) (SEQ ID NO:246)
ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVLHEALHSHYTQKSLSLSPGK >XENP023504 human_IL15_Q108E_(GGGGS)1-human_IL15Ra(Sushi)_(GGGGS)1_Fc(216)_IgG1_pl(-
)_Isosteric_A_C220S/PVA_/S267K/L368D/K370S/M428L/N434S-
Fc(216)_IgG1_C220S/PVA_/S267K/S364K/E357Q/M428L/N434S Chain 1 – human_IL15_Q108E_(GGGGS)1_Fc(216)_IgG1_pl(-
)_Isosteric_A_C220S/PVA_/S267K/L368D/K370S/M428L/N434S (SEQ ID NO:247)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVEMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVLHEALHSHYTQKSLSLSPGK Chain 2 – human_IL15Ra(Sushi)_(GGGGS)1_
Fc(216)_IgG1_C220S/PVA_/S267K/S364K/E357Q/M428L/N434S (SEQ ID NO:248)
ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVLHEALHSHYTQKSLSLSPGK

Figure 99B

>XENP024113 human_IL15_N4D/N65D_(GGGGS)1-human_IL15Rα(Sushi)_(GGGGS)1_Fc(216)_IgG1_pI(-
)_Isosteric_A_C220S/PVA_/S267K/L368D/K370S/M428L/N434S-
Fc(216)_IgG1_C220S/PVA_/S267K/S364K/E357Q/M428L/N434S Chain 1 – human_IL15_N4D/N65D_(GGGGS)1_Fc(216)_IgG1_pI(-
)_Isosteric_A_C220S/PVA_/S267K/L368D/K370S/M428L/N434S (SEQ ID NO:249)
NWVDVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS/GGGGS/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVLHEALHSHYTQKSLSLSPGK Chain 2 –
human_IL15Rα(Sushi)_(GGGGS)1_Fc(216)_IgG1_C220S/PVA_/S267K/S364K/E357Q/M428L/N434S
(SEQ ID NO:250)
ITCPPPMSVEHADIWVKSYSLYSRERYICNSGFKRKAGTSSLTECVLNKATNVAHWTTPSLKCIR/GGGGS/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVLHEALHSHYTQKSLSLSPGK >XENP024301 human_IL15_N4D/N65D-human_IL15Rα(Sushi)_Fc(216)_IgG1_pI(-
)_Isosteric_A_C220S/PVA_/S267K/L368D/K370S/M428L/N434S-
Fc(216)_IgG1_C220S/PVA_/S267K/S364K/E357Q/M428L/N434S Chain 1 – human_IL15_N4D/N65D_Fc(216)_IgG1_pI(-
)_Isosteric_A_C220S/PVA_/S267K/L368D/K370S/M428L/N434S (SEQ ID NO:251)
NWVDVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS/EPKSSDKTHTCPPCPAPPVAGPSVFLFPPKPKDTLMISRTPEVTCVVVD
VKHEDPEVKFNWYVDGVEVHNAKTKPREEEYNSTYRVVSVLTVLHQDWLNGKEYKCKVSNKALPAPIEKTISKAKGQP
REPQVYTLPPSREEMTKNQVSLTCDVSGFYPSDIAVEWESDGQPENNYKTTPPVLDSDGSFFLYSKLTVDKSRWEQGD
VFSCSVLHEALHSHYTQKSLSLSPGK Chain 2 – human_IL15Rα(Sushi)_ Fc(216)_IgG1_C220S/PVA_/S267K/S364K/E357Q/M428L/N434S
(SEQ ID NO:252)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREQMTKNQVKLTCLVKGFYPSDIAVEWESNGQP
ENNYKTTPPVLDSDGSFFLYSKLTVDKSRWQQGNVFSCSVLHEALHSHYTQKSLSLSPGK

Figure 99C

>XENP024306 human_IL15_D30N/E64Q/N65D_(GGGGS)1-
human_IL15Rα(Sushi)_(GGGGS)1_Fc(216)_IgG1_pI(-
)_Isosteric_A_C220S/PVA_/S267K/L368D/K370S/M428L/N434S-
Fc(216)_IgG1_C220S/PVA_/S267K/S364K/E357Q/M428L/N434S Chain 1 – human_IL15_D30N/E64Q/N65D_(GGGGS)1_Fc(216)_IgG1_pI(-
)_Isosteric_A_C220S/PVA_/S267K/L368D/K370S/M428L/N434S (SEQ ID NO:253)
<u>NWVNVISDLKKIEDLIQSMHIDATLYTESNVHPSCKVTAMKCFLLELQVISLESGDASIHDTVQDLIILANNSLSSNGNVTE
SGCKECEELEEKNIKEFLQSFVHIVQMFINTS</u>/<u>GGGGS</u>/EPKSSDKTHTCPPCPAPPVAGPSVFLFPPKPKDTLMISRTPEV
TCVVVDVKHEDPEVKFNWYVDGVEVHNAKTKPREEEYNSTYRVVSVLTVLHQDWLNGKEYKCKVSNKALPAPIEKTIS
KAKGQPREPQVYTLPPSREEMTKNQVSLTCDVSGFYPSDIAVEWESDGQPENNYKTTPPVLDSDGSFFLYSKLTVDKSR
WEQGDVFSCSVLHEALHSHYTQKSLSLSPGK Chain 2 –
human_IL15Rα(Sushi)_(GGGGS)1_Fc(216)_IgG1_C220S/PVA_/S267K/S364K/E357Q/M428L/N434S
(SEQ ID NO:254)
<u>ITCPPPMSVEHADIWVKSYSLYSRERYICNSGFKRKAGTSSLTECVLNKATNVAHWTTPSLKCIR</u>/<u>GGGGS</u>/EPKSSDKTH
TCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWE
SNGQPENNYKTTPPVLDSDGSFFLYSKLTVDKSRWQQGNVFSCSVLHEALHSHYTQKSLSLSPGK >XENP024341 human_IL15_N1D/N65D-human_IL15Rα(Sushi)_Fc(216)_IgG1_pI(-
)_Isosteric_A_C220S/PVA_/S267K/L368D/K370S/M428L/N434S-
Fc(216)_IgG1_C220S/PVA_/S267K/S364K/E357Q/M428L/N434S Chain 1 – human_IL15_N1D/N65D-human_Fc(216)_IgG1_pI(-
)_Isosteric_A_C220S/PVA_/S267K/L368D/K370S/M428L/N434S (SEQ ID NO:255)
<u>DWVNVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS</u>/EPKSSDKTHTCPPCPAPPVAGPSVFLFPPKPKDTLMISRTPEVTCVVVD
VKHEDPEVKFNWYVDGVEVHNAKTKPREEEYNSTYRVVSVLTVLHQDWLNGKEYKCKVSNKALPAPIEKTISKAKGQP
REPQVYTLPPSREEMTKNQVSLTCDVSGFYPSDIAVEWESDGQPENNYKTTPPVLDSDGSFFLYSKLTVDKSRWEQGD
VFSCSVLHEALHSHYTQKSLSLSPGK Chain 2 – human_IL15Rα(Sushi)_Fc(216)_IgG1_C220S/PVA_/S267K/S364K/E357Q/M428L/N434S
(SEQ ID NO:256)
<u>ITCPPPMSVEHADIWVKSYSLYSRERYICNSGFKRKAGTSSLTECVLNKATNVAHWTTPSLKCIR</u>/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREQMTKNQVKLTCLVKGFYPSDIAVEWESNGQP
ENNYKTTPPVLDSDGSFFLYSKLTVDKSRWQQGNVFSCSVLHEALHSHYTQKSLSLSPGK

Figure 100

>XENP025938 human_IL15Ra(sushi)_(GGGGS)5-human_IL15_N4D/N65D_(single-chain)-empty-Fc_Fc(216)_IgG1_pI(-)_Isosteric_A_C220S/PVA_/S267K/L368D/K370S/M428L/N434S-Fc(216)_IgG1_C220S/PVA_/S267K/S364K/E357Q/M428L/N434S Chain 1 – human_IL15Ra(sushi)_(GGGGS)5-human_IL15_N4D/N65D_(single-chain)-_Fc(216)_IgG1_pI(-)_Isosteric_A_C220S/PVA_/S267K/L368D/K370S/M428L/N434S (SEQ ID NO:257)
ITCPPPMSVEHADIWVKSYSLYSRERYICNSGFKRKAGTSSLTECVLNKATNVAHWTTPSLKCIR/<u>GGGGSGGGGSGGG</u>
<u>GSGGGGSGGGGS</u>/NWVDVISDLKKIEDLIQSMHIDATLYTESDVHPSCKVTAMKCFLLELQVISLESGDASIHDTVEDLII
LANNSLSSNGNVTESGCKECEELEEKNIKEFLQSFVHIVQMFINTS/EPKSSDKTHTCPPCPAPPVAGPSVFLFPPKPKDTL
MISRTPEVTCVVVDVKHEDPEVKFNWYVDGVEVHNAKTKPREEEYNSTYRVVSVLTVLHQDWLNGKEYKCKVSNKAL
PAPIEKTISKAKGQPREPQVYTLPPSREEMTKNQVSLTCDVSGFYPSDIAVEWESDGQPENNYKTTPPVLDSDGSFFLYS
KLTVDKSRWEQGDVFSCSVLHEALHSHYTQKSLSLSPGK Chain 2 – empty_Fc(216)_IgG1_C220S/PVA_/S267K/S364K/E357Q/M428L/N434S (SEQ ID NO:258)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVLHEALHSHYTQKSLSLSPGK

Figure 101

>XENP024383 IL15_Q108E_(non-covalent)-human_IL15Ra(Sushi)_empty-Fc_Fc(216)_IgG1_pI(-)_Isosteric_A_C220S/PVA_/S267K/L368D/K370S/M428L/N434S-Fc(216)_IgG1_C220S/PVA_/S267K/S364K/E357Q/M428L/N434S Chain 1 - IL15_Q108E (SEQ ID NO: 259)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVEMFINTS Chain 2 - human_IL15Ra(Sushi)_Fc(216)_IgG1_pI(-)_Isosteric_A_C220S/PVA_/S267K/L368D/K370S/M428L/N434S (SEQ ID NO:260)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEEYNSTYRVVSVLTVLH
QDWLNGKEYKCKVSNKALPAPIEKTISKAKGQPREPQVYTLPPSREEMTKNQVSLTCDVSGFYPSDIAVEWESDGQPE
NNYKTTPPVLDSDGSFFLYSKLTVDKSRWEQGDVFSCSVLHEALHSHYTQKSLSLSPGK Chain 3 – empty_ Fc(216)_IgG1_C220S/PVA_/S267K/S364K/E357Q/M428L/N434S (SEQ ID NO:261)
EPKSSDKTHTCPPCPAPPVAGPSVFLFPPKPKDTLMISRTPEVTCVVVDVKHEDPEVKFNWYVDGVEVHNAKTKPREE
QYNSTYRVVSVLTVLHQDWLNGKEYKCKVSNKALPAPIEKTISKAKGQPREPQVYTLPPSREQMTKNQVKLTCLVKGFY
PSDIAVEWESNGQPENNYKTTPPVLDSDGSFFLYSKLTVDKSRWQQGNVFSCSVLHEALHSHYTQKSLSLSPGK

Figure 102

>XENP024346 human_IL15(non-covalent; Q108E)-
human_IL15Rα(Sushi)_Fc(216)_IgG1_C220S/PVA_/S267K/M428L/N434S Chain 1 – human_IL15Rα(Sushi)_Fc(216)_IgG1_C220S/PVA_/S267K/M428L/N434S
(SEQ ID NO:262)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVLHEALHSHYTQKSLSLSPGK Chain 2 – human_IL15(non-covalent; Q108E) (SEQ ID NO:263)
NWVNVISDLKKIEDLIQSMHIDATLYTESDVHPSCKVTAMKCFLLELQVISLESGDASIHDTVENLIILANNSLSSNGNVTE
SGCKECEELEEKNIKEFLQSFVHIVEMFINTS >XENP024351 human_IL15(non-covalent; N4D/N65D)-
human_IL15Rα(Sushi)_Fc(216)_IgG1_C220S/PVA_/S267K/M428L/N434S Chain 1 – IL15(N4D/N65D) (SEQ ID NO:264)
NWVDVISDLKKIEDLIQSMHIDATLYTESDVHPSCKVTAMKCFLLELQVISLESGDASIHDTVEDLIILANNSLSSNGNVTE
SGCKECEELEEKNIKEFLQSFVHIVQMFINTS Chain 2 - human_IL15Rα(Sushi)_Fc(216)_IgG1_C220S/PVA_/S267K/M428L/N434S (SEQ ID NO:265)
ITCPPPMSVEHADIWVKSYSLYSRERYICNSGFKRKAGTSSLTECVLNKATNVAHWTTPSLKCIR/EPKSSDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVLHEALHSHYTQKSLSLSPGK igure 115E
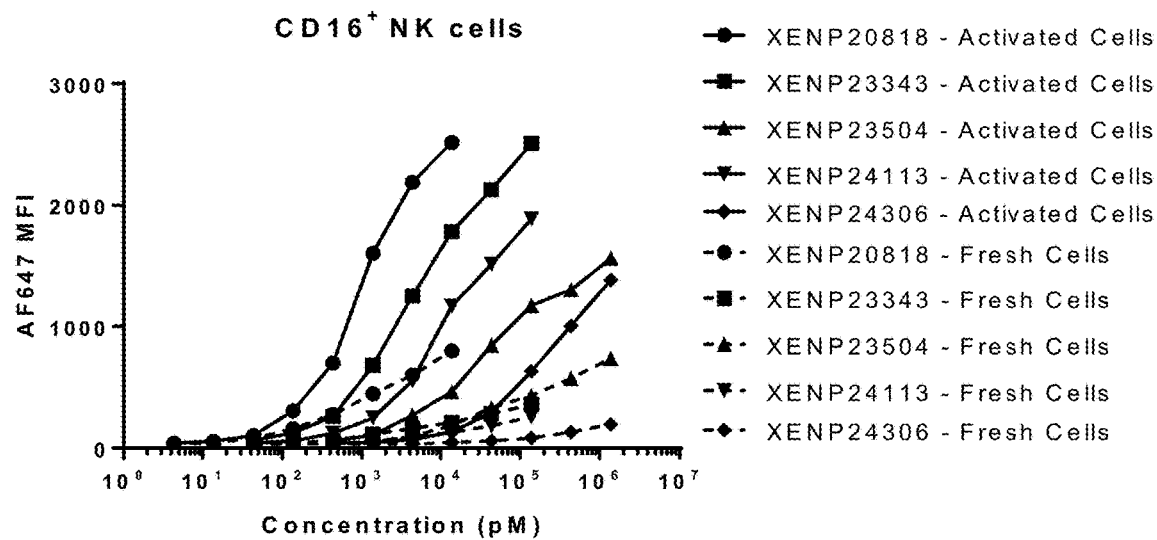
Figure 115F
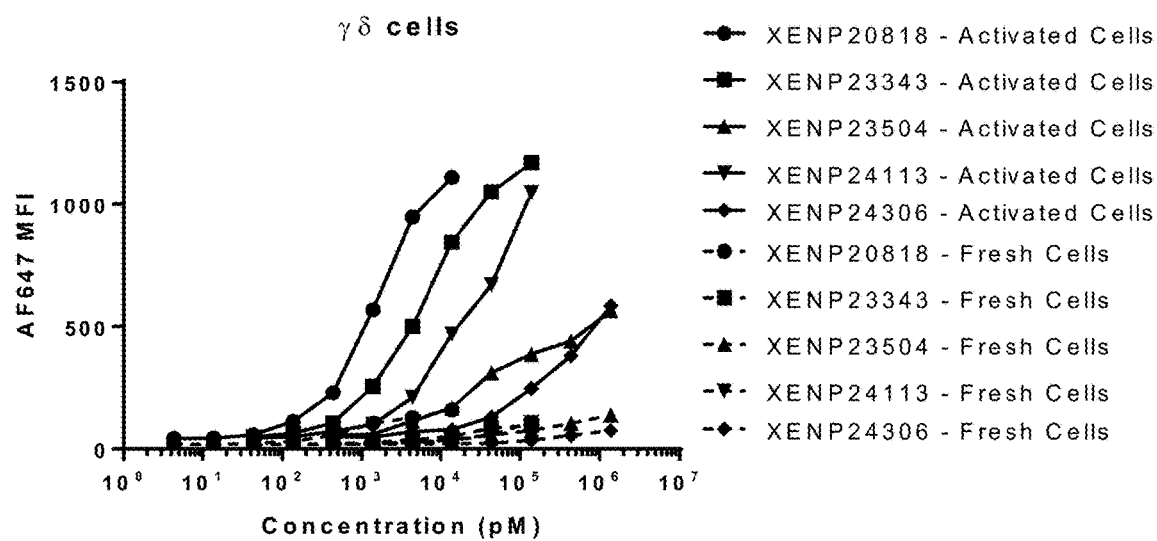

Figure 143D
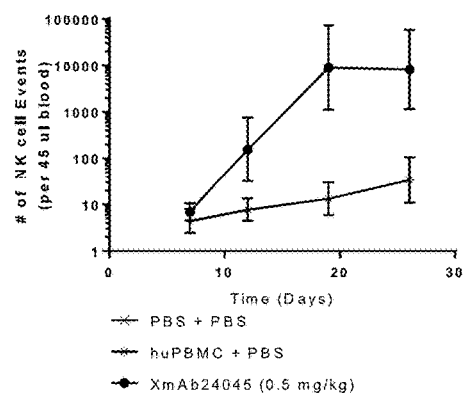
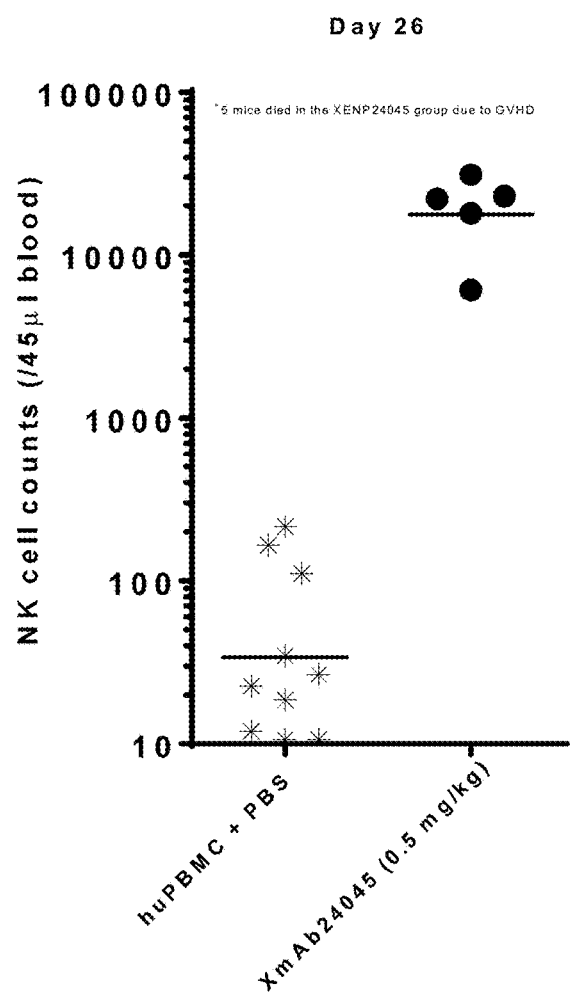

Figure 160

XENP016432 Nivolumab_H0L0_IgG1_PVA_/S267K Heavy Chain (SEQ ID NO: 266)

QVQLVESGGGVVQPGRSLRLDCKASGITFSNSGMHWVRQAPGKGLEWVAVIWYDGSKRYYADSVKGRFTISRDNSK
NTLFLQMNSLRAEDTAVYYCATNDDYWGQGTLVTVSS/ASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSCDKTHTCPPCPAPPVAG
PSVFLFPPKPKDTLMISRTPEVTCVVVDVKHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK

XENP016432 Nivolumab_H0L0_IgG1_PVA_/S267K Light Chain (SEQ ID NO: 267)

EIVLTQSPATLSLSPGERATLSCRASQSVSSYLAWYQQKPGQAPRLLIYDASNRATGIPARFSGSGSGTDFTLTISSLEPED
FAVYYCQQSSNWPRTFGQGTKVEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC

Figures 163A-163B depict CD45+ T cells in whole blood of mice on (Figure 163A) Day 6 and (Figure 163B) Day 10 after first dose of the indicated test articles.

Figure 186

>XENP21993 human_IL15Ra(sushi)_(GGGGS)5-human_IL15(single-Chain)-empty-Fc_Fc(216)_IgG1_pI(-
)_Isosteric_A_C220S/PVA_/S267K/L368D/K370S-Fc(216)_IgG1_C220S/PVA_/S267K/S364K/E357Q XENP21993 Chain 1 - human_IL15Ra(sushi)_(GGGGS)5-human_IL15(single-Chain)_Fc(216)_IgG1_pI(-
)_Isosteric_A_C220S/PVA_/S267K/L368D/K370S (SEQ ID NO:268)

ITCPPPMSVEHADIWVKSYSLYSRERYICNSGFKRKAGTSSLTECVLNKATNVAHWTTPSLKCIR/GGGG
SGGGGSGGGGSGGGGSGGGGS/NWVNVISDLKKIEDLIQSMHIDATLYTESDVHPSCKVTAMKCFLLELQ
VISLESGDASIHDTVENLIILANNSLSSNGNVTESGCKECEELEEKNIKEFLQSFVHIVQMFINTS/EPK
SSDKTHTCPPCPAPPVAGPSVFLFPPKPKDTLMISRTPEVTCVVVDVKHEDPEVKFNWYVDGVEVHNAKT
KPREEEYNSTYRVVSVLTVLHQDWLNGKEYKCKVSNKALPAPIEKTISKAKGQPREPQVYTLPPSREEMT
KNQVSLTCDVSGFYPSDIAVEWESDGQPENNYKTTPPVLDSDGSFFLYSKLTVDKSRWEQGDVFSCSVMH
EALHNHYTQKSLSLSPGK

XENP21993 Chain 2 - empty-Fc(216)_IgG1_C220S/PVA_/S267K/S364K/E357Q (SEQ ID NO:269)
EPKSSDKTHTCPPCPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPREPQVYTLPPSRE
QMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Figure 187

>XENP22853 human_IL15_(GGGGS)1-human_IL15Ra(Sushi)_(GGGGS)1_Fc(216)_IgG1_pI(-
)_Isosteric_A_C220S/PVA_/S267K/L368D/K370S/M428L/N434S-
Fc(216)_IgG1_C220S/PVA_/S267K/S364K/E357Q/M428L/N434S XENP22853 Chain 1 - human_IL15_(GGGGS)1-Fc(216)_IgG1_pI(-
)_Isosteric_A_C220S/PVA_/S267K/L368D/K370S/M428L/N434S (SEQ ID NO:270)
NWVNVISDLKKIEDLIQSMHIDATLYTESDVHPSCKVTAMKCFLLELQVISLESGDASIHDTVENLIILA
NNSLSSNGNVTESGCKECEELEEKNIKEFLQSFVHIVQMFINTS/GGGGS/EPKSSDKTHTCPPCPAPPV
AGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVLHEALHSHYTQKSLSLSP
GK XENP22853 Chain 2 - human_IL15Ra(Sushi)_(GGGGS)1-
Fc(216)_IgG1_C220S/PVA_/S267K/S364K/E357Q/M428L/N434S (SEQ ID NO:271)
ITCPPPMSVEHADIWVKSYSLYSRERYICNSGFKRKAGTSSLTECVLNKATNVAHWTTPSLKCIR/GGGG
S/EPKSSDKTHTCPPCPAPPVAGPSVFLFPPKPKDTLMISRTPEVTCVVVDVKHEDPEVKFNWYVDGVEV
HNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFS
CSVLHEALHSHYTQKSLSLSPGK

Figure 188

>XENP24294 human_IL15Ra(sushi)_(GGGGS)5-human_IL15_N4D/N65D_(single-Chain)-empty-
Fc_Fc(216)_IgG1_pI(-)_Isosteric_A_C220S/PVA_/S267K/L368D/K370S/M428L/N434S-
Fc(216)_IgG1_C220S/PVA_/S267K/S364K/E357Q/M428L/N434S XENP24294 Chain 1 - human_IL15Ra(sushi)_(GGGGS)5-human_IL15_N4D/N65D_(single-Chain)-
Fc(216)_IgG1_pI(-)_Isosteric_A_C220S/PVA_/S267K/L368D/K370S/M428L/N434S (SEQ ID NO:272)
ITCPPPMSVEHADIWVKSYSLYSRERYICNSGFKRKAGTSSLTECVLNKATNVAHWTTPSLKCIR/GGGG
SGGGGSGGGGSGGGGSGGGGS/NWVDVISDLKKIEDLIQSMHIDATLYTESDVHPSCKVTAMKCFLLELQ
VISLESGDASIHDTVEDLIILANNSLSSNGNVTESGCKECEELEEKNIKEFLQSFVHIVQMFINTS/EPK
SSDKTHTCPPCPAPPVAGPSVFLFPPKPKDTLMISRTPEVTCVVVDVKHEDPEVKFNWYVDGVEVHNAKT
KPREEEYNSTYRVVSVLTVLHQDWLNGKEYKCKVSNKALPAPIEKTISKAKGQPREPQVYTLPPSREEMT
KNQVSLTCDVSGFYPSDIAVEWESDGQPENNYKTTPPVLDSDGSFFLYSKLTVDKSRWEQGDVFSCSVLH
EALHSHYTQKSLSLSPGK XENP24294 Chain 2 - empty-Fc(216)_IgG1_C220S/PVA_/S267K/S364K/E357Q/M428L/N434S
(SEQ ID NO:273)
EPKSSDKTHTCPPCPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPREPQVYTLPPSRE
QMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Figure 191

D30N (SEQ ID NO:274)
NWVNVISDLKKIEDLIQSMHIDATLYTESNVHPSCKVTAMKCFLLELQVISLESGDASIHDTVENLIILA
NNSLSSNGNVTESGCKECEELEEKNIKEFLQSFVHIVQMFINTS

N1D/D30N (SEQ ID NO:275)
DWVNVISDLKKIEDLIQSMHIDATLYTESNVHPSCKVTAMKCFLLELQVISLESGDASIHDTVENLIILA
NNSLSSNGNVTESGCKECEELEEKNIKEFLQSFVHIVQMFINTS

N4D/D30N (SEQ ID NO:276)
NWVDVISDLKKIEDLIQSMHIDATLYTESNVHPSCKVTAMKCFLLELQVISLESGDASIHDTVENLIILA
NNSLSSNGNVTESGCKECEELEEKNIKEFLQSFVHIVQMFINTS

D30N/E64Q (SEQ ID NO:277)
NWVNVISDLKKIEDLIQSMHIDATLYTESNVHPSCKVTAMKCFLLELQVISLESGDASIHDTVQNLIILA
NNSLSSNGNVTESGCKECEELEEKNIKEFLQSFVHIVQMFINTS

D30N/N65D (SEQ ID NO:278)
NWVNVISDLKKIEDLIQSMHIDATLYTESNVHPSCKVTAMKCFLLELQVISLESGDASIHDTVEDLIILA
NNSLSSNGNVTESGCKECEELEEKNIKEFLQSFVHIVQMFINTS

D30N/E64Q/N65D (SEQ ID NO:279)
NWVNVISDLKKIEDLIQSMHIDATLYTESNVHPSCKVTAMKCFLLELQVISLESGDASIHDTVQDLIILA
NNSLSSNGNVTESGCKECEELEEKNIKEFLQSFVHIVQMFINTS

Figure 192A

>XENP29281 human_IL15Ra(sushi)_(GGGGS)5-human_IL15_D30N_(single-Chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q

XENP29281 Chain 1 - human_IL15Ra(sushi)_(GGGGS)5-human_IL15_D30N_(single-Chain)-Fc(216)_IgG1_pI(-)_Isosteric_A_C220S/PVA_/S267K/L368D/K370S (SEQ ID NO:280)
ITCPPPMSVEHADIWVKSYSLYSRERYICNSGFKRKAGTSSLTECVLNKATNVAHWTTPSLKCIR/GGGG
SGGGGSGGGGSGGGGSGGGGS/NWVNVISDLKKIEDLIQSMHIDATLYTESNVHPSCKVTAMKCFLLELQ
VISLESGDASIHDTVENLIILANNSLSSNGNVTESGCKECEELEEKNIKEFLQSFVHIVQMFINTS/EPK
SSDKTHTCPPCPAPPVAGPSVFLFPPKPKDTLMISRTPEVTCVVVDVKHEDPEVKFNWYVDGVEVHNAKT
KPREEEYNSTYRVVSVLTVLHQDWLNGKEYKCKVSNKALPAPIEKTISKAKGQPREPQVYTLPPSREEMT
KNQVSLTCDVSGFYPSDIAVEWESDGQPENNYKTTPPVLDSDGSFFLYSKLTVDKSRWEQGDVFSCSVMH
EALHNHYTQKSLSLSPGK

XENP29281 Chain 2 - empty-Fc(216)_IgG1_C220S/PVA_/S267K/S364K/E357Q (SEQ ID NO:281)
EPKSSDKTHTCPPCPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPREPQVYTLPPSRE
QMTKNQVKLTCLVKGFYPSDIAVEWESNGQPENNYKTTPPVLDSDGSFFLYSKLTVDKSRWQQGNVFSCS
VMHEALHNHYTQKSLSLSPGK

>XENP29282 human_IL15Ra(sushi)_(GGGGS)5-human_IL15_N1D/D30N_(single-Chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q

XENP29282 Chain 1 - human_IL15Ra(sushi)_(GGGGS)5-human_IL15_N1D/D30N_(single-Chain)-Fc(216)_IgG1_pI(-)_Isosteric_A_C220S/PVA_/S267K/L368D/K370S (SEQ ID NO:282)
ITCPPPMSVEHADIWVKSYSLYSRERYICNSGFKRKAGTSSLTECVLNKATNVAHWTTPSLKCIR/GGGG
SGGGGSGGGGSGGGGSGGGGS/DWVNVISDLKKIEDLIQSMHIDATLYTESNVHPSCKVTAMKCFLLELQ
VISLESGDASIHDTVENLIILANNSLSSNGNVTESGCKECEELEEKNIKEFLQSFVHIVQMFINTS/EPK
SSDKTHTCPPCPAPPVAGPSVFLFPPKPKDTLMISRTPEVTCVVVDVKHEDPEVKFNWYVDGVEVHNAKT
KPREEEYNSTYRVVSVLTVLHQDWLNGKEYKCKVSNKALPAPIEKTISKAKGQPREPQVYTLPPSREEMT
KNQVSLTCDVSGFYPSDIAVEWESDGQPENNYKTTPPVLDSDGSFFLYSKLTVDKSRWEQGDVFSCSVMH
EALHNHYTQKSLSLSPGK

XENP29282 Chain 2 - empty-Fc(216)_IgG1_C220S/PVA_/S267K/S364K/E357Q (SEQ ID NO:283)
EPKSSDKTHTCPPCPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPREPQVYTLPPSRE
QMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Figure 192B

>XENP29283 human_IL15Ra(sushi)_(GGGGS)5-human_IL15_N4D/D30N_(single-Chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q XENP29283 Chain 1 - human_IL15Ra(sushi)_(GGGGS)5-human_IL15_N4D/D30N_(single-Chain)-Fc(216)_IgG1_pI(-)_Isosteric_A_C220S/PVA_/S267K/L368D/K370S (SEQ ID NO:284)
ITCPPPMSVEHADIWVKSYSLYSRERYICNSGFKRKAGTSSLTECVLNKATNVAHWTTPSLKCIR/GGGG
SGGGGSGGGGSGGGGSGGGGS/NWVDVISDLKKIEDLIQSMHIDATLYTESNVHPSCKVTAMKCFLLELQ
VISLESGDASIHDTVENLIILANNSLSSNGNVTESGCKECEELEEKNIKEFLQSFVHIVQMFINTS/EPK
SSDKTHTCPPCPAPPVAGPSVFLFPPKPKDTLMISRTPEVTCVVVDVKHEDPEVKFNWYVDGVEVHNAKT
KPREEEYNSTYRVVSVLTVLHQDWLNGKEYKCKVSNKALPAPIEKTISKAKGQPREPQVYTLPPSREEMT
KNQVSLTCDVSGFYPSDIAVEWESDGQPENNYKTTPPVLDSDGSFFLYSKLTVDKSRWEQGDVFSCSVMH
EALHNHYTQKSLSLSPGK XENP29283 Chain 2 - empty-Fc(216)_IgG1_C220S/PVA_/S267K/S364K/E357Q (SEQ ID NO:285)
EPKSSDKTHTCPPCPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPREPQVYTLPPSRE
QMTKNQVKLTCLVKGFYPSDIAVEWESNGQPENNYKTTPPVLDSDGSFFLYSKLTVDKSRWQQGNVFSCS
VMHEALHNHYTQKSLSLSPGK >XENP29284 human_IL15Ra(sushi)_(GGGGS)5-human_IL15_D30N/E64Q_(single-Chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q XENP29284 Chain 1 - human_IL15Ra(sushi)_(GGGGS)5-human_IL15_D30N/E64Q_(single-Chain)-Fc(216)_IgG1_pI(-)_Isosteric_A_C220S/PVA_/S267K/L368D/K370S (SEQ ID NO:286)
ITCPPPMSVEHADIWVKSYSLYSRERYICNSGFKRKAGTSSLTECVLNKATNVAHWTTPSLKCIR/GGGG
SGGGGSGGGGSGGGGSGGGGS/NWVNVISDLKKIEDLIQSMHIDATLYTESNVHPSCKVTAMKCFLLELQ
VISLESGDASIHDTVQNLIILANNSLSSNGNVTESGCKECEELEEKNIKEFLQSFVHIVQMFINTS/EPK
SSDKTHTCPPCPAPPVAGPSVFLFPPKPKDTLMISRTPEVTCVVVDVKHEDPEVKFNWYVDGVEVHNAKT
KPREEEYNSTYRVVSVLTVLHQDWLNGKEYKCKVSNKALPAPIEKTISKAKGQPREPQVYTLPPSREEMT
KNQVSLTCDVSGFYPSDIAVEWESDGQPENNYKTTPPVLDSDGSFFLYSKLTVDKSRWEQGDVFSCSVMH
EALHNHYTQKSLSLSPGK XENP29284 Chain 2 - empty-Fc(216)_IgG1_C220S/PVA_/S267K/S364K/E357Q (SEQ ID NO:287)
EPKSSDKTHTCPPCPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPREPQVYTLPPSRE
QMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Figure 192C

>XENP29285 human_IL15Ra(sushi)_(GGGGS)5-human_IL15_D30N/N65D_(single-Chain)-empty-
Fc_Fc(216)_IgG1_pI(-)_Isosteric_A_C220S/PVA_/S267K/L368D/K370S-
Fc(216)_IgG1_C220S/PVA_/S267K/S364K/E357Q XENP29285 Chain 1 - human_IL15Ra(sushi)_(GGGGS)5-human_IL15_D30N/N65D_(single-Chain)-
Fc(216)_IgG1_pI(-)_Isosteric_A_C220S/PVA_/S267K/L368D/K370S (SEQ ID NO:288)
ITCPPPMSVEHADIWVKSYSLYSRERYICNSGFKRKAGTSSLTECVLNKATNVAHWTTPSLKCIR/GGGG
SGGGGSGGGGSGGGGSGGGGS/NWVNVISDLKKIEDLIQSMHIDATLYTESNVHPSCKVTAMKCFLLELQ
VISLESGDASIHDTVEDLIILANNSLSSNGNVTESGCKECEELEEKNIKEFLQSFVHIVQMFINTS/EPK
SSDKTHTCPPCPAPPVAGPSVFLFPPKPKDTLMISRTPEVTCVVVDVKHEDPEVKFNWYVDGVEVHNAKT
KPREEEYNSTYRVVSVLTVLHQDWLNGKEYKCKVSNKALPAPIEKTISKAKGQPREPQVYTLPPSREEMT
KNQVSLTCDVSGFYPSDIAVEWESDGQPENNYKTTPPVLDSDGSFFLYSKLTVDKSRWEQGDVFSCSVMH
EALHNHYTQKSLSLSPGK XENP29285 Chain 2 - empty-Fc(216)_IgG1_C220S/PVA_/S267K/S364K/E357Q (SEQ ID NO:289)
EPKSSDKTHTCPPCPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPREPQVYTLPPSRE
QMTKNQVKLTCLVKGFYPSDIAVEWESNGQPENNYKTTPPVLDSDGSFFLYSKLTVDKSRWQQGNVFSCS
VMHEALHNHYTQKSLSLSPGK >XENP29286 human_IL15Ra(sushi)_(GGGGS)5-human_IL15_D30N/E64Q/N65D_(single-Chain)-empty-
Fc_Fc(216)_IgG1_pI(-)_Isosteric_A_C220S/PVA_/S267K/L368D/K370S-
Fc(216)_IgG1_C220S/PVA_/S267K/S364K/E357Q XENP29286 Chain 1 - human_IL15Ra(sushi)_(GGGGS)5-human_IL15_D30N/E64Q/N65D_(single-Chain)-
Fc(216)_IgG1_pI(-)_Isosteric_A_C220S/PVA_/S267K/L368D/K370S (SEQ ID NO:290)
ITCPPPMSVEHADIWVKSYSLYSRERYICNSGFKRKAGTSSLTECVLNKATNVAHWTTPSLKCIR/GGGG
SGGGGSGGGGSGGGGSGGGGS/NWVNVISDLKKIEDLIQSMHIDATLYTESNVHPSCKVTAMKCFLLELQ
VISLESGDASIHDTVQDLIILANNSLSSNGNVTESGCKECEELEEKNIKEFLQSFVHIVQMFINTS/EPK
SSDKTHTCPPCPAPPVAGPSVFLFPPKPKDTLMISRTPEVTCVVVDVKHEDPEVKFNWYVDGVEVHNAKT
KPREEEYNSTYRVVSVLTVLHQDWLNGKEYKCKVSNKALPAPIEKTISKAKGQPREPQVYTLPPSREEMT
KNQVSLTCDVSGFYPSDIAVEWESDGQPENNYKTTPPVLDSDGSFFLYSKLTVDKSRWEQGDVFSCSVMH
EALHNHYTQKSLSLSPGK XENP29286 Chain 2 - empty-Fc(216)_IgG1_pI(-)_Isosteric_A_C220S/PVA_/S267K/L368D/K370S
(SEQ ID NO:291)
EPKSSDKTHTCPPCPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPREPQVYTLPPSRE
QMTKNQVKLTCLVKGFYPSDIAVEWESNGQPENNYKTTPPVLDSDGSFFLYSKLTVDKSRWQQGNVFSCS
VMHEALHNHYTQKSLSLSPGK × PBMC only
∗ PBMC + XENP16432 (3 mg/kg)
● PBMC + XENP16432 (3 mg/kg) + XENP24045 (0.5 mg/kg)

× PBMC
∗ PBMC + XENP16432 (3 mg/kg)
● PBMC + XENP16432 (3 mg/kg) + XENP24045 (0.5 mg/kg)

```
                            SEQUENCE LISTING

<160> NUMBER OF SEQ ID NOS: 294

<210> SEQ ID NO 1
    <211> LENGTH: 162
    <212> TYPE: PRT
    <213> ORGANISM: Homo sapiens

<400> SEQUENCE: 1

Met Arg Ile Ser Lys Pro His Leu Arg Ser Ile Ser Ile Gln Cys Tyr
    1               5                   10                  15

Leu Cys Leu Leu Leu Asn Ser His Phe Leu Thr Glu Ala Gly Ile His
                    20                  25                  30

Val Phe Ile Leu Gly Cys Phe Ser Ala Gly Leu Pro Lys Thr Glu Ala
                35                  40                  45

Asn Trp Val Asn Val Ile Ser Asp Leu Lys Lys Ile Glu Asp Leu Ile
            50                  55                  60

Gln Ser Met His Ile Asp Ala Thr Leu Tyr Thr Glu Ser Asp Val His
    65                  70                  75                  80

Pro Ser Cys Lys Val Thr Ala Met Lys Cys Phe Leu Leu Glu Leu Gln
                    85                  90                  95

Val Ile Ser Leu Glu Ser Gly Asp Ala Ser Ile His Asp Thr Val Glu
                    100                 105                 110

Asn Leu Ile Ile Leu Ala Asn Asn Ser Leu Ser Ser Asn Gly Asn Val
                115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
    145                 150                 155                 160

Thr Ser

<210> SEQ ID NO 2
    <211> LENGTH: 114
    <212> TYPE: PRT
    <213> ORGANISM: Homo sapiens

<400> SEQUENCE: 2

Asn Trp Val Asn Val Ile Ser Asp Leu Lys Lys Ile Glu Asp Leu Ile
    1               5                   10                  15

Gln Ser Met His Ile Asp Ala Thr Leu Tyr Thr Glu Ser Asp Val His
                    20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
                50                  55                  60

Asn Leu Ile Ile Leu Ala Asn Asn Ser Leu Ser Ser Asn Gly Asn Val
    65                  70                  75                  80

Thr Glu Ser Gly Cys Lys Glu Cys Glu Glu Leu Glu Glu Lys Asn Ile
```

```
                    85                  90                  95
Lys Glu Phe Leu Gln Ser Phe Val His Ile Val Gln Met Phe Ile Asn
                   100                 105                 110
Thr Ser

<210> SEQ ID NO 3
<211> LENGTH: 267
<212> TYPE: PRT
<213> ORGANISM: Homo sapiens

<400> SEQUENCE: 3

Met Ala Pro Arg Arg Ala Arg Gly Cys Arg Thr Leu Gly Leu Pro Ala
1               5                   10                  15

Leu Leu Leu Leu Leu Leu Arg Pro Pro Ala Thr Arg Gly Ile Thr
                20                  25                  30

Cys Pro Pro Pro Met Ser Val Glu His Ala Asp Ile Trp Val Lys Ser
                35                  40                  45

Tyr Ser Leu Tyr Ser Arg Glu Arg Tyr Ile Cys Asn Ser Gly Phe Lys
            50                  55                  60

Arg Lys Ala Gly Thr Ser Ser Leu Thr Glu Cys Val Leu Asn Lys Ala
65              70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
                100                 105                 110

Ala Gly Val Thr Pro Gln Pro Glu Ser Leu Ser Pro Ser Gly Lys Glu
                115                 120                 125

Pro Ala Ala Ser Ser Pro Ser Ser Asn Asn Thr Ala Ala Thr Thr Ala
            130                 135                 140

Ala Ile Val Pro Gly Ser Gln Leu Met Pro Ser Lys Ser Pro Ser Thr
145             150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
                180                 185                 190

Pro Pro Gly Val Tyr Pro Gln Gly His Ser Asp Thr Thr Val Ala Ile
                195                 200                 205

Ser Thr Ser Thr Val Leu Leu Cys Gly Leu Ser Ala Val Ser Leu Leu
            210                 215                 220

Ala Cys Tyr Leu Lys Ser Arg Gln Thr Pro Pro Leu Ala Ser Val Glu
225             230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
                260                 265

<210> SEQ ID NO 4
<211> LENGTH: 175
<212> TYPE: PRT
<213> ORGANISM: Homo sapiens

<400> SEQUENCE: 4

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30
```

Phe Lys Arg Lys Ala Gly Thr Ser Ser Leu Thr Glu Cys Val Leu Asn
           35                  40                  45

Lys Ala Thr Asn Val Ala His Trp Thr Thr Pro Ser Leu Lys Cys Ile
 50                  55                  60

Arg Asp Pro Ala Leu Val His Gln Arg Pro Ala Pro Pro Ser Thr Val
 65                  70                  75                  80

Thr Thr Ala Gly Val Thr Pro Gln Pro Glu Ser Leu Ser Pro Ser Gly
                 85                  90                  95

Lys Glu Pro Ala Ala Ser Ser Pro Ser Ser Asn Asn Thr Ala Ala Thr
                100                 105                 110

Thr Ala Ala Ile Val Pro Gly Ser Gln Leu Met Pro Ser Lys Ser Pro
            115                 120                 125

Ser Thr Gly Thr Thr Glu Ile Ser Ser His Glu Ser Ser His Gly Thr
        130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175

<210> SEQ ID NO 5
<211> LENGTH: 65
<212> TYPE: PRT
<213> ORGANISM: Homo sapiens

<400> SEQUENCE: 5

Ile Thr Cys Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
                 20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
 50                  55                  60

Arg
 65

<210> SEQ ID NO 6
<211> LENGTH: 551
<212> TYPE: PRT
<213> ORGANISM: Homo sapiens

<400> SEQUENCE: 6

Met Ala Ala Pro Ala Leu Ser Trp Arg Leu Pro Leu Leu Ile Leu Leu
 1               5                  10                  15

Leu Pro Leu Ala Thr Ser Trp Ala Ser Ala Ala Val Asn Gly Thr Ser
                 20                  25                  30

Gln Phe Thr Cys Phe Tyr Asn Ser Arg Ala Asn Ile Ser Cys Val Trp
            35                  40                  45

Ser Gln Asp Gly Ala Leu Gln Asp Thr Ser Cys Gln Val His Ala Trp
 50                  55                  60

Pro Asp Arg Arg Arg Trp Asn Gln Thr Cys Glu Leu Leu Pro Val Ser
 65                  70                  75                  80

Gln Ala Ser Trp Ala Cys Asn Leu Ile Leu Gly Ala Pro Asp Ser Gln
                 85                  90                  95

Lys Leu Thr Thr Val Asp Ile Val Thr Leu Arg Val Leu Cys Arg Glu
            100                 105                 110

```
Gly Val Arg Trp Arg Val Met Ala Ile Gln Asp Phe Lys Pro Phe Glu
            115                 120                 125

Asn Leu Arg Leu Met Ala Pro Ile Ser Leu Gln Val His Val Glu
        130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
            165                 170                 175

Thr Trp Glu Glu Ala Pro Leu Leu Thr Leu Lys Gln Lys Gln Glu Trp
        180                 185                 190

Ile Cys Leu Glu Thr Leu Thr Pro Asp Thr Gln Tyr Glu Phe Gln Val
            195                 200                 205

Arg Val Lys Pro Leu Gln Gly Glu Phe Thr Thr Trp Ser Pro Trp Ser
        210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
            245                 250                 255

Phe Ile Ile Leu Val Tyr Leu Leu Ile Asn Cys Arg Asn Thr Gly Pro
            260                 265                 270

Trp Leu Lys Lys Val Leu Lys Cys Asn Thr Pro Asp Pro Ser Lys Phe
        275                 280                 285

Phe Ser Gln Leu Ser Ser Glu His Gly Gly Asp Val Gln Lys Trp Leu
            290                 295                 300

Ser Ser Pro Phe Pro Ser Ser Ser Phe Ser Pro Gly Gly Leu Ala Pro
305                 310                 315                 320

Glu Ile Ser Pro Leu Glu Val Leu Glu Arg Asp Lys Val Thr Gln Leu
            325                 330                 335

Leu Leu Gln Gln Asp Lys Val Pro Glu Pro Ala Ser Leu Ser Ser Asn
        340                 345                 350

His Ser Leu Thr Ser Cys Phe Thr Asn Gln Gly Tyr Phe Phe Phe His
            355                 360                 365

Leu Pro Asp Ala Leu Glu Ile Glu Ala Cys Gln Val Tyr Phe Thr Tyr
        370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
            405                 410                 415

Ala Tyr Cys Thr Phe Pro Ser Arg Asp Asp Leu Leu Leu Phe Ser Pro
        420                 425                 430

Ser Leu Leu Gly Gly Pro Ser Pro Ser Thr Ala Pro Gly Gly Ser
            435                 440                 445

Gly Ala Gly Glu Glu Arg Met Pro Pro Ser Leu Gln Glu Arg Val Pro
450                 455                 460

Arg Asp Trp Asp Pro Gln Pro Leu Gly Pro Thr Pro Gly Val Pro
465                 470                 475                 480

Asp Leu Val Asp Phe Gln Pro Pro Glu Leu Val Leu Arg Glu Ala
            485                 490                 495

Gly Glu Glu Val Pro Asp Ala Gly Pro Arg Glu Gly Val Ser Phe Pro
        500                 505                 510

Trp Ser Arg Pro Pro Gly Gln Gly Glu Phe Arg Ala Leu Asn Ala Arg
            515                 520                 525
```

-continued

```
Leu Pro Leu Asn Thr Asp Ala Tyr Leu Ser Leu Gln Glu Leu Gln Gly
        530                 535                 540

Gln Asp Pro Thr His Leu Val
545                 550

<210> SEQ ID NO 7
<211> LENGTH: 214
<212> TYPE: PRT
<213> ORGANISM: Homo sapiens

<400> SEQUENCE: 7

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 8
<211> LENGTH: 369
<212> TYPE: PRT
<213> ORGANISM: Homo sapiens

<400> SEQUENCE: 8

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80
```

```
Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
        275                 280                 285

Arg Ile Pro Thr Leu Lys Asn Leu Glu Asp Leu Val Thr Glu Tyr His
    290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
        355                 360                 365

Thr

<210> SEQ ID NO 9
<211> LENGTH: 240
<212> TYPE: PRT
<213> ORGANISM: Homo sapiens

<400> SEQUENCE: 9

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
                20                  25                  30

Leu Pro Leu Pro Glu Val Gln Cys Phe Val Phe Asn Val Glu Tyr Met
            35                  40                  45

Asn Cys Thr Trp Asn Ser Ser Ser Glu Pro Gln Pro Thr Asn Leu Thr
        50                  55                  60

Leu His Tyr Trp Tyr Lys Asn Ser Asp Asn Asp Lys Val Gln Lys Cys
65                  70                  75                  80
```

```
Ser His Tyr Leu Phe Ser Glu Glu Ile Thr Ser Gly Cys Gln Leu Gln
             85                  90                  95

Lys Lys Glu Ile His Leu Tyr Gln Thr Phe Val Val Gln Leu Gln Asp
        100                 105                 110

Pro Arg Glu Pro Arg Gln Ala Thr Gln Met Leu Lys Leu Gln Asn
    115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
210                 215                 220

Gly Ser Asn Thr Ser Lys Glu Asn Pro Phe Leu Phe Ala Leu Glu Ala
225                 230                 235                 240

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(8)
<223> OTHER INFORMATION: This sequence may encompass 1-4 "Gly Ser"
      repeating units
<220> FEATURE:
<223> OTHER INFORMATION: See specification as filed for detailed
      description of substitutions and preferred embodiments

<400> SEQUENCE: 11

Gly Ser Gly Ser Gly Ser Gly Ser
1               5

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Ser Gly
      Gly Ser" repeating units
```

```
-continued

<220> FEATURE:
<223> OTHER INFORMATION: See specification as filed for detailed
      description of substitutions and preferred embodiments

<400> SEQUENCE: 12

Gly Ser Gly Gly Ser Gly Ser Gly Gly Ser Gly Ser Gly Gly Ser Gly
1               5                   10                  15

Ser Gly Gly Ser
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units
<220> FEATURE:
<223> OTHER INFORMATION: See specification as filed for detailed
      description of substitutions and preferred embodiments

<400> SEQUENCE: 13

Gly Gly Gly Gly Ser Gly Gly Gly Gly Ser Gly Gly Gly Gly Ser Gly
1               5                   10                  15

Gly Gly Gly Ser
            20

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 1-4 "Gly Gly Gly
      Ser" repeating units
<220> FEATURE:
<223> OTHER INFORMATION: See specification as filed for detailed
      description of substitutions and preferred embodiments

<400> SEQUENCE: 14

Gly Gly Gly Ser Gly Gly Gly Ser Gly Gly Gly Ser Gly Gly Gly Ser
1               5                   10                  15

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 1-5 "Gly Ser"
      repeating units
<220> FEATURE:
<223> OTHER INFORMATION: See specification as filed for detailed
      description of substitutions and preferred embodiments

<400> SEQUENCE: 15

Gly Ser Gly Ser Gly Ser Gly Ser Gly Ser
```

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 "Gly Ser Gly
      Gly Ser" repeating units
<220> FEATURE:
<223> OTHER INFORMATION: See specification as filed for detailed
      description of substitutions and preferred embodiments

<400> SEQUENCE: 16

Gly Ser Gly Gly Ser Gly Ser Gly Gly Ser Gly Ser Gly Gly Ser Gly
1               5                   10                  15

Ser Gly Gly Ser Gly Ser Gly Gly Ser
            20                  25

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 "Gly Gly Gly
      Gly Ser" repeating units
<220> FEATURE:
<223> OTHER INFORMATION: See specification as filed for detailed
      description of substitutions and preferred embodiments

<400> SEQUENCE: 17

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-5 "Gly Gly Gly
      Ser" repeating units
<220> FEATURE:
<223> OTHER INFORMATION: See specification as filed for detailed
      description of substitutions and preferred embodiments

<400> SEQUENCE: 18

Gly Gly Gly Ser Gly Gly Gly Ser Gly Gly Gly Ser Gly Gly Gly Ser
1               5                   10                  15

Gly Gly Gly Ser
            20

<210> SEQ ID NO 19

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 0-5 "Gly Ser"
      repeating units
<220> FEATURE:
<223> OTHER INFORMATION: See specification as filed for detailed
      description of substitutions and preferred embodiments

<400> SEQUENCE: 19

Gly Ser Gly Ser Gly Ser Gly Ser Gly Ser
1               5                   10

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 0-5 "Gly Ser Gly
      Gly Ser" repeating units
<220> FEATURE:
<223> OTHER INFORMATION: See specification as filed for detailed
      description of substitutions and preferred embodiments

<400> SEQUENCE: 20

Gly Ser Gly Gly Ser Gly Ser Gly Gly Ser Gly Ser Gly Gly Ser Gly
1               5                   10                  15

Ser Gly Gly Ser Gly Ser Gly Gly Ser
            20                  25

<210> SEQ ID NO 21
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 0-5 "Gly Gly Gly
      Gly Ser" repeating units
<220> FEATURE:
<223> OTHER INFORMATION: See specification as filed for detailed
      description of substitutions and preferred embodiments

<400> SEQUENCE: 21

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MISC_FEATURE
<222> LOCATION: (1)..(20)
<223> OTHER INFORMATION: This sequence may encompass 0-5 "Gly Gly Gly
      Ser" repeating units
<220> FEATURE:
<223> OTHER INFORMATION: See specification as filed for detailed
      description of substitutions and preferred embodiments

<400> SEQUENCE: 22

Gly Gly Gly Ser Gly Gly Gly Ser Gly Gly Gly Ser Gly Gly Gly Ser
1               5                   10                  15

Gly Gly Gly Ser
            20

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 0-5 "Gly Ser"
      repeating units
<220> FEATURE:
<223> OTHER INFORMATION: See specification as filed for detailed
      description of substitutions and preferred embodiments

<400> SEQUENCE: 23

Gly Ser Gly Ser Gly Ser Gly Ser Gly Ser
1               5                   10

<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 0-5 "Gly Ser Gly
      Gly Ser" repeating units
<220> FEATURE:
<223> OTHER INFORMATION: See specification as filed for detailed
      description of substitutions and preferred embodiments

<400> SEQUENCE: 24

Gly Ser Gly Gly Ser Gly Ser Gly Gly Ser Gly Ser Gly Gly Ser Gly
1               5                   10                  15

Ser Gly Gly Ser Gly Ser Gly Gly Ser
            20                  25

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 0-5 "Gly Gly Gly
      Gly Ser" repeating units
<220> FEATURE:
<223> OTHER INFORMATION: See specification as filed for detailed
      description of substitutions and preferred embodiments
```

```
<400> SEQUENCE: 25

Gly Gly Gly Gly Ser Gly Gly Gly Gly Ser Gly Gly Gly Gly Ser Gly
1               5                   10                  15
Gly Gly Gly Ser Gly Gly Gly Gly Ser
            20                  25

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 0-5 "Gly Gly Gly
      Ser" repeating units
<220> FEATURE:
<223> OTHER INFORMATION: See specification as filed for detailed
      description of substitutions and preferred embodiments

<400> SEQUENCE: 26

Gly Gly Gly Ser Gly Gly Gly Ser Gly Gly Gly Ser Gly Gly Gly Ser
1               5                   10                  15
Gly Gly Gly Ser
            20

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Gly Gly Ser
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser Gly Gly Gly Gly Ser
1               5                   10

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Gly Ser Gly Gly Gly Gly Ser Gly Gly Gly Gly Ser Gly
1               5                   10                  15
Gly Gly Gly Ser
            20
```

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Gly Gly Ser Gly Gly Gly Gly Ser Gly Gly Gly Gly Ser
1               5                   10                  15

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Lys Pro Gly Ser Gly Lys Pro Gly Ser Gly Lys Pro Gly Ser Gly
1               5                   10                  15

Lys Pro Gly Ser Gly Lys Pro Gly Ser Gly Lys Pro Gly Ser
            20                  25                  30

<210> SEQ ID NO 34
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Lys Pro Gly Ser Gly Lys Pro Gly Ser Gly Lys Pro Gly Ser Gly
1               5                   10                  15

```
Lys Pro Gly Ser Gly Lys Pro Gly Ser
            20              25

<210> SEQ ID NO 35
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly
            20              25                  30

Gly Gly Ser
        35

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Pro Ala Leu Val His Gln Arg Pro Ala Pro Gly Gly Gly Gly
1               5                   10                  15

Ser Gly Gly Gly Gly Ser Gly Gly Gly Gly Ser Gly Gly Gly
            20              25                  30

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Lys Pro Gly Ser
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Gly Glu Ser
1               5

<210> SEQ ID NO 39
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39
```

```
Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Lys Pro Lys
            20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Gln Met Thr Lys
        130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 40
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Lys Pro Lys
            20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125
```

```
Glu Pro Gln Val Tyr Thr Leu Pro Pro Ser Arg Glu Glu Met Thr Lys
        130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
        180                 185                 190

Lys Leu Thr Val Asp Lys Ser Arg Trp Gln Gln Gly Asp Val Phe Ser
        195                 200                 205

Cys Ser Val Met His Glu Ala Leu His Asn His Tyr Thr Gln Lys Ser
        210                 215                 220

Leu Ser Leu Ser Pro Gly Lys
225                 230
```

<210> SEQ ID NO 41
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
        210                 215                 220

Leu Ser Leu Ser Pro Gly Lys
225                 230
```

-continued

```
<210> SEQ ID NO 42
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 43
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80
```

```
                65                  70                  75                  80
Asn Ser Thr Tyr Arg Val Val Ser Val Leu Thr Val Leu His Gln Asp
                85                  90                  95
Trp Leu Asn Gly Lys Glu Tyr Lys Cys Lys Val Ser Asn Lys Ala Leu
            100                 105                 110
Pro Ala Pro Ile Glu Lys Thr Ile Ser Lys Ala Lys Gly Gln Pro Arg
        115                 120                 125
Glu Pro Gln Val Tyr Thr Leu Pro Pro Ser Arg Glu Glu Met Thr Lys
    130                 135                 140
Asn Gln Val Lys Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Val Leu Asp Ser Asp Gly Ser Phe Phe Leu Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
    210                 215                 220
Leu Ser Leu Ser Pro Gly Lys
225                 230

<210> SEQ ID NO 44
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Pro Lys Ser Ser Asp Lys Thr His Thr Cys Pro Pro Cys Pro Ala
1               5                   10                  15
Pro Pro Val Ala Gly Pro Ser Val Phe Leu Phe Pro Pro Lys Pro Lys
            20                  25                  30
Asp Thr Leu Met Ile Ser Arg Thr Pro Glu Val Thr Cys Val Val Val
        35                  40                  45
Asp Val Lys His Glu Asp Pro Glu Val Lys Phe Asn Trp Tyr Val Asp
    50                  55                  60
Gly Val Glu Val His Asn Ala Lys Thr Lys Pro Arg Glu Glu Glu Tyr
65                  70                  75                  80
Asn Ser Thr Tyr Arg Val Val Ser Val Leu Thr Val Leu His Gln Asp
                85                  90                  95
Trp Leu Asn Gly Lys Glu Tyr Lys Cys Lys Val Ser Asn Lys Ala Leu
            100                 105                 110
Pro Ala Pro Ile Glu Lys Thr Ile Ser Lys Ala Lys Gly Gln Pro Arg
        115                 120                 125
Glu Pro Gln Val Tyr Thr Leu Pro Pro Ser Arg Glu Glu Met Thr Lys
    130                 135                 140
Asn Gln Val Ser Leu Thr Cys Glu Val Ser Gly Phe Tyr Pro Ser Asp
145                 150                 155                 160
Ile Ala Val Glu Trp Glu Ser Asp Gly Gln Pro Glu Asn Asn Tyr Lys
                165                 170                 175
Thr Thr Pro Pro Val Leu Asp Ser Asp Gly Ser Phe Phe Leu Tyr Ser
            180                 185                 190
```

```
Lys Leu Thr Val Asp Lys Ser Arg Trp Glu Gln Gly Asp Val Phe Ser
            195                 200                 205

Cys Ser Val Met His Glu Ala Leu His Asn His Tyr Thr Gln Lys Ser
        210                 215                 220

Leu Ser Leu Ser Pro Gly Lys
225                 230

<210> SEQ ID NO 45
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Lys Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 46
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Pro Lys Ser Ser Asp Lys Thr His Thr Cys Pro Pro Cys Pro Ala
1               5                   10                  15
```

```
Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Glu Met Thr Glu
        130                 135                 140

Asn Glu Val Ser Leu Thr Cys Leu Val Lys Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Glu Val Asp Lys Ser Arg Trp Gln Gln Gly Asp Val Phe Ser
            195                 200                 205

Cys Ser Val Met His Glu Ala Leu His Asn His Tyr Thr Gln Lys Ser
        210                 215                 220

Leu Ser Leu Ser Pro Gly Lys
225                 230

<210> SEQ ID NO 47
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Gln Leu Thr Lys
        130                 135                 140
```

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
            210                 215                 220

Leu Ser Leu Ser Pro Gly Lys
225                 230

<210> SEQ ID NO 48
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asn Val Phe Ser
                195                 200                 205

Cys Ser Val Met His Glu Ala Leu His Asn His Tyr Thr Gln Lys Ser
            210                 215                 220

Leu Ser Leu Ser Pro Gly Lys
225                 230

<210> SEQ ID NO 49
<211> LENGTH: 231
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 49

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Ala Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 50
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Glu Tyr
65                  70                  75                  80

Ala Ser Thr Tyr Arg Val Val Ser Val Leu Thr Val Leu His Gln Asp

```
                    85                  90                  95
Trp Leu Asn Gly Lys Glu Tyr Lys Cys Lys Val Ser Asn Lys Ala Leu
                100                 105                 110
Pro Ala Pro Ile Glu Lys Thr Ile Ser Lys Ala Lys Gly Gln Pro Arg
            115                 120                 125
Glu Pro Gln Val Tyr Thr Leu Pro Pro Ser Arg Glu Glu Met Thr Lys
        130                 135                 140
Asn Gln Val Ser Leu Thr Cys Asp Val Ser Gly Phe Tyr Pro Ser Asp
145                 150                 155                 160
Ile Ala Val Glu Trp Glu Ser Asp Gly Gln Pro Glu Asn Asn Tyr Lys
                165                 170                 175
Thr Thr Pro Pro Val Leu Asp Ser Asp Gly Ser Phe Phe Leu Tyr Ser
                180                 185                 190
Lys Leu Thr Val Asp Lys Ser Arg Trp Glu Gln Gly Asp Val Phe Ser
            195                 200                 205
Cys Ser Val Met His Glu Ala Leu His Asn His Tyr Thr Gln Lys Ser
        210                 215                 220
Leu Ser Leu Ser Pro Gly Lys
225                 230

<210> SEQ ID NO 51
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Pro Lys Ser Ser Asp Lys Thr His Thr Cys Pro Pro Cys Pro Ala
1               5                   10                  15
Pro Pro Val Ala Gly Pro Ser Val Phe Leu Phe Pro Pro Lys Pro Lys
                20                  25                  30
Asp Thr Leu Met Ile Ser Arg Thr Pro Glu Val Thr Cys Val Val Val
            35                  40                  45
Asp Val Lys His Glu Asp Pro Glu Val Lys Phe Asn Trp Tyr Val Asp
        50                  55                  60
Gly Val Glu Val His Asn Ala Lys Thr Lys Pro Arg Glu Glu Gln Tyr
65                  70                  75                  80
Ser Ser Thr Tyr Arg Val Val Ser Val Leu Thr Val Leu His Gln Asp
                85                  90                  95
Trp Leu Asn Gly Lys Glu Tyr Lys Cys Lys Val Ser Asn Lys Ala Leu
                100                 105                 110
Pro Ala Pro Ile Glu Lys Thr Ile Ser Lys Ala Lys Gly Gln Pro Arg
            115                 120                 125
Glu Pro Gln Val Tyr Thr Leu Pro Pro Ser Arg Glu Gln Met Thr Lys
        130                 135                 140
Asn Gln Val Lys Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Val Leu Asp Ser Asp Gly Ser Phe Phe Leu Tyr Ser
                180                 185                 190
Lys Leu Thr Val Asp Lys Ser Arg Trp Gln Gln Gly Asn Val Phe Ser
            195                 200                 205
```

```
Cys Ser Val Met His Glu Ala Leu His Asn His Tyr Thr Gln Lys Ser
    210                 215                 220

Leu Ser Leu Ser Pro Gly Lys
225             230

<210> SEQ ID NO 52
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Glu Tyr
65                  70                  75                  80

Ser Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225             230

<210> SEQ ID NO 53
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30
```

Leu Met Ile Ser Arg Thr Pro Glu Val Thr Cys Val Val Asp Val
            35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Gln Met Thr Lys Asn Gln
130                 135                 140

Val Lys Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Lys
225

<210> SEQ ID NO 54
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Ser Lys Tyr Gly Pro Pro Cys Pro Pro Cys Pro Ala Pro Glu Phe
1                5                  10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Asp Val Ser Gly Phe Tyr Pro Ser Asp Ile Ala
145                 150                 155                 160

```
Val Glu Trp Glu Ser Asp Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Glu Glu Gly Asp Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 55
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Gln Met Thr Lys Asn Gln Val
    130                 135                 140

Lys Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
            165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 56
<211> LENGTH: 228
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 56

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Asp Val Ser Gly Phe Tyr Pro Ser Asp Ile Ala Val
145                 150                 155                 160

Glu Trp Glu Ser Asp Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Glu Gln Gly Asp Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 57
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Lys
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
```

```
                      100                 105                 110
Ile Glu Lys Thr Ile Ser Lys Thr Lys Gly Gln Pro Arg Glu Pro Gln
            115                 120                 125

Val Tyr Thr Leu Pro Pro Ser Arg Glu Gln Met Thr Lys Asn Gln Val
        130                 135                 140

Lys Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
        210                 215                 220

Ser Pro Gly Lys
225

<210> SEQ ID NO 58
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Lys
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Asp Val Ser Gly Phe Tyr Pro Ser Asp Ile Ala Val
145                 150                 155                 160

Glu Trp Glu Ser Asp Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asp Val Phe Ser Cys Ser Val
            195                 200                 205

Met His Glu Ala Leu His Asn His Tyr Thr Gln Lys Ser Leu Ser Leu
        210                 215                 220
```

Ser Pro Gly Lys
225

<210> SEQ ID NO 59
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Leu His Glu Ala Leu His Ser His Tyr Thr Gln Lys Ser
    210                 215                 220

Leu Ser Leu Ser Pro Gly Lys
225                 230

<210> SEQ ID NO 60
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

```
Asp Val Lys His Glu Asp Pro Glu Val Lys Phe Asn Trp Tyr Val Asp
         50                  55                  60

Gly Val Glu Val His Asn Ala Lys Thr Lys Pro Arg Glu Glu Glu Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
        195                 200                 205

Cys Ser Val Leu His Glu Ala Leu His Ser His Tyr Thr Gln Lys Ser
210                 215                 220

Leu Ser Leu Ser Pro Gly Lys
225                 230

<210> SEQ ID NO 61
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Pro Lys Ser Ser Asp Lys Thr His Thr Cys Pro Pro Cys Pro Ala
 1               5                  10                  15

Pro Pro Val Ala Gly Pro Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175
```

```
Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 62
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 63
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63
```

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 64
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Arg Lys Ser Ser Asp Lys Thr His Thr Cys Pro Arg Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Lys Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg

```
            115                 120                 125
Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 65
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Glu Pro Lys Ser Ser Asp Lys Thr His
        115                 120                 125

Thr Cys Pro Pro Cys Pro Ala Pro Val Ala Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240
```

```
Lys Ala Lys Gly Gln Pro Arg Glu Pro Gln Val Tyr Thr Leu Pro Pro
                    245                 250                 255

Ser Arg Glu Glu Met Thr Lys Asn Gln Val Ser Leu Thr Cys Asp Val
                260                 265                 270

Ser Gly Phe Tyr Pro Ser Asp Ile Ala Val Glu Trp Glu Ser Asp Gly
            275                 280                 285

Gln Pro Glu Asn Asn Tyr Lys Thr Thr Pro Val Leu Asp Ser Asp
        290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
                325                 330                 335

Asn His Tyr Thr Gln Lys Ser Leu Ser Leu Ser Pro Gly Lys
                340                 345                 350

<210> SEQ ID NO 66
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Pro Pro Val Leu Asp Ser Asp Gly
                245                 250                 255
```

Ser Phe Phe Leu Tyr Ser Lys Leu Thr Val Asp Lys Ser Arg Trp Gln
                260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
        290                 295                 300

<210> SEQ ID NO 67
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Glu Pro Lys Ser Ser Asp Lys Thr His Thr Cys Pro Pro Cys
        115                 120                 125

Pro Ala Pro Pro Val Ala Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Lys His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Glu Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Asp Val Ser Gly Phe Tyr Pro
            260                 265                 270

Ser Asp Ile Ala Val Glu Trp Glu Ser Asp Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Glu Gln Gly Asp Val 305                 310                 315                 320

Phe Ser Cys Ser Val Met His Glu Ala Leu His Asn His Tyr Thr Gln
              325                 330                 335

Lys Ser Leu Ser Leu Ser Pro Gly Lys
              340                 345

<210> SEQ ID NO 68
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Gln
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Gln Met Thr
        195                 200                 205

Lys Asn Gln Val Lys Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Met His Glu Ala Leu His Asn His Tyr Thr Gln Lys
        275                 280                 285

Ser Leu Ser Leu Ser Pro Gly Lys
    290                 295

<210> SEQ ID NO 69
<211> LENGTH: 440

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
                35                  40                  45

Lys Ala Thr Asn Val Ala His Trp Thr Thr Pro Ser Leu Lys Cys Ile
50                  55                  60

Arg Gly Gly Gly Ser Gly Gly Gly Ser Gly Gly Gly Ser
65                  70                  75                  80

Gly Gly Gly Gly Ser Gly Gly Gly Ser Gly Gly Gly Ser Asn
                85                  90                  95

Trp Val Asn Val Ile Ser Asp Leu Lys Lys Ile Glu Asp Leu Ile Gln
                100                 105                 110

Ser Met His Ile Asp Ala Thr Leu Tyr Thr Glu Ser Asp Val His Pro
            115                 120                 125

Ser Cys Lys Val Thr Ala Met Lys Cys Phe Leu Leu Glu Leu Gln Val
            130                 135                 140

Ile Ser Leu Glu Ser Gly Asp Ala Ser Ile His Asp Thr Val Glu Asn
145                 150                 155                 160

Leu Ile Ile Leu Ala Asn Asn Ser Leu Ser Ser Asn Gly Asn Val Thr
                165                 170                 175

Glu Ser Gly Cys Lys Glu Cys Glu Glu Leu Glu Glu Lys Asn Ile Lys
            180                 185                 190

Glu Phe Leu Gln Ser Phe Val His Ile Val Gln Met Phe Ile Asn Thr
            195                 200                 205

Ser Glu Pro Lys Ser Ser Asp Lys Thr His Thr Cys Pro Pro Cys Pro
210                 215                 220

Ala Pro Pro Val Ala Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Lys His Glu Asp Pro Glu Val Lys Phe Asn Trp Tyr Val
            260                 265                 270

Asp Gly Val Glu Val His Asn Ala Lys Thr Lys Pro Arg Glu Glu Glu
            275                 280                 285

Tyr Asn Ser Thr Tyr Arg Val Val Ser Val Leu Thr Val Leu His Gln
            290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
                325                 330                 335

Arg Glu Pro Gln Val Tyr Thr Leu Pro Pro Ser Arg Glu Glu Met Thr
            340                 345                 350

Lys Asn Gln Val Ser Leu Thr Cys Asp Val Ser Gly Phe Tyr Pro Ser
            355                 360                 365

Asp Ile Ala Val Glu Trp Glu Ser Asp Gly Gln Pro Glu Asn Asn Tyr
            370                 375                 380
```

```
Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Glu Gln Gly Asp Val Phe
            405                 410                 415

Ser Cys Ser Val Met His Glu Ala Leu His Asn His Tyr Thr Gln Lys
        420                 425                 430

Ser Leu Ser Leu Ser Pro Gly Lys
    435                 440

<210> SEQ ID NO 70
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 71
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71
```

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 72
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Glu Met Thr Lys
    130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
    195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 73
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Gln
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Gln Met Thr
        195                 200                 205

Lys Asn Gln Val Lys Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Met His Glu Ala Leu His Asn His Tyr Thr Gln Lys
        275                 280                 285

Ser Leu Ser Leu Ser Pro Gly Lys
    290                 295

<210> SEQ ID NO 74
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 75
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

```
<210> SEQ ID NO 76
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 77
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77
```

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 78
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Glu
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Glu Met Thr
        195                 200                 205

Lys Asn Gln Val Ser Leu Thr Cys Asp Val Ser Gly Phe Tyr Pro Ser
    210                 215                 220

Asp Ile Ala Val Glu Trp Glu Ser Asp Gly Gln Pro Glu Asn Asn Tyr
225                 230                 235                 240
```

```
Lys Thr Thr Pro Pro Val Leu Asp Ser Asp Gly Ser Phe Phe Leu Tyr
            245                 250                 255

Ser Lys Leu Thr Val Asp Lys Ser Arg Trp Glu Gln Gly Asp Val Phe
            260                 265                 270

Ser Cys Ser Val Met His Glu Ala Leu His Asn His Tyr Thr Gln Lys
        275                 280                 285

Ser Leu Ser Leu Ser Pro Gly Lys
    290                 295

<210> SEQ ID NO 79
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 80
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80
```

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Gln
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Glu Met Thr
        195                 200                 205

Lys Asn Gln Val Ser Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Met His Glu Ala Leu His Asn His Tyr Thr Gln Lys
        275                 280                 285

Ser Leu Ser Leu Ser Pro Gly Lys
    290                 295

<210> SEQ ID NO 81
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
```

```
              50                  55                  60
Asn Leu Ile Ile Leu Ala Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser
```

<210> SEQ ID NO 82
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Ile Thr Cys Pro Pro Met Ser Val Glu His Ala Asp Ile Trp Val
  1               5                  10                  15

Lys Ser Tyr Ser Leu Tyr Ser Arg Glu Arg Tyr Ile Cys Asn Ser Gly
                 20                  25                  30

Phe Lys Arg Lys Ala Gly Thr Ser Ser Leu Thr Glu Cys Val Leu Asn
             35                  40                  45

Lys Ala Thr Asn Val Ala His Trp Thr Thr Pro Ser Leu Lys Cys Ile
 50                  55                  60

Arg Gly Gly Gly Ser Asn Trp Val Asn Val Ile Ser Asp Leu Lys
 65                  70                  75                  80

Lys Ile Glu Asp Leu Ile Gln Ser Met His Ile Asp Ala Thr Leu Tyr
                 85                  90                  95

Thr Glu Ser Asp Val His Pro Ser Cys Lys Val Thr Ala Met Lys Cys
            100                 105                 110

Phe Leu Leu Glu Leu Gln Val Ile Ser Leu Glu Ser Gly Asp Ala Ser
            115                 120                 125

Ile His Asp Thr Val Glu Asn Leu Ile Ile Leu Ala Asn Asn Ser Leu
130                 135                 140

Ser Ser Asn Gly Asn Val Thr Glu Ser Gly Cys Lys Glu Cys Glu Glu
145                 150                 155                 160

Leu Glu Glu Lys Asn Ile Lys Glu Phe Leu Gln Ser Phe Val His Ile
                165                 170                 175

Val Gln Met Phe Ile Asn Thr Ser Glu Pro Lys Ser Ser Asp Lys Thr
            180                 185                 190

His Thr Cys Pro Pro Cys Pro Ala Pro Pro Val Ala Gly Pro Ser Val
            195                 200                 205

Phe Leu Phe Pro Pro Lys Pro Lys Asp Thr Leu Met Ile Ser Arg Thr
210                 215                 220

Pro Glu Val Thr Cys Val Val Val Asp Val Lys His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
            275                 280                 285

Cys Lys Val Ser Asn Lys Ala Leu Pro Ala Pro Ile Glu Lys Thr Ile
```

```
                290                 295                 300
Ser Lys Ala Lys Gly Gln Pro Arg Glu Pro Gln Val Tyr Thr Leu Pro
305                 310                 315                 320

Pro Ser Arg Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
                340                 345                 350

Gly Gln Pro Glu Asn Asn Tyr Lys Thr Thr Pro Pro Val Leu Asp Ser
                355                 360                 365

Asp Gly Ser Phe Phe Leu Tyr Ser Lys Leu Thr Val Asp Lys Ser Arg
                370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                405                 410                 415

<210> SEQ ID NO 83
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ser Arg Thr Pro Glu Val Thr Cys Val Val Val
                35                  40                  45

Asp Val Lys His Glu Asp Pro Glu Val Lys Phe Asn Trp Tyr Val Asp
            50                  55                  60

Gly Val Glu Val His Asn Ala Lys Thr Lys Pro Arg Glu Glu Glu Tyr
65              70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
                115                 120                 125

Glu Pro Gln Val Tyr Thr Leu Pro Pro Ser Arg Glu Glu Met Thr Lys
                130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asp Val Phe Ser
                195                 200                 205

Cys Ser Val Met His Glu Ala Leu His Asn His Tyr Thr Gln Lys Ser
                210                 215                 220

Leu Ser Leu Ser Pro Gly Lys Gly Gly Gly Ser Gly Gly Gly Gly
225                 230                 235                 240
```

```
Ser Ile Thr Cys Pro Pro Met Ser Val Glu His Ala Asp Ile Trp
            245                 250                 255

Val Lys Ser Tyr Ser Leu Tyr Ser Arg Glu Arg Tyr Ile Cys Asn Ser
        260                 265                 270

Gly Phe Lys Arg Lys Ala Gly Thr Ser Ser Leu Thr Glu Cys Val Leu
            275                 280                 285

Asn Lys Ala Thr Asn Val Ala His Trp Thr Thr Pro Ser Leu Lys Cys
        290                 295                 300

Ile Arg
305

<210> SEQ ID NO 84
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Arg Lys Ser Ser Asp Lys Thr His Thr Cys Pro Arg Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Lys Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 85
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 85

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 86
<211> LENGTH: 425
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
        195                 200                 205

Cys Ser Val Met His Glu Ala Leu His Asn His Tyr Thr Gln Lys Ser
210                 215                 220

```
Leu Ser Leu Ser Pro Gly Lys Gly Gly Gly Ser Gly Gly Gly Gly
225                 230                 235                 240

Ser Ile Thr Cys Pro Pro Met Ser Val Glu His Ala Asp Ile Trp
            245                 250                 255

Val Lys Ser Tyr Ser Leu Tyr Ser Arg Glu Arg Tyr Ile Cys Asn Ser
            260                 265                 270

Gly Phe Lys Arg Lys Ala Gly Thr Ser Ser Leu Thr Glu Cys Val Leu
            275                 280                 285

Asn Lys Ala Thr Asn Val Ala His Trp Thr Thr Pro Ser Leu Lys Cys
            290                 295                 300

Ile Arg Gly Gly Gly Ser Asn Trp Val Asn Val Ile Ser Asp Leu
305                 310                 315                 320

Lys Lys Ile Glu Asp Leu Ile Gln Ser Met His Ile Asp Ala Thr Leu
            325                 330                 335

Tyr Thr Glu Ser Asp Val His Pro Ser Cys Lys Val Thr Ala Met Lys
            340                 345                 350

Cys Phe Leu Leu Glu Leu Gln Val Ile Ser Leu Glu Ser Gly Asp Ala
            355                 360                 365

Ser Ile His Asp Thr Val Glu Asn Leu Ile Ile Leu Ala Asn Asn Ser
370                 375                 380

Leu Ser Ser Asn Gly Asn Val Thr Glu Ser Gly Cys Lys Glu Cys Glu
385                 390                 395                 400

Glu Leu Glu Glu Lys Asn Ile Lys Glu Phe Leu Gln Ser Phe Val His
            405                 410                 415

Ile Val Gln Met Phe Ile Asn Thr Ser
            420                 425

<210> SEQ ID NO 87
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Arg Lys Ser Ser Asp Lys Thr His Thr Cys Pro Arg Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Lys Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160
```

```
Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 88
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp
65

<210> SEQ ID NO 89
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro
65

<210> SEQ ID NO 90
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90
```

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Asp Pro Ala
65

<210> SEQ ID NO 91
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Cys Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 92
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Cys Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
```

<210> SEQ ID NO 93
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Cys Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 94
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 95
<211> LENGTH: 114
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 95

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Cys
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 96
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Cys Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 97
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Ser Phe Leu Leu Glu Leu Gln
```

```
                35                  40                  45
Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 98
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Cys Glu Leu Gln
                 35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 99
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
                 20                  25                  30

Phe Lys Arg Lys Ala Gly Thr Ser Ser Leu Thr Glu Cys Val Leu Asn
                 35                  40                  45

Lys Ala Thr Asn Val Ala His Trp Thr Thr Pro Ser Leu Lys Cys Ile
 50                  55                  60

Arg Asp Cys
 65

<210> SEQ ID NO 100
<211> LENGTH: 68
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Cys
65

<210> SEQ ID NO 101
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Cys Ala
65

<210> SEQ ID NO 102
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Cys Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 103
<211> LENGTH: 65
<212> TYPE: PRT

<213> ORGANISM: Artificial Sequence
<220> FEATURE:
<223> OTHER INFORMATION: Description of Artificial Sequence: Synthetic
     polypeptide

<400> SEQUENCE: 103

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Cys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 104
<211> LENGTH: 65
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 104

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Cys Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 105
<211> LENGTH: 65
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 105

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Cys Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 106
<211> LENGTH: 65
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 106

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Cys Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg
65

<210> SEQ ID NO 107
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 108
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg
```

<210> SEQ ID NO 109
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 110
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Cys
65

<210> SEQ ID NO 111
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

```
Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 112
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ile Thr Cys Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
             20                  25                  30

Phe Lys Arg Lys Ala Gly Thr Ser Ser Leu Thr Glu Cys Val Leu Asn
         35                  40                  45

Lys Ala Thr Asn Val Ala His Trp Thr Thr Pro Ser Leu Lys Cys Ile
     50                  55                  60

Arg Asp Pro Cys
 65

<210> SEQ ID NO 113
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
             20                  25                  30

Pro Ser Cys Lys Val Thr Ala Met Lys Cys Phe Leu Leu Glu Leu Gln
         35                  40                  45

Val Ile Ser Leu Glu Ser Gly Asp Ala Ser Ile His Asp Thr Val Glu
     50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 114
```

```
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Cys Ala
65

<210> SEQ ID NO 115
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Cys Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 116
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Cys Ser Leu Thr Glu Cys Val Leu Asn
        35                  40                  45

Lys Ala Thr Asn Val Ala His Trp Thr Thr Pro Ser Leu Lys Cys Ile
```

Arg
65

<210> SEQ ID NO 117
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Cys Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 118
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Cys Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 119
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Ile Thr Cys Pro Pro Pro Met Ser Val Glu His Ala Asp Ile Trp Val
1               5                   10                  15

```
Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
         35                  40                  45

Lys Ala Thr Asn Val Ala His Trp Thr Thr Pro Ser Leu Lys Cys Ile
 50                  55                  60

Arg Gly Gly Gly Gly Ser Gly Gly Gly Ser Gly Gly Gly Gly Gly Ser
 65                  70                  75                  80

Gly Gly Gly Gly Ser Gly Gly Gly Ser Gly Gly Gly Gly Gly Ser Asn
                 85                  90                  95

Trp Val Asn Val Ile Ser Asp Leu Lys Lys Ile Glu Asp Leu Ile Gln
                100                 105                 110

Ser Met His Ile Asp Ala Thr Leu Tyr Thr Glu Ser Asp Val His Pro
             115                 120                 125

Ser Cys Lys Val Thr Ala Met Lys Cys Phe Leu Leu Glu Leu Gln Val
 130                 135                 140

Ile Ser Leu Glu Ser Gly Asp Ala Ser Ile His Asp Thr Val Glu Asn
145                 150                 155                 160

Leu Ile Ile Leu Ala Asn Asn Ser Leu Ser Ser Asn Gly Asn Val Thr
                 165                 170                 175

Glu Ser Gly Cys Lys Glu Cys Glu Glu Leu Glu Glu Lys Asn Ile Lys
             180                 185                 190

Glu Phe Leu Gln Ser Phe Val His Ile Val Gln Met Phe Ile Asn Thr
         195                 200                 205

Ser

<210> SEQ ID NO 120
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
             35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Cys Glu Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser Gly Gly Gly Gly Ser Glu Pro Lys Ser Ser Asp Lys Thr His
             115                 120                 125

Thr Cys Pro Pro Cys Pro Ala Pro Pro Val Ala Gly Pro Ser Val Phe
 130                 135                 140

Leu Phe Pro Pro Lys Pro Lys Asp Thr Leu Met Ile Ser Arg Thr Pro
145                 150                 155                 160
```

```
Glu Val Thr Cys Val Val Asp Val Lys His Glu Asp Pro Glu Val
            165                 170                 175

Lys Phe Asn Trp Tyr Val Asp Gly Val Glu Val His Asn Ala Lys Thr
        180                 185                 190

Lys Pro Arg Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
        210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
        290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 121
<211> LENGTH: 303
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Cys Gly Gly Gly Ser Glu Pro Lys Ser Ser Asp Lys Thr
65                  70                  75                  80

His Thr Cys Pro Pro Cys Pro Ala Pro Pro Val Ala Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Asp Val Lys His Glu Asp Pro Glu
        115                 120                 125

Val Lys Phe Asn Trp Tyr Val Asp Gly Val Glu Val His Asn Ala Lys
        130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175
```

```
Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Arg Glu Gln Met Thr Lys Asn Gln Val Lys Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
    290                 295                 300

<210> SEQ ID NO 122
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Glu Pro Lys Ser Ser Asp Lys Thr His
            115                 120                 125

Thr Cys Pro Pro Cys Pro Ala Pro Val Ala Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Asp Val Lys His Glu Asp Pro Glu Val
            165                 170                 175

Lys Phe Asn Trp Tyr Val Asp Gly Val Glu Val His Asn Ala Lys Thr
        180                 185                 190

Lys Pro Arg Glu Glu Tyr Asn Ser Thr Tyr Arg Val Val Ser Val
    195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
```

```
            225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
                260                 265                 270

Ser Gly Phe Tyr Pro Ser Asp Ile Ala Val Glu Trp Glu Ser Asp Gly
                275                 280                 285

Gln Pro Glu Asn Asn Tyr Lys Thr Thr Pro Pro Val Leu Asp Ser Asp
        290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
                325                 330                 335

Asn His Tyr Thr Gln Lys Ser Leu Ser Leu Ser Pro Gly Lys
                340                 345                 350

<210> SEQ ID NO 123
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Pro Cys Gly Gly Gly Ser Glu Pro Lys Ser Ser Asp Lys
65                  70                  75                  80

Thr His Thr Cys Pro Pro Cys Pro Ala Pro Val Ala Gly Pro Ser
                85                  90                  95

Val Phe Leu Phe Pro Pro Lys Pro Lys Asp Thr Leu Met Ile Ser Arg
                100                 105                 110

Thr Pro Glu Val Thr Cys Val Val Val Asp Val Lys His Glu Asp Pro
            115                 120                 125

Glu Val Lys Phe Asn Trp Tyr Val Asp Gly Val Glu Val His Asn Ala
        130                 135                 140

Lys Thr Lys Pro Arg Glu Glu Gln Tyr Asn Ser Thr Tyr Arg Val Val
145                 150                 155                 160

Ser Val Leu Thr Val Leu His Gln Asp Trp Leu Asn Gly Lys Glu Tyr
                165                 170                 175

Lys Cys Lys Val Ser Asn Lys Ala Leu Pro Ala Pro Ile Glu Lys Thr
            180                 185                 190

Ile Ser Lys Ala Lys Gly Gln Pro Arg Glu Pro Gln Val Tyr Thr Leu
        195                 200                 205

Pro Pro Ser Arg Glu Gln Met Thr Lys Asn Gln Val Lys Leu Thr Cys
    210                 215                 220

Leu Val Lys Gly Phe Tyr Pro Ser Asp Ile Ala Val Glu Trp Glu Ser
225                 230                 235                 240
```

Asn Gly Gln Pro Glu Asn Asn Tyr Lys Thr Thr Pro Val Leu Asp
            245                 250                 255

Ser Asp Gly Ser Phe Phe Leu Tyr Ser Lys Leu Thr Val Asp Lys Ser
        260                 265                 270

Arg Trp Gln Gln Gly Asn Val Phe Ser Cys Ser Val Met His Glu Ala
        275                 280                 285

Leu His Asn His Tyr Thr Gln Lys Ser Leu Ser Leu Ser Pro Gly Lys
        290                 295                 300

<210> SEQ ID NO 124
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Cys Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Val Leu Asp Ser Asp
        290                 295                 300

```
Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
            325                 330                 335

Asn His Tyr Thr Gln Lys Ser Leu Ser Leu Ser Pro Gly Lys
            340                 345                 350

<210> SEQ ID NO 125
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
50                  55                  60

Arg Asp Cys Ala Gly Gly Gly Ser Glu Pro Lys Ser Ser Asp Lys
65                  70                  75                  80

Thr His Thr Cys Pro Pro Cys Pro Ala Pro Pro Val Ala Gly Pro Ser
                85                  90                  95

Val Phe Leu Phe Pro Pro Lys Pro Lys Asp Thr Leu Met Ile Ser Arg
                100                 105                 110

Thr Pro Glu Val Thr Cys Val Val Asp Val Lys His Glu Asp Pro
            115                 120                 125

Glu Val Lys Phe Asn Trp Tyr Val Asp Gly Val Glu Val His Asn Ala
            130                 135                 140

Lys Thr Lys Pro Arg Glu Glu Gln Tyr Asn Ser Thr Tyr Arg Val Val
145                 150                 155                 160

Ser Val Leu Thr Val Leu His Gln Asp Trp Leu Asn Gly Lys Glu Tyr
                165                 170                 175

Lys Cys Lys Val Ser Asn Lys Ala Leu Pro Ala Pro Ile Glu Lys Thr
            180                 185                 190

Ile Ser Lys Ala Lys Gly Gln Pro Arg Glu Pro Gln Val Tyr Thr Leu
            195                 200                 205

Pro Pro Ser Arg Glu Gln Met Thr Lys Asn Gln Val Lys Leu Thr Cys
210                 215                 220

Leu Val Lys Gly Phe Tyr Pro Ser Asp Ile Ala Val Glu Trp Glu Ser
225                 230                 235                 240

Asn Gly Gln Pro Glu Asn Asn Tyr Lys Thr Thr Pro Pro Val Leu Asp
                245                 250                 255

Ser Asp Gly Ser Phe Phe Leu Tyr Ser Lys Leu Thr Val Asp Lys Ser
            260                 265                 270

Arg Trp Gln Gln Gly Asn Val Phe Ser Cys Ser Val Met His Glu Ala
            275                 280                 285

Leu His Asn His Tyr Thr Gln Lys Ser Leu Ser Leu Ser Pro Gly Lys
290                 295                 300
```

```
<210> SEQ ID NO 126
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Cys Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 127
<211> LENGTH: 301
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Cys Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Gly Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
                85                  90                  95

Phe Pro Pro Lys Pro Lys Asp Thr Leu Met Ile Ser Arg Thr Pro Glu
                100                 105                 110

Val Thr Cys Val Val Val Asp Val Lys His Glu Asp Pro Glu Val Lys
            115                 120                 125

Phe Asn Trp Tyr Val Asp Gly Val Glu Val His Asn Ala Lys Thr Lys
        130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 128
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Asn Trp Val Asn Val Ile Ser Asp Leu Lys Lys Ile Glu Asp Leu Ile
1               5                   10                  15

-continued

```
Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Cys Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 129
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Pro Lys Ser Ser Asp Lys Thr His Thr Cys Pro Pro Cys Pro Ala
 1               5                  10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
 50                  55                  60

Gly Val Glu Val His Asn Ala Lys Thr Lys Pro Arg Glu Glu Glu Tyr
 65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Glu Met Thr Lys
130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asp Val Phe Ser
            195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 130
<211> LENGTH: 304
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
                35                  40                  45

Lys Ala Thr Asn Val Ala His Trp Thr Thr Pro Ser Leu Lys Cys Ile
    50                  55                  60

Arg Asp Pro Cys Gly Gly Gly Ser Glu Pro Lys Ser Ser Asp Lys
65                  70                  75                  80

Thr His Thr Cys Pro Pro Cys Pro Ala Pro Val Ala Gly Pro Ser
                85                  90                  95

Val Phe Leu Phe Pro Pro Lys Pro Lys Asp Thr Leu Met Ile Ser Arg
                100                 105                 110

Thr Pro Glu Val Thr Cys Val Val Val Asp Val Lys His Glu Asp Pro
            115                 120                 125

Glu Val Lys Phe Asn Trp Tyr Val Asp Gly Val Glu Val His Asn Ala
130                 135                 140

Lys Thr Lys Pro Arg Glu Glu Gln Tyr Asn Ser Thr Tyr Arg Val Val
145                 150                 155                 160

Ser Val Leu Thr Val Leu His Gln Asp Trp Leu Asn Gly Lys Glu Tyr
                165                 170                 175

Lys Cys Lys Val Ser Asn Lys Ala Leu Pro Ala Pro Ile Glu Lys Thr
            180                 185                 190

Ile Ser Lys Ala Lys Gly Gln Pro Arg Glu Pro Gln Val Tyr Thr Leu
        195                 200                 205

Pro Pro Ser Arg Glu Gln Met Thr Lys Asn Gln Val Lys Leu Thr Cys
210                 215                 220

Leu Val Lys Gly Phe Tyr Pro Ser Asp Ile Ala Val Glu Trp Glu Ser
225                 230                 235                 240

Asn Gly Gln Pro Glu Asn Asn Tyr Lys Thr Thr Pro Pro Val Leu Asp
                245                 250                 255

Ser Asp Gly Ser Phe Phe Leu Tyr Ser Lys Leu Thr Val Asp Lys Ser
            260                 265                 270

Arg Trp Gln Gln Gly Asn Val Phe Ser Cys Ser Val Met His Glu Ala
        275                 280                 285

Leu His Asn His Tyr Thr Gln Lys Ser Leu Ser Leu Ser Pro Gly Lys
    290                 295                 300

<210> SEQ ID NO 131
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Asn Trp Val Asn Val Ile Ser Asp Leu Lys Lys Ile Glu Asp Leu Ile
1               5                   10                  15

```
Gln Ser Met His Ile Asp Ala Thr Leu Tyr Thr Glu Ser Asp Val His
         20                  25                  30

Pro Ser Cys Lys Val Thr Ala Met Lys Cys Phe Leu Leu Glu Leu Gln
         35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Cys Cys Glu Glu Leu Glu Glu Lys Asn Ile
                 85                  90                  95

Lys Glu Phe Leu Gln Ser Phe Val His Ile Val Gln Met Phe Ile Asn
             100                 105                 110

Thr Ser
```

```
<210> SEQ ID NO 132
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
             20                  25                  30

Asp Thr Leu Met Ile Ser Arg Thr Pro Glu Val Thr Cys Val Val Val
         35                  40                  45

Asp Val Lys His Glu Asp Pro Glu Val Lys Phe Asn Trp Tyr Val Asp
 50                  55                  60

Gly Val Glu Val His Asn Ala Lys Thr Lys Pro Arg Glu Glu Glu Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
             100                 105                 110

Pro Ala Pro Ile Glu Lys Thr Ile Ser Lys Ala Lys Gly Gln Pro Arg
         115                 120                 125

Glu Pro Gln Val Tyr Thr Leu Pro Pro Ser Arg Glu Glu Met Thr Lys
130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asp Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230
```

```
<210> SEQ ID NO 133
<211> LENGTH: 304
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Cys Ala Gly Gly Gly Ser Glu Pro Lys Ser Ser Asp Lys
65                  70                  75                  80

Thr His Thr Cys Pro Pro Cys Pro Ala Pro Pro Val Ala Gly Pro Ser
                85                  90                  95

Val Phe Leu Phe Pro Pro Lys Pro Lys Asp Thr Leu Met Ile Ser Arg
            100                 105                 110

Thr Pro Glu Val Thr Cys Val Val Val Asp Val Lys His Glu Asp Pro
        115                 120                 125

Glu Val Lys Phe Asn Trp Tyr Val Asp Gly Val Glu Val His Asn Ala
    130                 135                 140

Lys Thr Lys Pro Arg Glu Glu Gln Tyr Asn Ser Thr Tyr Arg Val Val
145                 150                 155                 160

Ser Val Leu Thr Val Leu His Gln Asp Trp Leu Asn Gly Lys Glu Tyr
                165                 170                 175

Lys Cys Lys Val Ser Asn Lys Ala Leu Pro Ala Pro Ile Glu Lys Thr
            180                 185                 190

Ile Ser Lys Ala Lys Gly Gln Pro Arg Glu Pro Gln Val Tyr Thr Leu
        195                 200                 205

Pro Pro Ser Arg Glu Gln Met Thr Lys Asn Gln Val Lys Leu Thr Cys
    210                 215                 220

Leu Val Lys Gly Phe Tyr Pro Ser Asp Ile Ala Val Glu Trp Glu Ser
225                 230                 235                 240

Asn Gly Gln Pro Glu Asn Asn Tyr Lys Thr Thr Pro Pro Val Leu Asp
                245                 250                 255

Ser Asp Gly Ser Phe Phe Leu Tyr Ser Lys Leu Thr Val Asp Lys Ser
            260                 265                 270

Arg Trp Gln Gln Gly Asn Val Phe Ser Cys Ser Val Met His Glu Ala
        275                 280                 285

Leu His Asn His Tyr Thr Gln Lys Ser Leu Ser Leu Ser Pro Gly Lys
    290                 295                 300

<210> SEQ ID NO 134
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Asn Trp Val Asn Val Ile Ser Asp Leu Lys Lys Ile Glu Asp Leu Ile
1               5                   10                  15

```
Gln Ser Met His Ile Asp Ala Thr Leu Tyr Thr Glu Ser Asp Val His
             20                  25                  30

Pro Ser Cys Lys Val Thr Ala Met Lys Cys Phe Leu Leu Glu Leu Gln
         35                  40                  45

Val Ile Ser Cys Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
             85                  90                  95

Lys Glu Phe Leu Gln Ser Phe Val His Ile Val Gln Met Phe Ile Asn
        100                 105                 110

Thr Ser

<210> SEQ ID NO 135
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
             20                  25                  30

Asp Thr Leu Met Ile Ser Arg Thr Pro Glu Val Thr Cys Val Val Val
         35                  40                  45

Asp Val Lys His Glu Asp Pro Glu Val Lys Phe Asn Trp Tyr Val Asp
 50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
             85                  90                  95

Trp Leu Asn Gly Lys Glu Tyr Lys Cys Lys Val Ser Asn Lys Ala Leu
        100                 105                 110

Pro Ala Pro Ile Glu Lys Thr Ile Ser Lys Ala Lys Gly Gln Pro Arg
    115                 120                 125

Glu Pro Gln Val Tyr Thr Leu Pro Pro Ser Arg Glu Glu Met Thr Lys
130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asp Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 136
<211> LENGTH: 301
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Cys Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
            115                 120                 125

Phe Asn Trp Tyr Val Asp Gly Val Glu Val His Asn Ala Lys Thr Lys
        130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 137
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asn Trp Val Asn Val Ile Ser Asp Leu Lys Lys Ile Glu Asp Leu Ile
1               5                   10                  15

```
Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Cys Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 138
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Ile Thr Cys Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
 50                  55                  60

Arg Asp Cys Ala Glu Pro Lys Ser Ser Asp Lys Thr His Thr Cys Pro
 65                  70                  75                  80

Pro Cys Pro Ala Pro Pro Val Ala Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Lys His Glu Asp Pro Glu Val Lys Phe Asn
        115                 120                 125

Trp Tyr Val Asp Gly Val Glu Val His Asn Ala Lys Thr Lys Pro Arg
130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Gln Met Thr Lys Asn Gln Val Lys Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255
```

```
Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
            275                 280                 285

Thr Gln Lys Ser Leu Ser Leu Ser Pro Gly Lys
            290                 295

<210> SEQ ID NO 139
<211> LENGTH: 298
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Cys Glu Pro Lys Ser Ser Asp Lys Thr His Thr Cys Pro Pro
65                  70                  75                  80

Cys Pro Ala Pro Pro Val Ala Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Lys His Glu Asp Pro Glu Val Lys Phe Asn Trp
            115                 120                 125

Tyr Val Asp Gly Val Glu Val His Asn Ala Lys Thr Lys Pro Arg Glu
        130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
            165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
            195                 200                 205

Met Thr Lys Asn Gln Val Ser Leu Thr Cys Leu Val Lys Gly Phe Tyr
        210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
            245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
            275                 280                 285

Gln Lys Ser Leu Ser Leu Ser Pro Gly Lys
            290                 295

<210> SEQ ID NO 140
```

```
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Cys Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 141
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Cys Ala Glu Pro Lys Ser Ser Asp Lys Thr His Thr Cys Pro
65                  70                  75                  80

Pro Cys Pro Ala Pro Pro Val Ala Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Lys His Glu Asp Pro Glu Val Lys Phe Asn
        115                 120                 125

Trp Tyr Val Asp Gly Val Glu Val His Asn Ala Lys Thr Lys Pro Arg
    130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190
```

```
Gly Gln Pro Arg Glu Pro Gln Val Tyr Thr Leu Pro Pro Ser Arg Glu
            195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Lys Leu Thr Val Asp Lys Ser Arg Trp Gln Gln Gly
                260                 265                 270

Asn Val Phe Ser Cys Ser Val Met His Glu Ala Leu His Asn His Tyr
                275                 280                 285

Thr Gln Lys Ser Leu Ser Leu Ser Pro Gly Lys
                290                 295

<210> SEQ ID NO 142
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 143
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Cys Ser Leu Thr Glu Cys Val Leu Asn
            35                  40                  45

Lys Ala Thr Asn Val Ala His Trp Thr Thr Pro Ser Leu Lys Cys Ile
    50                  55                  60

Arg Glu Pro Lys Ser Ser Asp Lys Thr His Thr Cys Pro Pro Cys Pro
```

```
            65                  70                  75                  80
Ala Pro Pro Val Ala Gly Pro Ser Val Phe Leu Phe Pro Pro Lys Pro
                    85                  90                  95

Lys Asp Thr Leu Met Ile Ser Arg Thr Pro Glu Val Thr Cys Val Val
                100                 105                 110

Val Asp Val Lys His Glu Asp Pro Glu Val Lys Phe Asn Trp Tyr Val
            115                 120                 125

Asp Gly Val Glu Val His Asn Ala Lys Thr Lys Pro Arg Glu Glu Gln
        130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
                180                 185                 190

Arg Glu Pro Gln Val Tyr Thr Leu Pro Pro Ser Arg Glu Glu Met Thr
            195                 200                 205

Lys Asn Gln Val Ser Leu Thr Cys Leu Val Lys Gly Phe Tyr Pro Ser
        210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
                260                 265                 270

Ser Cys Ser Val Met His Glu Ala Leu His Asn His Tyr Thr Gln Lys
            275                 280                 285

Ser Leu Ser Leu Ser Pro Gly Lys
        290                 295

<210> SEQ ID NO 144
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Cys Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser
```

<210> SEQ ID NO 145
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Gly Gly Gly Ser Gly Gly Gly Gly
225                 230                 235                 240

Ser Ile Thr Cys Pro Pro Pro Met Ser Val Glu His Ala Asp Ile Trp
                245                 250                 255

Val Lys Ser Tyr Ser Leu Tyr Ser Arg Glu Arg Tyr Ile Cys Asn Ser
            260                 265                 270

Gly Phe Lys Arg Lys Ala Gly Thr Ser Ser Leu Thr Glu Cys Val Leu
        275                 280                 285

Asn Lys Ala Thr Asn Val Ala His Trp Thr Thr Pro Ser Leu Lys Cys
    290                 295                 300

Ile Arg Asp Cys
305

<210> SEQ ID NO 146
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Arg Lys Ser Ser Asp Lys Thr His Thr Cys Pro Arg Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Lys Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 147
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Cys Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 148
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Cys Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 149
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

```
Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
            195                 200                 205

Cys Ser Val Met His Glu Ala Leu His Asn His Tyr Thr Gln Lys Ser
            210                 215                 220

Leu Ser Leu Ser Pro Gly Lys
225                 230

<210> SEQ ID NO 150
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 151
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110
```

Thr Ser

<210> SEQ ID NO 152
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asn Trp Val Asn Val Ile Ser Asn Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 153
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 154
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 154

Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
                20                  25                  30
Pro Ser Cys Lys Val Thr Ala Met Lys Cys Phe Leu Leu Glu Leu Gln
            35                  40                  45
Val Ile Ser Leu Glu Ser Gly Asp Ala Ser Ile His Asn Thr Val Glu
    50                  55                  60
Asn Leu Ile Ile Leu Ala Asn Asn Ser Leu Ser Ser Asn Gly Asn Val
65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
Thr Ser

<210> SEQ ID NO 155
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
                20                  25                  30
Pro Ser Cys Lys Val Thr Ala Met Lys Cys Phe Leu Leu Glu Leu Gln
            35                  40                  45
Val Ile Ser Leu Glu Ser Gly Asp Ala Ser Ile His Asp Thr Val Gln
    50                  55                  60
Asn Leu Ile Ile Leu Ala Asn Asn Ser Leu Ser Ser Asn Gly Asn Val
65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
Thr Ser

<210> SEQ ID NO 156
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
                20                  25                  30
Pro Ser Cys Lys Val Thr Ala Met Lys Cys Phe Leu Leu Glu Leu Gln
            35                  40                  45

```
Val Ile Ser Leu Glu Ser Gly Asp Ala Ser Ile His Asp Thr Val Glu
 50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 157
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Glu Met Phe Ile Asn
                100                 105                 110

Thr Ser

<210> SEQ ID NO 158
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Asp Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asn Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
                100                 105                 110
```

Thr Ser

<210> SEQ ID NO 159
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Gln
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 160
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asn Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 161
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Gln
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 162
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asn Trp Val Asn Val Ile Ser Asn Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 163
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Asn Trp Val Asn Val Ile Ser Asn Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Gln
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 164
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asn Thr Val Gln
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 165
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Gln
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Leu Glu Glu Lys Asn Ile
                85                  90                  95

Lys Glu Phe Leu Gln Ser Phe Val His Ile Val Glu Met Phe Ile Asn

-continued

```
                100                 105                 110
Thr Ser

<210> SEQ ID NO 166
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Trp Val Asp Val Ile Ser Asn Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 167
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Gln
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 168
<211> LENGTH: 114
<212> TYPE: PRT
<213> ORGANISM: Artificial Sequence
<220> FEATURE:
<223> OTHER INFORMATION: Description of Artificial Sequence: Synthetic
```

-continued

```
         polypeptide

<400> SEQUENCE: 168

Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Gln
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser

<210> SEQ ID NO 169
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Gln
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser

<210> SEQ ID NO 170
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
```

```
              35                  40                  45

Val Ile Ser Leu Glu Ser Gly Asp Ala Ser Ile His Asp Thr Val Glu
 50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser

<210> SEQ ID NO 171
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Asp Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
                 35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Glu Met Phe Ile Asn
                100                 105                 110

Thr Ser

<210> SEQ ID NO 172
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Asn Trp Val Asp Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
                 35                  40                  45

Val Ile Ser Leu Glu Ser Gly Asp Ala Ser Ile His Asp Thr Val Glu
 50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95
```

```
Lys Glu Phe Leu Gln Ser Phe Val His Ile Val Gln Met Phe Ile Asn
                100                 105                 110
Thr Ser

<210> SEQ ID NO 173
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
        50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110
Thr Ser

<210> SEQ ID NO 174
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110
Thr Ser

<210> SEQ ID NO 175
<211> LENGTH: 114
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 175

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser

<210> SEQ ID NO 176
<211> LENGTH: 114
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 176

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Gln
50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 177
<211> LENGTH: 114
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 177

Asp Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

```
Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
 50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 178
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asn Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Gln
 50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 179
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Asn Trp Val Asp Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asn Thr Val Glu
 50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                85                  90                  95
```

```
Lys Glu Phe Leu Gln Ser Phe Val His Ile Val Gln Met Phe Ile Asn
            100                 105                 110
Thr Ser

<210> SEQ ID NO 180
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Glu Pro Lys Ser Ser Asp Lys Thr His
            115                 120                 125

Thr Cys Pro Pro Cys Pro Ala Pro Pro Val Ala Gly Pro Ser Val Phe
        130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
                325                 330                 335
```

```
Asn His Tyr Thr Gln Lys Ser Leu Ser Leu Ser Pro Gly Lys
            340                 345                 350

<210> SEQ ID NO 181
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Ser Glu Pro Lys Ser Ser Asp Lys Thr His Thr
65                  70                  75                  80

Cys Pro Pro Cys Pro Ala Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 182
<211> LENGTH: 350
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 182

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 183
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 183

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Ser Glu Pro Lys Ser Ser Asp Lys Thr His Thr
65                  70                  75                  80

Cys Pro Pro Cys Pro Ala Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 184
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45
```

```
Val Ile Ser Leu Glu Ser Gly Asp Ala Ser Ile His Asp Thr Val Gln
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 185
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Ile Thr Cys Pro Pro Met Ser Val Glu His Ala Asp Ile Trp Val
  1               5                  10                  15

Lys Ser Tyr Ser Leu Tyr Ser Arg Glu Arg Tyr Ile Cys Asn Ser Gly
             20                  25                  30

Phe Lys Arg Lys Ala Gly Thr Ser Ser Leu Thr Glu Cys Val Leu Asn
         35                  40                  45

Lys Ala Thr Asn Val Ala His Trp Thr Thr Pro Ser Leu Lys Cys Ile
 50                  55                  60
```

```
Arg Gly Gly Gly Gly Ser Glu Pro Lys Ser Ser Asp Lys Thr His Thr
 65                  70                  75                  80

Cys Pro Pro Cys Pro Ala Pro Val Ala Gly Pro Ser Val Phe Leu
                 85                  90                  95

Phe Pro Pro Lys Pro Lys Asp Thr Leu Met Ile Ser Arg Thr Pro Glu
             100                 105                 110

Val Thr Cys Val Val Val Asp Val Lys His Glu Asp Pro Glu Val Lys
             115                 120                 125

Phe Asn Trp Tyr Val Asp Gly Val Glu Val His Asn Ala Lys Thr Lys
             130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                 165                 170                 175

Val Ser Asn Lys Ala Leu Pro Ala Pro Ile Glu Lys Thr Ile Ser Lys
             180                 185                 190

Ala Lys Gly Gln Pro Arg Glu Pro Gln Val Tyr Thr Leu Pro Pro Ser
             195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                 245                 250                 255

Ser Phe Phe Leu Tyr Ser Lys Leu Thr Val Asp Lys Ser Arg Trp Gln
                 260                 265                 270

Gln Gly Asn Val Phe Ser Cys Ser Val Met His Glu Ala Leu His Asn
             275                 280                 285

His Tyr Thr Gln Lys Ser Leu Ser Leu Ser Pro Gly Lys
        290                 295                 300

<210> SEQ ID NO 186
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                 20                  25                  30

Pro Ser Cys Lys Val Thr Ala Met Lys Cys Phe Leu Leu Glu Leu Gln
             35                  40                  45

Val Ile Ser Leu Glu Ser Gly Asp Ala Ser Ile His Asp Thr Val Glu
         50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
             100                 105                 110

Thr Ser Gly Gly Gly Gly Ser Glu Pro Lys Ser Ser Asp Lys Thr His
```

```
                115                 120                 125
Thr Cys Pro Pro Cys Pro Ala Pro Pro Val Ala Gly Pro Ser Val Phe
        130                 135                 140
Leu Phe Pro Pro Lys Pro Lys Asp Thr Leu Met Ile Ser Arg Thr Pro
145                 150                 155                 160
Glu Val Thr Cys Val Val Val Asp Val Lys His Glu Asp Pro Glu Val
                165                 170                 175
Lys Phe Asn Trp Tyr Val Asp Gly Val Glu Val His Asn Ala Lys Thr
            180                 185                 190
Lys Pro Arg Glu Glu Glu Tyr Asn Ser Thr Tyr Arg Val Val Ser Val
        195                 200                 205
Leu Thr Val Leu His Gln Asp Trp Leu Asn Gly Lys Glu Tyr Lys Cys
    210                 215                 220
Lys Val Ser Asn Lys Ala Leu Pro Ala Pro Ile Glu Lys Thr Ile Ser
225                 230                 235                 240
Lys Ala Lys Gly Gln Pro Arg Glu Pro Gln Val Tyr Thr Leu Pro Pro
                245                 250                 255
Ser Arg Glu Glu Met Thr Lys Asn Gln Val Ser Leu Thr Cys Asp Val
            260                 265                 270
Ser Gly Phe Tyr Pro Ser Asp Ile Ala Val Glu Trp Glu Ser Asp Gly
        275                 280                 285
Gln Pro Glu Asn Asn Tyr Lys Thr Thr Pro Pro Val Leu Asp Ser Asp
    290                 295                 300
Gly Ser Phe Phe Leu Tyr Ser Lys Leu Thr Val Asp Lys Ser Arg Trp
305                 310                 315                 320
Glu Gln Gly Asp Val Phe Ser Cys Ser Val Met His Glu Ala Leu His
                325                 330                 335
Asn His Tyr Thr Gln Lys Ser Leu Ser Leu Ser Pro Gly Lys
            340                 345                 350

<210> SEQ ID NO 187
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
                20                  25                  30
Phe Lys Arg Lys Ala Gly Thr Ser Ser Leu Thr Glu Cys Val Leu Asn
            35                  40                  45
Lys Ala Thr Asn Val Ala His Trp Thr Thr Pro Ser Leu Lys Cys Ile
        50                  55                  60
Arg Gly Gly Gly Gly Ser Glu Pro Lys Ser Ser Asp Lys Thr His Thr
65                  70                  75                  80
Cys Pro Pro Cys Pro Ala Pro Pro Val Ala Gly Pro Ser Val Phe Leu
                85                  90                  95
Phe Pro Pro Lys Pro Lys Asp Thr Leu Met Ile Ser Arg Thr Pro Glu
            100                 105                 110
Val Thr Cys Val Val Val Asp Val Lys His Glu Asp Pro Glu Val Lys
        115                 120                 125
```

```
Phe Asn Trp Tyr Val Asp Gly Val Glu Val His Asn Ala Lys Thr Lys
            130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
                195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
                275                 280                 285

His Tyr Thr Gln Lys Ser Leu Ser Leu Ser Pro Gly Lys
            290                 295                 300

<210> SEQ ID NO 188
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser Gly Gly Gly Ser Glu Pro Lys Ser Ser Asp Lys Thr His
            115                 120                 125

Thr Cys Pro Pro Cys Pro Ala Pro Pro Val Ala Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190
```

```
Lys Pro Arg Glu Glu Tyr Asn Ser Thr Tyr Arg Val Val Ser Val
            195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
            245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
            275                 280                 285

Gln Pro Glu Asn Asn Tyr Lys Thr Thr Pro Pro Val Leu Asp Ser Asp
290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
            325                 330                 335

Asn His Tyr Thr Gln Lys Ser Leu Ser Leu Ser Pro Gly Lys
            340                 345                 350

<210> SEQ ID NO 189
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Gly Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
            85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
            165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
```

```
                195                 200                 205
Arg Glu Gln Met Thr Lys Asn Gln Val Lys Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 190
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Gln
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255
```

```
Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 191
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Gly Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270
```

```
Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 192
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asn Thr Val Gln
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
```

325                 330                 335
Asn His Tyr Thr Gln Lys Ser Leu Ser Leu Ser Pro Gly Lys
            340                 345                 350

<210> SEQ ID NO 193
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
                35                  40                  45

Lys Ala Thr Asn Val Ala His Trp Thr Thr Pro Ser Leu Lys Cys Ile
            50                  55                  60

Arg Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
            115                 120                 125

Phe Asn Trp Tyr Val Asp Gly Val Glu Val His Asn Ala Lys Thr Lys
        130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 194
<211> LENGTH: 350
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 194

Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 195
<211> LENGTH: 301
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 195

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 196
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asp Leu Ile Ile Leu Ala Asn Asn Ser Leu Ser Asn Gly Asn Val
65                  70                  75                  80

Thr Glu Ser Gly Cys Lys Glu Cys Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser Gly Gly Gly Ser Glu Pro Lys Ser Ser Asp Lys Thr His
                115                 120                 125

Thr Cys Pro Pro Cys Pro Ala Pro Pro Val Ala Gly Pro Ser Val Phe
                130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
                180                 185                 190

Lys Pro Arg Glu Glu Gln Tyr Asn Ser Thr Tyr Arg Val Val Ser Val
                195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
                260                 265                 270

Ser Gly Phe Tyr Pro Ser Asp Ile Ala Val Glu Trp Glu Ser Asp Gly
                275                 280                 285

Gln Pro Glu Asn Asn Tyr Lys Thr Thr Pro Pro Val Leu Asp Ser Asp
                290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
                325                 330                 335

Asn His Tyr Thr Gln Lys Ser Leu Ser Leu Ser Pro Gly Lys
                340                 345                 350

<210> SEQ ID NO 197
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
                35                  40                  45

Lys Ala Thr Asn Val Ala His Trp Thr Thr Pro Ser Leu Lys Cys Ile

Arg Gly Gly Gly Ser Glu Pro Lys Ser Ser Asp Lys Thr His Thr
65                  70                  75                  80

Cys Pro Pro Cys Pro Ala Pro Val Ala Gly Pro Ser Val Phe Leu
                85                  90                  95

Phe Pro Pro Lys Pro Lys Asp Thr Leu Met Ile Ser Arg Thr Pro Glu
                100                 105                 110

Val Thr Cys Val Val Val Asp Val Lys His Glu Asp Pro Glu Val Lys
            115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
    195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
                260                 265                 270

Gln Gly Asn Val Phe Ser Cys Ser Val Met His Glu Ala Leu His Asn
            275                 280                 285

His Tyr Thr Gln Lys Ser Leu Ser Leu Ser Pro Gly Lys
    290                 295                 300

<210> SEQ ID NO 198
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
                100                 105                 110

```
Thr Ser Gly Gly Gly Ser Glu Pro Lys Ser Ser Asp Lys Thr His
            115                 120                 125

Thr Cys Pro Pro Cys Pro Ala Pro Pro Val Ala Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 199
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Ser Glu Pro Lys Ser Ser Asp Lys Thr His Thr
65                  70                  75                  80

Cys Pro Pro Cys Pro Ala Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125
```

```
Phe Asn Trp Tyr Val Asp Gly Val Glu Val His Asn Ala Lys Thr Lys
            130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 200
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Glu Pro Lys Ser Ser Asp Lys Thr His Thr Cys Pro Pro Cys
        115                 120                 125

Pro Ala Pro Pro Val Ala Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Lys His Glu Asp Pro Glu Val Lys Phe Asn Trp Tyr
                165                 170                 175

Val Asp Gly Val Glu Val His Asn Ala Lys Thr Lys Pro Arg Glu Glu
```

```
                180                 185                 190
Glu Tyr Asn Ser Thr Tyr Arg Val Val Ser Val Leu Thr Val Leu His
            195                 200                 205

Gln Asp Trp Leu Asn Gly Lys Glu Tyr Lys Cys Lys Val Ser Asn Lys
        210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
            245                 250                 255

Thr Lys Asn Gln Val Ser Leu Thr Cys Asp Val Ser Gly Phe Tyr Pro
        260                 265                 270

Ser Asp Ile Ala Val Glu Trp Glu Ser Asp Gly Gln Pro Glu Asn Asn
    275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Glu Gln Gly Asp Val
305                 310                 315                 320

Phe Ser Cys Ser Val Met His Glu Ala Leu His Asn His Tyr Thr Gln
            325                 330                 335

Lys Ser Leu Ser Leu Ser Pro Gly Lys
            340                 345

<210> SEQ ID NO 201
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
            85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Gln
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
            165                 170                 175

Leu Pro Ala Pro Ile Glu Lys Thr Ile Ser Lys Ala Lys Gly Gln Pro
        180                 185                 190
```

```
Arg Glu Pro Gln Val Tyr Thr Leu Pro Pro Ser Arg Glu Gln Met Thr
            195                 200                 205

Lys Asn Gln Val Lys Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Met His Glu Ala Leu His Asn His Tyr Thr Gln Lys
            275                 280                 285

Ser Leu Ser Leu Ser Pro Gly Lys
            290                 295

<210> SEQ ID NO 202
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser Glu Pro Lys Ser Ser Asp Lys Thr His Thr Cys Pro Pro Cys
        115                 120                 125

Pro Ala Pro Pro Val Ala Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Lys His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Glu Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255
```

```
Thr Lys Asn Gln Val Ser Leu Thr Cys Asp Val Ser Gly Phe Tyr Pro
            260                 265                 270

Ser Asp Ile Ala Val Glu Trp Glu Ser Asp Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asp Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 203
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Gln
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Gln Met Thr
        195                 200                 205

Lys Asn Gln Val Lys Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
```

```
                260                 265                 270
Ser Cys Ser Val Met His Glu Ala Leu His Asn His Tyr Thr Gln Lys
        275                 280                 285

Ser Leu Ser Leu Ser Pro Gly Lys
        290             295

<210> SEQ ID NO 204
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Gln
50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320
```

Glu Gln Gly Asp Val Phe Ser Cys Ser Val Met His Glu Ala Leu His
            325                 330                 335

Asn His Tyr Thr Gln Lys Ser Leu Ser Leu Ser Pro Gly Lys
            340                 345                 350

<210> SEQ ID NO 205
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
50                  55                  60

Arg Gly Gly Gly Gly Ser Glu Pro Lys Ser Ser Asp Lys Thr His Thr
65                  70                  75                  80

Cys Pro Pro Cys Pro Ala Pro Val Ala Gly Pro Ser Val Phe Leu
                85                  90                  95

Phe Pro Pro Lys Pro Lys Asp Thr Leu Met Ile Ser Arg Thr Pro Glu
                100                 105                 110

Val Thr Cys Val Val Val Asp Val Lys His Glu Asp Pro Glu Val Lys
            115                 120                 125

Phe Asn Trp Tyr Val Asp Gly Val Glu Val His Asn Ala Lys Thr Lys
        130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
            290                 295                 300

<210> SEQ ID NO 206
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

```
Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Glu Pro Lys Ser Ser Asp Lys Thr His Thr Cys Pro Pro Cys
        115                 120                 125

Pro Ala Pro Pro Val Ala Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Lys His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Asp Val Ser Gly Phe Tyr Pro
            260                 265                 270

Ser Asp Ile Ala Val Glu Trp Glu Ser Asp Gly Gln Pro Glu Asn Asn
        275                 280                 285

Tyr Lys Thr Thr Pro Pro Val Leu Asp Ser Asp Gly Ser Phe Phe Leu
290                 295                 300

Tyr Ser Lys Leu Thr Val Asp Lys Ser Arg Trp Gln Gln Gly Asp Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345
```

<210> SEQ ID NO 207
<211> LENGTH: 296
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 207

```
Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys Ile
    50                  55                  60
Arg Glu Pro Lys Ser Ser Asp Lys Thr His Thr Cys Pro Pro Cys Pro
65                  70                  75                  80
Ala Pro Pro Val Ala Gly Pro Ser Val Phe Leu Phe Pro Pro Lys Pro
                85                  90                  95
Lys Asp Thr Leu Met Ile Ser Arg Thr Pro Glu Val Thr Cys Val Val
            100                 105                 110
Val Asp Val Lys His Glu Asp Pro Glu Val Lys Phe Asn Trp Tyr Val
        115                 120                 125
Asp Gly Val Glu Val His Asn Ala Lys Thr Lys Pro Arg Glu Glu Gln
    130                 135                 140
Tyr Asn Ser Thr Tyr Arg Val Val Ser Val Leu Thr Val Leu His Gln
145                 150                 155                 160
Asp Trp Leu Asn Gly Lys Glu Tyr Lys Cys Lys Val Ser Asn Lys Ala
                165                 170                 175
Leu Pro Ala Pro Ile Glu Lys Thr Ile Ser Lys Ala Lys Gly Gln Pro
            180                 185                 190
Arg Glu Pro Gln Val Tyr Thr Leu Pro Pro Ser Arg Glu Gln Met Thr
        195                 200                 205
Lys Asn Gln Val Lys Leu Thr Cys Leu Val Lys Gly Phe Tyr Pro Ser
    210                 215                 220
Asp Ile Ala Val Glu Trp Glu Ser Asn Gly Gln Pro Glu Asn Asn Tyr
225                 230                 235                 240
Lys Thr Thr Pro Pro Val Leu Asp Ser Asp Gly Ser Phe Phe Leu Tyr
                245                 250                 255
Ser Lys Leu Thr Val Asp Lys Ser Arg Trp Gln Gln Gly Asn Val Phe
            260                 265                 270
Ser Cys Ser Val Met His Glu Ala Leu His Asn His Tyr Thr Gln Lys
        275                 280                 285
Ser Leu Ser Leu Ser Pro Gly Lys
    290                 295
```

<210> SEQ ID NO 208
<211> LENGTH: 345
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 208

```
Asn Trp Val Asp Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
            20                  25                  30
Pro Ser Cys Lys Val Thr Ala Met Lys Cys Phe Leu Leu Glu Leu Gln
```

```
              35                  40                  45
Val Ile Ser Leu Glu Ser Gly Asp Ala Ser Ile His Asp Thr Val Glu
 50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser Glu Pro Lys Ser Ser Asp Lys Thr His Thr Cys Pro Pro Cys
                115                 120                 125

Pro Ala Pro Pro Val Ala Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Lys His Glu Asp Pro Glu Val Lys Phe Asn Trp Tyr
                165                 170                 175

Val Asp Gly Val Glu Val His Asn Ala Lys Thr Lys Pro Arg Glu Glu
                180                 185                 190

Glu Tyr Asn Ser Thr Tyr Arg Val Val Ser Val Leu Thr Val Leu His
                195                 200                 205

Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Asp Val Ser Gly Phe Tyr Pro
                260                 265                 270

Ser Asp Ile Ala Val Glu Trp Glu Ser Asp Gly Gln Pro Glu Asn Asn
                275                 280                 285

Tyr Lys Thr Thr Pro Pro Val Leu Asp Ser Asp Gly Ser Phe Phe Leu
                290                 295                 300

Tyr Ser Lys Leu Thr Val Asp Lys Ser Arg Trp Gln Gln Gly Asp Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
                340                 345

<210> SEQ ID NO 209
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
                35                  40                  45
```

```
Lys Ala Thr Asn Val Ala His Trp Thr Thr Pro Ser Leu Lys Cys Ile
 50                  55                  60

Arg Glu Pro Lys Ser Ser Asp Lys Thr His Thr Cys Pro Pro Cys Pro
 65                  70                  75                  80

Ala Pro Pro Val Ala Gly Pro Ser Val Phe Leu Phe Pro Pro Lys Pro
                 85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
            115                 120                 125

Asp Gly Val Glu Val His Asn Ala Lys Thr Lys Pro Arg Glu Glu Gln
130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Gln Met Thr
        195                 200                 205

Lys Asn Gln Val Lys Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Met His Glu Ala Leu His Asn His Tyr Thr Gln Lys
        275                 280                 285

Ser Leu Ser Leu Ser Pro Gly Lys
    290                 295

<210> SEQ ID NO 210
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
             20                  25                  30

Phe Lys Arg Lys Ala Gly Thr Ser Ser Leu Thr Glu Cys Val Leu Asn
         35                  40                  45

Lys Ala Thr Asn Val Ala His Trp Thr Thr Pro Ser Leu Lys Cys Ile
 50                  55                  60

Arg Gly Gly Gly Ser Gly Gly Gly Ser Gly Gly Gly Ser
 65                  70                  75                  80

Gly Gly Gly Gly Ser Gly Gly Gly Ser Asn Trp Val Asn Val Ile
                 85                  90                  95

Ser Asp Leu Lys Lys Ile Glu Asp Leu Ile Gln Ser Met His Ile Asp
            100                 105                 110
```

Ala Thr Leu Tyr Thr Glu Ser Asp Val His Pro Ser Cys Lys Val Thr
115                 120                 125

Ala Met Lys Cys Phe Leu Leu Glu Leu Gln Val Ile Ser Leu Glu Ser
130                 135                 140

Gly Asp Ala Ser Ile His Asp Thr Val Glu Asn Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Glu Met Phe Ile Asn Thr Ser Glu Pro Lys Ser
        195                 200                 205

Ser Asp Lys Thr His Thr Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 211
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys

```
                    20                  25                  30
Asp Thr Leu Met Ile Ser Arg Thr Pro Glu Val Thr Cys Val Val Val
                35                  40                  45

Asp Val Lys His Glu Asp Pro Glu Val Lys Phe Asn Trp Tyr Val Asp
 50                  55                  60

Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
                115                 120                 125

Glu Pro Gln Val Tyr Thr Leu Pro Pro Ser Arg Glu Gln Met Thr Lys
                130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
                210                 215                 220

Leu Ser Leu Ser Pro Gly Lys
225                 230

<210> SEQ ID NO 212
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
                35                  40                  45

Lys Ala Thr Asn Val Ala His Trp Thr Thr Pro Ser Leu Lys Cys Ile
 50                  55                  60

Arg Gly Gly Gly Ser Gly Gly Gly Ser Gly Gly Gly Ser
 65                  70                  75                  80

Gly Gly Gly Gly Ser Gly Gly Gly Ser Asn Trp Val Asp Val Ile
                85                  90                  95

Ser Asp Leu Lys Lys Ile Glu Asp Leu Ile Gln Ser Met His Ile Asp
                100                 105                 110

Ala Thr Leu Tyr Thr Glu Ser Asp Val His Pro Ser Cys Lys Val Thr
                115                 120                 125

Ala Met Lys Cys Phe Leu Leu Glu Leu Gln Val Ile Ser Leu Glu Ser
                130                 135                 140
```

-continued

```
Gly Asp Ala Ser Ile His Asp Thr Val Glu Asp Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Tyr Asn Ser Thr Tyr
        275                 280                 285

Arg Val Val Ser Val Leu Thr Val Leu His Gln Asp Trp Leu Asn Gly
290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 213
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60
```

```
Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Gln Met Thr Lys
130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 214
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Ile Thr Cys Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
                 20                  25                  30

Phe Lys Arg Lys Ala Gly Thr Ser Ser Leu Thr Glu Cys Val Leu Asn
             35                  40                  45

Lys Ala Thr Asn Val Ala His Trp Thr Thr Pro Ser Leu Lys Cys Ile
 50                  55                  60

Arg Gly Gly Gly Gly Ser Gly Gly Gly Ser Gly Gly Gly Gly Ser
 65                  70                  75                  80

Gly Gly Gly Gly Ser Gly Gly Gly Ser Gly Gly Gly Gly Ser Asn
                 85                  90                  95

Trp Val Asn Val Ile Ser Asp Leu Lys Lys Ile Glu Asp Leu Ile Gln
                100                 105                 110

Ser Met His Ile Asp Ala Thr Leu Tyr Thr Glu Ser Asp Val His Pro
            115                 120                 125

Ser Cys Lys Val Thr Ala Met Lys Cys Phe Leu Leu Glu Leu Gln Val
130                 135                 140

Ile Ser Leu Glu Ser Gly Asp Ala Ser Ile His Asp Thr Val Glu Asn
145                 150                 155                 160

Leu Ile Ile Leu Ala Asn Asn Ser Leu Ser Ser Asn Gly Asn Val Thr
                165                 170                 175

Glu Ser Gly Cys Lys Glu Cys Glu Glu Leu Glu Glu Lys Asn Ile Lys
```

```
                180             185              190
Glu Phe Leu Gln Ser Phe Val His Ile Val Glu Met Phe Ile Asn Thr
        195                 200             205

Ser Glu Pro Lys Ser Ser Asp Lys Thr His Thr Cys Pro Pro Cys Pro
    210                 215             220

Ala Pro Pro Val Ala Gly Pro Ser Val Phe Leu Phe Pro Pro Lys Pro
225                 230             235                 240

Lys Asp Thr Leu Met Ile Ser Arg Thr Pro Glu Val Thr Cys Val Val
                245             250             255

Val Asp Val Lys His Glu Asp Pro Glu Val Lys Phe Asn Trp Tyr Val
            260             265             270

Asp Gly Val Glu Val His Asn Ala Lys Thr Lys Pro Arg Glu Glu Glu
        275             280             285

Tyr Asn Ser Thr Tyr Arg Val Val Ser Val Leu Thr Val Leu His Gln
    290             295             300

Asp Trp Leu Asn Gly Lys Glu Tyr Lys Cys Lys Val Ser Asn Lys Ala
305             310             315                 320

Leu Pro Ala Pro Ile Glu Lys Thr Ile Ser Lys Ala Lys Gly Gln Pro
                325             330             335

Arg Glu Pro Gln Val Tyr Thr Leu Pro Pro Ser Arg Glu Glu Met Thr
            340             345             350

Lys Asn Gln Val Ser Leu Thr Cys Asp Val Ser Gly Phe Tyr Pro Ser
        355             360             365

Asp Ile Ala Val Glu Trp Glu Ser Asp Gly Gln Pro Glu Asn Asn Tyr
    370             375             380

Lys Thr Thr Pro Pro Val Leu Asp Ser Asp Gly Ser Phe Phe Leu Tyr
385             390             395                 400

Ser Lys Leu Thr Val Asp Lys Ser Arg Trp Glu Gln Gly Asp Val Phe
                405             410             415

Ser Cys Ser Val Met His Glu Ala Leu His Asn His Tyr Thr Gln Lys
            420             425             430

Ser Leu Ser Leu Ser Pro Gly Lys
        435             440

<210> SEQ ID NO 215
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Glu Pro Lys Ser Ser Asp Lys Thr His Thr Cys Pro Pro Cys Pro Ala
1               5                  10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95
```

```
Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 216
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
50                  55                  60

Arg Gly Gly Gly Gly Ser Gly Gly Gly Gly Ser Gly Gly Gly Gly Ser
65                  70                  75                  80

Gly Gly Gly Gly Ser Gly Gly Gly Ser Gly Gly Gly Gly Ser Asn
                85                  90                  95

Trp Val Asp Val Ile Ser Asp Leu Lys Lys Ile Glu Asp Leu Ile Gln
                100                 105                 110

Ser Met His Ile Asp Ala Thr Leu Tyr Thr Glu Ser Asp Val His Pro
            115                 120                 125

Ser Cys Lys Val Thr Ala Met Lys Cys Phe Leu Leu Glu Leu Gln Val
        130                 135                 140

Ile Ser Leu Glu Ser Gly Asp Ala Ser Ile His Asp Thr Val Glu Asp
145                 150                 155                 160

Leu Ile Ile Leu Ala Asn Asn Ser Leu Ser Ser Asn Gly Asn Val Thr
                165                 170                 175

Glu Ser Gly Cys Lys Glu Cys Glu Glu Leu Glu Glu Lys Asn Ile Lys
            180                 185                 190

Glu Phe Leu Gln Ser Phe Val His Ile Val Gln Met Phe Ile Asn Thr
        195                 200                 205

Ser Glu Pro Lys Ser Ser Asp Lys Thr His Thr Cys Pro Pro Cys Pro
210                 215                 220
```

```
Ala Pro Pro Val Ala Gly Pro Ser Val Phe Leu Phe Pro Lys Pro
225                 230                 235                 240

Lys Asp Thr Leu Met Ile Ser Arg Thr Pro Glu Val Thr Cys Val Val
                245                 250                 255

Val Asp Val Lys His Glu Asp Pro Glu Val Lys Phe Asn Trp Tyr Val
            260                 265                 270

Asp Gly Val Glu Val His Asn Ala Lys Thr Lys Pro Arg Glu Glu Glu
        275                 280                 285

Tyr Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
                325                 330                 335

Arg Glu Pro Gln Val Tyr Thr Leu Pro Pro Ser Arg Glu Glu Met Thr
            340                 345                 350

Lys Asn Gln Val Ser Leu Thr Cys Asp Val Ser Gly Phe Tyr Pro Ser
        355                 360                 365

Asp Ile Ala Val Glu Trp Glu Ser Asp Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Glu Gln Gly Asp Val Phe
                405                 410                 415

Ser Cys Ser Val Met His Glu Ala Leu His Asn His Tyr Thr Gln Lys
                420                 425                 430

Ser Leu Ser Leu Ser Pro Gly Lys
                435                 440

<210> SEQ ID NO 217
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Lys Pro Lys
                20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
```

```
            130                 135                 140
Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
            210                 215                 220

Leu Ser Leu Ser Pro Gly Lys
225                 230

<210> SEQ ID NO 218
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
50                  55                  60

Arg Gly Gly Gly Ser Gly Gly Gly Ser Gly Gly Gly Gly Ser
65                  70                  75                  80

Gly Gly Gly Gly Ser Gly Gly Gly Ser Gly Gly Gly Gly Ser Gly
                85                  90                  95

Gly Gly Gly Ser Asn Trp Val Asn Val Ile Ser Asp Leu Lys Lys Ile
            100                 105                 110

Glu Asp Leu Ile Gln Ser Met His Ile Asp Ala Thr Leu Tyr Thr Glu
            115                 120                 125

Ser Asp Val His Pro Ser Cys Lys Val Thr Ala Met Lys Cys Phe Leu
            130                 135                 140

Leu Glu Leu Gln Val Ile Ser Leu Glu Ser Gly Asp Ala Ser Ile His
145                 150                 155                 160

Asp Thr Val Glu Asn Leu Ile Ile Leu Ala Asn Asn Ser Leu Ser Ser
                165                 170                 175

Asn Gly Asn Val Thr Glu Ser Gly Cys Lys Glu Cys Glu Glu Leu Glu
            180                 185                 190

Glu Lys Asn Ile Lys Glu Phe Leu Gln Ser Phe Val His Ile Val Glu
            195                 200                 205

Met Phe Ile Asn Thr Ser Glu Pro Lys Ser Ser Asp Lys Thr His Thr
            210                 215                 220

Cys Pro Pro Cys Pro Ala Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255
```

```
Val Thr Cys Val Val Asp Val Lys His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Glu Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Asp Val Ser
        355                 360                 365

Gly Phe Tyr Pro Ser Asp Ile Ala Val Glu Trp Glu Ser Asp Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Glu
                405                 410                 415

Gln Gly Asp Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 219
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175
```

```
Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225             230

<210> SEQ ID NO 220
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Gly Ser Gly Gly Gly Gly Ser Gly Gly Gly Gly Ser
65                  70                  75                  80

Gly Gly Gly Gly Ser Gly Gly Gly Ser Gly Gly Gly Gly Ser Gly
                85                  90                  95

Gly Gly Gly Ser Asn Trp Val Asp Val Ile Ser Asp Leu Lys Lys Ile
                100                 105                 110

Glu Asp Leu Ile Gln Ser Met His Ile Asp Ala Thr Leu Tyr Thr Glu
            115                 120                 125

Ser Asp Val His Pro Ser Cys Lys Val Thr Ala Met Lys Cys Phe Leu
130                 135                 140

Leu Glu Leu Gln Val Ile Ser Leu Glu Ser Gly Asp Ala Ser Ile His
145                 150                 155                 160

Asp Thr Val Glu Asp Leu Ile Ile Leu Ala Asn Asn Ser Leu Ser Ser
                165                 170                 175

Asn Gly Asn Val Thr Glu Ser Gly Cys Lys Glu Cys Glu Glu Leu Glu
            180                 185                 190

Glu Lys Asn Ile Lys Glu Phe Leu Gln Ser Phe Val His Ile Val Gln
        195                 200                 205

Met Phe Ile Asn Thr Ser Glu Pro Lys Ser Ser Asp Lys Thr His Thr
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Lys His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Glu Tyr Asn Ser Thr Tyr Arg Val Val Ser Val Leu
```

```
                290                 295                 300
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Asp Val Ser
                355                 360                 365

Gly Phe Tyr Pro Ser Asp Ile Ala Val Glu Trp Glu Ser Asp Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Glu
                405                 410                 415

Gln Gly Asp Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 221
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ser Arg Thr Pro Glu Val Thr Cys Val Val Val
                35                  40                  45

Asp Val Lys His Glu Asp Pro Glu Val Lys Phe Asn Trp Tyr Val Asp
                50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
                115                 120                 125

Glu Pro Gln Val Tyr Thr Leu Pro Pro Ser Arg Glu Gln Met Thr Lys
                130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
                195                 200                 205
```

```
Cys Ser Val Met His Glu Ala Leu His Asn His Tyr Thr Gln Lys Ser
    210                 215                 220
Leu Ser Leu Ser Pro Gly Lys
225                 230

<210> SEQ ID NO 222
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
50                  55                  60

Arg Asp Pro Ala Leu Val His Gln Arg Pro Ala Pro Pro Gly Gly Gly
65                  70                  75                  80

Gly Ser Gly Gly Gly Ser Gly Gly Gly Ser Gly Gly Gly Asn
                85                  90                  95

Trp Val Asn Val Ile Ser Asp Leu Lys Lys Ile Glu Asp Leu Ile Gln
                100                 105                 110

Ser Met His Ile Asp Ala Thr Leu Tyr Thr Glu Ser Asp Val His Pro
            115                 120                 125

Ser Cys Lys Val Thr Ala Met Lys Cys Phe Leu Leu Glu Leu Gln Val
        130                 135                 140

Ile Ser Leu Glu Ser Gly Asp Ala Ser Ile His Asp Thr Val Glu Asn
145                 150                 155                 160

Leu Ile Ile Leu Ala Asn Asn Ser Leu Ser Ser Asn Gly Asn Val Thr
                165                 170                 175

Glu Ser Gly Cys Lys Glu Cys Glu Glu Leu Glu Glu Lys Asn Ile Lys
            180                 185                 190

Glu Phe Leu Gln Ser Phe Val His Ile Val Glu Met Phe Ile Asn Thr
        195                 200                 205

Ser Glu Pro Lys Ser Ser Asp Lys Thr His Thr Cys Pro Pro Cys Pro
    210                 215                 220

Ala Pro Pro Val Ala Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Lys His Glu Asp Pro Glu Val Lys Phe Asn Trp Tyr Val
            260                 265                 270

Asp Gly Val Glu Val His Asn Ala Lys Thr Lys Pro Arg Glu Glu Glu
        275                 280                 285

Tyr Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
                325                 330                 335
```

```
Arg Glu Pro Gln Val Tyr Thr Leu Pro Pro Ser Arg Glu Glu Met Thr
                340                 345                 350

Lys Asn Gln Val Ser Leu Thr Cys Asp Val Ser Gly Phe Tyr Pro Ser
                355                 360                 365

Asp Ile Ala Val Glu Trp Glu Ser Asp Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asp Val Phe
                405                 410                 415

Ser Cys Ser Val Met His Glu Ala Leu His Asn His Tyr Thr Gln Lys
                420                 425                 430

Ser Leu Ser Leu Ser Pro Gly Lys
                435                 440

<210> SEQ ID NO 223
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Gln Met Thr Lys
        130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
        210                 215                 220

Leu Ser Leu Ser Pro Gly Lys
225                 230
```

<210> SEQ ID NO 224
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Glu
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Glu Met Thr
        195                 200                 205

Lys Asn Gln Val Ser Leu Thr Cys Asp Val Ser Gly Phe Tyr Pro Ser
    210                 215                 220

Asp Ile Ala Val Glu Trp Glu Ser Asp Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Glu Gln Gly Asp Val Phe
            260                 265                 270

Ser Cys Ser Val Met His Glu Ala Leu His Asn His Tyr Thr Gln Lys
        275                 280                 285

Ser Leu Ser Leu Ser Pro Gly Lys
    290                 295

<210> SEQ ID NO 225
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Glu Pro Lys Ser Ser Asp Lys Thr His Thr Cys Pro Pro Cys Pro Ala

```
  1               5                  10                 15
Pro Pro Val Ala Gly Pro Ser Val Phe Leu Phe Pro Pro Lys Pro Lys
                20                 25                 30
Asp Thr Leu Met Ile Ser Arg Thr Pro Glu Val Thr Cys Val Val Val
                35                 40                 45
Asp Val Lys His Glu Asp Pro Glu Val Lys Phe Asn Trp Tyr Val Asp
 50                 55                 60
Gly Val Glu Val His Asn Ala Lys Thr Lys Pro Arg Glu Glu Gln Tyr
 65                 70                 75                 80
Asn Ser Thr Tyr Arg Val Val Ser Val Leu Thr Val Leu His Gln Asp
                85                 90                 95
Trp Leu Asn Gly Lys Glu Tyr Lys Cys Lys Val Ser Asn Lys Ala Leu
                100                105                110
Pro Ala Pro Ile Glu Lys Thr Ile Ser Lys Ala Lys Gly Gln Pro Arg
                115                120                125
Glu Pro Gln Val Tyr Thr Leu Pro Pro Ser Arg Glu Gln Met Thr Lys
                130                135                140
Asn Gln Val Lys Leu Thr Cys Leu Val Lys Gly Phe Tyr Pro Ser Asp
145                150                155                160
Ile Ala Val Glu Trp Glu Ser Asn Gly Gln Pro Glu Asn Asn Tyr Lys
                165                170                175
Thr Thr Pro Pro Val Leu Asp Ser Asp Gly Ser Phe Phe Leu Tyr Ser
                180                185                190
Lys Leu Thr Val Asp Lys Ser Arg Trp Gln Gln Gly Asn Val Phe Ser
                195                200                205
Cys Ser Val Met His Glu Ala Leu His Asn His Tyr Thr Gln Lys Ser
                210                215                220
Leu Ser Leu Ser Pro Gly Lys
225                230

<210> SEQ ID NO 226
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Asn Trp Val Asn Val Ile Ser Asp Leu Lys Lys Ile Glu Asp Leu Ile
1               5                  10                 15
Gln Ser Met His Ile Asp Ala Thr Leu Tyr Thr Glu Ser Asp Val His
                20                 25                 30
Pro Ser Cys Lys Val Thr Ala Met Lys Cys Phe Leu Leu Glu Leu Gln
                35                 40                 45
Val Ile Ser Leu Glu Ser Gly Asp Ala Ser Ile His Asp Thr Val Glu
 50                 55                 60
Asn Leu Ile Ile Leu Ala Asn Asn Ser Leu Ser Ser Asn Gly Asn Val
65                  70                 75                 80
Thr Glu Ser Gly Cys Lys Glu Cys Glu Glu Leu Glu Glu Lys Asn Ile
                85                 90                 95
Lys Glu Phe Leu Gln Ser Phe Val His Ile Val Glu Met Phe Ile Asn
                100                105                110
Thr Ser
```

```
<210> SEQ ID NO 227
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Glu
130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Glu Met Thr
        195                 200                 205

Lys Asn Gln Val Ser Leu Thr Cys Asp Val Ser Gly Phe Tyr Pro Ser
210                 215                 220

Asp Ile Ala Val Glu Trp Glu Ser Asp Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Glu Gln Gly Asp Val Phe
            260                 265                 270

Ser Cys Ser Val Met His Glu Ala Leu His Asn His Tyr Thr Gln Lys
        275                 280                 285

Ser Leu Ser Leu Ser Pro Gly Lys
    290                 295

<210> SEQ ID NO 228
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Ile Thr Cys Pro Pro Pro Met Ser Val Glu His Ala Asp Ile Trp Val
```

```
                1               5                   10                  15
Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
                35                  40                  45

Lys Ala Thr Asn Val Ala His Trp Thr Thr Pro Ser Leu Lys Cys Ile
 50                      55                  60

Arg Glu Pro Lys Ser Ser Asp Lys Thr His Thr Cys Pro Pro Cys Pro
 65                  70                  75                  80

Ala Pro Pro Val Ala Gly Pro Ser Val Phe Leu Phe Pro Pro Lys Pro
                    85                  90                  95

Lys Asp Thr Leu Met Ile Ser Arg Thr Pro Glu Val Thr Cys Val Val
                100                 105                 110

Val Asp Val Lys His Glu Asp Pro Glu Val Lys Phe Asn Trp Tyr Val
                115                 120                 125

Asp Gly Val Glu Val His Asn Ala Lys Thr Lys Pro Arg Glu Glu Glu
        130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                    165                 170                 175

Leu Pro Ala Pro Ile Glu Lys Thr Ile Ser Lys Ala Lys Gly Gln Pro
                180                 185                 190

Arg Glu Pro Gln Val Tyr Thr Leu Pro Pro Ser Arg Glu Glu Met Thr
                195                 200                 205

Lys Asn Gln Val Ser Leu Thr Cys Asp Val Ser Gly Phe Tyr Pro Ser
        210                 215                 220

Asp Ile Ala Val Glu Trp Glu Ser Asp Gly Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asp Val Phe
                260                 265                 270

Ser Cys Ser Val Met His Glu Ala Leu His Asn His Tyr Thr Gln Lys
                275                 280                 285

Ser Leu Ser Leu Ser Pro Gly Lys
                290                 295

<210> SEQ ID NO 229
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Glu Pro Lys Ser Ser Asp Lys Thr His Thr Cys Pro Pro Cys Pro Ala
 1               5                  10                  15

Pro Pro Val Ala Gly Pro Ser Val Phe Leu Phe Pro Pro Lys Pro Lys
                20                  25                  30

Asp Thr Leu Met Ile Ser Arg Thr Pro Glu Val Thr Cys Val Val Val
                35                  40                  45

Asp Val Lys His Glu Asp Pro Glu Val Lys Phe Asn Trp Tyr Val Asp
 50                      55                  60
```

-continued

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 230
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Gln
        50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 231
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Ile Thr Cys Pro Pro Pro Met Ser Val Glu His Ala Asp Ile Trp Val

```
                1               5                       10                      15
        Lys Ser Tyr Ser Leu Tyr Ser Arg Glu Arg Tyr Ile Cys Asn Ser Gly
                        20                      25                      30

Phe Lys Arg Lys Ala Gly Thr Ser Ser Leu Thr Glu Cys Val Leu Asn
                        35                      40                      45

Lys Ala Thr Asn Val Ala His Trp Thr Thr Pro Ser Leu Lys Cys Ile
                50                      55                      60

Arg Glu Pro Lys Ser Ser Asp Lys Thr His Thr Cys Pro Pro Cys Pro
        65                      70                      75                      80

Ala Pro Pro Val Ala Gly Pro Ser Val Phe Leu Phe Pro Pro Lys Pro
                                85                      90                      95

Lys Asp Thr Leu Met Ile Ser Arg Thr Pro Glu Val Thr Cys Val Val
                        100                     105                     110

Val Asp Val Lys His Glu Asp Pro Glu Val Lys Phe Asn Trp Tyr Val
                        115                     120                     125

Asp Gly Val Glu Val His Asn Ala Lys Thr Lys Pro Arg Glu Glu Glu
                130                     135                     140

Tyr Asn Ser Thr Tyr Arg Val Val Ser Val Leu Thr Val Leu His Gln
        145                     150                     155                     160

Asp Trp Leu Asn Gly Lys Glu Tyr Lys Cys Lys Val Ser Asn Lys Ala
                                165                     170                     175

Leu Pro Ala Pro Ile Glu Lys Thr Ile Ser Lys Ala Lys Gly Gln Pro
                        180                     185                     190

Arg Glu Pro Gln Val Tyr Thr Leu Pro Pro Ser Arg Glu Glu Met Thr
                        195                     200                     205

Lys Asn Gln Val Ser Leu Thr Cys Asp Val Ser Gly Phe Tyr Pro Ser
                210                     215                     220

Asp Ile Ala Val Glu Trp Glu Ser Asp Gly Gln Pro Glu Asn Asn Tyr
        225                     230                     235                     240

Lys Thr Thr Pro Pro Val Leu Asp Ser Asp Gly Ser Phe Phe Leu Tyr
                                245                     250                     255

Ser Lys Leu Thr Val Asp Lys Ser Arg Trp Gln Gln Gly Asp Val Phe
                        260                     265                     270

Ser Cys Ser Val Met His Glu Ala Leu His Asn His Tyr Thr Gln Lys
                        275                     280                     285

Ser Leu Ser Leu Ser Pro Gly Lys
                290                     295

<210> SEQ ID NO 232
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Glu Pro Lys Ser Ser Asp Lys Thr His Thr Cys Pro Pro Cys Pro Ala
        1               5                       10                      15

Pro Pro Val Ala Gly Pro Ser Val Phe Leu Phe Pro Pro Lys Pro Lys
                        20                      25                      30

Asp Thr Leu Met Ile Ser Arg Thr Pro Glu Val Thr Cys Val Val Val
                        35                      40                      45

Asp Val Lys His Glu Asp Pro Glu Val Lys Phe Asn Trp Tyr Val Asp
                50                      55                      60
```

```
Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 233
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 234
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Ile Thr Cys Pro Pro Pro Met Ser Val Glu His Ala Asp Ile Trp Val
```

```
                1               5                  10                 15
Lys Ser Tyr Ser Leu Tyr Ser Arg Glu Arg Tyr Ile Cys Asn Ser Gly
            20                  25                 30

Phe Lys Arg Lys Ala Gly Thr Ser Ser Leu Thr Glu Cys Val Leu Asn
            35                  40                 45

Lys Ala Thr Asn Val Ala His Trp Thr Thr Pro Ser Leu Lys Cys Ile
            50                  55                 60

Arg
65

<210> SEQ ID NO 235
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser

<210> SEQ ID NO 236
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg
65

<210> SEQ ID NO 237
<211> LENGTH: 296
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 237

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Gln
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Glu Met Thr
        195                 200                 205

Lys Asn Gln Val Ser Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Met His Glu Ala Leu His Asn His Tyr Thr Gln Lys
        275                 280                 285

Ser Leu Ser Leu Ser Pro Gly Lys
    290                 295

<210> SEQ ID NO 238
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30
```

```
Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Glu Met Phe Ile Asn
            100                 105                 110

Thr Ser

<210> SEQ ID NO 239
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Glu Pro Lys Ser Ser Asp Lys Thr His Thr Cys Pro Pro Cys Pro Ala
 1               5                  10                  15

Pro Pro Val Ala Gly Pro Ser Val Phe Leu Phe Pro Pro Lys Pro Lys
                 20                  25                  30

Asp Thr Leu Met Ile Ser Arg Thr Pro Glu Val Thr Cys Val Val Val
             35                  40                  45

Asp Val Lys His Glu Asp Pro Glu Val Lys Phe Asn Trp Tyr Val Asp
 50                  55                  60

Gly Val Glu Val His Asn Ala Lys Thr Lys Pro Arg Glu Glu Glu Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 240
<211> LENGTH: 114
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 240

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asp Leu Ile Ile Leu Ala Asn Asn Ser Leu Ser Ser Asn Gly Asn Val
65                  70                  75                  80

Thr Glu Ser Gly Cys Lys Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 241
<211> LENGTH: 298
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Asp Cys Glu Pro Lys Ser Ser Asp Lys Thr His Thr Cys Pro Pro
65                  70                  75                  80

Cys Pro Ala Pro Pro Val Ala Gly Pro Ser Val Phe Leu Phe Pro Pro
                85                  90                  95

Lys Pro Lys Asp Thr Leu Met Ile Ser Arg Thr Pro Glu Val Thr Cys
                100                 105                 110

Val Val Val Asp Val Lys His Glu Asp Pro Glu Val Lys Phe Asn Trp
                115                 120                 125

Tyr Val Asp Gly Val Glu Val His Asn Ala Lys Thr Lys Pro Arg Glu
            130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
                180                 185                 190

Gln Pro Arg Glu Pro Gln Val Tyr Thr Leu Pro Pro Ser Arg Glu Gln
            195                 200                 205
```

Met Thr Lys Asn Gln Val Lys Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
                260                 265                 270

Val Phe Ser Cys Ser Val Met His Glu Ala Leu His Asn His Tyr Thr
                275                 280                 285

Gln Lys Ser Leu Ser Leu Ser Pro Gly Lys
    290                 295

<210> SEQ ID NO 242
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ser Arg Thr Pro Glu Val Thr Cys Val Val Val
                35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Glu Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Glu Met Thr Lys
    130                 135                 140

Asn Gln Val Ser Leu Thr Cys Asp Val Ser Gly Phe Tyr Pro Ser Asp
145                 150                 155                 160

Ile Ala Val Glu Trp Glu Ser Asp Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Glu Gln Gly Asp Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 243
<211> LENGTH: 114
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 243

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Cys Glu Ser Gly Asp Ala Ser Ile His Asp Thr Val Glu
50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 244
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Cys Ser Leu Thr Glu Cys Val Leu Asn
            35                  40                  45

Lys Ala Thr Asn Val Ala His Trp Thr Thr Pro Ser Leu Lys Cys Ile
50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
            115                 120                 125

Asp Gly Val Glu Val His Asn Ala Lys Thr Lys Pro Arg Glu Glu Gln
130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Gln Met Thr
        195                 200                 205
```

Lys Asn Gln Val Lys Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Met His Glu Ala Leu His Asn His Tyr Thr Gln Lys
                275                 280                 285

Ser Leu Ser Leu Ser Pro Gly Lys
290                 295

<210> SEQ ID NO 245
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

```
Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
        290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Leu His Glu Ala Leu His
                325                 330                 335

Ser His Tyr Thr Gln Lys Ser Leu Ser Leu Ser Pro Gly Lys
            340                 345                 350

<210> SEQ ID NO 246
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Gly Ser Glu Pro Lys Ser Ser Asp Lys Thr His Thr
65                  70                  75                  80

Cys Pro Pro Cys Pro Ala Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Leu His Glu Ala Leu His Ser
```

```
                275                 280                 285
His Tyr Thr Gln Lys Ser Leu Ser Leu Ser Pro Gly Lys
    290                 295                 300

<210> SEQ ID NO 247
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Leu His Glu Ala Leu His
                325                 330                 335
```

Ser His Tyr Thr Gln Lys Ser Leu Ser Leu Ser Pro Gly Lys
            340                 345                 350

<210> SEQ ID NO 248
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Ser Glu Pro Lys Ser Ser Asp Lys Thr His Thr
65                  70                  75                  80

Cys Pro Pro Cys Pro Ala Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Leu His Glu Ala Leu His Ser
        275                 280                 285

His Tyr Thr Gln Lys Ser Leu Ser Leu Ser Pro Gly Lys
    290                 295                 300

<210> SEQ ID NO 249
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

```
Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Leu His Glu Ala Leu His
                325                 330                 335

Ser His Tyr Thr Gln Lys Ser Leu Ser Leu Ser Pro Gly Lys
            340                 345                 350
```

<210> SEQ ID NO 250
<211> LENGTH: 301
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 250

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Gly Gly Gly Ser Glu Pro Lys Ser Ser Asp Lys Thr His Thr
65                  70                  75                  80

Cys Pro Pro Cys Pro Ala Pro Val Ala Gly Pro Ser Val Phe Leu
                85                  90                  95

Phe Pro Pro Lys Pro Lys Asp Thr Leu Met Ile Ser Arg Thr Pro Glu
                100                 105                 110

Val Thr Cys Val Val Val Asp Val Lys His Glu Asp Pro Glu Val Lys
            115                 120                 125

Phe Asn Trp Tyr Val Asp Gly Val Glu Val His Asn Ala Lys Thr Lys
        130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Leu His Glu Ala Leu His Ser
        275                 280                 285

His Tyr Thr Gln Lys Ser Leu Ser Leu Ser Pro Gly Lys
290                 295                 300

<210> SEQ ID NO 251
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
```

```
            50                  55                  60
Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser Glu Pro Lys Ser Ser Asp Lys Thr His Thr Cys Pro Pro Cys
        115                 120                 125

Pro Ala Pro Pro Val Ala Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Lys His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Glu Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Asp Val Ser Gly Phe Tyr Pro
            260                 265                 270

Ser Asp Ile Ala Val Glu Trp Glu Ser Asp Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Glu Gln Gly Asp Val
305                 310                 315                 320

Phe Ser Cys Ser Val Leu His Glu Ala Leu His Ser His Tyr Thr Gln
                325                 330                 335

Lys Ser Leu Ser Leu Ser Pro Gly Lys
            340                 345

<210> SEQ ID NO 252
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Ile Thr Cys Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
                 20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
 50                  55                  60
```

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Gln
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Gln Met Thr
        195                 200                 205

Lys Asn Gln Val Lys Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Leu His Glu Ala Leu His Ser His Tyr Thr Gln Lys
        275                 280                 285

Ser Leu Ser Leu Ser Pro Gly Lys
    290                 295

<210> SEQ ID NO 253
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Gln
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Glu Pro Lys Ser Ser Asp Lys Thr His
        115                 120                 125

```
Thr Cys Pro Cys Pro Ala Pro Pro Val Ala Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Leu His Glu Ala Leu His
                325                 330                 335

Ser His Tyr Thr Gln Lys Ser Leu Ser Leu Ser Pro Gly Lys
            340                 345                 350

<210> SEQ ID NO 254
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Gly Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
```

```
                130                 135                 140
Pro Arg Glu Glu Gln Tyr Asn Ser Thr Tyr Arg Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
                180                 185                 190

Ala Lys Gly Gln Pro Arg Glu Pro Gln Val Tyr Thr Leu Pro Pro Ser
            195                 200                 205

Arg Glu Gln Met Thr Lys Asn Gln Val Lys Leu Thr Cys Leu Val Lys
        210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
                260                 265                 270

Gln Gly Asn Val Phe Ser Cys Ser Val Leu His Glu Ala Leu His Ser
            275                 280                 285

His Tyr Thr Gln Lys Ser Leu Ser Leu Ser Pro Gly Lys
        290                 295                 300

<210> SEQ ID NO 255
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser Glu Pro Lys Ser Ser Asp Lys Thr His Thr Cys Pro Pro Cys
            115                 120                 125

Pro Ala Pro Pro Val Ala Gly Pro Ser Val Phe Leu Phe Pro Pro Lys
        130                 135                 140

Pro Lys Asp Thr Leu Met Ile Ser Arg Thr Pro Glu Val Thr Cys Val
145                 150                 155                 160

Val Val Asp Val Lys His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190
```

```
Glu Tyr Asn Ser Thr Tyr Arg Val Val Ser Val Leu Thr Val Leu His
            195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Asp Val Ser Gly Phe Tyr Pro
            260                 265                 270

Ser Asp Ile Ala Val Glu Trp Glu Ser Asp Gly Gln Pro Glu Asn Asn
        275                 280                 285

Tyr Lys Thr Thr Pro Pro Val Leu Asp Ser Asp Gly Ser Phe Phe Leu
290                 295                 300

Tyr Ser Lys Leu Thr Val Asp Lys Ser Arg Trp Gln Gln Gly Asp Val
305                 310                 315                 320

Phe Ser Cys Ser Val Leu His Glu Ala Leu His Ser His Tyr Thr Gln
                325                 330                 335

Lys Ser Leu Ser Leu Ser Pro Gly Lys
            340                 345

<210> SEQ ID NO 256
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Gln
130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Gln Met Thr
        195                 200                 205
```

```
Lys Asn Gln Val Lys Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
        260                 265                 270

Ser Cys Ser Val Leu His Glu Ala Leu His Ser His Tyr Thr Gln Lys
    275                 280                 285

Ser Leu Ser Leu Ser Pro Gly Lys
    290                 295

<210> SEQ ID NO 257
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
    50                  55                  60

Arg Gly Gly Gly Gly Ser Gly Gly Gly Gly Ser Gly Gly Gly Gly Ser
65                  70                  75                  80

Gly Gly Gly Gly Ser Gly Gly Gly Ser Asn Trp Val Asp Val Ile
                85                  90                  95

Ser Asp Leu Lys Lys Ile Glu Asp Leu Ile Gln Ser Met His Ile Asp
                100                 105                 110

Ala Thr Leu Tyr Thr Glu Ser Asp Val His Pro Ser Cys Lys Val Thr
            115                 120                 125

Ala Met Lys Cys Phe Leu Leu Glu Leu Gln Val Ile Ser Leu Glu Ser
    130                 135                 140

Gly Asp Ala Ser Ile His Asp Thr Val Glu Asp Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
    195                 200                 205

Ser Asp Lys Thr His Thr Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
```

```
                    260                 265                 270
His Asn Ala Lys Thr Lys Pro Arg Glu Glu Tyr Asn Ser Thr Tyr
            275                 280                 285

Arg Val Val Ser Val Leu Thr Val Leu His Gln Asp Trp Leu Asn Gly
            290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
            325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
            355                 360                 365

Trp Glu Ser Asp Gly Gln Pro Glu Asn Asn Tyr Lys Thr Thr Pro Pro
            370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Leu
            405                 410                 415

His Glu Ala Leu His Ser His Tyr Thr Gln Lys Ser Leu Ser Leu Ser
            420                 425                 430

Pro Gly Lys
        435

<210> SEQ ID NO 258
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175
```

```
Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Leu His Glu Ala Leu His Ser His Tyr Thr Gln Lys Ser
    210                 215                 220

Leu Ser Leu Ser Pro Gly Lys
225             230

<210> SEQ ID NO 259
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser

<210> SEQ ID NO 260
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
```

```
                115                 120                 125
Asp Gly Val Glu Val His Asn Ala Lys Thr Lys Pro Arg Glu Glu
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
                180                 185                 190

Arg Glu Pro Gln Val Tyr Thr Leu Pro Pro Ser Arg Glu Glu Met Thr
            195                 200                 205

Lys Asn Gln Val Ser Leu Thr Cys Asp Val Ser Gly Phe Tyr Pro Ser
    210                 215                 220

Asp Ile Ala Val Glu Trp Glu Ser Asp Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Glu Gln Gly Asp Val Phe
                260                 265                 270

Ser Cys Ser Val Leu His Glu Ala Leu His Ser His Tyr Thr Gln Lys
            275                 280                 285

Ser Leu Ser Leu Ser Pro Gly Lys
    290                 295

<210> SEQ ID NO 261
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Lys Pro Lys
            20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175
```

```
Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Leu His Glu Ala Leu His Ser His Tyr Thr Gln Lys Ser
    210                 215                 220

Leu Ser Leu Ser Pro Gly Lys
225             230
```

<210> SEQ ID NO 262
<211> LENGTH: 296
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 262

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Gln
130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Glu Met Thr
        195                 200                 205

Lys Asn Gln Val Ser Leu Thr Cys Leu Val Lys Gly Phe Tyr Pro Ser
210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Leu His Glu Ala Leu His Ser His Tyr Thr Gln Lys
        275                 280                 285

Ser Leu Ser Leu Ser Pro Gly Lys
    290                 295
```

<210> SEQ ID NO 263
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Glu Met Phe Ile Asn
            100                 105                 110

Thr Ser

<210> SEQ ID NO 264
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 265
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Glu Pro Lys Ser Ser Asp Lys Thr His Thr Cys Pro Pro Cys Pro
65                  70                  75                  80

Ala Pro Pro Val Ala Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Lys His Glu Asp Pro Glu Val Lys Phe Asn Trp Tyr Val
        115                 120                 125

Asp Gly Val Glu Val His Asn Ala Lys Thr Lys Pro Arg Glu Glu Gln
130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Glu Met Thr
        195                 200                 205

Lys Asn Gln Val Ser Leu Thr Cys Leu Val Lys Gly Phe Tyr Pro Ser
210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Leu His Glu Ala Leu His Ser His Tyr Thr Gln Lys
        275                 280                 285

Ser Leu Ser Leu Ser Pro Gly Lys
    290                 295

<210> SEQ ID NO 266
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val

```
                50                  55                  60
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Lys His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 267
<211> LENGTH: 214
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 267

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 268
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
50                  55                  60

Arg Gly Gly Gly Ser Gly Gly Gly Ser Gly Gly Gly Ser
65                  70                  75                  80

Gly Gly Gly Gly Ser Gly Gly Gly Ser Asn Trp Val Asn Val Ile
                85                  90                  95

Ser Asp Leu Lys Lys Ile Glu Asp Leu Ile Gln Ser Met His Ile Asp
            100                 105                 110
```

```
Ala Thr Leu Tyr Thr Glu Ser Asp Val His Pro Ser Cys Lys Val Thr
        115                 120                 125
Ala Met Lys Cys Phe Leu Leu Glu Leu Gln Val Ile Ser Leu Glu Ser
        130                 135                 140
Gly Asp Ala Ser Ile His Asp Thr Val Glu Asn Leu Ile Ile Leu Ala
145                 150                 155                 160
Asn Asn Ser Leu Ser Ser Asn Gly Asn Val Thr Glu Ser Gly Cys Lys
                165                 170                 175
Glu Cys Glu Glu Leu Glu Glu Lys Asn Ile Lys Glu Phe Leu Gln Ser
            180                 185                 190
Phe Val His Ile Val Gln Met Phe Ile Asn Thr Ser Glu Pro Lys Ser
        195                 200                 205
Ser Asp Lys Thr His Thr Cys Pro Pro Cys Pro Ala Pro Pro Val Ala
210                 215                 220
Gly Pro Ser Val Phe Leu Phe Pro Pro Lys Pro Asp Thr Leu Met
225                 230                 235                 240
Ile Ser Arg Thr Pro Glu Val Thr Cys Val Val Asp Val Lys His
                245                 250                 255
Glu Asp Pro Glu Val Lys Phe Asn Trp Tyr Val Asp Gly Val Glu Val
            260                 265                 270
His Asn Ala Lys Thr Lys Pro Arg Glu Glu Glu Tyr Asn Ser Thr Tyr
        275                 280                 285
Arg Val Val Ser Val Leu Thr Val Leu His Gln Asp Trp Leu Asn Gly
        290                 295                 300
Lys Glu Tyr Lys Cys Lys Val Ser Asn Lys Ala Leu Pro Ala Pro Ile
305                 310                 315                 320
Glu Lys Thr Ile Ser Lys Ala Lys Gly Gln Pro Arg Glu Pro Gln Val
                325                 330                 335
Tyr Thr Leu Pro Pro Ser Arg Glu Glu Met Thr Lys Asn Gln Val Ser
            340                 345                 350
Leu Thr Cys Asp Val Ser Gly Phe Tyr Pro Ser Asp Ile Ala Val Glu
        355                 360                 365
Trp Glu Ser Asp Gly Gln Pro Glu Asn Asn Tyr Lys Thr Thr Pro Pro
        370                 375                 380
Val Leu Asp Ser Asp Gly Ser Phe Phe Leu Tyr Ser Lys Leu Thr Val
385                 390                 395                 400
Asp Lys Ser Arg Trp Glu Gln Gly Asp Val Phe Ser Cys Ser Val Met
                405                 410                 415
His Glu Ala Leu His Asn His Tyr Thr Gln Lys Ser Leu Ser Leu Ser
            420                 425                 430
Pro Gly Lys
        435

<210> SEQ ID NO 269
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
```

```
                20                  25                  30
Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 270
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
    130                 135                 140
```

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Glu Gln Gly Asp Val Phe Ser Cys Ser Val Leu His Glu Ala Leu His
                325                 330                 335

Ser His Tyr Thr Gln Lys Ser Leu Ser Leu Ser Pro Gly Lys
            340                 345                 350

<210> SEQ ID NO 271
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Gly Gly Gly Gly Ser Glu Pro Lys Ser Ser Asp Lys Thr His Thr
65                  70                  75                  80

Cys Pro Pro Cys Pro Ala Pro Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

```
Thr Val Leu His Gln Asp Trp Leu Asn Gly Lys Glu Tyr Lys Cys Lys
            165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
            195                 200                 205

Arg Glu Gln Met Thr Lys Asn Gln Val Lys Leu Thr Cys Leu Val Lys
            210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
            245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Leu His Glu Ala Leu His Ser
            275                 280                 285

His Tyr Thr Gln Lys Ser Leu Ser Leu Ser Pro Gly Lys
            290                 295                 300

<210> SEQ ID NO 272
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
50                  55                  60

Arg Gly Gly Gly Ser Gly Gly Gly Ser Gly Gly Gly Ser
65                  70                  75                  80

Gly Gly Gly Gly Ser Gly Gly Gly Ser Asn Trp Val Asp Val Ile
                85                  90                  95

Ser Asp Leu Lys Lys Ile Glu Asp Leu Ile Gln Ser Met His Ile Asp
                100                 105                 110

Ala Thr Leu Tyr Thr Glu Ser Asp Val His Pro Ser Cys Lys Val Thr
            115                 120                 125

Ala Met Lys Cys Phe Leu Leu Glu Leu Gln Val Ile Ser Leu Glu Ser
130                 135                 140

Gly Asp Ala Ser Ile His Asp Thr Val Glu Asp Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
            195                 200                 205

Ser Asp Lys Thr His Thr Cys Pro Pro Cys Pro Ala Pro Pro Val Ala
```

```
                210                 215                 220
Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
                260                 265                 270

His Asn Ala Lys Thr Lys Pro Arg Glu Glu Tyr Asn Ser Thr Tyr
            275                 280                 285

Arg Val Val Ser Val Leu Thr Val Leu His Gln Asp Trp Leu Asn Gly
            290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
                340                 345                 350

Leu Thr Cys Asp Val Ser Gly Phe Tyr Pro Ser Asp Ile Ala Val Glu
            355                 360                 365

Trp Glu Ser Asp Gly Gln Pro Glu Asn Asn Tyr Lys Thr Thr Pro Pro
            370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Leu
                405                 410                 415

His Glu Ala Leu His Ser His Tyr Thr Gln Lys Ser Leu Ser Leu Ser
            420                 425                 430

Pro Gly Lys
        435

<210> SEQ ID NO 273
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Lys His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125
```

-continued

```
Glu Pro Gln Val Tyr Thr Leu Pro Pro Ser Arg Glu Gln Met Thr Lys
            130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
                195                 200                 205

Cys Ser Val Leu His Glu Ala Leu His Ser His Tyr Thr Gln Lys Ser
            210                 215                 220

Leu Ser Leu Ser Pro Gly Lys
225                 230

<210> SEQ ID NO 274
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 275
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Asp Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
```

```
                65                  70                  75                  80
Thr Glu Ser Gly Cys Lys Glu Cys Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 276
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Asn Trp Val Asp Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 277
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Gln
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

```
<210> SEQ ID NO 278
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 279
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Gln
        50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 280
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Ile Thr Cys Pro Pro Pro Met Ser Val Glu His Ala Asp Ile Trp Val
```

-continued

```
1               5                   10                  15
Lys Ser Tyr Ser Leu Tyr Ser Arg Glu Arg Tyr Ile Cys Asn Ser Gly
                20                  25                  30
Phe Lys Arg Lys Ala Gly Thr Ser Leu Thr Glu Cys Val Leu Asn
        35                  40                  45
Lys Ala Thr Asn Val Ala His Trp Thr Thr Pro Ser Leu Lys Cys Ile
    50                  55                  60
Arg Gly Gly Gly Ser Gly Gly Gly Ser Gly Gly Gly Ser
65                  70                  75                  80
Gly Gly Gly Gly Ser Gly Gly Gly Ser Asn Trp Val Asn Val Ile
                85                  90                  95
Ser Asp Leu Lys Lys Ile Glu Asp Leu Ile Gln Ser Met His Ile Asp
            100                 105                 110
Ala Thr Leu Tyr Thr Glu Ser Asn Val His Pro Ser Cys Lys Val Thr
            115                 120                 125
Ala Met Lys Cys Phe Leu Leu Glu Leu Gln Val Ile Ser Leu Glu Ser
            130                 135                 140
Gly Asp Ala Ser Ile His Asp Thr Val Glu Asn Leu Ile Ile Leu Ala
145                 150                 155                 160
Asn Asn Ser Leu Ser Ser Asn Gly Asn Val Thr Glu Ser Gly Cys Lys
                165                 170                 175
Glu Cys Glu Glu Leu Glu Glu Lys Asn Ile Lys Glu Phe Leu Gln Ser
            180                 185                 190
Phe Val His Ile Val Gln Met Phe Ile Asn Thr Ser Glu Pro Lys Ser
            195                 200                 205
Ser Asp Lys Thr His Thr Cys Pro Pro Cys Pro Ala Pro Pro Val Ala
            210                 215                 220
Gly Pro Ser Val Phe Leu Phe Pro Pro Lys Pro Lys Asp Thr Leu Met
225                 230                 235                 240
Ile Ser Arg Thr Pro Glu Val Thr Cys Val Val Val Asp Val Lys His
                245                 250                 255
Glu Asp Pro Glu Val Lys Phe Asn Trp Tyr Val Asp Gly Val Glu Val
            260                 265                 270
His Asn Ala Lys Thr Lys Pro Arg Glu Glu Glu Tyr Asn Ser Thr Tyr
            275                 280                 285
Arg Val Val Ser Val Leu Thr Val Leu His Gln Asp Trp Leu Asn Gly
        290                 295                 300
Lys Glu Tyr Lys Cys Lys Val Ser Asn Lys Ala Leu Pro Ala Pro Ile
305                 310                 315                 320
Glu Lys Thr Ile Ser Lys Ala Lys Gly Gln Pro Arg Glu Pro Gln Val
                325                 330                 335
Tyr Thr Leu Pro Pro Ser Arg Glu Glu Met Thr Lys Asn Gln Val Ser
            340                 345                 350
Leu Thr Cys Asp Val Ser Gly Phe Tyr Pro Ser Asp Ile Ala Val Glu
            355                 360                 365
Trp Glu Ser Asp Gly Gln Pro Glu Asn Asn Tyr Lys Thr Thr Pro Pro
        370                 375                 380
Val Leu Asp Ser Asp Gly Ser Phe Phe Leu Tyr Ser Lys Leu Thr Val
385                 390                 395                 400
Asp Lys Ser Arg Trp Glu Gln Gly Asp Val Phe Ser Cys Ser Val Met
                405                 410                 415
His Glu Ala Leu His Asn His Tyr Thr Gln Lys Ser Leu Ser Leu Ser
            420                 425                 430
```

Pro Gly Lys
    435

<210> SEQ ID NO 281
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 282
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

```
Lys Ala Thr Asn Val Ala His Trp Thr Thr Pro Ser Leu Lys Cys Ile
 50                  55                  60

Arg Gly Gly Gly Ser Gly Gly Gly Ser Gly Gly Gly Ser
 65                  70                  75                  80

Gly Gly Gly Gly Ser Gly Gly Gly Ser Asp Trp Val Asn Val Ile
                 85                  90                  95

Ser Asp Leu Lys Lys Ile Glu Asp Leu Ile Gln Ser Met His Ile Asp
                100                 105                 110

Ala Thr Leu Tyr Thr Glu Ser Asn Val His Pro Ser Cys Lys Val Thr
                115                 120                 125

Ala Met Lys Cys Phe Leu Leu Glu Leu Gln Val Ile Ser Leu Glu Ser
130                 135                 140

Gly Asp Ala Ser Ile His Asp Thr Val Glu Asn Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
                180                 185                 190

Phe Val His Ile Val Gln Met Phe Ile Asn Thr Ser Glu Pro Lys Ser
                195                 200                 205

Ser Asp Lys Thr His Thr Cys Pro Pro Cys Pro Ala Pro Pro Val Ala
210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
                260                 265                 270

His Asn Ala Lys Thr Lys Pro Arg Glu Glu Glu Tyr Asn Ser Thr Tyr
                275                 280                 285

Arg Val Val Ser Val Leu Thr Val Leu His Gln Asp Trp Leu Asn Gly
                290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
                340                 345                 350

Leu Thr Cys Asp Val Ser Gly Phe Tyr Pro Ser Asp Ile Ala Val Glu
                355                 360                 365

Trp Glu Ser Asp Gly Gln Pro Glu Asn Asn Tyr Lys Thr Thr Pro Pro
                370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
                405                 410                 415

His Glu Ala Leu His Asn His Tyr Thr Gln Lys Ser Leu Ser Leu Ser
                420                 425                 430

Pro Gly Lys
435

<210> SEQ ID NO 283
<211> LENGTH: 231
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 284
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Gly Ser Gly Gly Gly Ser Gly Gly Gly Gly Ser
65                  70                  75                  80
```

Gly Gly Gly Gly Ser Gly Gly Gly Ser Asn Trp Val Asp Val Ile
            85                  90                  95

Ser Asp Leu Lys Lys Ile Glu Asp Leu Ile Gln Ser Met His Ile Asp
        100                 105                 110

Ala Thr Leu Tyr Thr Glu Ser Asn Val His Pro Ser Cys Lys Val Thr
        115                 120                 125

Ala Met Lys Cys Phe Leu Leu Glu Leu Gln Val Ile Ser Leu Glu Ser
    130                 135                 140

Gly Asp Ala Ser Ile His Asp Thr Val Glu Asn Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Glu Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 285
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

```
Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 286
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Ser Gly Gly Gly Ser Gly Gly Gly Ser
65                  70                  75                  80

Gly Gly Gly Gly Ser Gly Gly Gly Ser Asn Trp Val Asn Val Ile
                85                  90                  95

Ser Asp Leu Lys Lys Ile Glu Asp Leu Ile Gln Ser Met His Ile Asp
                100                 105                 110

Ala Thr Leu Tyr Thr Glu Ser Asn Val His Pro Ser Cys Lys Val Thr
```

```
                    115                 120                 125
Ala Met Lys Cys Phe Leu Leu Glu Leu Gln Val Ile Ser Leu Glu Ser
        130                 135                 140

Gly Asp Ala Ser Ile His Asp Thr Val Gln Asn Leu Ile Ile Leu Ala
145                 150                 155                 160

Asn Asn Ser Leu Ser Ser Asn Gly Asn Val Thr Glu Ser Gly Cys Lys
                165                 170                 175

Glu Cys Glu Glu Leu Glu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Glu Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asp Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
    435

<210> SEQ ID NO 287
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30
```

```
Asp Thr Leu Met Ile Ser Arg Thr Pro Glu Val Thr Cys Val Val Val
                 35                  40                  45

Asp Val Lys His Glu Asp Pro Glu Val Lys Phe Asn Trp Tyr Val Asp
 50                  55                  60

Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Gln Met Thr Lys
130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
            210                 215                 220

Leu Ser Leu Ser Pro Gly Lys
225                 230

<210> SEQ ID NO 288
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
             20                  25                  30

Phe Lys Arg Lys Ala Gly Thr Ser Ser Leu Thr Glu Cys Val Leu Asn
                 35                  40                  45

Lys Ala Thr Asn Val Ala His Trp Thr Thr Pro Ser Leu Lys Cys Ile
 50                  55                  60

Arg Gly Gly Gly Gly Ser Gly Gly Gly Gly Ser Gly Gly Gly Gly Ser
 65                  70                  75                  80

Gly Gly Gly Gly Ser Gly Gly Gly Gly Ser Asn Trp Val Asn Val Ile
             85                  90                  95

Ser Asp Leu Lys Lys Ile Glu Asp Leu Ile Gln Ser Met His Ile Asp
                100                 105                 110

Ala Thr Leu Tyr Thr Glu Ser Asn Val His Pro Ser Cys Lys Val Thr
            115                 120                 125

Ala Met Lys Cys Phe Leu Leu Glu Leu Gln Val Ile Ser Leu Glu Ser
130                 135                 140

Gly Asp Ala Ser Ile His Asp Thr Val Glu Asp Leu Ile Ile Leu Ala
145                 150                 155                 160
```

Asn Asn Ser Leu Ser Ser Asn Gly Asn Val Thr Glu Ser Gly Cys Lys
                165                 170                 175

Glu Cys Glu Glu Leu Glu Lys Asn Ile Lys Glu Phe Leu Gln Ser
            180                 185                 190

Phe Val His Ile Val Gln Met Phe Ile Asn Thr Ser Glu Pro Lys Ser
        195                 200                 205

Ser Asp Lys Thr His Thr Cys Pro Pro Cys Pro Ala Pro Pro Val Ala
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Gln Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asp Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 289
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr

```
                65                  70                  75                  80
Asn Ser Thr Tyr Arg Val Val Ser Val Leu Thr Val Leu His Gln Asp
                    85                  90                  95

Trp Leu Asn Gly Lys Glu Tyr Lys Cys Lys Val Ser Asn Lys Ala Leu
                    100                 105                 110

Pro Ala Pro Ile Glu Lys Thr Ile Ser Lys Ala Lys Gly Gln Pro Arg
                    115                 120                 125

Glu Pro Gln Val Tyr Thr Leu Pro Pro Ser Arg Glu Gln Met Thr Lys
            130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                    165                 170                 175

Thr Thr Pro Pro Val Leu Asp Ser Asp Gly Ser Phe Phe Leu Tyr Ser
                    180                 185                 190

Lys Leu Thr Val Asp Lys Ser Arg Trp Gln Gln Gly Asn Val Phe Ser
                    195                 200                 205

Cys Ser Val Met His Glu Ala Leu His Asn His Tyr Thr Gln Lys Ser
            210                 215                 220

Leu Ser Leu Ser Pro Gly Lys
225                 230

<210> SEQ ID NO 290
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                    20                  25                  30

Phe Lys Arg Lys Ala Gly Thr Ser Ser Leu Thr Glu Cys Val Leu Asn
                    35                  40                  45

Lys Ala Thr Asn Val Ala His Trp Thr Thr Pro Ser Leu Lys Cys Ile
            50                  55                  60

Arg Gly Gly Gly Gly Ser Gly Gly Gly Gly Ser Gly Gly Gly Gly Ser
65                  70                  75                  80

Gly Gly Gly Gly Ser Gly Gly Gly Ser Asn Trp Val Asn Val Ile
                    85                  90                  95

Ser Asp Leu Lys Lys Ile Glu Asp Leu Ile Gln Ser Met His Ile Asp
                    100                 105                 110

Ala Thr Leu Tyr Thr Glu Ser Asn Val His Pro Ser Cys Lys Val Thr
            115                 120                 125

Ala Met Lys Cys Phe Leu Leu Glu Leu Gln Val Ile Ser Leu Glu Ser
            130                 135                 140

Gly Asp Ala Ser Ile His Asp Thr Val Gln Asp Leu Ile Ile Leu Ala
145                 150                 155                 160

Asn Asn Ser Leu Ser Ser Asn Gly Asn Val Thr Glu Ser Gly Cys Lys
                    165                 170                 175

Glu Cys Glu Glu Leu Glu Glu Lys Asn Ile Lys Glu Phe Leu Gln Ser
                    180                 185                 190
```

Phe Val His Ile Val Gln Met Phe Ile Asn Thr Ser Glu Pro Lys Ser
            195                 200                 205

Ser Asp Lys Thr His Thr Cys Pro Pro Cys Pro Ala Pro Pro Val Ala
        210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Lys His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Glu Glu Met Thr Lys Asn Gln Val Ser
            340                 345                 350

Leu Thr Cys Asp Val Ser Gly Phe Tyr Pro Ser Asp Ile Ala Val Glu
        355                 360                 365

Trp Glu Ser Asp Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Glu Gln Gly Asp Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 291
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Gln Met Thr Lys
    130                 135                 140

Asn Gln Val Lys Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 292
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Glu Pro Lys Ser
1

<210> SEQ ID NO 293
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Glu Pro Lys Ser Cys
1               5

<210> SEQ ID NO 294
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gly Lys Pro Gly Ser Gly Lys Pro Gly Ser Gly Lys Pro Gly Ser Gly
1               5                   10                  15

Lys Pro Gly Ser
            20

IL-15/IL-15RA HETERODIMERIC Fc FUSION PROTEINS AND USES THEREOF

CROSS-REFERENCE TO RELATED APPLICATIONS

This application is a continuation of U.S. patent application Ser. No. 16/388,174, filed Apr. 18, 2019 which claims priority to U.S. Provisional Application No. 62/659,563 filed Apr. 18, 2018, U.S. Provisional Application No. 62/684,143 filed Jun. 12, 2018, U.S. Provisional Application No. 62/724,396 filed Aug. 29, 2018, and U.S. Provisional Application No. 62/756,800, filed Nov. 7, 2018, the disclosures are incorporated by reference in their entirety.

SEQUENCE LISTING

The instant application contains a Sequence Listing which has been submitted electronically in ASCII format and is hereby incorporated by reference in its entirety. Said ASCII copy, created on Jun. 11, 2019, is named 067461-5203-US_SL.txt and is 561,630 bytes in size.

BACKGROUND OF THE INVENTION

Two very promising approaches in cancer immunotherapy include cytokine-based treatments and blockade of immune checkpoint proteins such as PD-1.

Cytokines such as IL-2 and IL-15 function in aiding the proliferation and differentiation of B cells, T cells, and NK cells. Both cytokines exert their cell signaling function through binding to a trimeric complex consisting of two shared receptors, the common gamma chain (γc; CD132) and IL-2 receptor beta-chain (IL-2Rß; CD122), as well as an alpha chain receptor unique to each cytokine: IL-2 receptor alpha (IL-2Rα; CD25) or IL-15 receptor alpha (IL-15Rα; CD215). Both cytokines are considered as potentially valuable therapeutics in oncology, and IL-2 has been approved for use in patients with metastatic renal-cell carcinoma and malignant melanoma. Currently, there are no approved uses of recombinant IL-15, although several clinical trials are ongoing. However, as potential drugs, both cytokines suffer from a very fast clearance, with half-lives measured in minutes. IL-2 immunotherapy has been associated with systemic toxicity when administered in high doses to overcome fast clearance. Such systemic toxicity has also been reported with IL-15 immunotherapy in recent clinical trials (Guo et al., J Immunol, 2015, 195(5):2353-64).

Immune checkpoint proteins such as PD-1 are up-regulated following T cell activation to preclude autoimmunity by exhausting activated T cells upon binding to immune checkpoint ligands such as PD-L1. However, immune checkpoint proteins are also up-regulated in tumor-infiltrating lymphocytes (TILs), and immune checkpoint ligands are overexpressed on tumor cells, contributing to immune escape by tumor cells. De-repression of TILs by blockade of immune checkpoint interactions by drugs such as Opdivo® (nivolumab) and Keytruda® (pembrolizumab) have proven highly effective in treatment of cancer. Despite the promise of checkpoint blockade therapies such as nivolumab and pembrolizumab, many patients still fail to achieve sufficient response to checkpoint blockade alone.

Therefore, there remains an unmet need in oncology treatment for therapeutic strategies with cytokines which do not require high doses and are targeted to tumors to avoid systemic toxicity. Further, there is a need to identify additional therapeutic modalities to stack with checkpoint blockade that could increase patient response rate. The present invention addresses these needs and caveats by providing reduced potency IL-15/Rα-Fc fusion proteins with enhanced pharmacokinetics and pharmacodynamics, and which synergistically combine with checkpoint blockade antibodies.

BRIEF SUMMARY OF THE INVENTION

The present invention is directed to administering a novel IL-15/IL-15Rα heterodimeric Fc fusion protein in combination with a checkpoint blockade antibody. In some embodiments, the checkpoint blockade antibody selected from the group consisting of an anti-PD-1 antibody, an anti-PD-L1 antibody, an anti-TIM3 antibody, an anti-TIGIT antibody, an anti-LAG3 antibody, and an anti-CTLA-4 antibody.

In some aspects, provided herein is a method of treating cancer in a patient in need thereof comprising administering:
a therapeutically effective amount of an IL-15/IL-15Rα heterodimeric Fc fusion protein comprising:
  a) a first monomer comprising, from N- to C-terminal:
    i) an IL-15 receptor alpha (IL-15Rα) sushi domain;
    ii) a first domain linker; and
    iii) a first variant Fc domain comprising CH2-CH3; and
  b) a second monomer comprising from N- to C-terminal:
    i) a variant IL-15 domain comprising the amino acid sequence of SEQ ID NO:2 and any one of the amino acid substitutions selected from the group consisting of N4D/N65D, D30N/N65D, and D30N/E64Q/N65D;
    ii) a second domain linker; and
    iii) a second variant Fc domain comprising CH2-CH3;
wherein the first and second variant Fc domains have a set of amino acid substitutions selected from the group consisting of S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering; and a therapeutically effective amount of a checkpoint blockade antibody selected from the group consisting of an anti-PD-1 antibody, an anti-PD-L1 antibody, an anti-TIM3 antibody, an anti-TIGIT antibody, an anti-LAG3 antibody, and an anti-CTLA-4 antibody.

In some embodiments, the variant IL-15 domain comprises the amino acid sequence of SEQ ID NO:2 and the amino acid substitutions D30N/E64Q/N65D. In some embodiments, the variant IL-15 domain comprises the amino acid sequence of SEQ ID NO:2 and the amino acid substitutions D30N/N65D. In some embodiments, the variant IL-15 domain comprises the amino acid sequence of SEQ ID NO:2 and the amino acid substitutions N4D/N65D.

In some embodiments, the IL-15Rα sushi domain comprises the amino acid sequence of SEQ ID NO:4.

In some embodiments, the first and second variant Fc domains have S364K/E357Q. L368D/K370S substitutions. In some embodiments, the first variant Fc domain has S364K/E357Q substitutions and the second variant Fc domain L368D/K370S substitutions.

In some embodiments, the first and second variant Fc domains each comprise M428L/N434S substitutions.

In some embodiments, the first and second variant Fc domains each comprise E233P/L234V/L235A/G236del/S267K substitutions.

In some embodiments, the IL-15/IL-15Rα heterodimeric Fc fusion protein and the checkpoint blockade antibody are administered concomitantly or sequentially.

In some embodiments, the anti-PD-1 antibody is nivolumab, pembrolizumab, or pidilizumab.

In some embodiments, the IL-15/IL-15Rα heterodimeric Fc fusion protein comprises the amino acid sequence of XENP24306 or XENP24045.

In some embodiments, the IL-15/IL-15Rα heterodimeric Fc fusion protein comprises the amino acid sequence of XENP24306 (SEQ ID NOS 253 and 254) and the anti-PD-1 antibody is nivolumab. In some embodiments, the IL-15/IL-15Rα heterodimeric Fc fusion protein comprises the amino acid sequence of XENP24306 (SEQ ID NOS 253 and 254) and the anti-PD-1 antibody is pembrolizumab. In some embodiments, the IL-15/IL-15Rα heterodimeric Fc fusion protein comprises the amino acid sequence of XENP24306 (SEQ ID NOS 253 and 254) and the anti-PD-1 antibody is pidilizumab.

In some embodiments, the IL-15/IL-15Rα heterodimeric Fc fusion protein comprises the amino acid sequence of XENP24045 (SEQ ID NOS 204 and 205) and the anti-PD-1 antibody is nivolumab. In some embodiments, the IL-15/IL-15Rα heterodimeric Fc fusion protein comprises the amino acid sequence of XENP24045 (SEQ ID NOS 204 and 205) and the anti-PD-1 antibody is pembrolizumab. In some embodiments, the IL-15/IL-15Rα heterodimeric Fc fusion protein comprises the amino acid sequence of XENP24045 (SEQ ID NOS 204 and 205) and the anti-PD-1 antibody is pidilizumab.

In some embodiments, the cancer is metastatic cancer. In some embodiments, the cancer is selected from the group consisting of breast cancer, lung cancer, colon cancer, ovarian cancer, melanoma cancer, bladder cancer, renal cancer, kidney cancer, liver cancer, head and neck cancer, colorectal cancer, melanoma, pancreatic cancer, gastric carcinoma cancer, esophageal cancer, mesothelioma, prostate cancer, leukemia, lymphoma, and myeloma.

In some embodiments, the method of treating cancer outlined herein results in a minimal level of vascular leakage in the patient.

In some embodiments, the level of vascular leakage ranges from a 20% reduction or less in serum albumin in the patient following administration.

In some aspects, provided herein is a method of treating cancer in a patient, the method comprising administering a combination therapy comprising an IL-15/IL-15Rα heterodimeric Fc fusion protein and a checkpoint blockade antibody to the patient, wherein the IL-15/IL-15Rα heterodimeric Fc fusion comprises:
 a) a first monomer comprising, from N- to C-terminal:
  i) an IL-15 receptor alpha (IL-15Rα) sushi domain;
  ii) a first domain linker; and
  iii) a first variant Fc domain comprising CH2-CH3; and
 b) a second monomer comprising from N- to C-terminal:
  i) a variant IL-15 domain comprising the amino acid sequence of SEQ ID NO:2 and any one of the amino acid substitutions selected from the group consisting of N4D/N65D, D30N/N65D, and D30N/E64Q/N65D;
  ii) a second domain linker; and
  iii) a second variant Fc domain comprising CH2-CH3;
wherein the first and second variant Fc domains have a set of amino acid substitutions selected from the group consisting of S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357Q and K370S:S364K/E357Q, according to EU numbering; and the checkpoint blockade antibody is selected from the group consisting of an anti-PD-1 antibody, an anti-PD-L1 antibody, an anti-TIM3 antibody, an anti-TIGIT antibody, an anti-LAG3 antibody, and an anti-CTLA-4 antibody.

In some embodiments, the variant IL-15 domain comprises the amino acid sequence of SEQ ID NO:2 and the amino acid substitutions D30N/E64Q/N65D. In some embodiments, the variant IL-15 domain comprises the amino acid sequence of SEQ ID NO:2 and the amino acid substitutions D30N/N65D. In some embodiments, the variant IL-15 domain comprises the amino acid sequence of SEQ ID NO:2 and the amino acid substitutions N4D/N65D.

In some embodiments, the IL-15Rα sushi domain comprises the amino acid sequence of SEQ ID NO:4.

In some embodiments, the first and second variant Fc domains have S364K/E357Q:L368D/K370S substitutions. In some embodiments, the first variant Fc domain has S364K/E357Q substitutions and the second variant Fc domain L368D/K370S substitutions.

In some embodiments, the first and second variant Fc domains each comprise M428L/N434S substitutions.

In some embodiments, the first and second variant Fc domains each comprise E233P/L234V/L235A/G236del/S267K substitutions.

In some embodiments, the anti-PD-1 antibody is nivolumab, pembrolizumab, or pidilizumab.

In some embodiments, the IL-15/IL-15Rα heterodimeric Fc fusion protein comprises the amino acid sequence of XENP24306 (SEQ ID NOS 253 and 254) or XENP24045 (SEQ ID NOS 204 and 205).

In some embodiments, the IL-15/IL-15Rα heterodimeric Fc fusion protein comprises the amino acid sequence of XENP24306 (SEQ ID NOS 253 and 254) and the anti-PD-1 antibody is nivolumab. In some embodiments, the IL-15/IL-15Rα heterodimeric Fc fusion protein comprises the amino acid sequence of XENP24306 (SEQ ID NOS 253 and 254) and the anti-PD-1 antibody is pembrolizumab. In some embodiments, the IL-15/IL-15Rα heterodimeric Fc fusion protein comprises the amino acid sequence of XENP24306 (SEQ ID NOS 253 and 254) and the anti-PD-1 antibody is pidilizumab.

In some embodiments, the IL-15/IL-15Rα heterodimeric Fc fusion protein comprises the amino acid sequence of XENP24045 (SEQ ID NOS 204 and 205) and the anti-PD-1 antibody is nivolumab. In some embodiments, the IL-15/IL-15Rα heterodimeric Fc fusion protein comprises the amino acid sequence of XENP24045 (SEQ ID NOS 204 and 205) and the anti-PD-1 antibody is pembrolizumab. In some embodiments, the IL-15/IL-15Rα heterodimeric Fc fusion protein comprises the amino acid sequence of XENP24045 (SEQ ID NOS 204 and 205) and the anti-PD-1 antibody is pidilizumab.

In some embodiments, the cancer is metastatic cancer. In some embodiments, the cancer is selected from the group consisting of breast cancer, lung cancer, colon cancer, ovarian cancer, melanoma cancer, bladder cancer, renal cancer, kidney cancer, liver cancer, head and neck cancer, colorectal cancer, melanoma, pancreatic cancer, gastric carcinoma cancer, esophageal cancer, mesothelioma, prostate cancer, leukemia, lymphoma, and myeloma.

In some embodiments, the method of treating cancer described herein results in a minimal level of vascular leakage in the patient.

In some embodiments, the level of vascular leakage ranges from a 20% reduction or less in serum albumin in the patient following administration.

In some aspects, provided herein is a method of inducing T cell expansion in a patient comprising administering:

a therapeutically effective amount of an IL-15/IL-15Rα heterodimeric Fc fusion protein comprising:
a) a first monomer comprising, from N- to C-terminal:
  i) an IL-15 receptor alpha (IL-15Rα) sushi domain;
  ii) a first domain linker; and
  iii) a first variant Fc domain comprising CH2-CH3; and
b) a second monomer comprising from N- to C-terminal:
  i) a variant IL-15 domain comprising the amino acid sequence of SEQ ID NO:2 and any one of the amino acid substitutions selected from the group consisting of N4D/N65D, D30N/N65D, and D30N/E64Q/N65D;
  ii) a second domain linker; and
  iii) a second variant Fc domain comprising CH2-CH3; wherein the first and second variant Fc domains have a set of amino acid substitutions selected from the group consisting of S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S S364K/E357L and K370S:S364K/E357Q, according to EU numbering; and a therapeutically effective amount of a checkpoint blockade antibody selected from the group consisting of an anti-PD-1 antibody, an anti-PD-L1 antibody, an anti-TIM3 antibody, an anti-TIGIT antibody, an anti-LAG3 antibody, and an anti-CTLA-4 antibody.

In some embodiments, the variant IL-15 domain comprises the amino acid sequence of SEQ ID NO:2 and the amino acid substitutions D30N/E64Q/N65D. In some embodiments, the variant IL-15 domain comprises the amino acid sequence of SEQ ID NO:2 and the amino acid substitutions D30N/N65D. In some embodiments, the variant IL-15 domain comprises the amino acid sequence of SEQ ID NO:2 and the amino acid substitutions N4D/N65D.

In some embodiments, the IL-15Rα sushi domain comprises the amino acid sequence of SEQ ID NO:4.

In some embodiments, the first and second variant Fc domains have S364K/E357Q:L368D/K370S substitutions. In some embodiments, the first variant Fc domain has S364K/E357Q substitutions and the second variant Fc domain L368D/K370S substitutions.

In some embodiments, the first and second variant Fc domains each comprise M428L/N434S substitutions.

In some embodiments, the first and second variant Fc domains each comprise E233P/L234V/L235A/G236del/S267K substitutions.

In some embodiments, the IL-15/IL-15Rα heterodimeric Fc fusion protein and the checkpoint blockade antibody are administered concomitantly or sequentially.

In some embodiments, the e anti-PD-1 antibody is nivolumab, pembrolizumab, or pidilizumab. In some embodiments, the IL-15/IL-15Rα heterodimeric Fc fusion protein comprises the amino acid sequence of XENP24306 (SEQ ID NOS 253 and 254) or XENP24045 (SEQ ID NOS 204 and 205).

In some embodiments, the IL-15/IL-15Rα heterodimeric Fc fusion protein comprises the amino acid sequence of XENP24306 (SEQ ID NOS 253 and 254) and the anti-PD-1 antibody is nivolumab. In some embodiments, the IL-15/IL-15Rα heterodimeric Fc fusion protein comprises the amino acid sequence of XENP24306 (SEQ ID NOS 253 and 254) and the anti-PD-1 antibody is pembrolizumab. In some embodiments, the IL-15/IL-15Rα heterodimeric Fc fusion protein comprises the amino acid sequence of XENP24306 (SEQ ID NOS 253 and 254) and the anti-PD-1 antibody is pidilizumab.

In some embodiments, the IL-15/IL-15Rα heterodimeric Fc fusion protein comprises the amino acid sequence of XENP24045 (SEQ ID NOS 204 and 205) and the anti-PD-1 antibody is nivolumab. In some embodiments, the IL-15/IL-15Rα heterodimeric Fc fusion protein comprises the amino acid sequence of XENP24045 (SEQ ID NOS 204 and 205) and the anti-PD-1 antibody is pembrolizumab. In some embodiments, the IL-15/IL-15Rα heterodimeric Fc fusion protein comprises the amino acid sequence of XENP24045 (SEQ ID NOS 204 and 205) and the anti-PD-1 antibody is pidilizumab.

In some embodiments, the patient has cancer. In some embodiments, the cancer is metastatic cancer. In some embodiments, the cancer is selected from the group consisting of breast cancer, lung cancer, colon cancer, ovarian cancer, melanoma cancer, bladder cancer, renal cancer, kidney cancer, liver cancer, head and neck cancer, colorectal cancer, melanoma, pancreatic cancer, gastric carcinoma cancer, esophageal cancer, mesothelioma, prostate cancer, leukemia, lymphoma, and myeloma.

In some embodiments, the T cell expansion is at least a 2-fold increase in T cells. In some embodiments, the T cell expansion ranges from a 2-fold to a 15-fold increase in T cells.

In some embodiments, the method does not increase the likelihood of inducing hypoalbuminemia.

In some embodiments, the T cells comprise tumor infiltrating lymphocytes.

In some aspects, the present invention provides a combination therapy comprising an IL-15/IL-15Rα heterodimeric Fc fusion protein and a checkpoint blockade antibody selected from an anti-PD-1 antibody, an anti-PD-L1 antibody, an anti-TIM3 antibody, an anti-TIGIT antibody, an anti-LAG3 antibody, and an anti-CTLA-4 antibody. In some embodiments, the IL-15/IL-15Rα heterodimeric Fc fusion protein comprises:
a) a first monomer comprising, from N- to C-terminal:
  i) an IL-15 receptor alpha (IL-15Rα) sushi domain;
  ii) a first domain linker; and
  iii) a first variant Fc domain comprising CH2-CH3; and
b) a second monomer comprising from N- to C-terminal:
  i) a variant IL-15 domain comprising the amino acid sequence of SEQ ID NO:2 and any one of the amino acid substitutions selected from the group consisting of N4D/N65D, D30N/N65D, and D30N/E64Q/N65D;
  ii) a second domain linker; and
  iii) a second variant Fc domain comprising CH2-CH3; wherein the first and second variant Fc domains have a set of amino acid substitutions selected from the group consisting of S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering.

In some embodiments, the variant IL-15 domain comprises the amino acid sequence of SEQ ID NO:2 and the amino acid substitutions D30N/E64Q/N65D. In some embodiments, the variant IL-15 domain comprises the amino acid sequence of SEQ ID NO:2 and the amino acid substitutions D30N/N65D. In some embodiments, the variant IL-15 domain comprises the amino acid sequence of SEQ ID NO:2 and the amino acid substitutions N4D/N65D.

In some embodiments, the IL-15Rα sushi domain comprises the amino acid sequence of SEQ ID NO:4.

In some embodiments, the first and second variant Fc domains have S364K/E357Q. L368D/K370S substitutions.

In some embodiments, the first variant Fc domain has S364K/E357Q substitutions and the second variant Fc domain L368D/K370S substitutions.

In some embodiments, the first and second variant Fc domains each comprise M428L/N434S substitutions.

In some embodiments, the first and second variant Fc domains each comprise E233P/L234V/L235A/G236del/S267K substitutions.

In some embodiments, the anti-PD-1 antibody is nivolumab, pembrolizumab, or pidilizumab.

In some embodiments, the IL-15/IL-15Rα heterodimeric Fc fusion protein comprises the amino acid sequence of XENP24306 (SEQ ID NOS 253 and 254) or XENP24045 (SEQ ID NOS 204 and 205).

In some embodiments, the IL-15/IL-15Rα heterodimeric Fc fusion protein comprises the amino acid sequence of XENP24306 (SEQ ID NOS 253 and 254) and the anti-PD-1 antibody is nivolumab.

In some embodiments, the IL-15/IL-15Rα heterodimeric Fc fusion protein comprises the amino acid sequence of XENP24306 (SEQ ID NOS 253 and 254) and the anti-PD-1 antibody is pembrolizumab.

In some embodiments, the IL-15/IL-15Rα heterodimeric Fc fusion protein comprises the amino acid sequence of XENP24306 (SEQ ID NOS 253 and 254) and the anti-PD-1 antibody is pidilizumab.

In some embodiments, the IL-15/IL-15Rα heterodimeric Fc fusion protein comprises the amino acid sequence of XENP24045 (SEQ ID NOS 204 and 205) and the anti-PD-1 antibody is nivolumab.

In some embodiments, the IL-15/IL-15Rα heterodimeric Fc fusion protein comprises the amino acid sequence of XENP24045 (SEQ ID NOS 204 and 205) and the anti-PD-1 antibody is pembrolizumab.

In some embodiments, the IL-15/IL-15Rα heterodimeric Fc fusion protein comprises the amino acid sequence of XENP24045 (SEQ ID NOS 204 and 205) and the anti-PD-1 antibody is pidilizumab.

BRIEF DESCRIPTION OF THE DRAWINGS

FIG. 2A and FIG. 2B depict the sequences for IL-15 and its receptors.

FIG. 3A-FIG. 3E depict useful pairs of Fc heterodimerization variant sets (including skew and pI variants). On FIG. 3D and FIG. 3E, there are variants for which there are no corresponding "monomer 2" variants; these are pI variants which can be used alone on either monomer.

FIG. 4 depict a list of isosteric variant antibody constant regions and their respective substitutions. pI_( ) indicates lower pI variants, while pI_(+) indicates higher pI variants. These can be optionally and independently combined with other heterodimerization variants of the inventions (and other variant types as well, as outlined herein).

FIG. 5 depict useful ablation variants that ablate FcγR binding (sometimes referred to as "knock outs" or "KO" variants). Generally, ablation variants are found on both monomers, although in some cases they may be on only one monomer.

FIG. 6A-FIG. 6E show particularly useful embodiments of "non-cytokine" components of the invention.

FIG. 7 depicts a number of exemplary variable length linkers. In some embodiments, these linkers find use linking the C-terminus of IL-15 and/or IL-15Rα(sushi) to the N-terminus of the Fc region. In some embodiments, these linkers find use fusing IL-15 to the IL-15Rα(sushi).

FIG. 8A-FIG. 8D show the sequences of several useful IL-15/Rα-Fc format backbones based on human IgG1, without the cytokine sequences (e.g., the Il-15 and/or IL-15Rα (sushi)). Backbone 1 is based on human IgG1 (356E/358M allotype), and includes C220S on both chain, the S364K/E357Q:L368D/K370S skew variants, the Q295E/N384D/Q418E/N421D pI variants on the chain with L368D/K370S skew variants and the E233P/L234V/L235A/G236del/S267K ablation variants on both chains. Backbone 2 is based on human IgG1 (356E/358M allotype), and includes C220S on both chain, the S364K:L368D/K370S skew variants, the Q295E/N384D/Q418E/N421D pI variants on the chain with L368D/K370S skew variants and the E233P/L234V/L235A/G236del/S267K ablation variants on both chains. Backbone 3 is based on human IgG1 (356E/358M allotype), and includes C220S on both chain, the S364K:L368E/K370S skew variants, the Q295E/N384D/Q418E/N421D pI variants on the chain with L368E/K370S skew variants and the E233P/L234V/L235A/G236del/S267K ablation variants on both chains. Backbone 4 is based on human IgG1 (356E/358M allotype), and includes C220S on both chain, the D401K:K360E/Q362E/T411E skew variants, the Q295E/N384D/Q418E/N421D pI variants on the chain with K360E/Q362E/T411E skew variants and the E233P/L234V/L235A/G236del/S267K ablation variants on both chains. Backbone 5 is based on human IgG1 (356D/358L allotype), and includes C220S on both chain, the S364K/E357Q:L368D/K370S skew variants, the Q295E/N384D/Q418E/N421D pI variants on the chain with L368D/K370S skew variants and the E233P/L234V/L235A/G236del/S267K ablation variants on both chains. Backbone 6 is based on human IgG1 (356E/358M allotype), and includes C220S on both chain, the S364K/E357Q:L368D/K370S skew variants, Q295E/N384D/Q418E/N421D pI variants on the chain with L368D/K370S skew variants and the E233P/L234V/L235A/G236del/S267K ablation variants on both chains, as well as an N297A variant on both chains. Backbone 7 is identical to 6 except the mutation is N297S. Alternative formats for backbones 6 and 7 can exclude the ablation variants E233P/L234V/L235A/G236del/S267K in both chains. Backbone 8 is based on human IgG4, and includes the S364K/E357Q:L368D/K370S skew variants, the Q295E/N384D/Q418E/N421D pI variants on the chain with L368D/K370S skew variants, as well as a S228P (EU numbering, this is S241P in Kabat) variant on both chains that ablates Fab arm exchange as is known in the art. Backbone 9 is based on human IgG2, and includes the S364K/E357Q:L368D/K370S skew variants, the Q295E/N384D/Q418E/N421D pI variants on the chain with L368D/K370S skew variants. Backbone 10 is based on human IgG2, and includes the S364K/E357Q:L368D/K370S skew variants, the Q295E/N384D/Q418E/N421D pI variants on the chain with L368D/K370S skew variants as well as a S267K variant on both chains. Backbone 11 is identical to backbone 1, except it includes M428L/N434S Xtend mutations. Backbone 12 is based on human IgG1 (356E/358M allotype), and includes C220S on both identical chain, the E233P/L234V/L235A/G236del/S267K ablation variants on both identical chains. Backbone 13 is based on human IgG1 (356E/358M allotype), and includes C220S on both chain, the S364K/E357Q. L368D/K370S skew variants, the P217R/P229R/N276K pI variants on the chain with S364K/E357Q skew variants and the E233P/L234V/L235A/G236del/S267K ablation variants on both chains.

Figure 1:
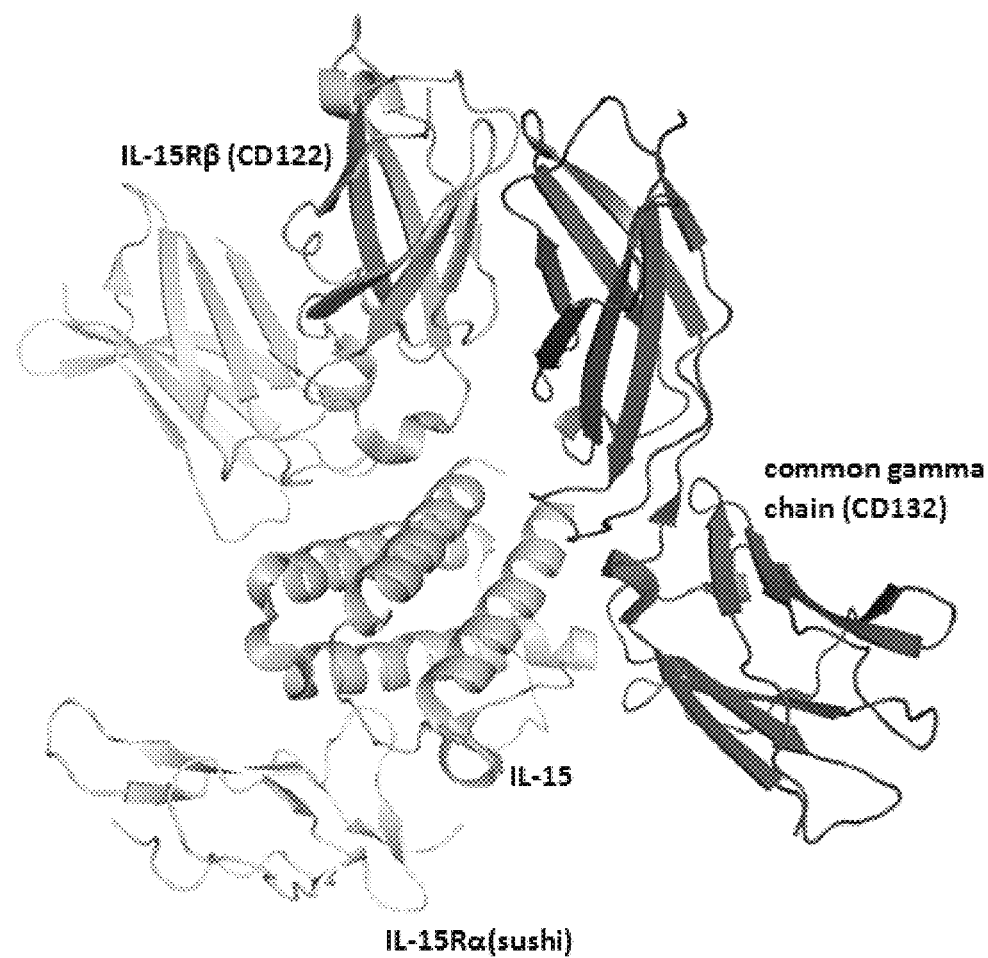
FIG. 1 depicts the structure of IL-15 in complex with its receptors IL-15Rα (CD215), IL-15RP (CD122), and the common gamma chain (CD132).

As will be appreciated by those in the art and outlined below, these sequences can be used with any IL-15 and IL-15Rα(sushi) pairs outlined herein, including but not limited to IL-15/Rα-heteroFc, ncIL-15/Rα, scIL-15/Rα, and dsIL-15/Rα as schematically depicted in FIGS. 9A-9G and 39. Additionally, any IL-15 and/or IL-15Rα(sushi) variants can be incorporated into these FIG. 8A-8D backbones in any combination.

Included within each of these backbones are sequences that are 90, 95, 98 and 99% identical (as defined herein) to the recited sequences, and/or contain from 1, 2, 3, 4, 5, 6, 7, 8, 9 or 10 additional amino acid substitutions (as compared to the "parent" of the Figure, which, as will be appreciated by those in the art, already contain a number of amino acid modifications as compared to the parental human IgG1 (or IgG2 or IgG4, depending on the backbone). That is, the recited backbones may contain additional amino acid modifications (generally amino acid substitutions) in addition to the skew, pI and ablation variants contained within the backbones of this figure.

FIG. 9A-FIG. 9G depict several formats for the IL-15/Rα-Fc fusion proteins of the present invention. IL-15Rα Heterodimeric Fc fusion or "IL-15/Rα-heteroFc" (FIG. 9A) comprises IL-15 recombinantly fused to one side of a heterodimeric Fc and IL-15Rα(sushi) recombinantly fused to the other side of a heterodimeric Fc. The IL-15 and IL-15Rα(sushi) may have a variable length Gly-Ser linker between the C-terminus and the N-terminus of the Fc region. Single-chain IL-15/Rα-Fc fusion or "scIL-15/Rα-Fc" (FIG. 9B) comprises IL-15Rα(sushi) fused to IL-15 by a variable length linker (termed a "single-chain" IL-15/IL-15Rα(sushi) complex or "scIL-15/Rα") which is then fused to the N-terminus of a heterodimeric Fc-region, with the other side of the molecule being "Fc-only" or "empty Fc". Non-covalent IL-15/Rα-Fc or "ncIL-15/Rα-Fc" (FIG. 9C) comprises IL-15Rα(sushi) fused to a heterodimeric Fc region, while IL-15 is transfected separatedly so that a non-covalent IL-15/Rα complex is formed, with the other side of the molecule being "Fc-only" or "empty Fc". Bivalent non-covalent IL-15/Rα-Fc fusion or "bivalent ncIL-15/Rα-Fc" (FIG. 9D) comprises IL-15Rα(sushi) fused to the N-terminus of a homodimeric Fc region, while IL-15 is transfected separately so that a non-covalent IL-15/Rα complex is formed. Bivalent single-chain IL-15/Rα-Fc fusion or "bivalent scIL-15/Rα-Fc" (FIG. 9E) comprises IL-15 fused to IL-15Rα(sushi) by a variable length linker (termed a "single-chain" IL-15/IL-15Rα(sushi) complex or "scIL-15/Rα") which is then fused to the N-terminus of a homodimeric Fc-region. Fc-non-covalent IL-15/Rα fusion or "Fc-ncIL-15/Rα" (FIG. 9F) comprises IL-15Rα(sushi) fused to the C-terminus of a heterodimeric Fc region, while IL-15 is transfected separately so that a non-covalent IL-15/Rα complex is formed, with the other side of the molecule being "Fc-only" or "empty Fc". Fc-single-chain IL-15/Rα fusion or "Fc-scIL-15/Rα" (FIG. 9G) comprises IL-15 fused to IL-15Rα(sushi) by a variable length linker (termed a "single-chain" IL-15/IL-15Rα(sushi) complex or "scIL-15/Rα") which is then fused to the C-terminus of a heterodimeric Fc region, with the other side of the molecule being "Fc-only" or "empty Fc".

FIG. 10 depicts sequences of XENP20818 and XENP21475, illustrative IL-15/Rα-Fc fusion proteins of the "IL-15/Rα-heteroFc" format, with additional sequences of XENP20819, XENP21471, XENP21472, XENP21473, XENP21474, XENP21476, XENP21477 being listed in WO2018071919 in FIGS. 104A-104D, respectively and as SEQ ID NOS: 418-423, 424-429, 430-435, 436-441, 442-447, 454-459, and 460-465, respectively. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

Figure 104A:
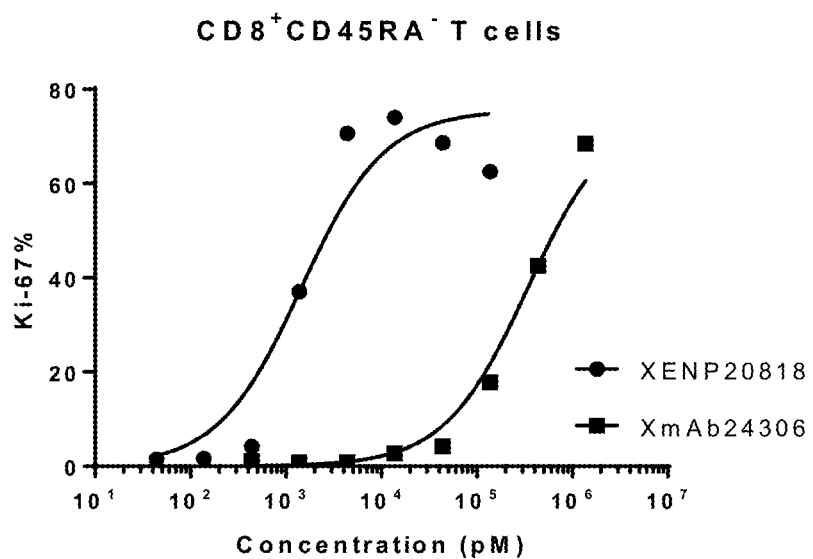
Figure 104B:
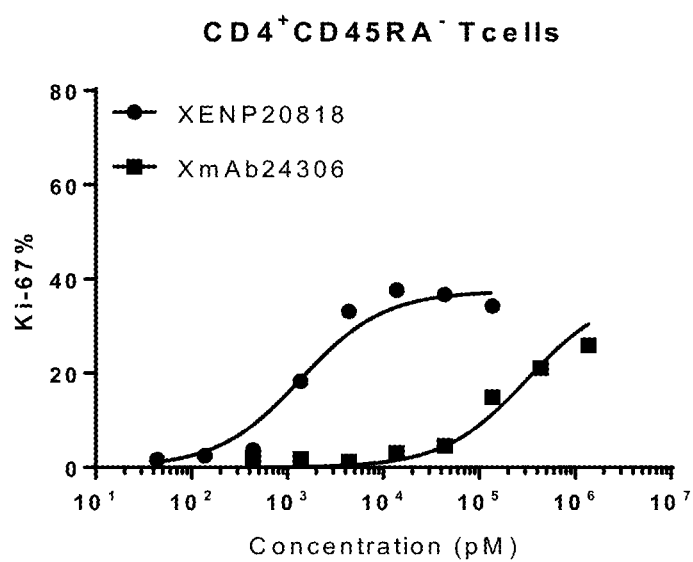
Figure 104C:
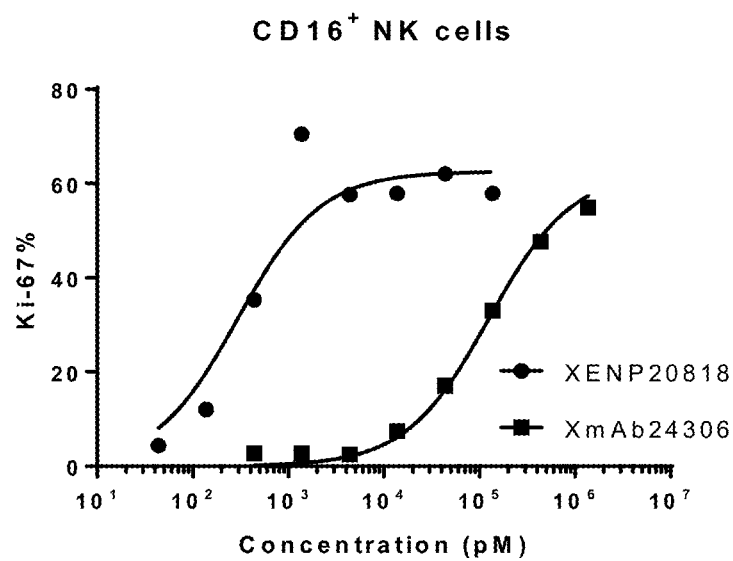
Figure 104D:
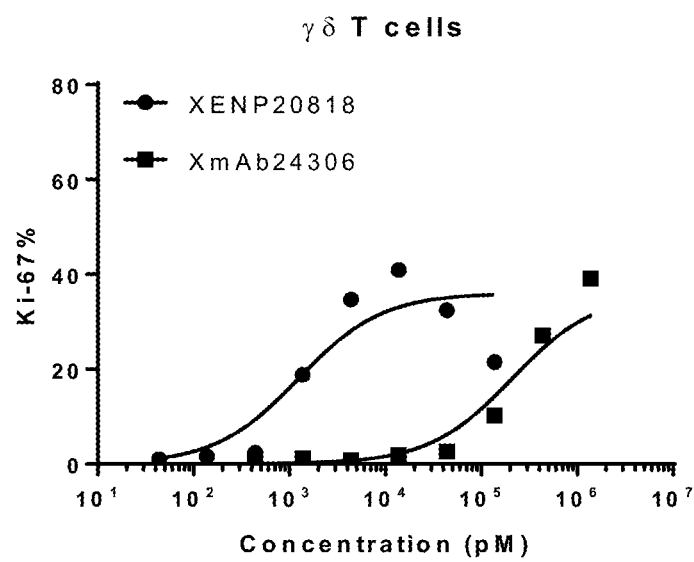

FIG. 11 depicts sequences of XENP21478, an illustrative IL-15/Rα-Fc fusion protein of the "scIL-15/Rα-Fc" format, with additional sequences of XENP21993, XENP21994, XENP21995, XENP23174, XENP23175, XENP24477, and XENP24480 being listed in WO2018071919 in FIGS. 104G, 104H, 104AG, 104AU, and 104AV, respectively and as SEQ ID NOS: 514-518, 519-523, 524-528, 849-853, 1063-1067, and 1078-1082, respectively. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 12A-FIG. 12B depict sequences of XENP21479, XENP22366 and XENP24348, illustrative IL-15/Rα-Fc fusion proteins of the "ncIL-15/Rα-Fc" format. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 13 depicts sequences of XENP21978, an illustrative IL-15/Rα-Fc fusion protein of the "bivalent ncIL-15/Rα-Fc" format, with additional sequences of XENP21979 being listed in WO2018071919 in FIG. 104E and as SEQ ID NOS: 480-483. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 14 depicts sequences of an illustrative IL-15/Rα-Fc fusion protein of the "bivalent scIL-15/Rα-Fc" format. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 15 depicts sequences of XENP22637, an illustrative IL-15/Rα-Fc fusion protein of the "Fc-ncIL-15/Rα" format, with additional sequences of XENP22638 being listed in WO2018071919 in FIG. 104T and as SEQ ID NOS: 668-672. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 16 depicts sequences of an illustrative IL-15/Rα-Fc fusion protein of the "Fc-scIL-15/Rα" format. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

Figure 17D:
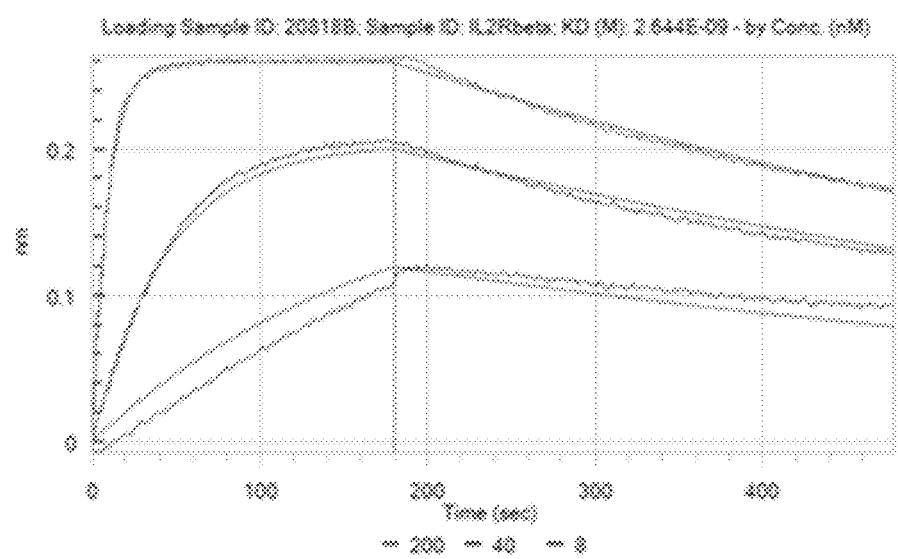

FIG. 17A-FIG. 17E provide data for an illustrative IL-15/Rα-Fc fusion protein format for XENP20818. FIG. 17A depicts the IL-15/Rα-Fc fusion protein format for XENP20818. FIG. 17B depicts the purity and homogeneity of XENP20818 as determined by SEC. FIG. 17C depicts the purity and homogeneity of XENP20818 as determined by CEF.

Figure 17E:
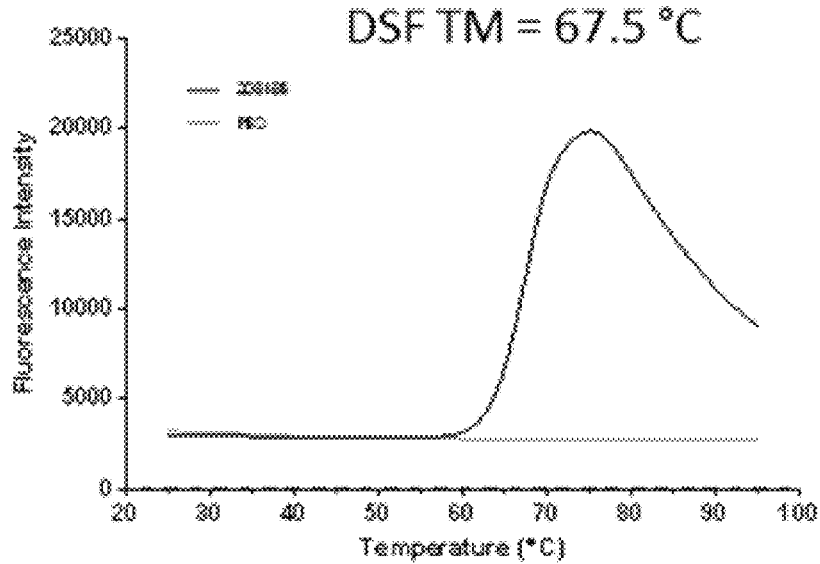

FIG. 17D depicts the affinity of XENP20818 for IL-2RB as determined by Octet. FIG. 17E depicts the stability of XENP20818 as determined by DSF.

Figure 18D:
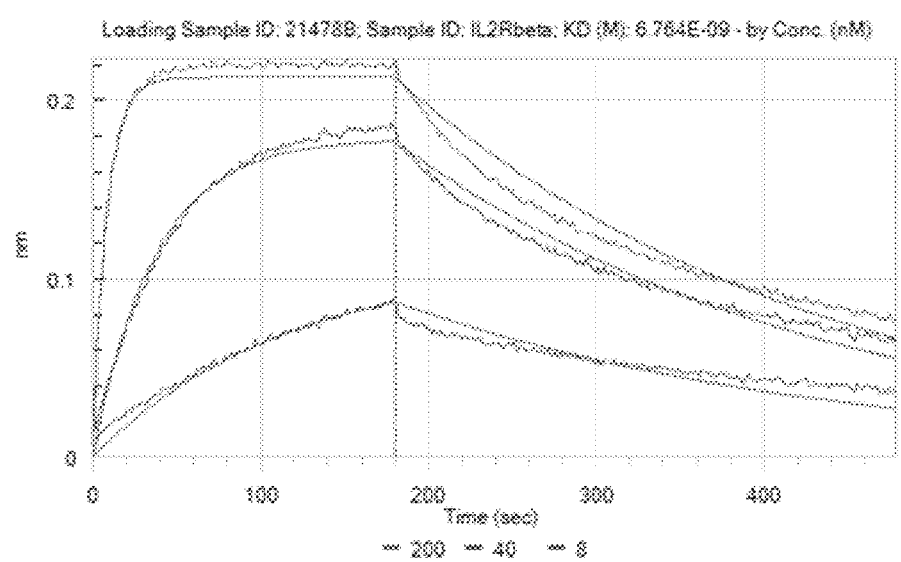

FIG. 18A-FIG. 18E provide data for an illustrative IL-15/Rα-Fc fusion protein format for XENP21478. FIG. 18A depicts the IL-15/Rα-Fc fusion protein format for XENP21478. FIG. 18B depicts the purity and homogeneity of XENP21478 as determined by SEC. FIG. 18C depicts the purity and homogeneity of XENP21478 as determined by CEF.

Figure 18E:
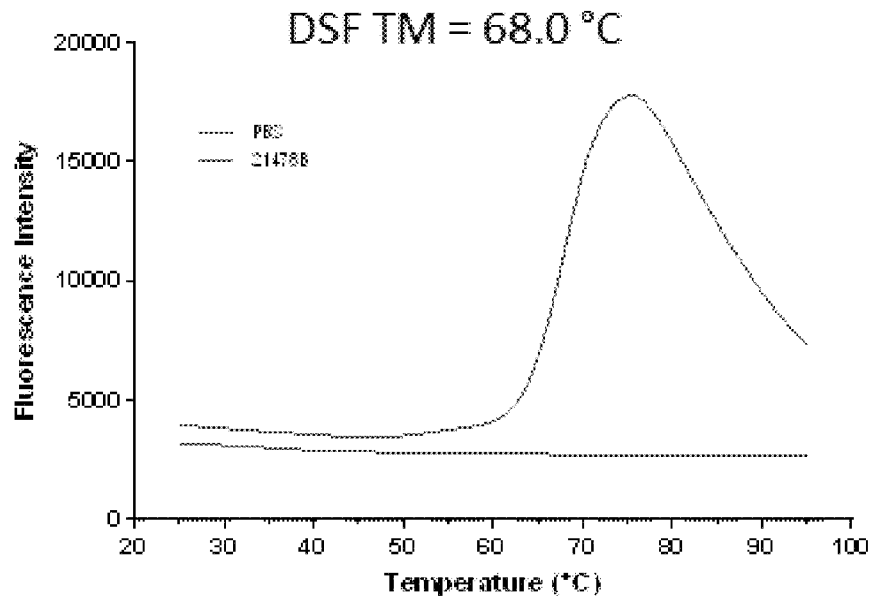

FIG. 18D depicts the affinity of XENP21478 for IL-2RB as determined by Octet. FIG. 18E depicts the stability of XENP21478 as determined by DSF.

Figure 19D:
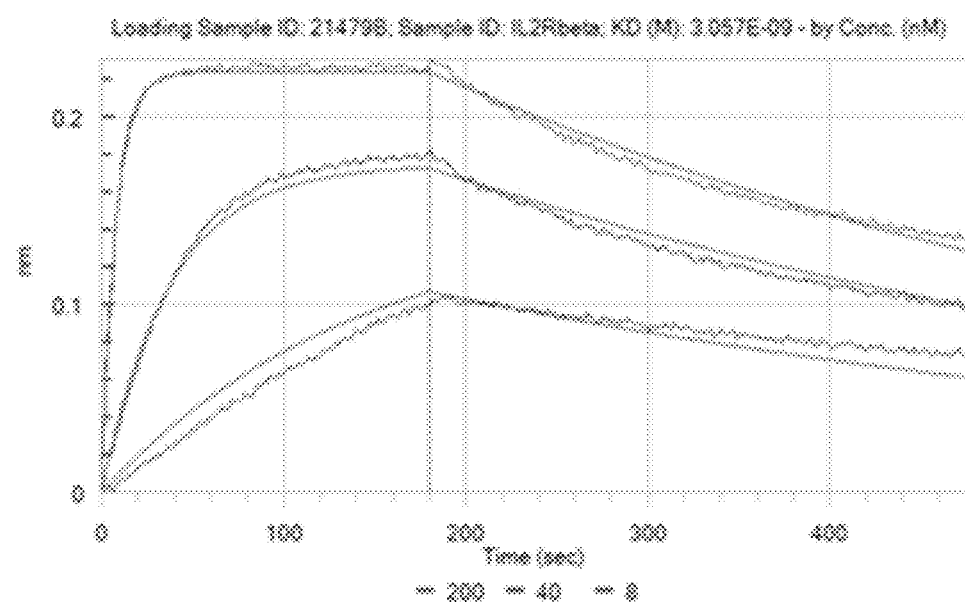

FIG. 19A-FIG. 19E provide data for an illustrative IL-15/Rα-Fc fusion protein format for XENP21479. FIG. 19A depicts the IL-15/Rα-Fc fusion protein format for XENP21479. FIG. 19B depicts the purity and homogeneity of XENP21479 as determined by SEC. FIG. 19C depicts the purity and homogeneity of XENP21479 as determined by CEF.

Figure 19E:
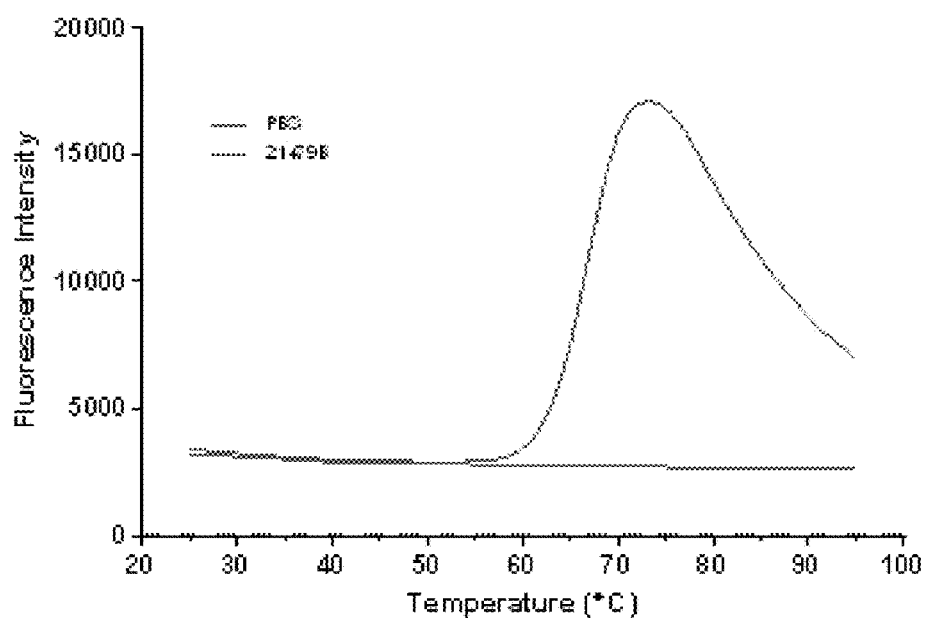

FIG. 19D depicts the affinity of XENP21479 for IL-2RB as determined by Octet. FIG. 19E depicts the stability of XENP21479 as determined by DSF.

Figure 20A:
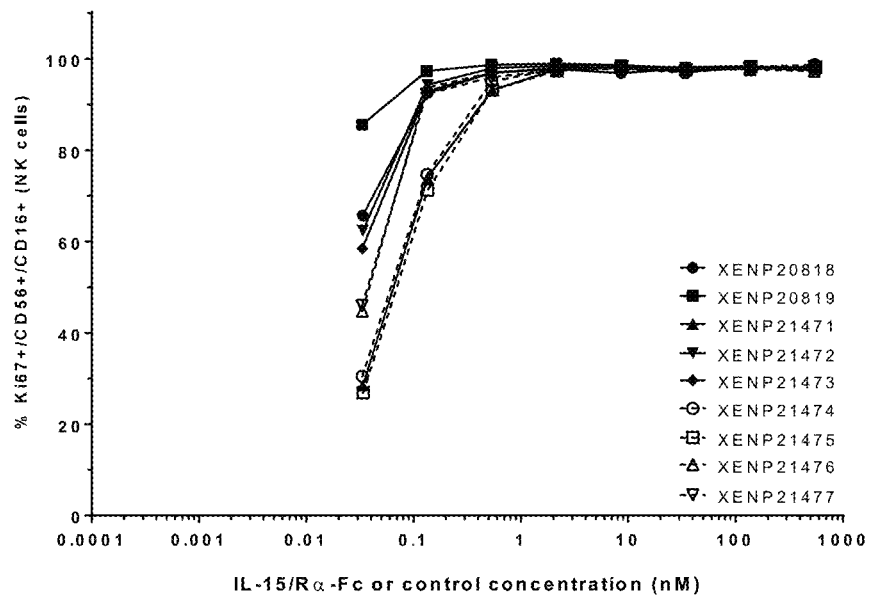
Figure 20B:
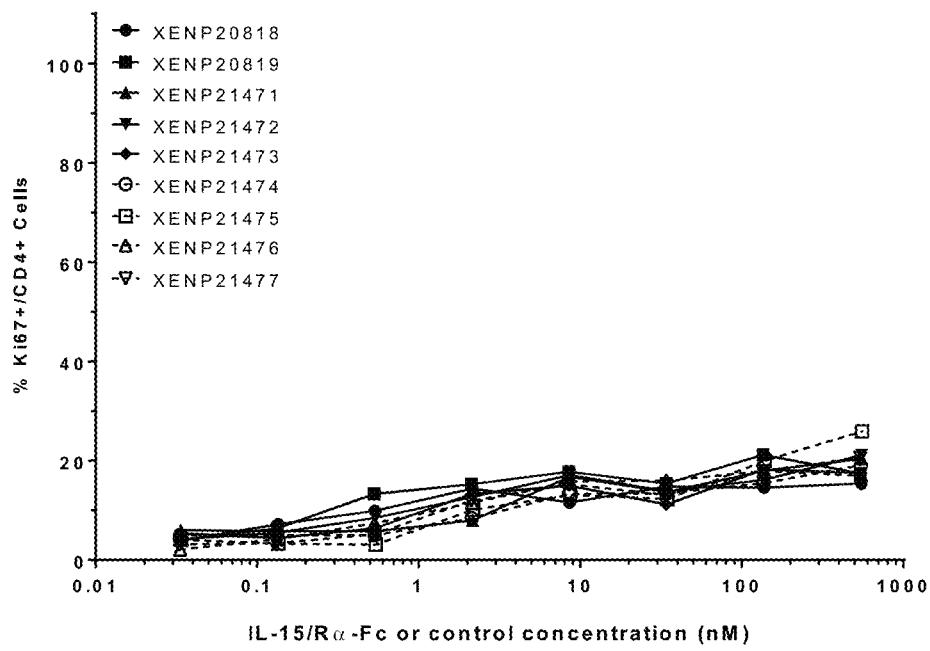
Figure 20C:
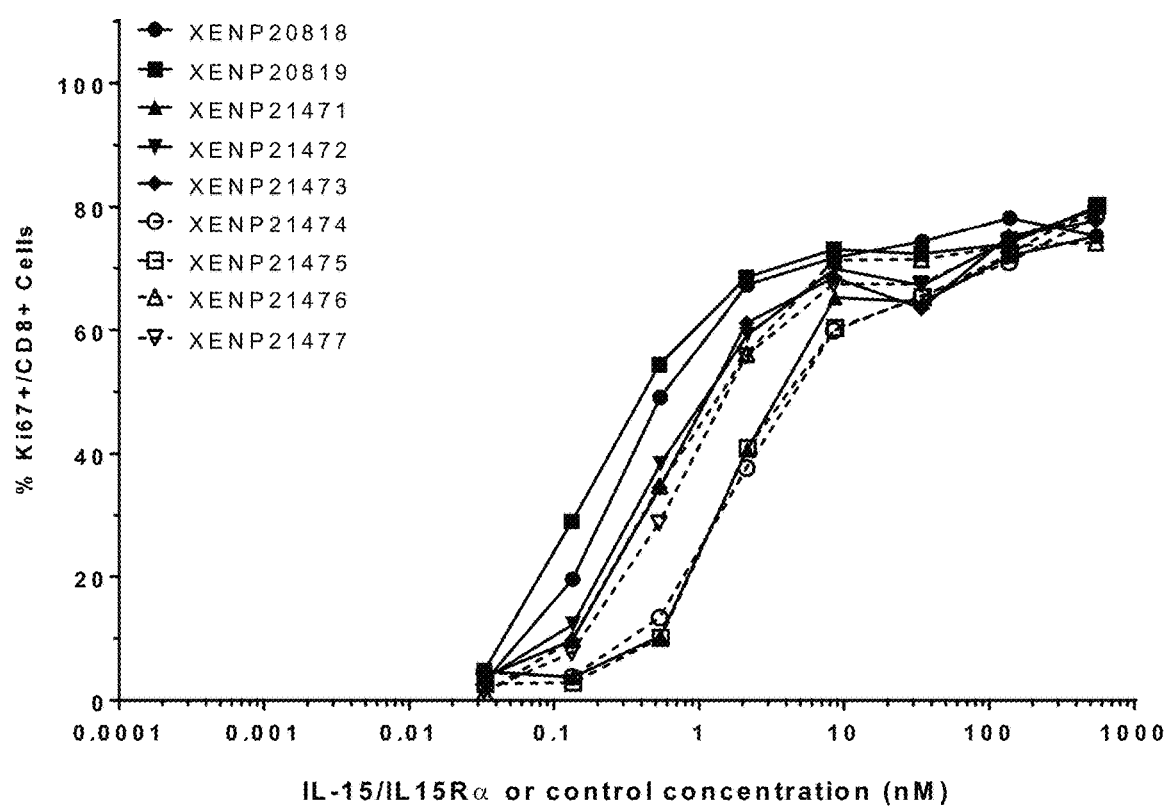

FIG. 20A-FIG. 20C depict the induction of NK (CD56+/CD16*) cells (FIG. 20A), CD4+ T cells (FIG. 20B), and CD8+ T cells (FIG. 20C) proliferation by illustrative IL-15/Rα-Fc fusion proteins of the TL-15/Rα-heteroFc format with different linker lengths based on Ki67 expression as measured by FACS.

Figure 21A:
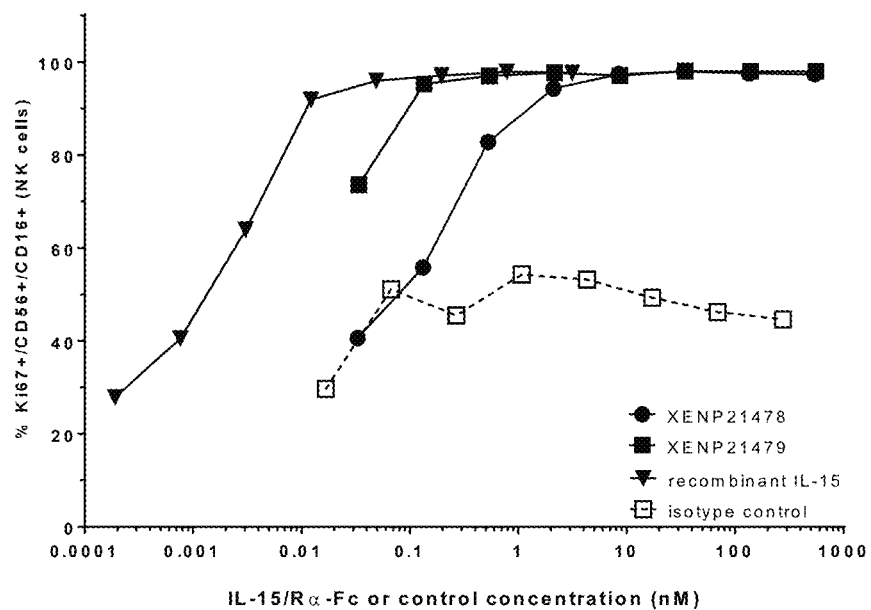
Figure 21B:
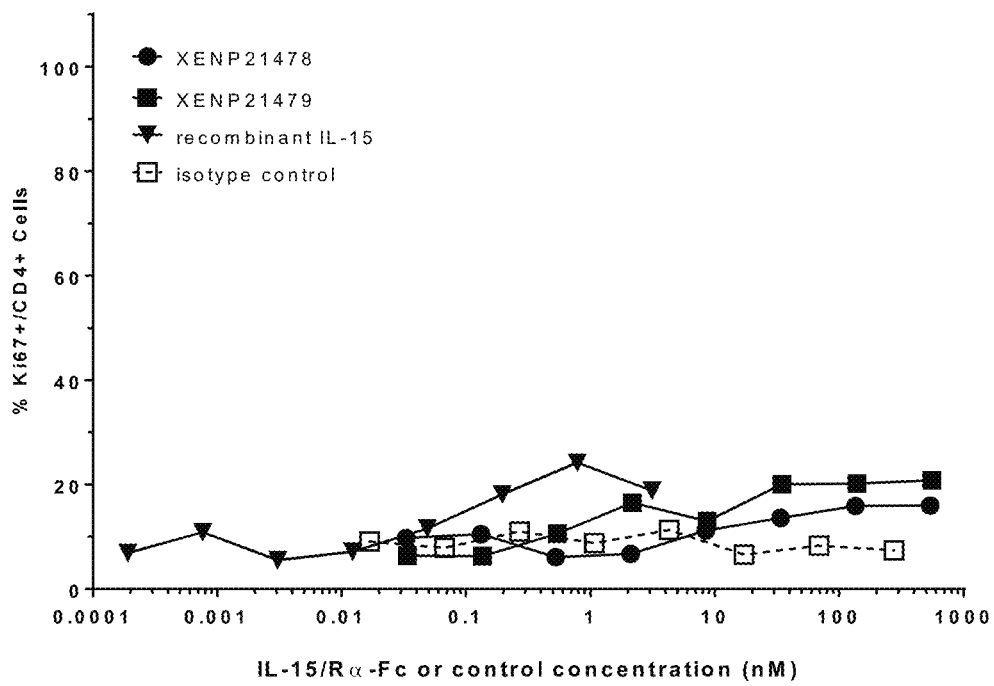
Figure 21C:
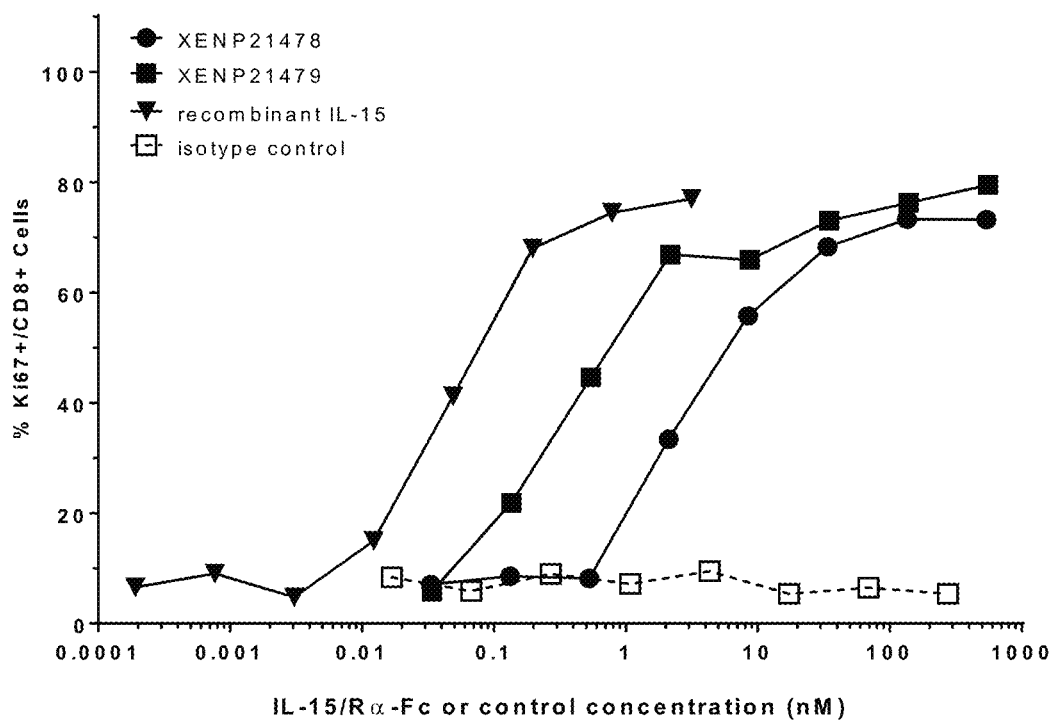

FIG. 21A-FIG. 21C depict the induction of NK (CD56+/CD16*) cells (FIG. 21A), CD4+ T cells (FIG. 21B), and CD8+ T cells (FIG. 21C) proliferation by illustrative IL-15/Rα-Fc fusion proteins of the scIL-15/Rα-Fc format (XENP21478) and the ncIL-15/Rα-Fc format (XENP21479) based on Ki67 expression as measured by FACS.

Figure 22:
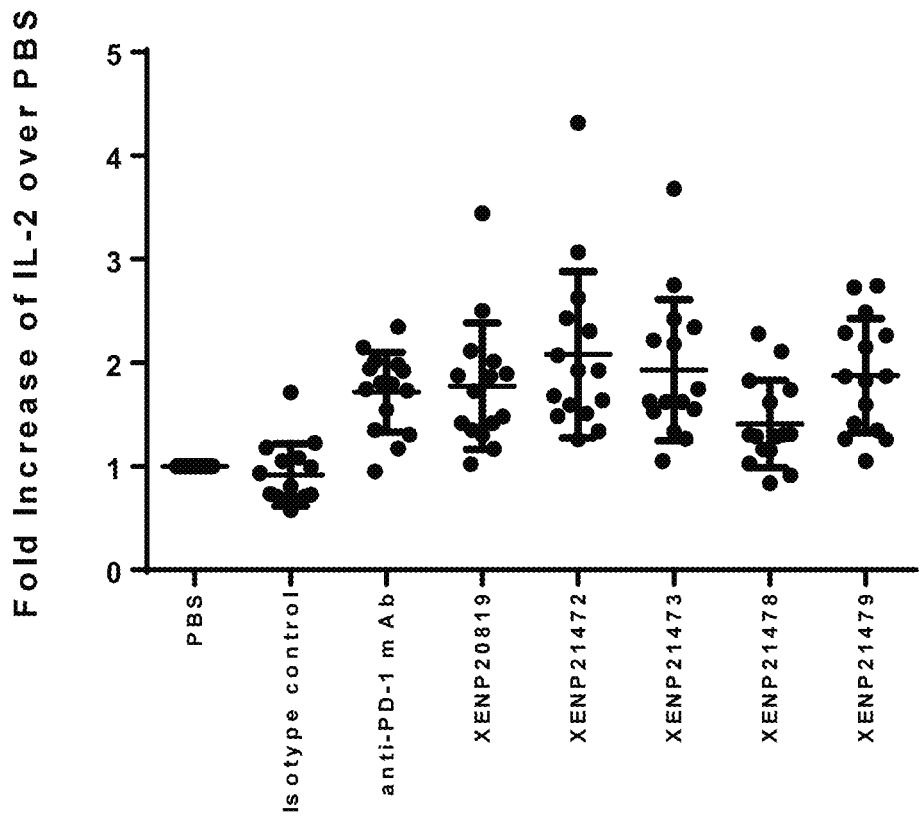

FIG. 22 depicts enhancement of IL-2 secretion by illustrative IL-15/Rα-Fc fusion proteins, an isotype control, and a bivalent anti-PD-1 antibody over PBS control in an SEB-stimulated PBMC assay.

Figure 23:
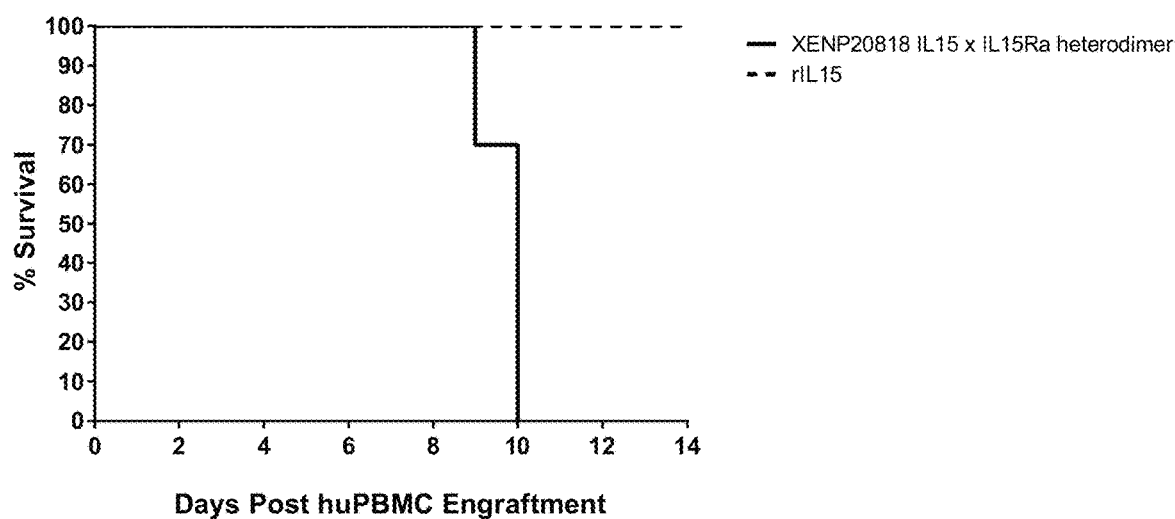

FIG. 23 depicts the survival curve for PBMC-engrafted NSG mice following treatment with XENP20818 and recombinant IL-15.

Figure 24:
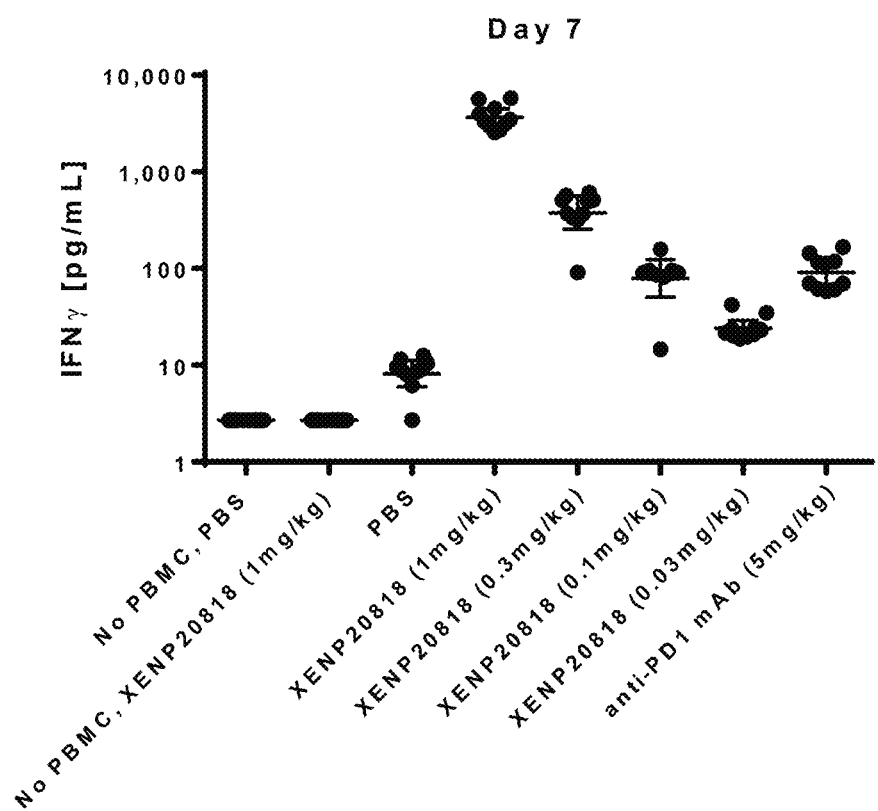

FIG. 24 depicts the concentration of IFNγ in serum of NSG mice on Day 7 after engraftment with human PBMCs and treatment with XENP20818 at the indicated concentrations.

Figure 25A:
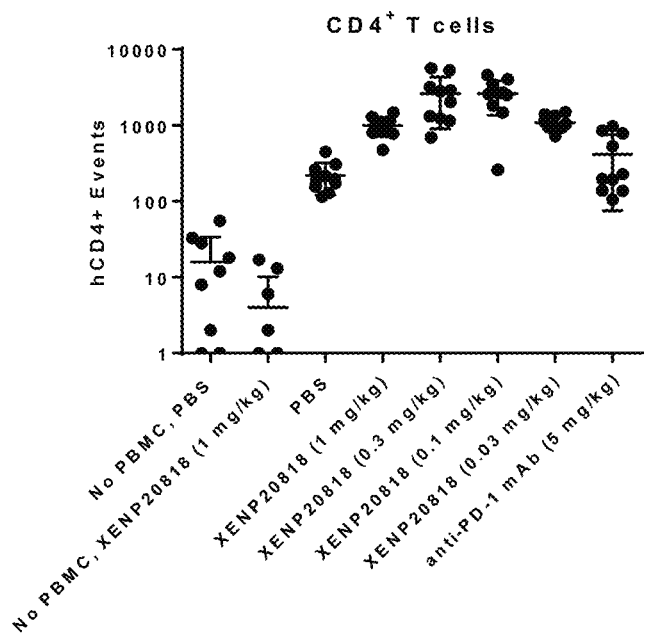
Figure 25B:
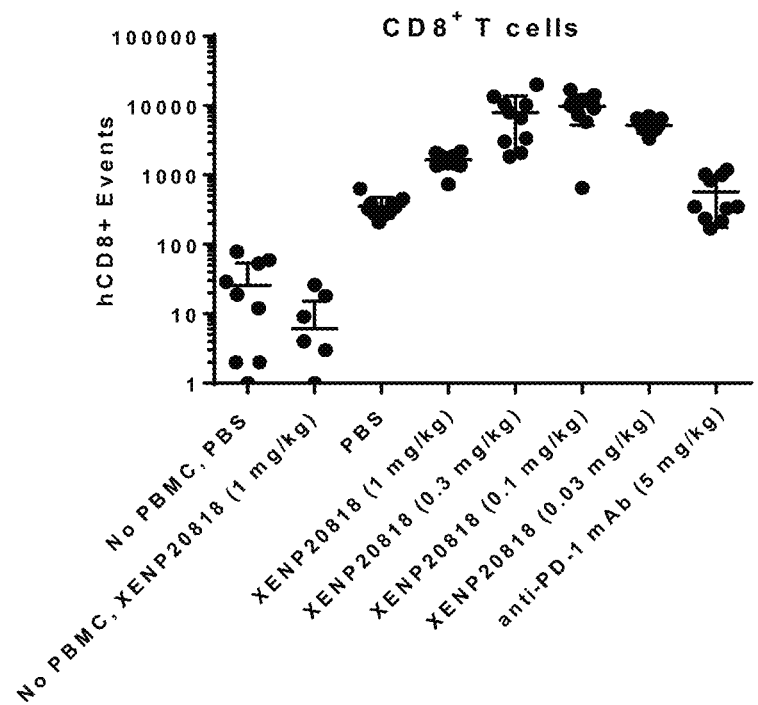
Figure 25C:
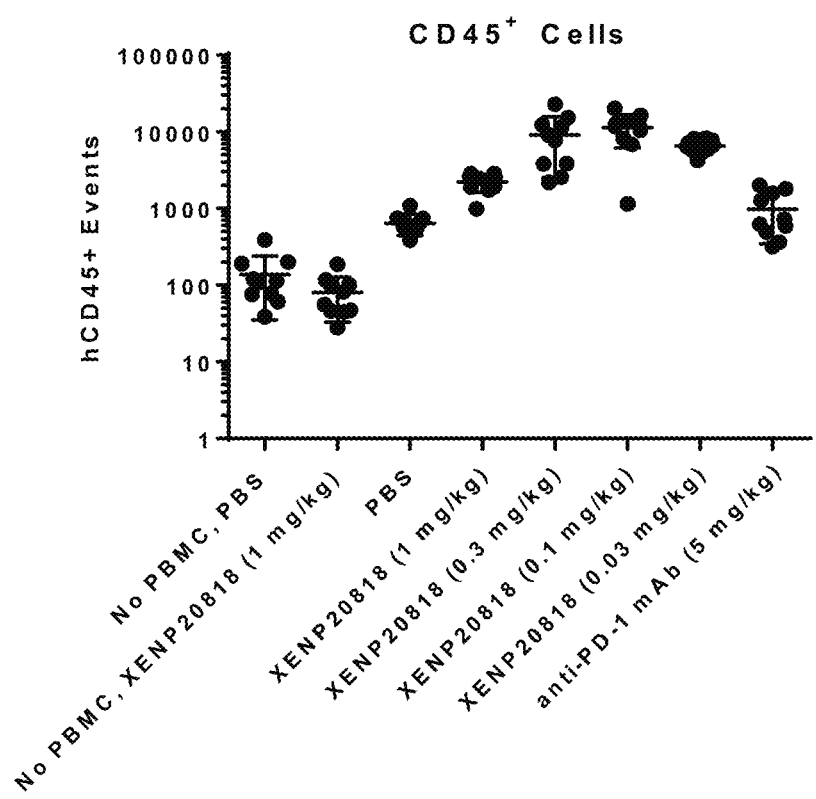

FIGS. 25A-25C depict CD4+ T cell (FIG. 25A), CD8+ T cell (FIG. 25B), and CD45+ cell (FIG. 25C) counts in whole blood of human PBMC-engrafted NSG mice 7 days after treatment with XENP20818 at the indicated concentrations.

Figure 26:
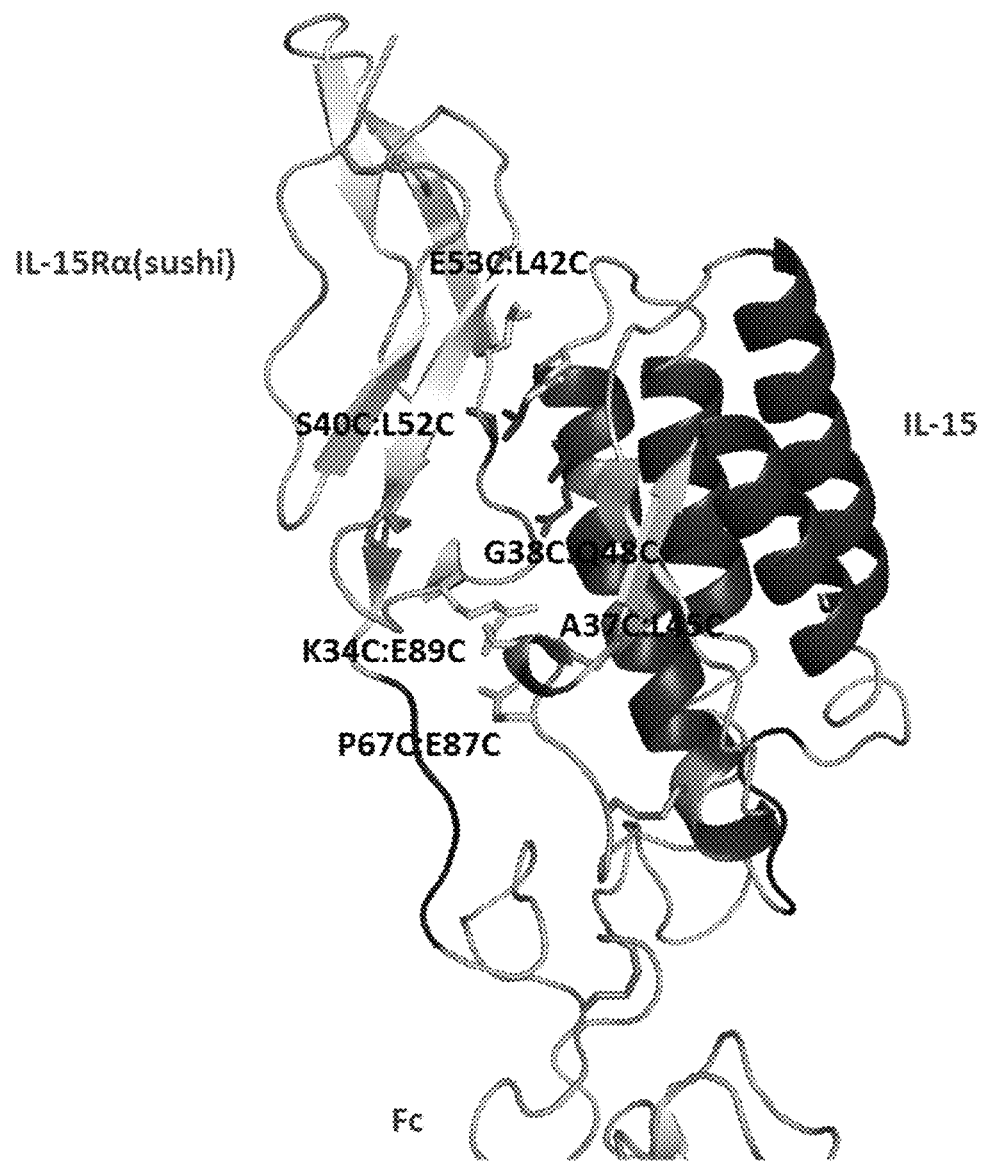

FIG. 26 depicts a structural model of the IL-15/Rα heterodimer showing locations of engineered disulfide bond pairs.

FIG. 27 depicts sequences for illustrative IL-15Rα(sushi) variants engineered with additional residues at the C-terminus to serve as a scaffold for engineering cysteine residues.

FIG. 28 depicts sequences for illustrative IL-15 variants engineered with cysteines in order to form covalent disulfide bonds with IL-15Rα(sushi) variants engineered with cysteines.

FIG. 29 depicts sequences for illustrative IL-15Rα(sushi) variants engineered with cysteines in order to form covalent disulfide bonds with IL-15 variants engineered with cysteines.

Figure 30A:
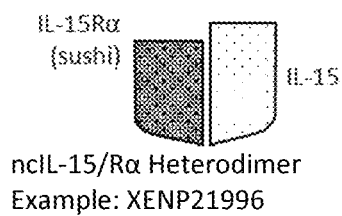
Figure 30B:
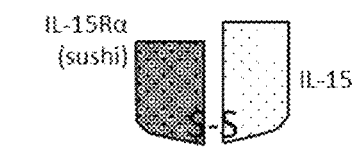
Figure 30C:
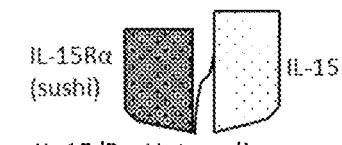

FIG. 30A-FIG. 30C depict IL-15/Rα heterodimers with and without engineered disulfide bonds between IL-15 and IL-15Rα(sushi). Non-covalent IL-15/Rα heterodimer or "ncIL-15/Rα heterodimer" (FIG. 30A) comprises IL-15Rα(sushi) and IL-15 transfected separately and non-covalently linked. Disulfide-bonded IL-15/Rα heterodimer or "dsIL-15/Rα heterodimer" (FIG. 30B) comprises IL-15Rα(sushi) and IL-15 transfected separately and covalently linked as a result of engineered cysteines. Single-chain IL-15/Rα heterodimer or "scIL-15/Rα Heterodimer" (FIG. 30C) comprises IL-15Rα(sushi) fused to IL-15 by a variable length Gly-Ser linker.

FIG. 31 depicts sequences of XENP21996, an illustrative ncIL-15/Rα heterodimer. It is important to note that these sequences were generated using polyhistidine (His×6 or HHHHHH (SEQ ID NO: 10)) C-terminal tags at the C-terminus of IL-15Rα(sushi).

FIG. 32 depicts sequences of XENP22004, XENP22005, XENP22006, XENP22008, and XENP22494, illustrative dsIL-15/Rα heterodimers, with additional sequences of XENP22007, XENP22009, XENP22010, XENP22011, XENP22012, and XENP22493 depicted in WO2018071919 in FIGS. 104J, 104K, and 104I, respectively and as SEQ ID NOS: 543-544, 545-546, 547-548, 551-552, 553-554, AND 647-648, respectively. It is important to note that these sequences were generated using polyhistidine (His×6 or HHHHHH (SEQ ID NO: 10)) C-terminal tags at the C-terminus of IL-15Rα(sushi).

FIG. 33 depicts the sequence for XENP22049, an illustrative scIL-15/Rα Heterodimer. It is important to note that these sequences were generated using polyhistidine (His×6 or HHHHHH (SEQ ID NO: 10)) C-terminal tags at the C-terminus of IL-15. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, and linker.

Figure 34:
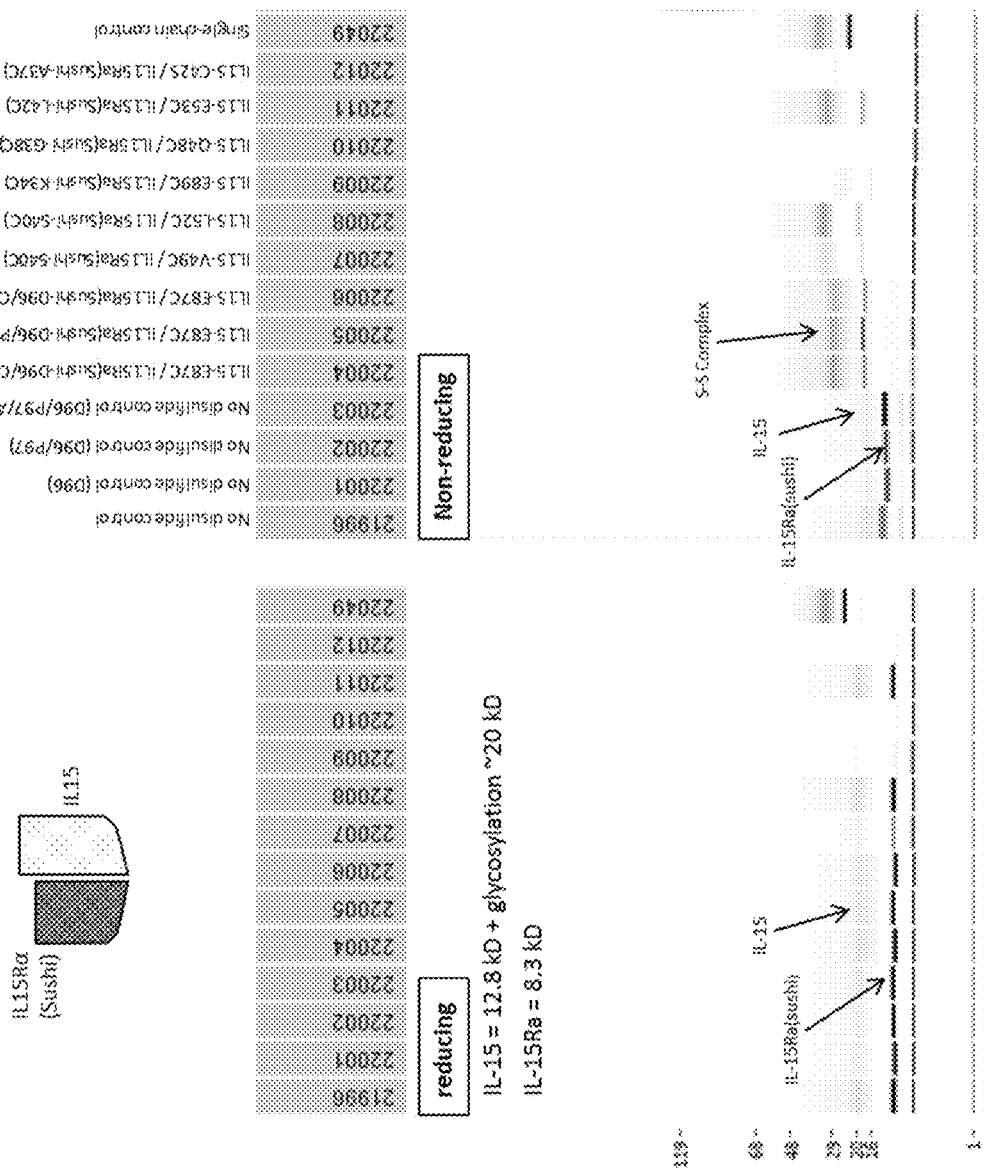

FIG. 34 depicts the purity and homogeneity of illustrative IL-15/Rα heterodimers with and without engineered disulfide bonds as determined by CEF.

Figure 35:
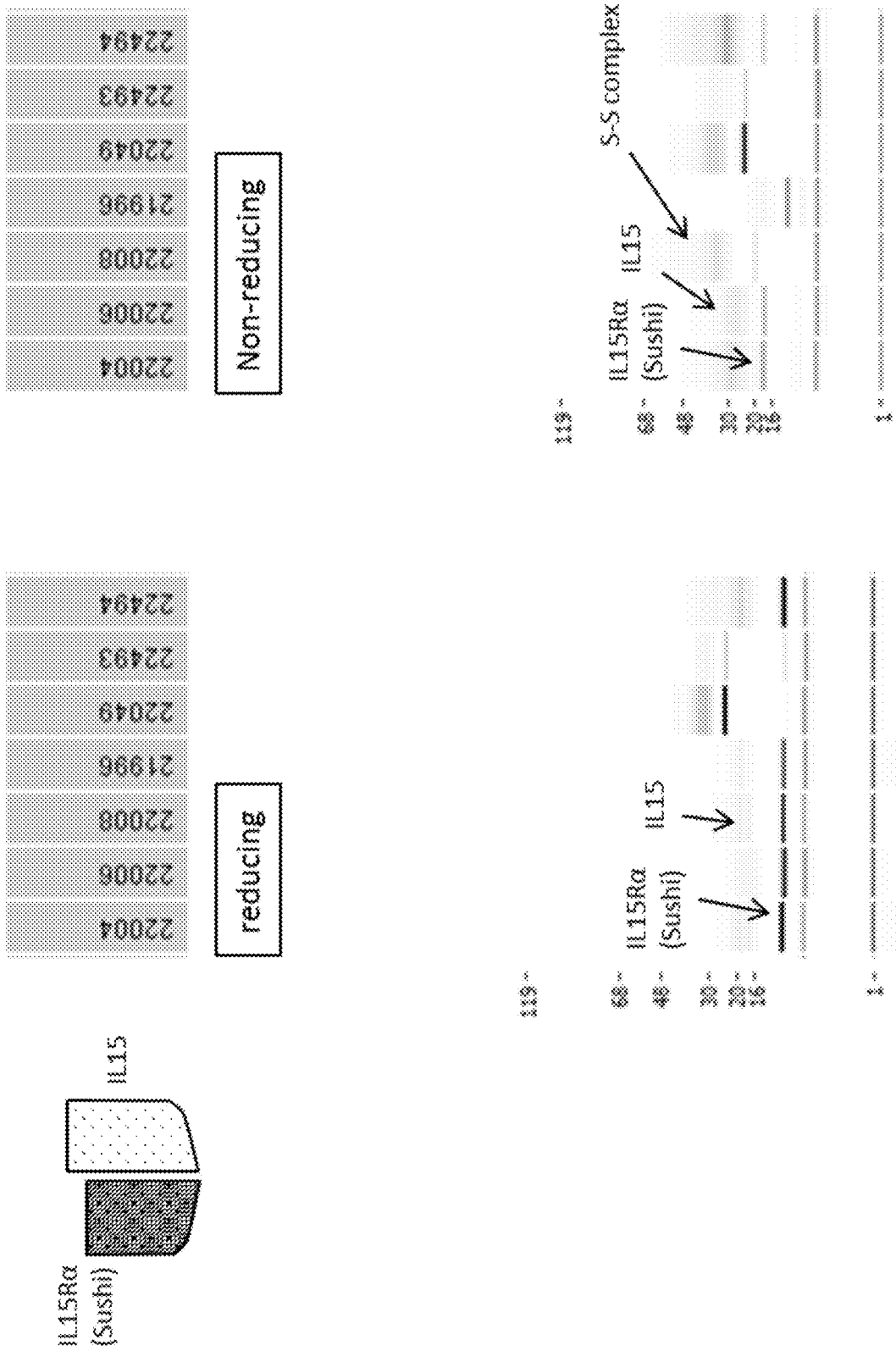

FIG. 35 depicts the purity and homogeneity of illustrative IL-15/Rα heterodimers with and without engineered disulfide bonds as determined by CEF.

Figure 36:
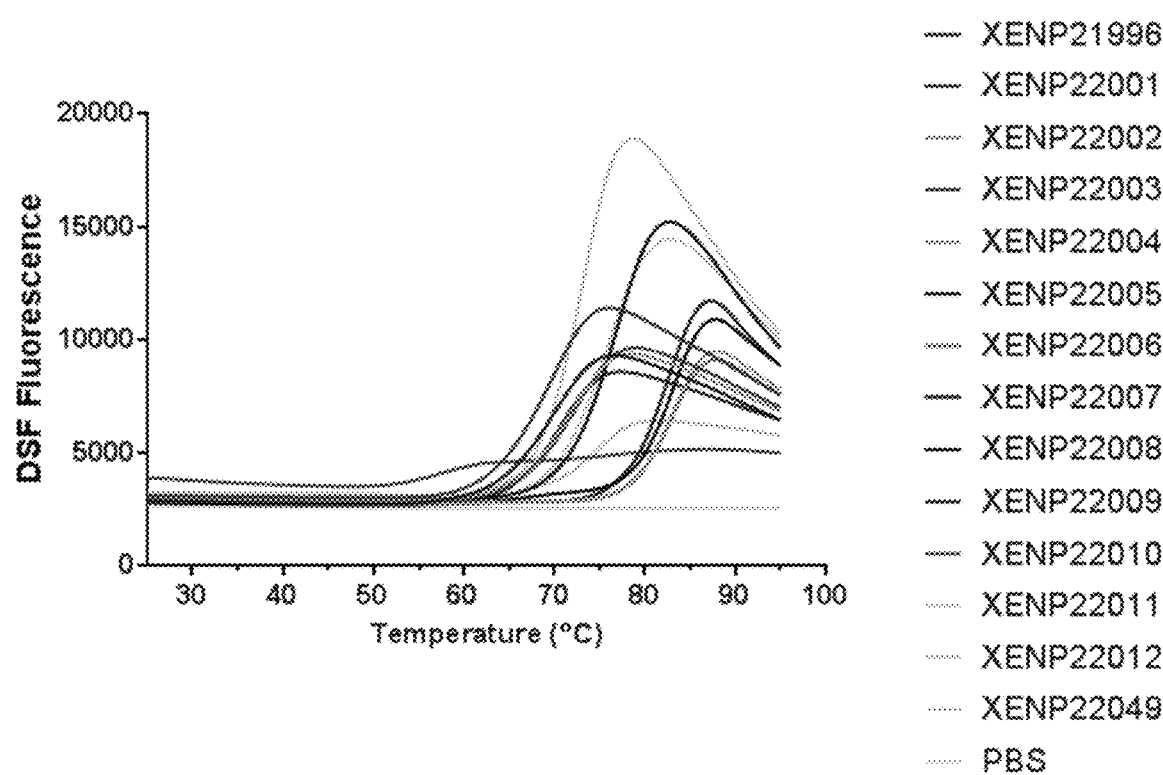

FIG. 36 depicts the stability and melting temperatures of illustrative IL-15/Rα heterodimers with and without engineered disulfide bonds as indicated by melting curves from DSF.

Figure 37:
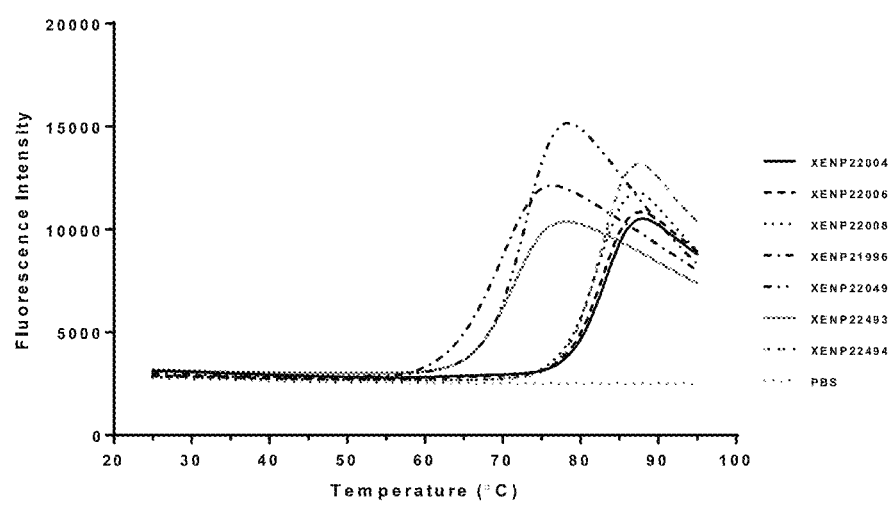
Figure 39A:
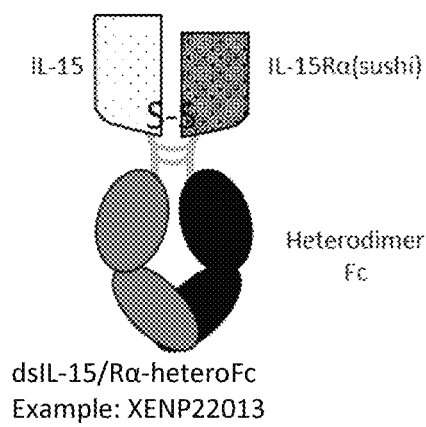
Figure 39B:
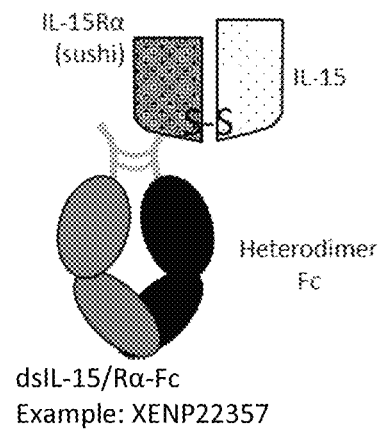
Figure 39C:
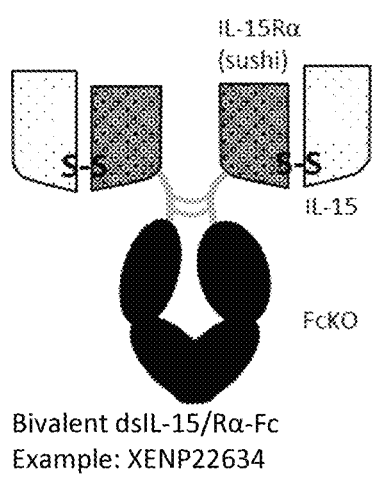
Figure 39D:
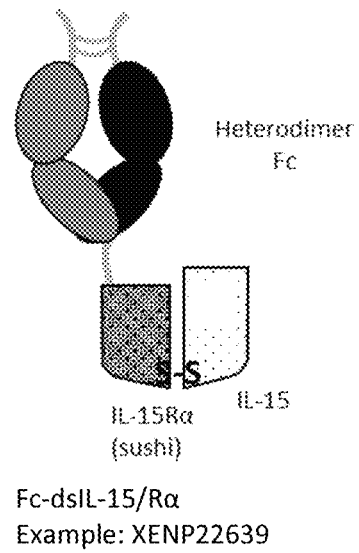

FIG. 37 depicts the stability and melting temperatures of illustrative IL-15/Rα heterodimers with and without engineered disulfide bonds as indicated by melting curves from DSF.

FIG. 38 depicts the expression yield, molecular weight, predicted change in affinity between IL-15 and IL-15Rα (sushi) as calculated by MOE software, melting temperature, and affinity for IL-2Rβ for IL-15/Rα heterodimers with and without engineered disulfide bonds. Mutations are indicated in parentheses after the relevant monomer.

FIG. 39A-FIG. 39D depict additional formats for the IL-15/Rα-Fc fusion proteins of the present invention with engineered disulfide bonds. Disulfide-bonded IL-15/Rα heterodimeric Fc fusion or "dsIL-15/Rα-heteroFc" (FIG. 39A) is the same as "IL-15/Rα-heteroFc", but wherein IL-15Rα (sushi) and IL-15 are further covalently linked as a result of engineered cysteines. Disulfide-bonded IL-15/Rα Fc fusion or "dsIL-15/Rα-Fc" (FIG. 39B) is the same as "ncIL-15/Rα-Fc", but wherein IL-15Rα(sushi) and IL-15 are further covalently linked as a result of engineered cysteines. Bivalent disulfide-bonded IL-15/Rα-Fc or "bivalent dsIL-15/Rα-

Fc" (FIG. 39C) is the same as "bivalent ncIL-15/Rα-Fc", but wherein IL-15Rα(sushi) and IL-15 are further covalently linked as a result of engineered cysteines. Fc-disulfide-bonded IL-15/Rα fusion or "Fc-dsIL-15/Rα" (FIG. 39D) is the same as "Fc-ncIL-15/Rα", but wherein IL-15Rα(sushi) and IL-15 are further covalently linked as a result of engineered cysteines.

FIG. 40A-FIG. 40B depict sequences of XENP22013, XENP22014, XENP22015, and XENP22017, illustrative IL-15/Rα-Fc fusion protein of the "dsIL-15/Rα-heteroFc" format. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 41A-FIG. 41B depict sequences of XENP22357, XENP22358, XENP22359, XENP22684, and XENP22361, illustrative IL-15/Rα-Fc fusion proteins of the "dsIL-15/Rα-Fc" format. Additional sequences of XENPs 22360, 22362, 22363, 22364, 22365, 22366 are depicted in WO2018/071919 in FIGS. 104O, 104P, 104Q, and 104R, respectively, and as SEQ ID NOS:612-616, 622-626, 627-631, 632-636, 637-641, and 642-646, respectively, herein incorporated by reference in its entirety. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 42 depicts sequences of XENP22634, XENP22635, and XENP22636, illustrative IL-15/Rα-Fc fusion proteins of the "bivalent dsIL-15/Rα-Fc" format. Additional sequences of XENP22687 are depicted in WO2018/071919 in FIG. 104V and as SEQ ID NOS:685-688, herein incorporated by reference in its entirety. IL-15 and IL-15Rα (sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 43 depicts sequences of XENP22639 and XENP22640, illustrative IL-15/Rα-Fc fusion proteins of the "Fc-dsIL-15/Rα" format. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

Figure 44:
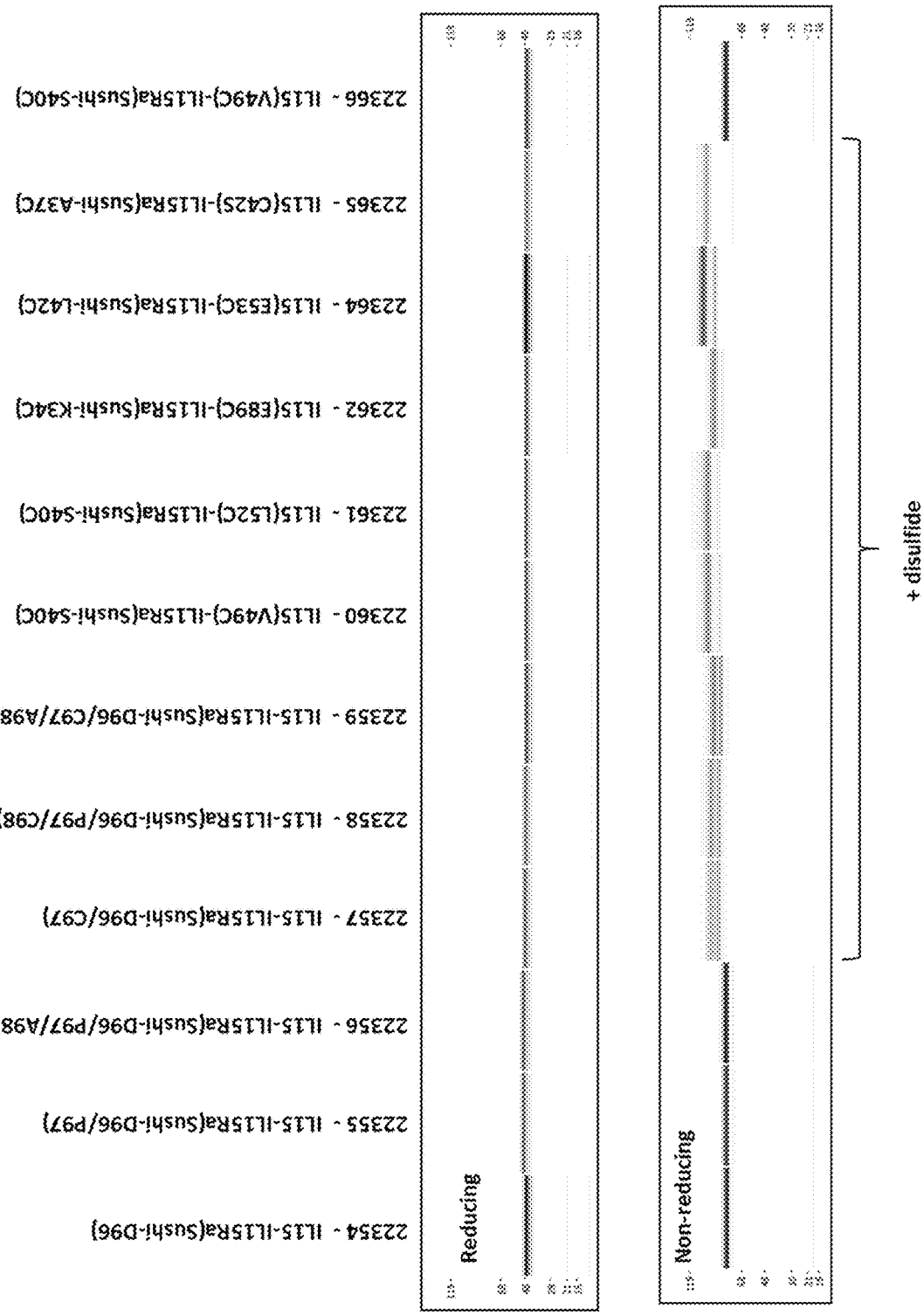

FIG. 44 depicts the purity and homogeneity of illustrative IL-15/Rα-Fc fusion proteins with and without engineered disulfide bonds as determined by CEF.

Figure 45A:
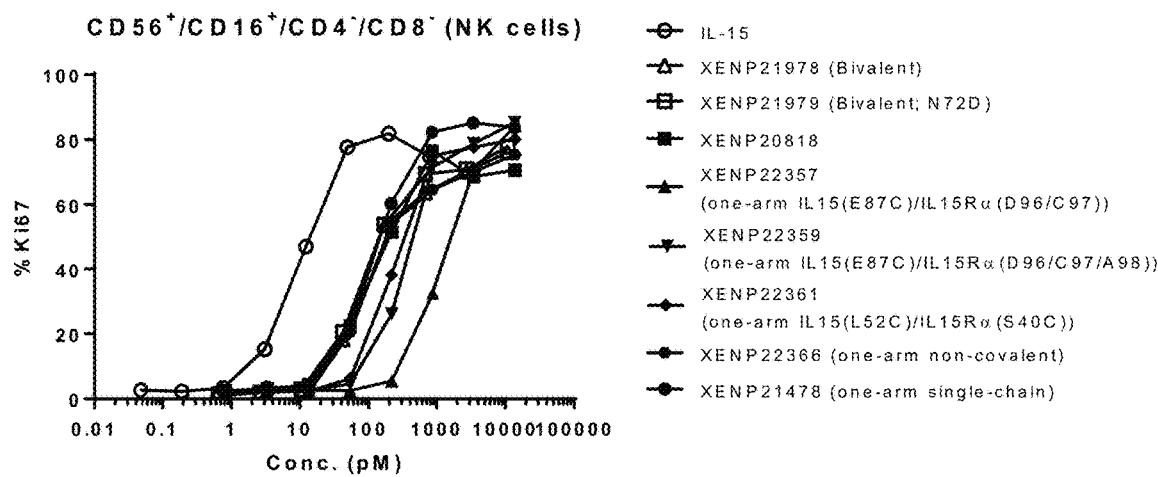
Figure 45B:
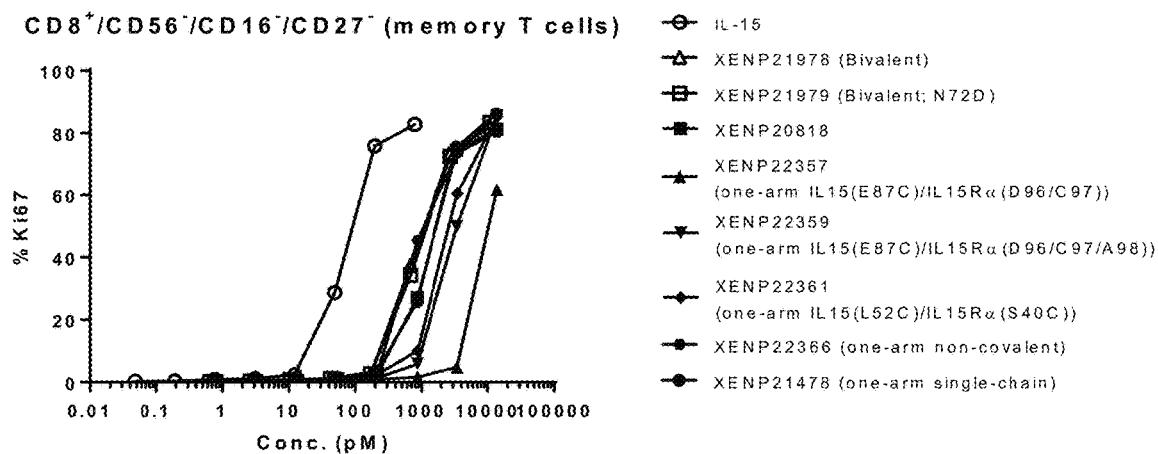
Figure 45C:
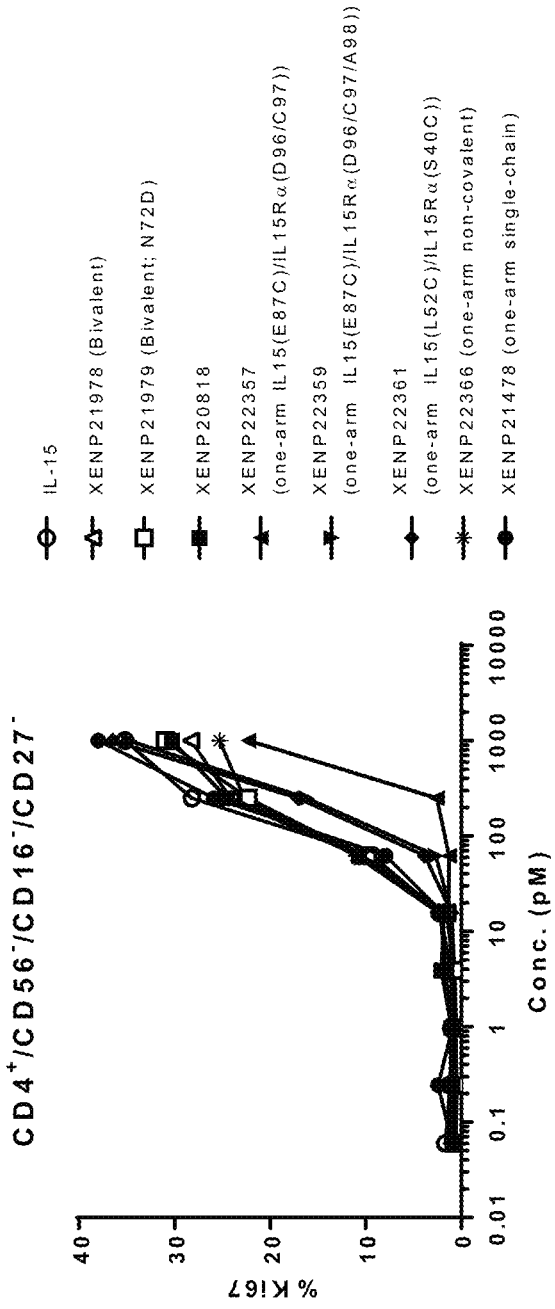

FIG. 45A-FIG. 45C depict the induction of NK (CD56+/CD16+) cell (FIG. 45A), CD8+ T cell (FIG. 45B), and CD4+ T cell (FIG. 45C) proliferation by illustrative IL-15/Rα-Fc fusion proteins with and without engineered disulfide bonds based on Ki67 expression as measured by FACS.

Figure 46:
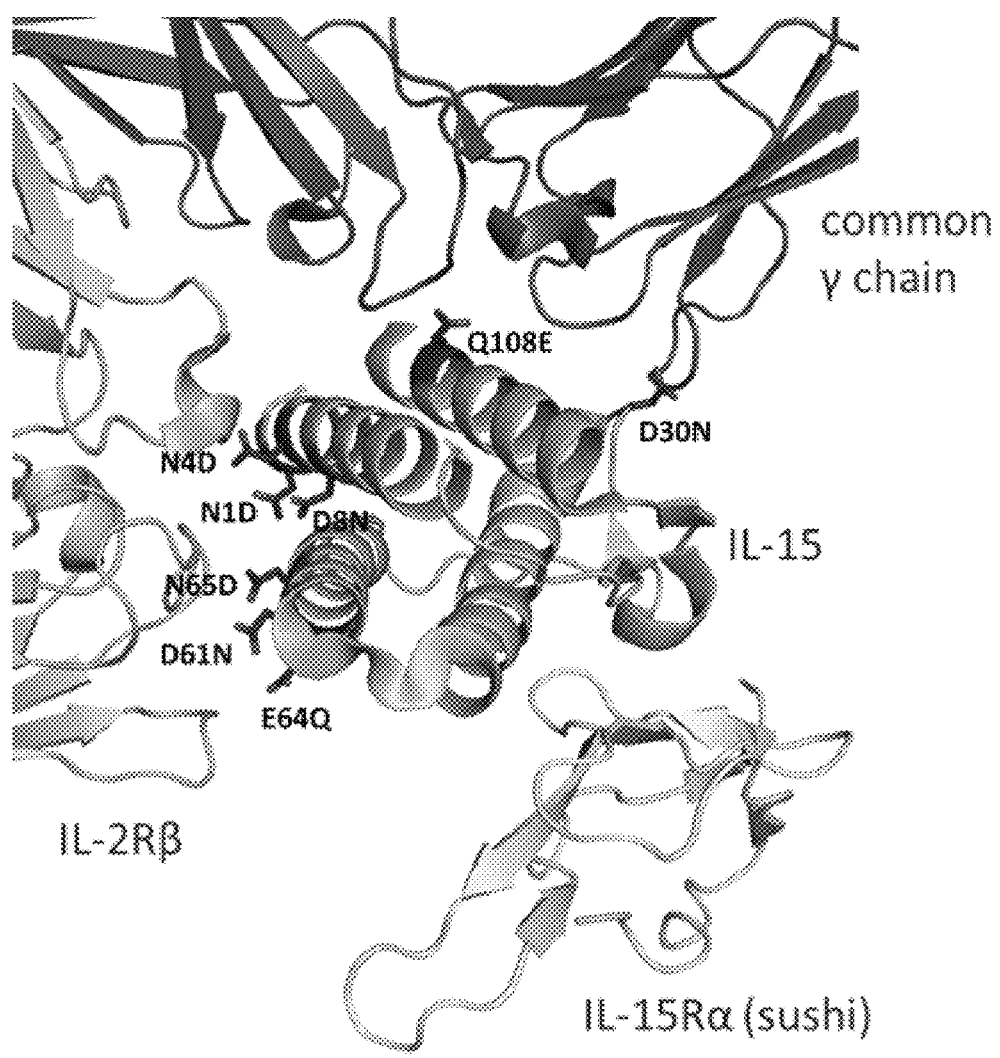

FIG. 46 depicts the structure of IL-15 complexed with IL-15Rα, IL-2Rβ, and common gamma chain. Locations of substitutions designed to reduce potency are shown.

FIG. 47A-FIG. 47C depict sequences for illustrative IL-15 variants engineered for reduced potency. Included within each of these variant IL-15 sequences are sequences that are 90%, 95%, 98% and 99% identical (as defined herein) to the recited sequences, and/or contain from 1, 2, 3, 4, 5, 6, 7, 8, 9 or 10 additional amino acid substitutions. In a non-limiting example, the recited sequences may contain additional amino acid modifications such as those contributing to formation of covalent disulfide bonds as described in Example 2.

FIG. 48A-FIG. 48H depict sequences of XENP22816, XENP22819, XENP22820, XENP22821, XENP22822, XENP22829, XENP22834, XENP23554, XENP23557, XENP23561, XENP24018, XENP24019, XENP24045, XENP24051, and XENP24052, illustrative IL-15/Rα-Fc fusion proteins of the "IL-15/Rα-heteroFc" format engineered for lower potency. Additional sequences of XENPs 22815, 22817, 22818, 22823, 22824, 22825, 22826, 22827, 22828, 22830, 22831, 22832, 22833, 23555, 23559, 23560, 24017, 24020, 24043, and 24048 are depicted in WO2018071919 in FIGS. 104Z, 104AA, 104AC, 104AD, 104AE, 104AF, 104AJ, 104AK, 104AM, 104AN, and 104AO, and as SEQ ID NOS: 729-734, 741-746, 747-752, 777-782, 783-788, 789-794, 795-800, 801-806, 807-812, 819-824, 825-830, 831-836, 837-842, 887-892, 899-904, 905-910, 937-942, 955-960, 961-966, and 979-984, respectively. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 49A-FIG. 49D depict sequences of XENP24015, XENP24050, XENP24475, XENP24476, XENP24478, XENP24479, and XENP24481, illustrative IL-15/Rα-Fc fusion proteins of the "scIL-15/Rα-Fc" format engineered for lower potency. Additional sequences of XENPs 24013, 24014, 24016 are depicted in WO2018071919 in FIG. 104AK and 104AL and as SEQ ID NOS: 914-921, 922-926, and 932-936. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 50A-FIG. 50B depict sequences of XENP24349, XENP24890, and XENP25138, illustrative IL-15/Rα-Fc fusion proteins of the "ncIL-15/Rα-Fc" format engineered for lower potency. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 51 depicts sequences of XENP22801 and XENP22802, illustrative ncIL-15/Rα heterodimers engineered for lower potency. Additional sequences of XENPs 22791, 22792, 22793, 22794, 22795, 22796, 22803, 22804, 22805, 22806, 22807, 22808, 22809, 22810, 22811, 22812, 22813, 22814 are depicted in WO2018071919 in FIGS. 104V, 104W, 104X, 104Y, and 104Z and as SEQ ID NOS: 689-690, 691-692, 693-694, 695-696, 697-698, 699-700, 705-706, 707-708, 709-710, 711-712, 713-714, 715-716, 717-718, 719-720, 721-722, 723-724, 725-726, and 727-728, respectively. It is important to note that these sequences were generated using polyhistidine (His×6 or HHHHHH (SEQ ID NO: 10)) C-terminal tags at the C-terminus of IL-15Rα(sushi).

FIG. 52 depicts sequences of XENP24342, an illustrative IL-15/Rα-Fc fusion protein of the "bivalent ncIL-15/Rα-Fc" format engineered for lower potency. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 53 depicts sequences of XENP23472 and XENP23473, illustrative IL-15/Rα-Fc fusion proteins of the "dsIL-15/Rα-Fc" format engineered for lower potency. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

Figure 54A:
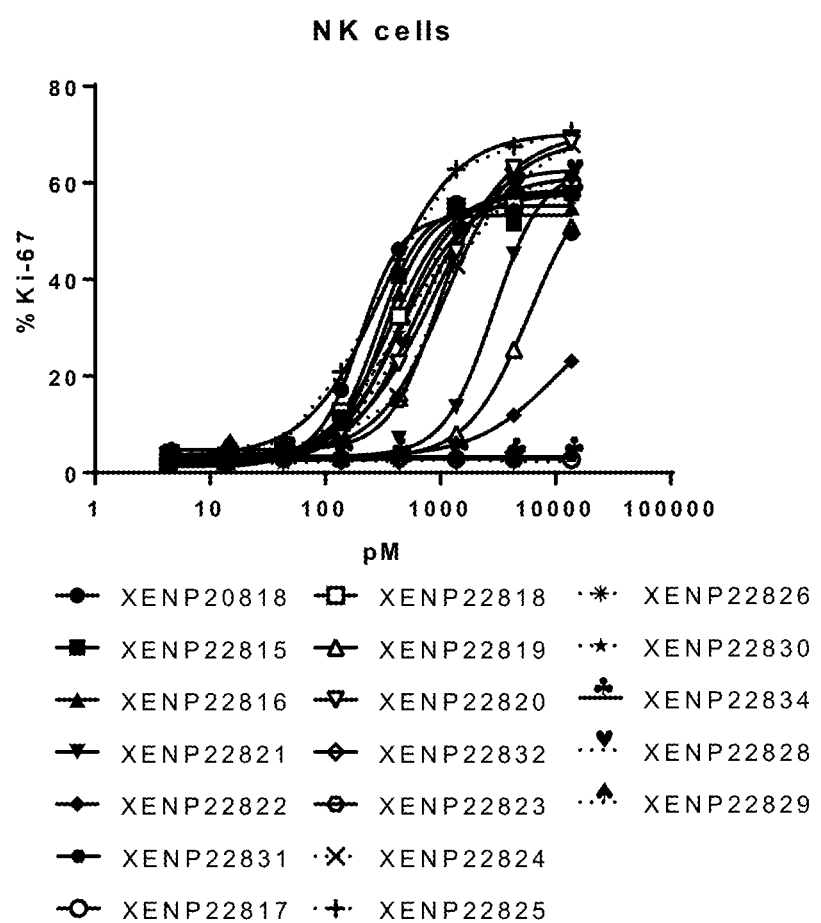
Figure 54B:
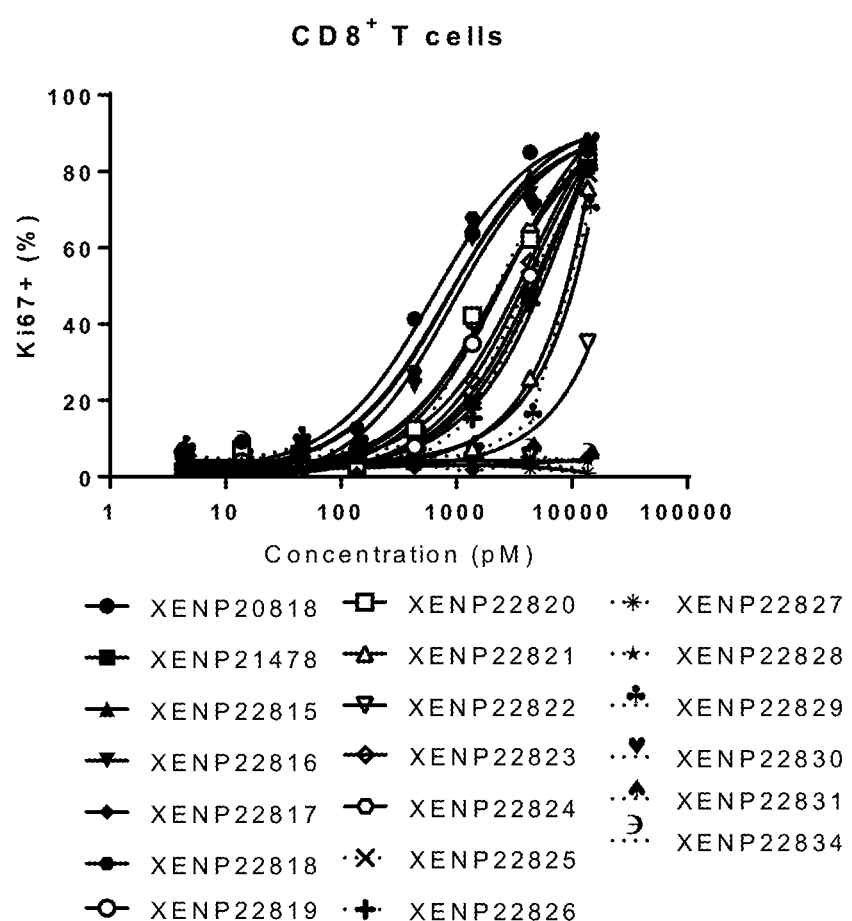
Figure 54C:
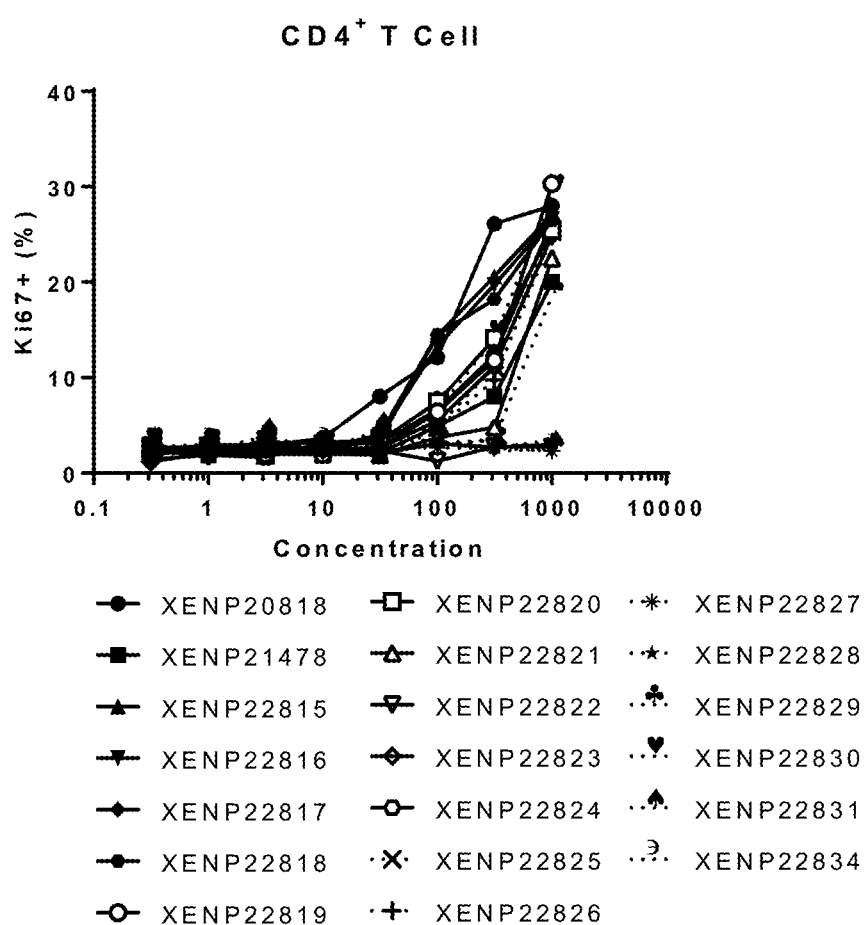

FIG. 54A-FIG. 54C depict the induction of NK cell (FIG. 54A), CD8$^+$ (CD45RA−) T cell (FIG. 54B), and CD4+ (CD45RA−) T cell (FIG. 54C) proliferation by variant IL-15/Rα-Fc fusion proteins based on Ki67 expression as measured by FACS.

FIG. 55 depicts EC50 for induction of NK and CD8$^+$ T cells proliferation by variant IL-15/Rα-Fc fusion proteins, and fold reduction in EC50 relative to XENP20818.

Figure 56B:
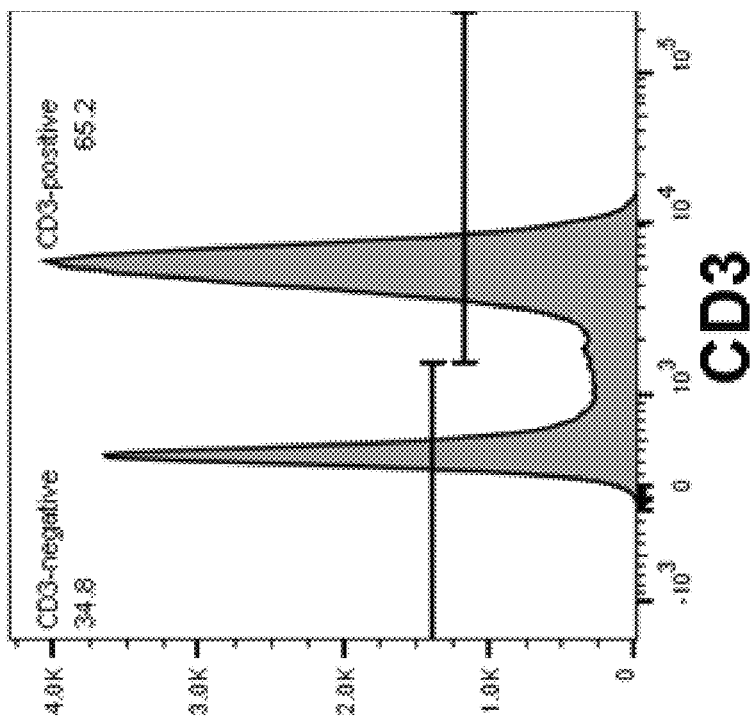
Figure 56A:
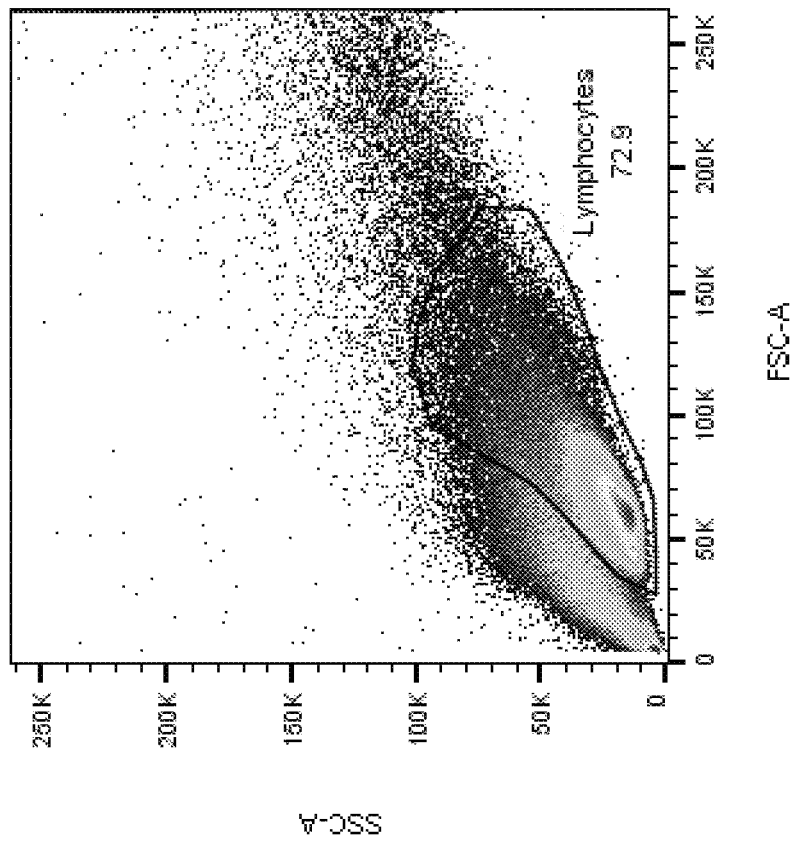
Figure 56C:
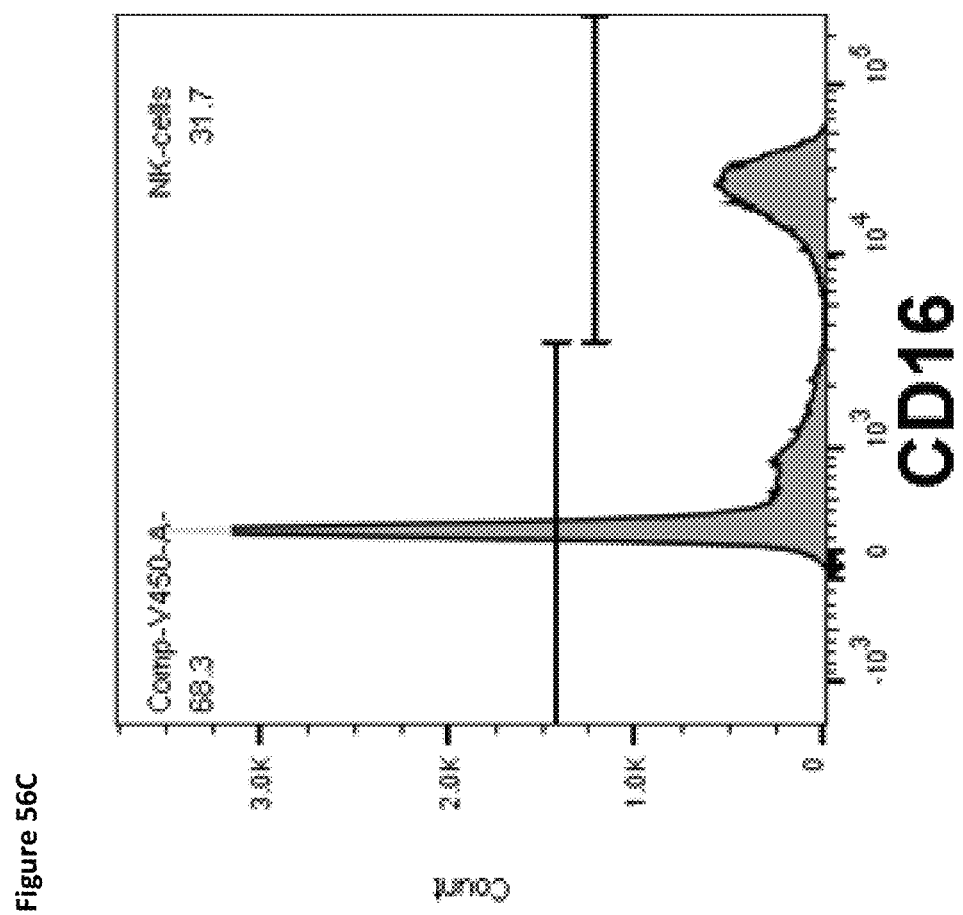

FIG. 56A-FIG. 56C depict the gating of lymphocytes and subpopulations for the experiments depicted in FIGS. 59A-59D. FIG. 56A shows the gated lymphocyte population. FIG. 56B shows the CD3-negative and CD3-positive subpopulations. FIG. 56C shows the CD16-negative and CD16-positive subpopulations of the CD3-negative cells.

Figure 57B:
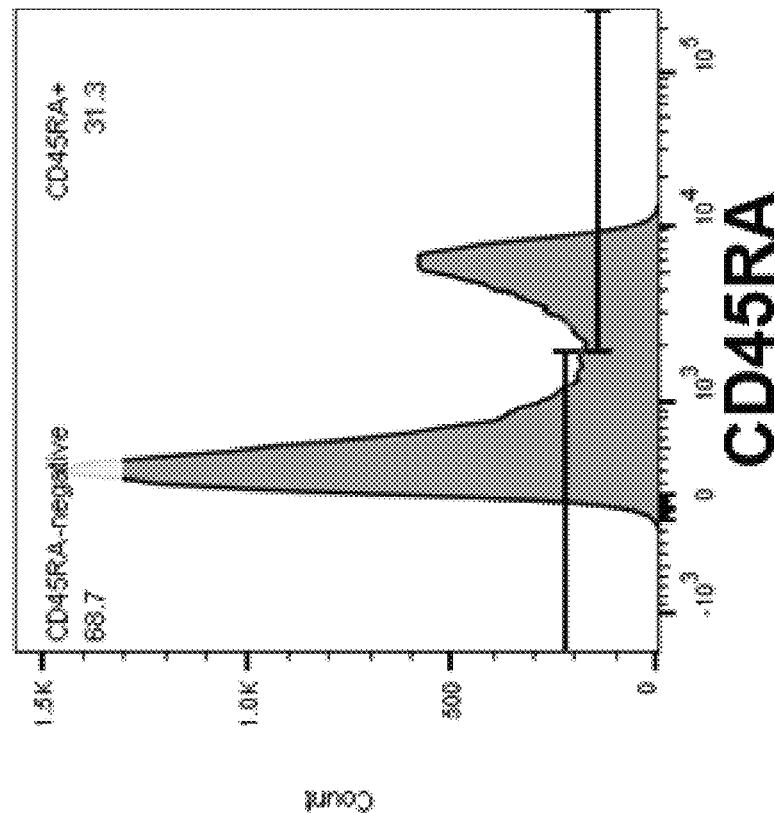
Figure 57A:
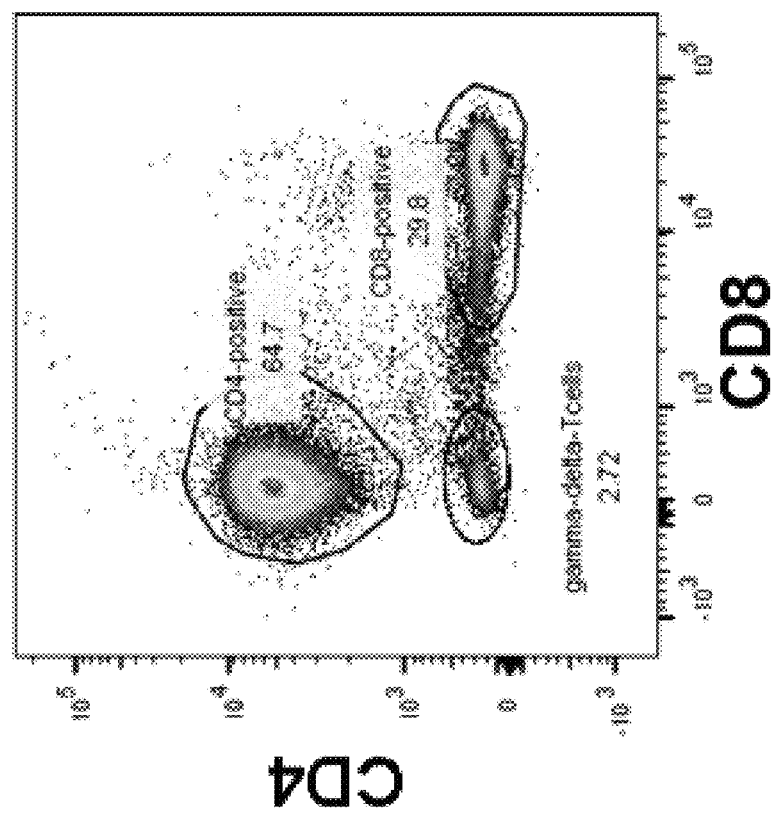
Figure 57C:
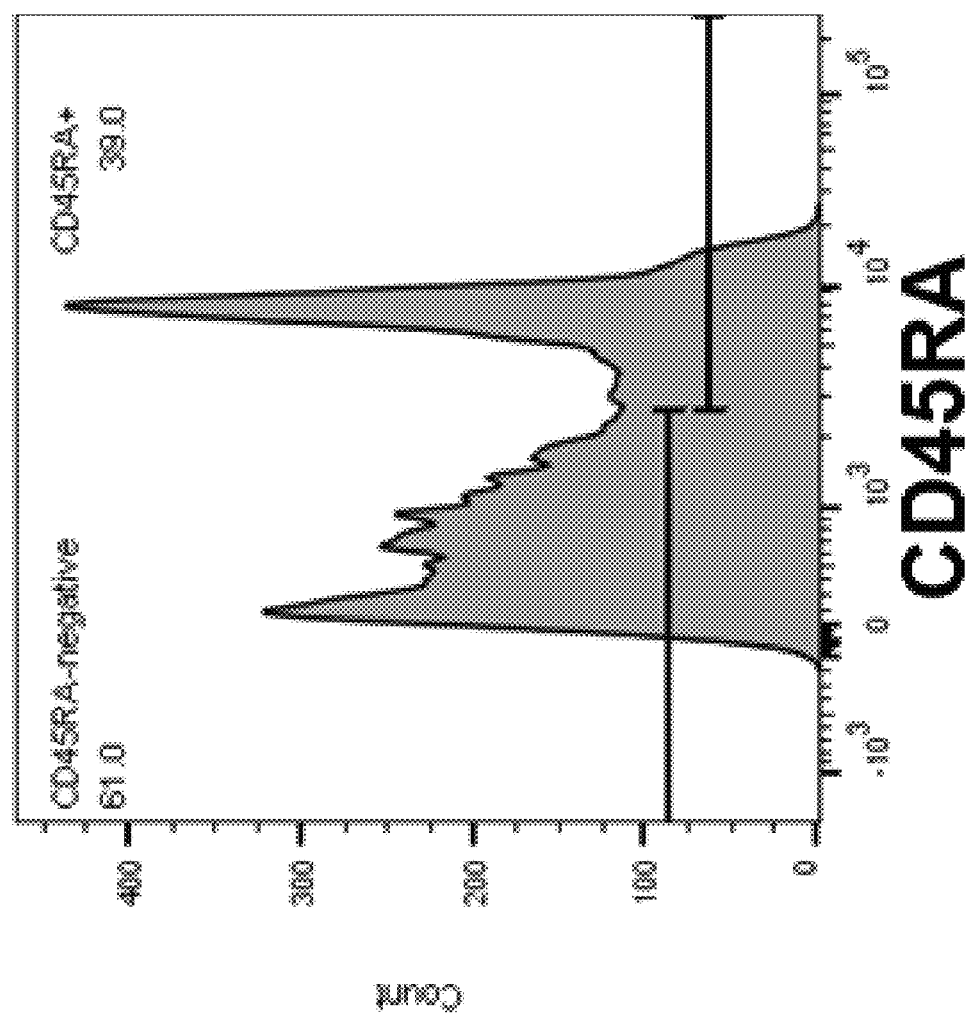

FIG. 57A-FIG. 57C depict the gating of CD3$^+$ lymphocyte subpopulations for the experiments depicted in FIGS. 59A-59D. FIG. 57A shows the CD4$^+$, CD8$^+$ and γδ T cell subpopulations of the CD3$^+$ T cells. FIG. 57B shows the CD45RA(−) and CD45RA(+) subpopulations of the CD4$^+$ T cells. FIG. 57C shows the CD45RA(−) and CD45RA(+) subpopulations of the CD8$^+$ T cells.

Figure 58A:
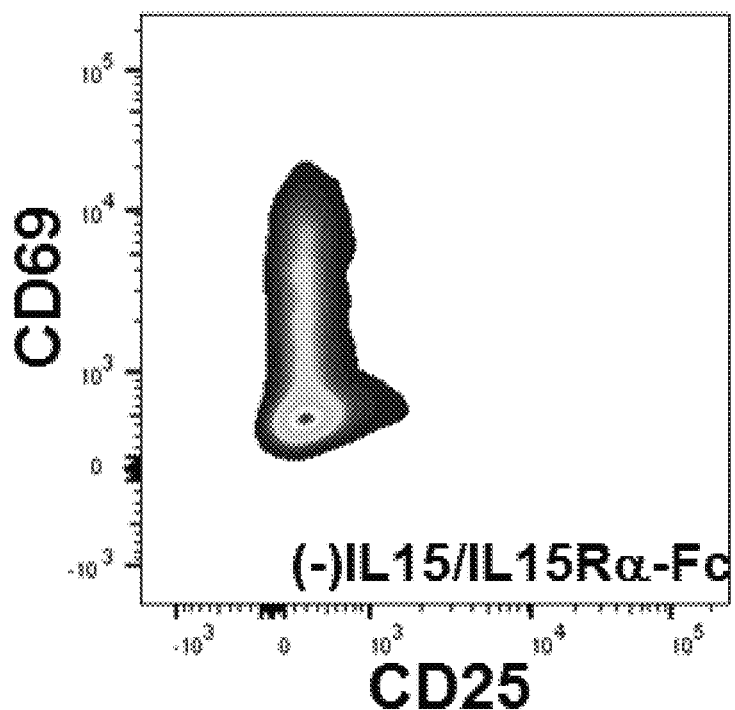
Figure 58B:
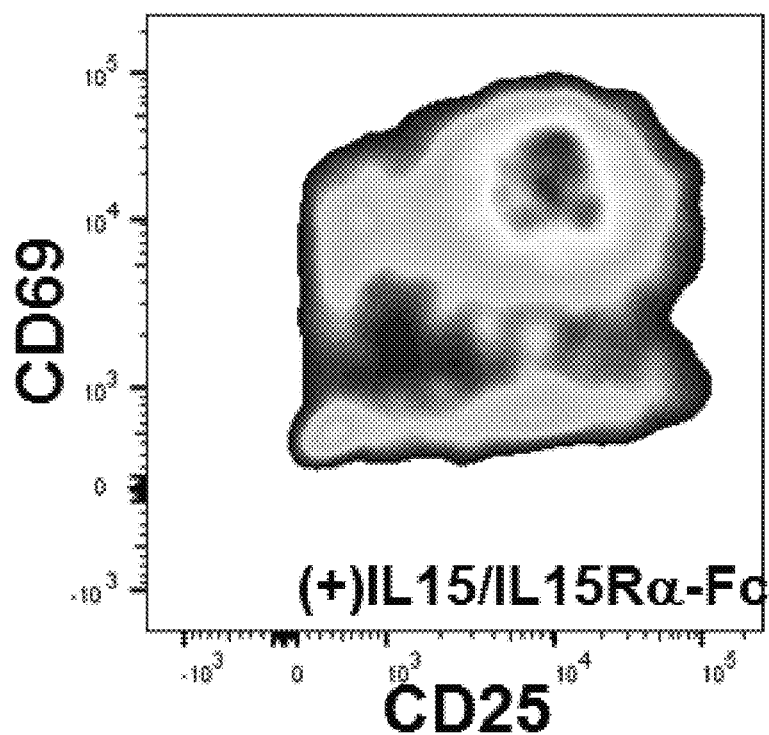

FIG. 58A-FIG. 58B depict CD69 and CD25 expression before (FIG. 58A) and after (FIG. 58B) incubation of human PBMCs with XENP22821.

Figure 59C:
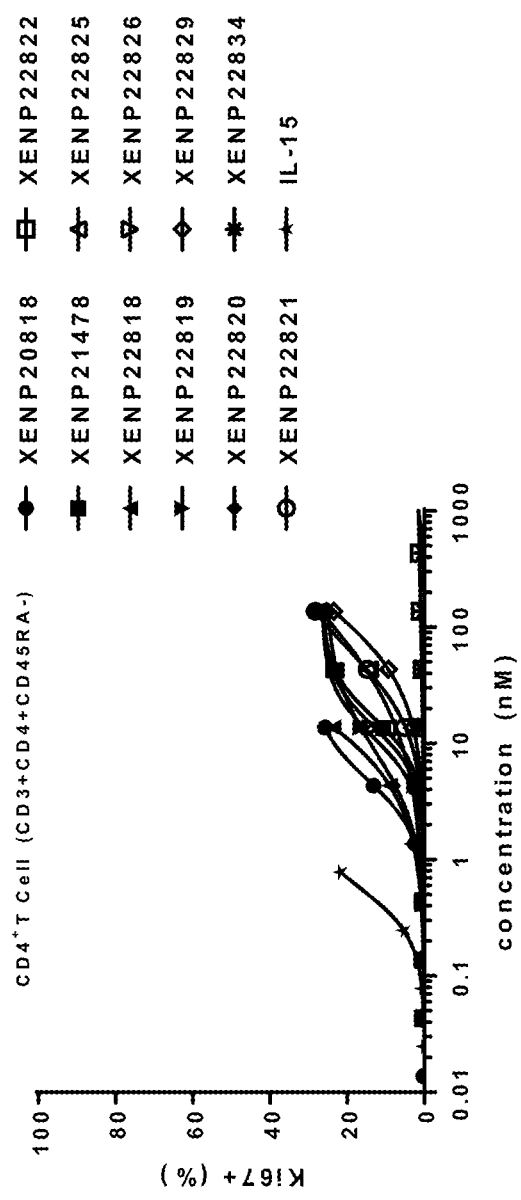

FIG. 59A-FIG. 59D depict cell proliferation in human PBMCs incubated for four days with the indicated variant IL-15/Rα-Fc fusion proteins. FIGS. 59A-C show the percentage of proliferating NK cells (CD3−CD16+) (FIG. 59A), CD8+ T cells (CD3+CD8+CD45RA−) (FIG. 59B) and CD4+ T cells (CD3+CD4+CD45RA−) (FIG. 59C). FIG. 59D shows the fold change in EC50 of various IL-15/IL-15Rα Fc heterodimers relative to control (XENP20818).

Figure 60A:
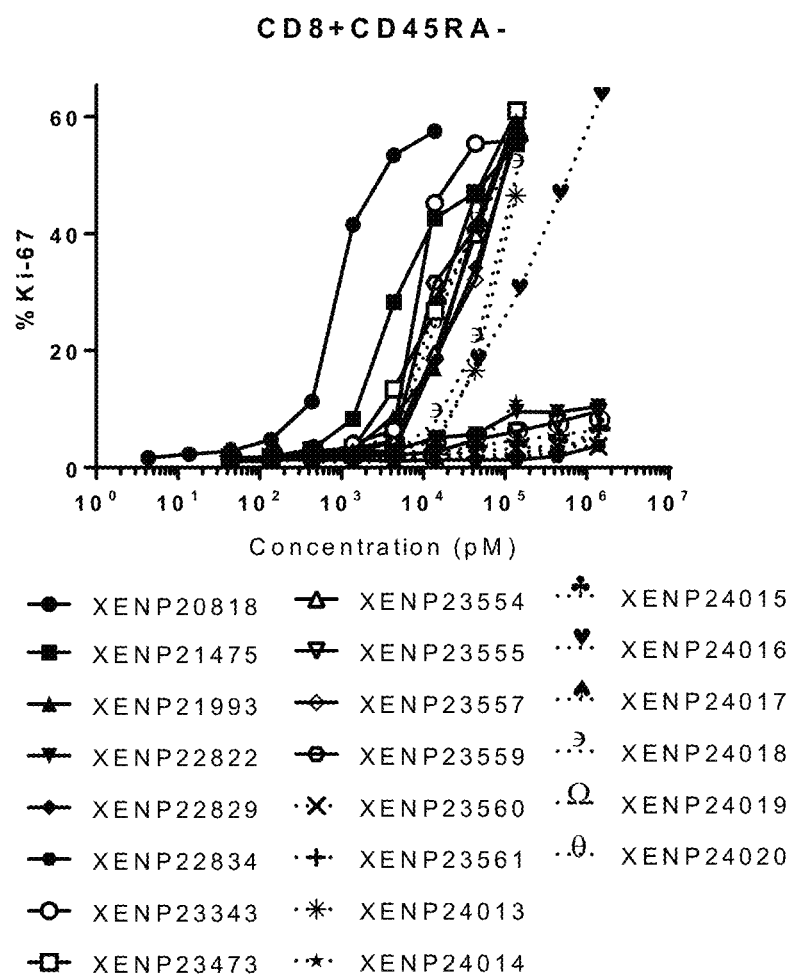
Figure 60B:
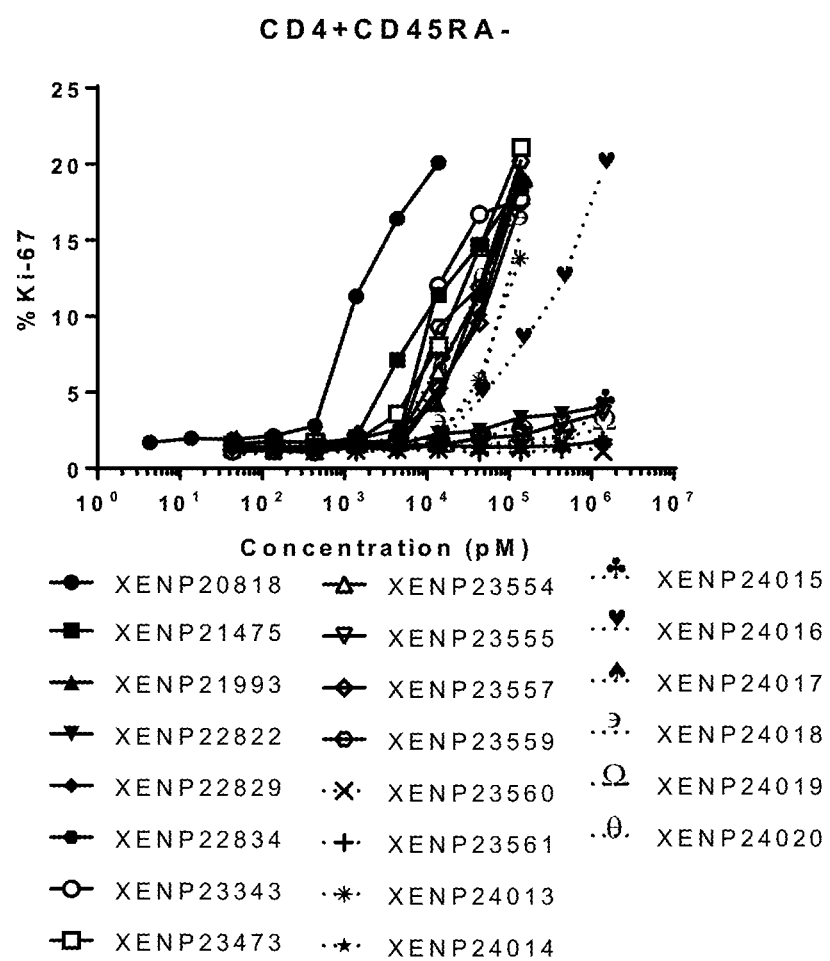
Figure 60C:
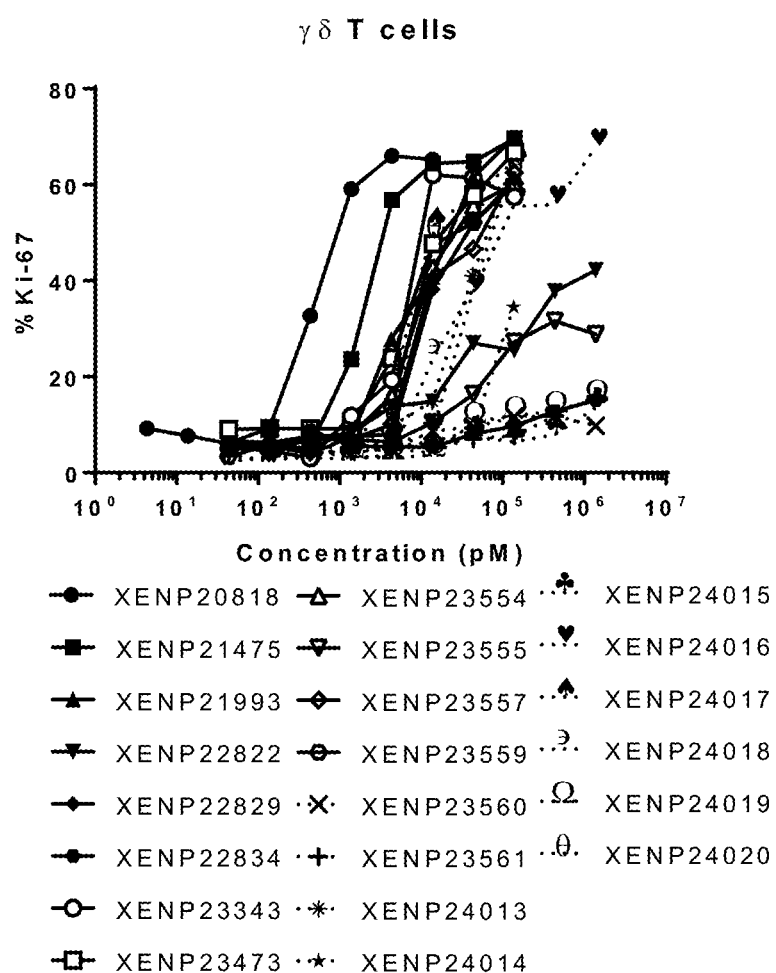
Figure 60D:
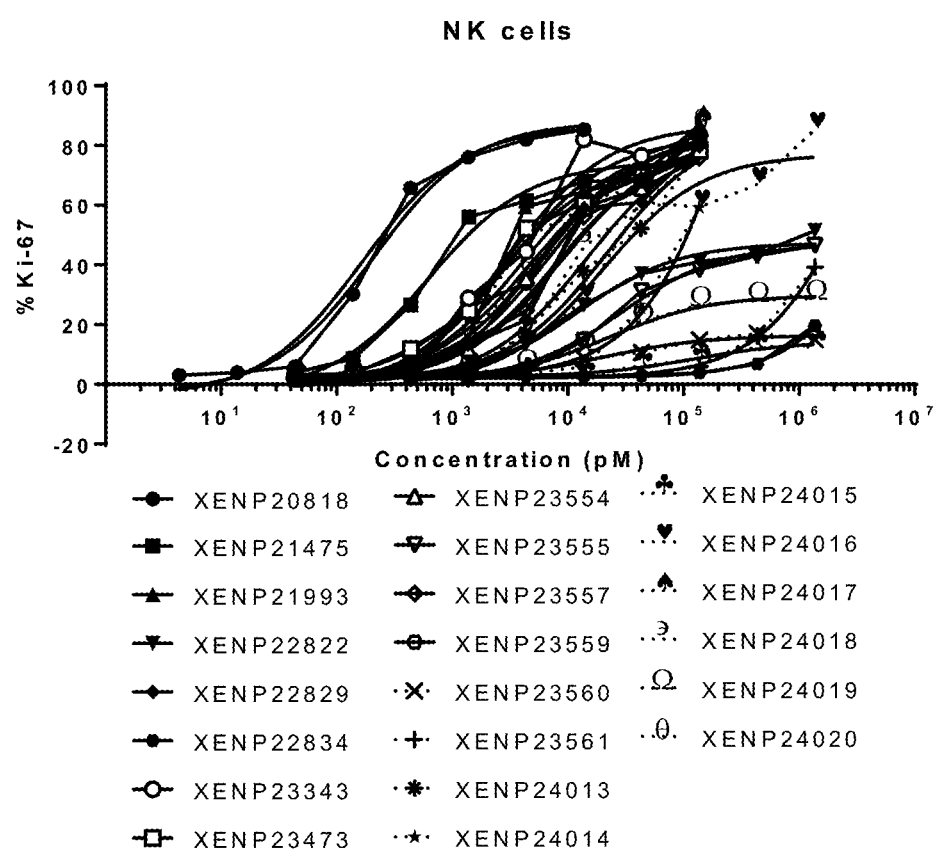

FIG. 60A-FIG. 60D depict cell proliferation in human PBMCs incubated for three days with the indicated variant IL-15/Rα-Fc fusion proteins. FIGS. 60A-C show the percentage of proliferating CD8$^+$ (CD45RA−) T cells (FIG. 60A), CD4$^+$ (CD45RA−) T cells (FIG. 60B), γδ T cells (FIG. 60C), and NK cells (FIG. 60D).

Figure 61A:
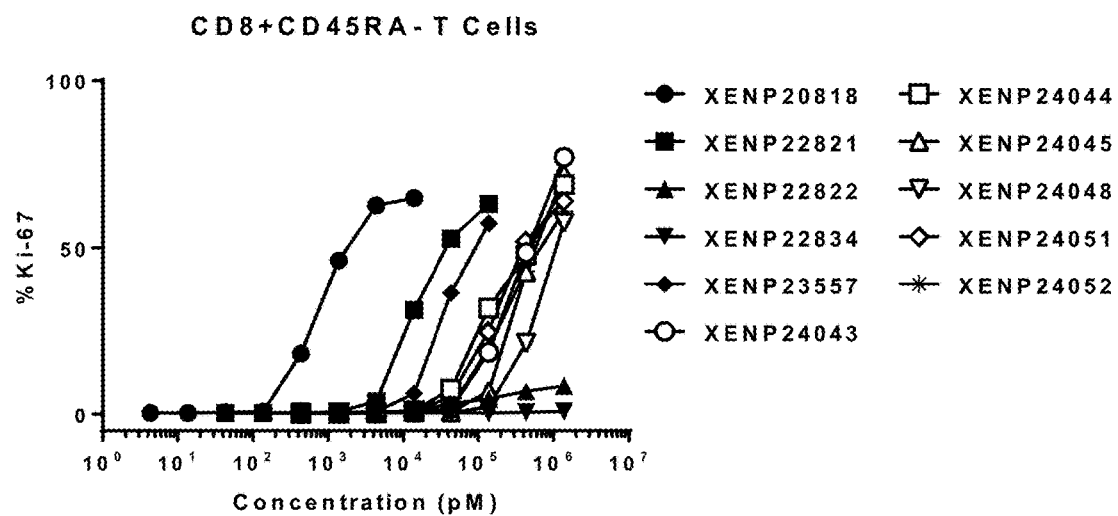
Figure 61B:
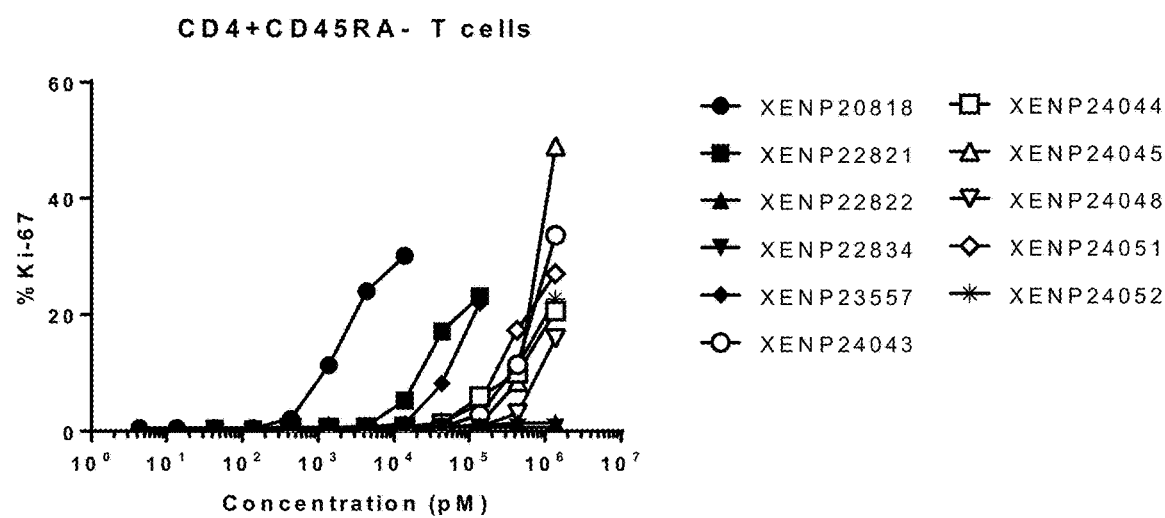
Figure 61C:
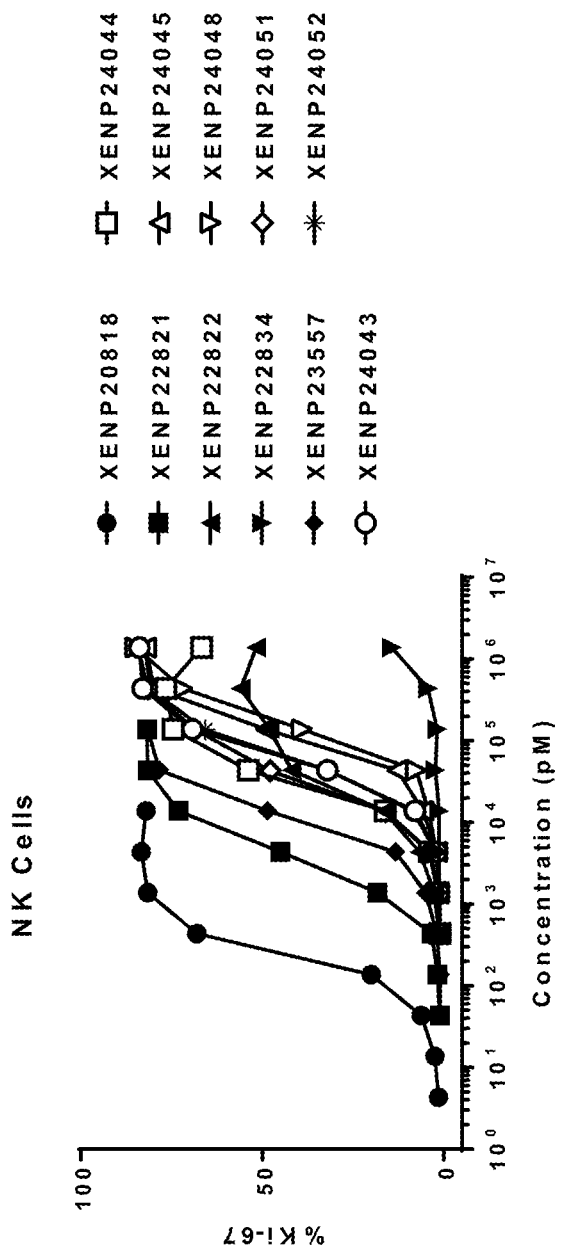
Figure 62A:
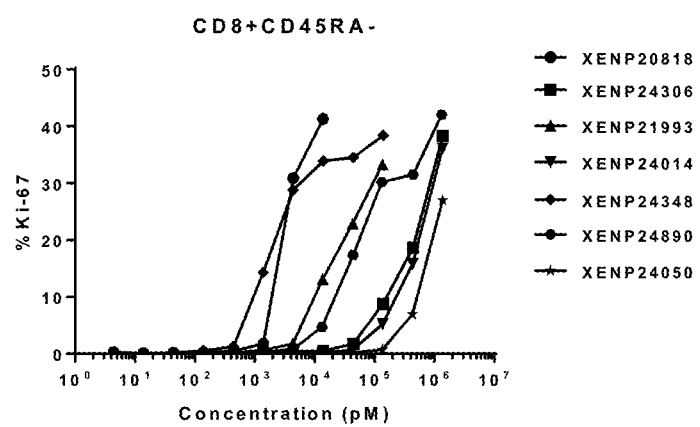
Figure 62B:
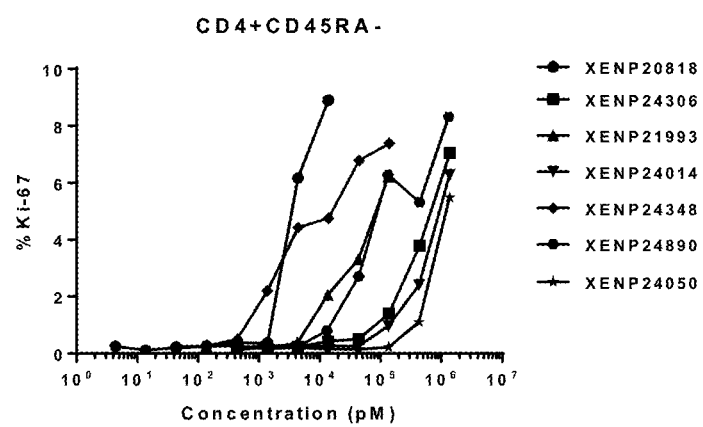
Figure 62C:
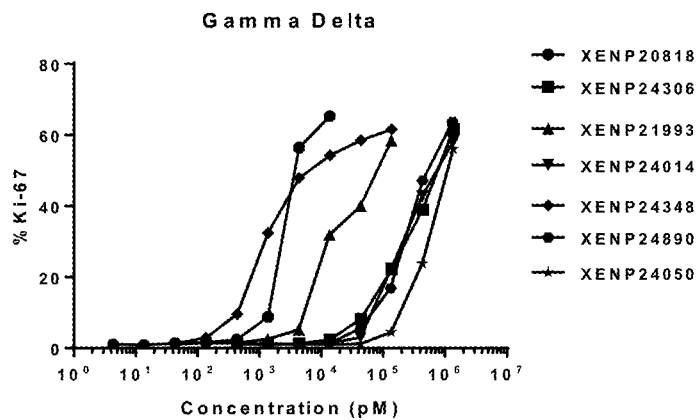
Figure 62D:
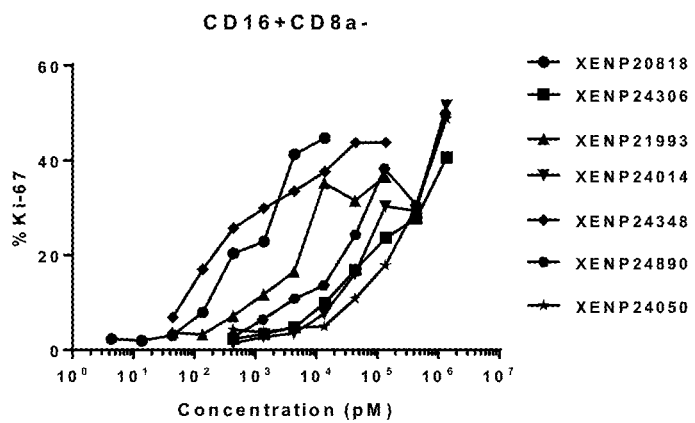
Figure 62E:
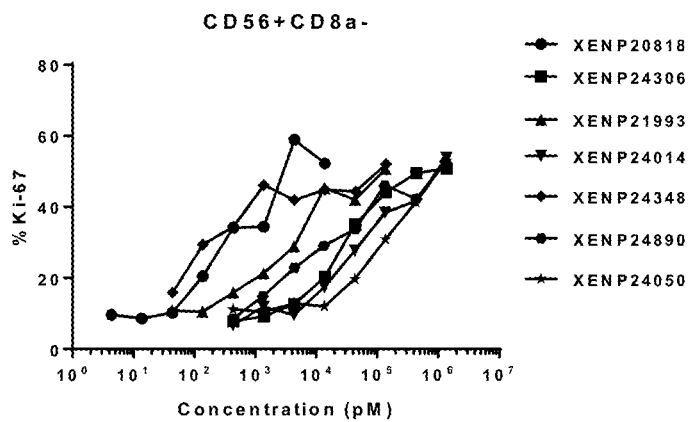
Figure 63A:
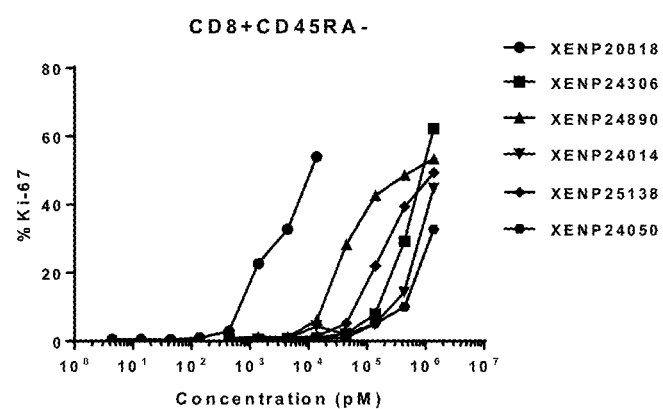
Figure 63B:
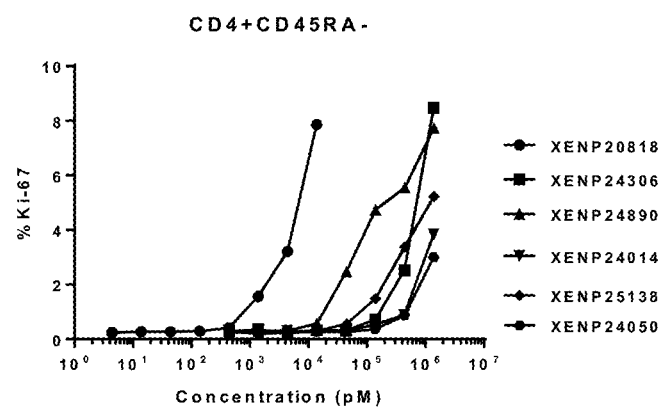
Figure 63C:
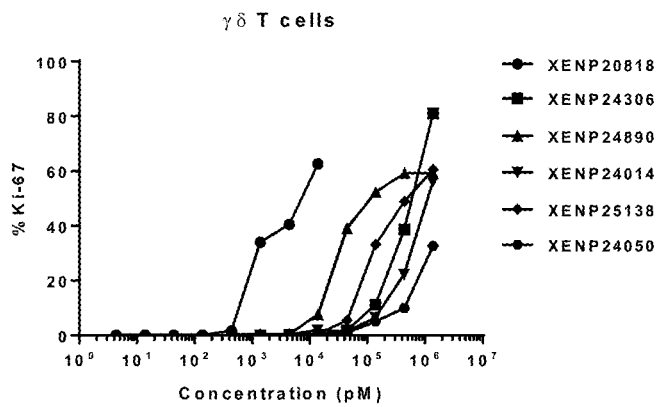
Figure 63D:
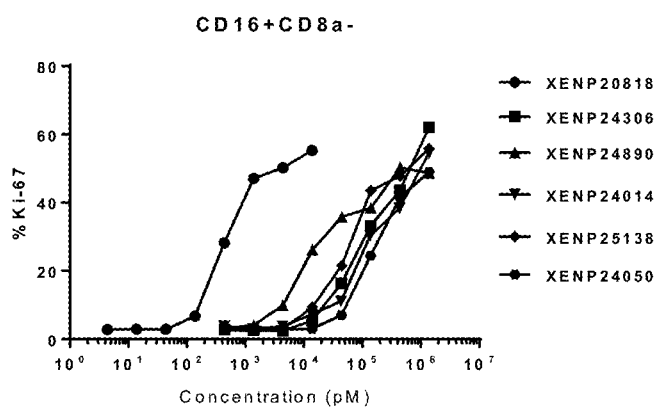
Figure 63E:
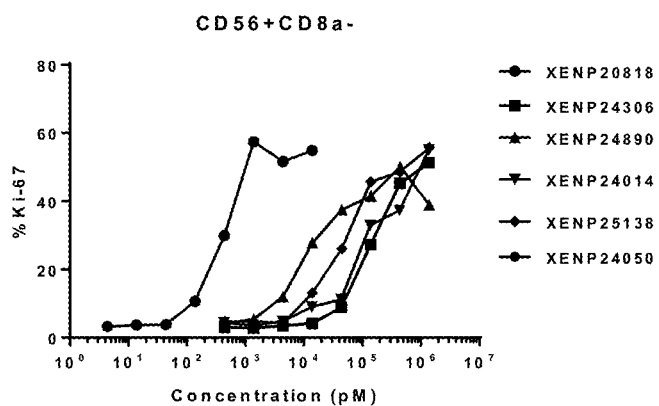
Figure 64A:
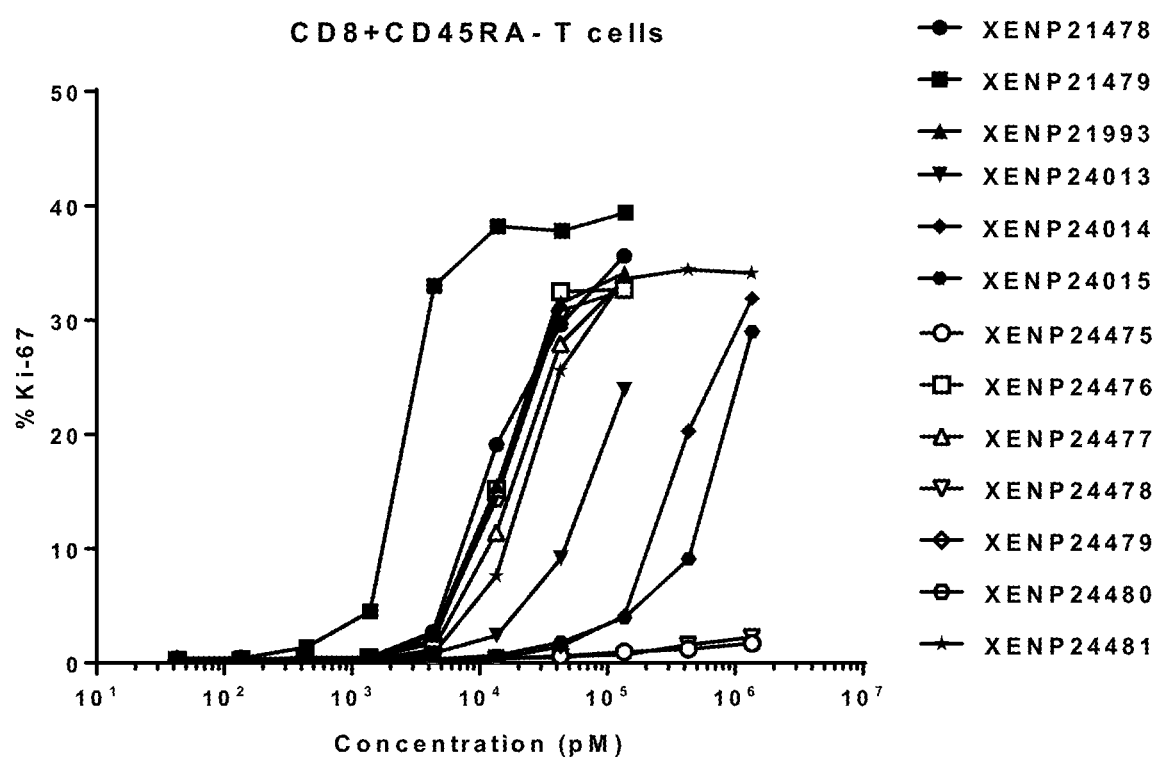
Figure 64B:
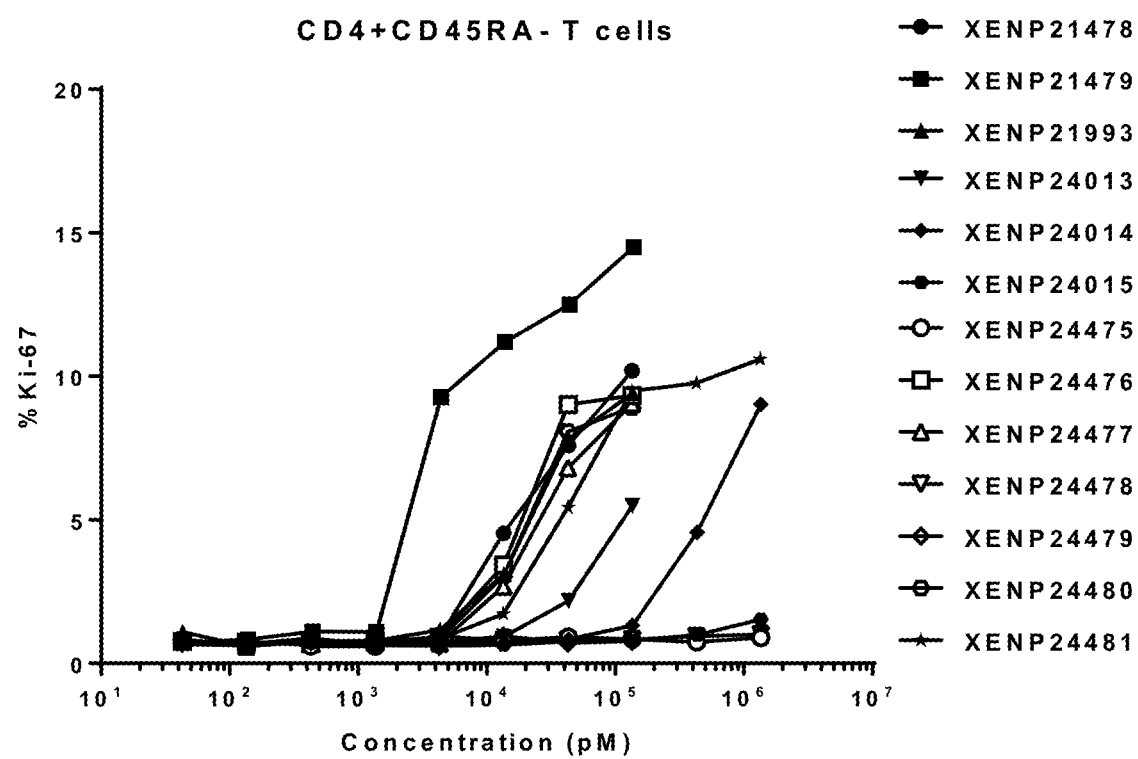
Figure 64C:
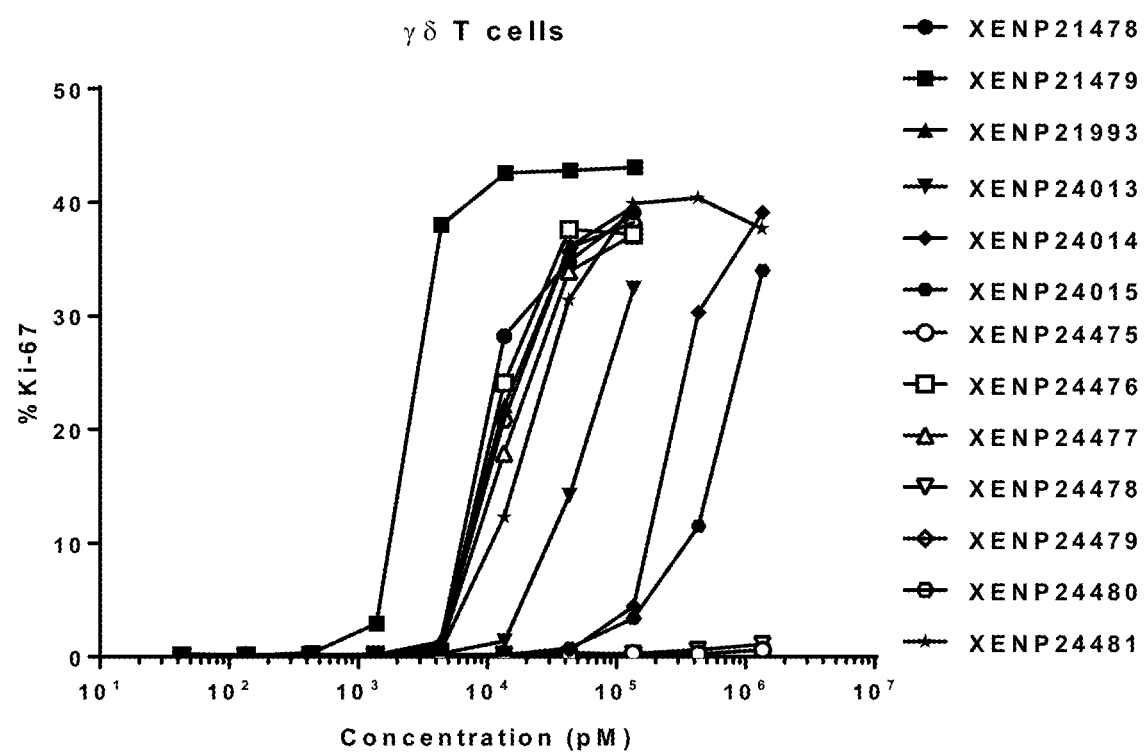
Figure 64D:
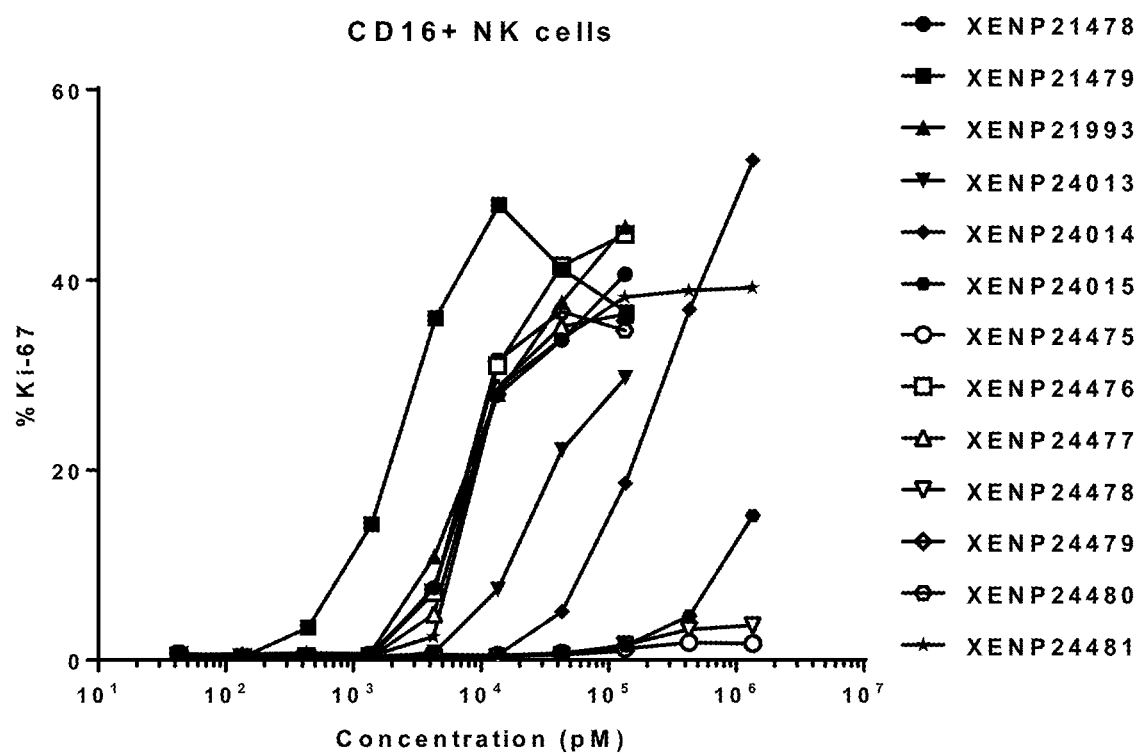
Figure 65A:
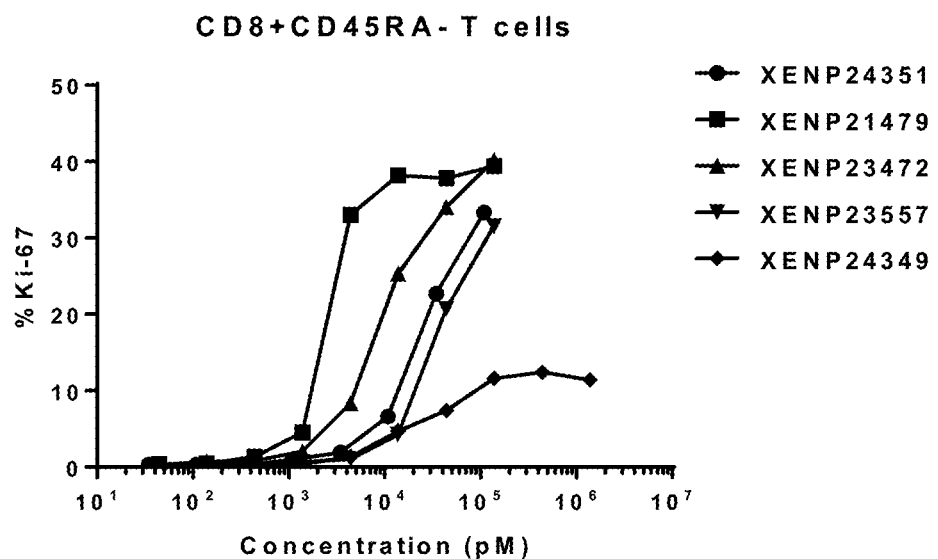
Figure 65B:
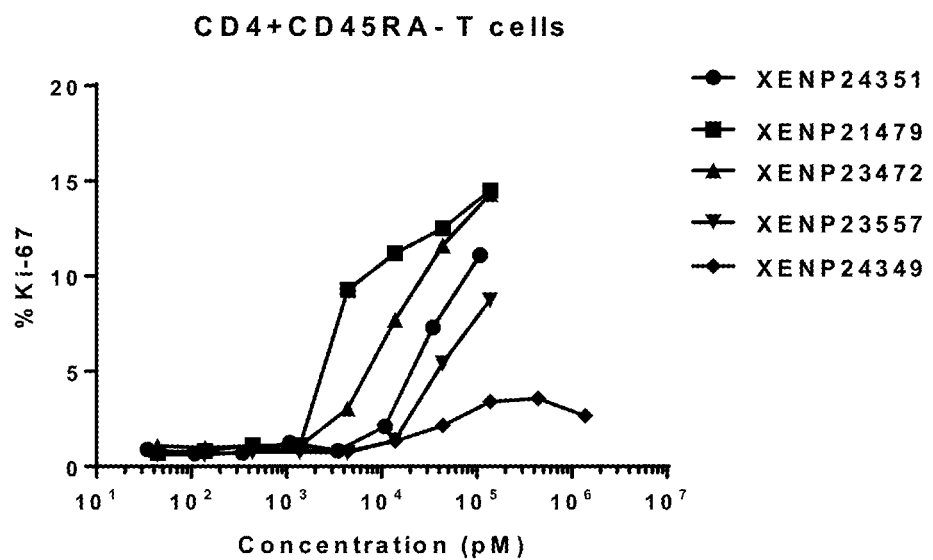
Figure 65C:
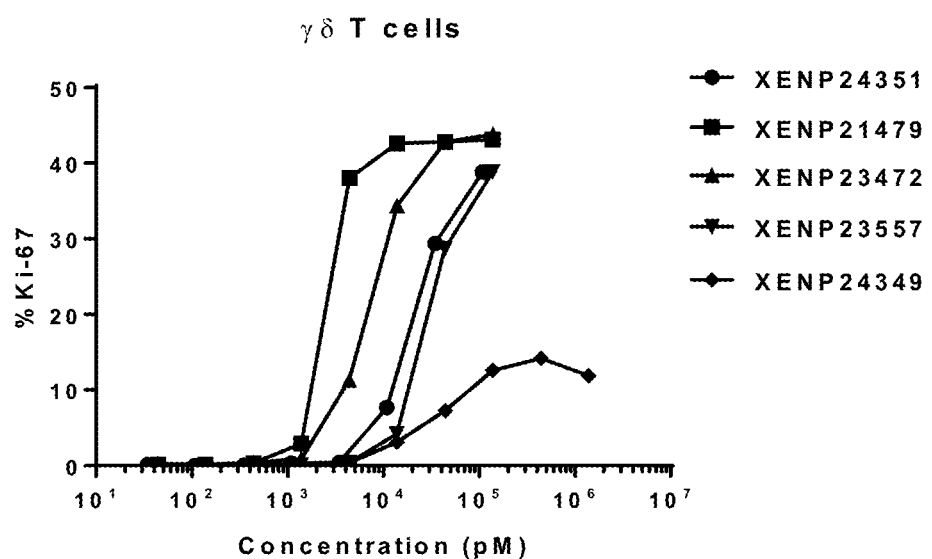
Figure 65D:
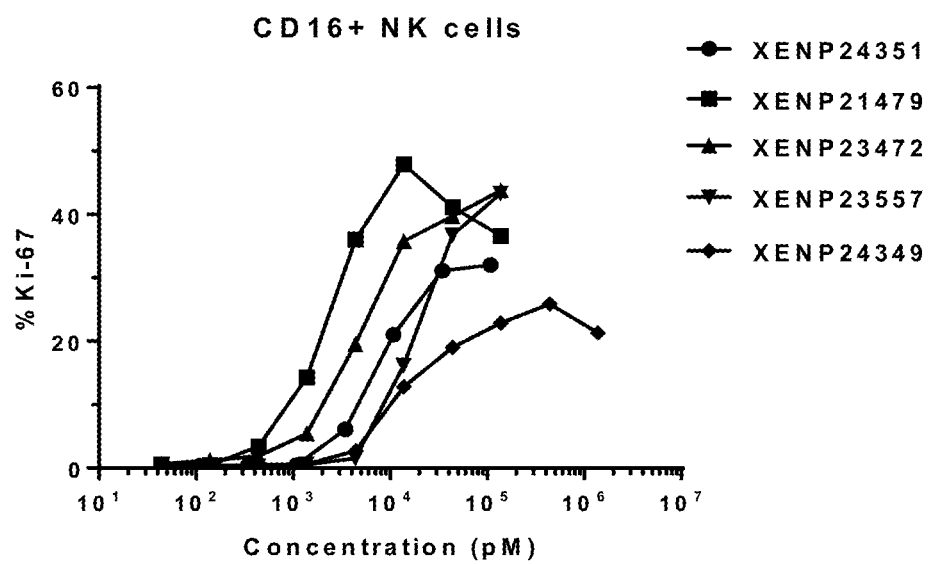

FIG. 61A-FIG. 61C depict the percentage of Ki67 expression on CD8+ T cells (FIG. 61A), CD4+ T cells (FIG. 61B), and NK cells (FIG. 61C) following treatment with additional IL-15/Rα variants.

FIG. 62A-FIG. 62E depict the percentage of Ki67 expression on (FIG. 62A) CD8+(CD45RA−) T cells, (FIG. 62B) CD4+(CD45RA−) T cells, (FIG. 62C) γδ T cells, (FIG. 62D) NK (CD16+CD8α−) cells, and (FIG. 62E) NK (CD56+CD8α−) cells following treatment with IL-15/Rα variants.

FIG. 63A-FIG. 63E depict the percentage of Ki67 expression on CD8$^+$ (CD45RA−) T cells (FIG. 63A), CD4$^+$ (CD45RA−) T cells (FIG. 63B), γδ T cells (FIG. 63C), NK (CD16+CD8α−) cells (FIG. 63D), and NK (CD56+CD8α−) cells (FIG. 63E) following treatment with IL-15/Rα variants.

FIG. 64A-FIG. 64D depict the percentage of Ki67 expression on (FIG. 64A) CD8+ T cells, (FIG. 64B) CD4+ T cells, (FIG. 64C) γδ T cells and (FIG. 64D) NK (CD16+) cells following treatment with additional IL-15/Rα variants engineered for decreased potency with different linker lengths.

FIG. 65A-FIG. 65D depict the percentage of Ki67 expression on (FIG. 65A) CD8$^+$ T cells, (FIG. 65B) CD4$^+$ T cells, (FIG. 65C) γδ T cells and (FIG. 65D) NK (CD16+) cells following treatment with additional IL-15/Rα variants.

Figure 66B:
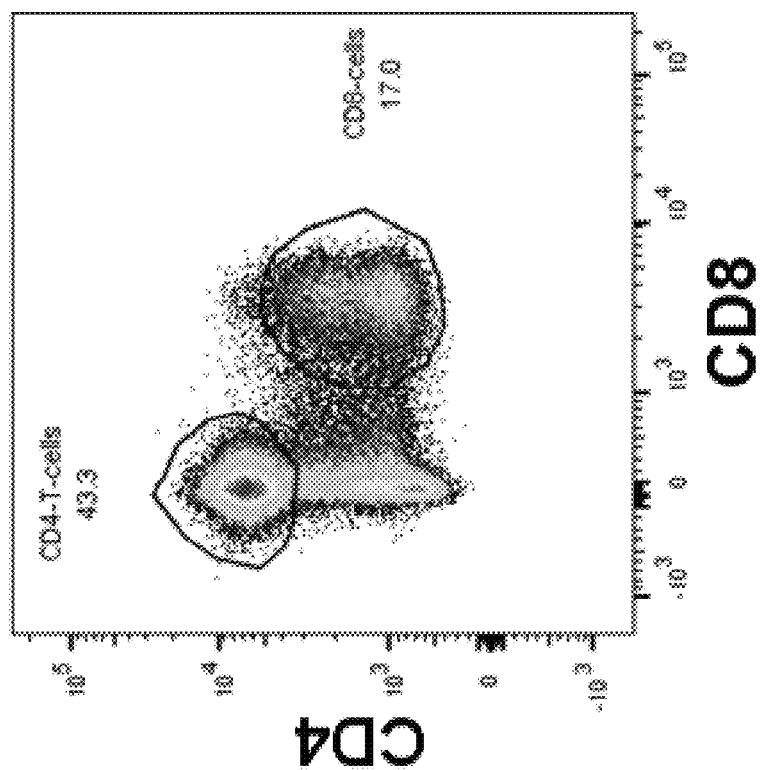
Figure 66A:
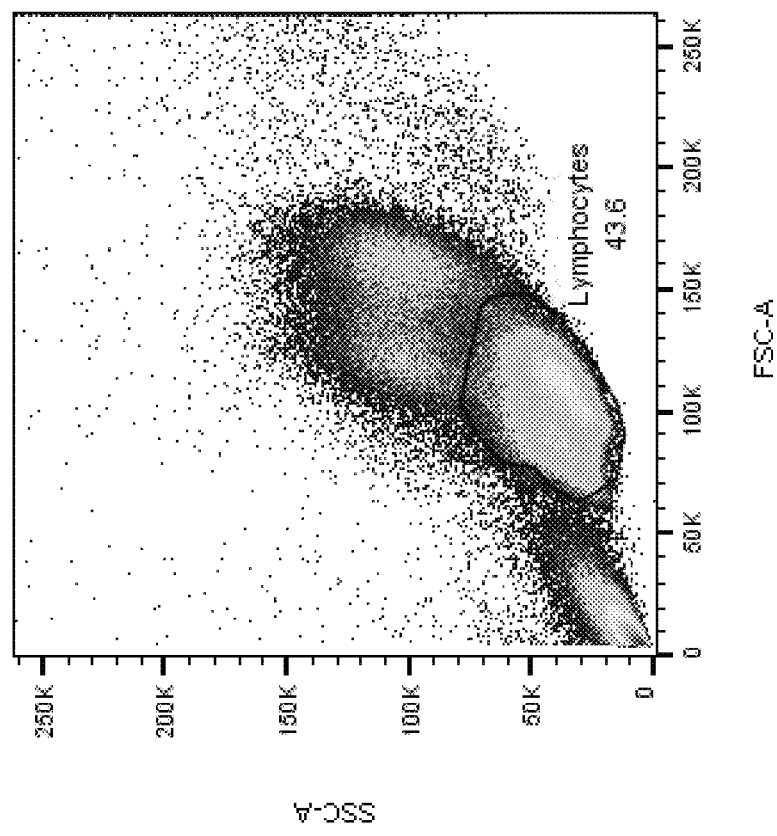
Figure 66D:
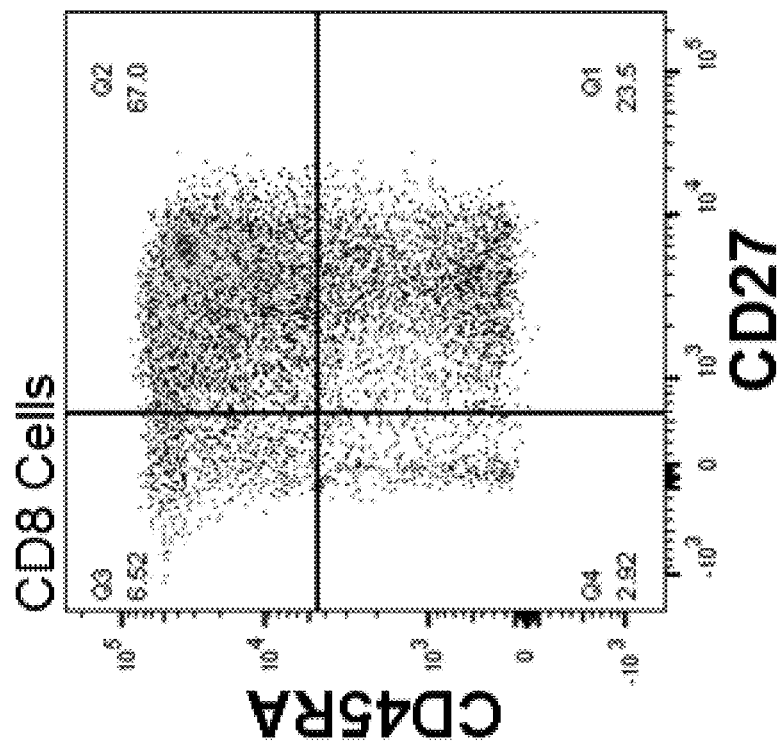
Figure 66C:
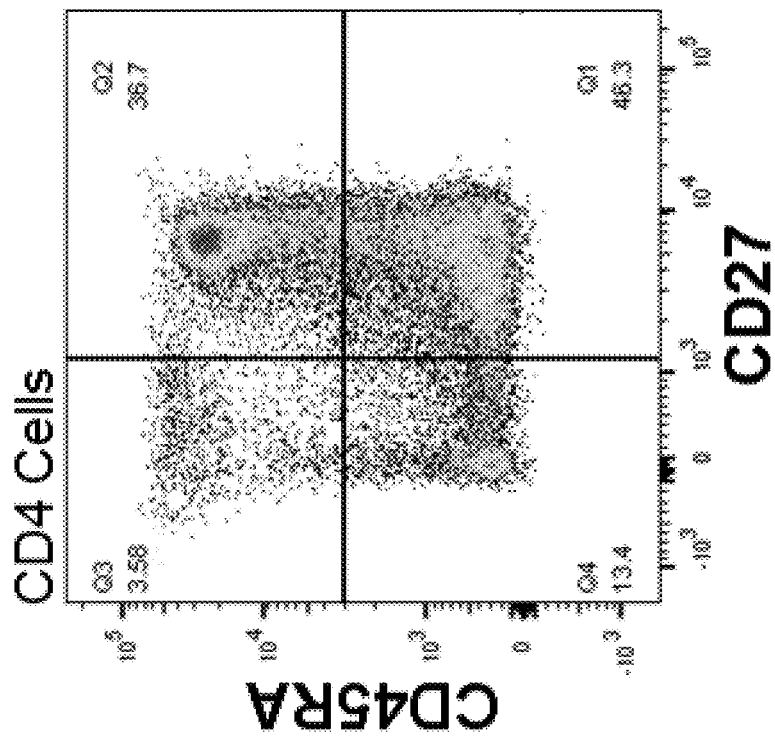
Figure 67A:
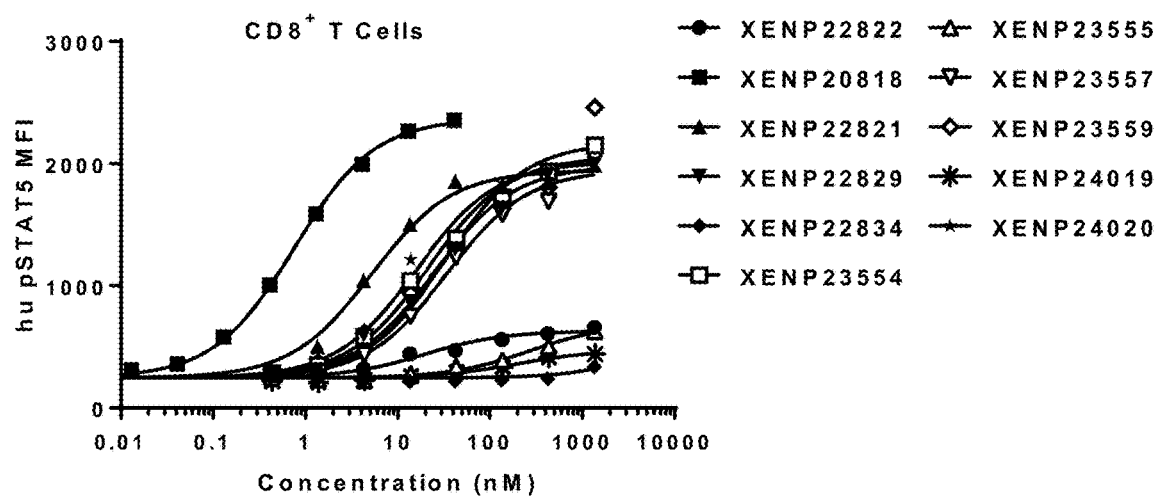
Figure 67B:
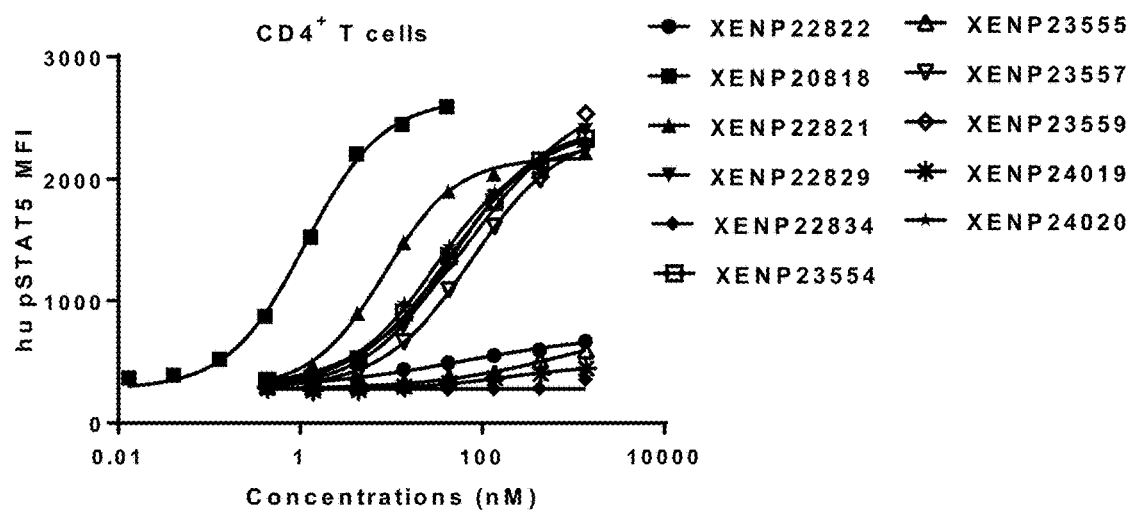

FIG. 66A-FIG. 66D depict gating of lymphocytes and subpopulations thereof for the experiments depicted in FIGS. 67A-67C. FIG. 66A shows gating of the lymphocyte population. FIG. 66B shows CD4+ and CD8+ T cells. FIG. 66C shows the CD45RA and CD27 expressing subpopulations of CD4+ T cells. FIG. 66D shows the CD45RA and CD27 expressing subpopulations of CD8+ T cells.

FIG. 67A-FIG. 67C depict STAT5 phosphorylation on CD8$^+$ T cells (CD45RA−CD27−) (FIG. 67A) and CD4$^+$ T cells (CD45RA−CD27−) (FIG. 67B) following incubation of PBMCs for 4 days with the indicated variant IL-15/IL-15Rα-Fc fusion proteins at the indicated concentrations. FIG. 67C shows the fold change in EC50 of various IL-15/IL-15Rα Fc heterodimers relative to control (XENP20818).

Figure 68A:
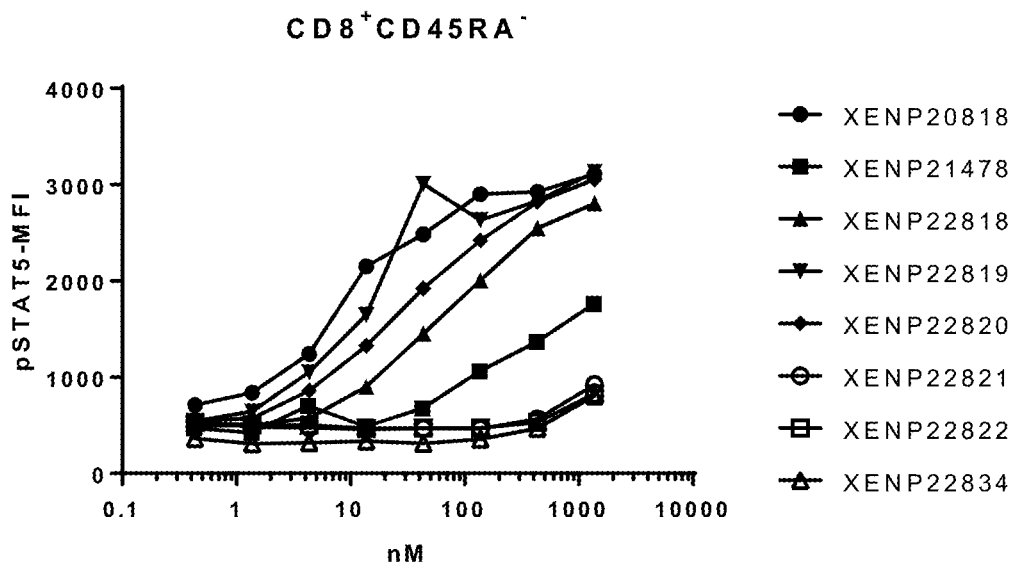
Figure 68B:
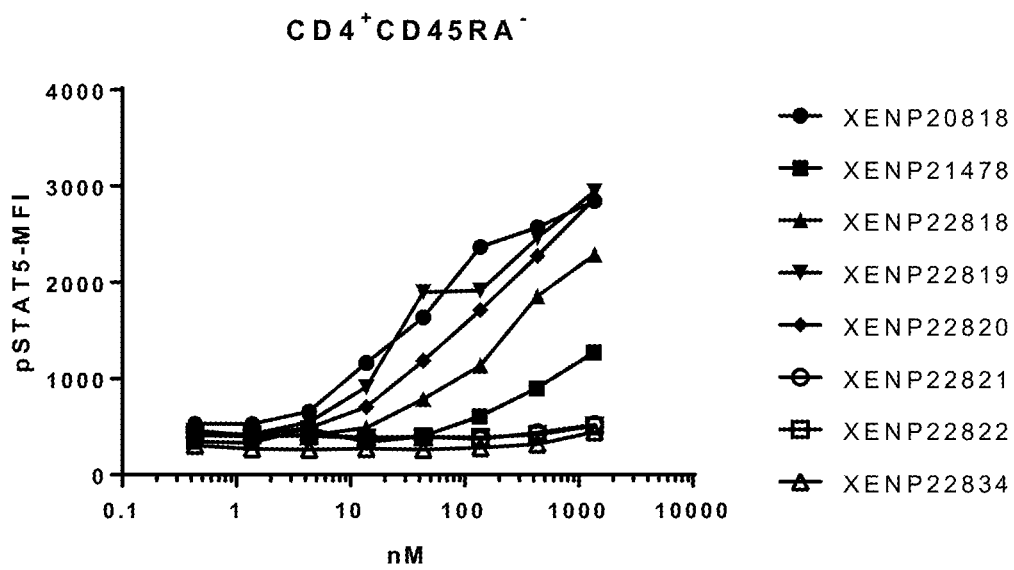

FIG. 68A-FIG. 68B depict STAT5 phosphorylation on CD8$^+$CD45RA$^-$ T cells (FIG. 68A) and CD4$^+$CD45RA$^-$ T cells (FIG. 68B) in mouse splenocytes following incubation with the indicated test articles.

Figure 69:
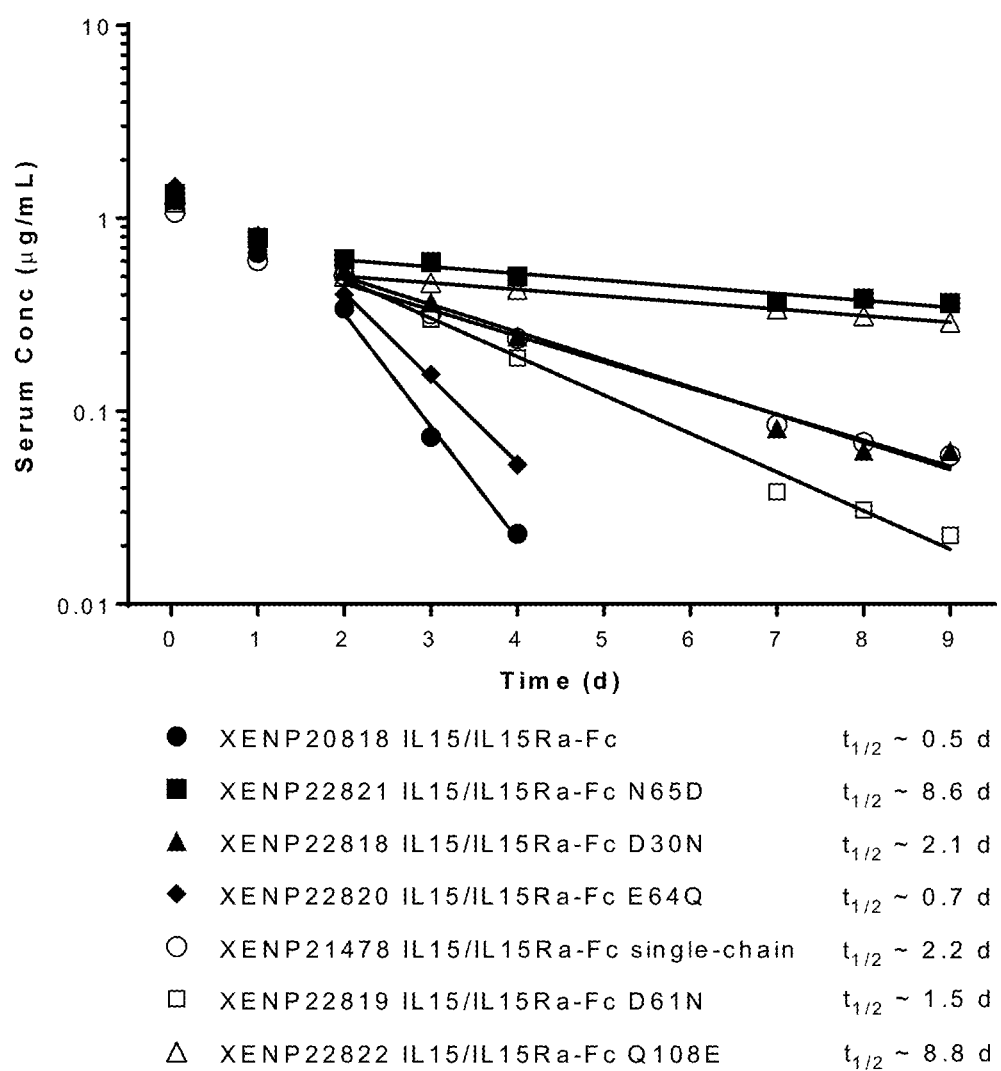

FIG. 69 depicts IV-TV Dose PK of various IL-15/Rα-Fc fusion proteins or controls in C57BL/6 mice at 0.1 mg/kg single dose.

Figure 70:
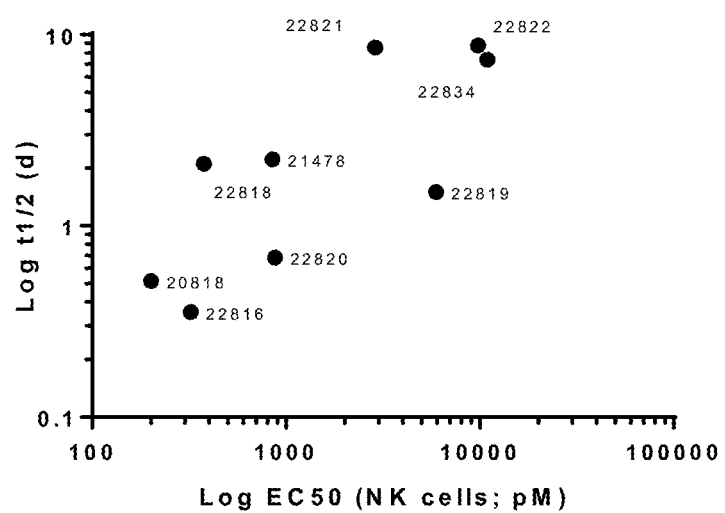

FIG. 70 depicts the correlation of half-life vs NK cell potency.

Figure 71:
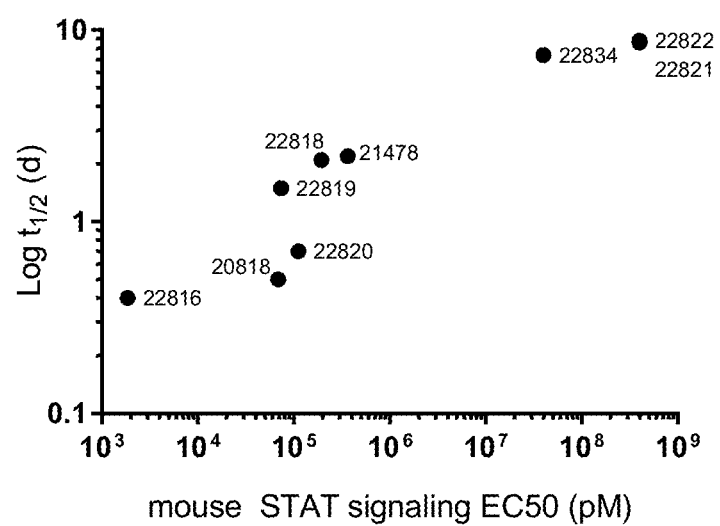

FIG. 71 depicts the correlation of half-life vs mouse STAT5 signaling for IL-15/Rα-Fc affinity variants.

Figure 72:
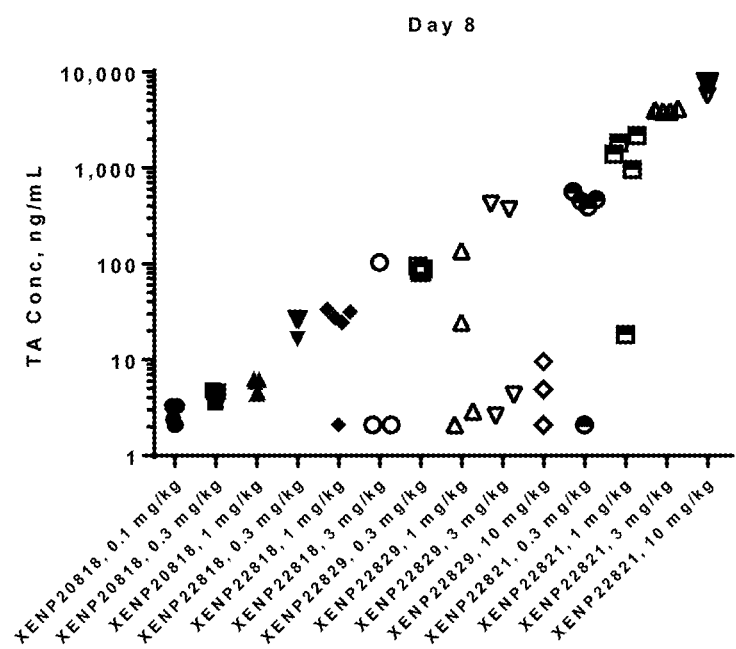

FIG. 72 depicts the serum concentration of test articles 8 days after dosing of C57BL/6 albino mice.

Figure 73:
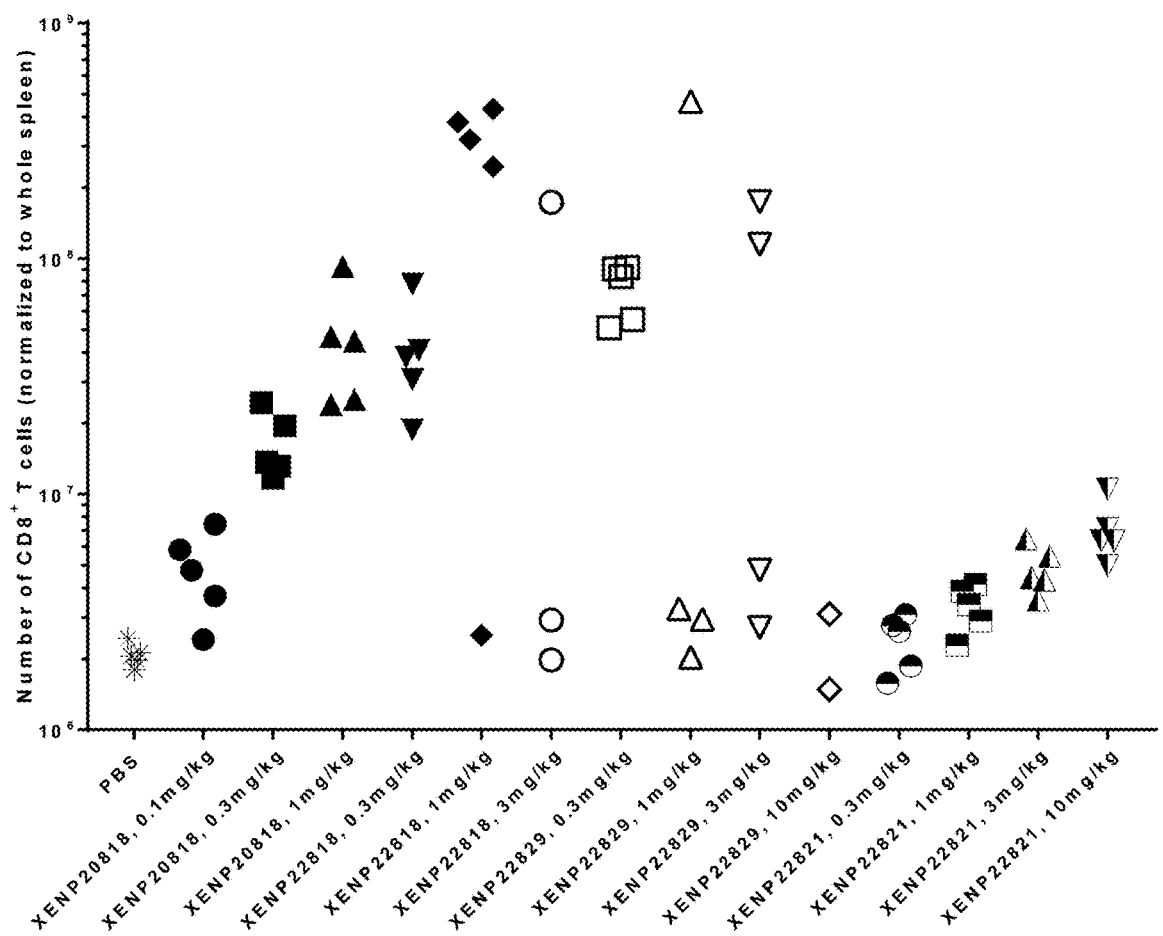

FIG. 73 depicts the CD8+ T cell count in the spleen of C57BL/6 albino mice 8 days after dosing with the indicated test articles.

Figure 74:
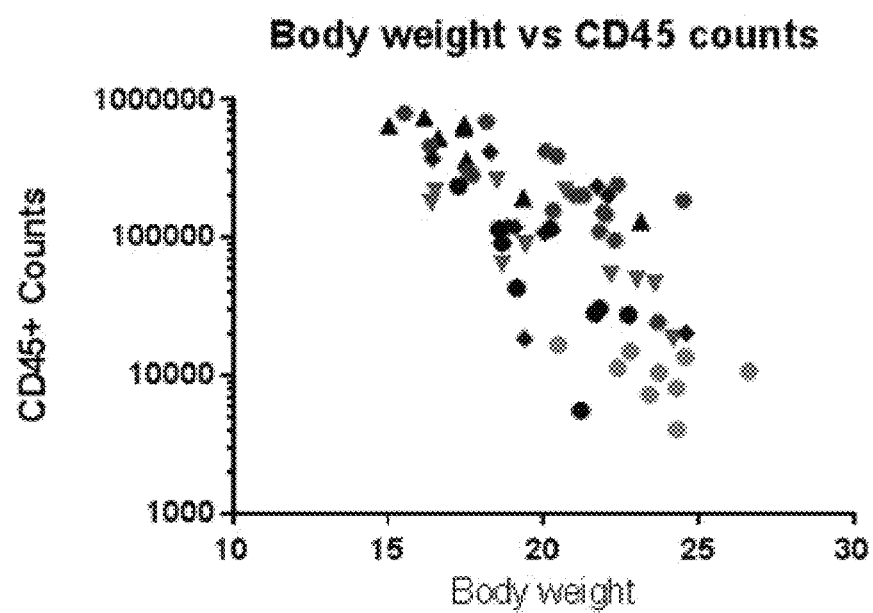

FIG. 74 shows that CD45$^+$ cell levels are predictive of disease.

Figure 75A:
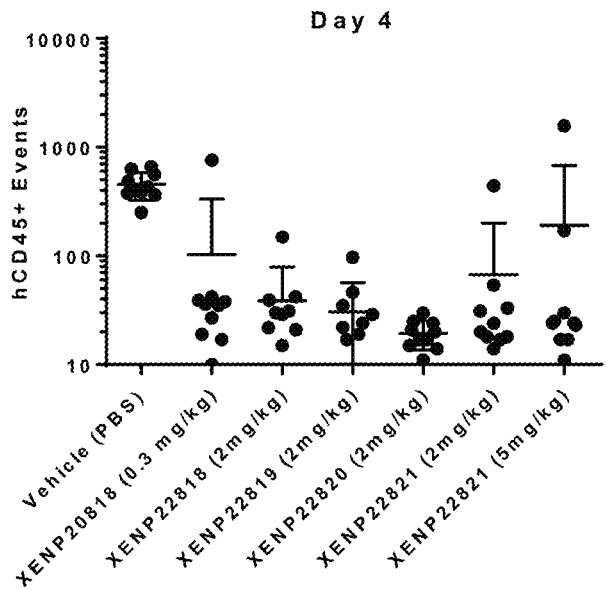
Figure 75B:
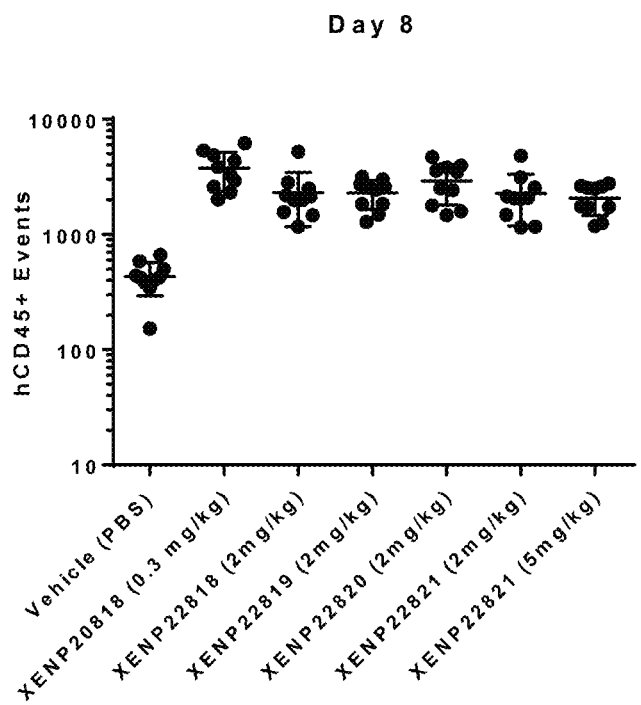

FIG. 75A-FIG. 75B depict the enhancement of engraftment by variant IL-15/Rα-Fc fusion proteins as indicated by CD45$^+$ cell counts on Day 4 (FIG. 75A) and Day 8 (FIG. 75B).

Figure 76A:
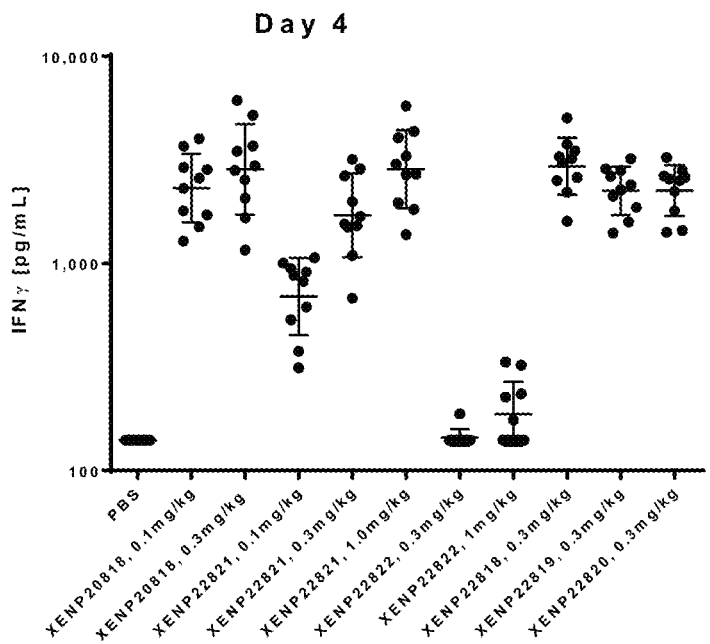
Figure 76B:
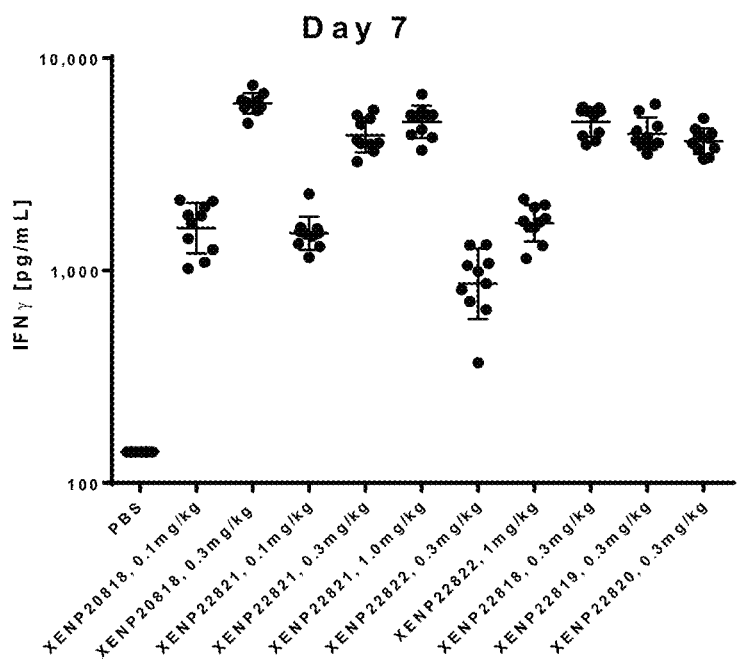
Figure 76C:
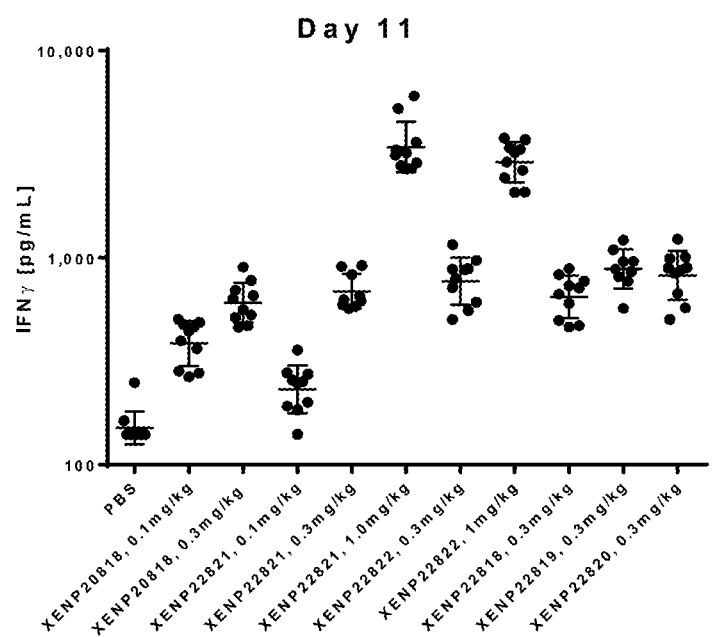

FIG. 76A-FIG. 76C depict IFNγ levels on Day 4 (FIG. 76A), Day 7 (FIG. 76B), and Day 11 (FIG. 76C) after treatment of NSG mice engrafted with human PBMCs with the indicated variant IL-15/Rα-Fc fusion proteins or control.

Figure 77A:
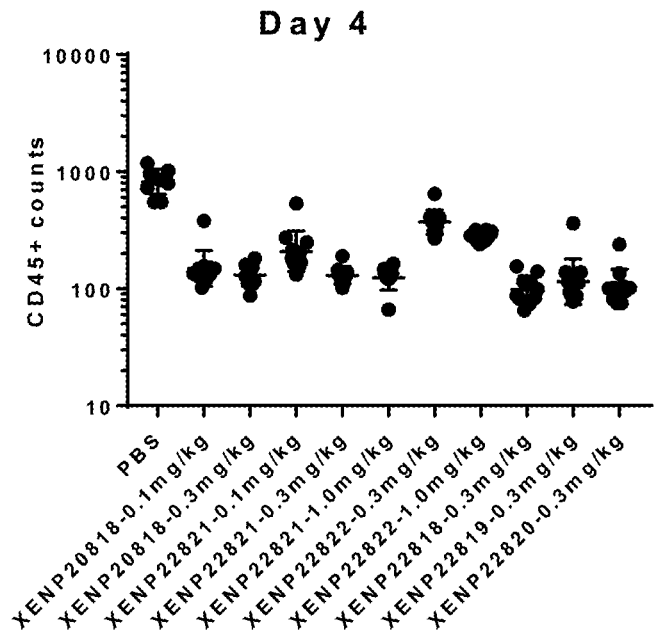
Figure 77B:
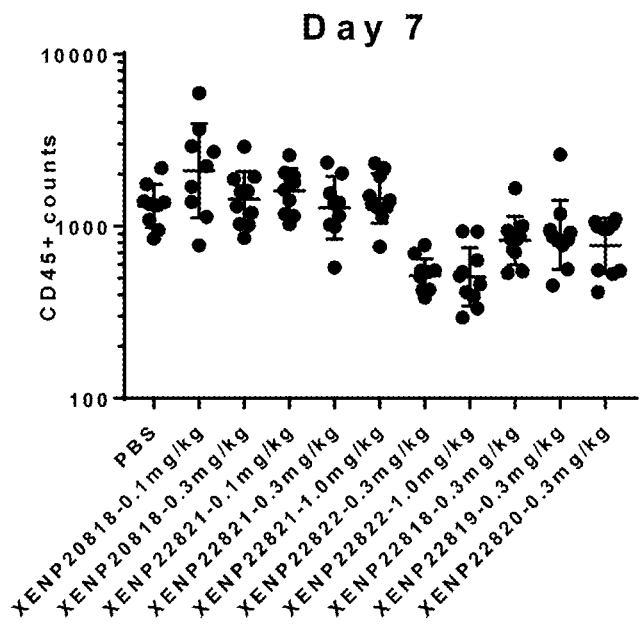
Figure 77C:
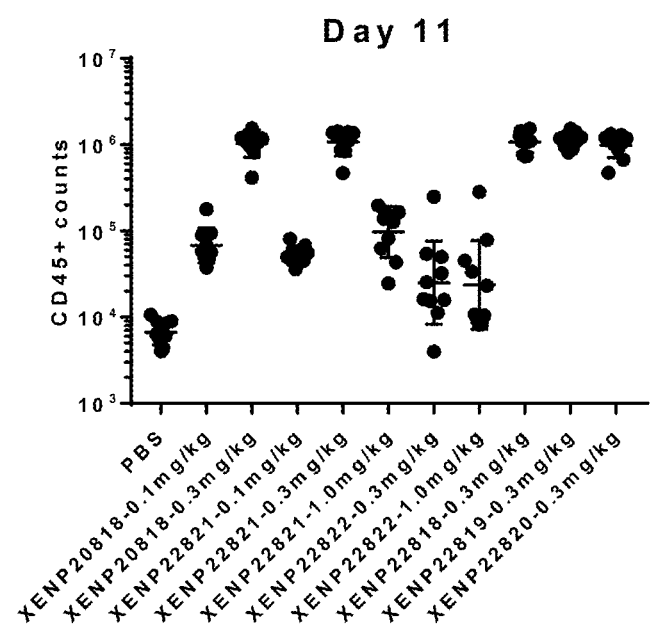

FIG. 77A-FIG. 77C depict CD45+ lymphocyte cell counts on Day 4 (FIG. 77A), Day 7 (FIG. 77B), and Day 11 (FIG. 77C) after treatment of NSG mice engrafted with human PBMCs with the indicated variant IL-15/Rα-Fc fusion proteins or control.

Figure 78A:
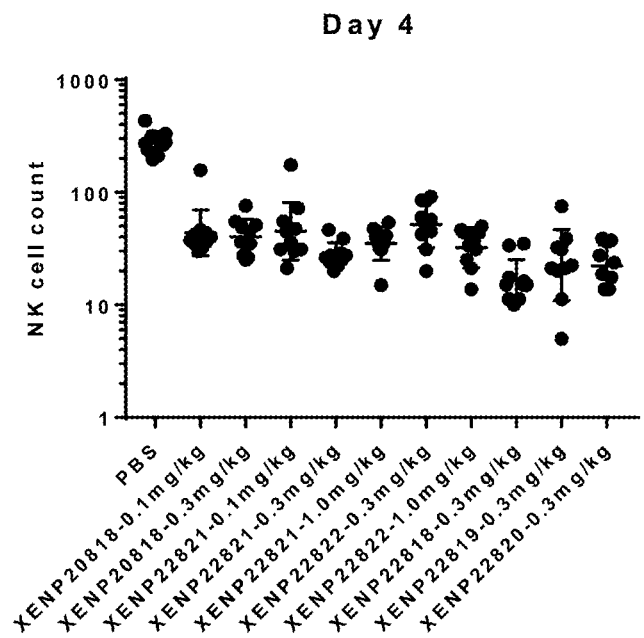
Figure 78B:
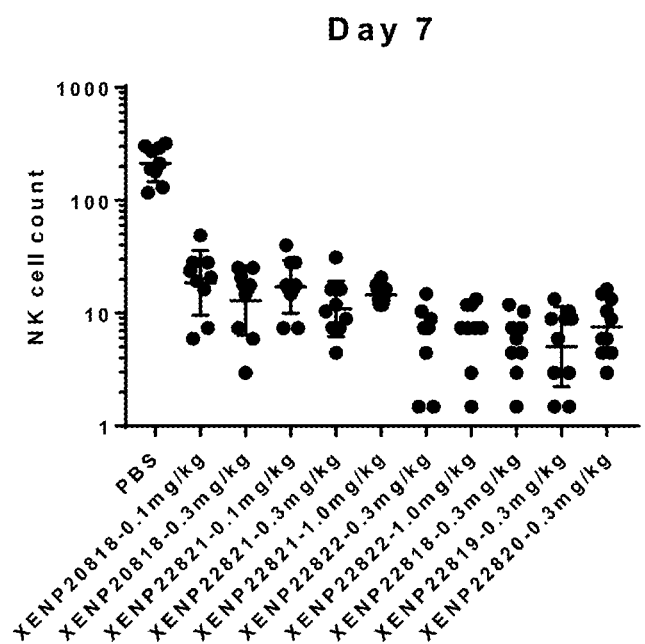
Figure 78C:
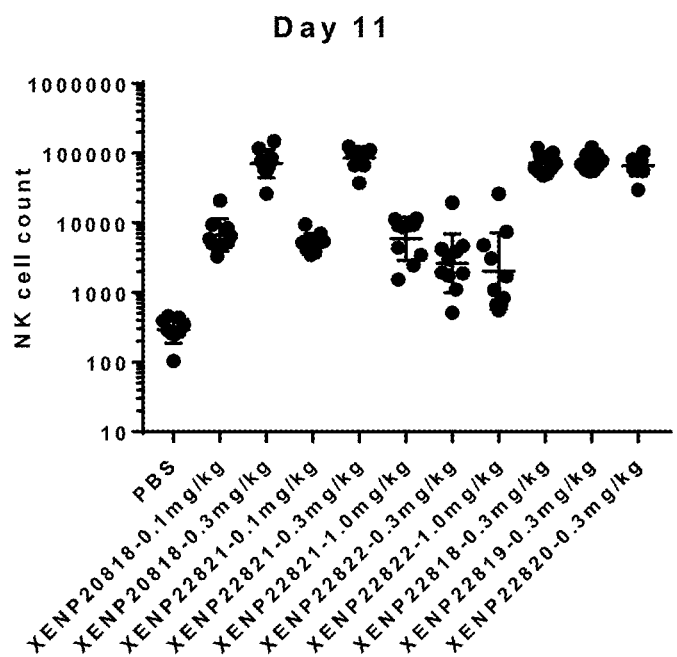

FIG. 78A-FIG. 78C depict NK cell (CD16+CD56+CD45RA+) counts on Day 4 (FIG. 78A), Day 7 (FIG. 78B) and Day 11 (FIG. 78C) after treatment of NSG mice engrafted with human PBMCs with the indicated IL-15/Rα-Fc fusion proteins or control.

Figure 79A:
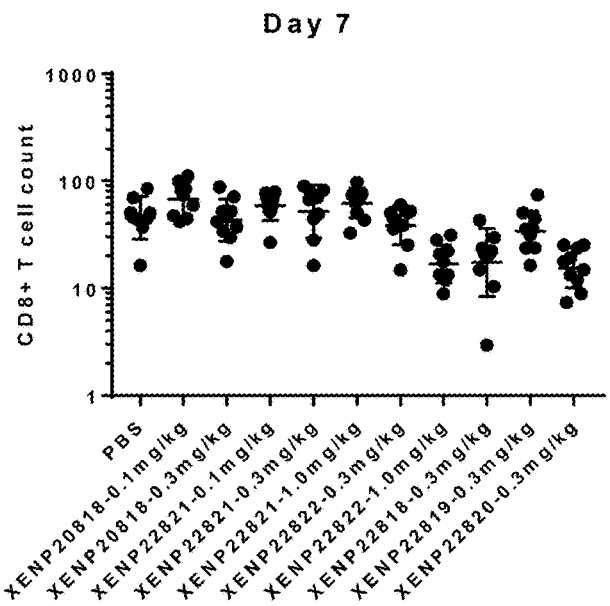
Figure 79B:
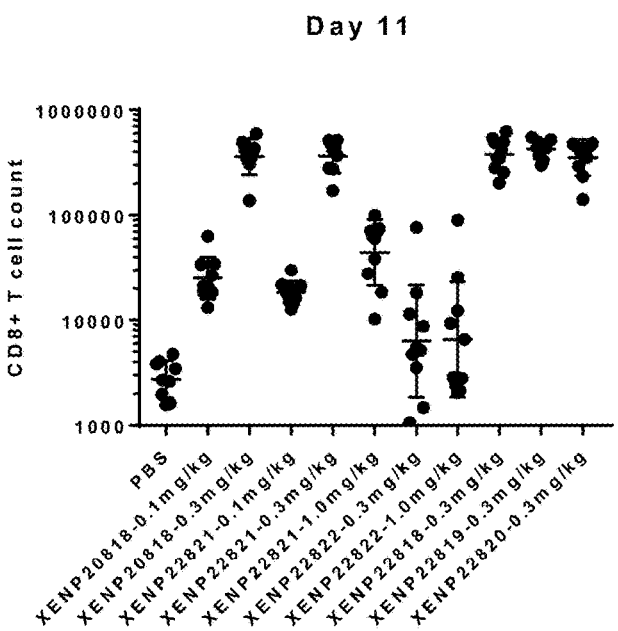

FIG. 79A-FIG. 79B depict CD8$^+$ T cell (CD8+CD45RA+) counts on Day 7 (FIG. 79A) and Day 11 (FIG. 79B) after treatment of NSG mice engrafted with human PBMCs with the indicated IL-15/Rα-Fc fusion proteins or control.

Figure 80A:
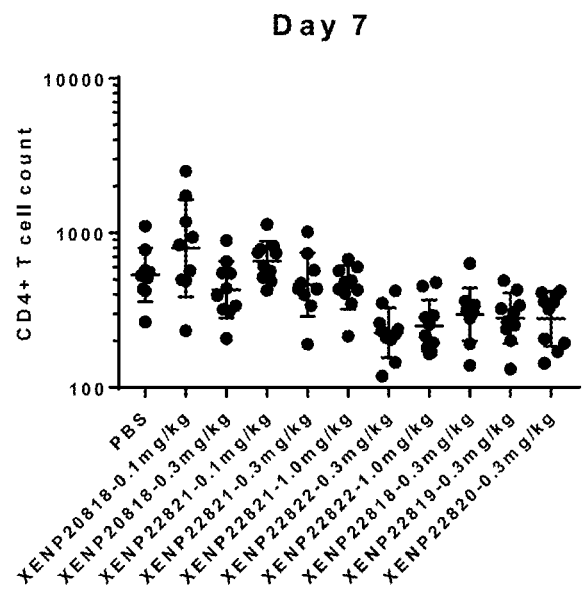
Figure 80B:
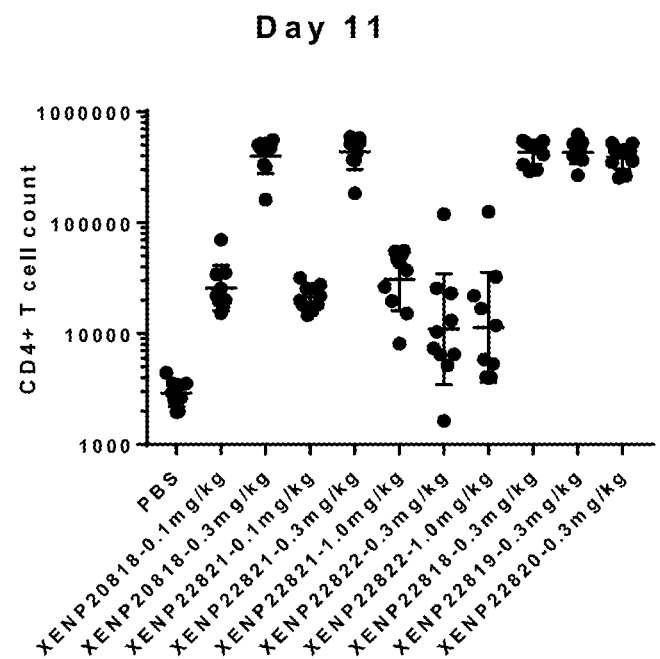

FIG. 80A-FIG. 80B depict CD4+ T cell (CD4+CD45RA+) counts on Day 7 (FIG. 80A) and Day 11 (FIG. 80B) after treatment of NSG mice engrafted with human PBMCs with the indicated IL-15/Rα-Fc fusion proteins or control.

Figure 81:
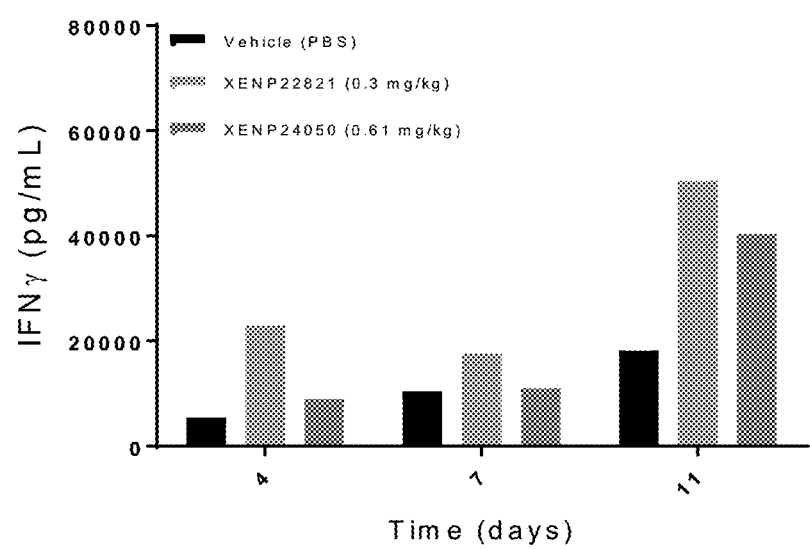

FIG. 81 depicts IFNγ level on Days 4, 7, and 11 in serum of huPBMC engrafted mice following treatment with additional variant IL-15/Rα-Fc fusion proteins.

Figure 82A:
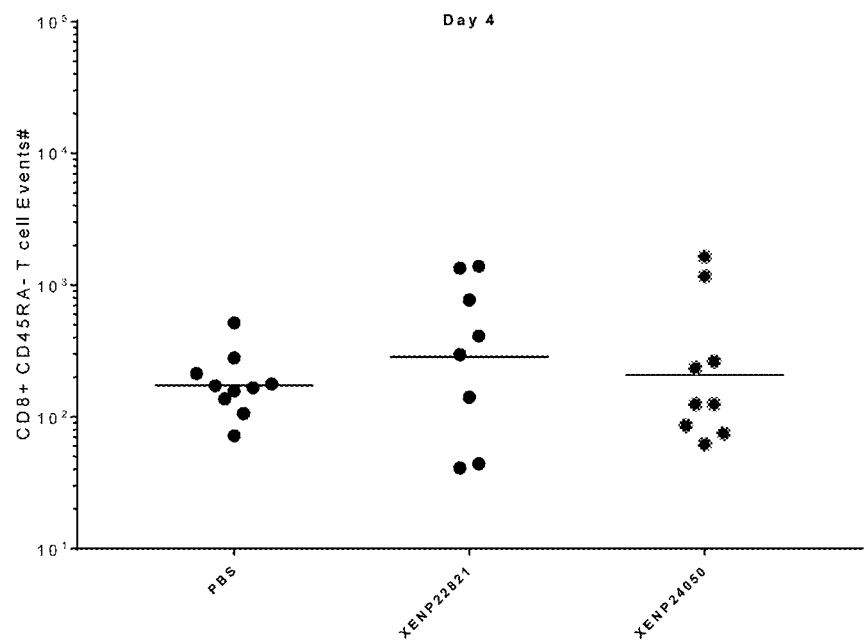
Figure 82B:
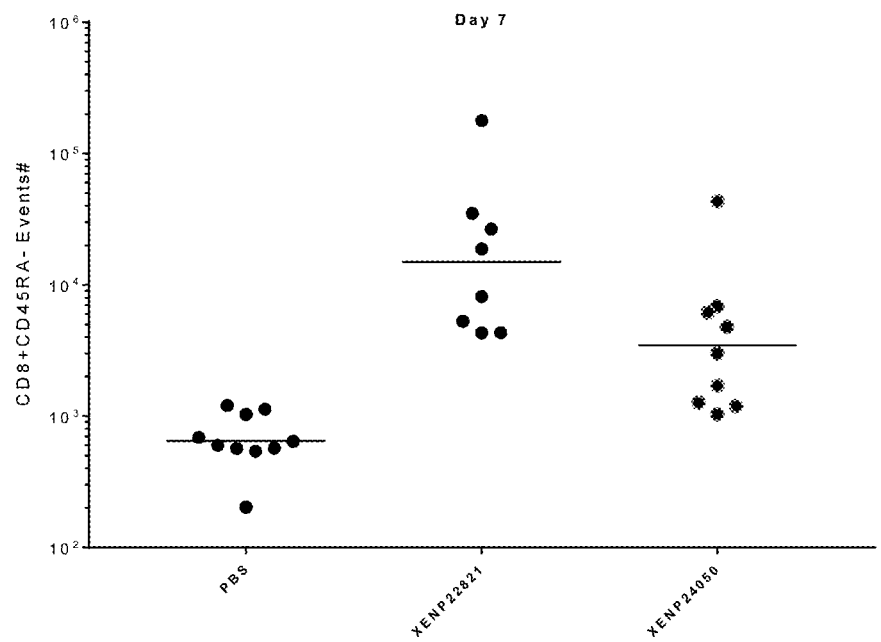
Figure 82C:
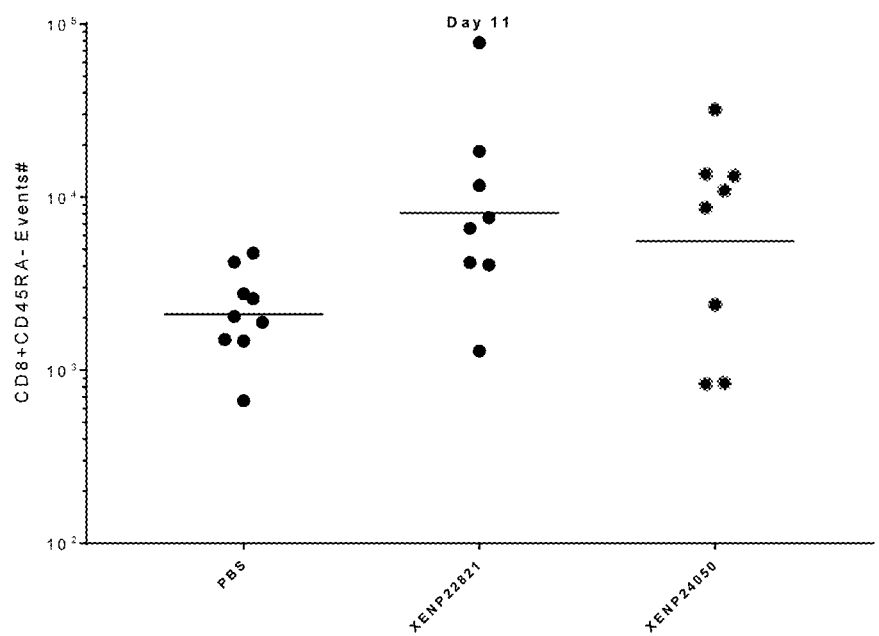

FIG. 82A-FIG. 82C depict CD8+ T cell count on Day 4 (FIG. 82A), Day 7 (FIG. 82B), and Day 11 (FIG. 82C) in whole blood of huPBMC engrafted mice following treatment with additional variant IL-15/Rα-Fc fusion proteins.

Figure 83A:
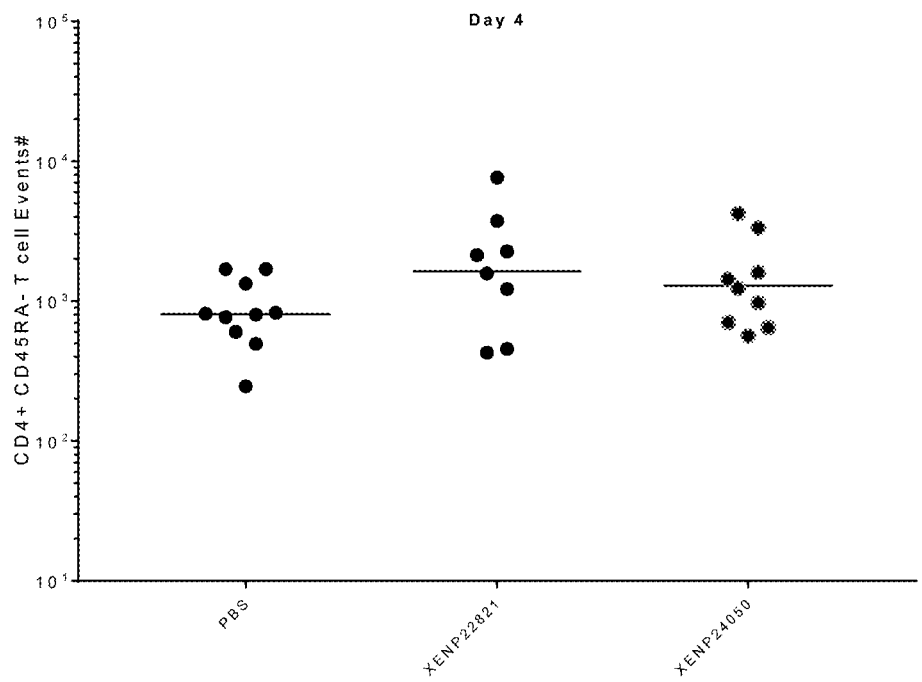
Figure 83B:
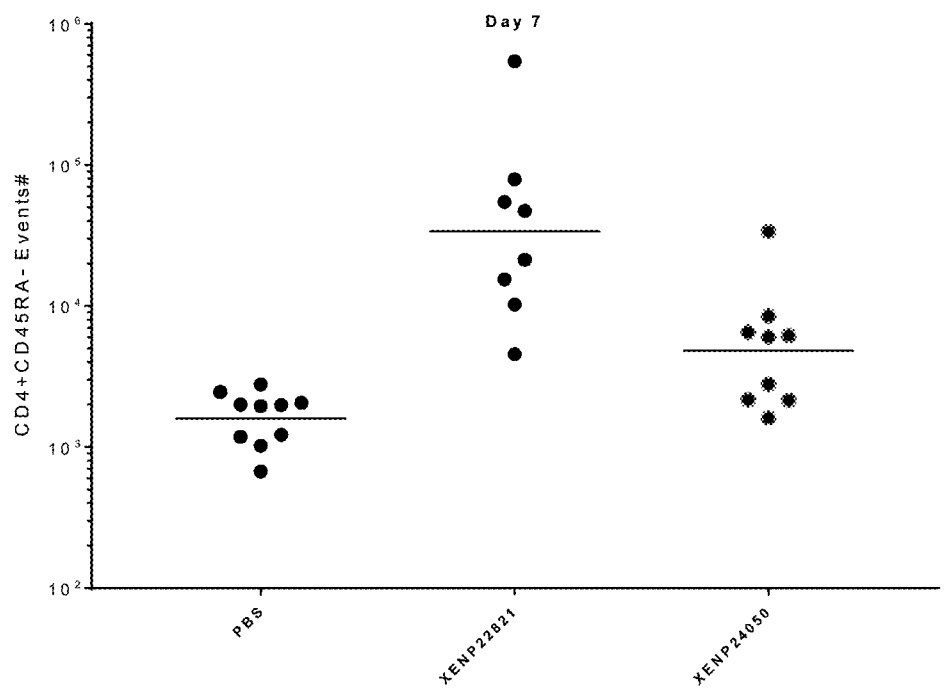
Figure 83C:
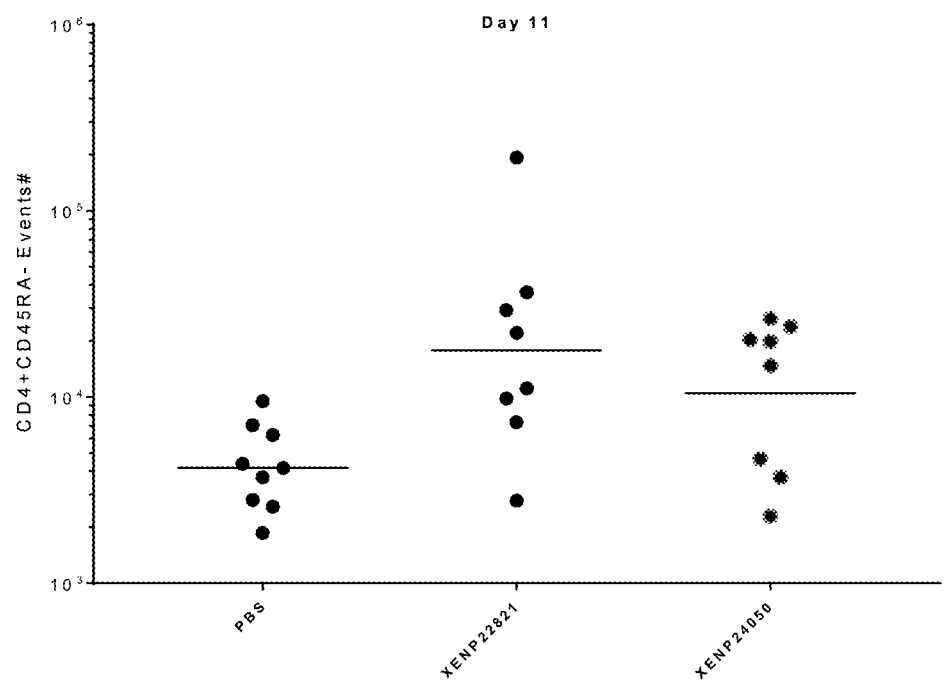

FIG. 83A-FIG. 83C depict CD4+ T cell count on Day 4 (FIG. 83A), Day 7 (FIG. 83B), and Day 11 (FIG. 83C) in whole blood of huPBMC engrafted mice following treatment with additional variant IL-15/Rα-Fc fusion proteins.

Figure 84A:
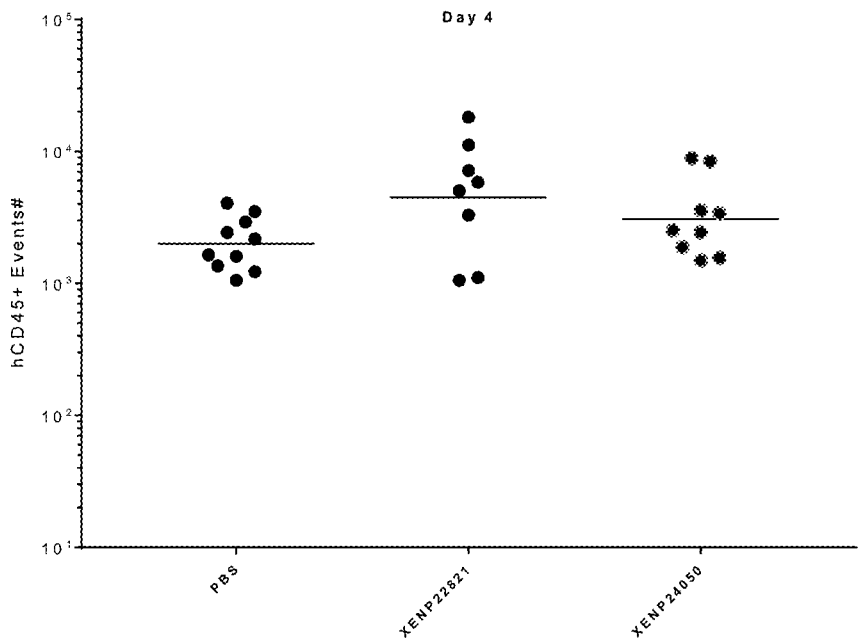
Figure 84B:
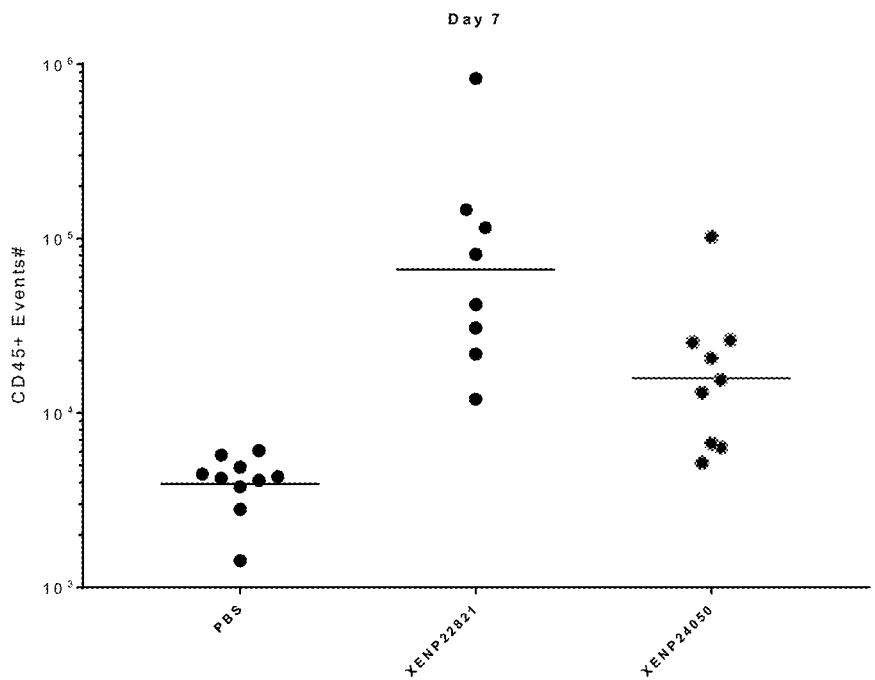
Figure 84C:
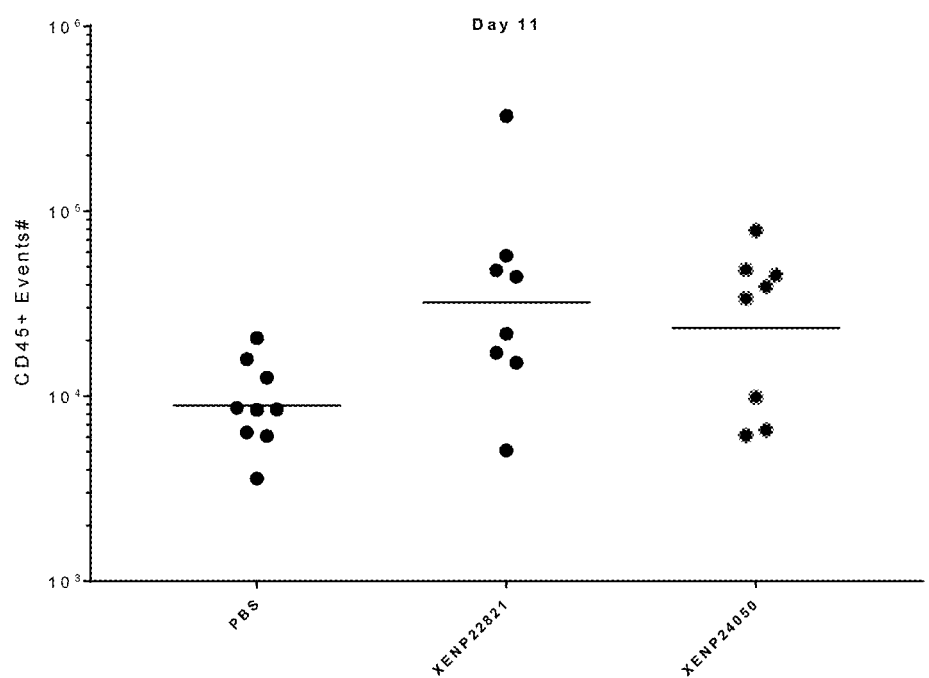

FIG. 84A-FIG. 84C depict CD45+ cell count on Day 4 (FIG. 84A), Day 7 (FIG. 84B), and Day 11 (FIG. 84C) in whole blood of huPBMC engrafted mice following treatment with additional variant IL-15/Rα-Fc fusion proteins.

Figure 85A:
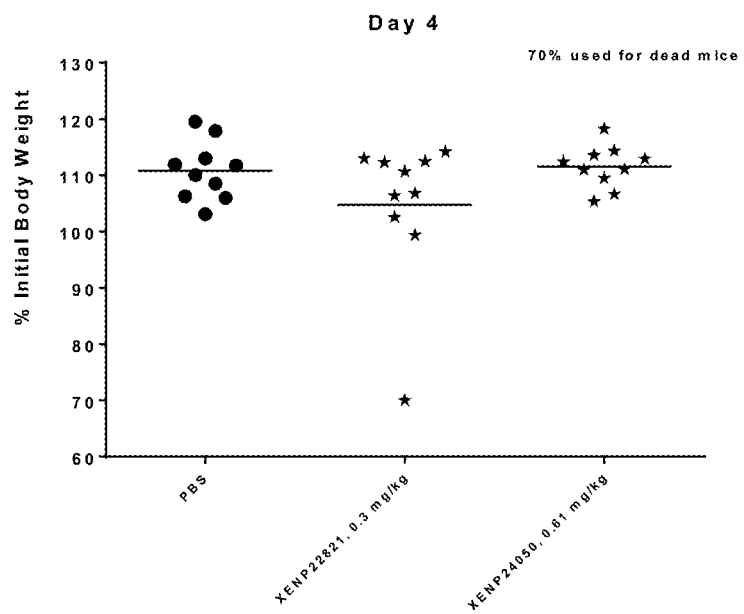
Figure 85B:
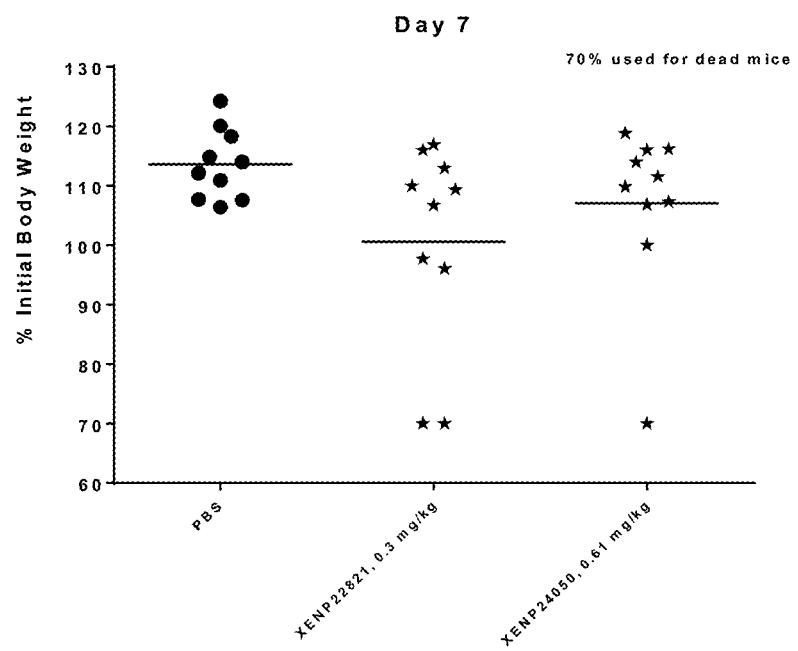
Figure 85C:
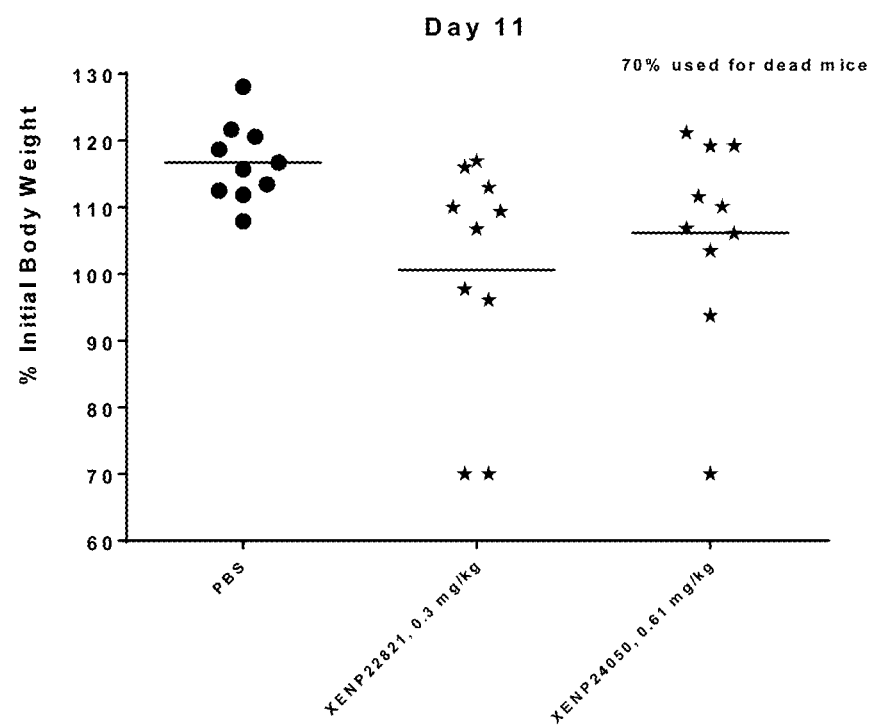

FIG. 85A-FIG. 85C depict the body weight as a percentage of initial body weight of huPBMC engrafted mice on Day 4 (FIG. 85A), Day 7 (FIG. 85B), and Day 11 (FIG. 85C) following treatment with additional IL-15/Rα variants. Each point represents a single NSG mouse. Mice whose body weights dropped below 70% initial body weight were euthanized. Dead mice are represented as 70%.

Figure 86A:
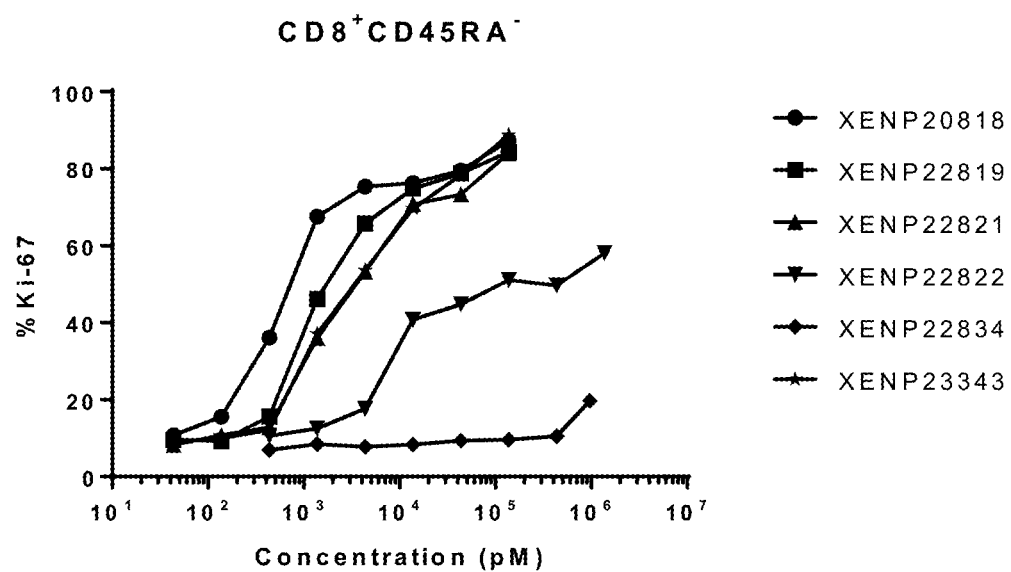
Figure 86B:
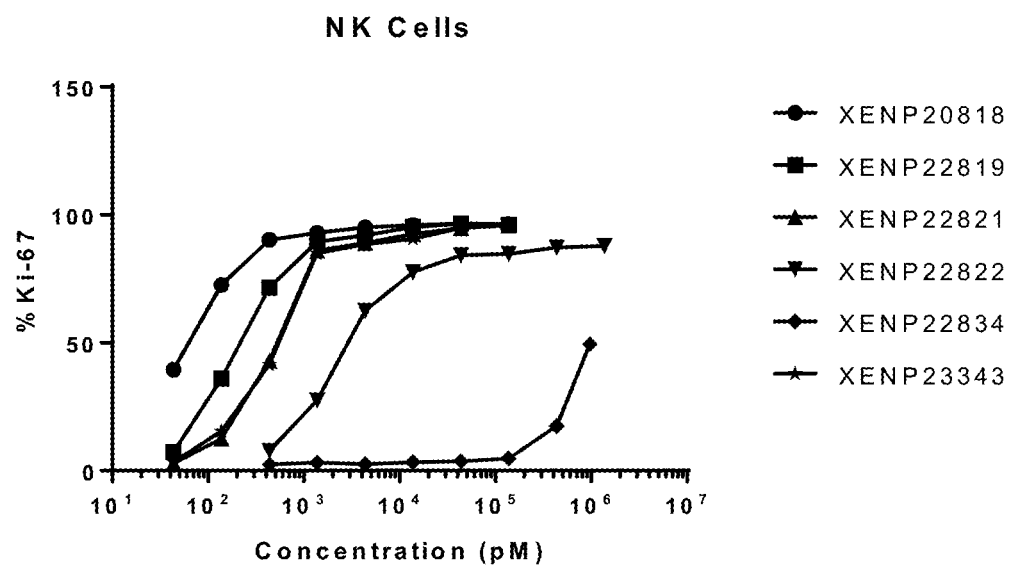

FIG. 86A-FIG. 86B depict percentage cyno CD8$^+$ T cell (FIG. 86A) and cyno NK cell (FIG. 86B) expressing Ki67 following incubation with the indicated test articles.

Figure 87A:
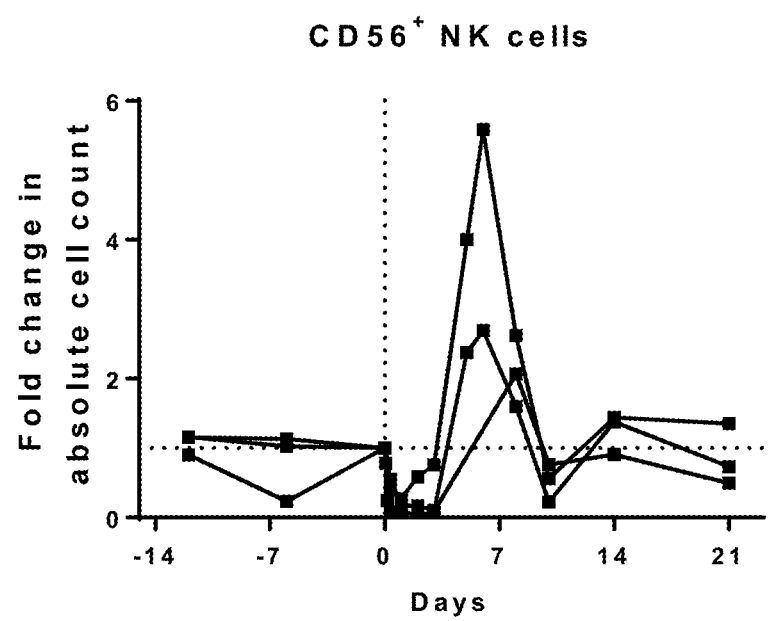
Figure 87B:
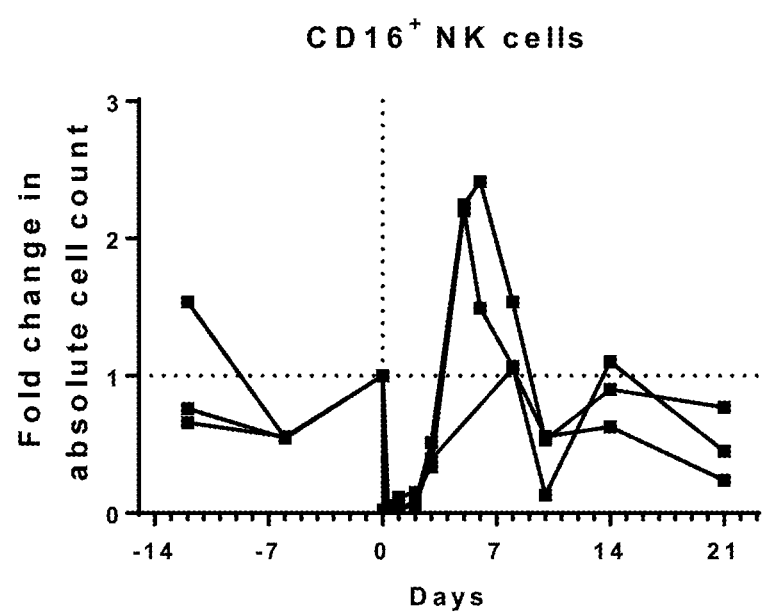
Figure 87C:
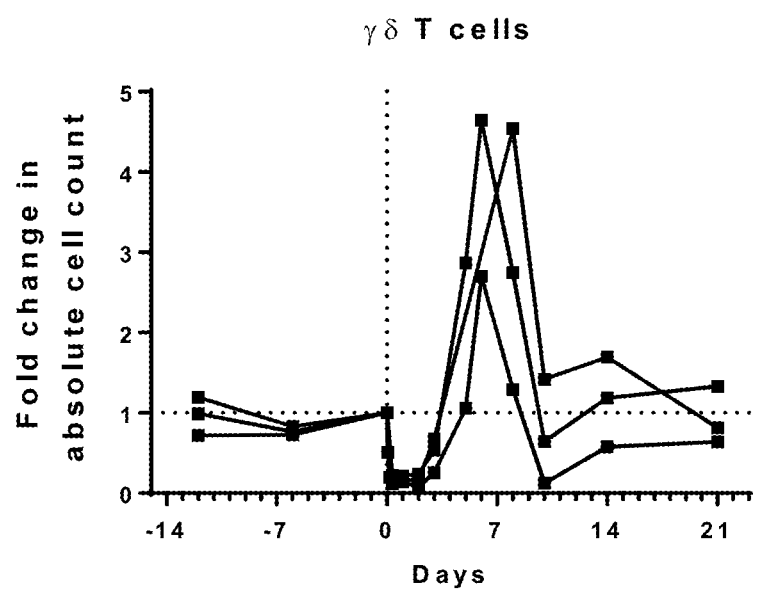
Figure 87D:
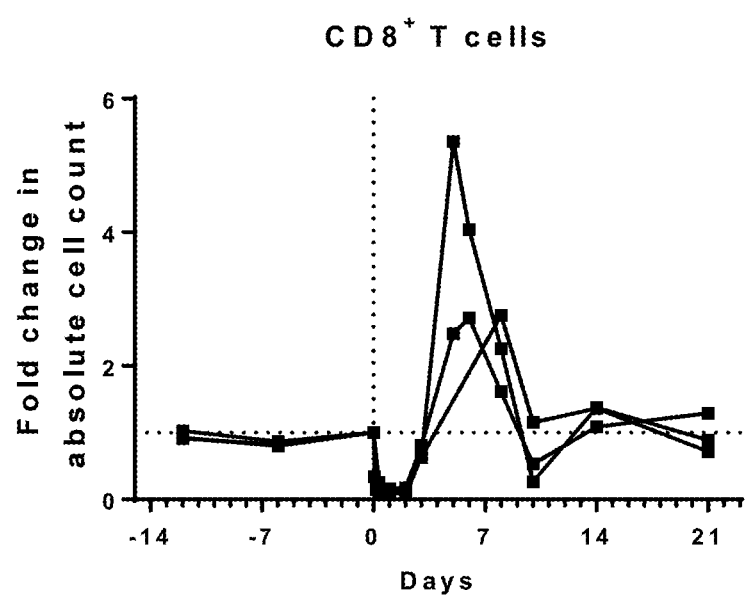
Figure 87E:
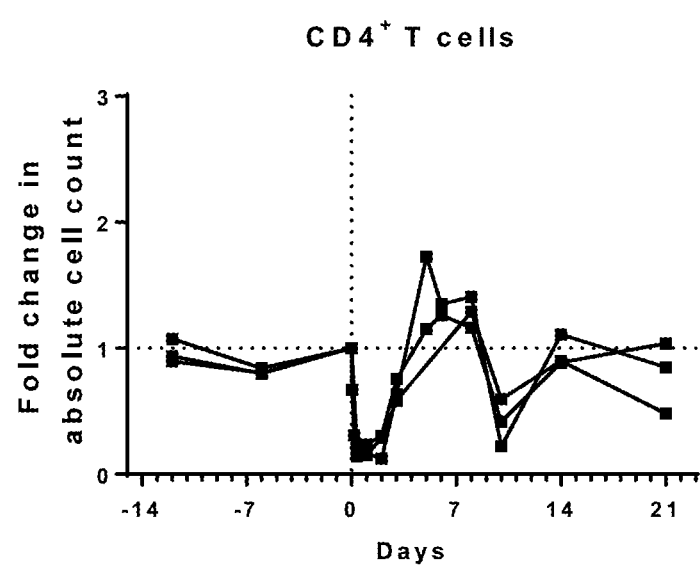
Figure 88A:
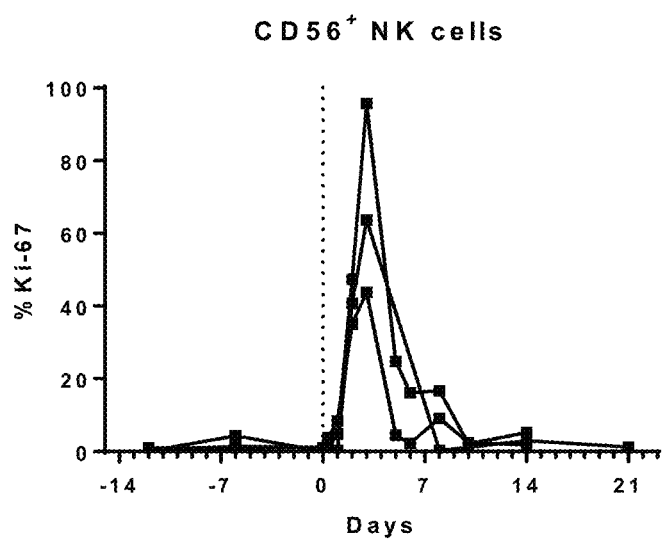
Figure 88B:
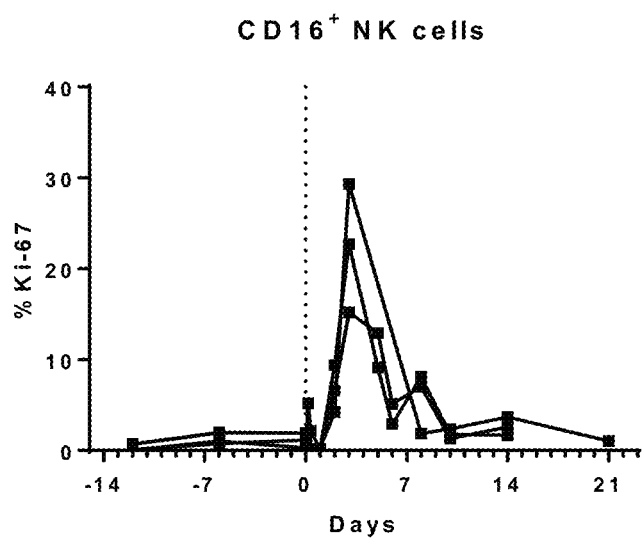
Figure 88C:
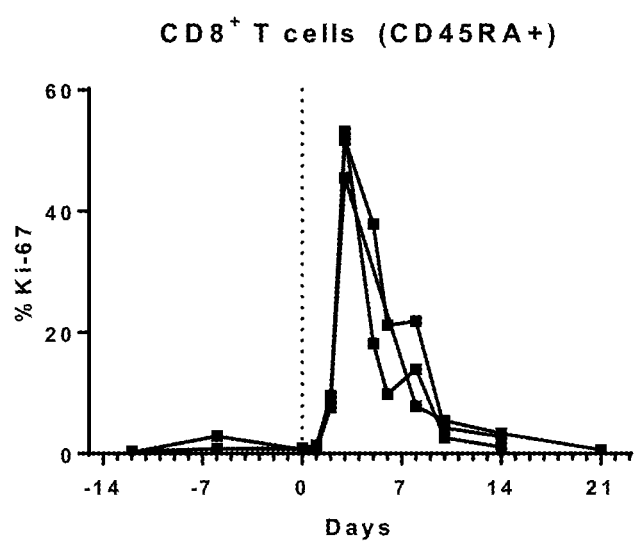
Figure 88D:
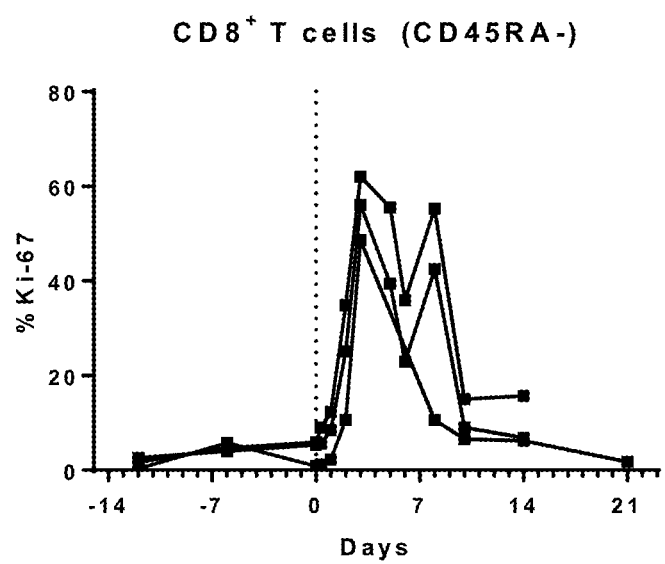
Figure 88E:
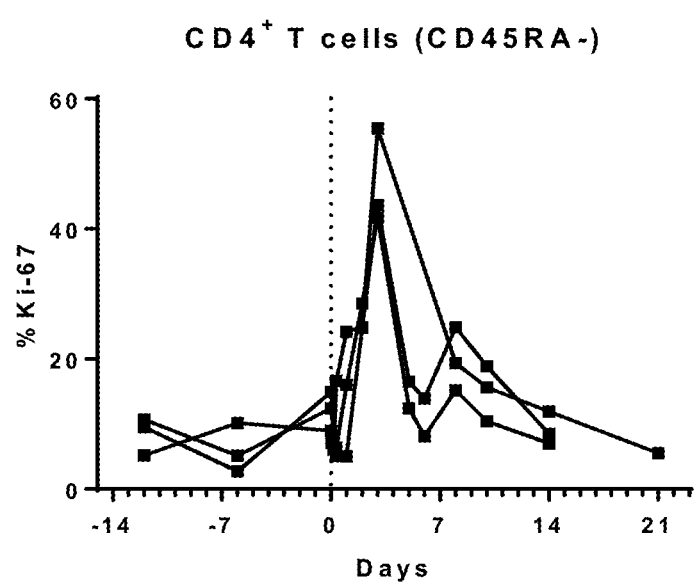

FIG. 87A-FIG. 87E depict lymphocyte counts after dosing cynomolgus monkeys with XENP20818. FIGS. 87A-E respectively show the fold change in absolute count of CD56+ NK cells (FIG. 87A), CD16+ NK cells (FIG. 87B), γδ T cells (CD45RA+CD3+CD4−CD8−) (FIG. 87C), CD8+ T cells (FIG. 87D), and CD4+ T cells (FIG. 87E).

FIG. 88A-FIG. 88E depict proliferation of CD56+ NK cells (FIG. 88A), CD16+ NK cells (FIG. 88B), CD8+ T cells (CD45RA+) (FIG. 88C), CD8+ T cells (CD45RA−) (FIG. 88D), and CD4+ T cells (CD45RA−) (FIG. 88E) after dosing cynomolgus monkeys with XENP20818.

Figure 89A:
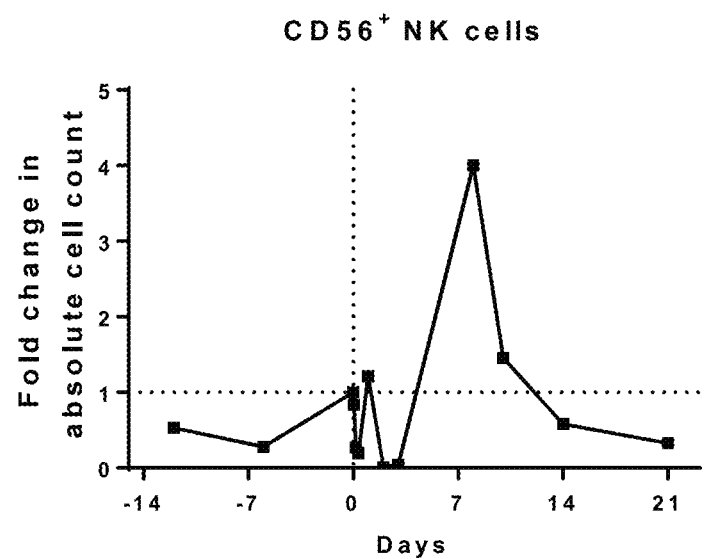
Figure 89B:
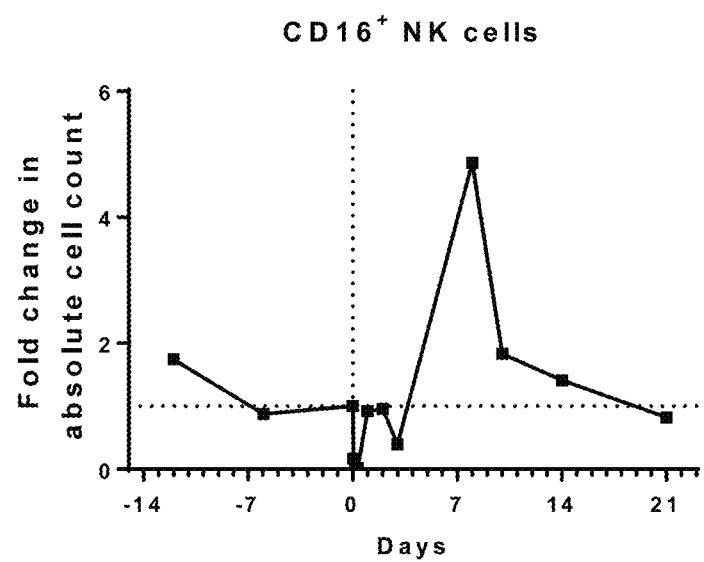
Figure 89C:
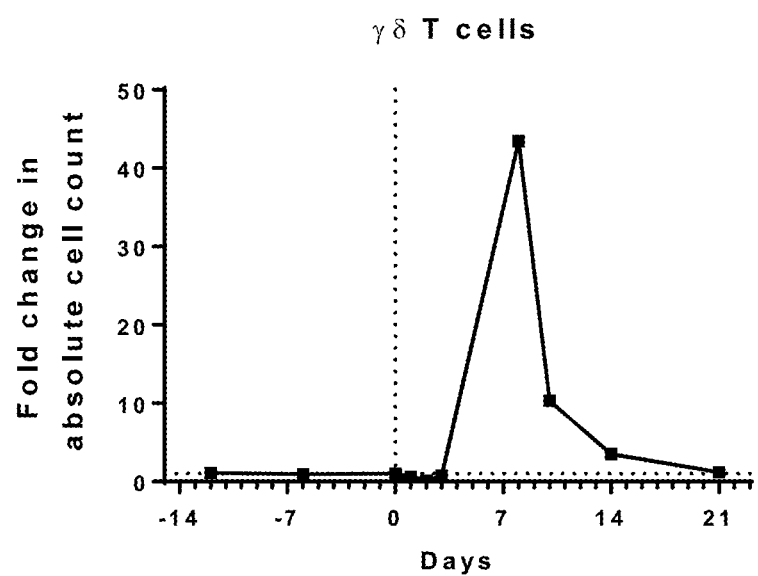
Figure 89D:
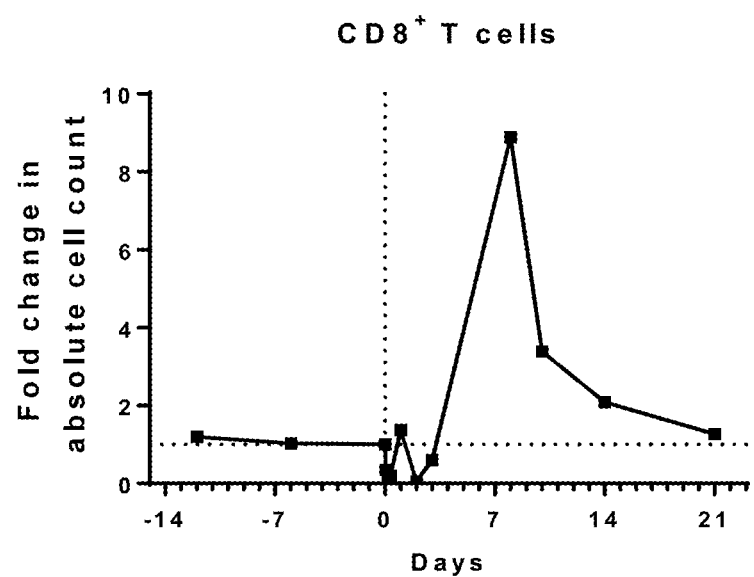
Figure 89E:
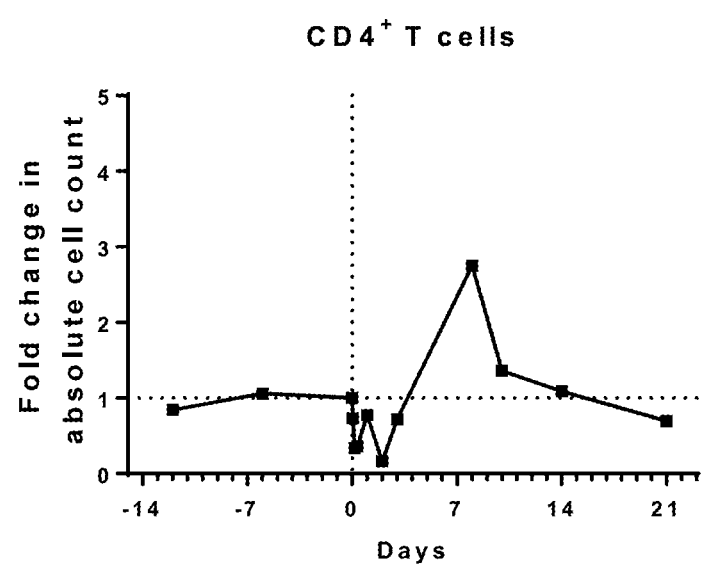
Figure 90A:
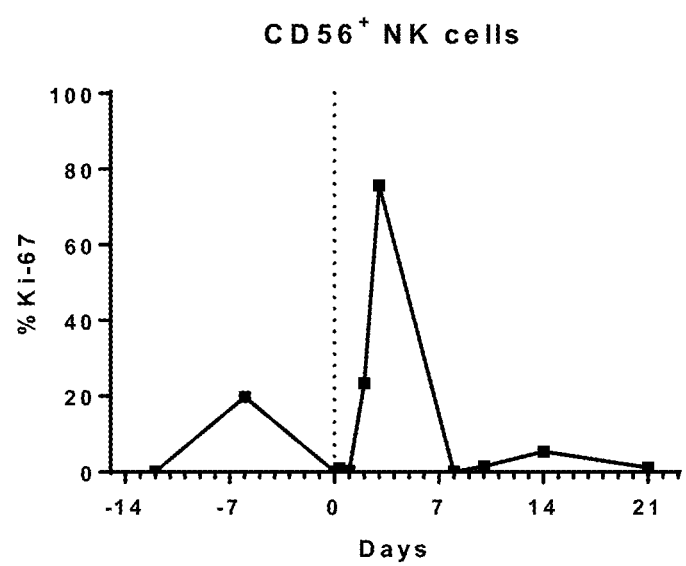
Figure 90B:
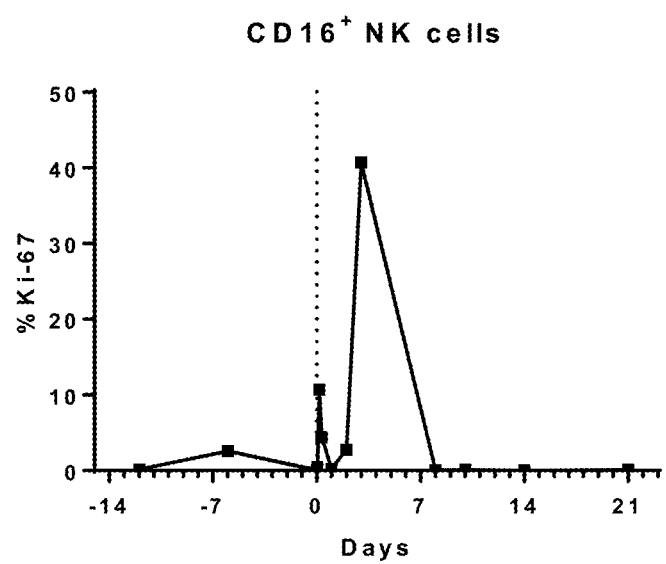
Figure 90C:
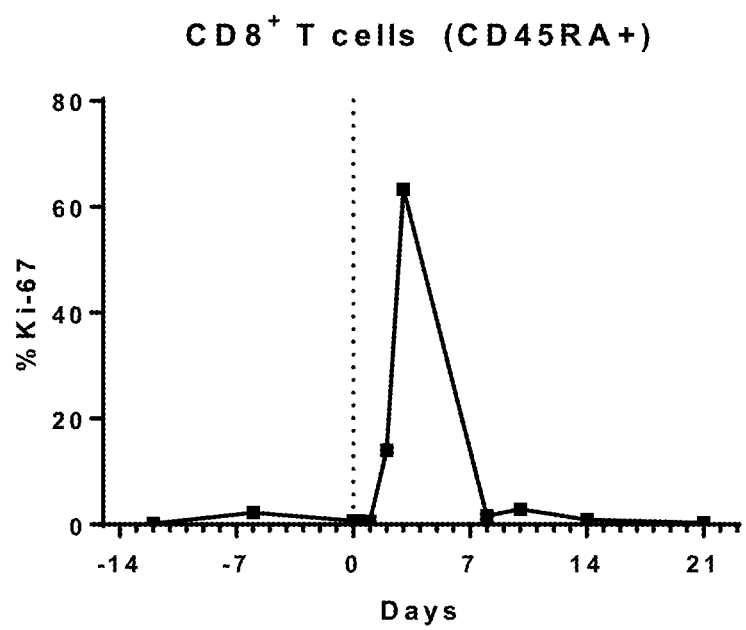
Figure 90D:
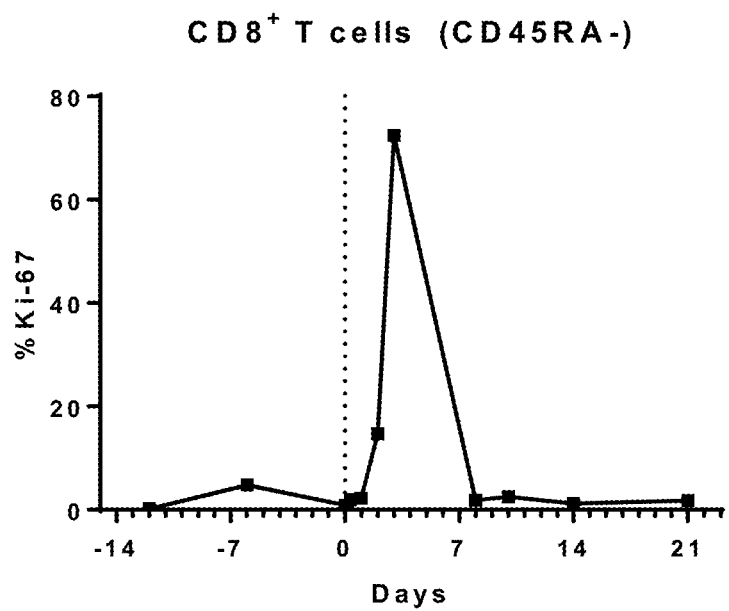
Figure 90E:
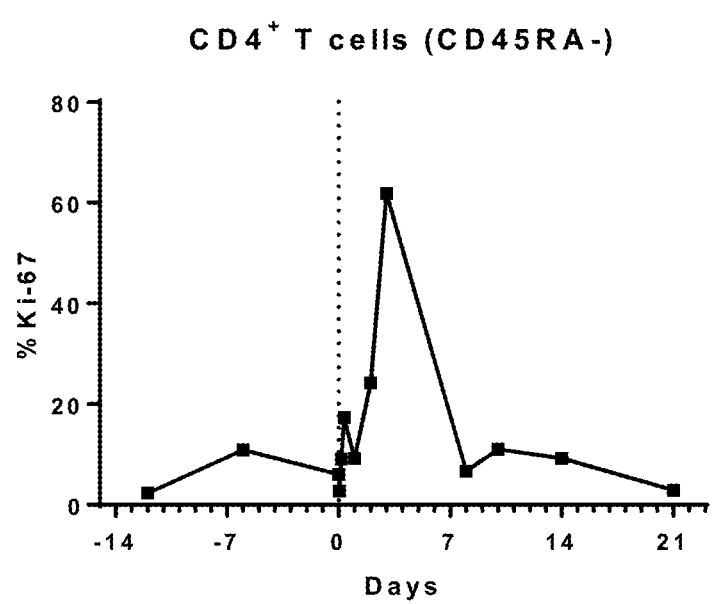

FIG. 89A-FIG. 89E depict lymphocyte counts after dosing cynomolgus monkeys with XENP22819. FIGS. 89A-89E show the fold change in absolute count of CD56+ NK cells (FIG. 89A), CD16+ NK cells (FIG. 89B), γδ T cells (CD45RA+CD3+CD4−CD8−) (FIG. 89C), CD8+ T cells (FIG. 89D), and CD4+ T cells (FIG. 89E).

FIG. 90A-FIG. 90E depict proliferation of CD56+ NK cells (FIG. 90A), CD16+ NK cells (FIG. 90B), CD8+ T cells (CD45RA+) (FIG. 90C), CD8+ T cells (CD45RA−) (FIG. 90D), and CD4+ T cells (CD45RA−) (FIG. 90E) after dosing cynomolgus monkeys with XENP22819.

Figure 91A:
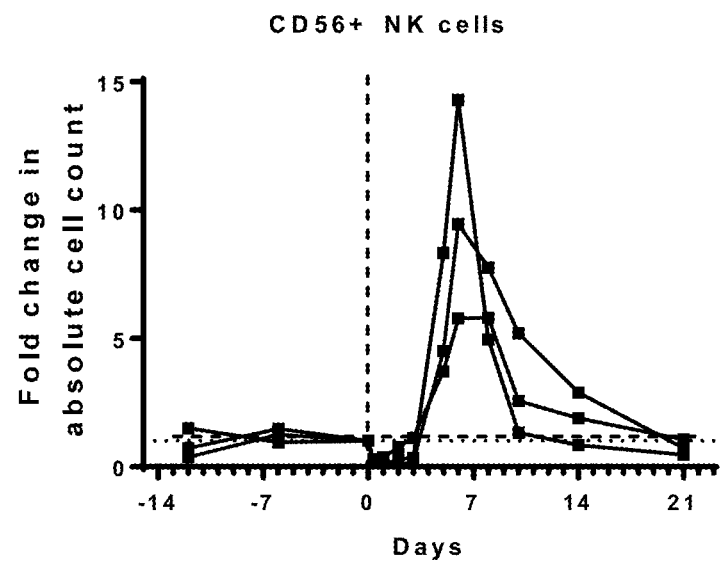
Figure 91B:
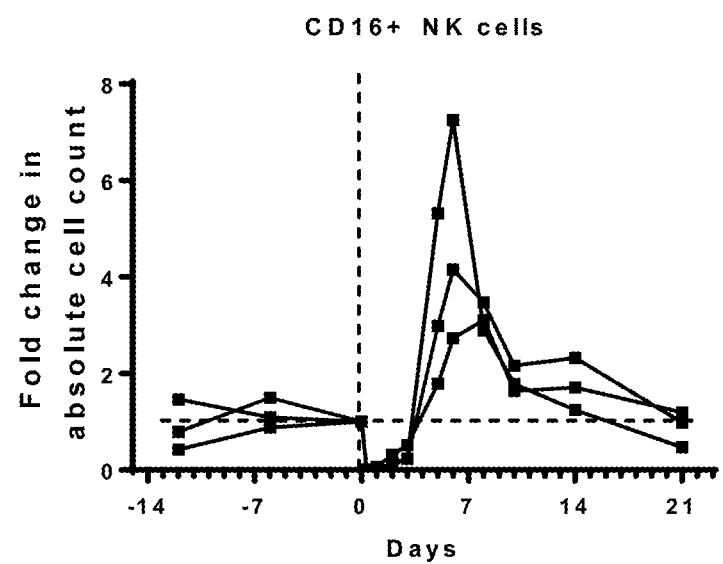
Figure 91C:
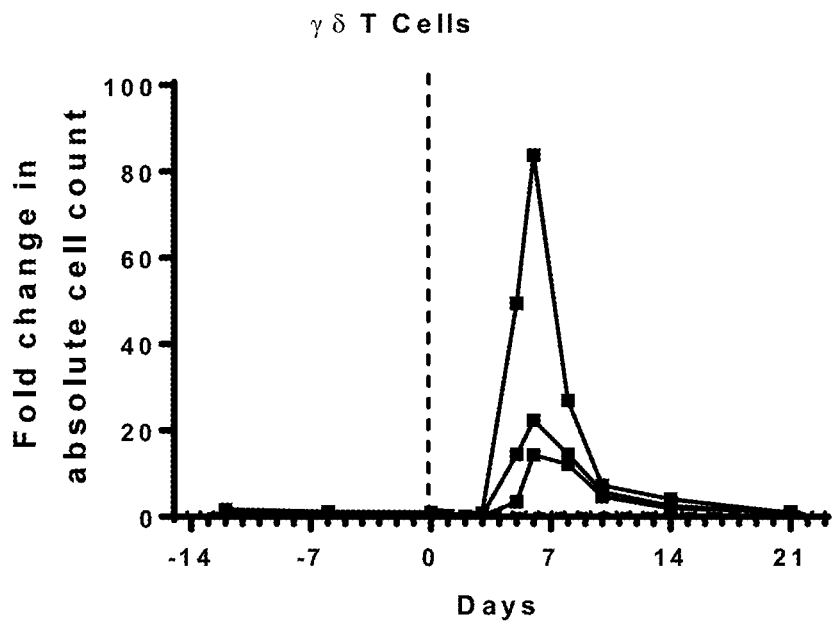
Figure 91D:
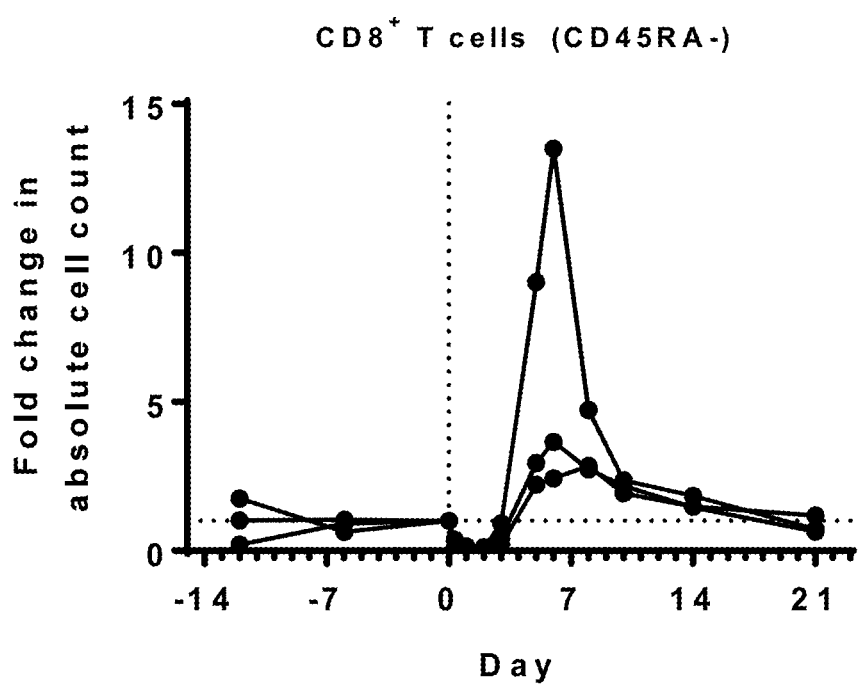
Figure 91E:
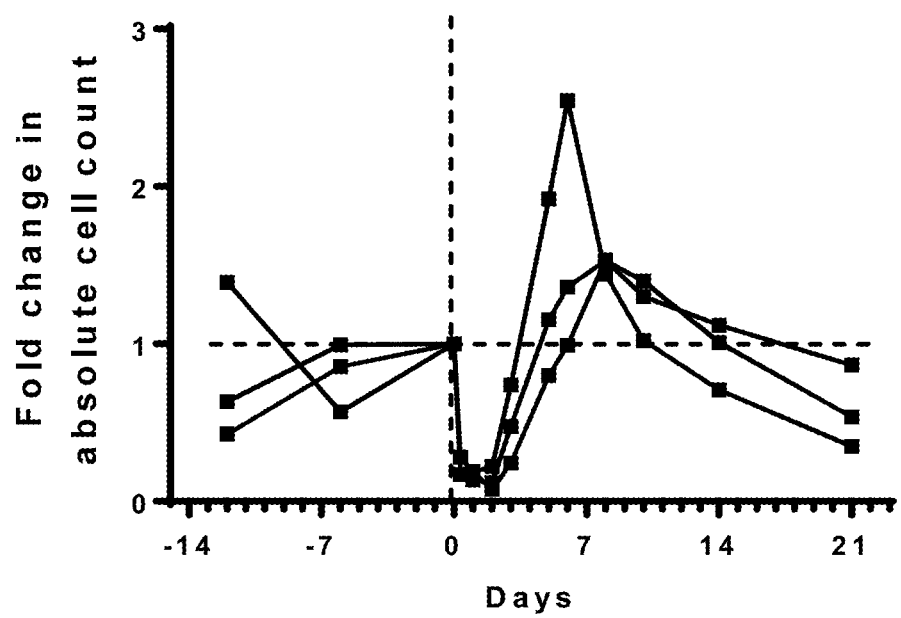
Figure 92A:
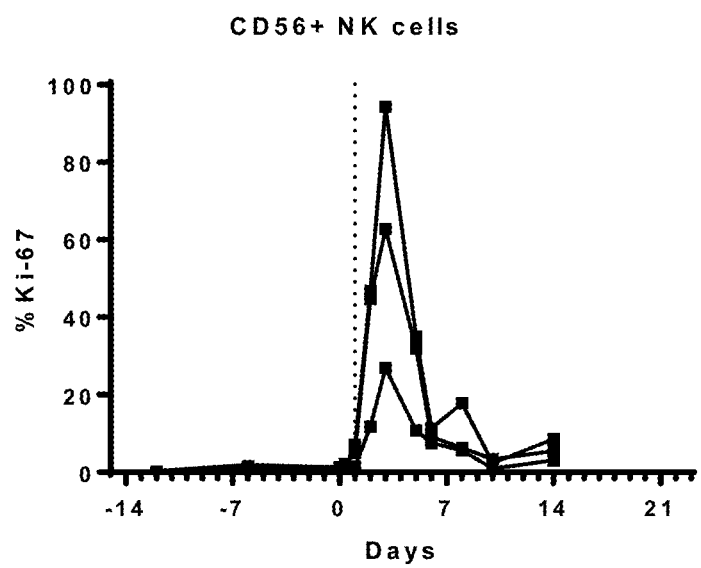
Figure 92B:
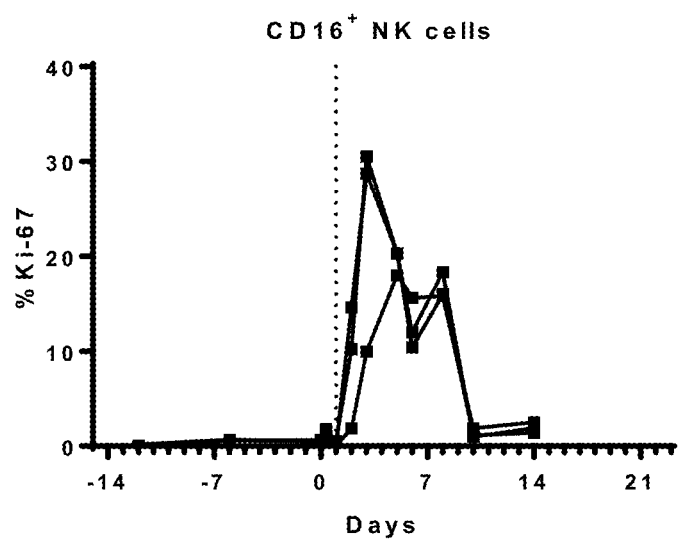
Figure 92C:
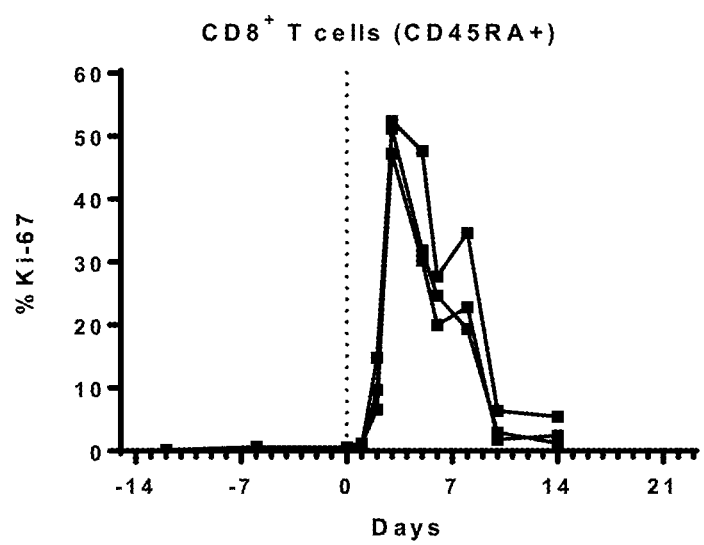
Figure 92D:
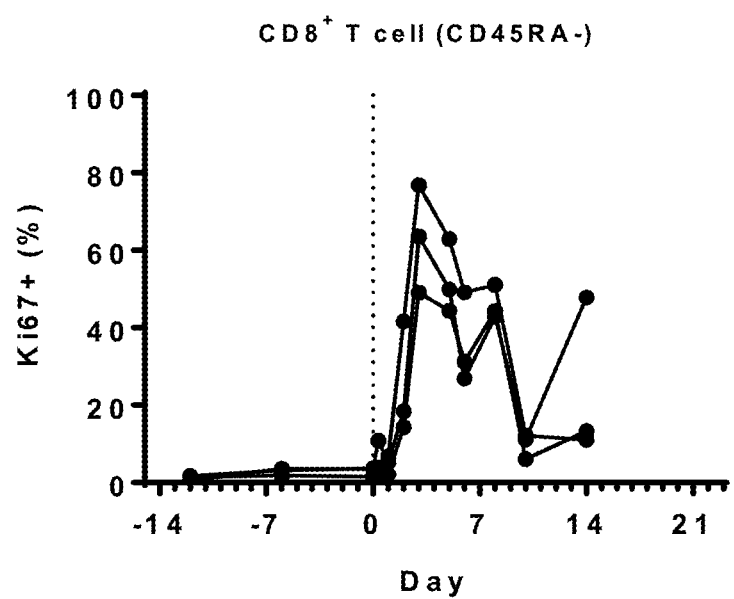
Figure 92E:
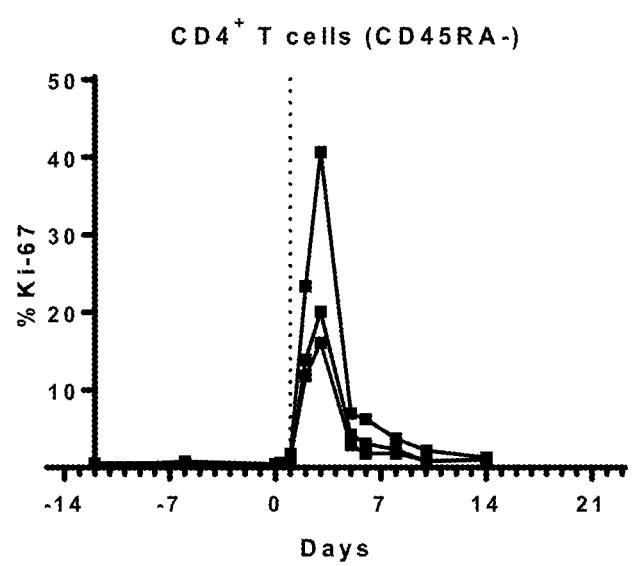

FIG. 91A-FIG. 91E depict lymphocyte counts after dosing cynomolgus monkeys with XENP22821. FIGS. 91A-91E show the fold change in absolute count of CD56+ NK cells (FIG. 91A), CD16+ NK cells (FIG. 91B), γδ T cells (CD45RA+CD3+CD4−CD8−) (FIG. 91C), CD8+ T cells (FIG. 91D), and CD4+ T cells (FIG. 91E).

FIG. 92A-FIG. 92E depict proliferation of CD56+ NK cells (FIG. 92A), CD16+ NK cells (FIG. 92B), CD8+ T cells (CD45RA+) (FIG. 92C), CD8+ T cells (CD45RA−) (FIG. 92D), and CD4+ T cells (CD45RA−) (FIG. 92E) after dosing cynomolgus monkeys with XENP22821.

Figure 93A:
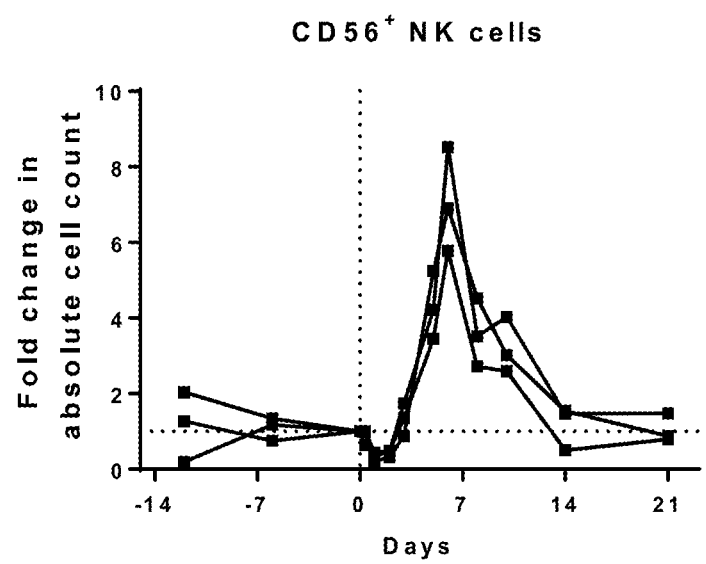
Figure 93B:
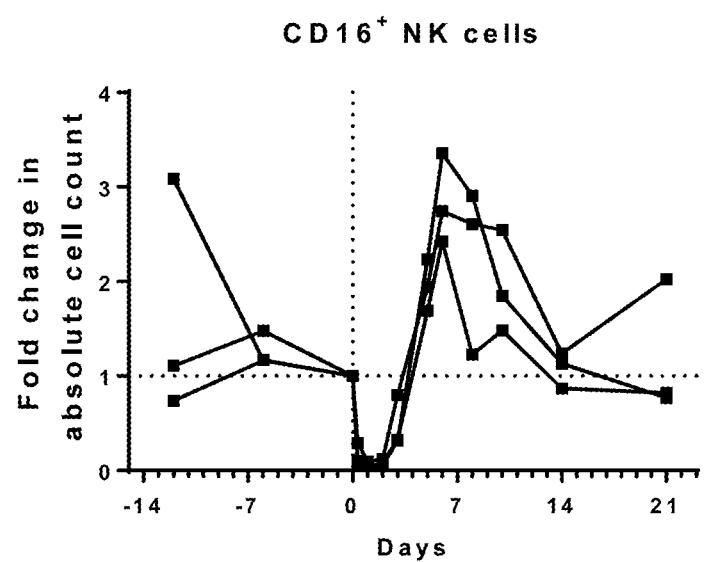
Figure 93C:
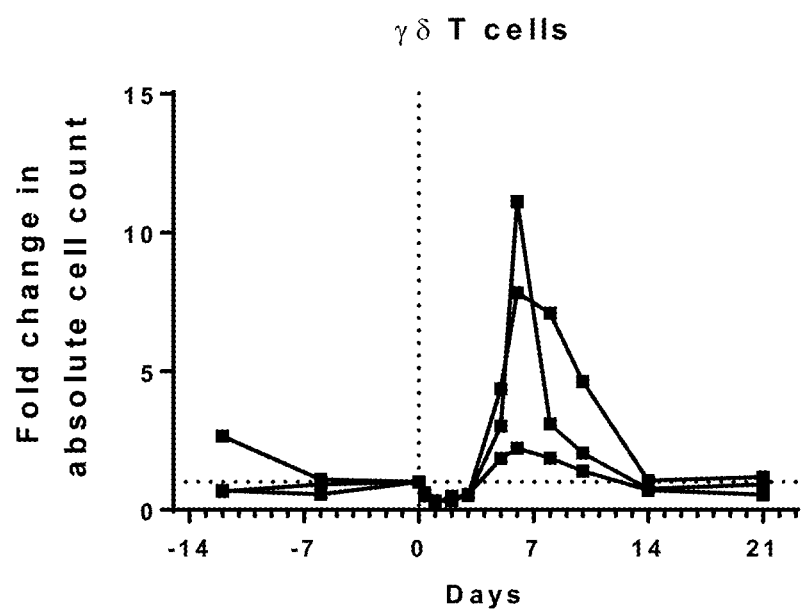
Figure 93D:
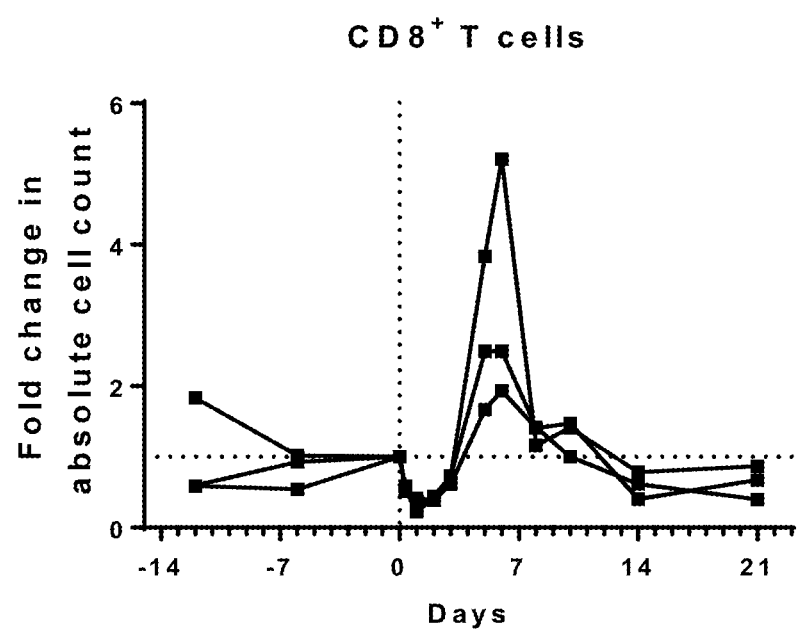
Figure 93E:
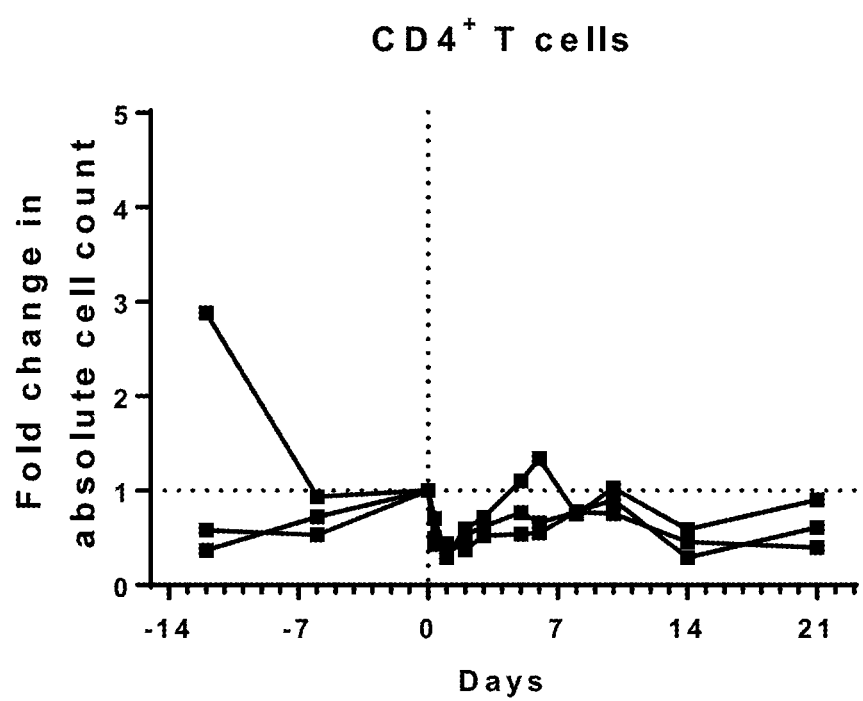

FIG. 93A-FIG. 93E depict lymphocyte counts after dosing cynomolgus monkeys with XENP22822. FIGS. 93A-E, respectively show the fold change in absolute count of CD56+ NK cells (FIG. 93A), CD16+ NK cells (FIG. 93B), γδ T cells (CD45RA+CD3+CD4−CD8−) (FIG. 93C), CD8+ T cells (FIG. 93D), and CD4+ T cells (FIG. 93E).

FIG. 94A-FIG. 94E depict proliferation of CD56+ NK cells (FIG. 94A), CD16+ NK cells (FIG. 94B), CD8+ T cells (CD45RA+) (FIG. 94C), CD8+ T cells (CD45RA−) (FIG. 94D), and CD4+ T cells (CD45RA−) (FIG. 94E) after dosing cynomolgus monkeys with XENP22822.

Figure 95A:
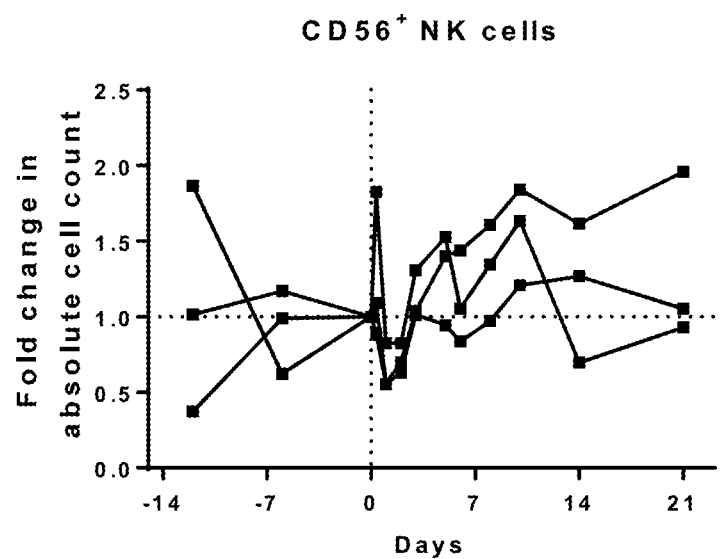
Figure 95B:
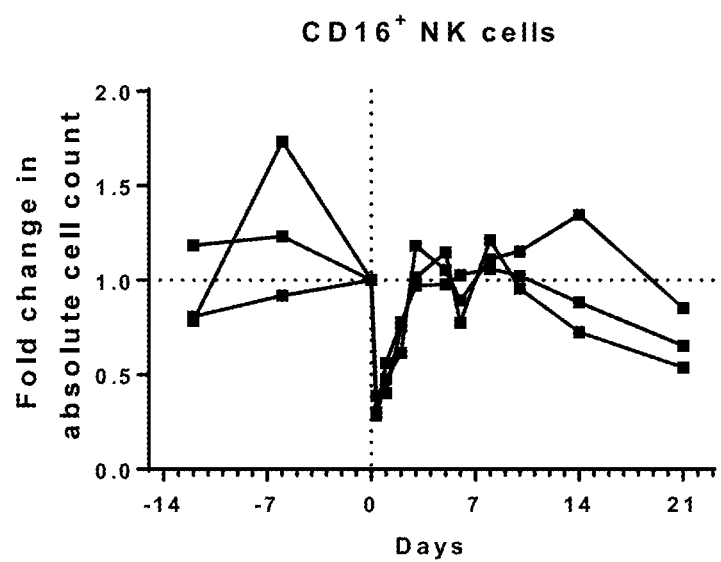
Figure 95C:
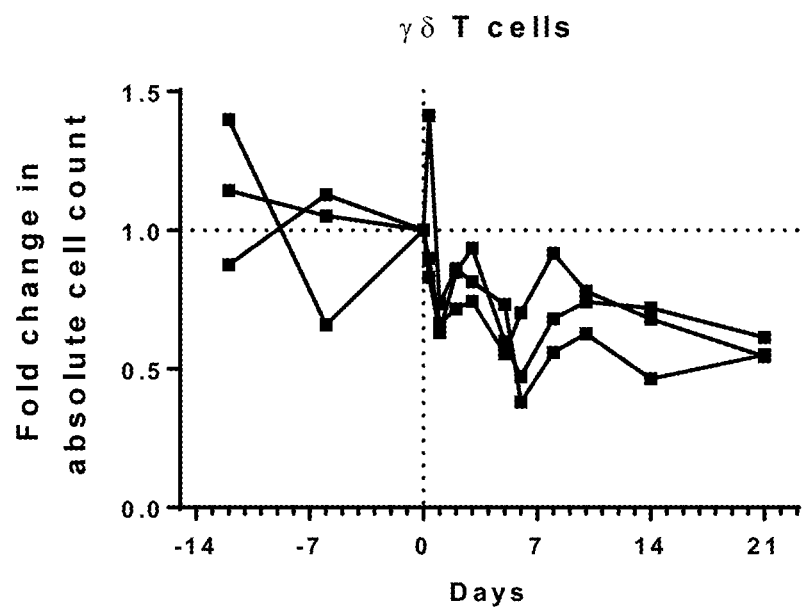
Figure 95D:
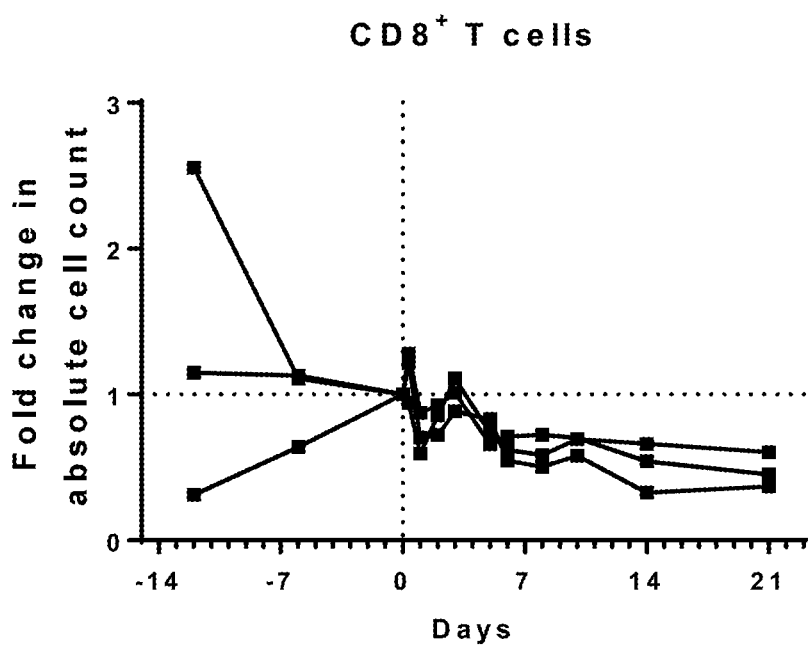
Figure 95E:
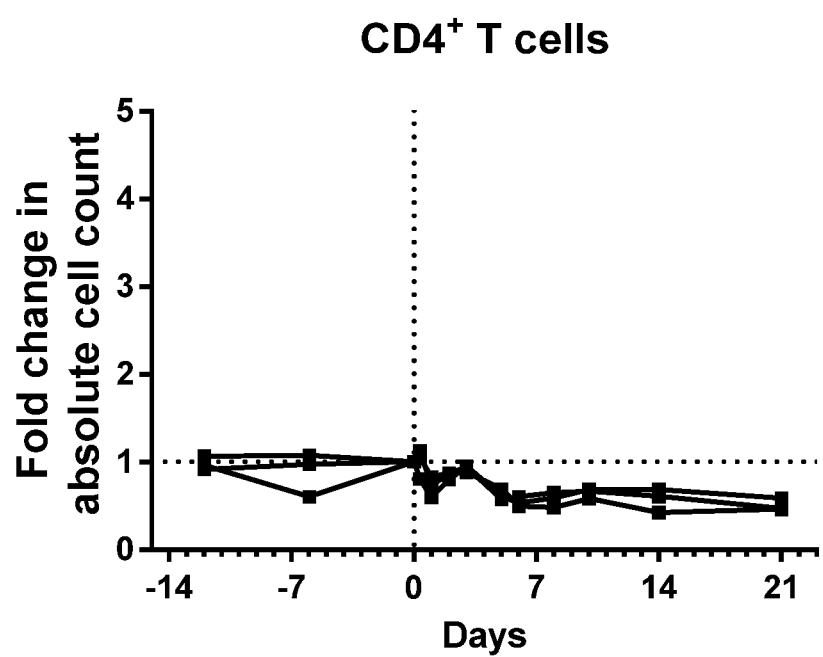
Figure 96A:
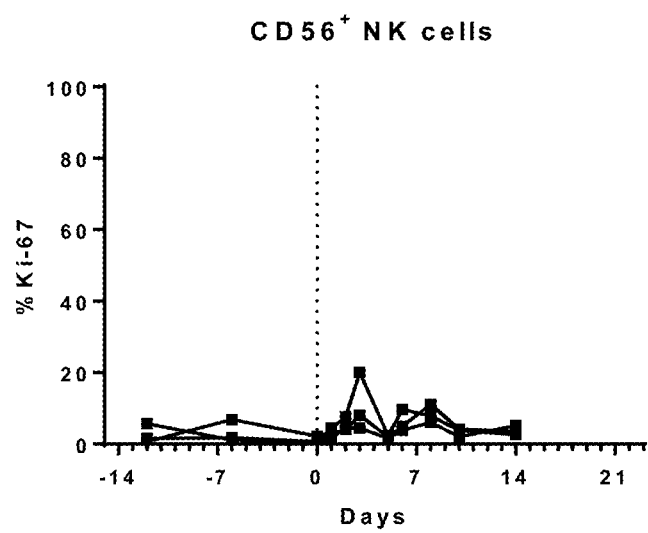
Figure 96B:
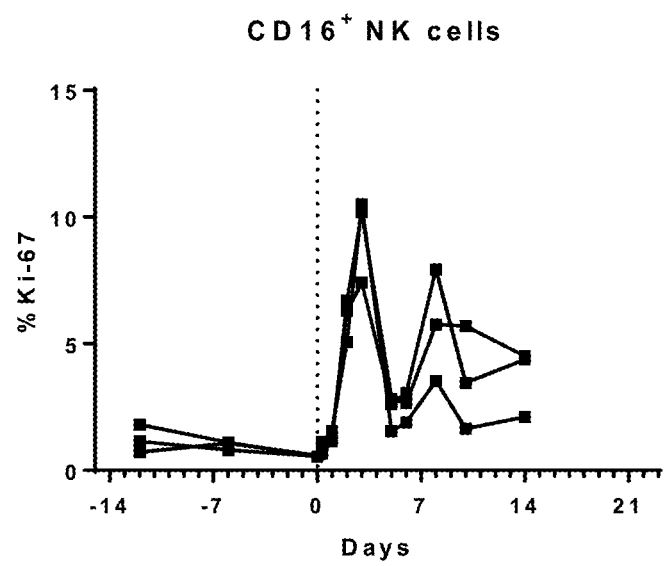
Figure 96C:
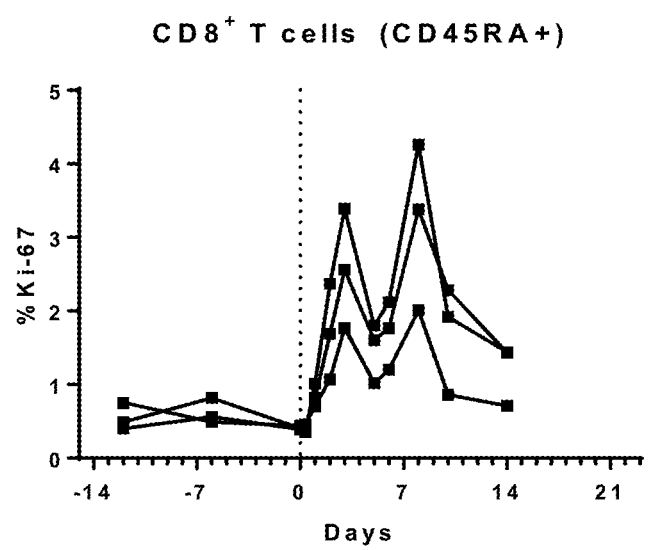
Figure 96D:
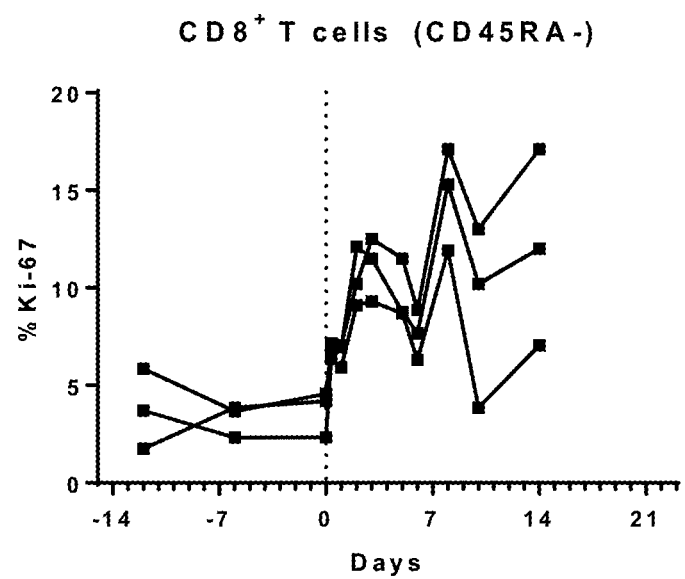
Figure 96E:
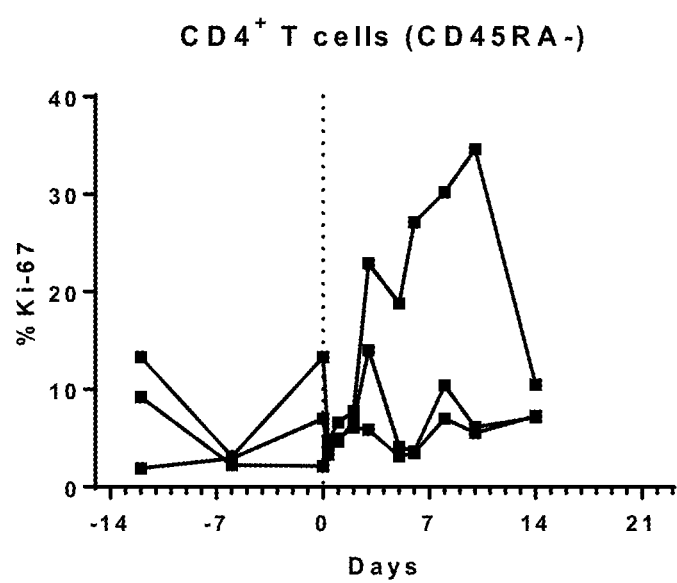

FIG. 95A-FIG. 95E depict lymphocyte counts after dosing cynomolgus monkeys with XENP22834. FIGS. 95A-E respectively show the fold change in absolute count of CD56+NK cells (FIG. 95A), CD16+ NK cells (FIG. 95B), γδ T cells (CD45RA+CD3+CD4−CD8−) (FIG. 95C), CD8+ T cells (FIG. 95D), and CD4+ T cells (FIG. 95E).

FIG. 96A-FIG. 96E depict proliferation of CD56+ NK cells (FIG. 96A), CD16+ NK cells (FIG. 96B), CD8+ T cells (CD45RA+) (FIG. 96C), CD8+ T cells (CD45RA−) (FIG. 96D), and CD4+ T cells (CD45RA−) (FIG. 96E) after dosing cynomolgus monkeys with XENP22834.

Figure 97A:
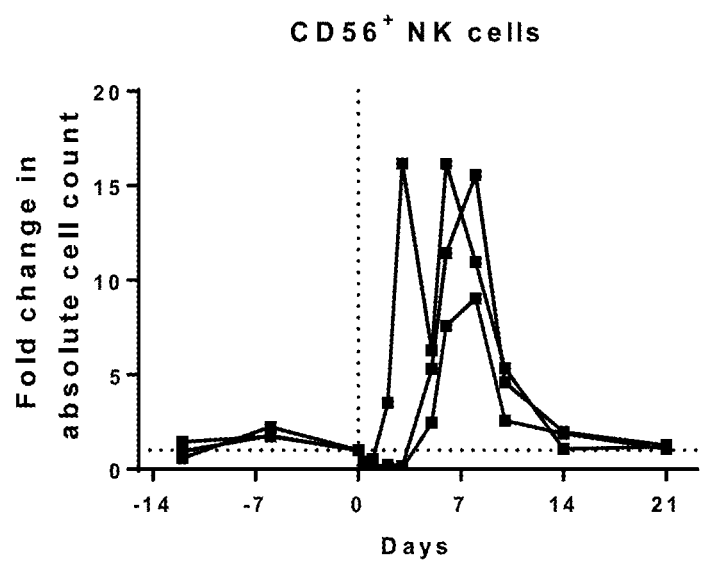
Figure 97B:
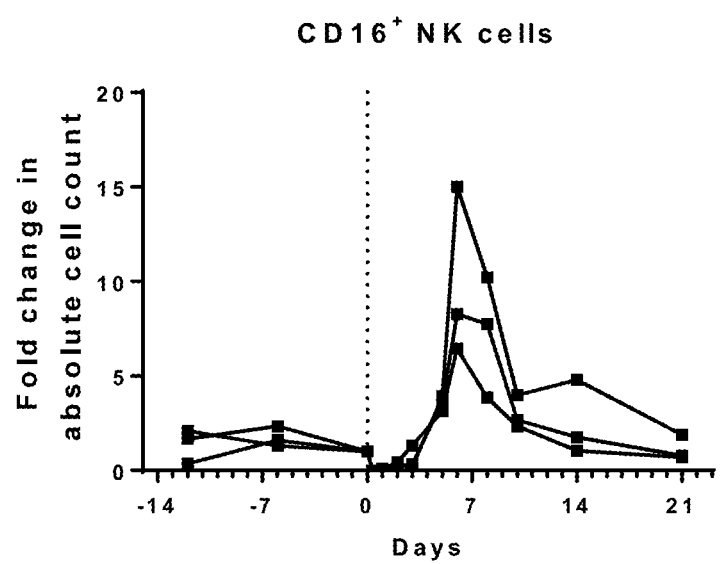
Figure 97C:
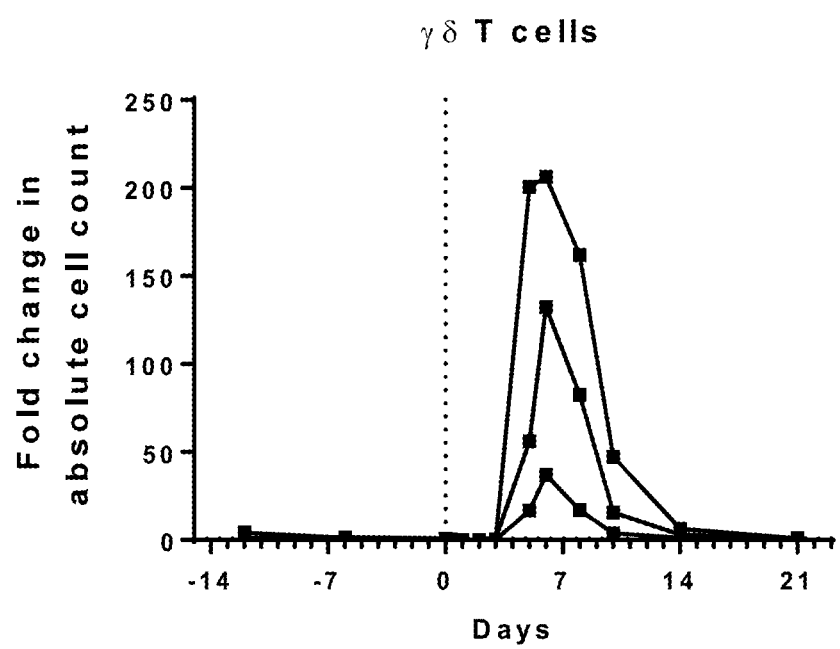
Figure 97D:
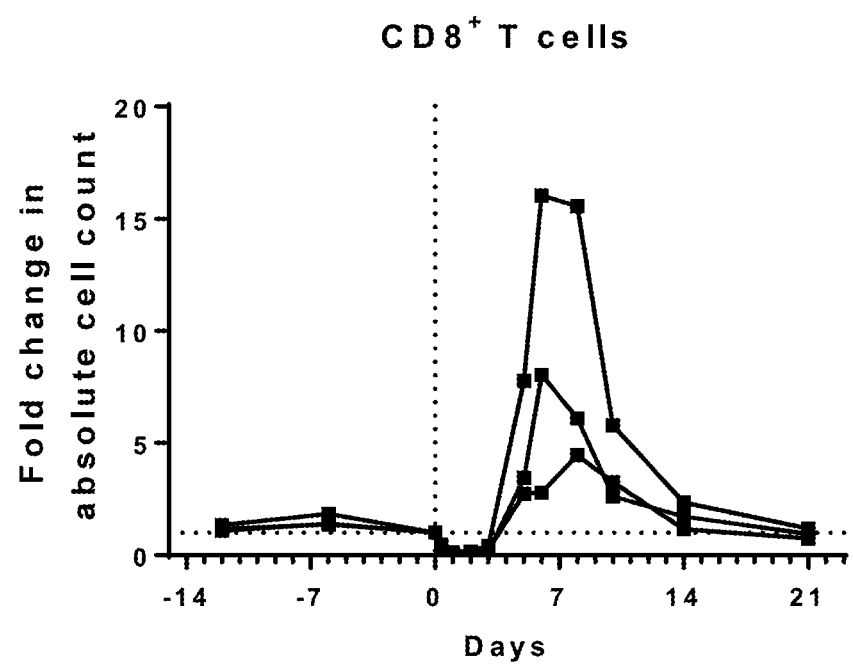
Figure 97E:
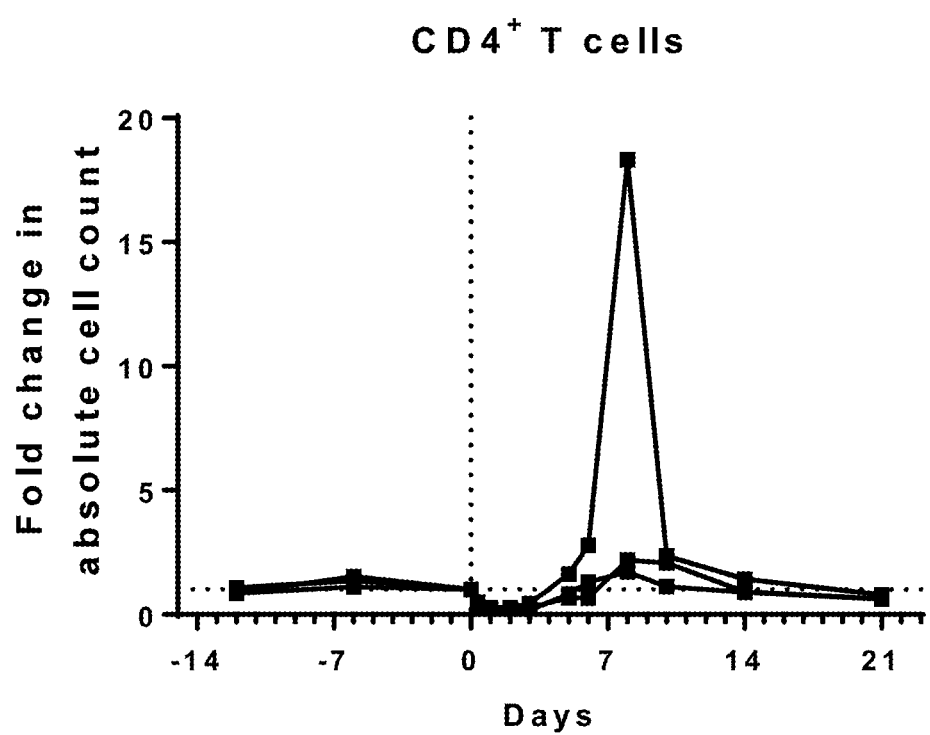
Figure 98A:
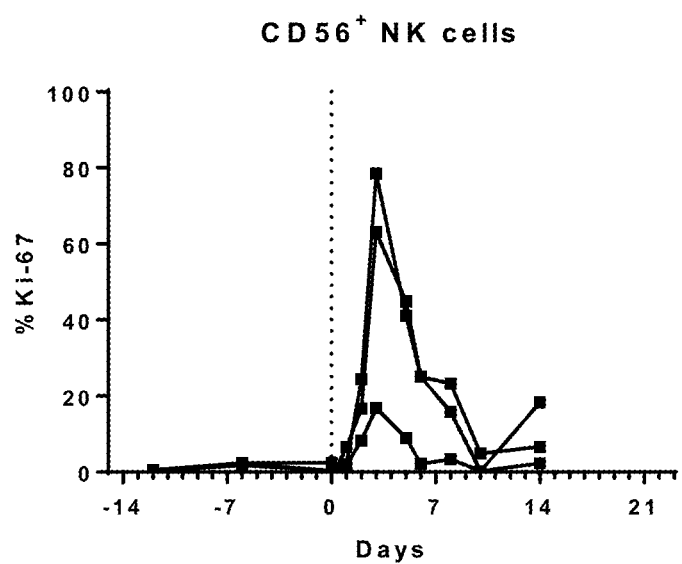
Figure 98B:
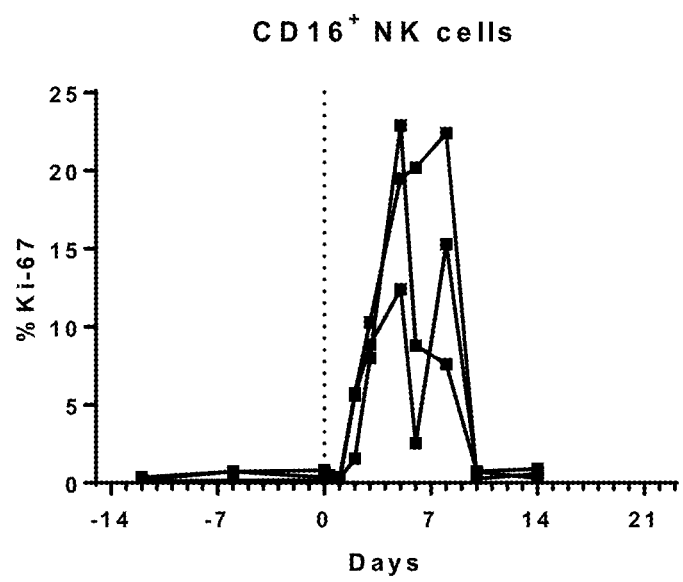
Figure 98C:
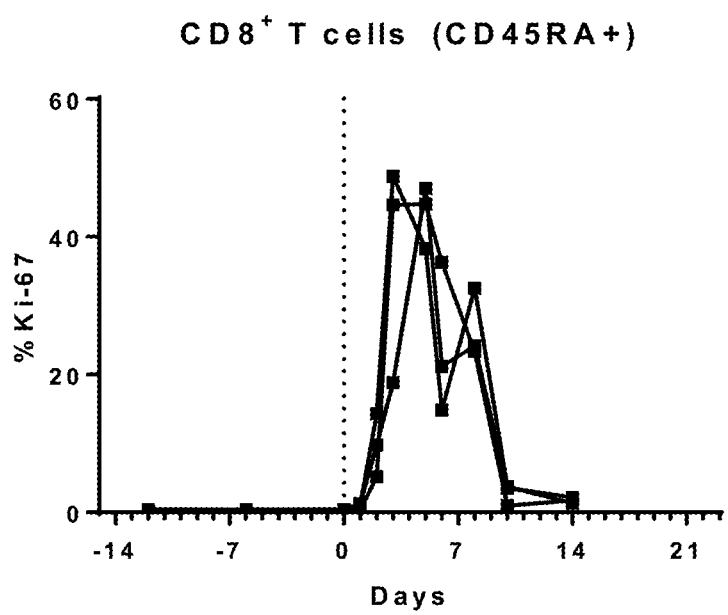
Figure 98D:
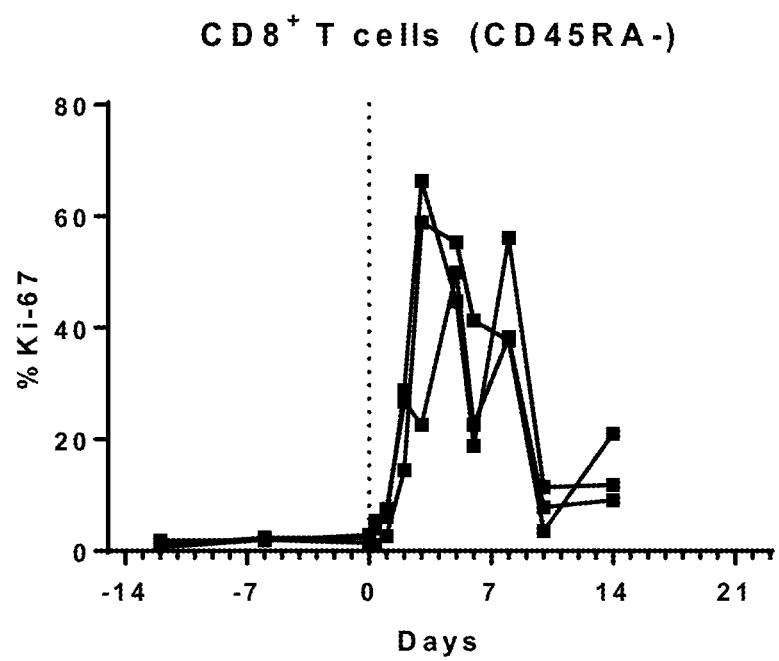
Figure 98E:
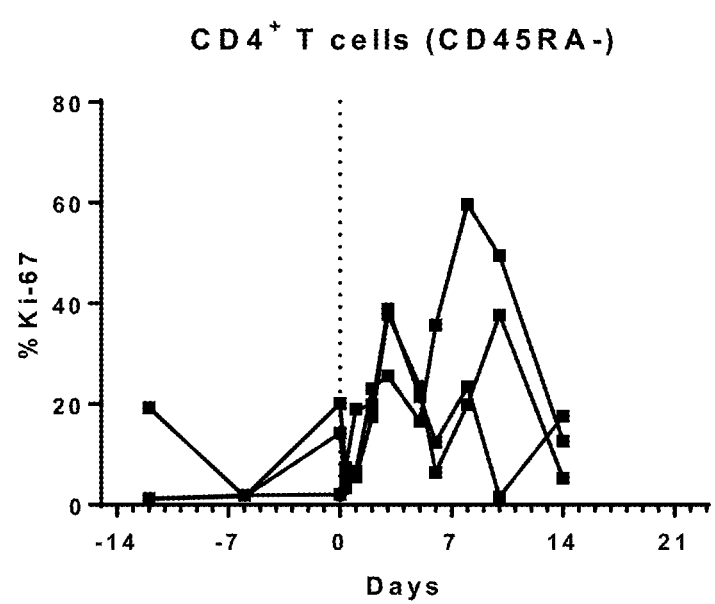

FIG. 97A-FIG. 97E depict lymphocyte counts after dosing cynomolgus monkeys with XENP23343. FIGS. 97A-E respectively show the fold change in absolute count of CD56+NK cells (FIG. 97A), CD16+ NK cells (FIG. 97B), γδ T cells (CD45RA+CD3+CD4−CD8−) (FIG. 97C), CD8+ T cells (FIG. 97D), and CD4+ T cells (FIG. 97E).

FIG. 98A-FIG. 98E depict proliferation of CD56+ NK cells (FIG. 98A), CD16+ NK cells (FIG. 98B), CD8+ T cells (CD45RA+) (FIG. 98C), CD8+ T cells (CD45RA−) (FIG. 98D), and CD4+ T cells (CD45RA−) (FIG. 98E) after dosing cynomolgus monkeys with XENP23343.

FIG. 99A-FIG. 99C depict sequences of XENP23343, XENP23504, XENP24113, XENP24301, XENP24306, and XENP24341, illustrative IL-15/Rα-Fc fusion proteins of the "IL-15/Rα-heteroFc" format with M428L/N434S substitutions. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

FIG. 100 depicts sequences of XENP25938 (also referred to as XENP24294), an illustrative IL-15/Rα-Fc fusion protein of the "scIL-15/Rα-Fc" format with M428L/N434S substitutions.

FIG. 101 depicts sequences of XENP24383, an illustrative IL-15/Rα-Fc fusion protein of the "ncIL-15/Rα-Fc" format with M428L/N434S substitutions. IL-15 and IL-15Rα(sushi) are underlined, linkers are double underlined (although as will be appreciated by those in the art, the linkers can be replaced by other linkers, some of which are depicted in FIG. 7 and slashes (/) indicate the border(s) between IL-15, IL-15Rα, linkers, and Fc regions.

FIG. 102 depicts sequences of XENP24346 and XENP24351, illustrative IL-15/Rα-Fc fusion proteins of the "bivalent ncIL-15/Rα-Fc" format with M428L/N434S substitutions. IL-15 and IL-15Rα(sushi) are underlined, linkers are double underlined (although as will be appreciated by those in the art, the linkers can be replaced by other linkers, some of which are depicted in FIG. 7), and slashes (/) indicate the border(s) between IL-15, IL-15Rα, linkers, and Fc regions.

Figure 103A:
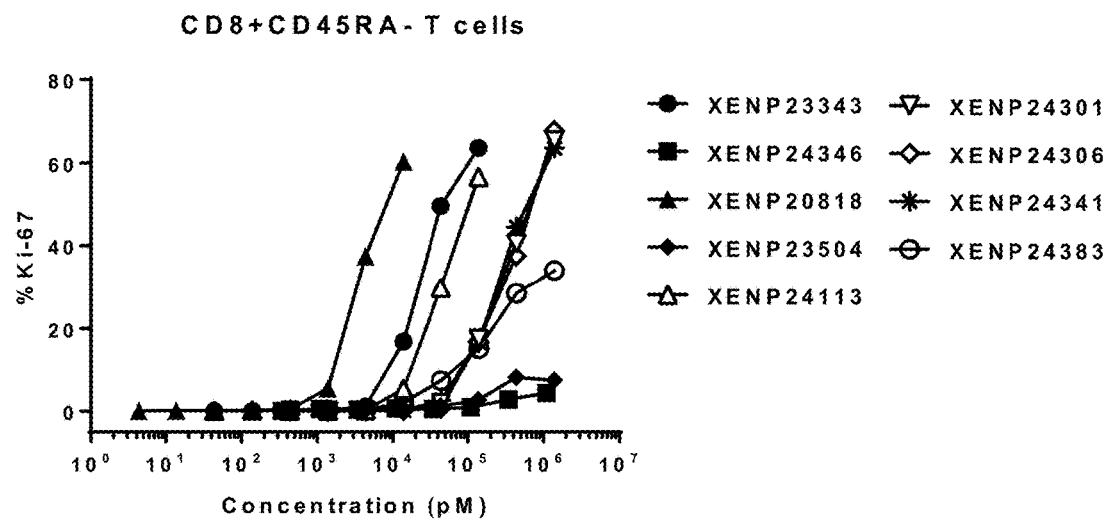
Figure 103B:
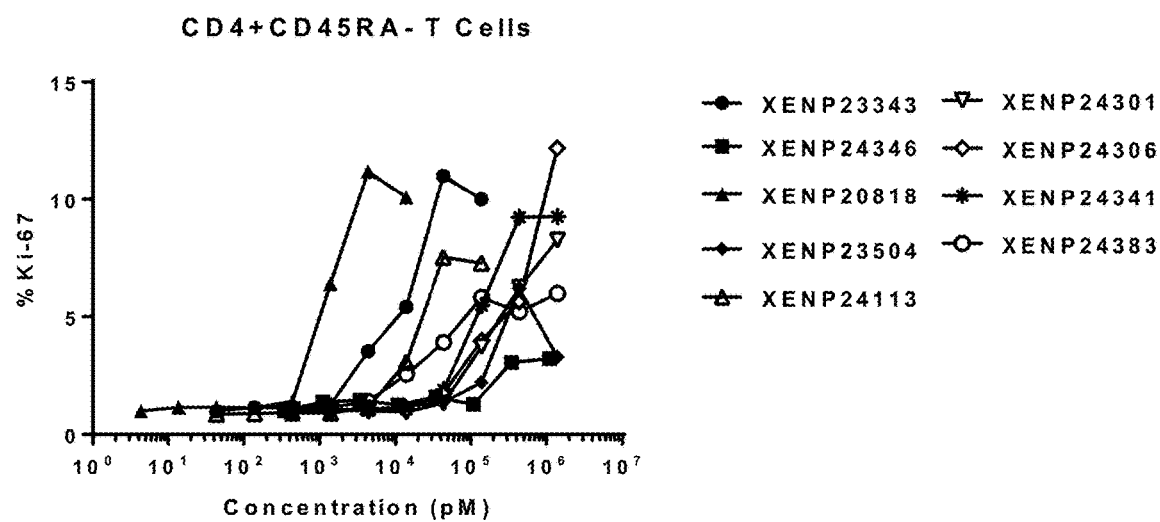
Figure 103C:
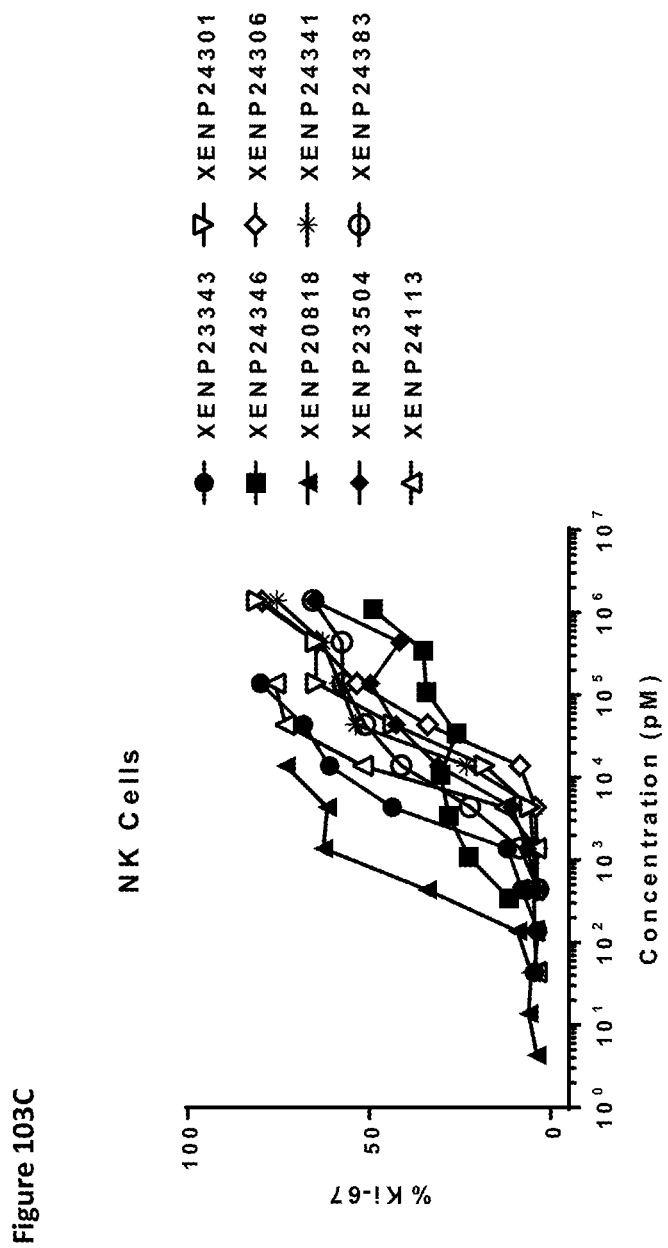

FIG. 103A-FIG. 103C depict the percentage of Ki67 expression on human CD8$^+$ T cells (FIG. 103A), human CD4$^+$ T cells (FIG. 103B) and human NK cells (FIG. 103C) following treatment with IL-15/Rα variants with M428L/N434S Fc mutations.

FIG. 104A-FIG. 104D depict the percentage of Ki67 expression on human CD8$^+$ T cells (FIG. 104A), human CD4$^+$ T cells (FIG. 104B), human NK cells (FIG. 104C), and human γδ T cells (FIG. 104D) following treatment with XmAb24306 (also referred to as XENP24306).

Figure 105A:
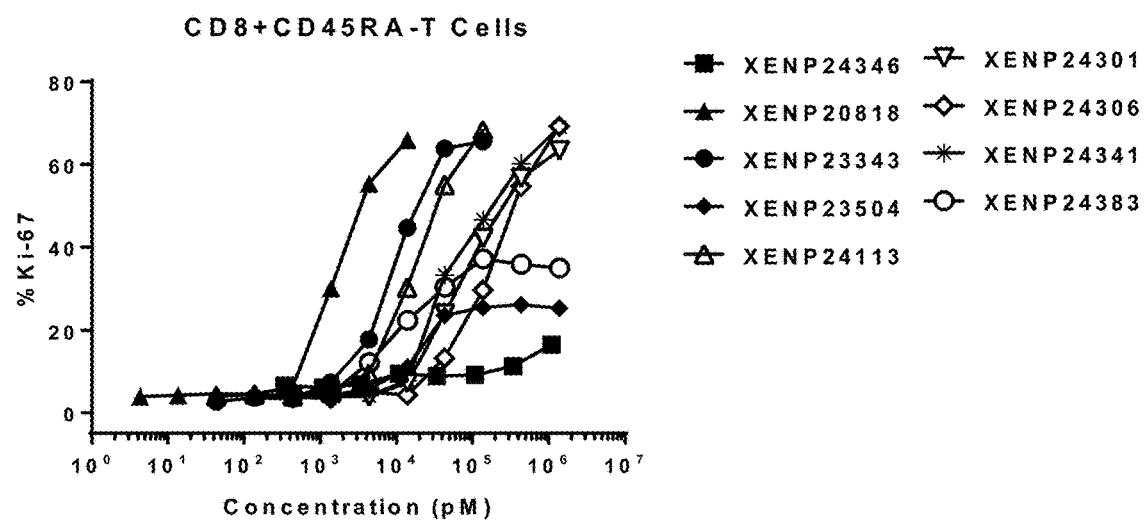
Figure 105B:
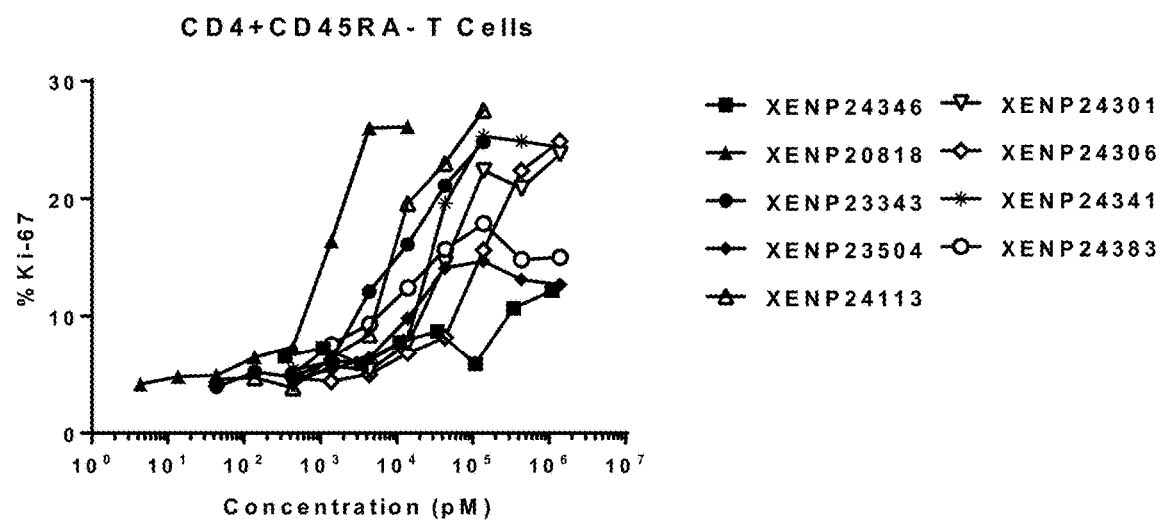
Figure 105C:
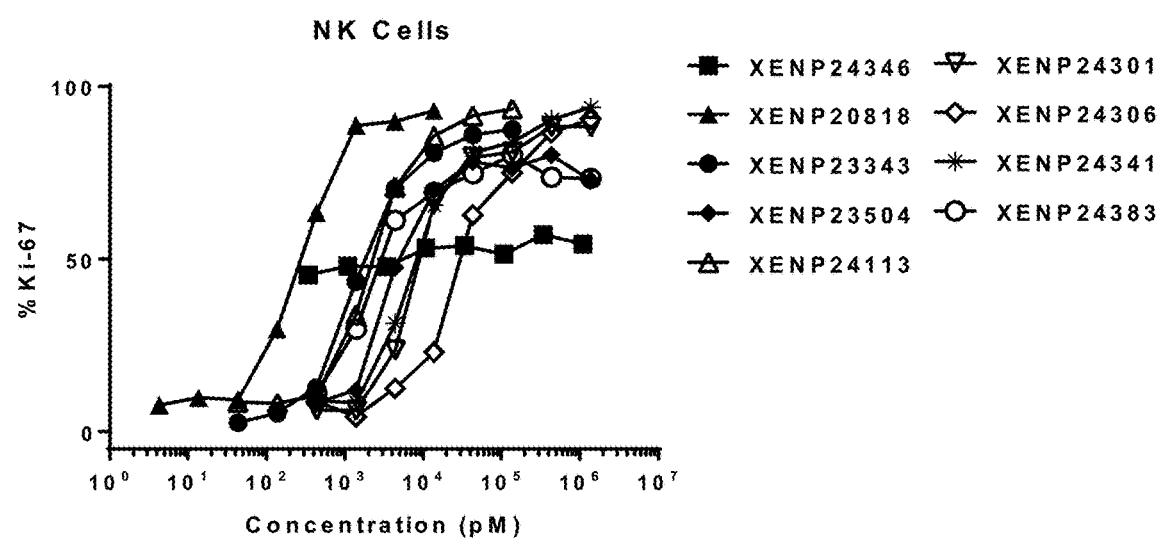

FIG. 105A-FIG. 105C depict the percentage of Ki67 expression on cyno CD8$^+$ T cells (FIG. 105A), cyno CD4$^+$ T cells (FIG. 105B) and cyno NK cells (FIG. 105C) following treatment with WT IL-15/Rα-Fc and potency-reduced IL-15/Rα variants with M428L/N434S Fc mutations.

Figure 106:
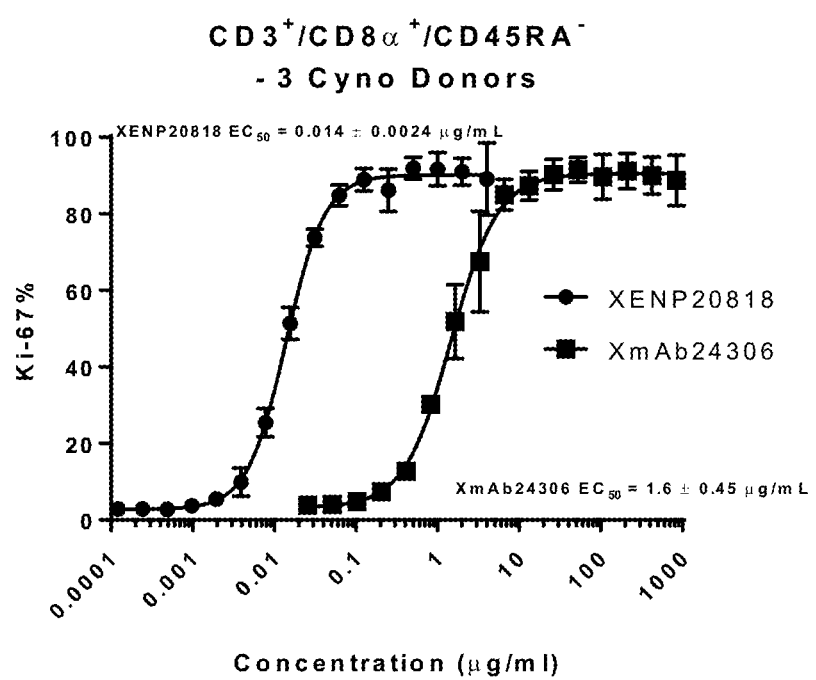

FIG. 106 depicts the percentage of Ki67 expression on cyno CD8α$^+$CD45RA$^-$ T cells following treatment with XENP20818 or XmAb24306.

Figure 107A:
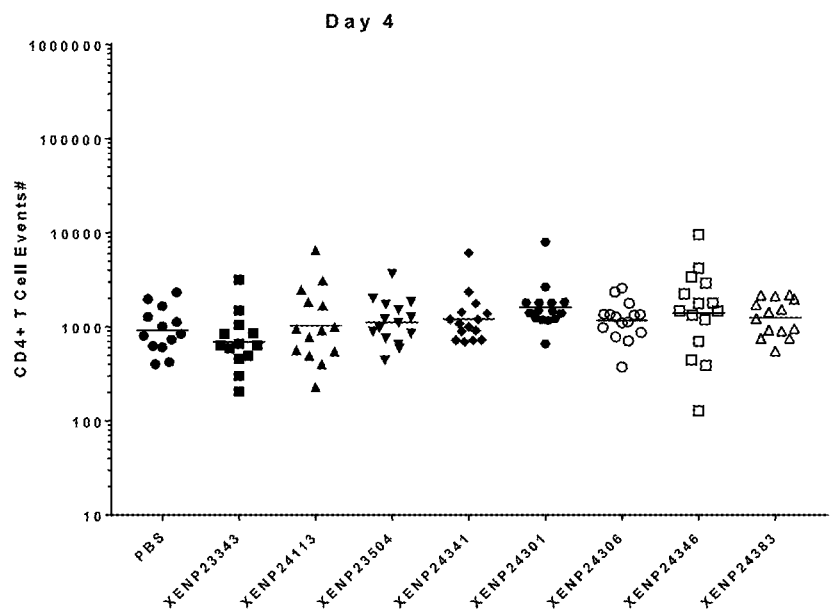
Figure 107B:
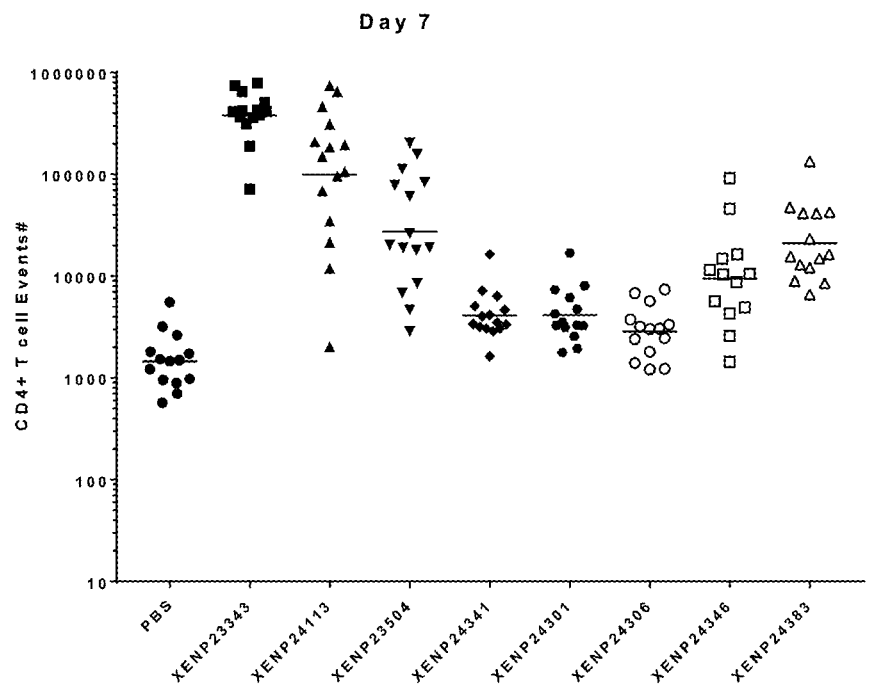
Figure 107C:
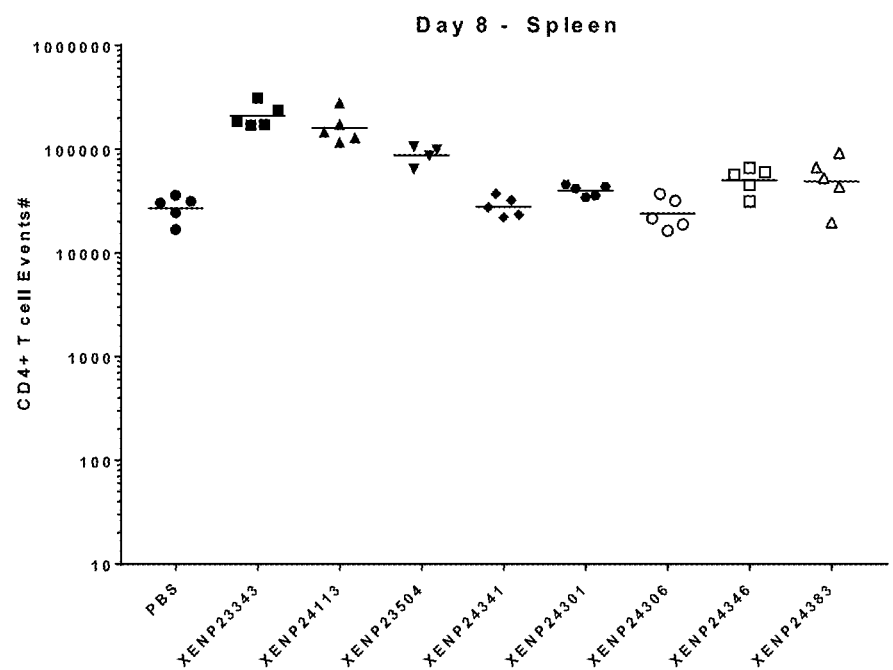

FIG. 107A-FIG. 107C depicts CD4+ T cell count on Day 4 (FIG. 107A) and Day 7 (FIG. 107B) in whole blood and Day 8 (FIG. 107C) in spleen of huPBMC engrafted mice following treatment with additional variant IL-15/Rα-Fc fusion proteins.

Figure 108A:
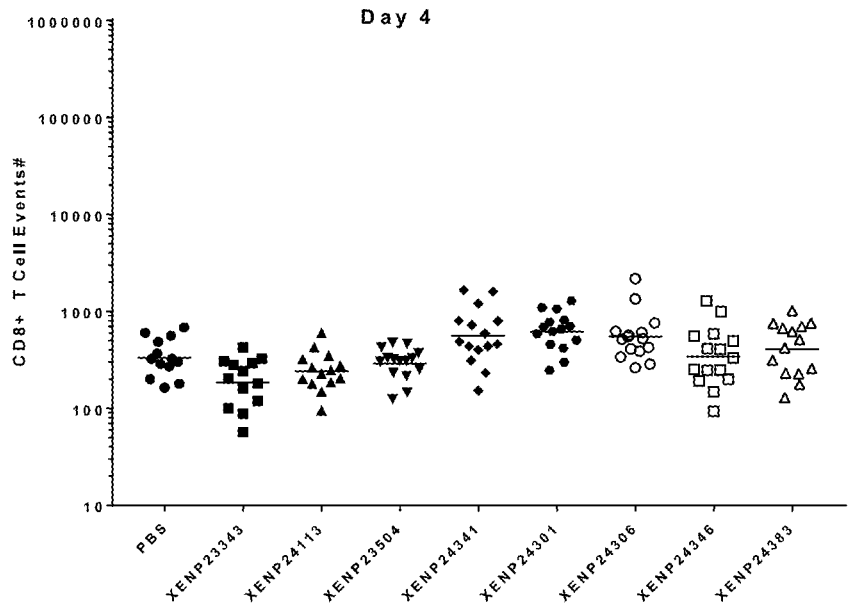
Figure 108B:
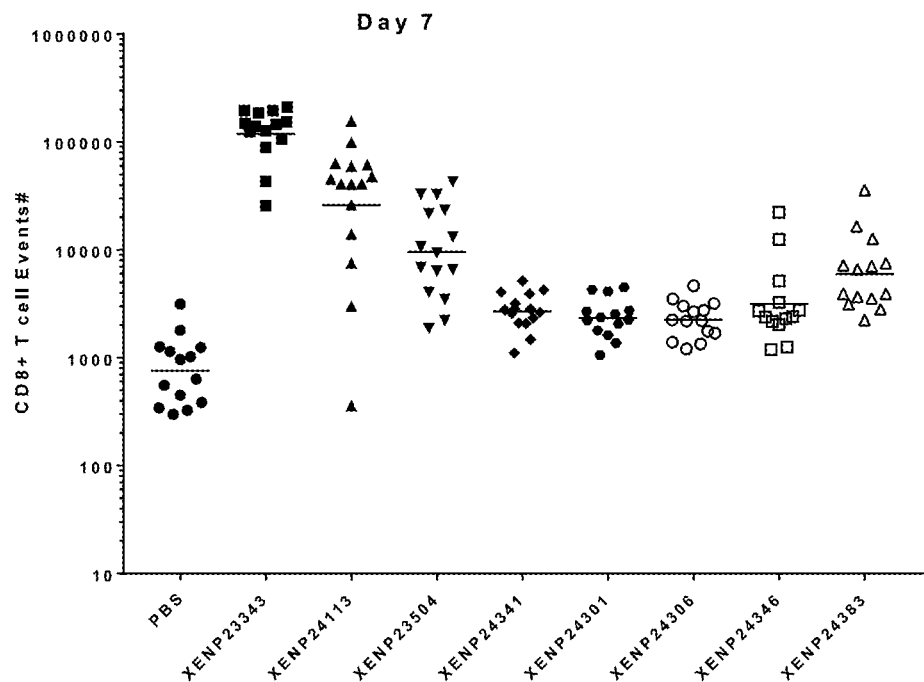
Figure 108C:
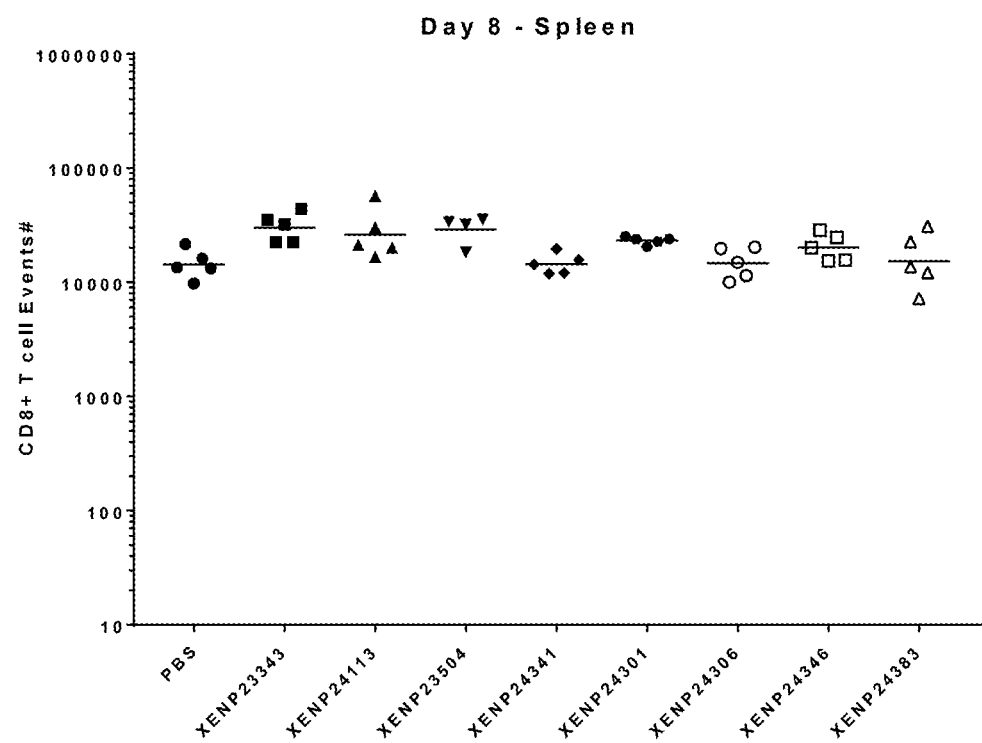

FIG. 108A-FIG. 108C depict CD8$^+$ T cell count on (FIG. 108A) Day 4 and (FIG. 108B) Day 7 in whole blood and (FIG. 108C) Day 8 in spleen of huPBMC engrafted mice following treatment with additional variant IL-15/Rα-Fc fusion proteins.

Figure 109A:
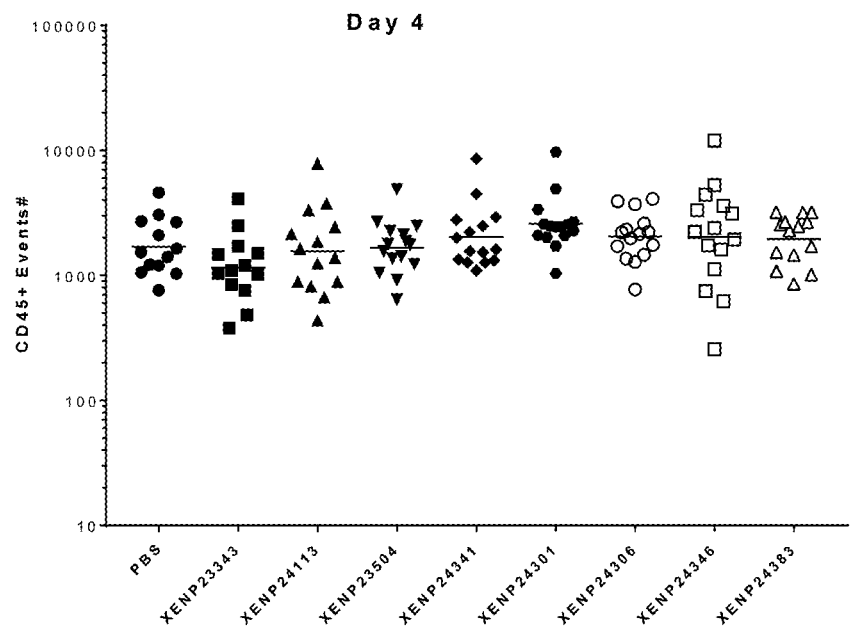
Figure 109B:
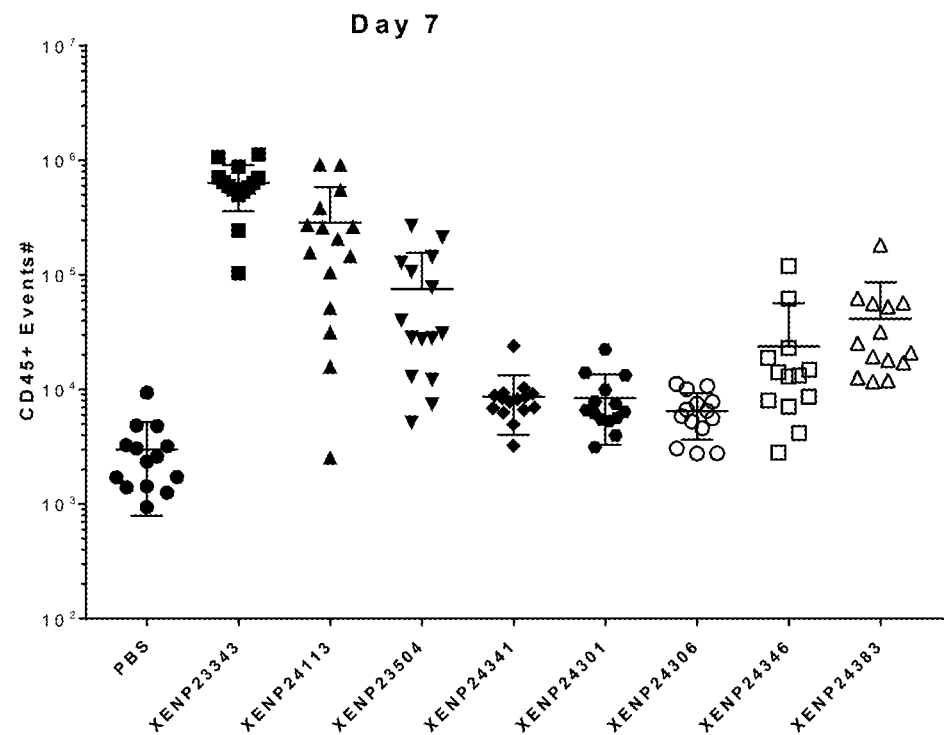
Figure 109C:
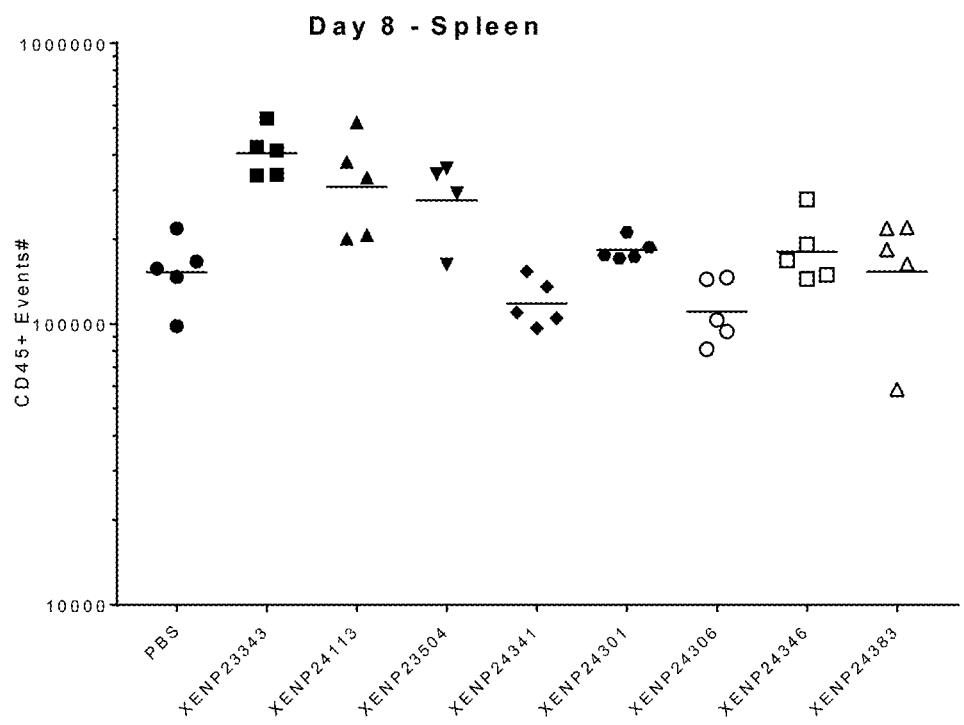

FIG. 109A-FIG. 109C depict CD8+ T cell count on Day 4 (FIG. 109A) and Day 7 (FIG. 109B) in whole blood and Day 8 (FIG. 109C) in spleen of huPBMC engrafted mice following treatment with additional variant IL-15/Rα-Fc fusion proteins.

Figure 110A:
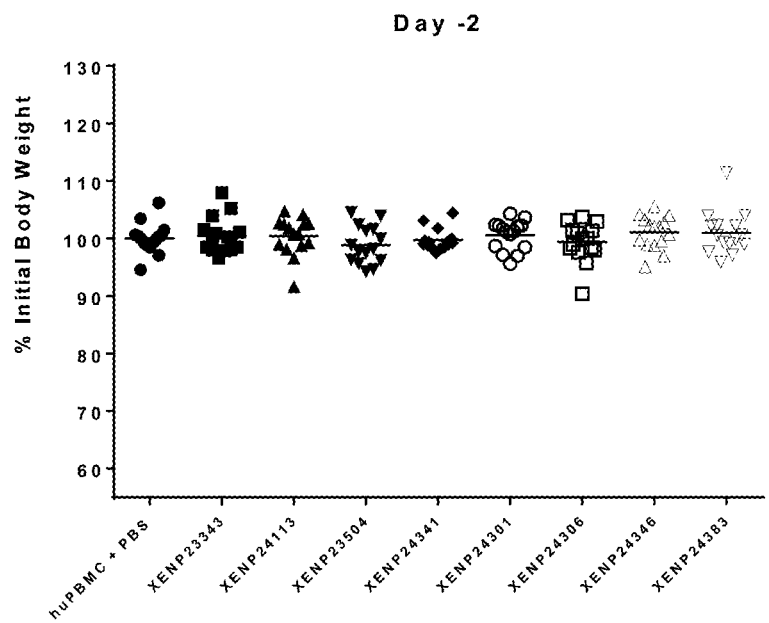
Figure 110B:
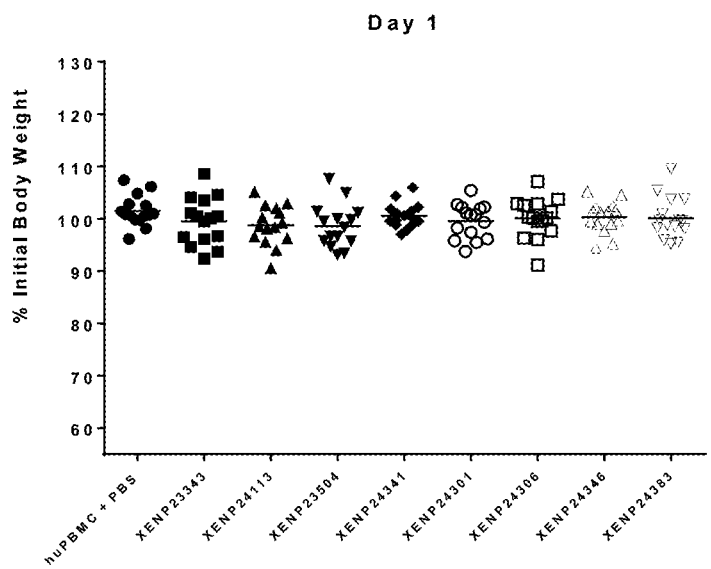
Figure 110C:
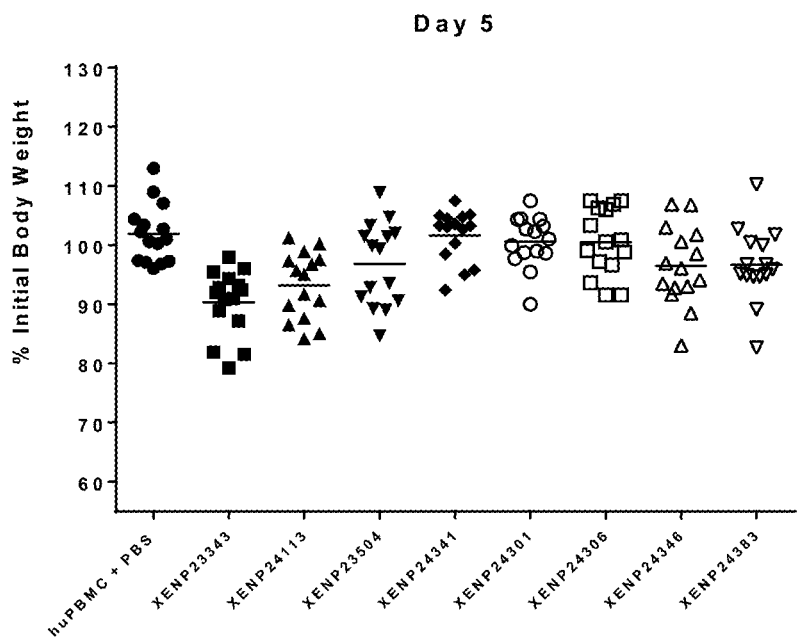
Figure 110D:
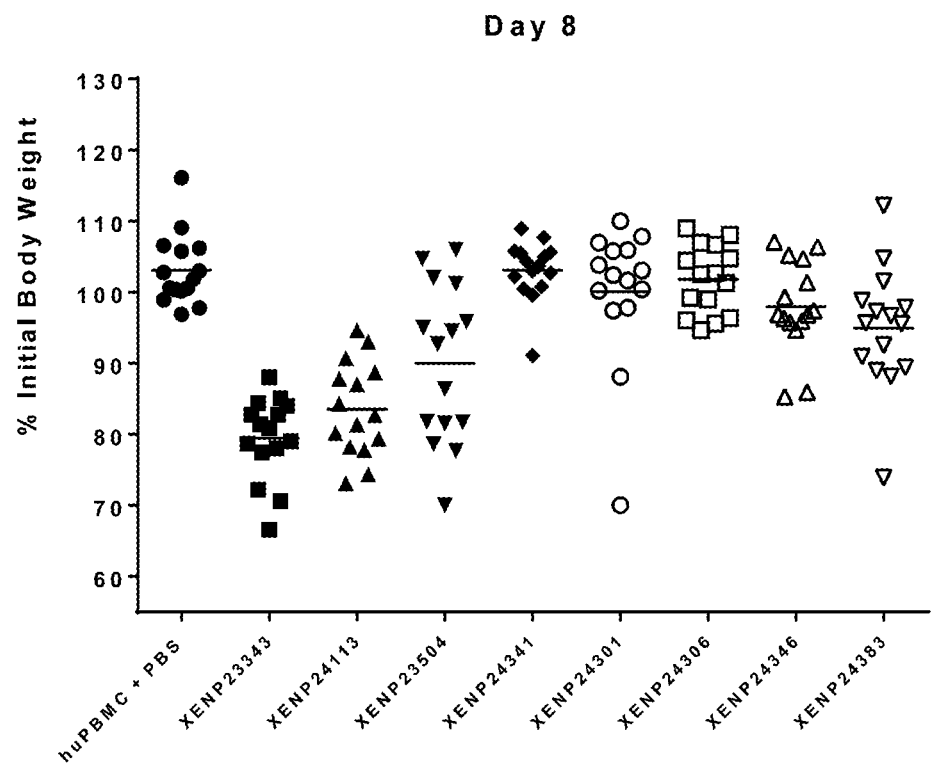
Figure 110E:
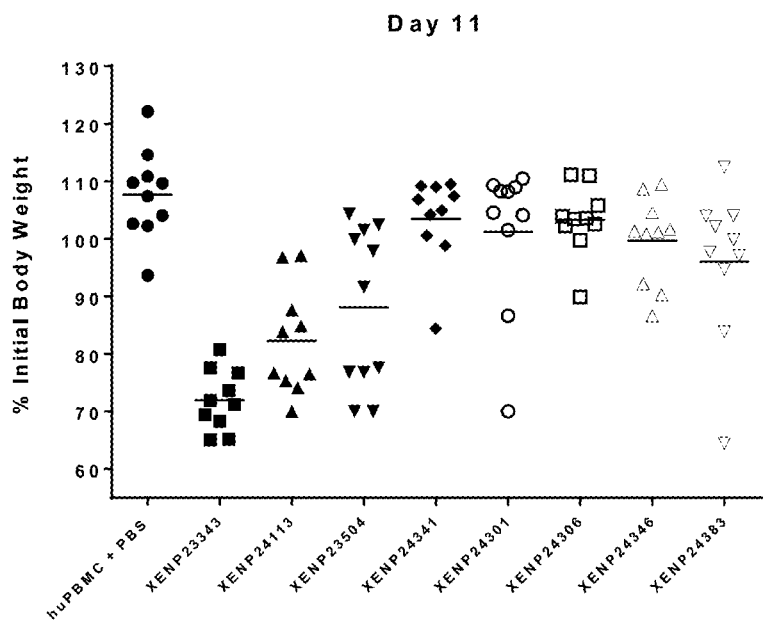
Figure 110F:
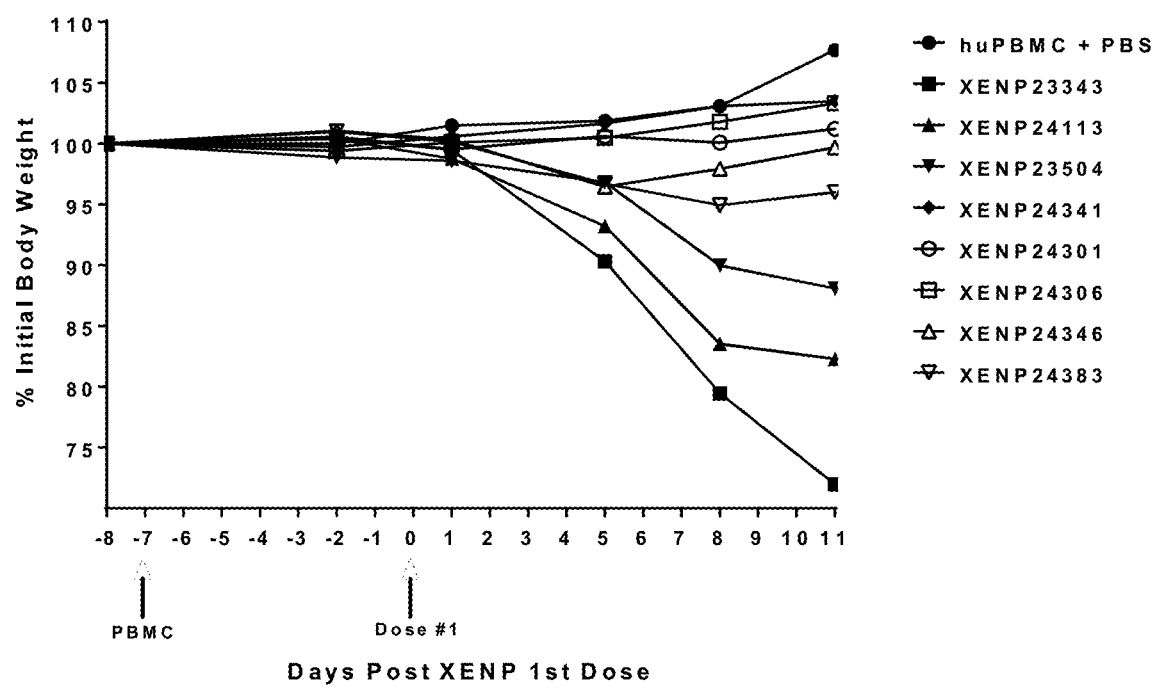
Figure 111A:
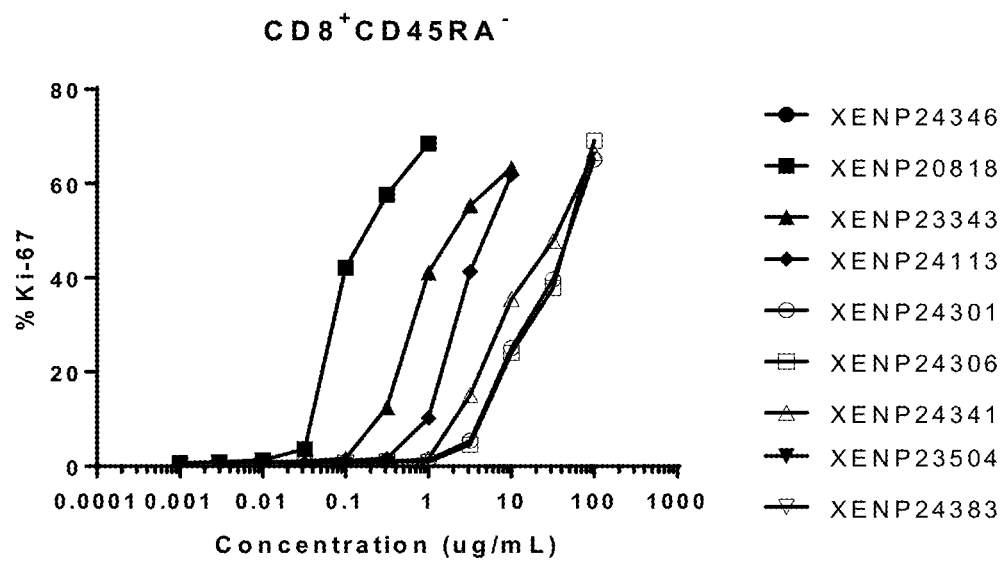
Figure 111B:
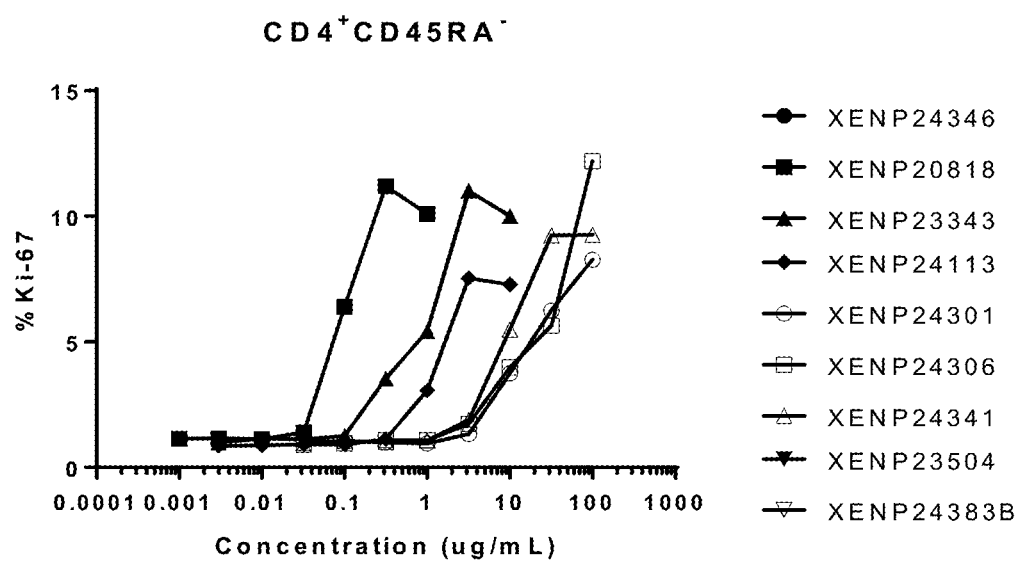
Figure 111C:
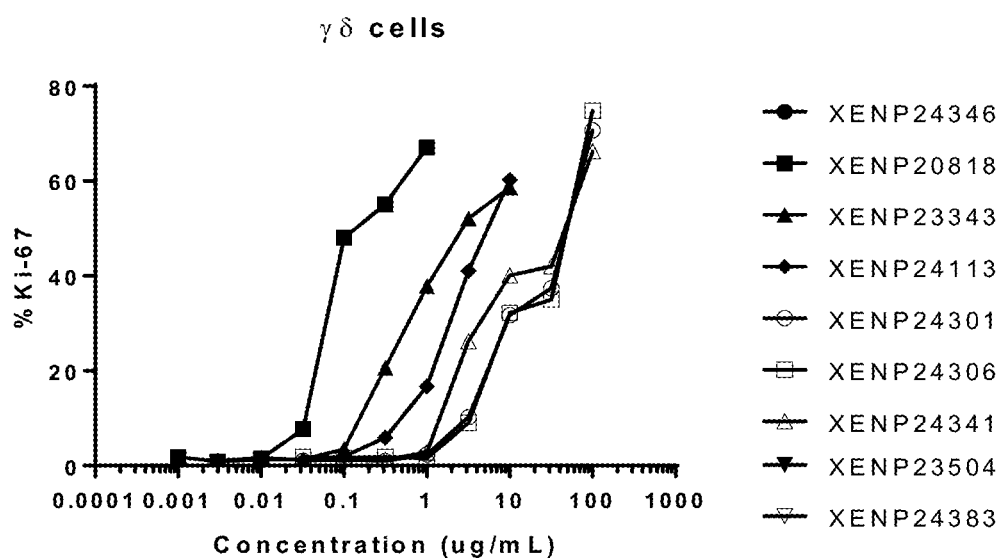
Figure 111D:
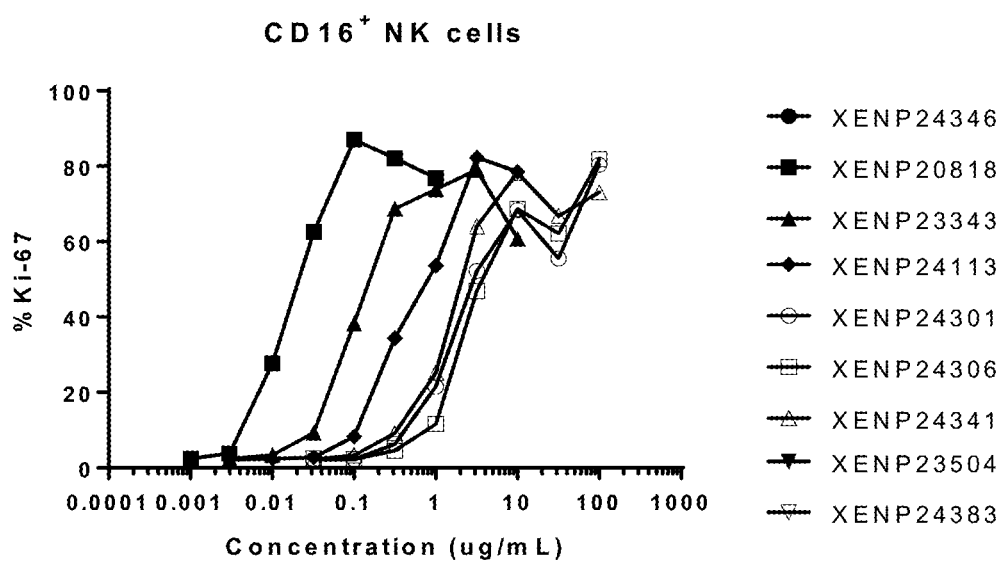
Figure 112A:
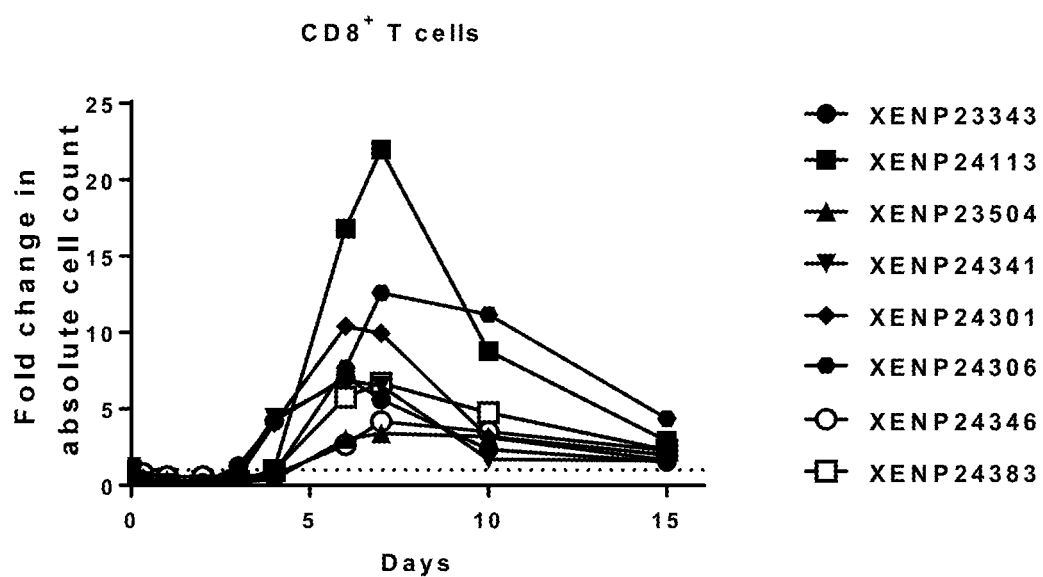
Figure 112B:
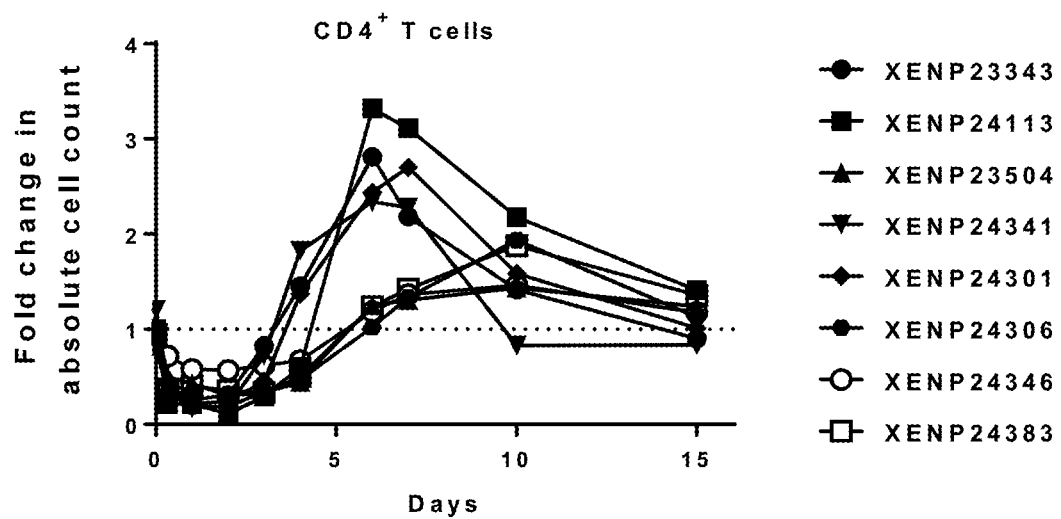
Figure 112C:
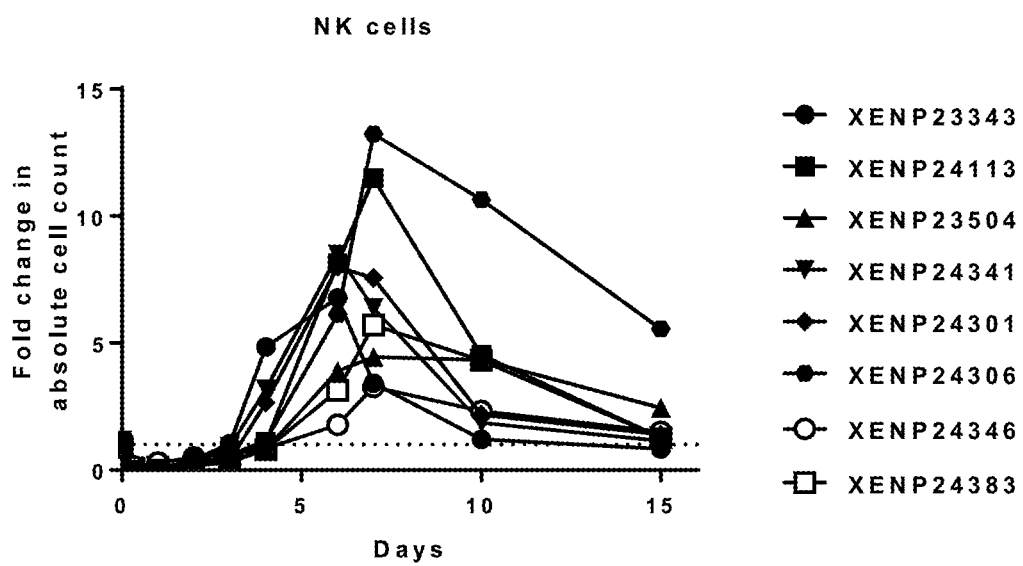
Figure 112D:
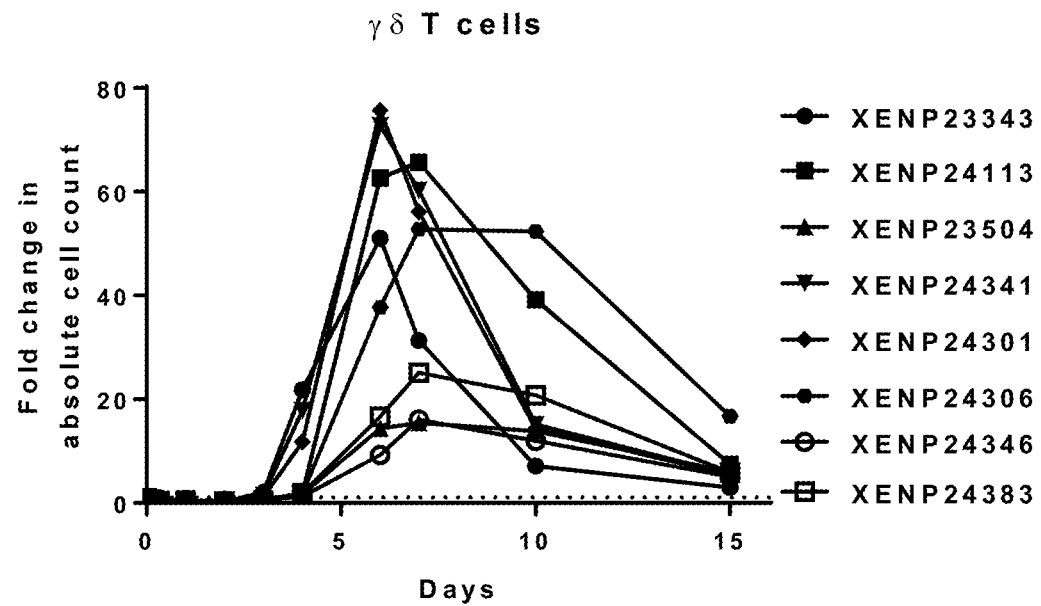
Figure 113A:
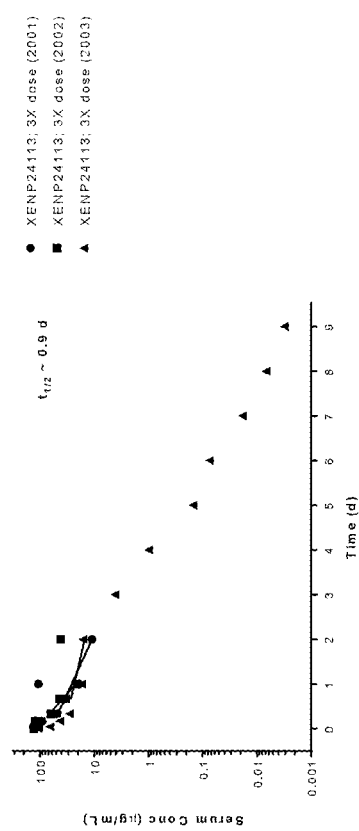
Figure 113B:
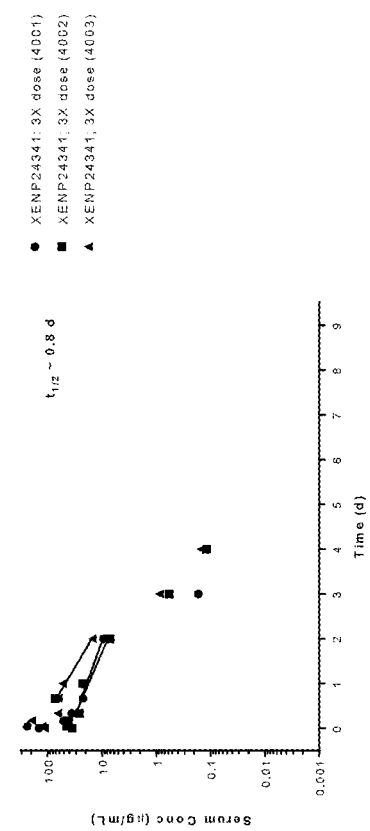
Figure 113C:
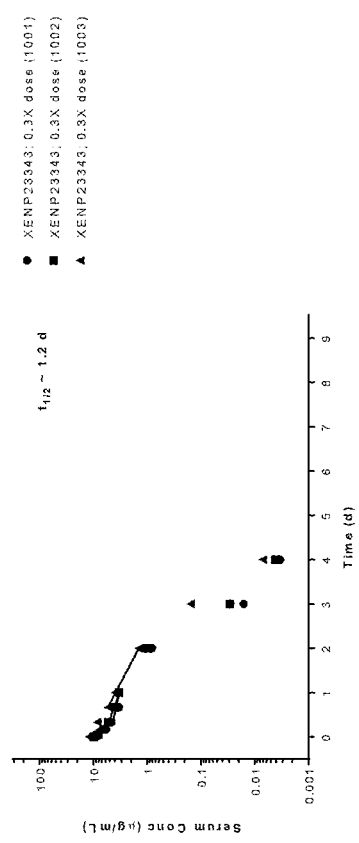
Figure 113D:
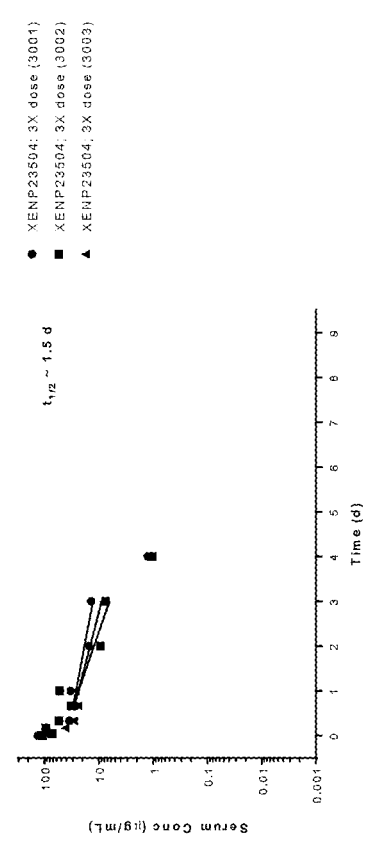
Figure 113E:
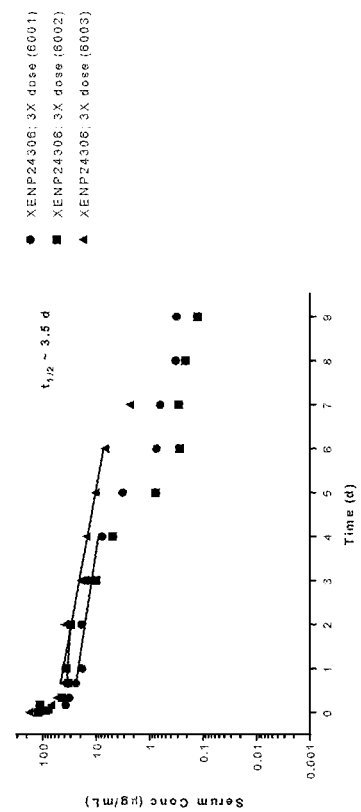
Figure 113F:
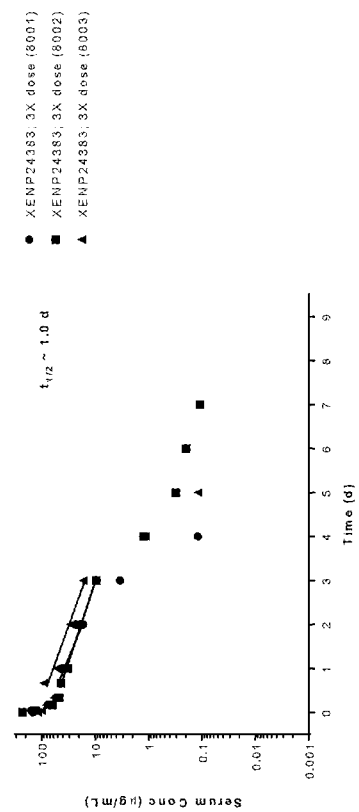
Figure 113G:
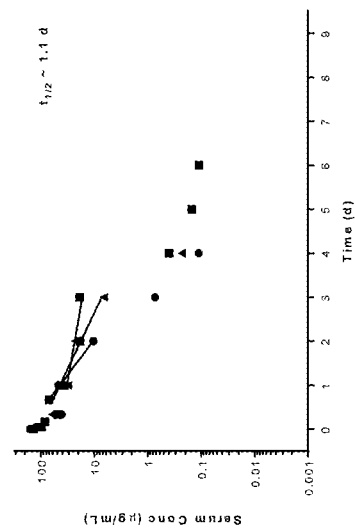
Figure 113H:
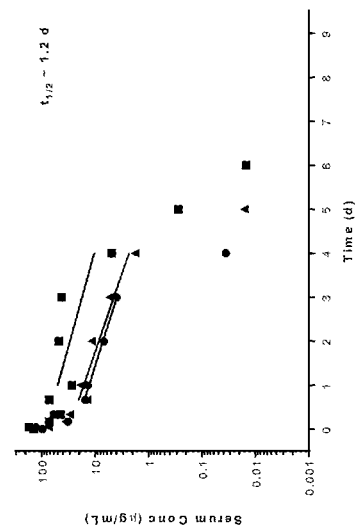
Figure 114A:
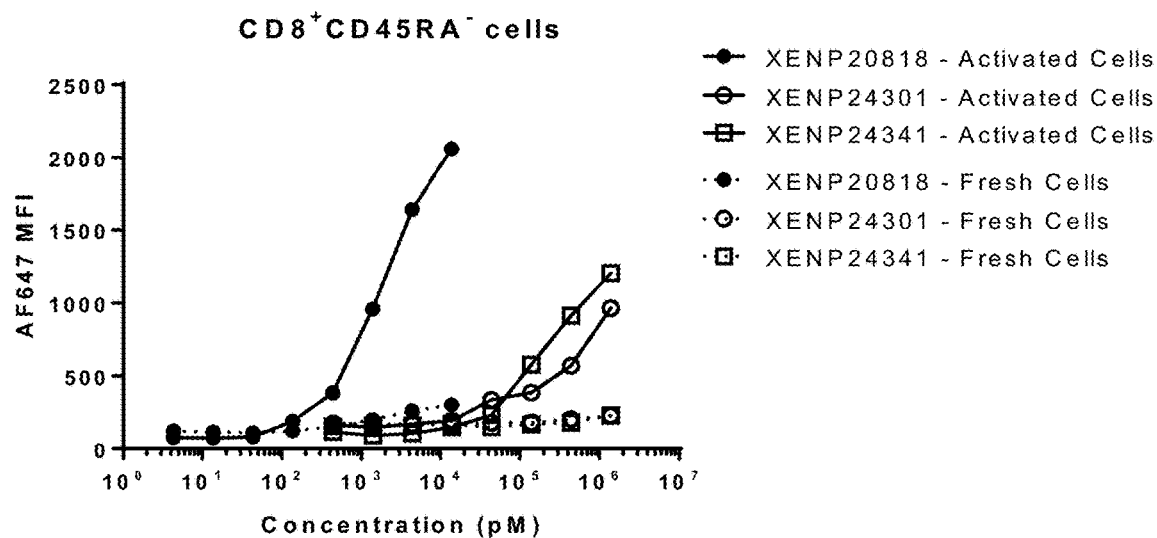
Figure 114B:
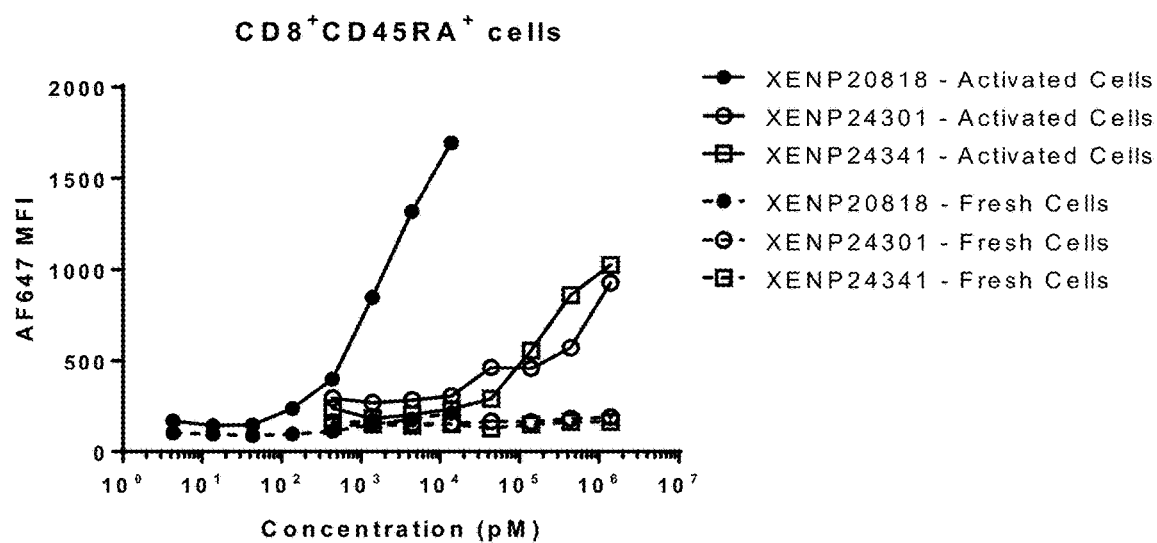
Figure 114C:
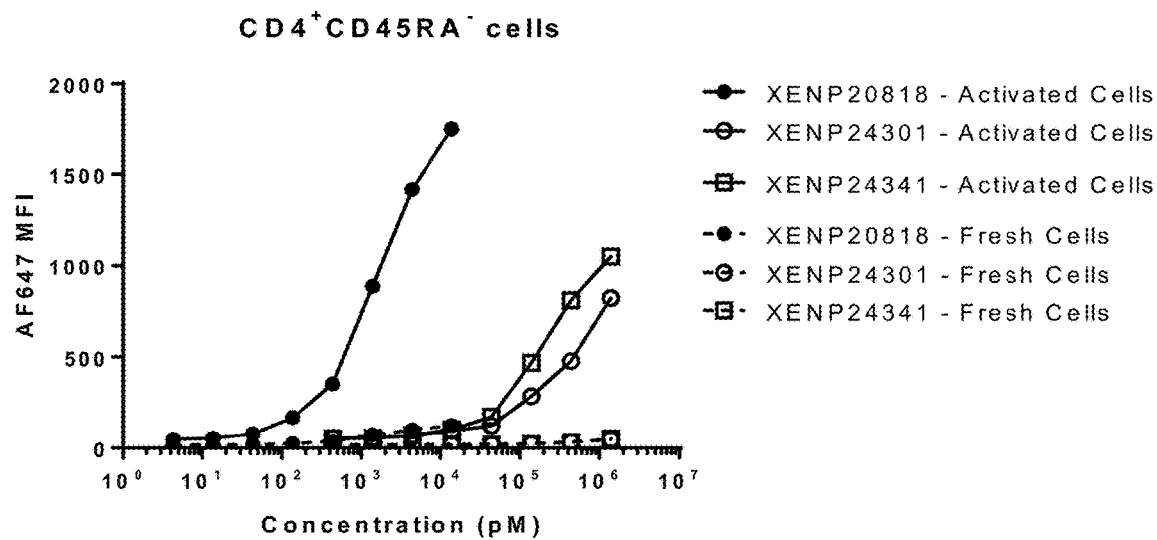
Figure 114D:
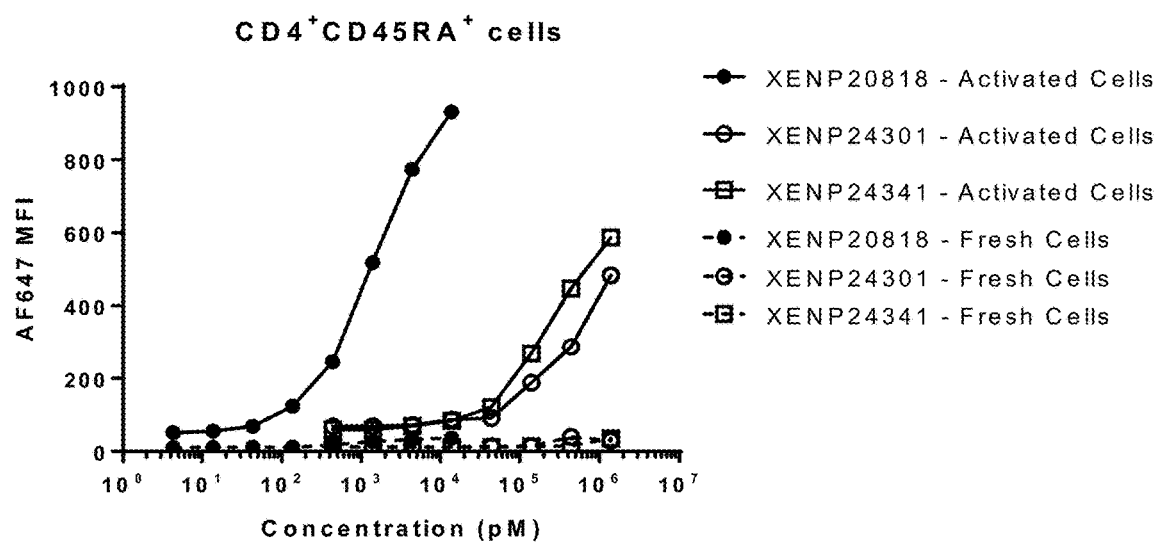
Figure 114E:
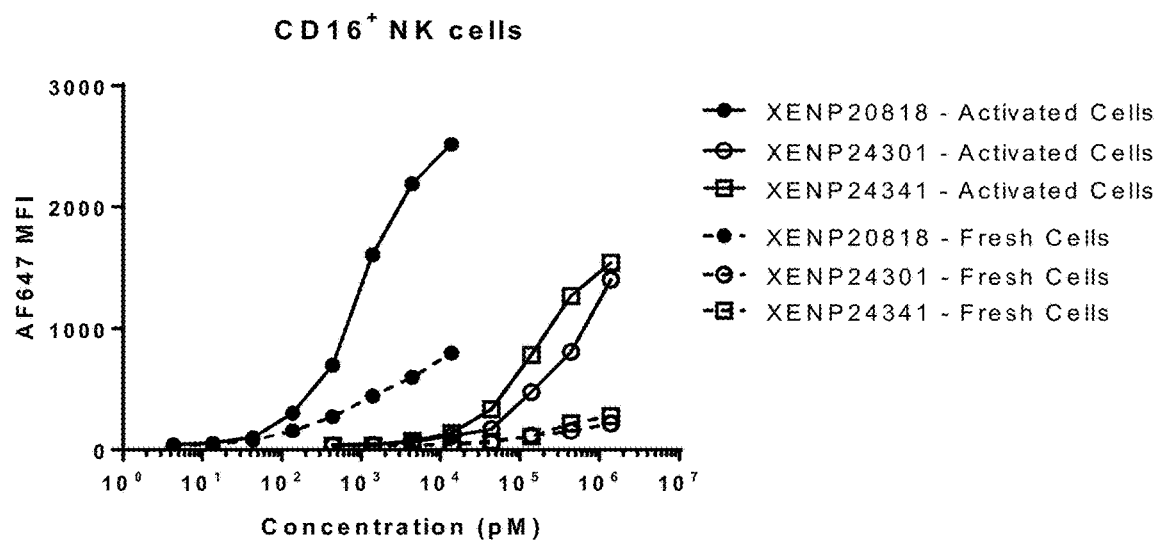
Figure 114F:
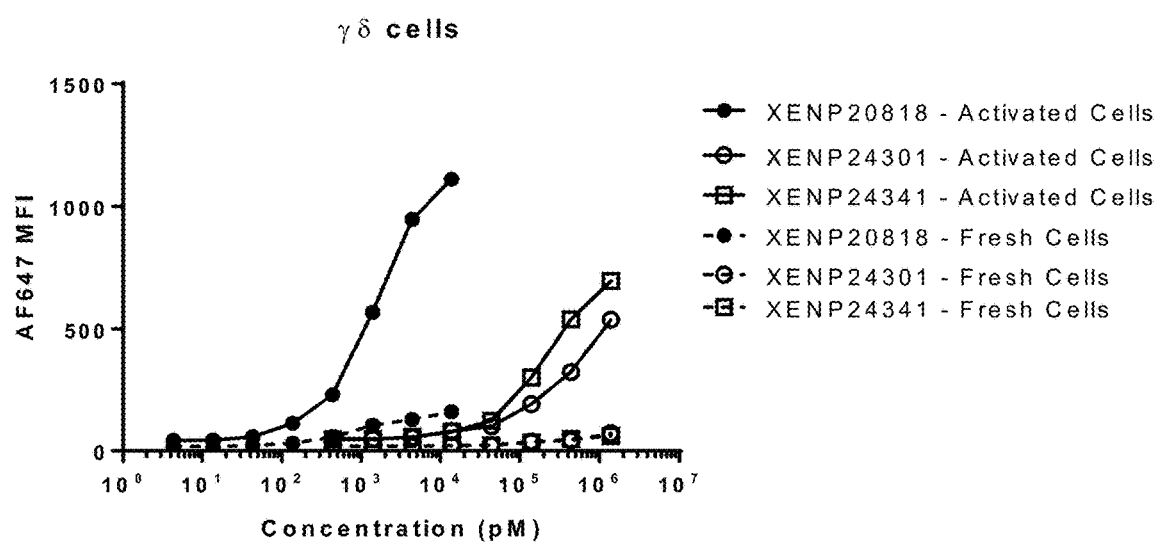
Figure 115A:
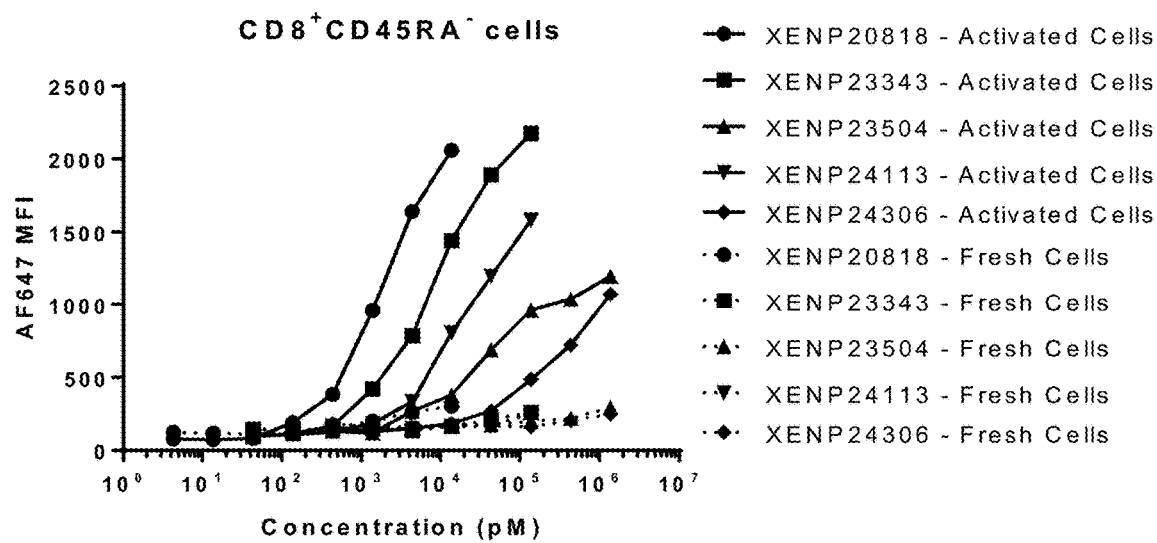
Figure 115B:
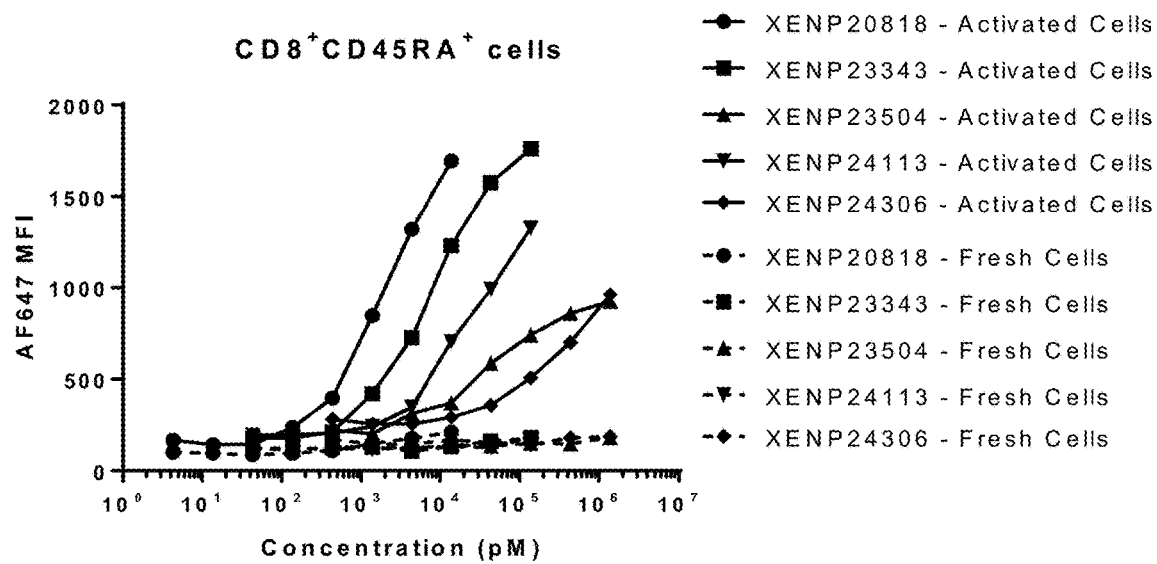
Figure 115C:
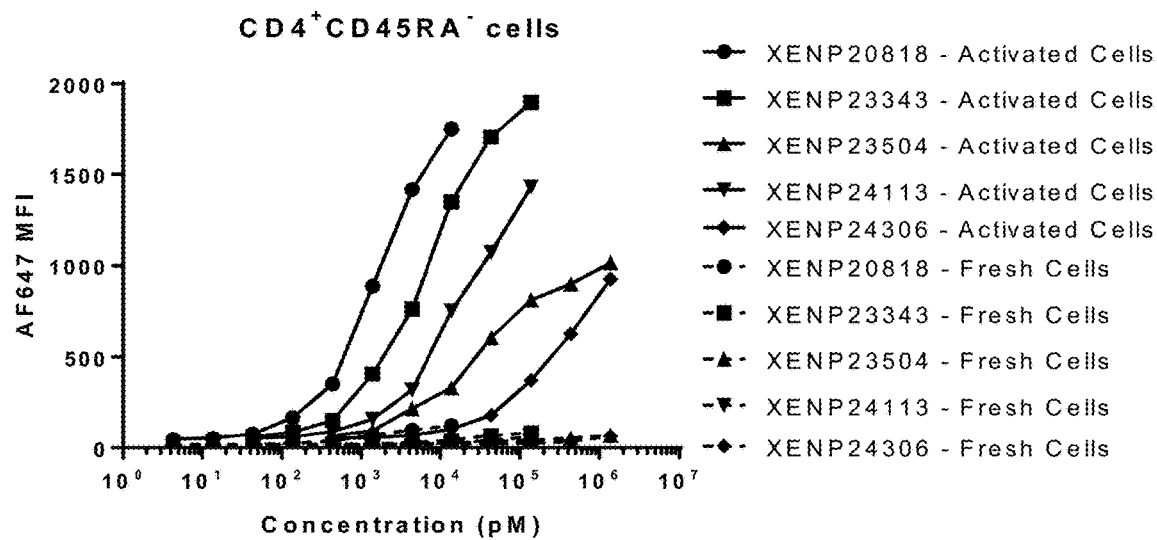
Figure 115D:
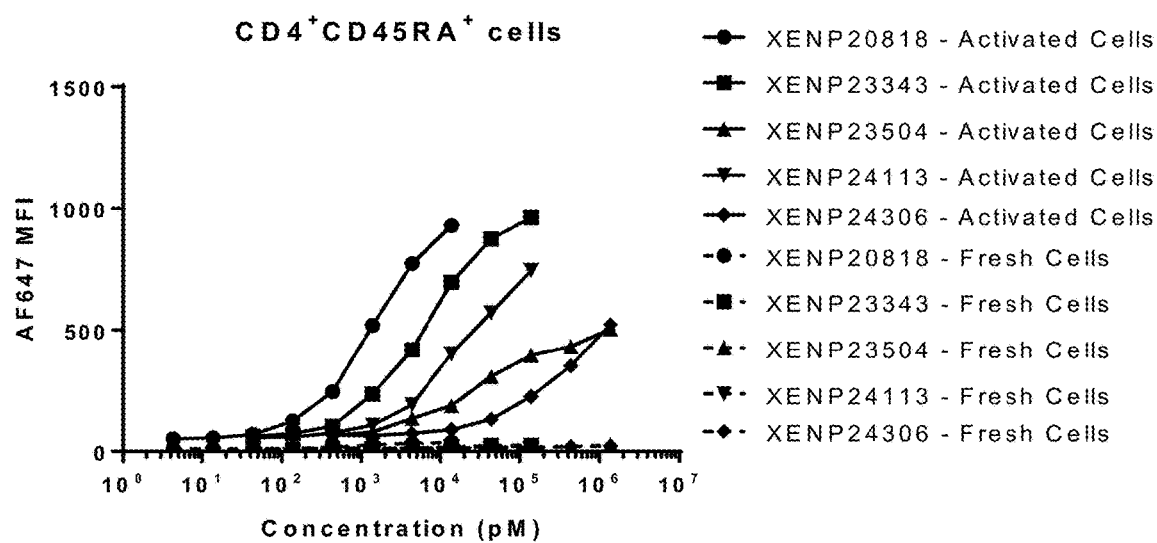
Figure 116A:
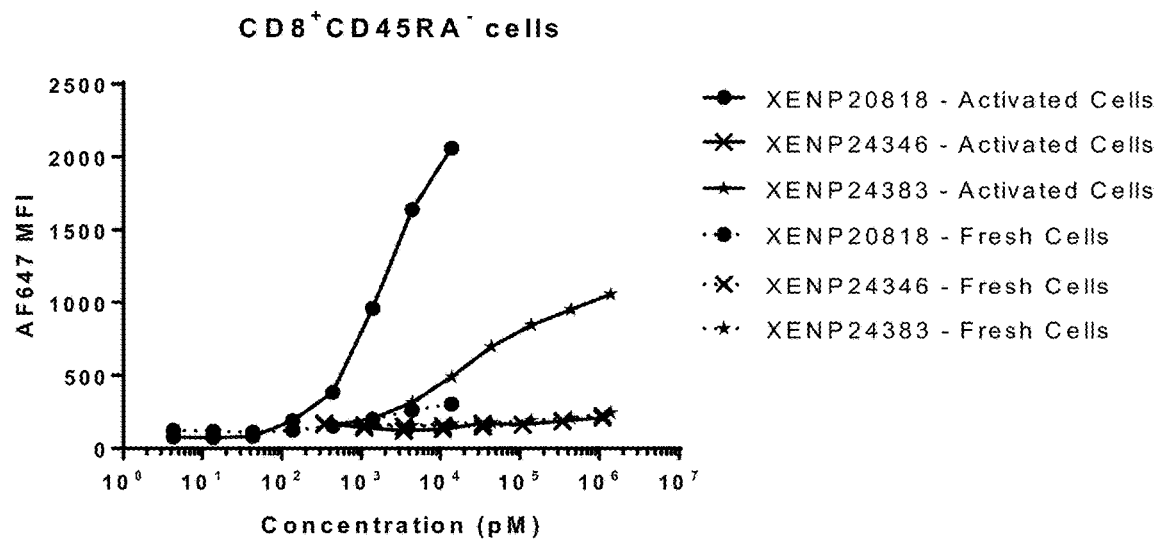
Figure 116B:
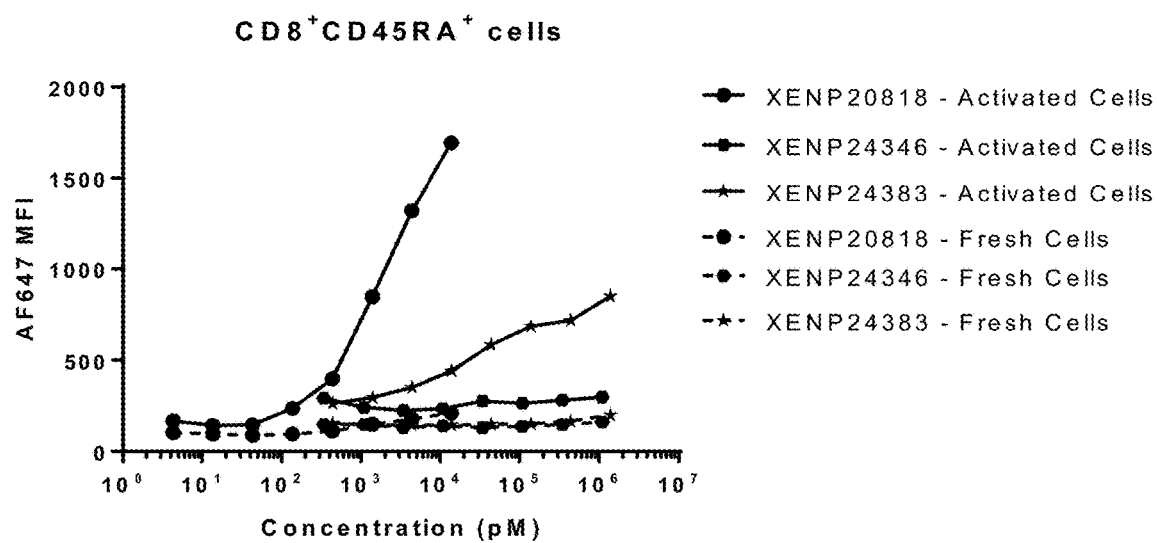
Figure 116C:
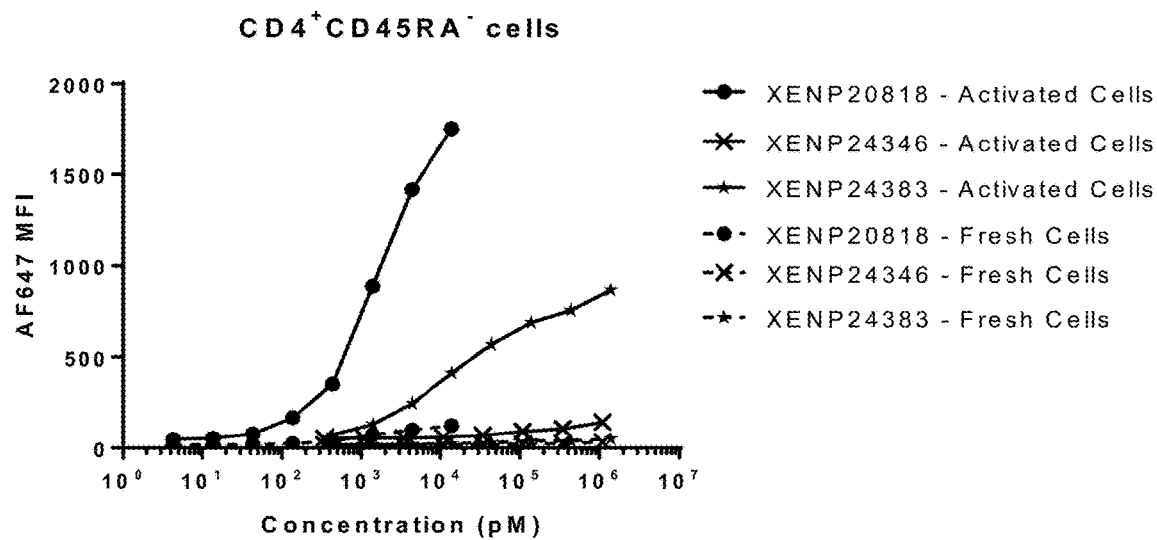
Figure 116D:
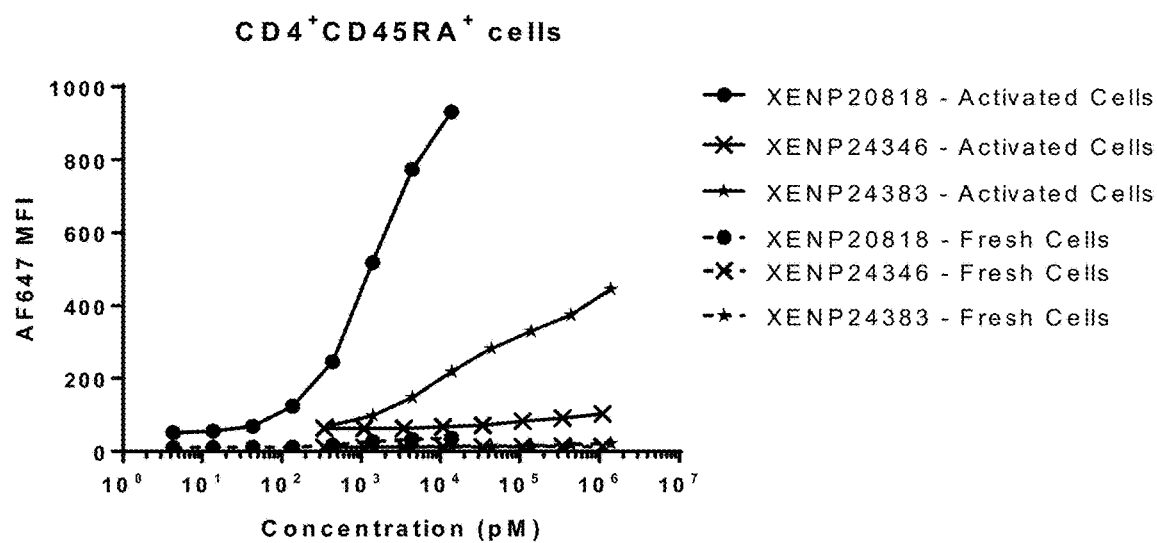
Figure 116E:
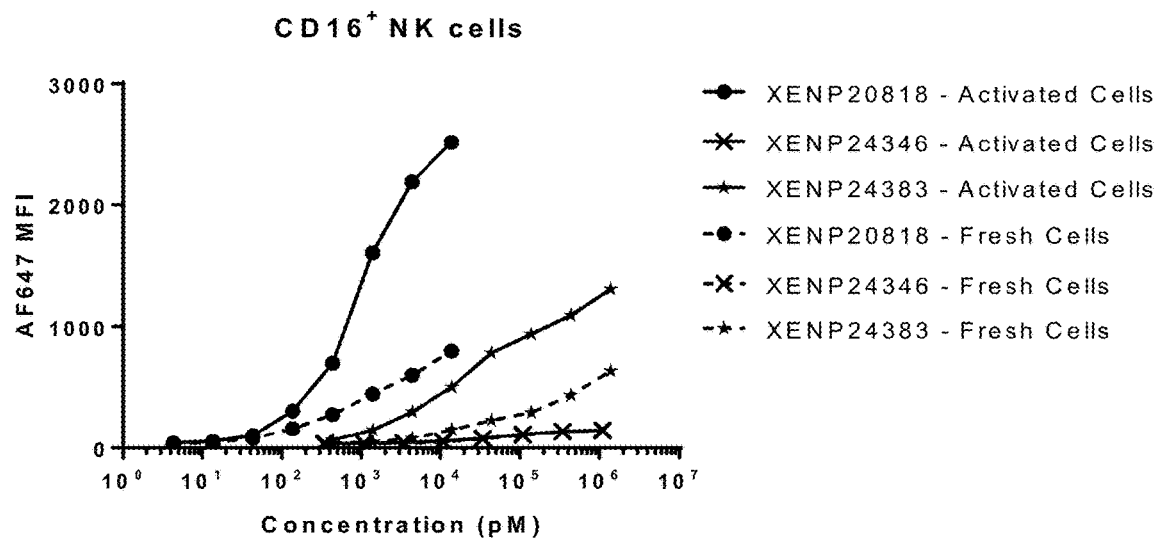
Figure 116F:
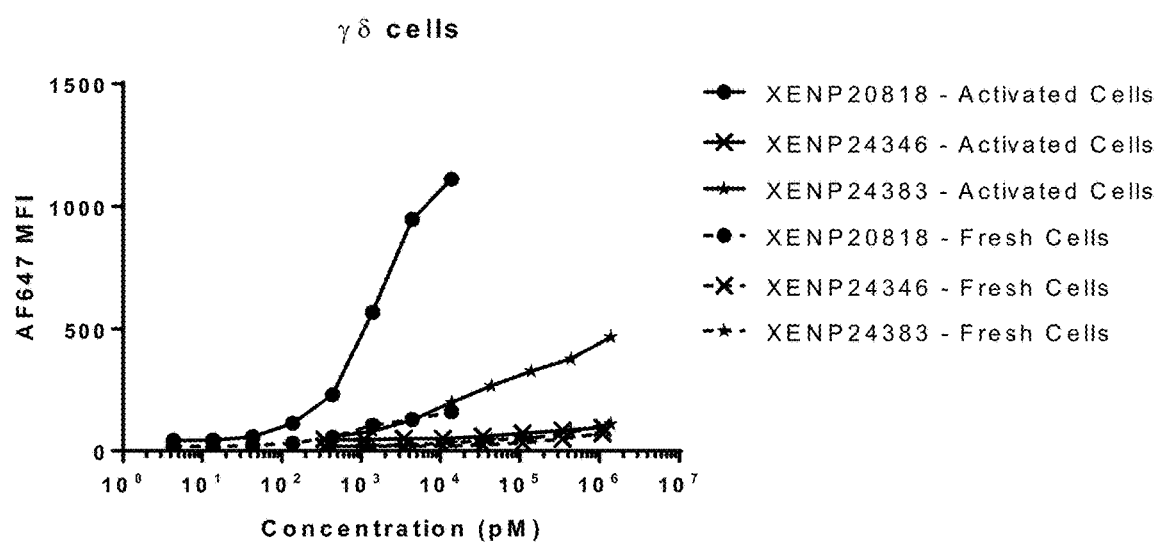

FIG. 110A-FIG. 110F depicts the body weight as a percentage of initial body weight of huPBMC engrafted mice on Day −2 (FIG. 110A), Day 1 (FIG. 110B), Day 5 (FIG. 110C), Day 8 (FIG. 110D) and Day 11 (FIG. 110E) following treatment with additional IL-15/Rα variants. Each point represents a single NSG mouse. FIG. 110F depicts a time-course of body weight in huPBMC engrafted mice following treatment with the IL-15/Rα variants.

FIG. 111A-FIG. 111D depict the percentage of CD8+ CD45RA− T cell (FIG. 111A), CD4+CD45RA− T cell (FIG. 111B), γδ T cell (FIG. 111C), and CD16+ NK cell (FIG. 111D) expressing Ki67 following incubation with the indicated test articles.

FIG. 112A-FIG. 112D depict CD8+ T cell (FIG. 112A), CD4+ T cell (FIG. 112B), NK cell (FIG. 112C) and γδ T cell (FIG. 112D) counts in cynomolgus monkeys after treatment with IL-15/Rα variants.

FIG. 113A-113H depicts the serum concentrations over time and half-lives of the indicated test articles in cynomolgus monkeys.

FIG. 114A-FIG. 114F depict the binding of AF647-labeled test articles (WT IL-15/Rα-Fc and IL-15/Rα-Fc affinity variants with Xtend and without domain linkers) to CD8+CD45RA− T cells (FIG. 114A), CD8+CD45RA+ T cells (FIG. 114B), CD4+CD45RA− T cells (FIG. 114C), CD4+CD45RA+ T cells (FIG. 114D), CD16+ NK cells (FIG. 114E), and γδ T cells (FIG. 114F) in fresh and activated PBMC.

FIG. 115A-FIG. 115F depict the binding of AF647-labeled test articles (WT IL-15/Rα-Fc and IL-15/Rα-Fc affinity variants with Xtend and with domain linkers) to (FIG. 115A) CD8$^+$CD45RA$^-$ T cells, (FIG. 115B) CD8$^+$CD45RA$^+$ T cells, (FIG. 115C) CD4$^+$CD45RA$^-$ T cells, (FIG. 115D) CD4$^+$CD45RA$^+$ T cells, (FIG. 115E) CD16$^+$ NK cells, and (FIG. 115F) γδ T cells in fresh and activated PBMC.

FIG. 116A-FIG. 116F depicts the binding of AF647-labeled test articles (WT IL-15/Rα-Fc and IL-15/Rα-Fc fusion proteins in additional formats with Xtend variants such as FcRn variants) to (FIG. 116A) CD8$^+$CD45RA$^-$ T cells, (FIG. 116B) CD8$^+$CD45RA$^+$ T cells, (FIG. 116C) CD4$^+$CD45RA$^-$ T cells, (FIG. 116D) CD4$^+$CD45RA$^+$ T cells, (FIG. 116E) CD16$^+$ NK cells, and (FIG. 116F) γδ T cells in fresh and activated PBMC.

Figure 117:
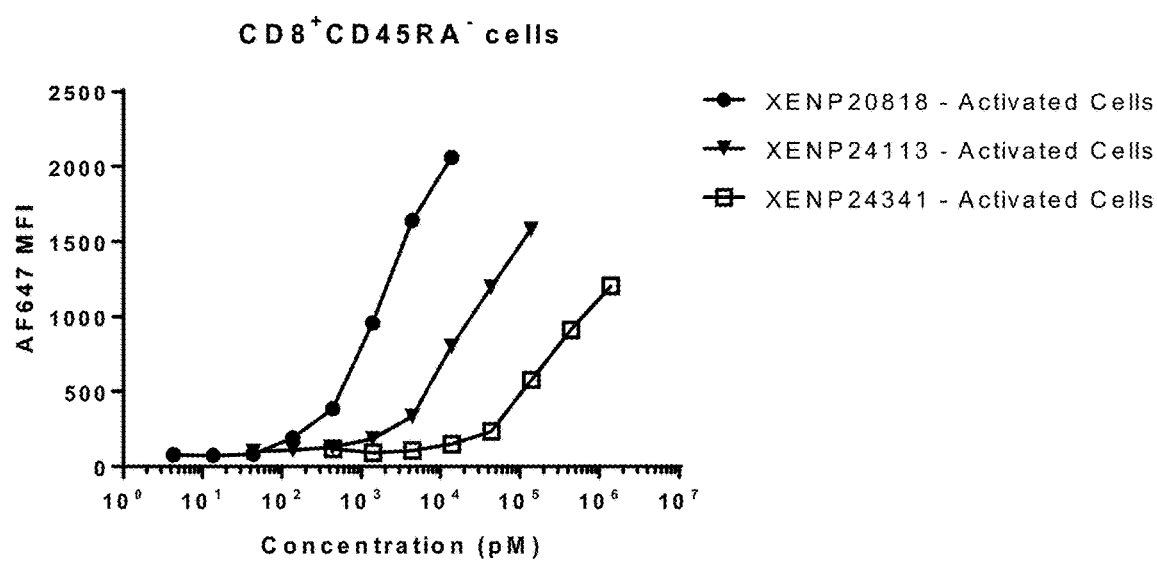

FIG. 117 depicts the binding of AF647-labeled test articles (including XENP24341 and XENP24113) to CD8$^+$CD45RA$^-$ T cells in activated PBMC.

Figure 118A:
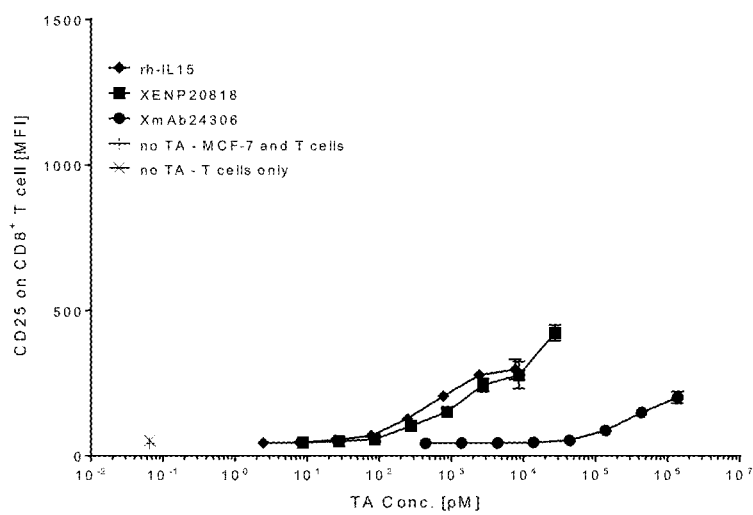
Figure 118B:
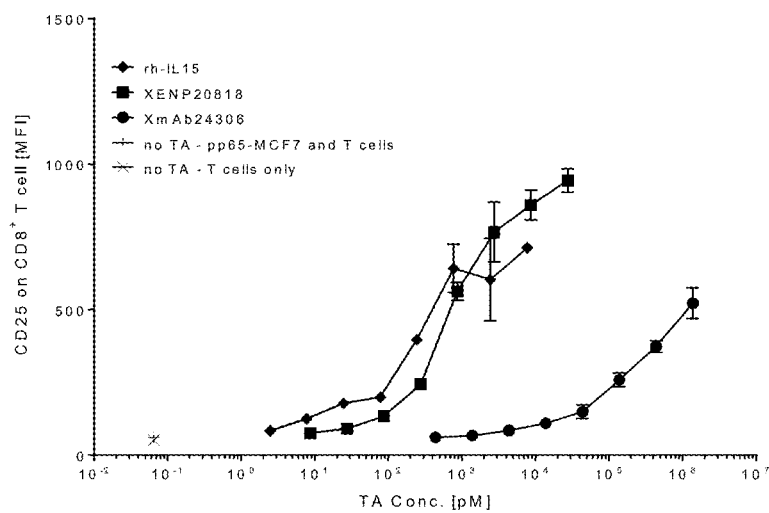

FIG. 118A-FIG. 118B depicts CD25 expression on CD8$^+$ T cells in (FIG. 118A) Group 1 (purified T cells incubated with parental MCF-7 tumor cells and indicated test articles) and (FIG. 118B) Group 2 (purified T cells incubated with pp65-expressing MCF-7 tumor cells and indicated test articles).

Figure 119A:
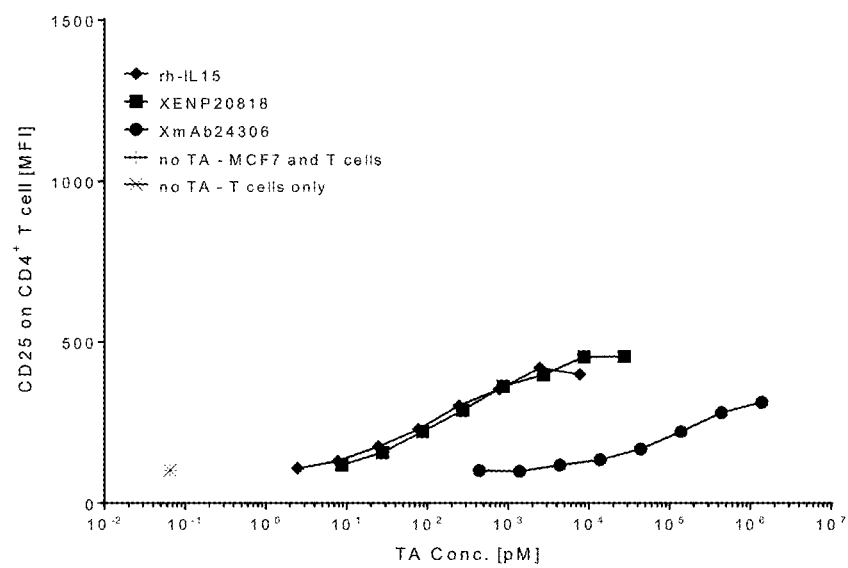
Figure 119B:
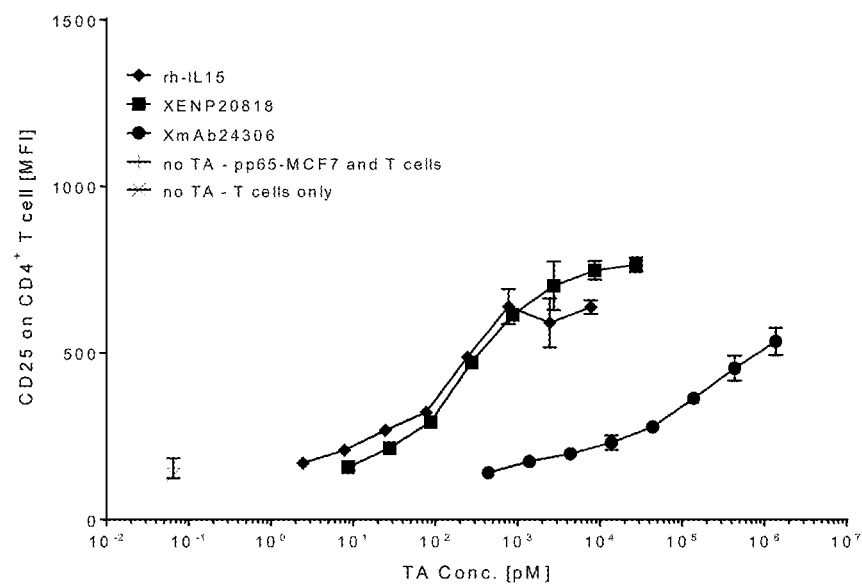

FIG. 119A-FIG. 119B depicts CD25 expression on CD4$^+$ T cells in (FIG. 119A) Group 1 (purified T cells incubated with parental MCF-7 tumor cells and indicated test articles) and (FIG. 119B) Group 2 (purified T cells incubated with pp65-expressing MCF-7 tumor cells and indicated test articles).

Figure 120A:
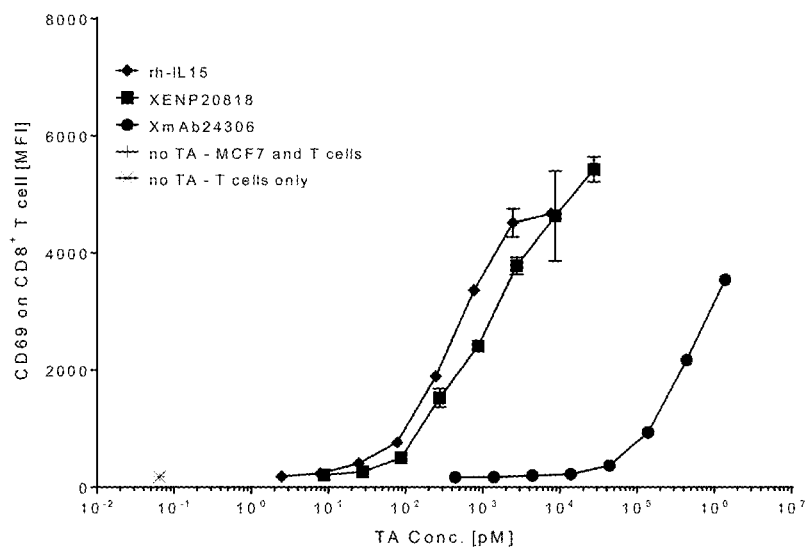
Figure 120B:
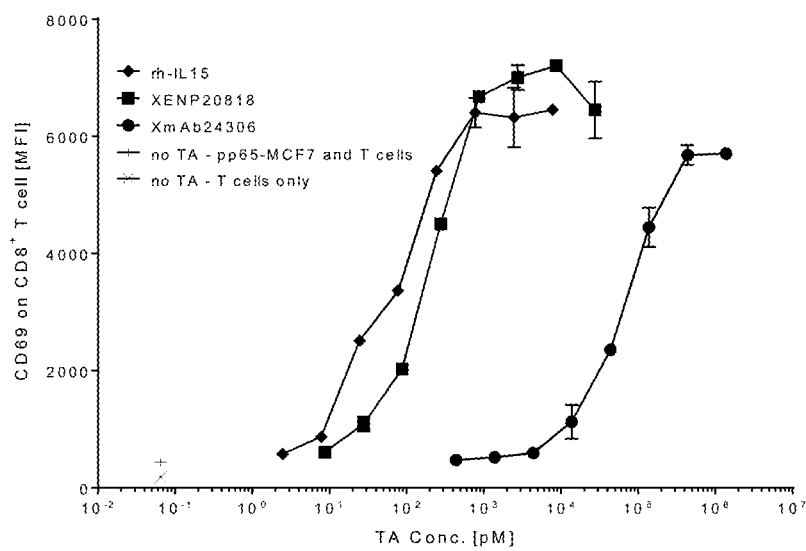

FIG. 120A-FIG. 120B depict CD69 expression on CD8$^+$ T cells in (FIG. 120A) Group 1 (purified T cells incubated with parental MCF-7 tumor cells and indicated test articles) and (FIG. 120B) Group 2 (purified T cells incubated with pp65-expressing MCF-7 tumor cells and indicated test articles).

Figure 121A:
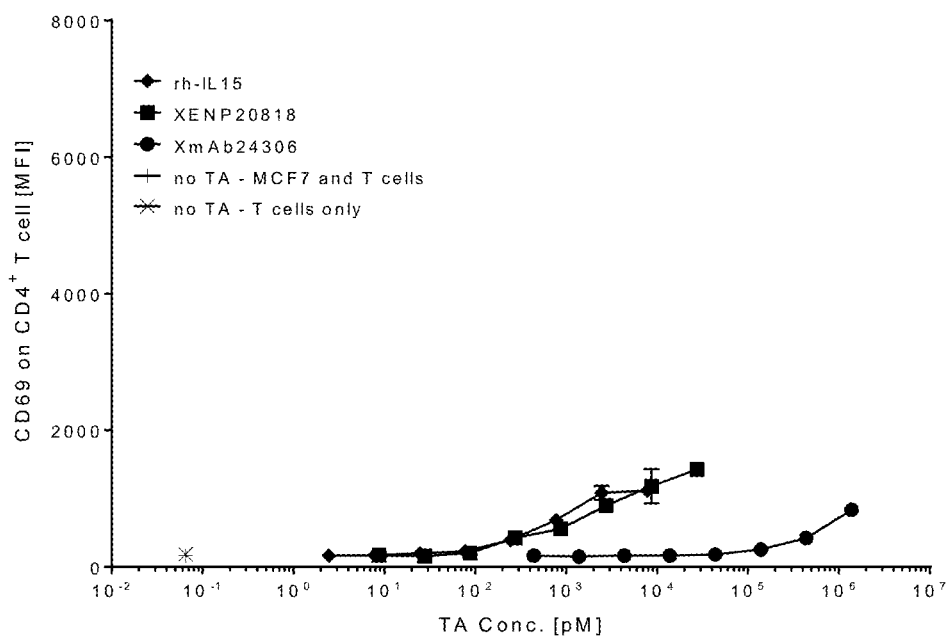
Figure 121B:
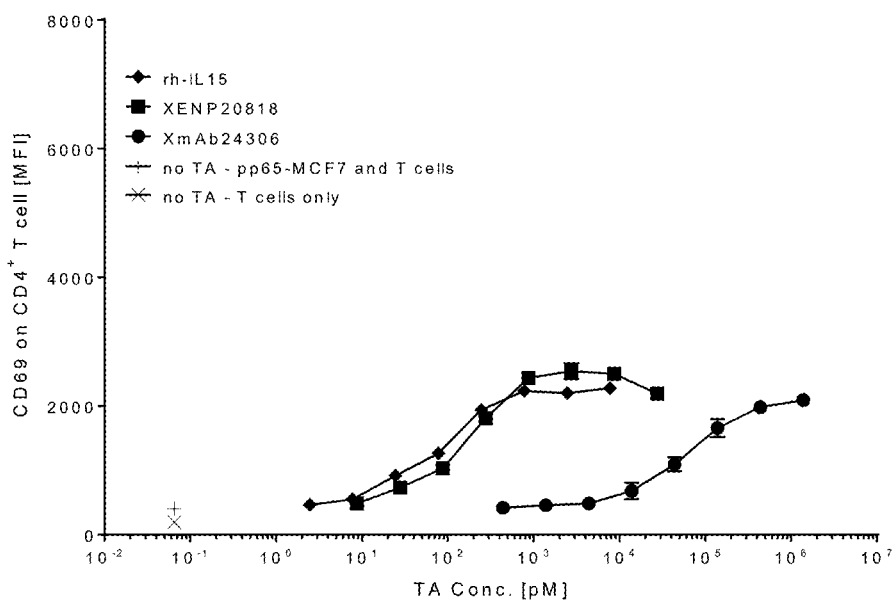

FIG. 121A-FIG. 121B depict CD69 expression on CD4$^+$ T cells in (FIG. 121A) Group 1 (purified T cells incubated with parental MCF-7 tumor cells and indicated test articles) and (FIG. 121B) Group 2 (purified T cells incubated with pp65-expressing MCF-7 tumor cells and indicated test articles).

Figure 122A:
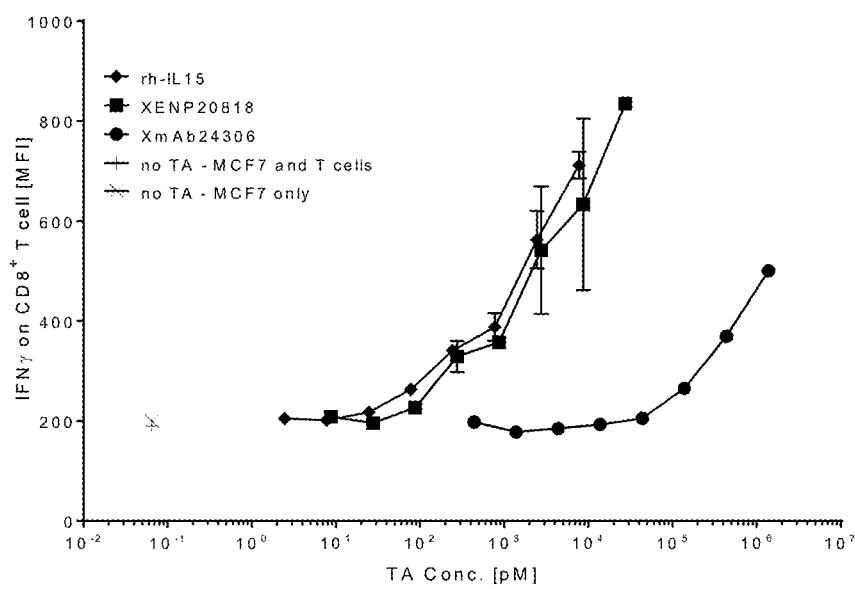
Figure 122B:
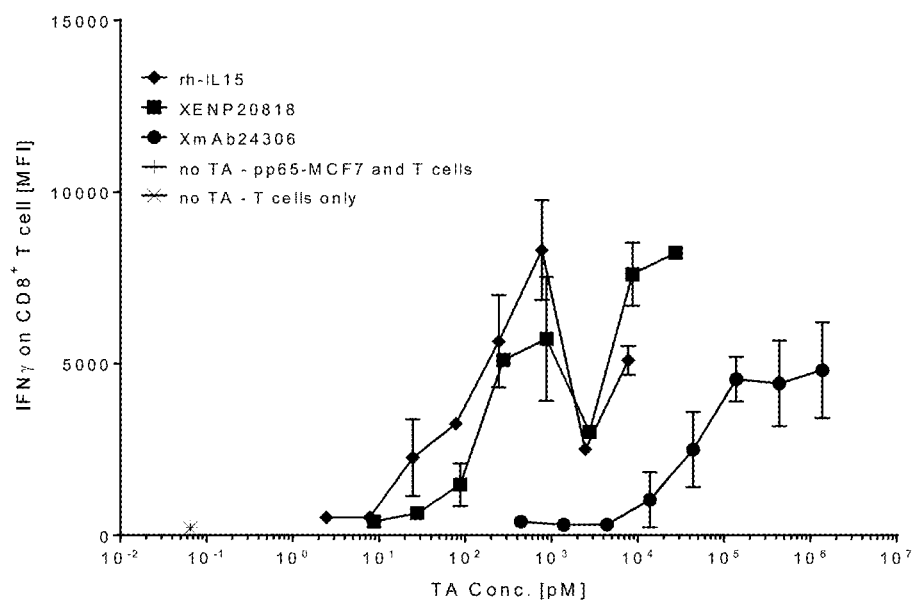

FIG. 122A-FIG. 122B depict intracellular IFNγ expression in CD8$^+$ T cells in (FIG. 122A) Group 1 (purified T cells incubated with parental MCF-7 tumor cells and indicated test articles) and (FIG. 122B) Group 2 (purified T cells incubated with pp65-expressing MCF-7 tumor cells and indicated test articles).

Figure 123A:
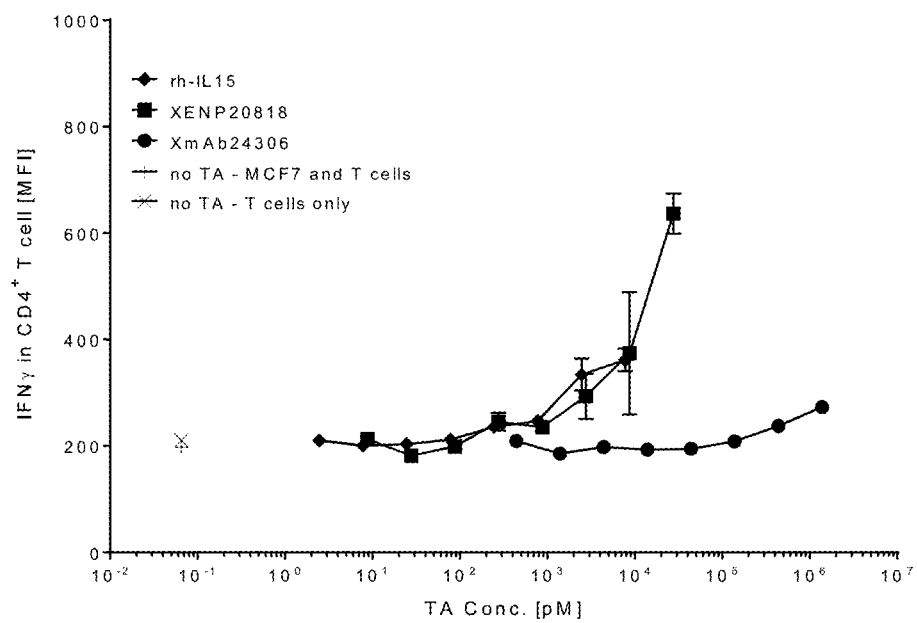
Figure 123B:
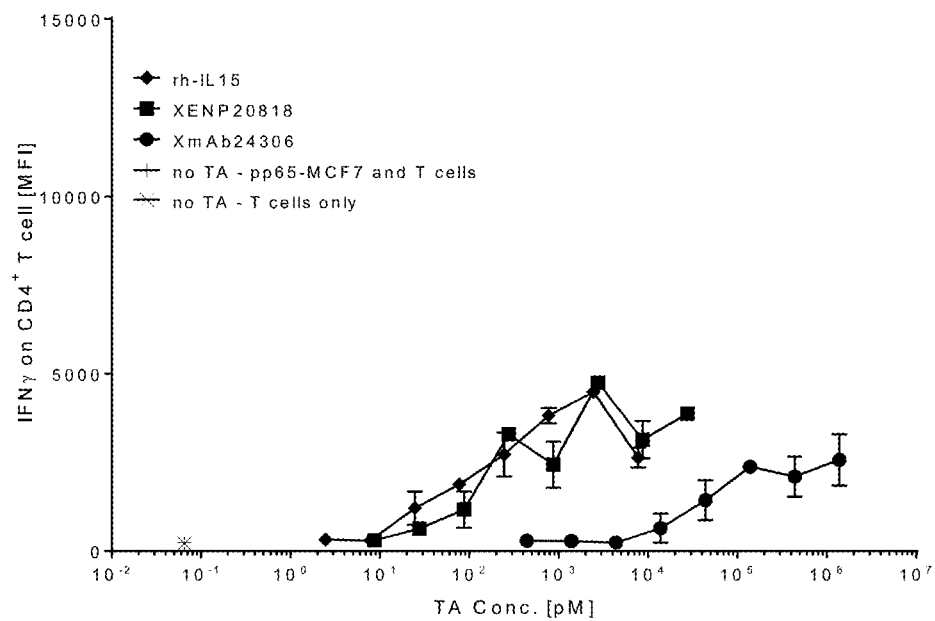

FIG. 123A-FIG. 123B depict intracellular IFNγ expression in CD4$^+$ T cells in (FIG. 123A) Group 1 (purified T cells incubated with parental MCF-7 tumor cells and indicated test articles) and (FIG. 123B) Group 2 (purified T cells incubated with pp65-expressing MCF-7 tumor cells and indicated test articles).

Figure 124A:
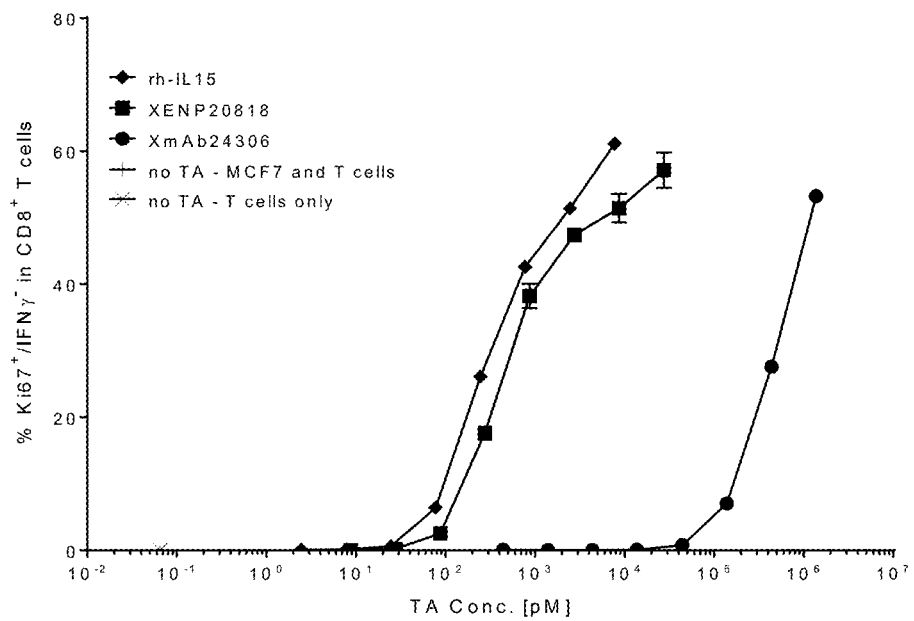
Figure 124B:
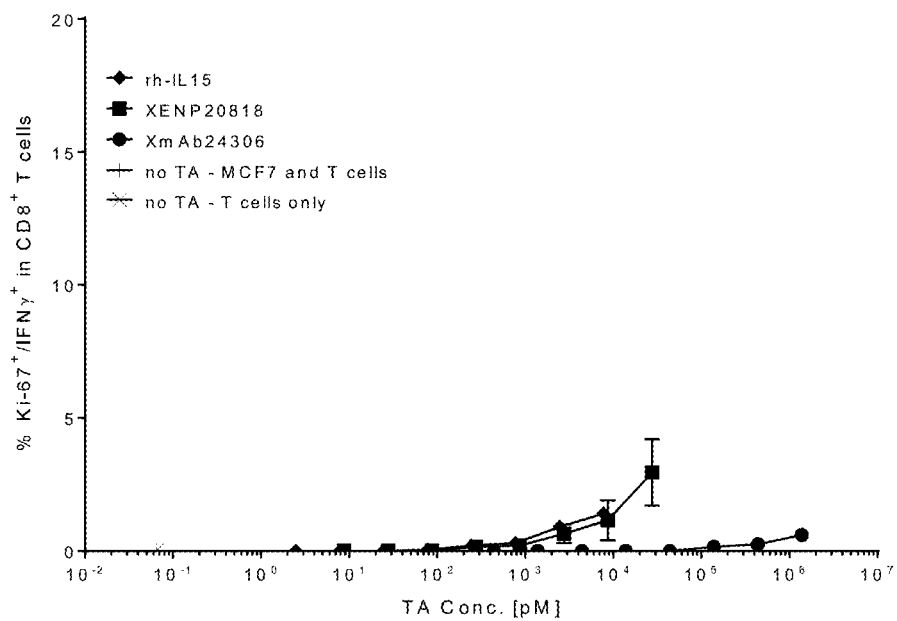
Figure 124C:
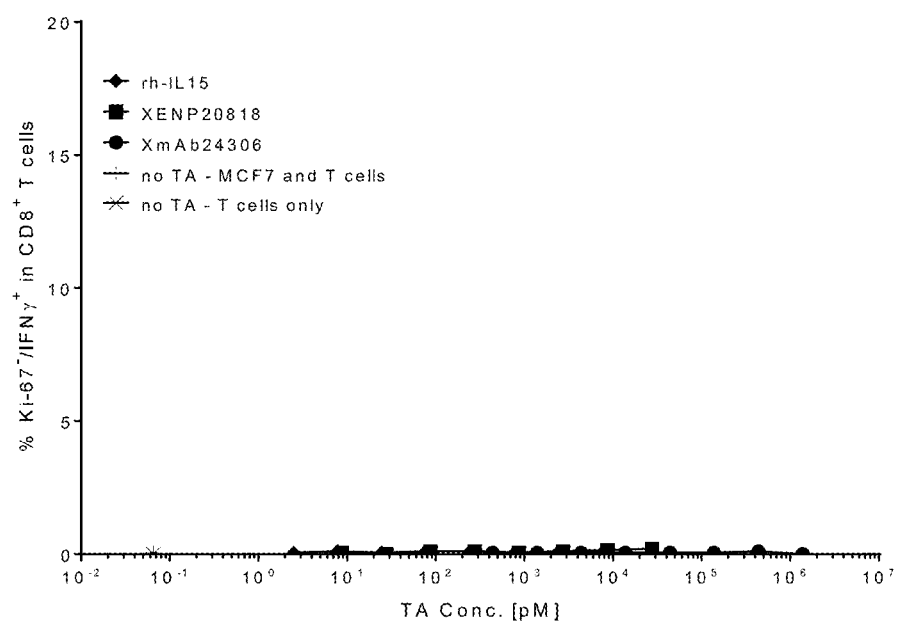

FIG. 124A-FIG. 124C depict percentage of (FIG. 124A) Ki-67$^+$/IFNγ$^-$, (FIG. 124B) Ki-67$^+$/IFNγ$^+$, and (FIG. 124C) Ki-67$^-$/IFNγ$^+$ fractions of CD8$^+$ T cells in Group 1 (purified T cells incubated with parental MCF-7 tumor cells and indicated test articles).

Figure 125A:
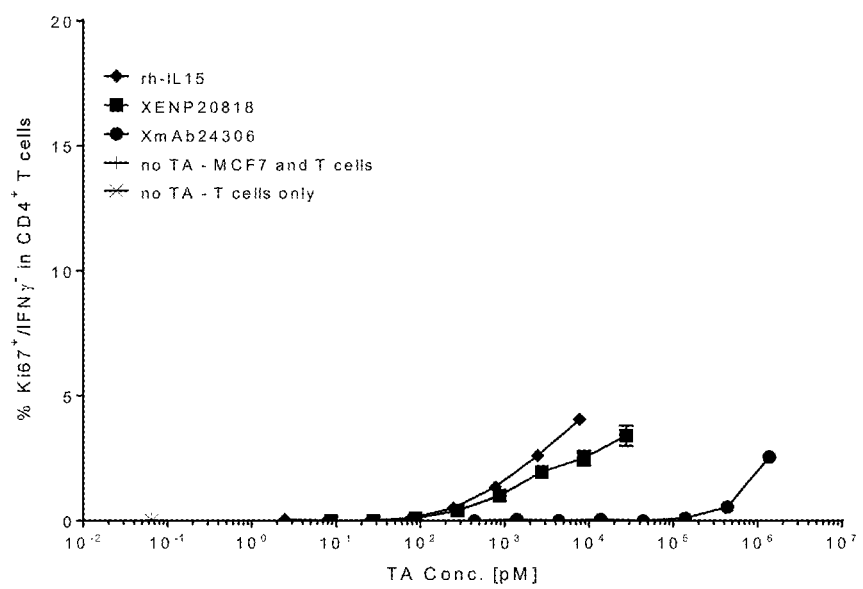
Figure 125B:
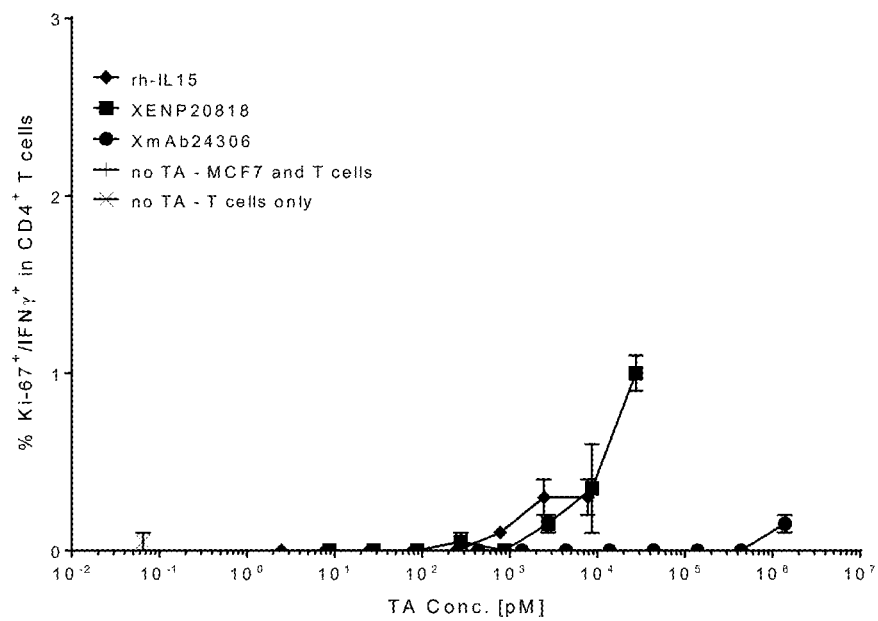
Figure 125C:
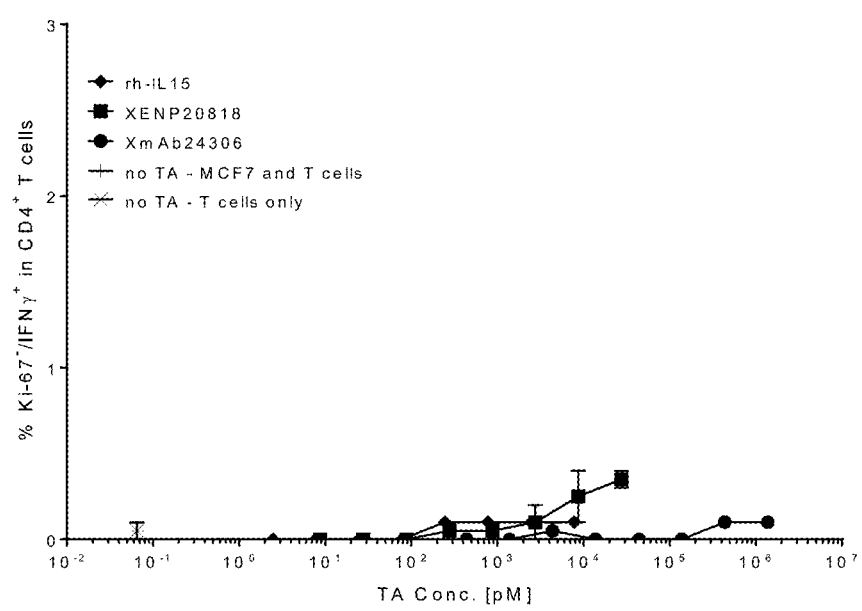

FIG. 125A-FIG. 125C depicts percentage of (FIG. 125A) Ki-67$^+$/IFNγ$^-$, (FIG. 125B) Ki-67$^+$/IFNγ$^+$, and (FIG. 125C) Ki-67$^-$/IFNγ$^+$ fractions of CD4$^+$ T cells in Group 1 (purified T cells incubated with parental MCF-7 tumor cells and indicated test articles).

Figure 126A:
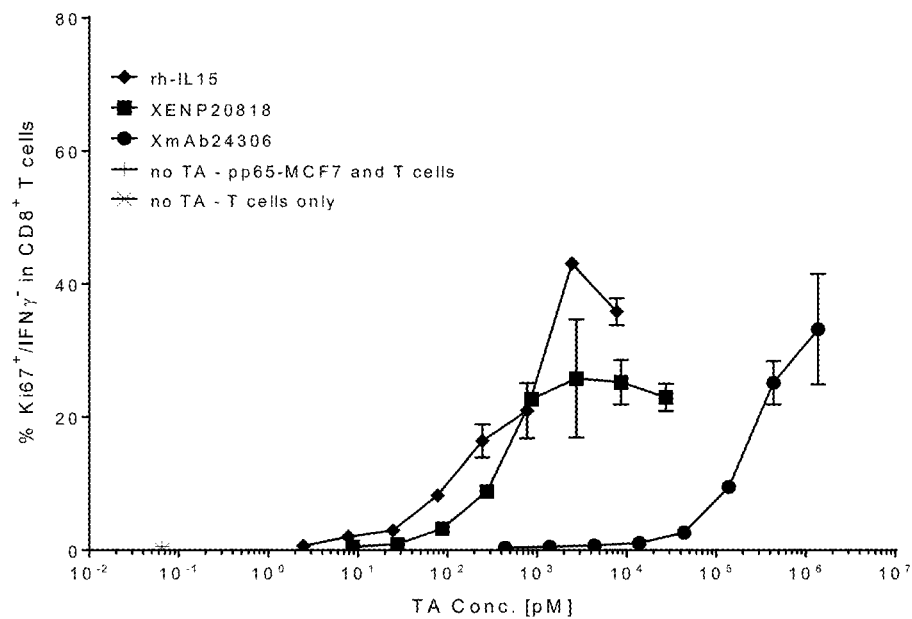
Figure 126B:
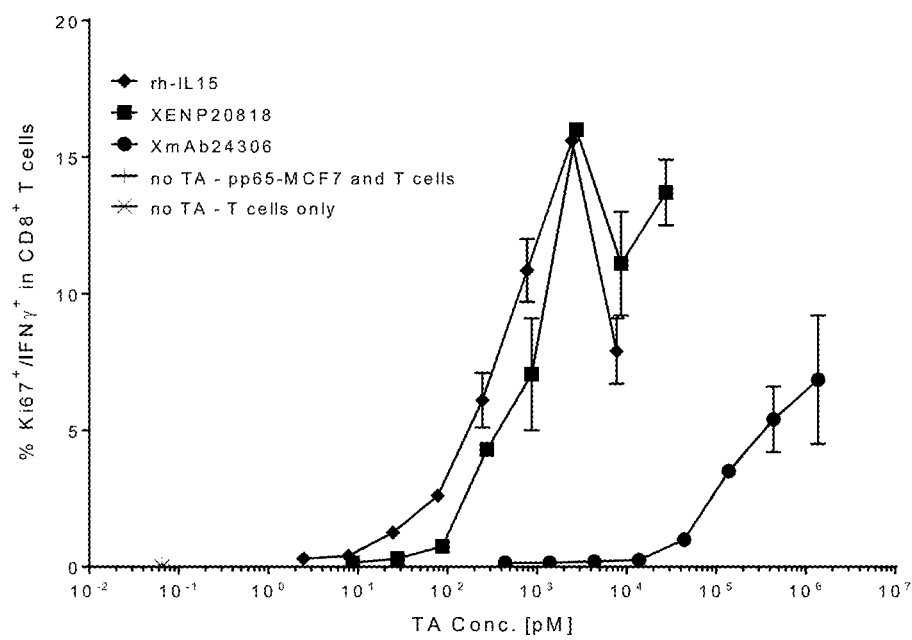
Figure 126C:
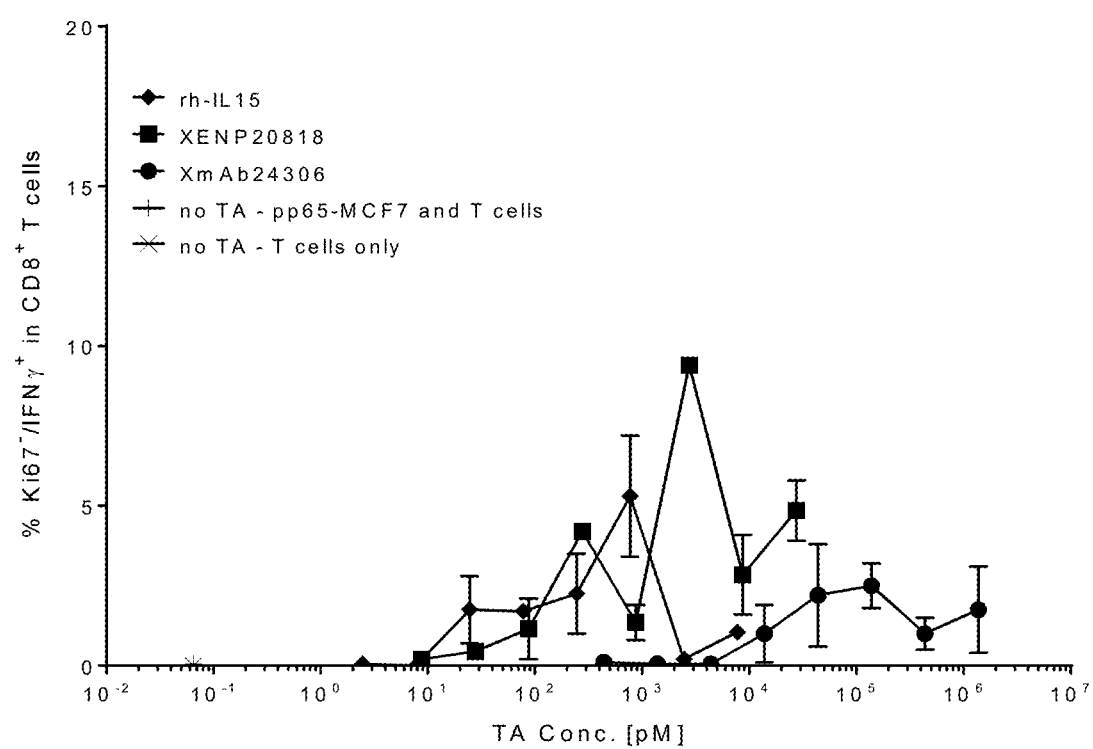

FIG. 126A-FIG. 126C depict percentage of (FIG. 126A) Ki-67$^+$/IFNγ$^-$, (FIG. 126B) Ki-67$^+$/IFNγ$^+$, and (FIG. 126C) Ki-67$^-$/IFNγ$^+$ fractions of CD8$^+$ T cells in Group 1 (purified T cells incubated with pp65-expressing MCF-7 tumor cells and indicated test articles).

Figure 127A:
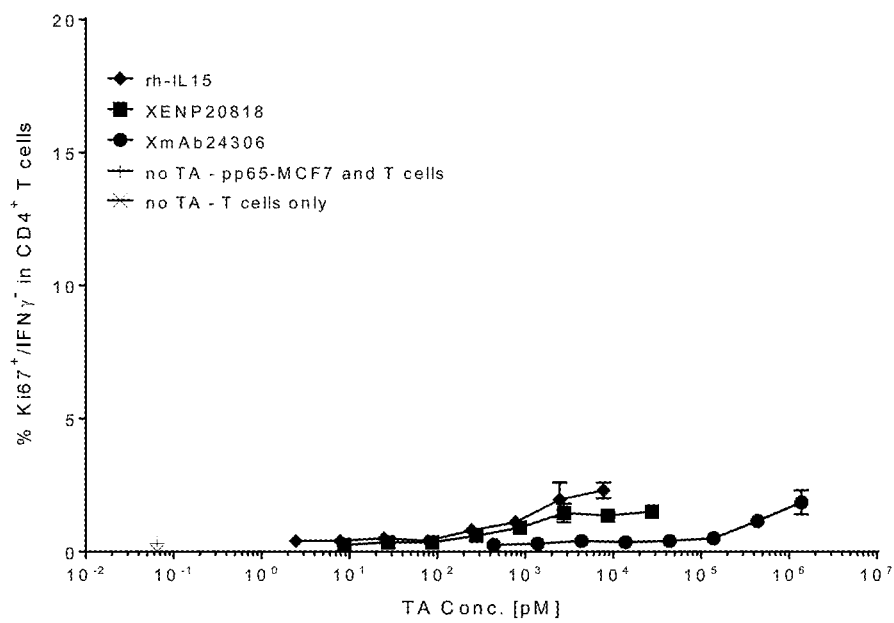
Figure 127B:
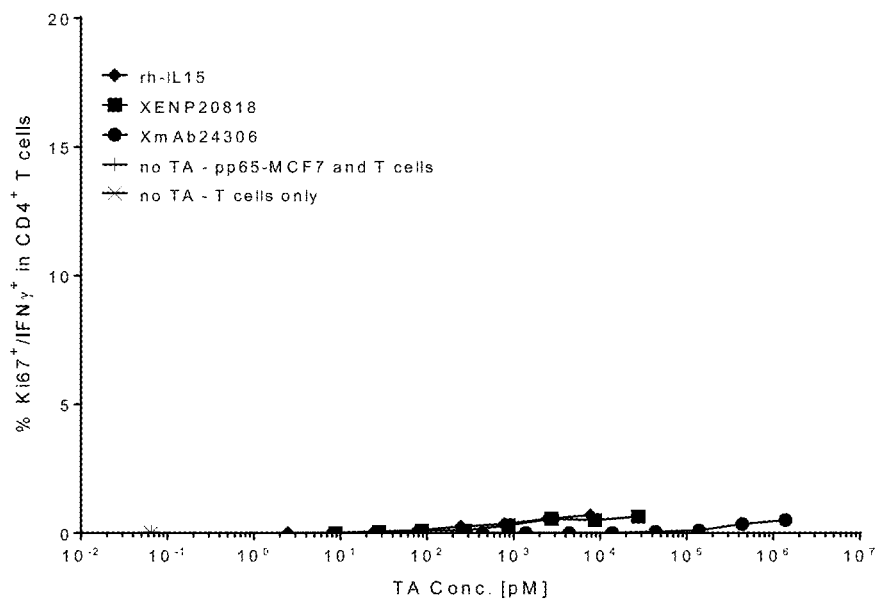
Figure 127C:
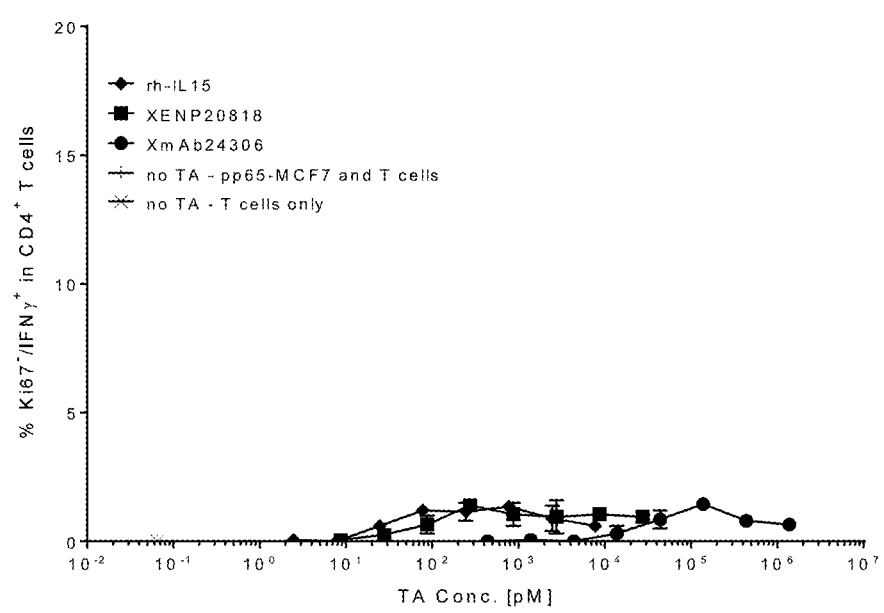

FIG. 127A-FIG. 127C depict percentage of (FIG. 127A) Ki-67$^+$/IFNγ$^-$, (FIG. 127B) Ki-67$^+$/IFNγ$^+$, and (FIG. 127C) Ki-67$^-$/IFNγ$^+$ fractions of CD4$^+$ T cells in Group 1 (purified T cells incubated with pp65-expressing MCF-7 tumor cells and indicated test articles).

Figure 128A:
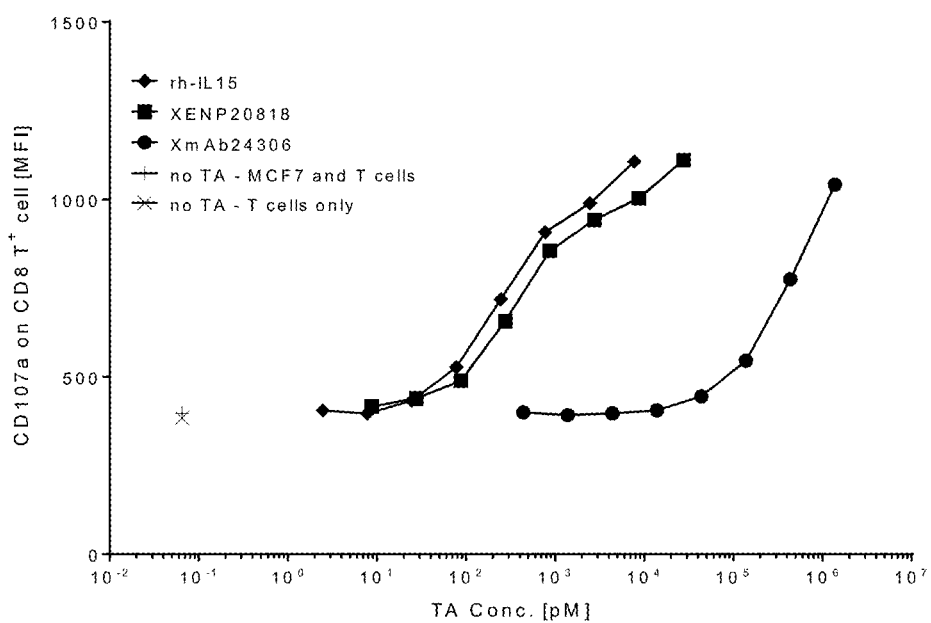
Figure 128B:
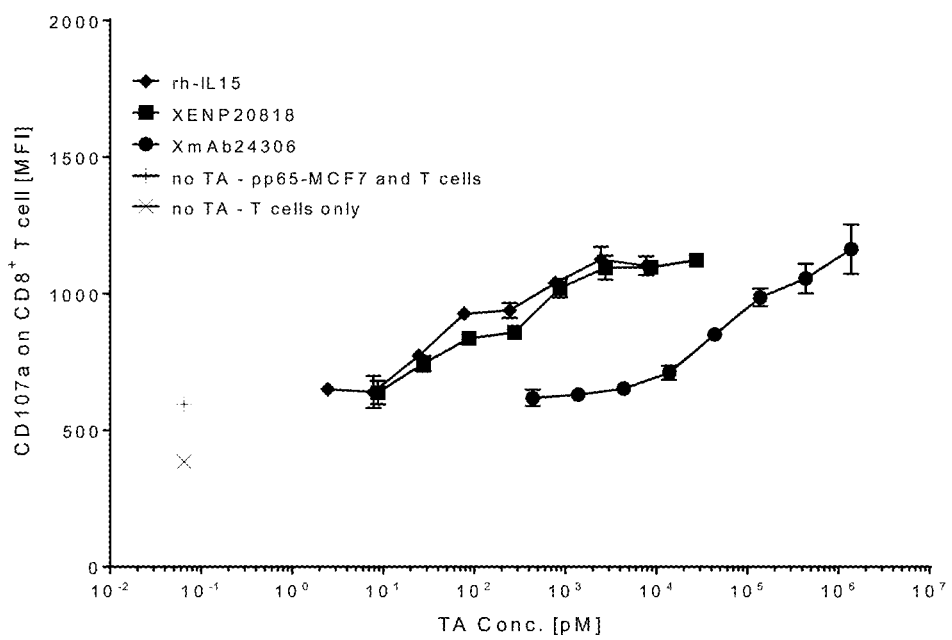

FIG. 128A-FIG. 128B depict CD107a expression on CD8$^+$ T cells in (FIG. 128A) Group 1 (purified T cells incubated with parental MCF-7 tumor cells and indicated test articles) and (FIG. 128B) Group 2 (purified T cells incubated with pp65-expressing MCF-7 tumor cells and indicated test articles).

Figure 129A:
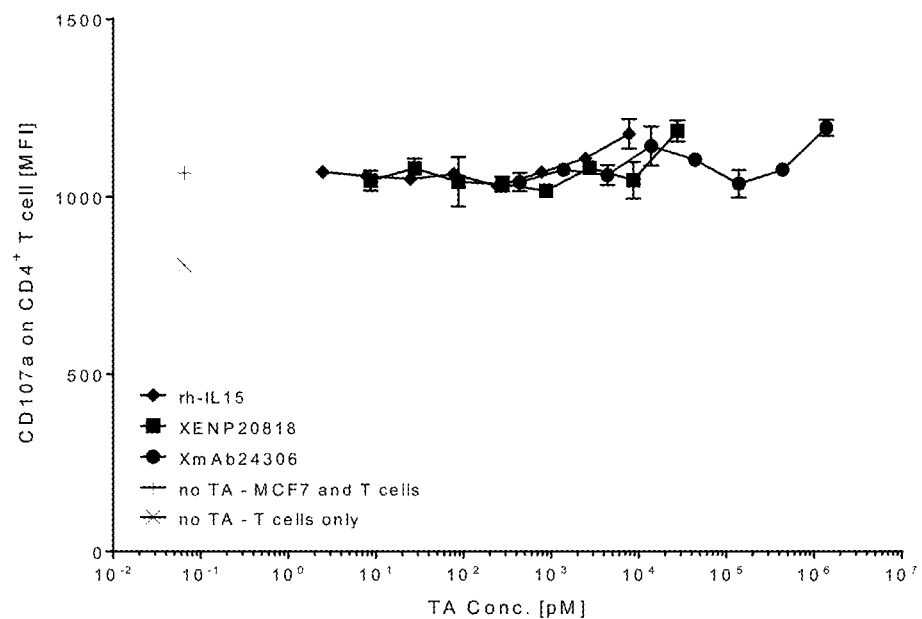
Figure 129B:
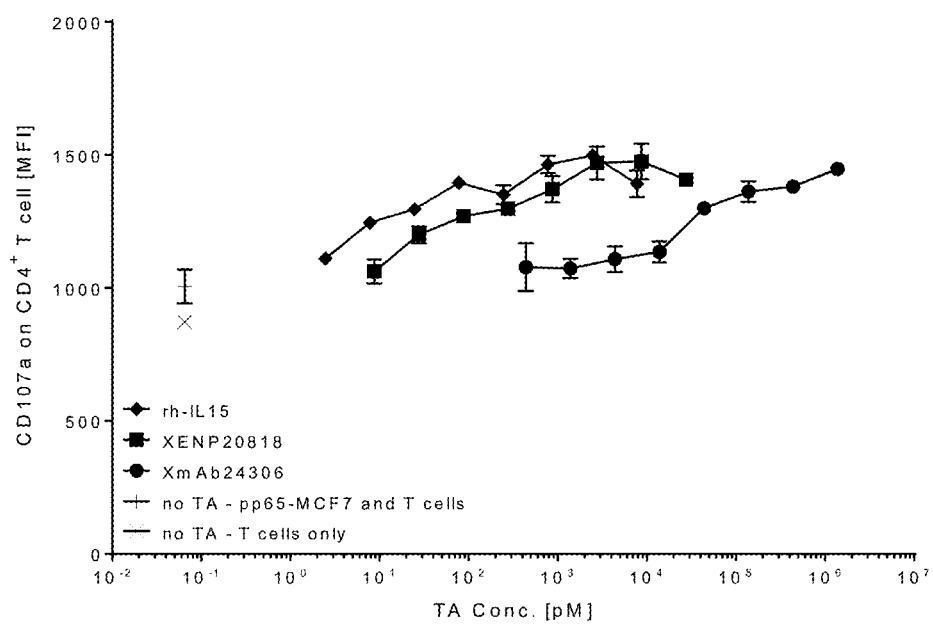

FIG. 129A-FIG. 129B depict CD107a expression on CD4$^+$ T cells in (FIG. 129A) Group 1 (purified T cells incubated with parental MCF-7 tumor cells and indicated test articles) and (FIG. 129B) Group 2 (purified T cells incubated with pp65-expressing MCF-7 tumor cells and indicated test articles).

Figure 130A:
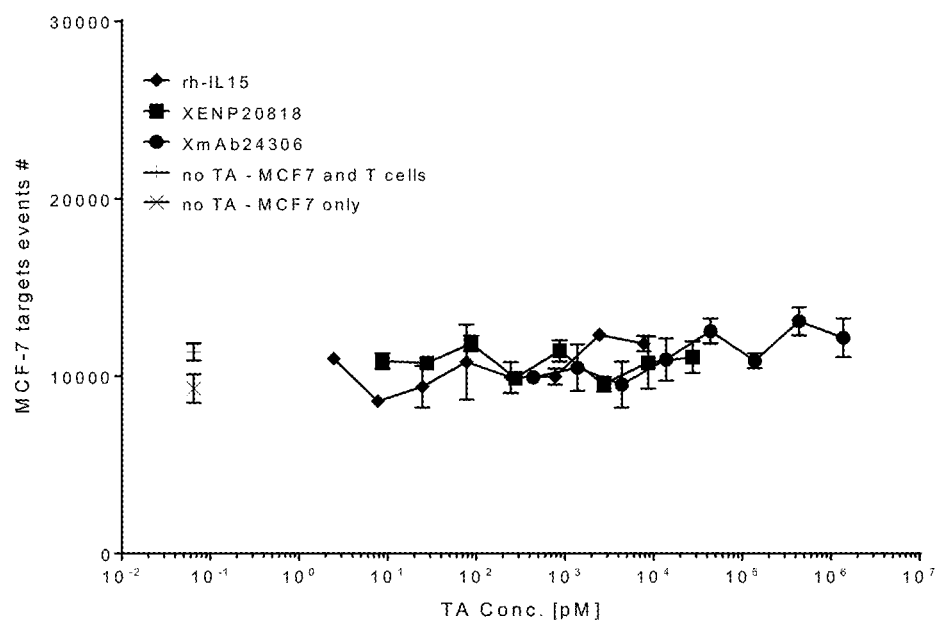
Figure 130B:
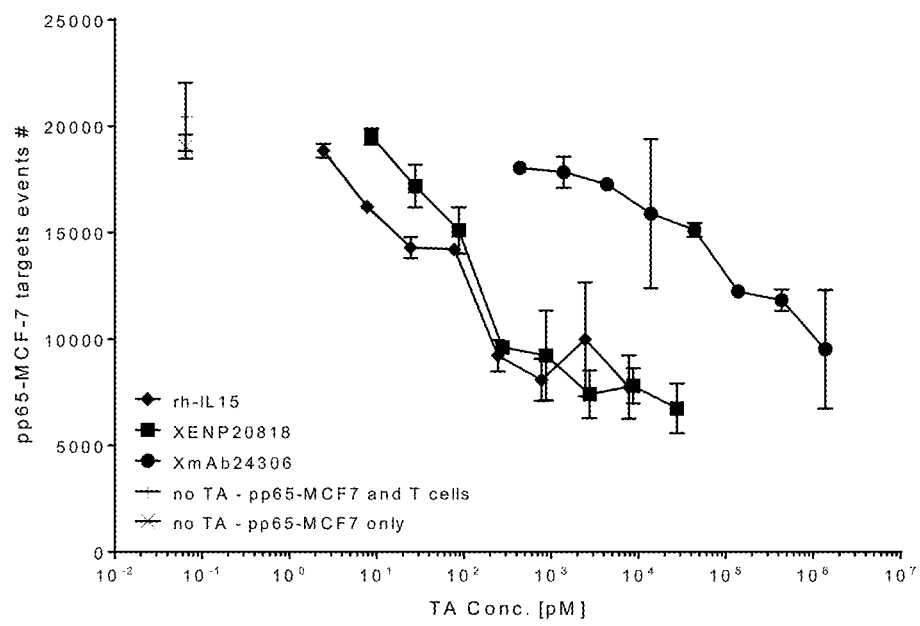

FIG. 130A-FIG. 130B depict remaining target cells [FIG. 130A: parental MCF-7 tumor cells; FIG. 130B: pp65-expressing MCF-7 tumor cells] following incubation with purified T cells and indicated test articles.

Figure 131A:
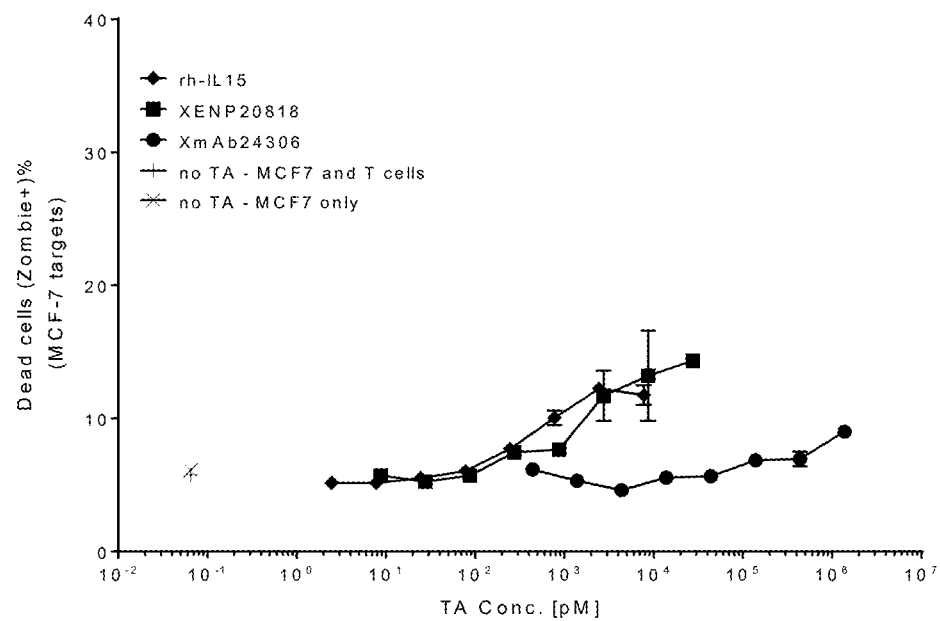
Figure 131B:
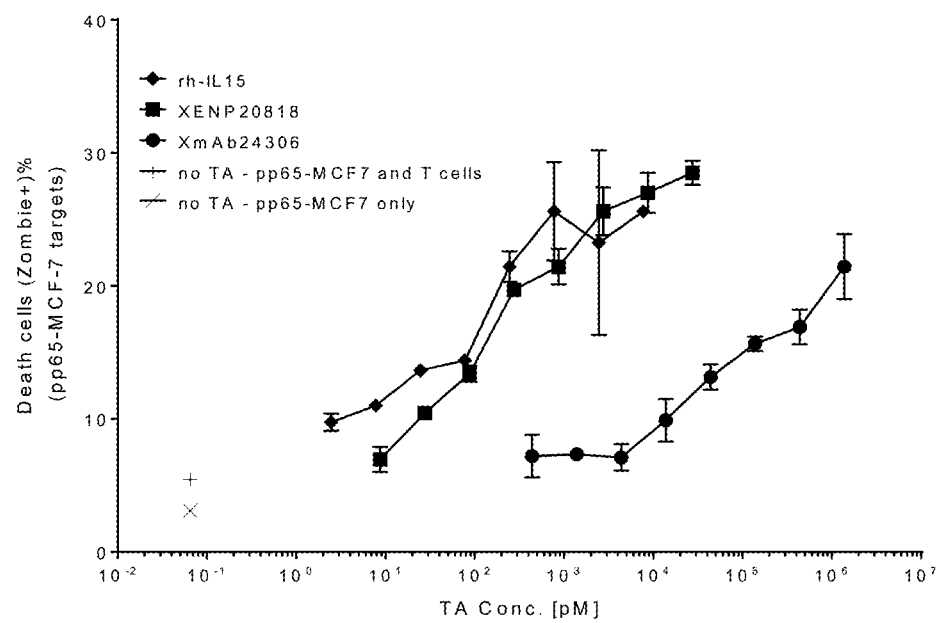

FIG. 131A-FIG. 131B depict number of dead cells [FIG. 131A: parental MCF-7 tumor cells; FIG. 131B: pp65-expressing MCF-7 tumor cells] following incubation with purified T cells and indicated test articles.

Figure 132:
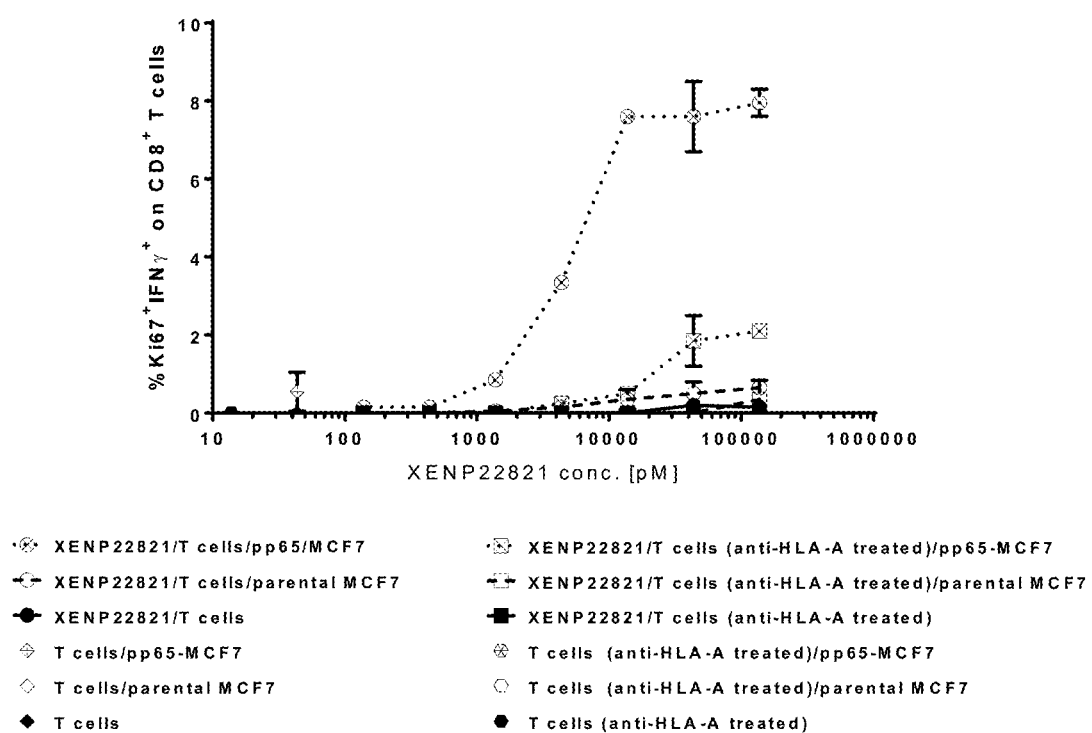

FIG. 132 depicts percentage of Ki-67$^+$/IFN$\gamma^+$ fractions of CD8$^+$ T cells following incubation of purified T cells with parental MCF-7 tumor cells or pp65-expressing MCF-7 tumor cells, with or without anti-HLA-A antibodies.

Figure 133:
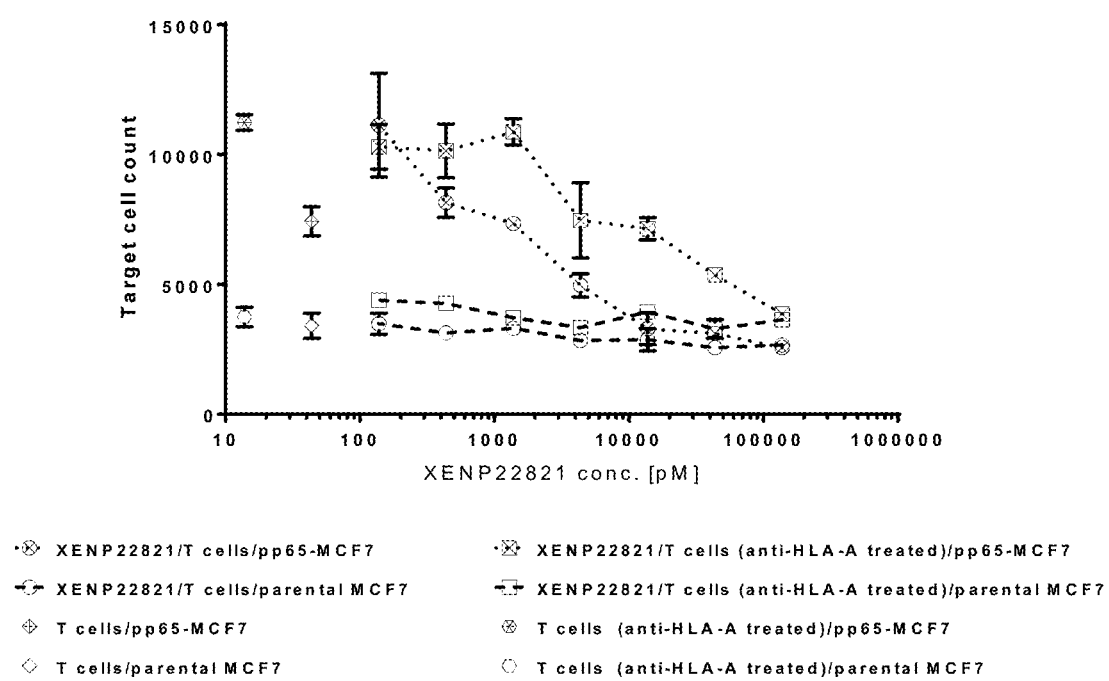

FIG. 133 depicts number of target cells (i.e. parental MCF-7 tumor cells or pp65-expressing MCF-7 tumor cells) following incubation of purified T cells with parental MCF-7 tumor cells or pp65-expressing MCF-7 tumor cells, with or without anti-HLA-A antibodies.

Figure 134A:
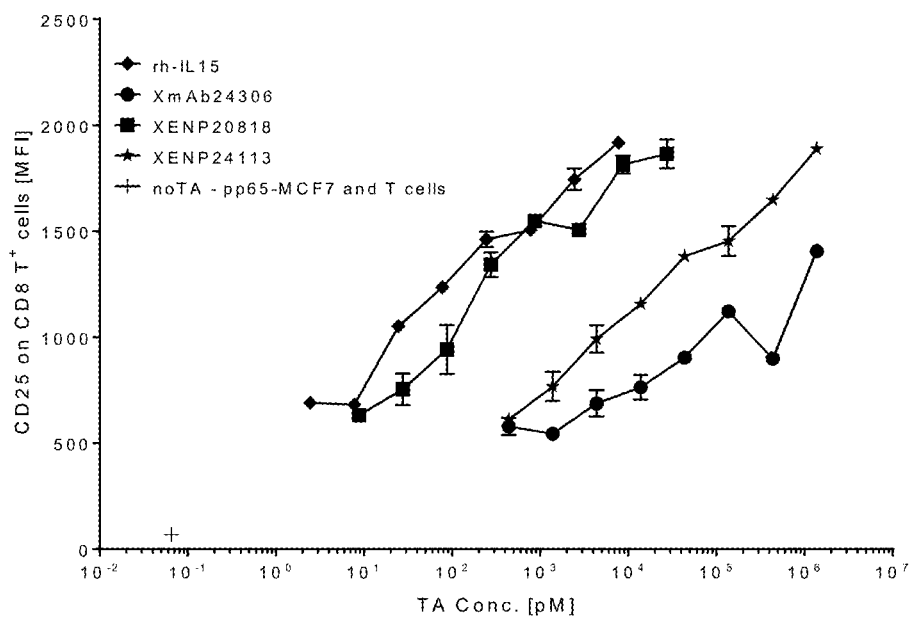
Figure 134B:
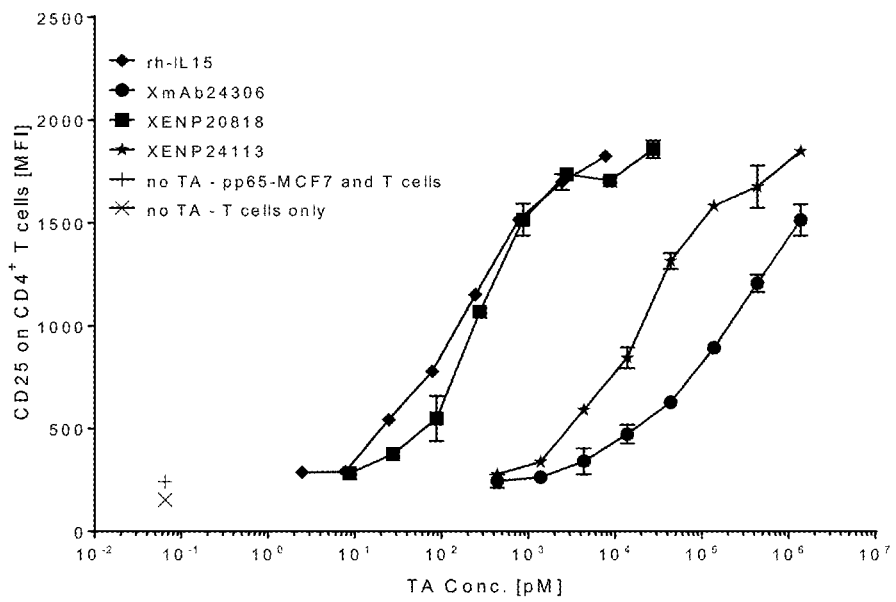

FIG. 134A-FIG. 134B depict CD25 expression on (FIG. 134A) CD8$^+$ T cells and (FIG. 134B) CD4$^+$ T cells following incubation of purified T cells with pp65-expressing MCF-7 tumor cells and indicated test articles.

Figure 135A:
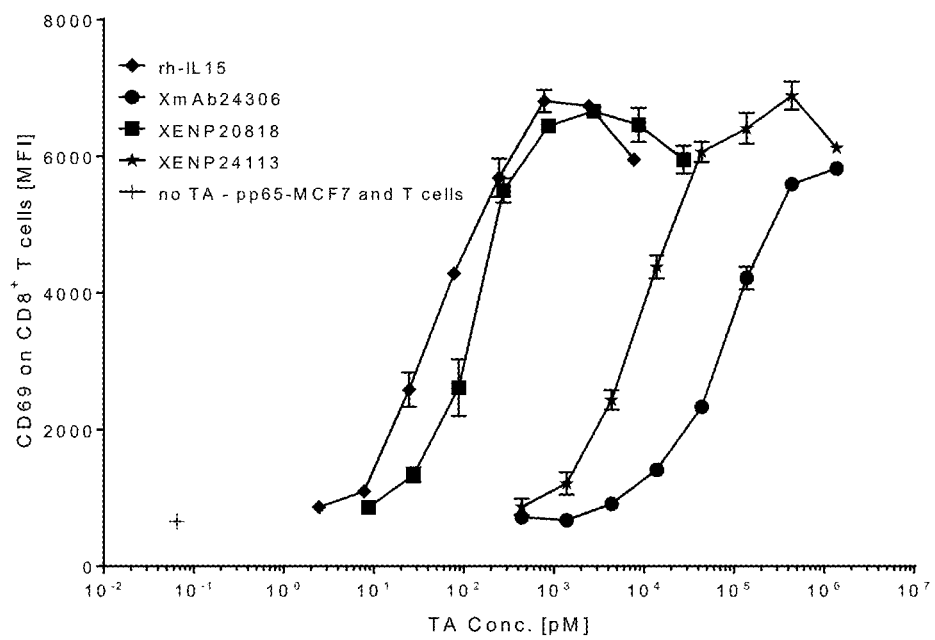
Figure 135B:
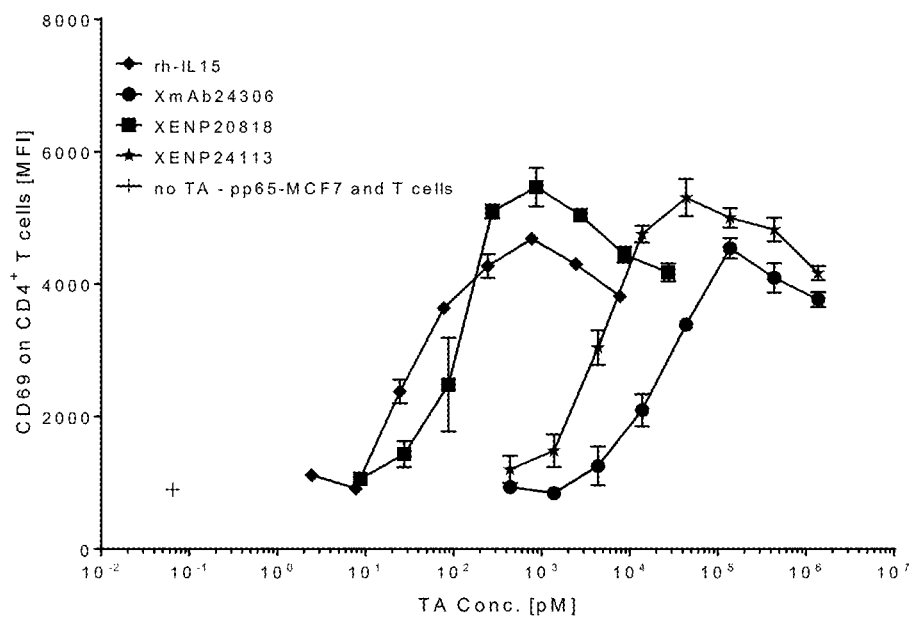

FIG. 135A-FIG. 135B depict CD69 expression on (FIG. 135A) CD8$^+$ T cells and (FIG. 135B) CD4$^+$ T cells following incubation of purified T cells with pp65-expressing MCF-7 tumor cells and indicated test articles.

Figure 136A:
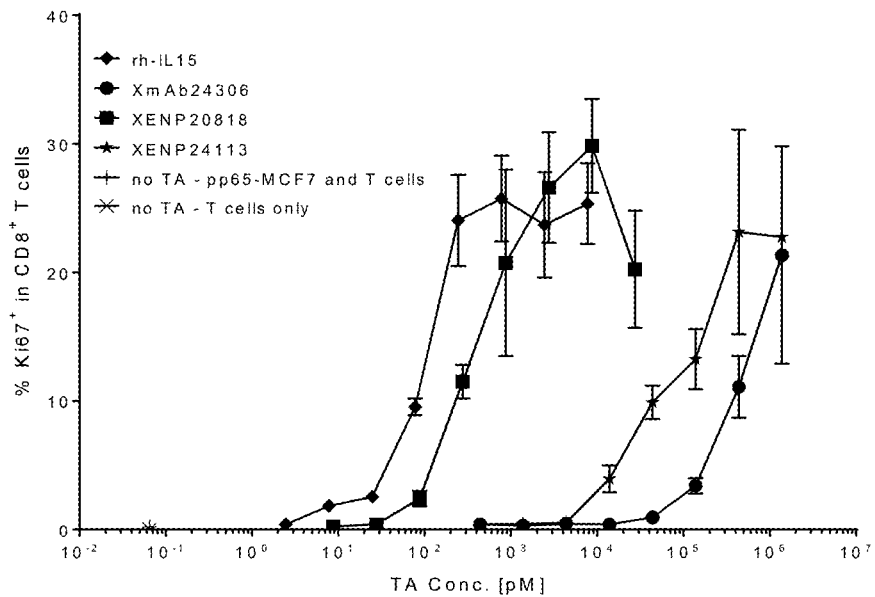
Figure 136B:
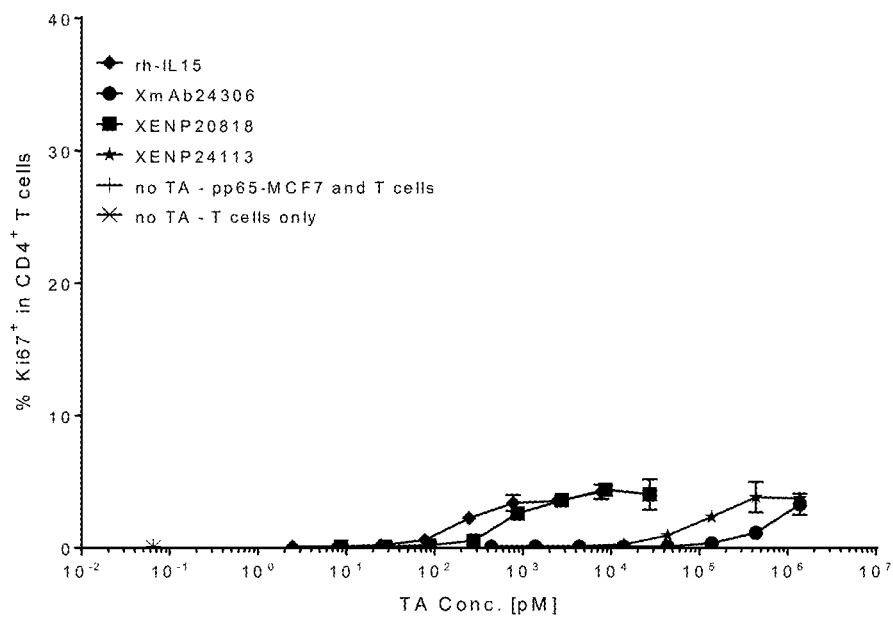

FIG. 136A-FIG. 136B depict Ki67 expression on (FIG. 136A) CD8$^+$ T cells and (FIG. 136B) CD4$^+$ T cells following incubation of purified T cells with pp65-expressing MCF-7 tumor cells and indicated test articles.

Figure 137A:
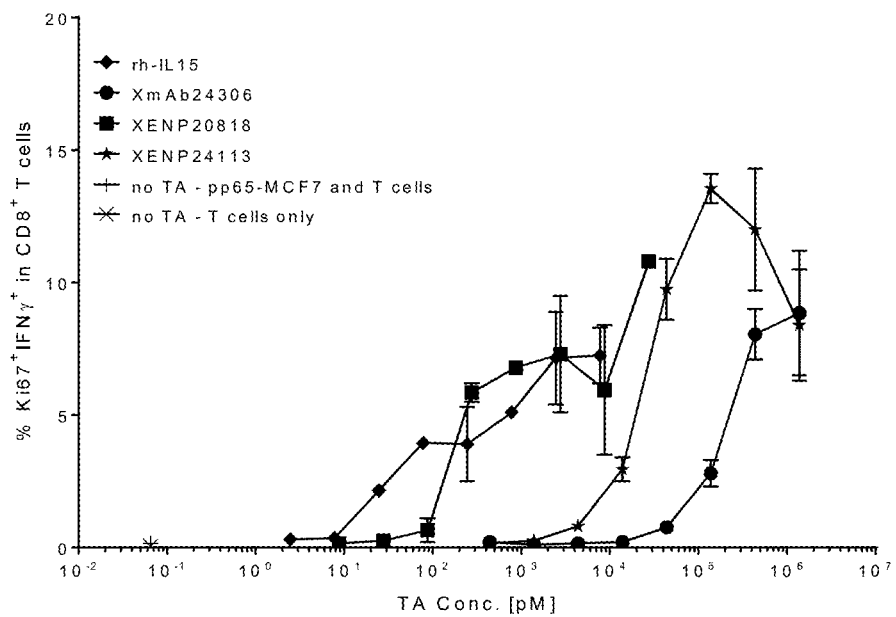
Figure 137B:
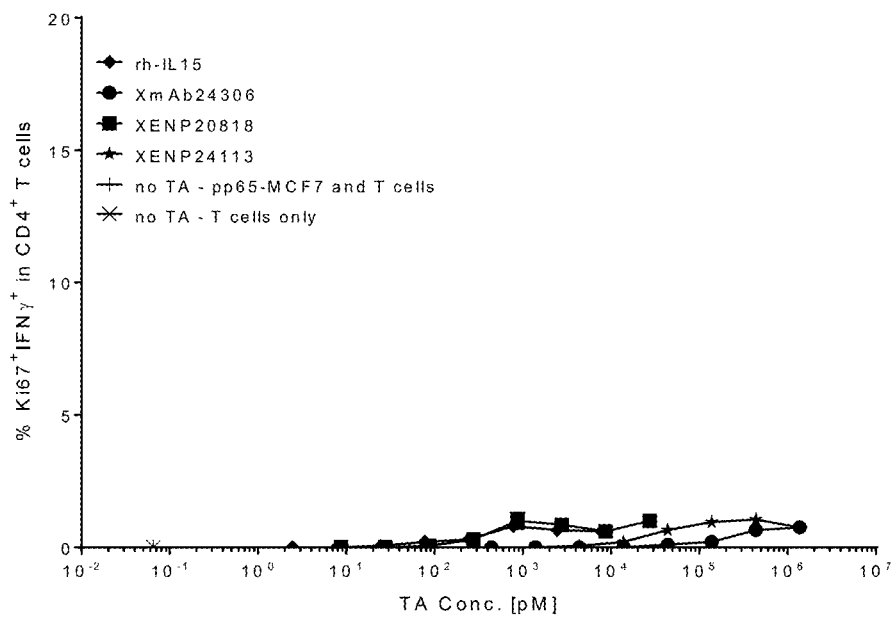

FIG. 137A-FIG. 137B depict percentage of Ki-67$^+$/IFN$\gamma^+$ fractions of (FIG. 137A) CD8$^+$ T cells and (FIG. 137B) CD4$^+$ T cells following incubation of purified T cells with pp65-expressing MCF-7 tumor cells and indicated test articles.

Figure 138A:
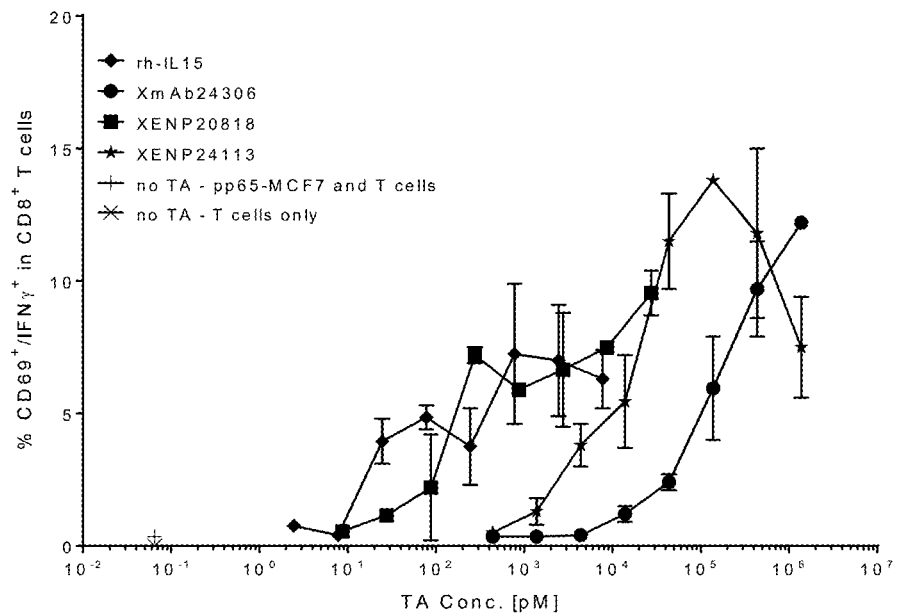
Figure 138B:
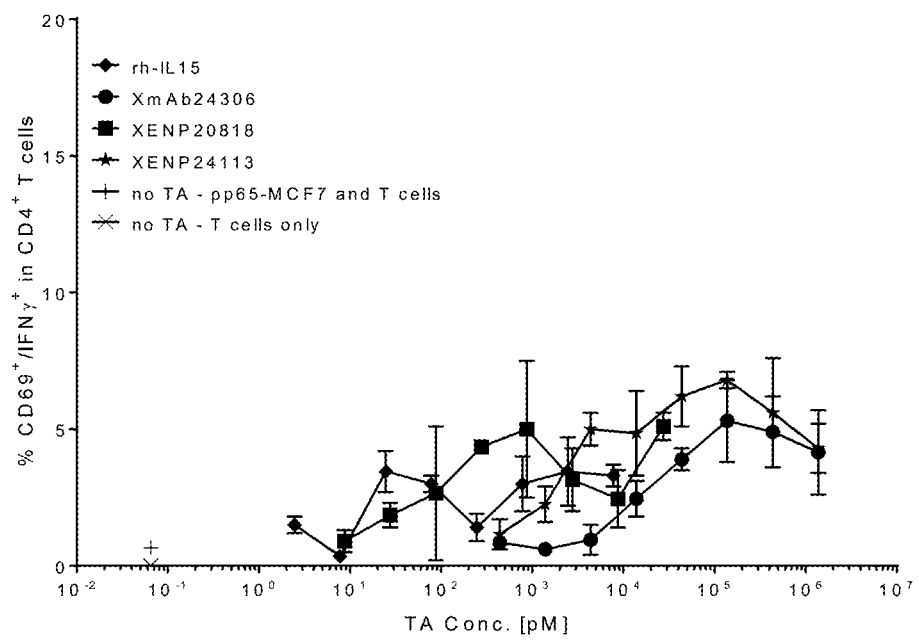

FIG. 138A-FIG. 138B depict percentage of CD69$^+$/IFN$\gamma^+$ fractions of (FIG. 138A) CD8$^+$ T cells and (FIG. 138B) CD4$^+$ T cells following incubation of purified T cells with pp65-expressing MCF-7 tumor cells and indicated test articles.

Figure 139A:
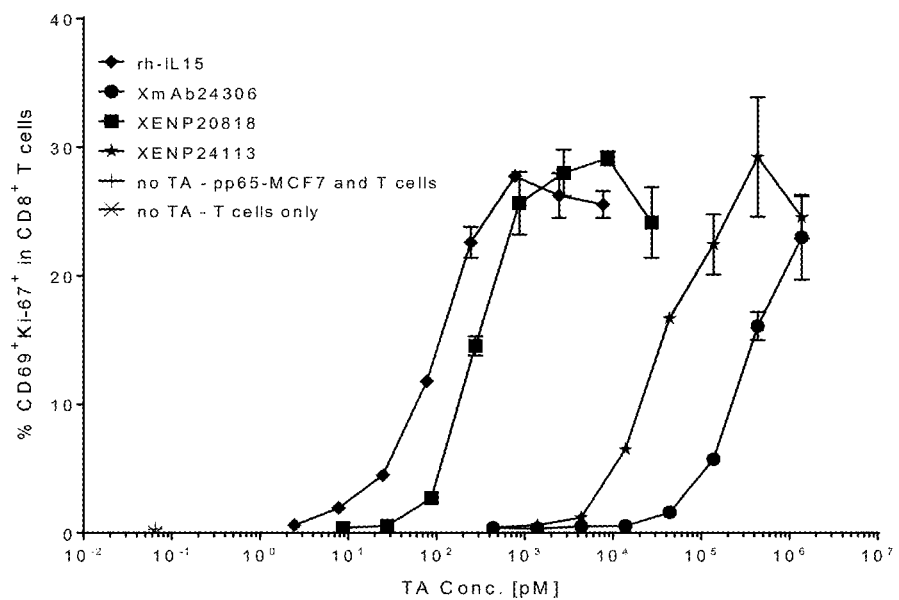
Figure 139B:
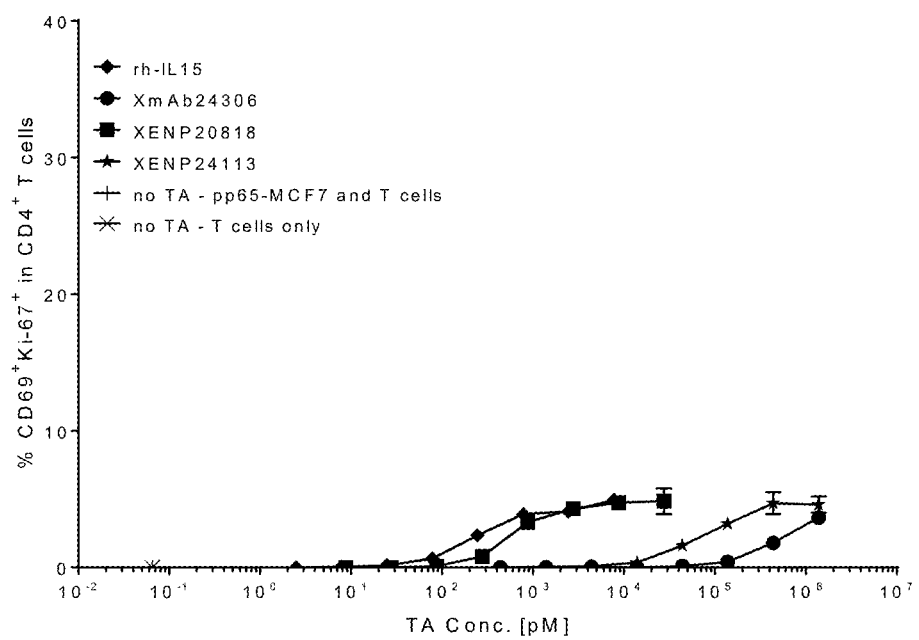

FIG. 139A-FIG. 139B depict percentage of CD69$^+$/Ki67$^+$ fractions of (FIG. 139A) CD8$^+$ T cells and (FIG. 139B) CD4$^+$ T cells following incubation of purified T cells with pp65-expressing MCF-7 tumor cells and indicated test articles.

Figure 140:
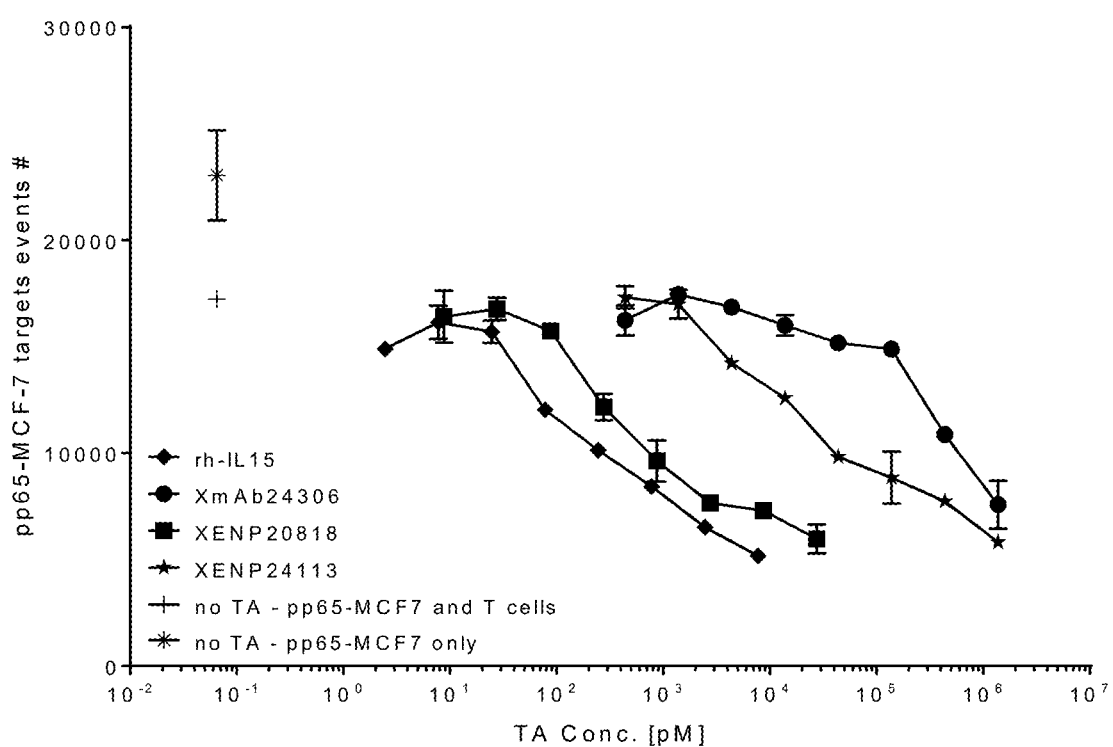

FIG. 140 depicts remaining target cells (pp65-expressing MCF-7 tumor cells) following incubation with purified T cells and indicated test articles.

Figure 141:
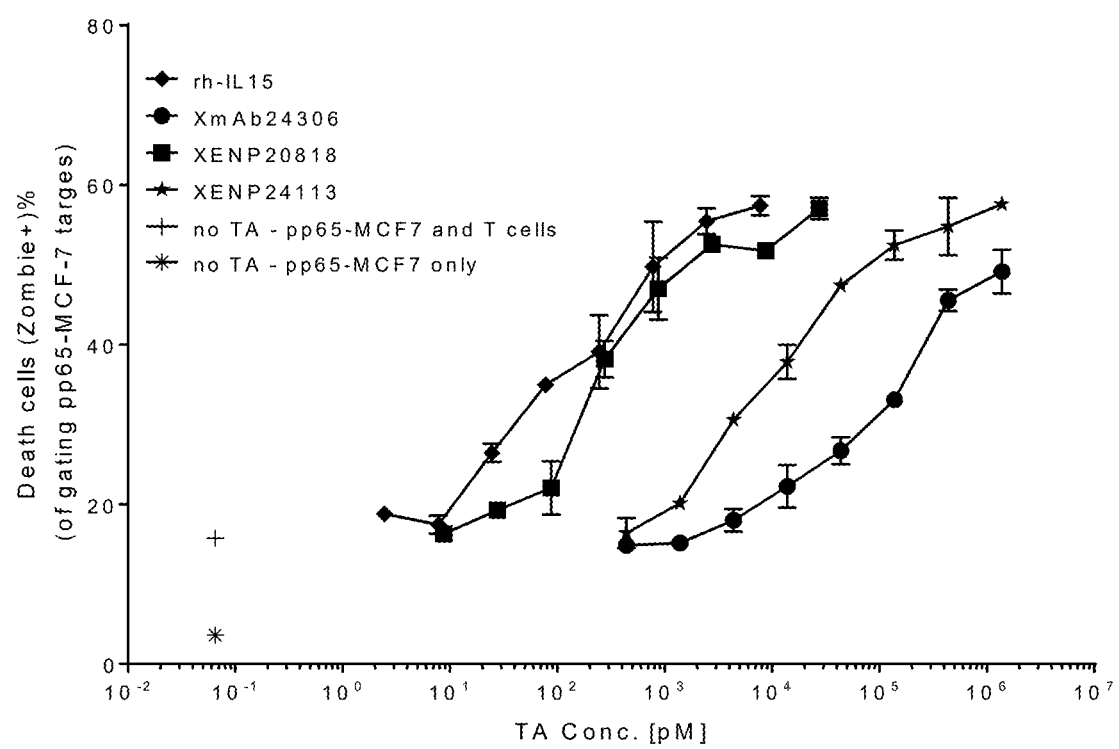

FIG. 141 depicts number of dead cells (pp65-expressing MCF-7 tumor cells) following incubation with purified T cells and indicated test articles.

Figure 142A:
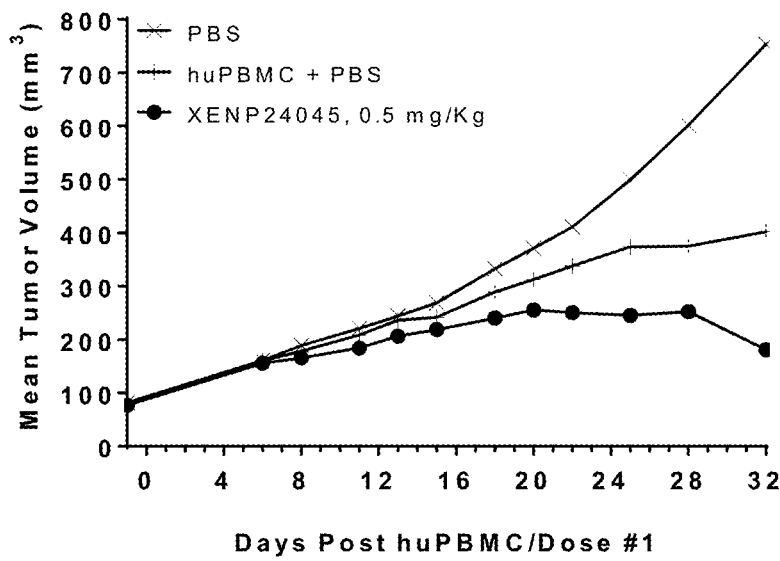
Figure 142B:
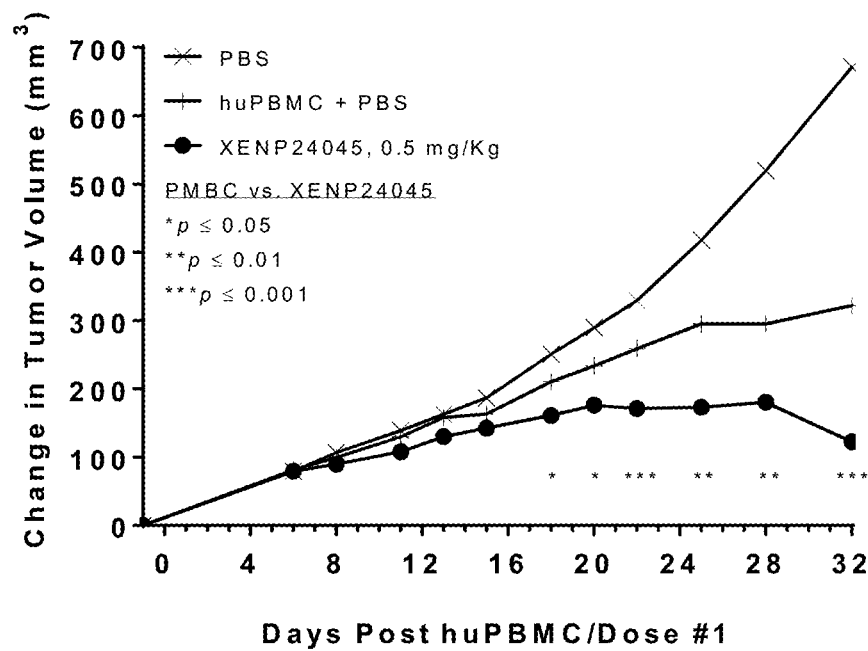
Figure 143A:
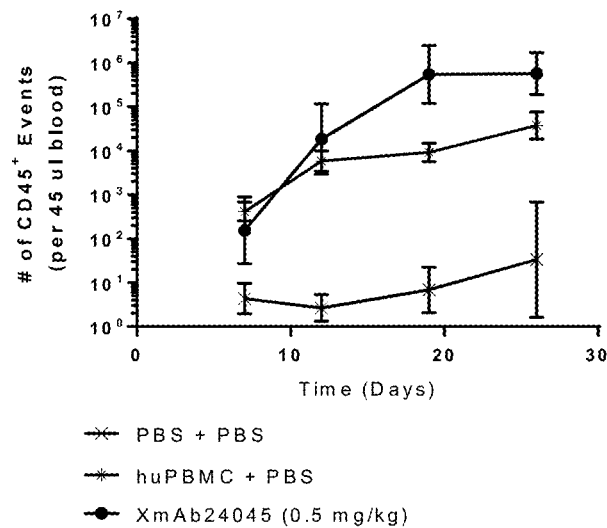
Figure 143B:
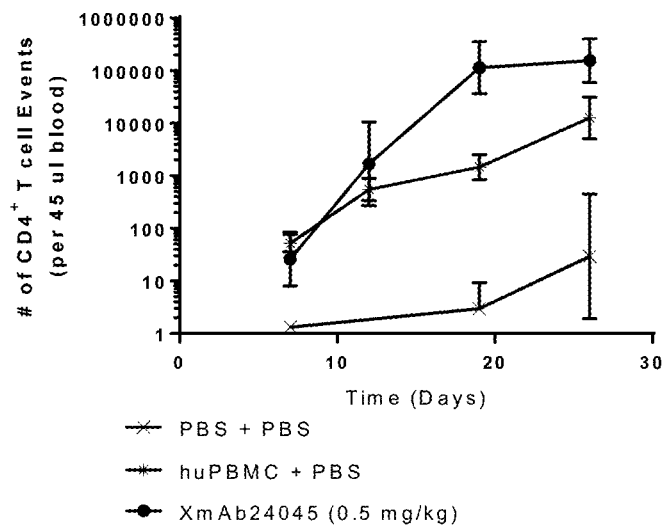
Figure 143C:
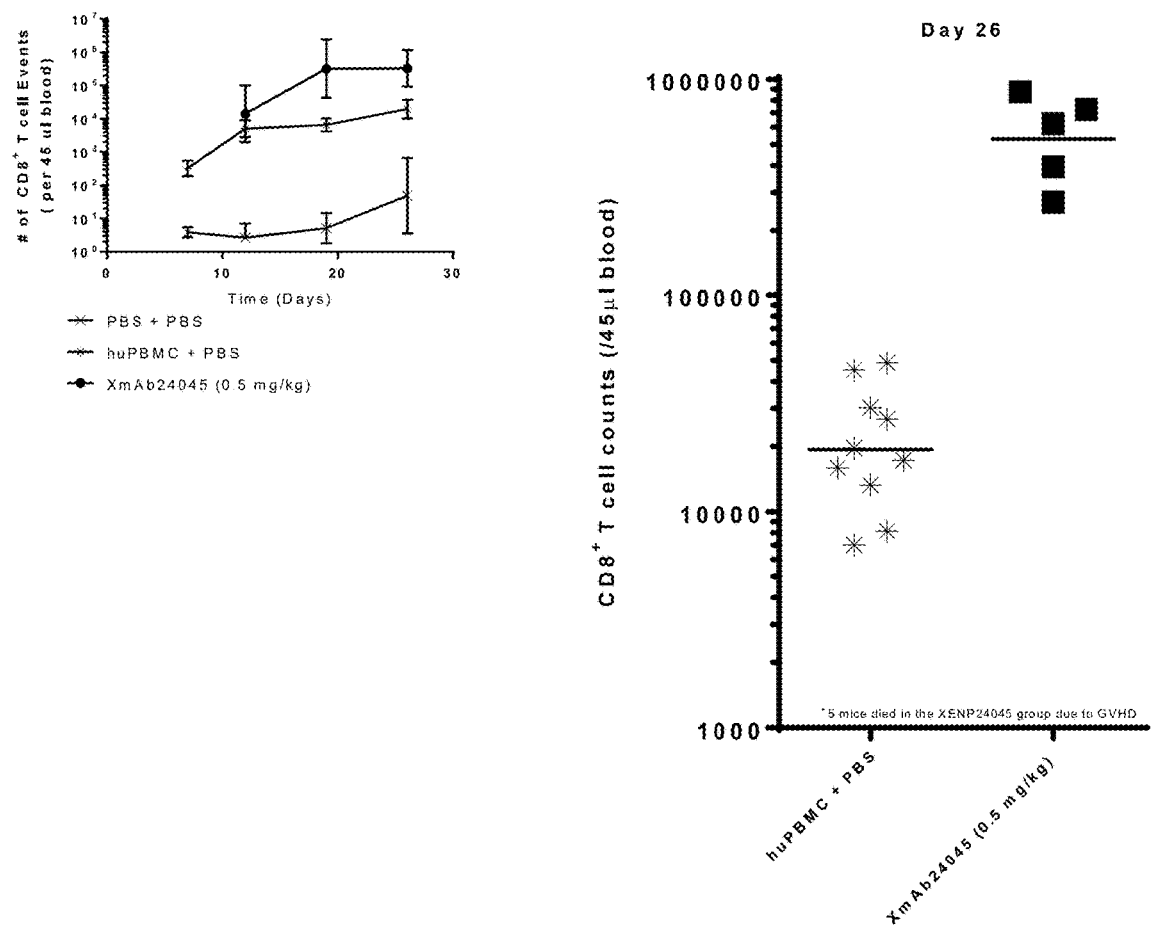

FIG. 142A-FIG. 142B depict mean tumor volume (FIG. 142A) and change in tumor volume (FIG. 142B) in mice engrafted with pp65-expressing MCF-7 tumor cells and pp65-reactive human PBMCs following treatment with XENP24045, the non-Xtend analog of XmAb24306.

FIG. 143A-FIG. 143D depict CD45$^+$ cell (FIG. 143A), CD4$^+$ cell (FIG. 143B), CD8$^+$ cell (FIG. 143C), and NK cell (FIG. 143D) counts in whole blood of mice engrafted with pp65-expressing MCF-7 tumor cells and pp65-reactive human PBMCs following treatment with XENP24045, the non-Xtend analog of XmAb24306.

Figure 144:
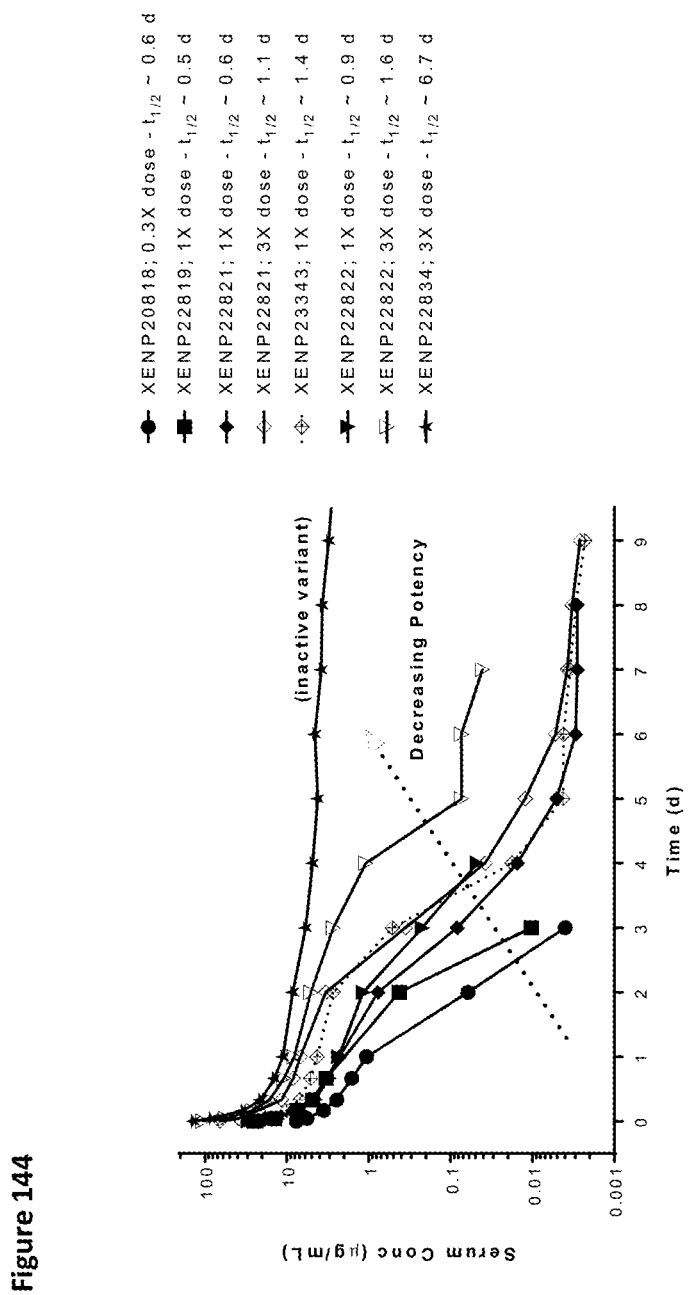

FIG. 144 depicts the serum concentrations over time and half-lives of various test articles at various concentrations in cynomolgus monkeys.

Figure 145:
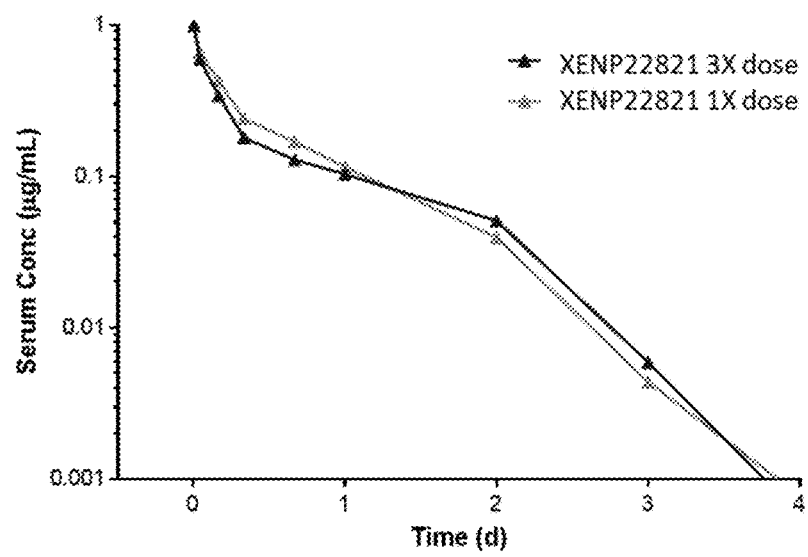
Figure 146A:
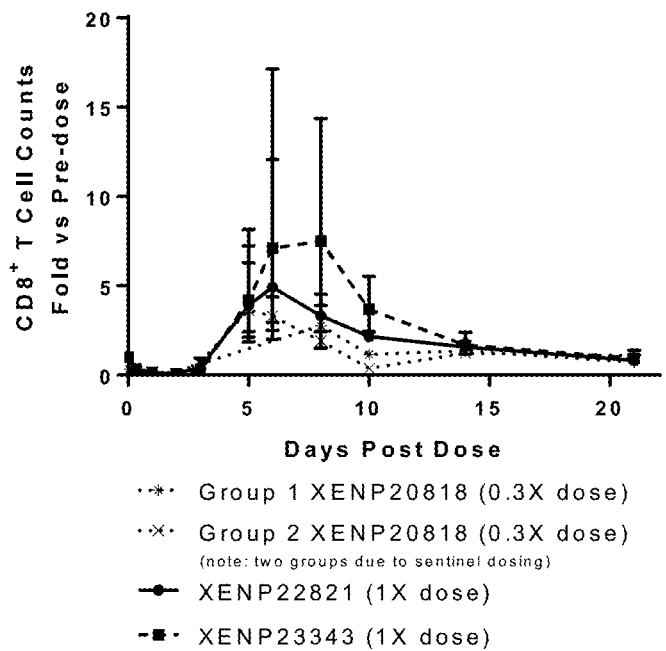
Figure 146B:
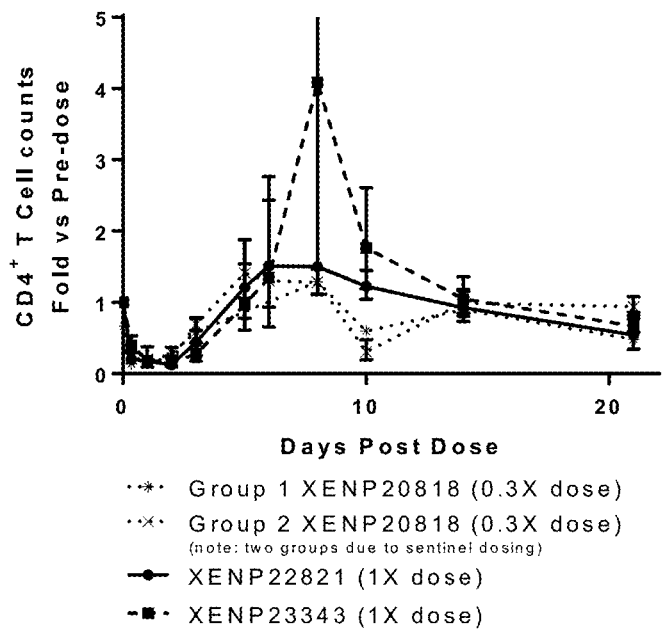
Figure 146C:
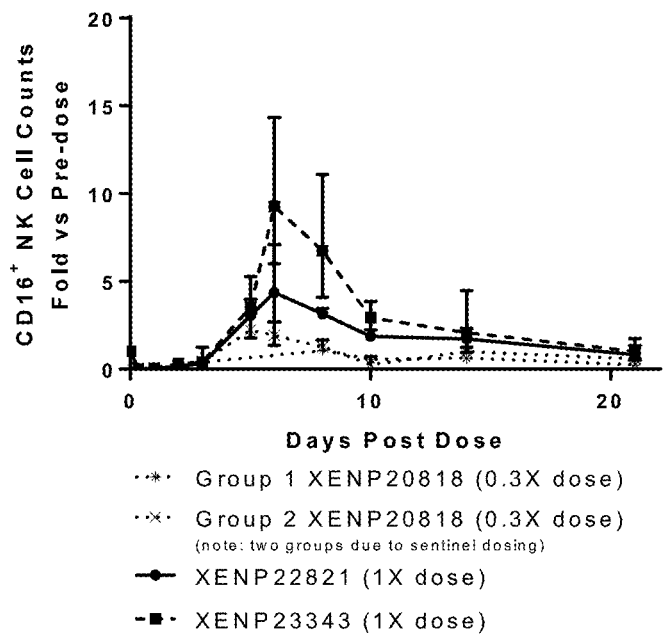
Figure 146D:
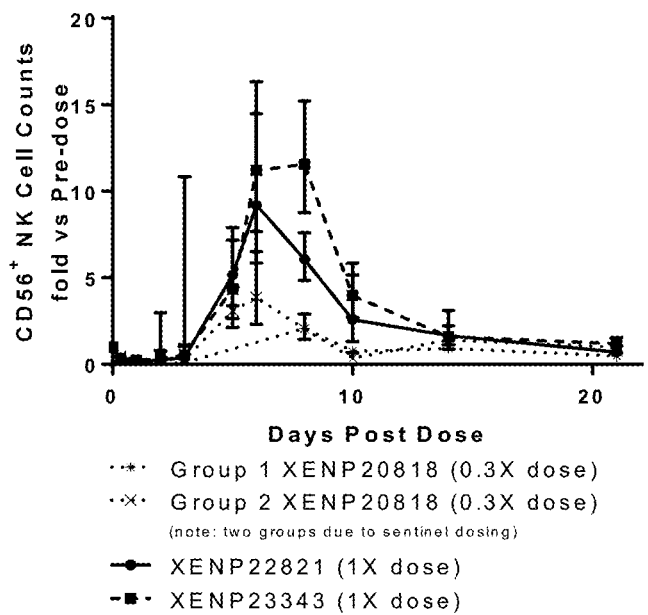
Figure 146E:
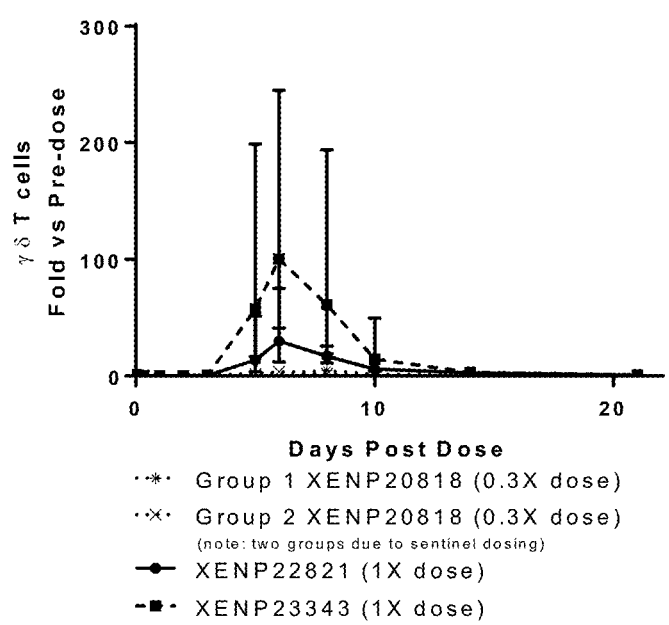

FIG. 145 depicts the Cmax normalized serum concentrations over time of XENP22821 at 1× and 3× dose in cynomolgus monkeys.

FIG. 146A-FIG. 146E depict the mean fold-change in CD8$^+$ T cell (FIG. 146A), CD4$^+$ T cell (FIG. 146B), CD16$^+$ NK cell (FIG. 146C), CD56$^+$ NK cell (FIG. 146D), and $\gamma\delta$ T cell (FIG. 146E) counts in cynomolgus monkeys following dosing with the indicated test articles.

Figure 147A:
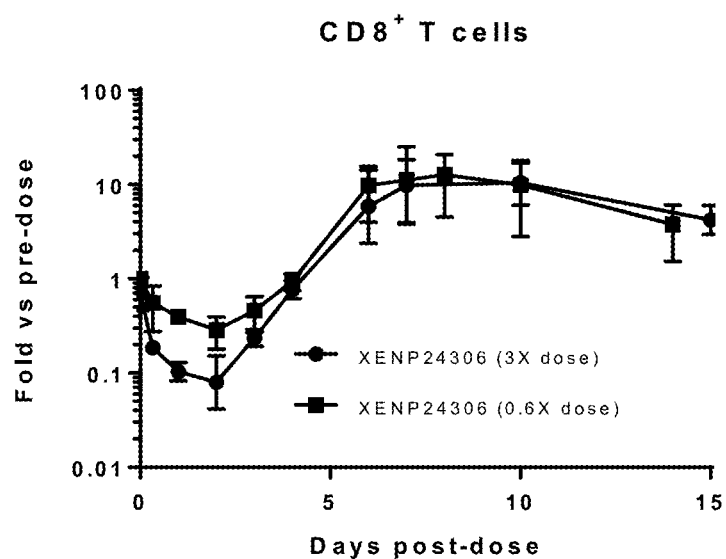
Figure 147B:
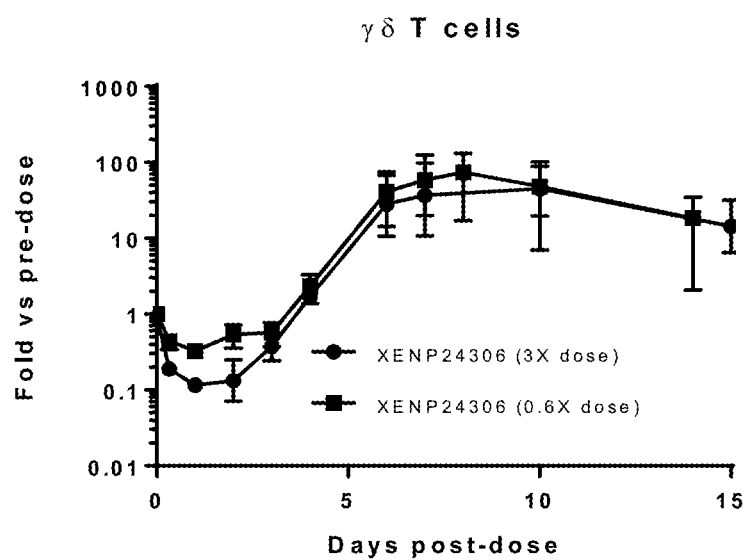

FIG. 147A-FIG. 147B depict fold change in CD8$^+$ T cells (FIG. 147A) and $\gamma\delta$ T cells (FIG. 147B) in cyno whole blood over time following dosing with either 3× dose or 0.6× dose of XENP24306.

Figure 148:
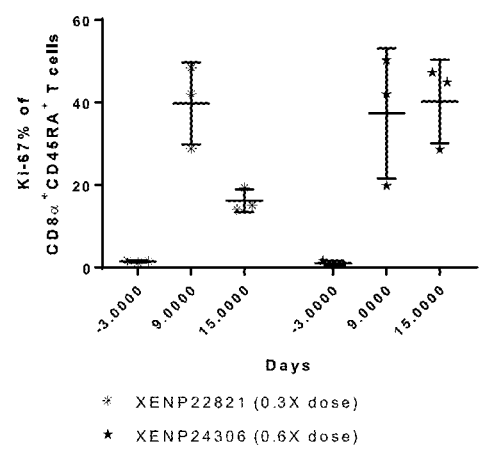

FIG. 148 depicts the percentage of CD8$\alpha^+$CD45RA$^+$ T cells in cyno lymph nodes expressing Ki67 following dosing with 0.3× dose XENP22821 and 0.6× dose XENP24306.

Figure 149:
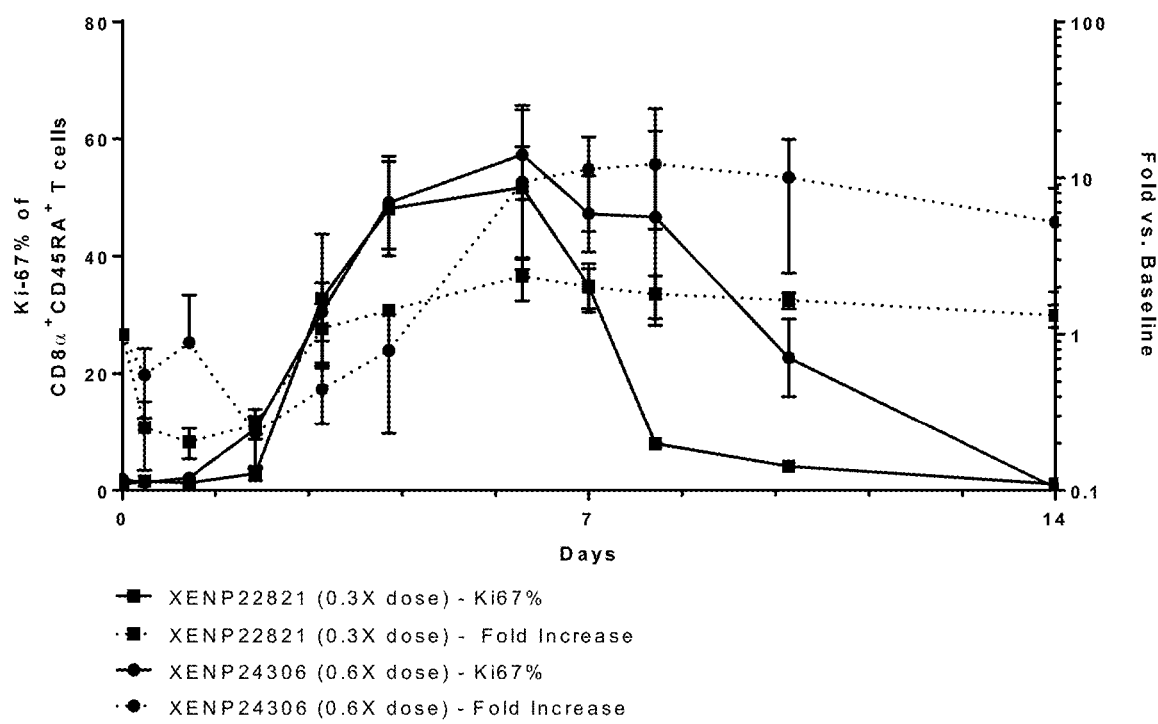

FIG. 149 depicts the percentage of CD8$\alpha^+$CD45RA$^+$ T cells in cyno whole blood expressing Ki67 (left axis) and the fold change in cell counts (right axis) following dosing with 0.3× dose XENP22821 and 0.6× dose XENP24306.

Figure 150:
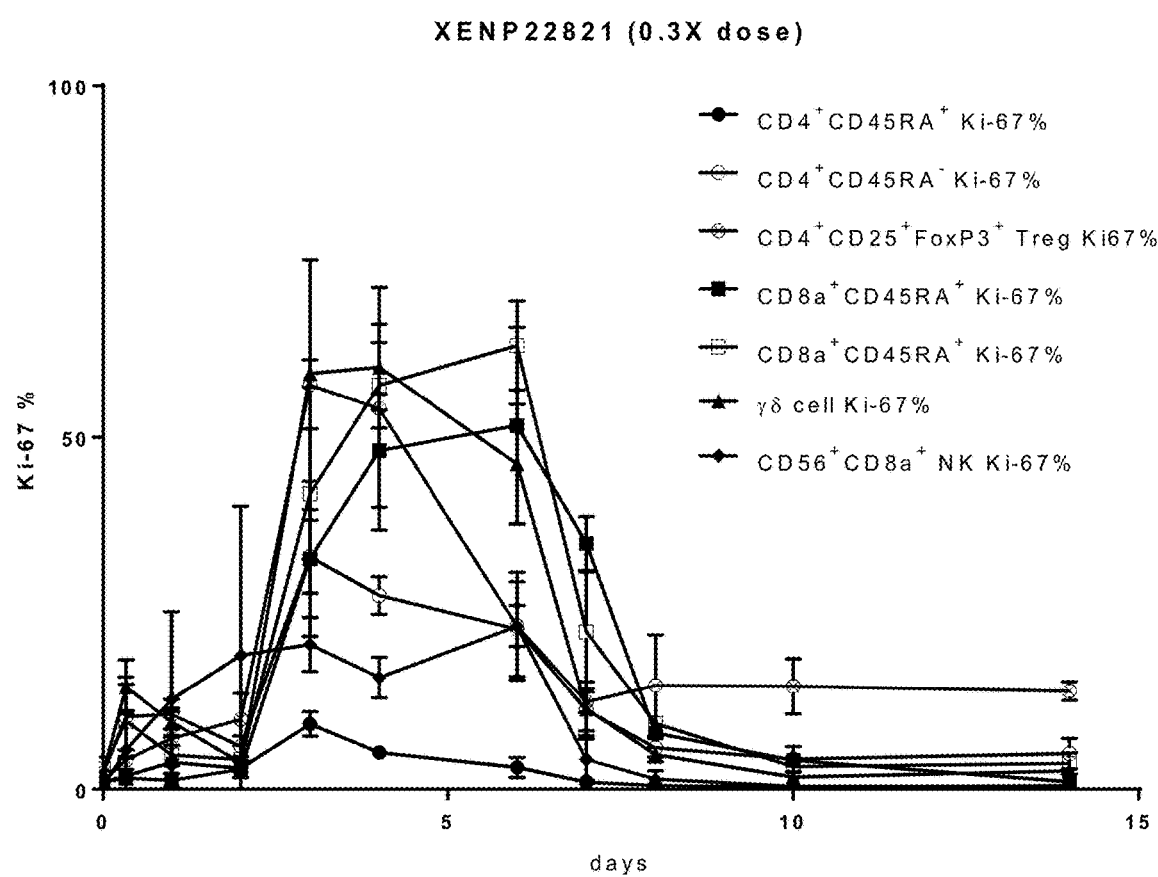

FIG. 150 depicts the percentage of various lymphocyte populations in cyno PBMC expressing Ki67 after dosing with 0.3× dose XENP22821.

Figure 151:
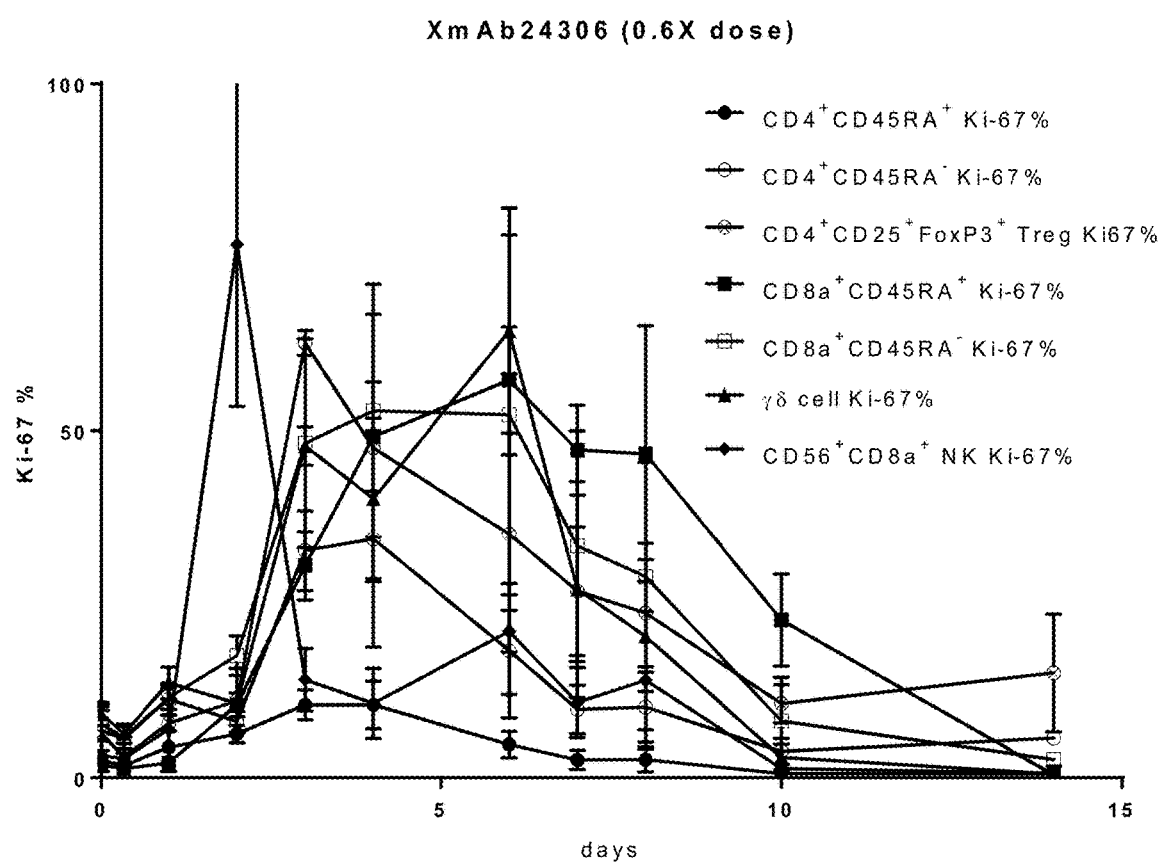

FIG. 151 depicts the percentage of various lymphocyte populations in cyno PBMC expressing Ki67 after dosing with 0.6× dose XmAb24306.

Figure 152:
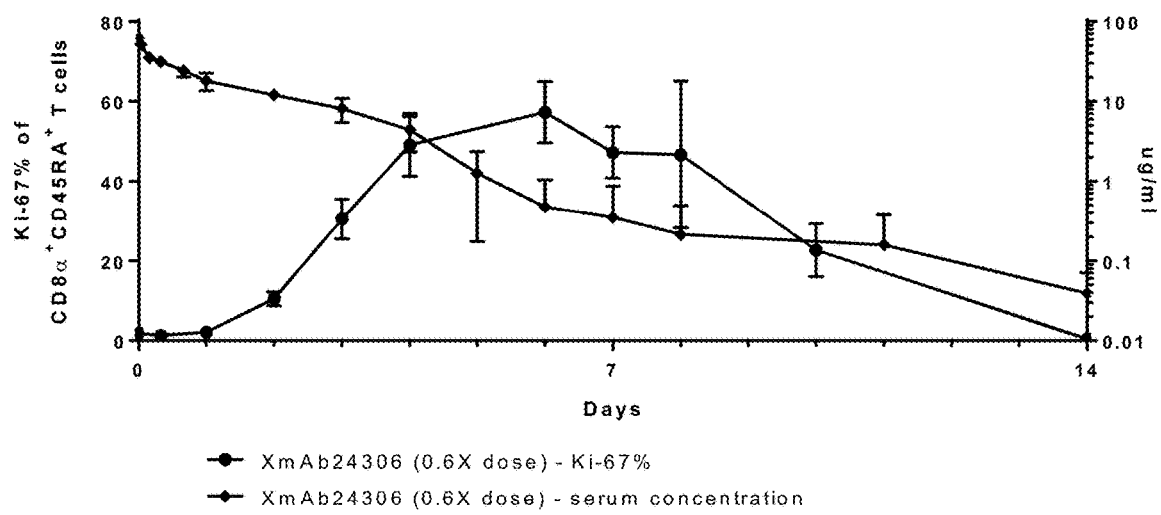

FIG. 152 depicts an overlay of the percentage of CD8$\alpha$+ CD45RA+ T cells in cyno whole blood expressing Ki67 and the serum concentration of XmAb24306 over time following dosing with 0.6× dose XmAb24306.

Figure 153:
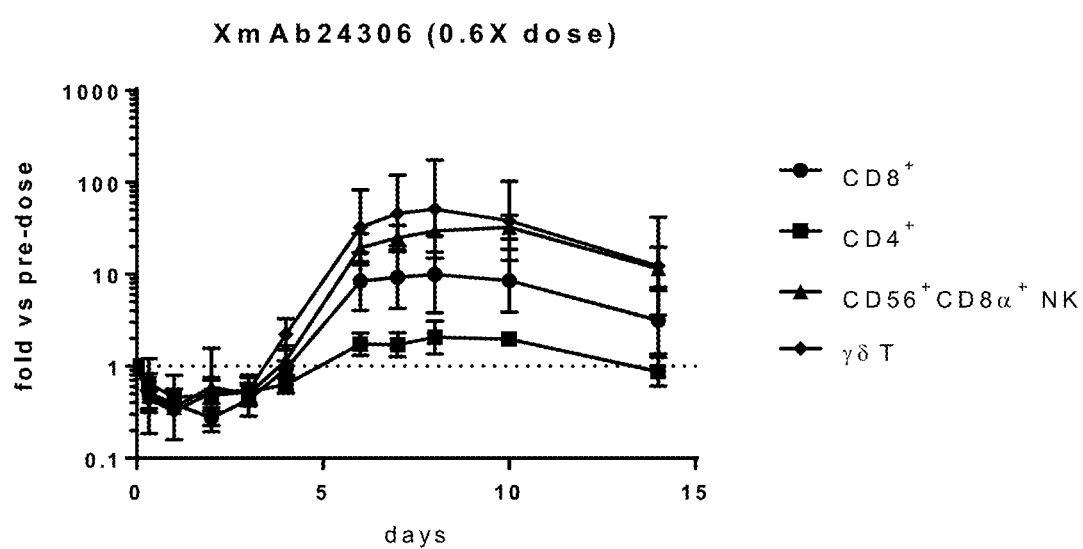

FIG. 153 depicts fold-change in counts of CD8$^+$ T cell, CD4$^+$ T cell, CD56$^+$CD8$\alpha^+$ NK cell and $\gamma\delta$ T cell in cyno whole blood over time following dosing with 0.6× dose XmAb24306.

Figure 154:
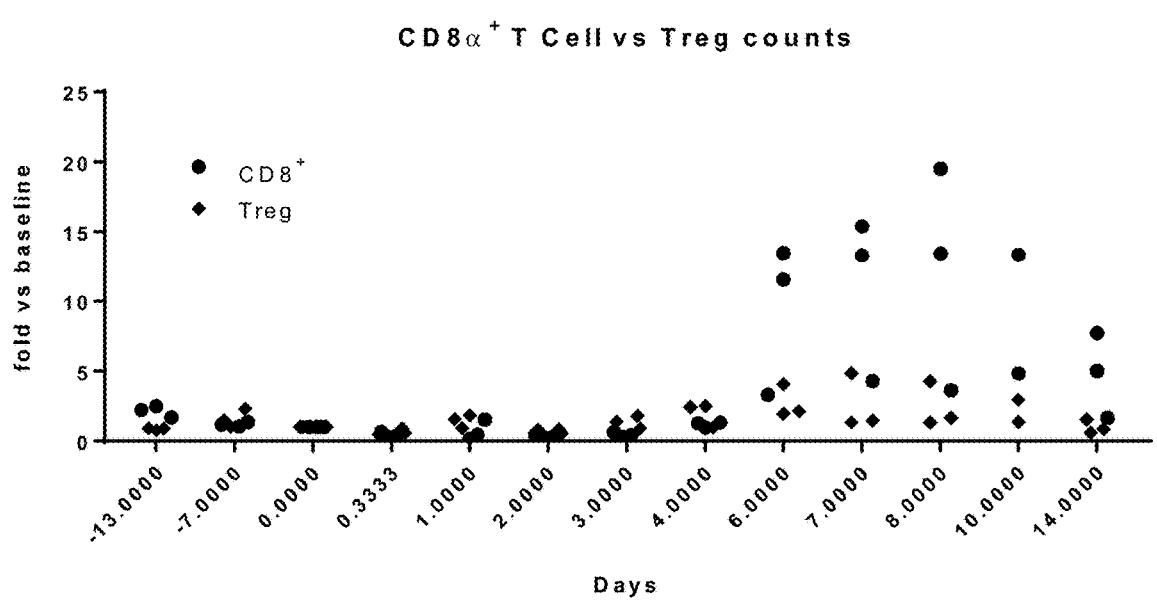

FIG. 154 depicts fold-change in counts of CD8$^+$ T cell and Treg in cyno whole blood over time following dosing with 0.6× dose XmAb24306.

Figure 155A:
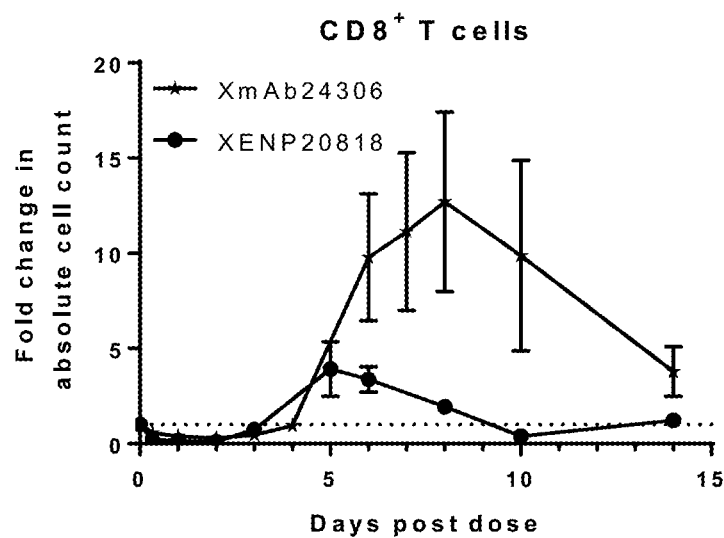
Figure 155B:
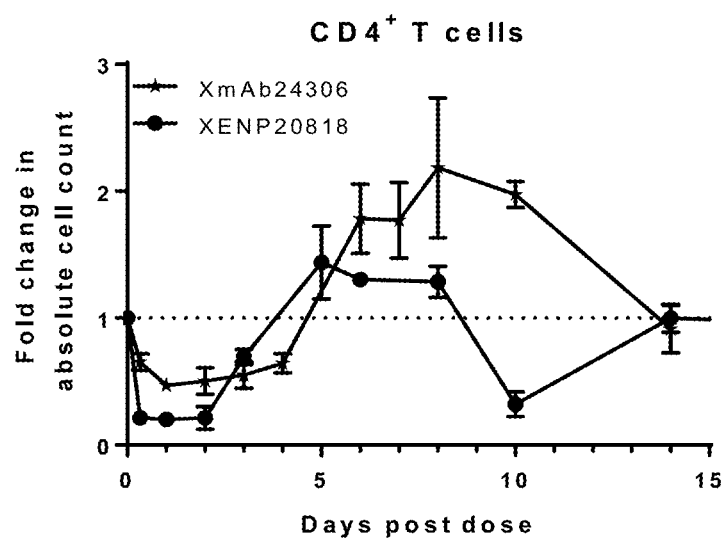
Figure 155C:
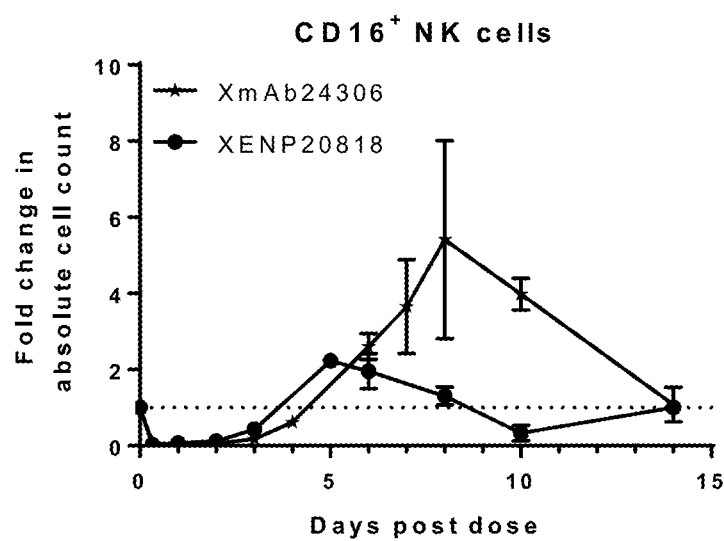

FIG. 155A-FIG. 155C depict overlays of CD8$^+$ T cell (FIG. 155A), CD4$^+$ T cell (FIG. 155B), and CD16$^+$ NK cell (FIG. 155C) counts over time in whole blood of cynomolgus monkeys following dosing with either XENP20818 or XmAb24306.

Figure 156A:
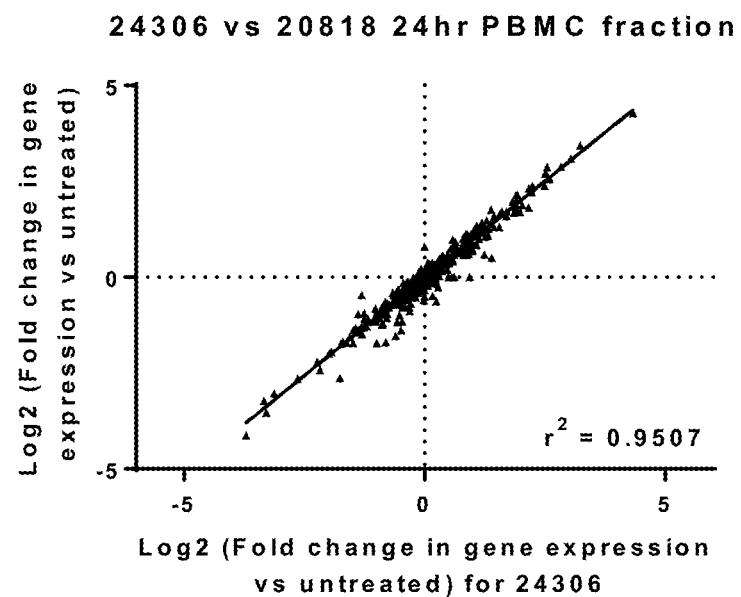
Figure 156B:
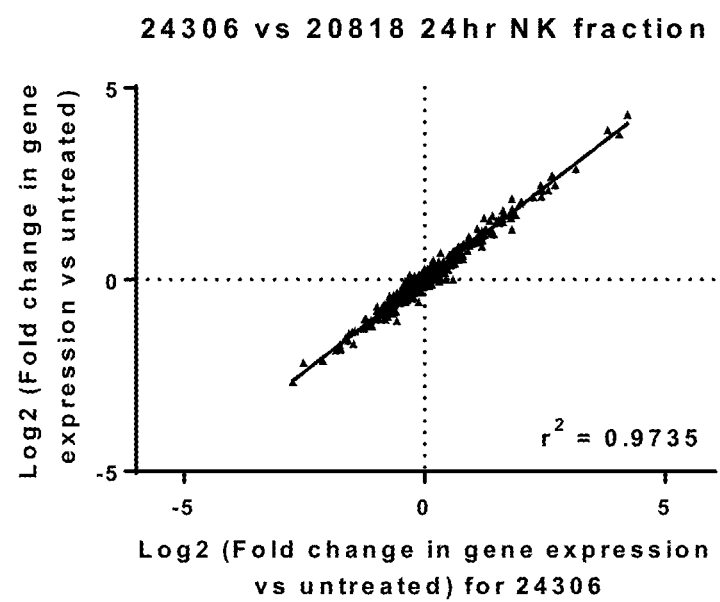
Figure 156C:
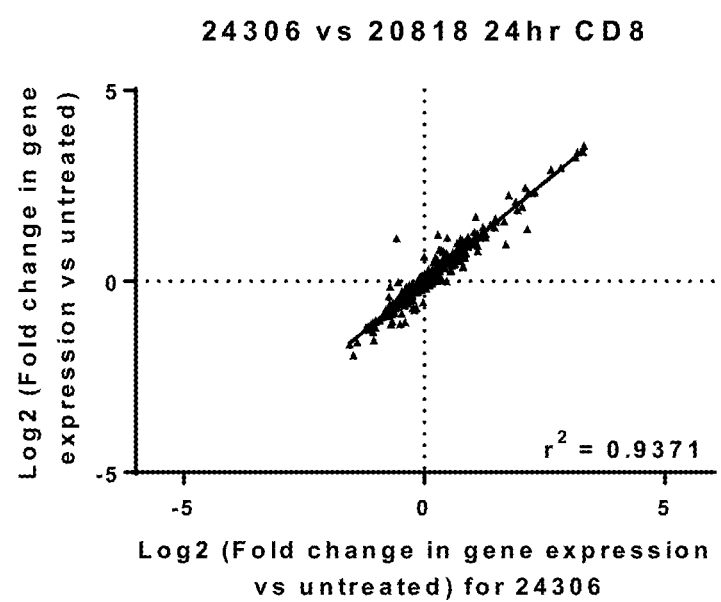

FIG. 156A-FIG. 156C depict the fold change in immune-related gene expression in (FIG. 156A) whole PBMC, (FIG. 156B) purified NK cells, and (FIG. 156C) purified CD8$^+$ T cells following 24 hour treatment with either XENP20818 or XmAb24306 at their EC$_{50}$ concentrations as compared to untreated.

Figure 157A:
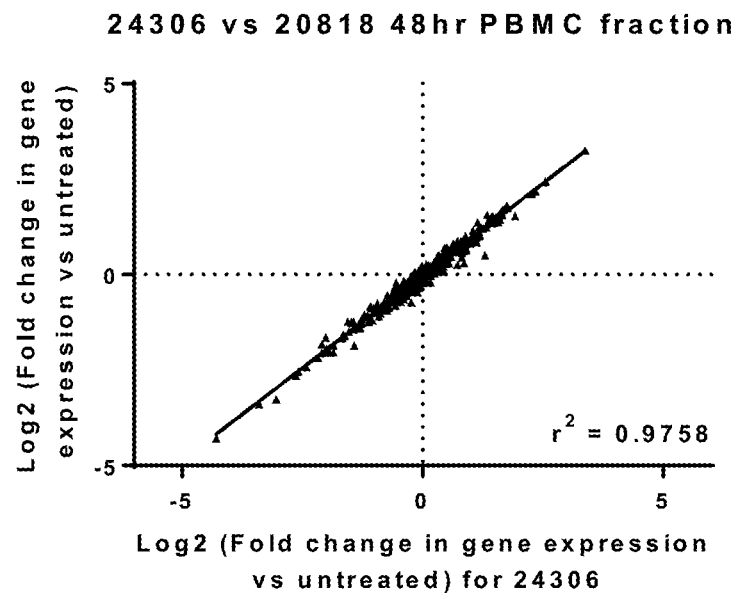
Figure 157B:
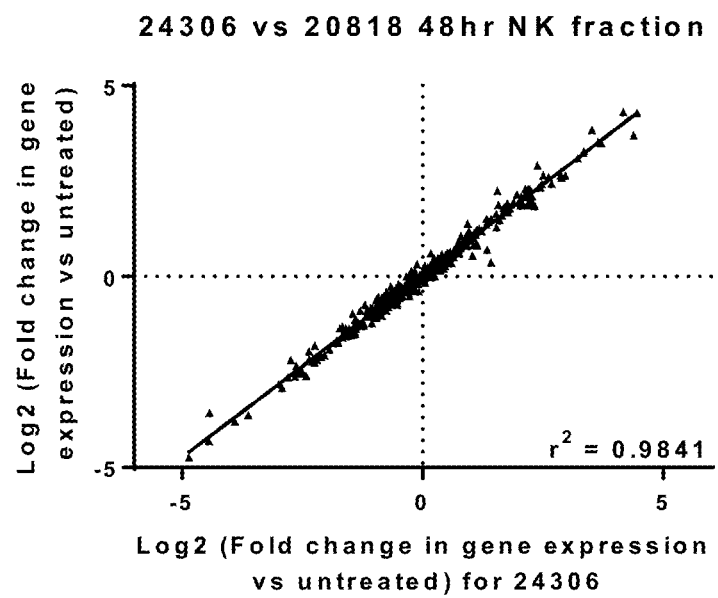
Figure 157C:
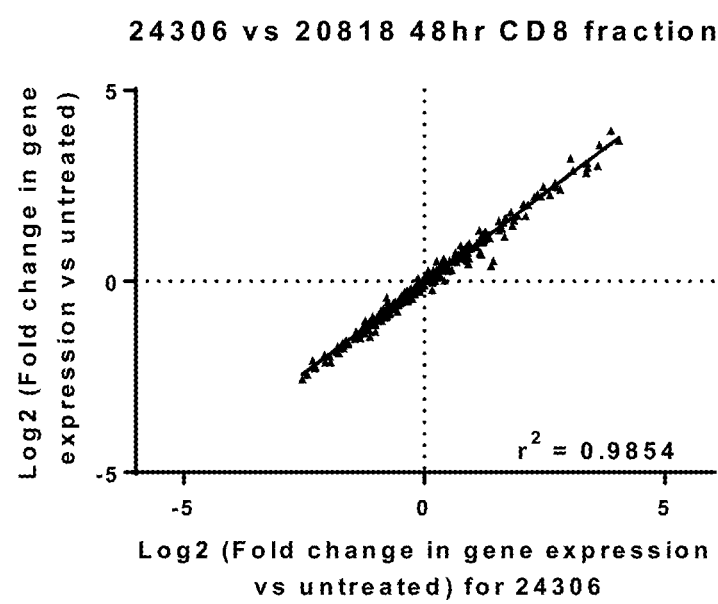

FIG. 157A-FIG. 157C depict the fold change in gene expression in (FIG. 157A) whole PBMC, (FIG. 157B) purified NK cells, and (FIG. 157C) purified CD8$^+$ T cells following 48 hour treatment with either XENP20818 or XmAb24306 at their EC$_{50}$ concentrations as compared to untreated.

Figure 158A:
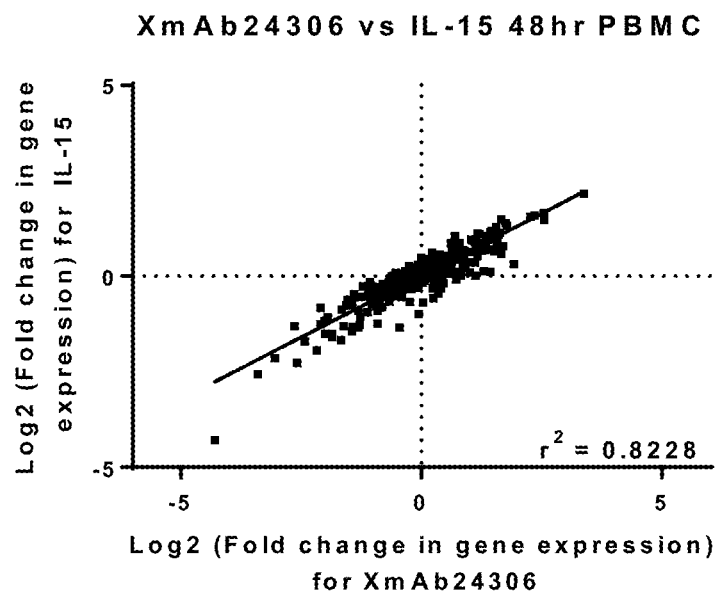
Figure 158B:
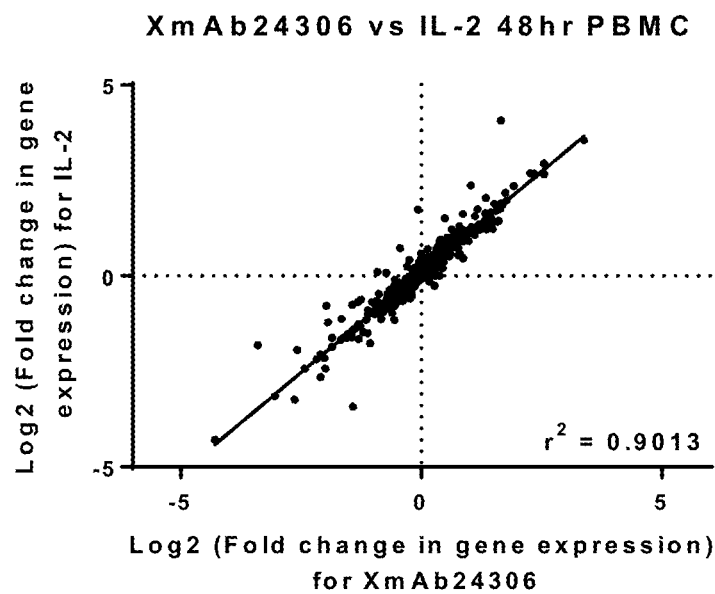

FIG. 158A-FIG. 158B depict the fold change in gene expression in whole PBMC following 48 hour treatment with (FIG. 158A) XmAb24306 or IL-15 and (FIG. 158B) XmAb24306 or IL-2 at their EC50 concentrations as compared to untreated.

Figure 159A:
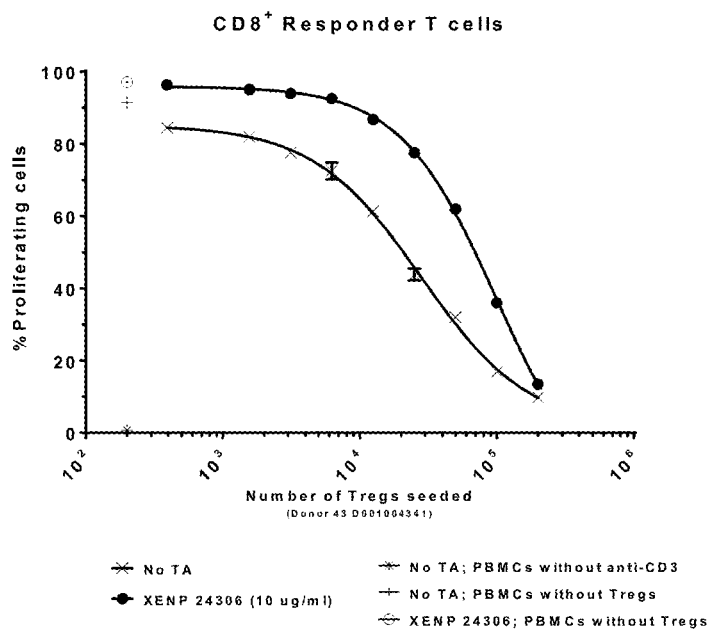
Figure 159B:
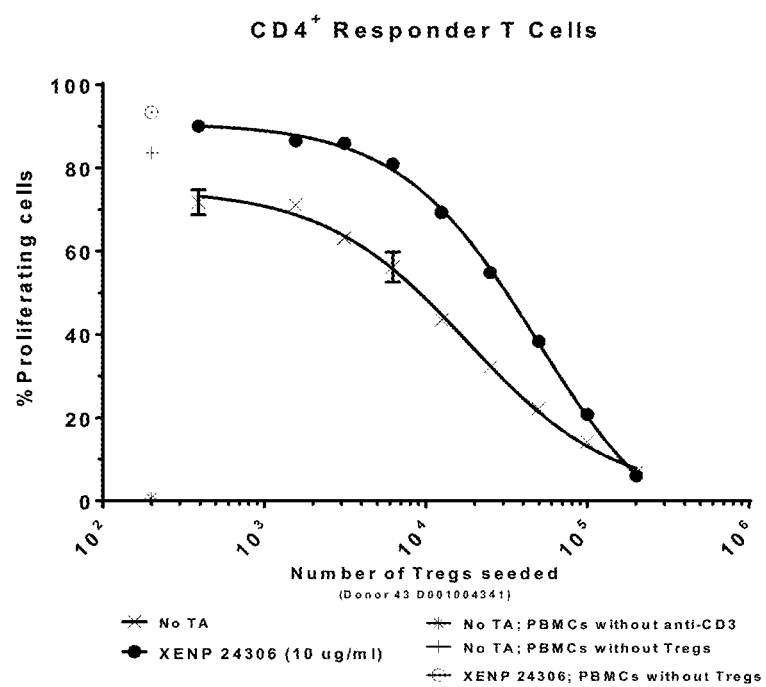

FIG. 159A-FIG. 159B depict the proliferation of (FIG. 159A) CD8$^+$ and (FIG. 159B) CD4+ responder T cells in the presence of XmAb24306 and various concentrations of rapamycin expanded Treg.

FIG. 160 depicts the sequences for XENP16432, a bivalent anti-PD-1 mAb with an ablation variant (E233P/L234V/ L235A/G236del/S267K, "IgG1_PVA_/S267k"). The CDRs are underlined. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems. Additionally, each CDR has its own SEQ ID NO: or sequence identifier in the sequence listing, and each VH and VL domain has its own SEQ ID NO: or sequence identifier in the sequence listing.

Figure 161A:
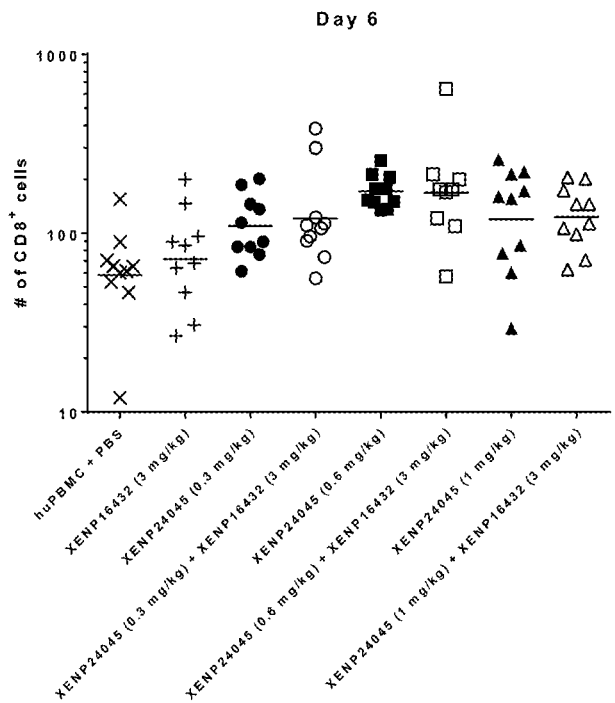
Figure 161B:
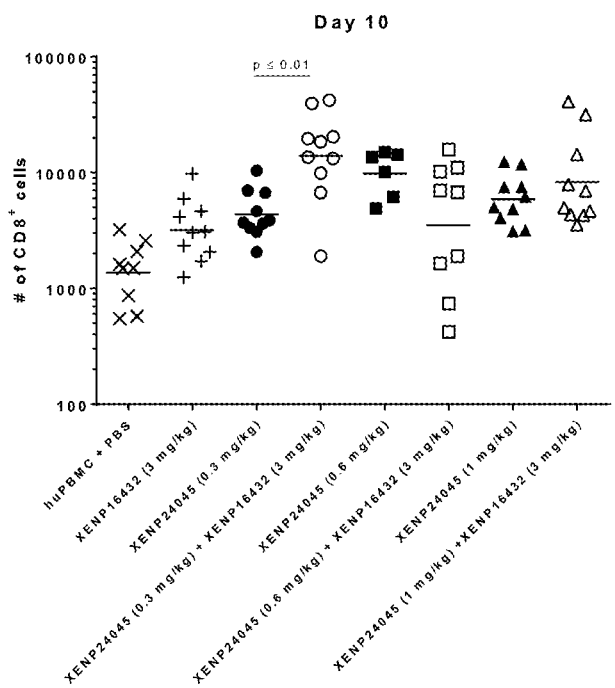

FIG. 161A-FIG. 161B depict CD8+ T cells in whole blood of mice on (FIG. 161A) Day 6 and (FIG. 161B) Day 10 after first dose of the indicated test articles.

Figure 162A:
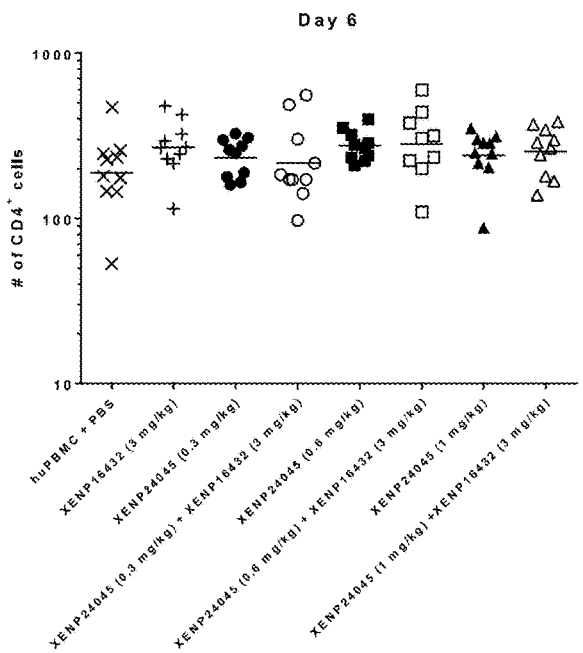
Figure 162B:
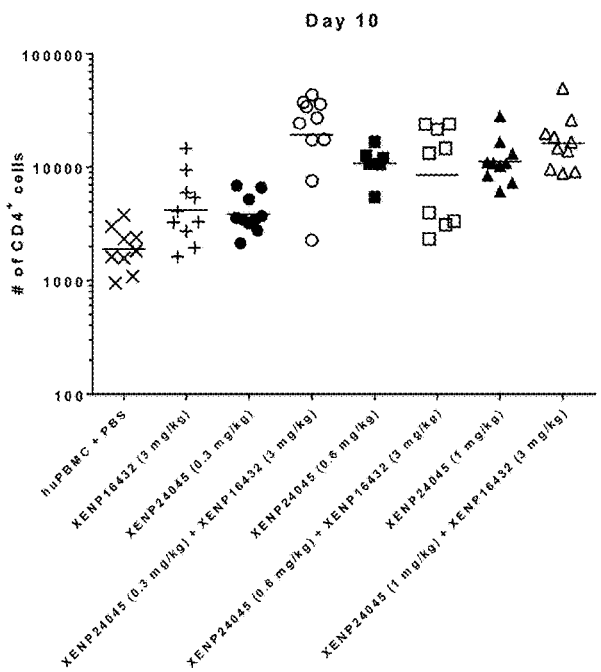

FIG. 162A-FIG. 162B depict CD4+ T cells in whole blood of mice on (FIG. 162A) Day 6 and (FIG. 162B) Day 10 after first dose of the indicated test articles.

Figure 163A:
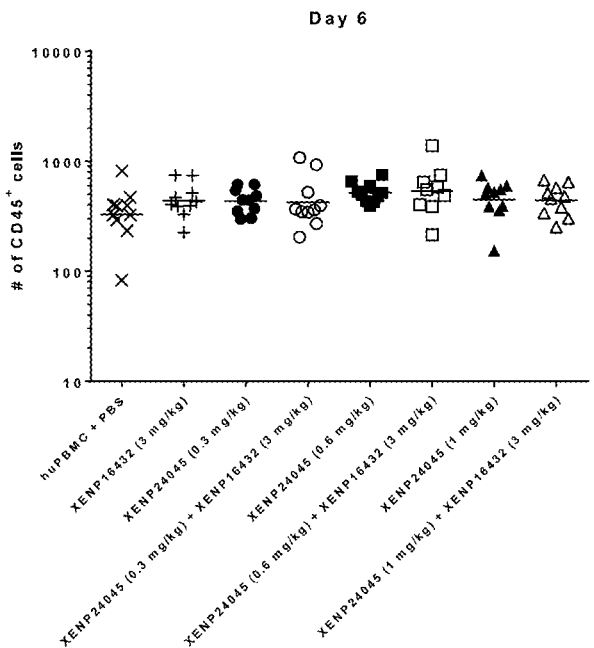
Figure 163B:
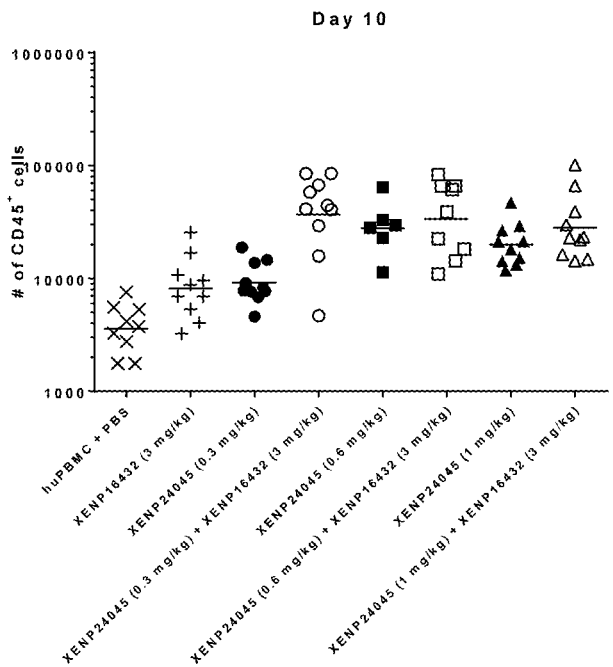

FIG. 163A-FIG. 163B depict CD45+ T cells in whole blood of mice on (FIG. 163A) Day 6 and (FIG. 163B) Day 10 after first dose of the indicated test articles.

Figure 164A:
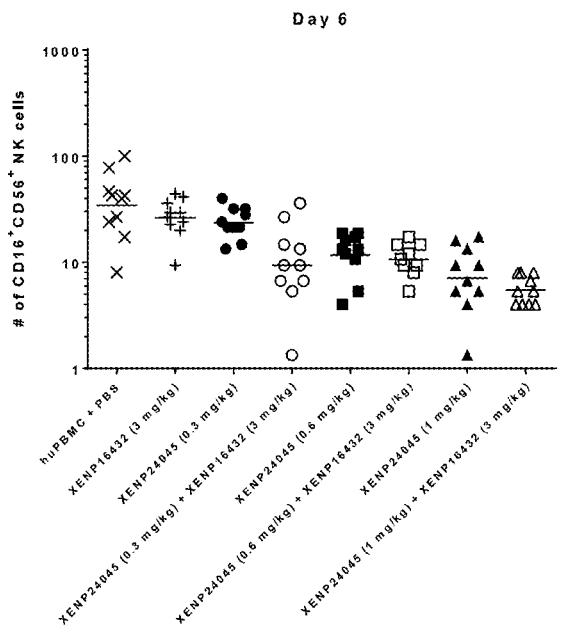
Figure 164B:
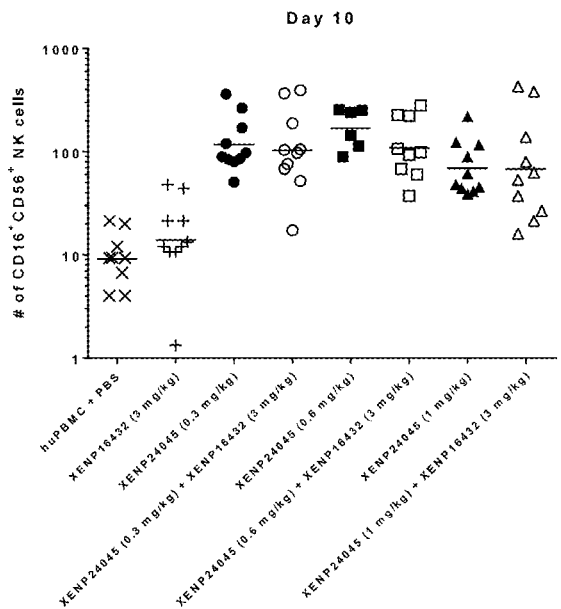

FIG. 164A-FIG. 164B depict NK cells in whole blood of mice on (FIG. 164A) Day 6 and (FIG. 164B) Day 10 after first dose of the indicated test articles.

Figure 165:
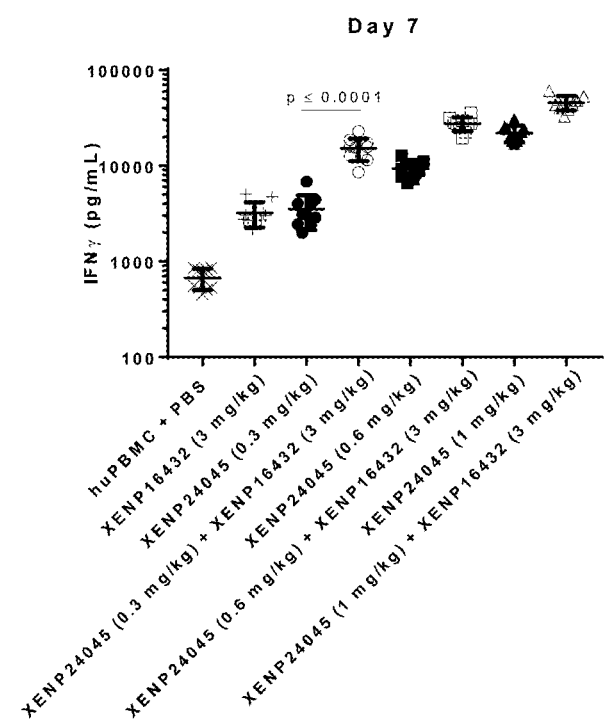
Figure 166A:
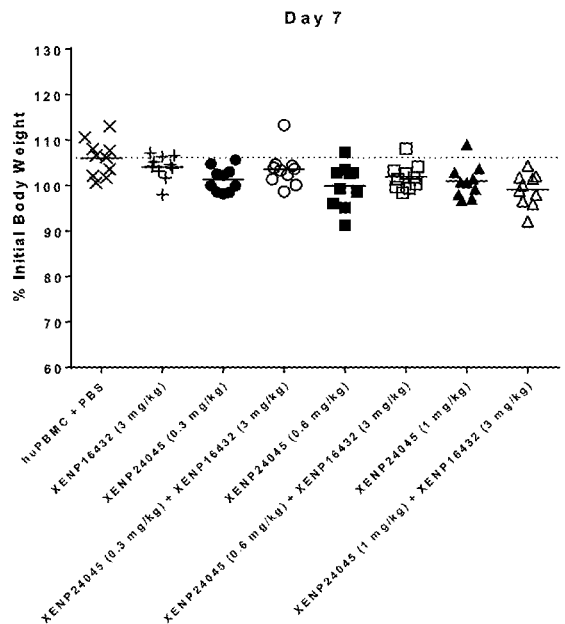
Figure 166B:
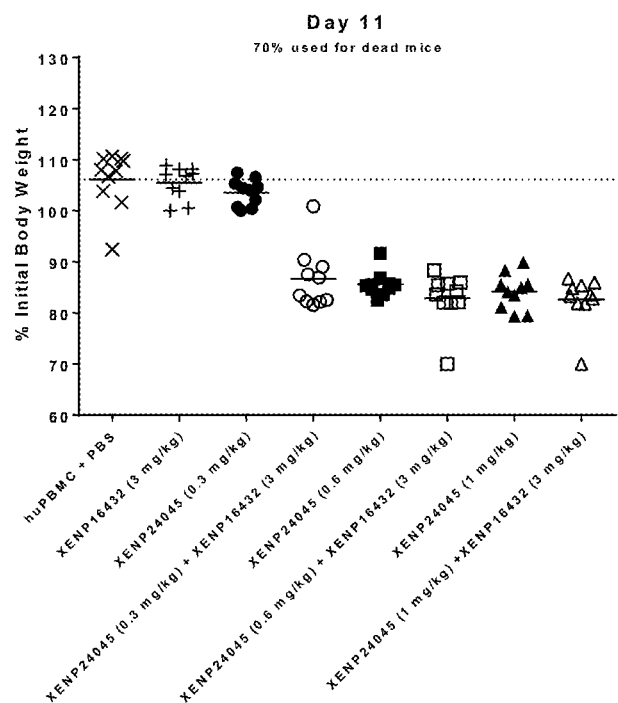
Figure 166C:
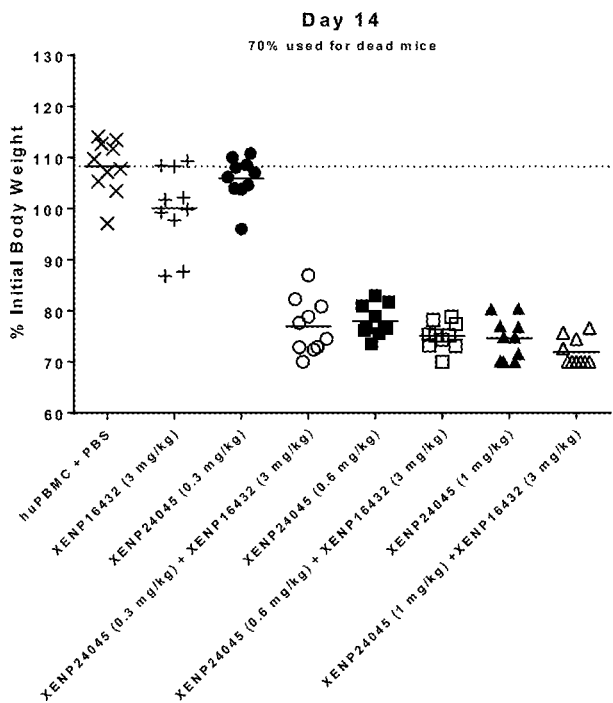
Figure 166D:
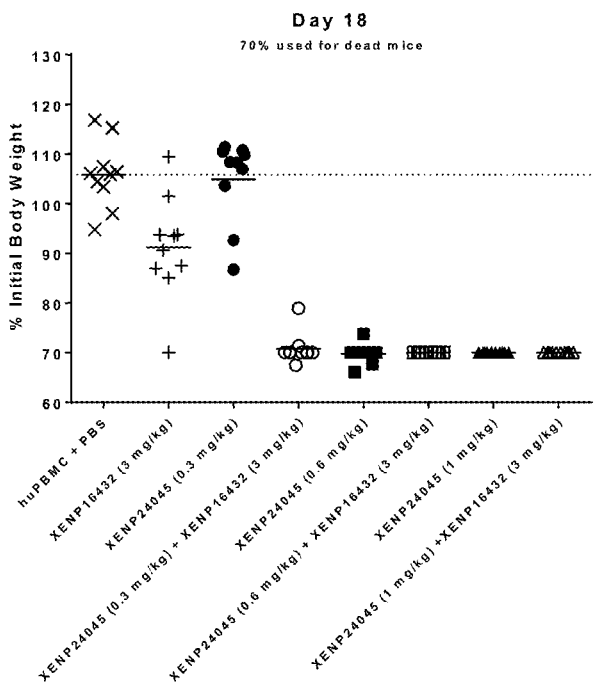

FIG. 165 depicts IFNγ in serum of NSG mice on Day 7 after first dose of the indicated test articles.

FIG. 166A-FIG. 166D depict body weight of mice on Day 7 (FIG. 166A), Day 11 (FIG. 166B), Day 14 (FIG. 166C), and Day 18 (FIG. 166D) after first dose of the indicated test articles.

Figure 167:
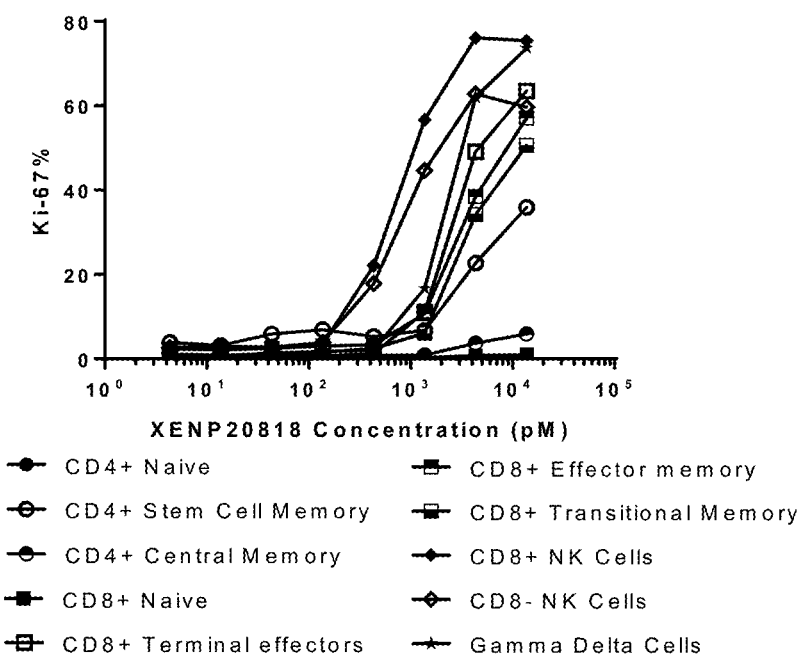

FIG. 167 depicts percentage of indicated lymphocyte populations expressing Ki67 following incubation with XENP20818.

Figure 168:
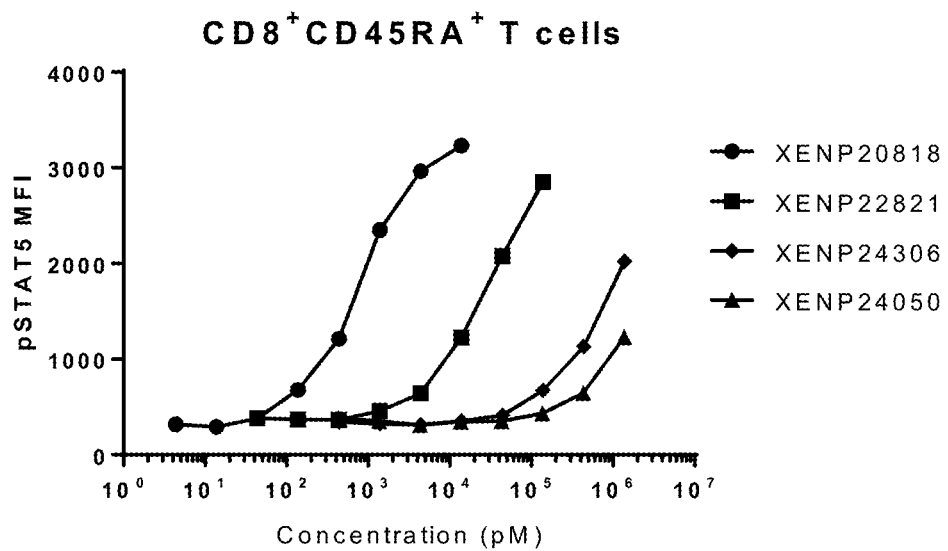

FIG. 168 depicts STAT5 phosphorylation on CD8+ CD45RA+ T cells following incubation with XENP20818, XENP22821, XENP24050, and XENP24306.

Figure 169:
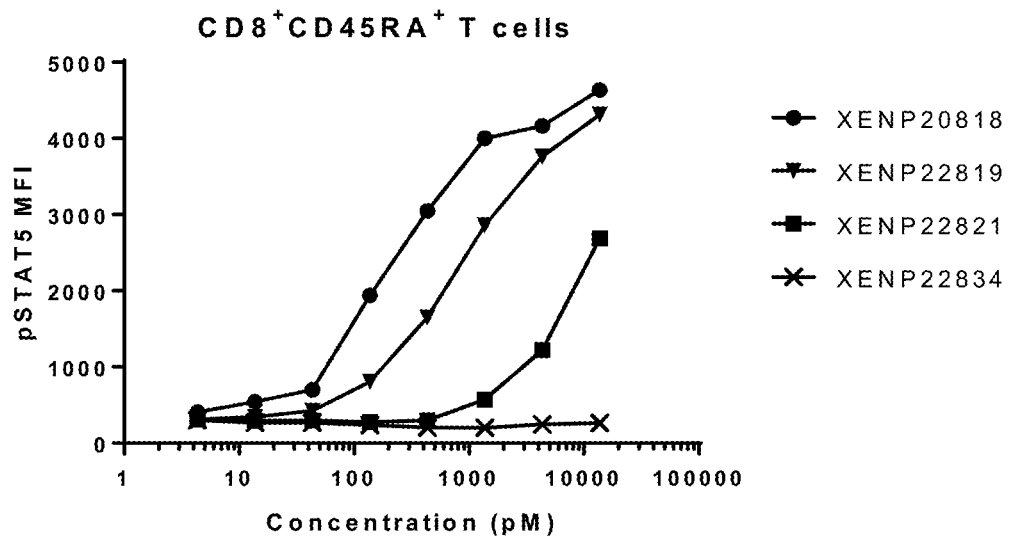

FIG. 169 depicts STAT5 phosphorylation on CD8+ CD45RA+ T cells following incubation with XENP20818, XENP22819, XENP22821, and XENP22834.

Figure 170:
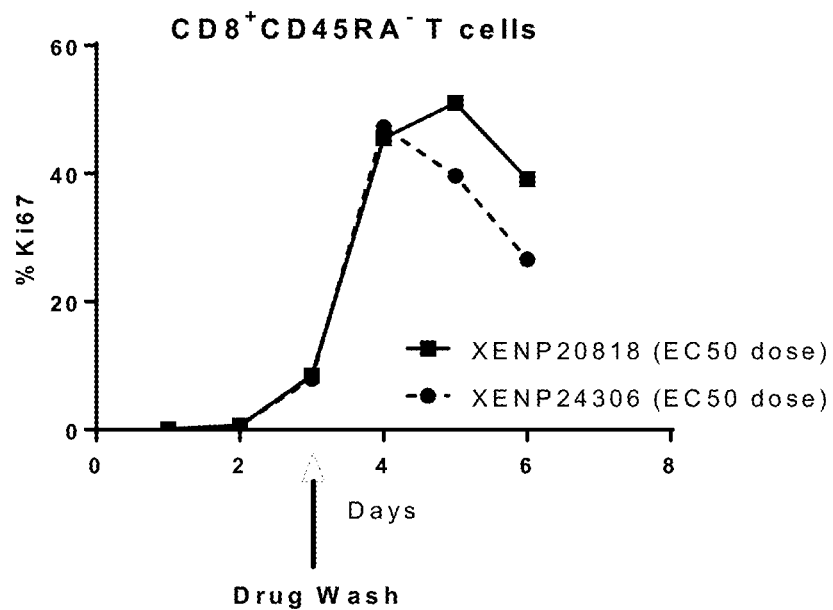

FIG. 170 depicts percentage CD8+CD45RA− T cells expressing Ki67 over time following incubation with XENP20818 or XENP24306 at their respective EC50.

Figure 171:
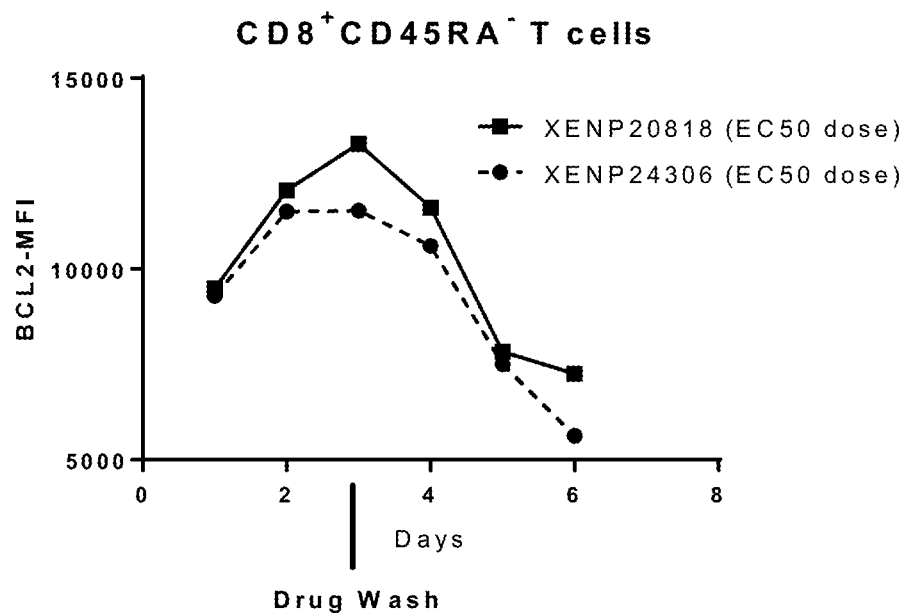

FIG. 171 depicts BCL2 expression on CD8+CD45RA− T cells over time following incubation with XENP20818 or XENP24306 at their respective EC50.

Figure 172:
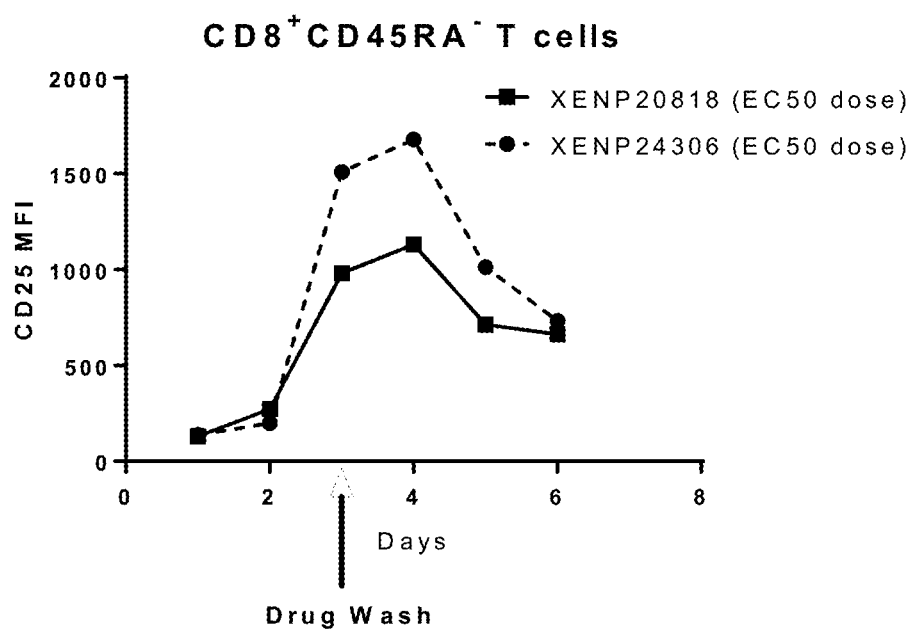

FIG. 172 depicts CD25 expression on CD8+CD45RA− T cells over time following incubation with XENP20818 or XENP24306 at their respective EC50.

Figure 173:
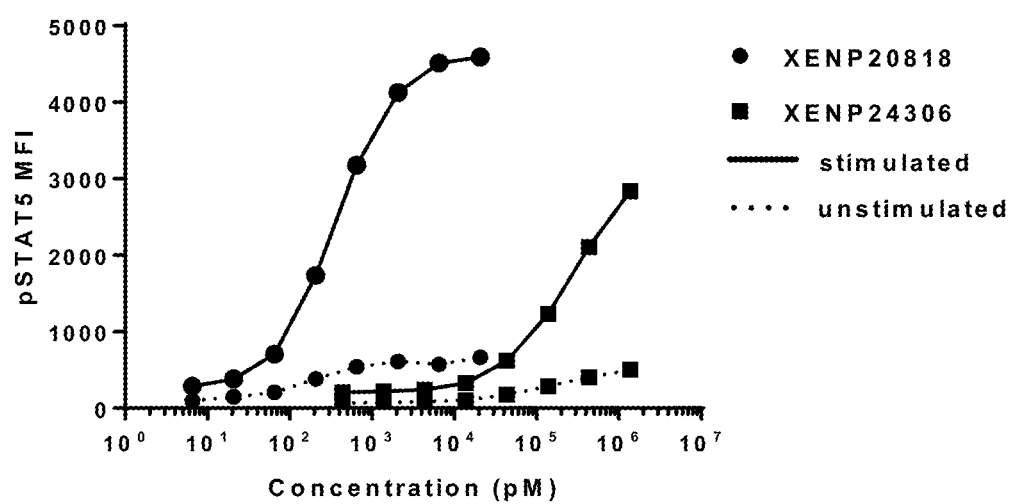

FIG. 173 depicts STAT5 phosphorylation on CD8+ T cells in fresh versus stimulated human PBMCs following incubation with XENP24045 or XENP20818.

Figure 174:
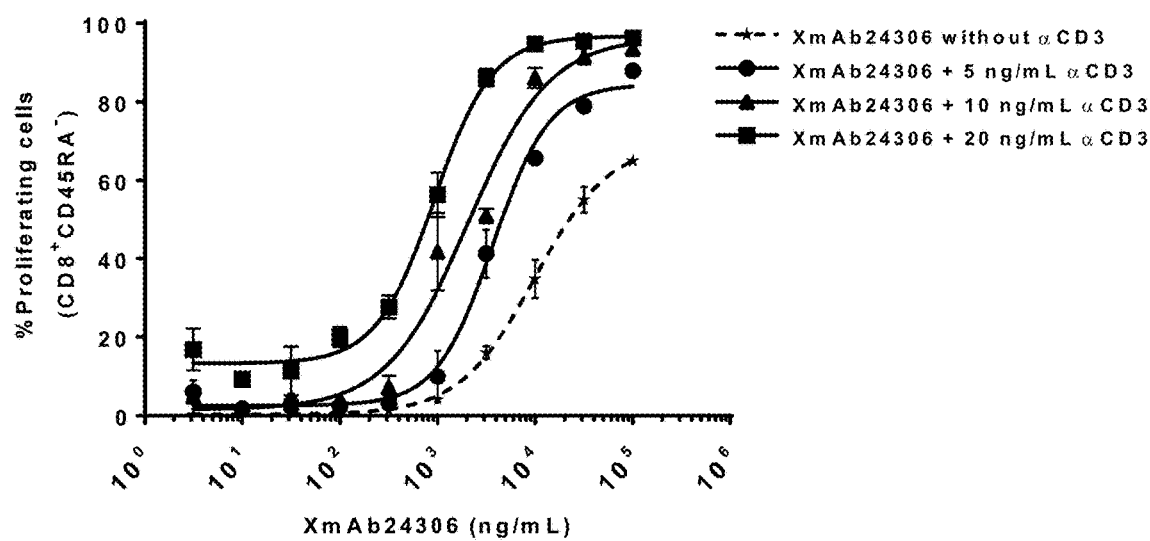

FIG. 174 depicts percent proliferating CD8+CD45RA− (as determined by CFSE dilution) following incubation of human PBMCs with indicated dose of XENP24306 and indicated dose of plate bound anti-CD3 (OKT3).

Figure 175:
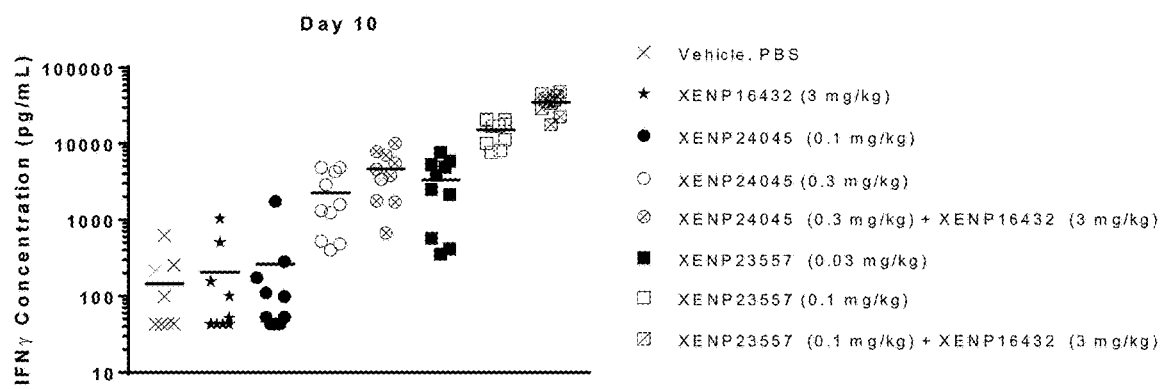

FIG. 175 depicts serum IFNγ concentration in huPBMC-engrafted NSG mice on Day 10 after the first dosing with the indicated test articles at the indicated concentrations.

Figure 176:
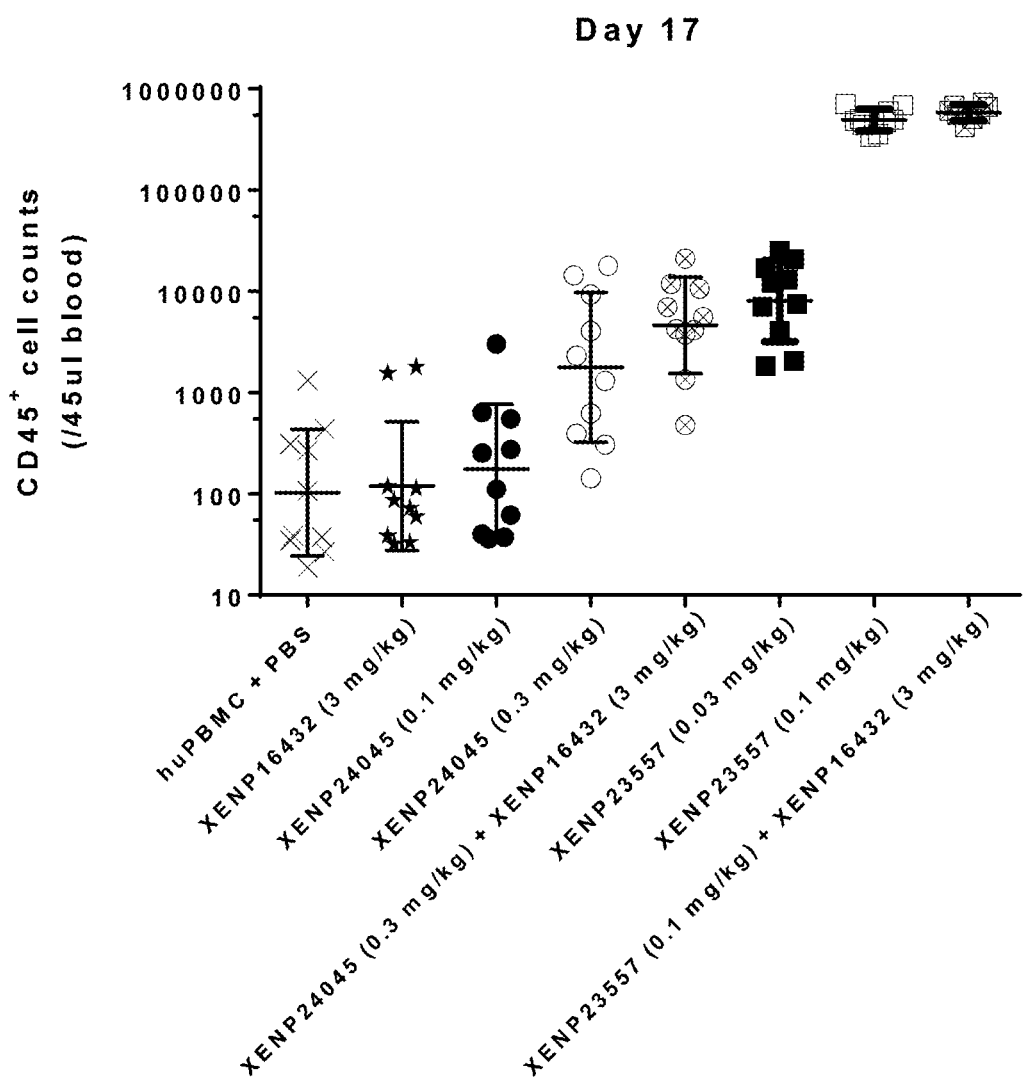

FIG. 176 depicts CD45+ cell count in blood of huPBMC-engrafted NSG mice on Day 17 after the first dosing with the indicated test articles at the indicated concentrations.

Figure 177:
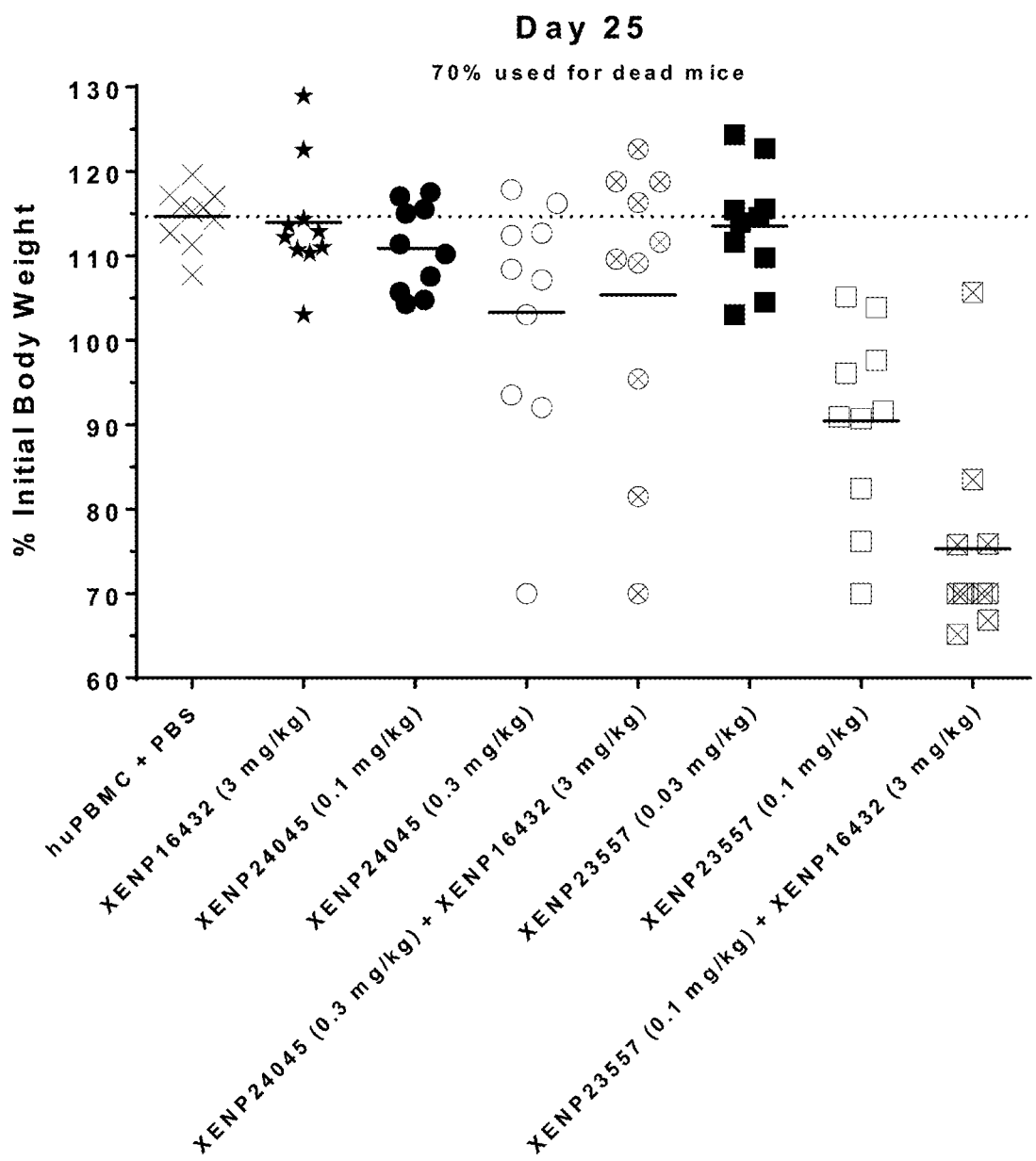

FIG. 177 depicts body weight (as a percentage of initial body weight) of huPBMC-engrafted NSG mice on Day 25 after the first dosing with the indicated test articles at the indicated concentrations.

Figure 178:
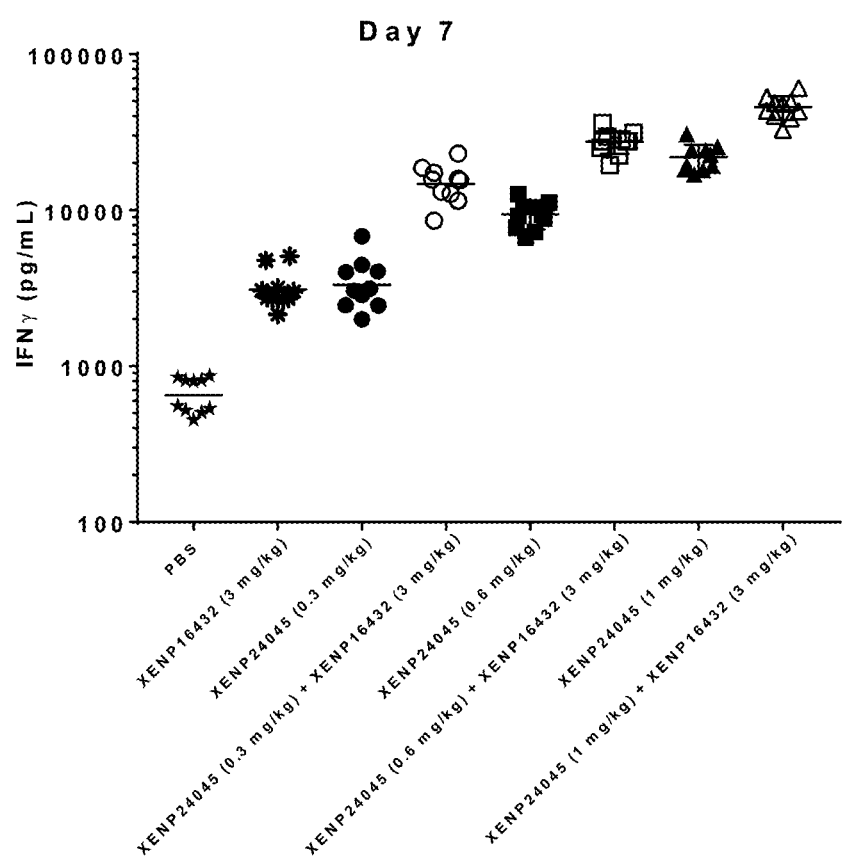
Figure 179A:
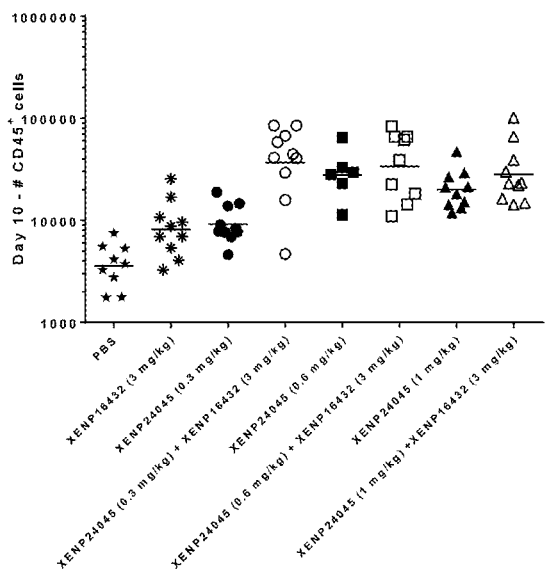
Figure 179B:
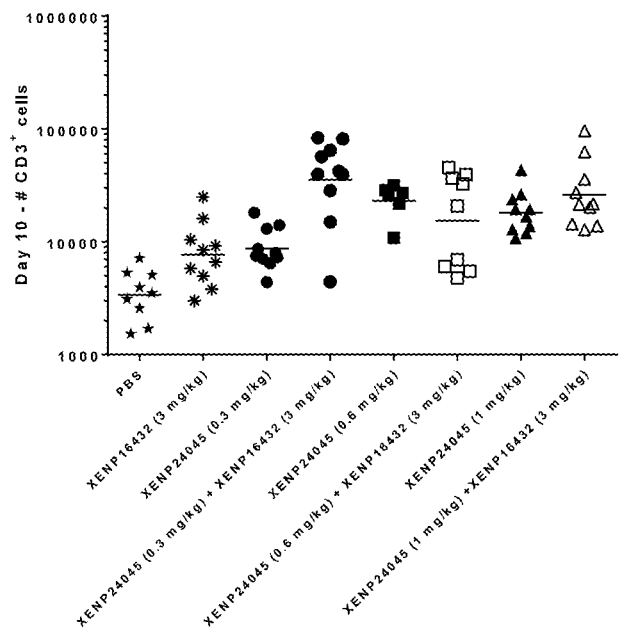
Figure 179C:
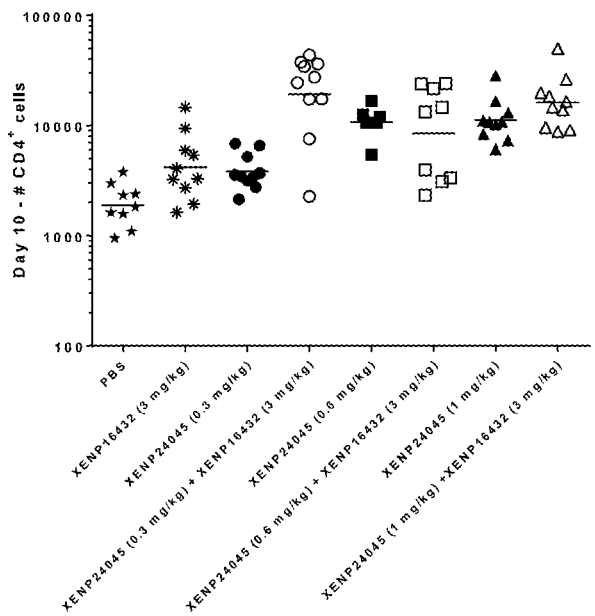
Figure 179D:
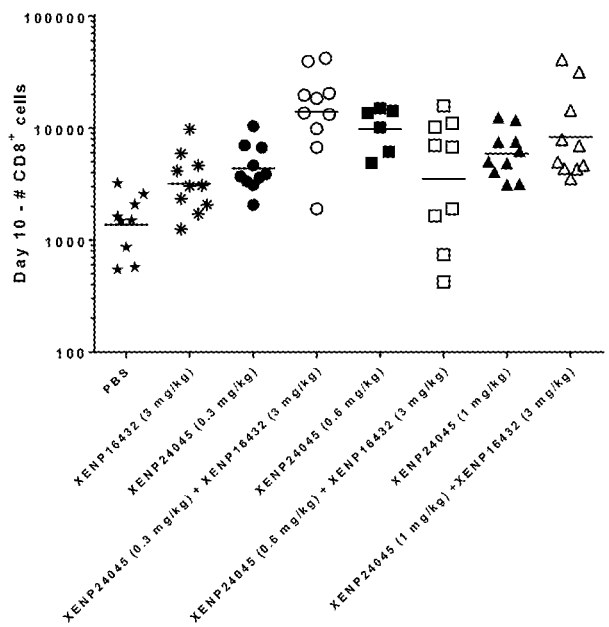

FIG. 178 depicts serum IFNγ concentration in huPBMC-engrafted NSG mice on Day 7 after the first dosing with the indicated test articles at the indicated concentrations.

FIG. 179A, FIG. 179B, FIG. 179C, and FIG. 179D depicts A) CD45+ cell, B) CD3+ T cell, C) CD4+ T cell, D) CD8+ T cell counts in blood of huPBMC-engrafted NSG mice on Day 10 after the first dosing with the indicated test articles at the indicated concentrations.

Figure 180:
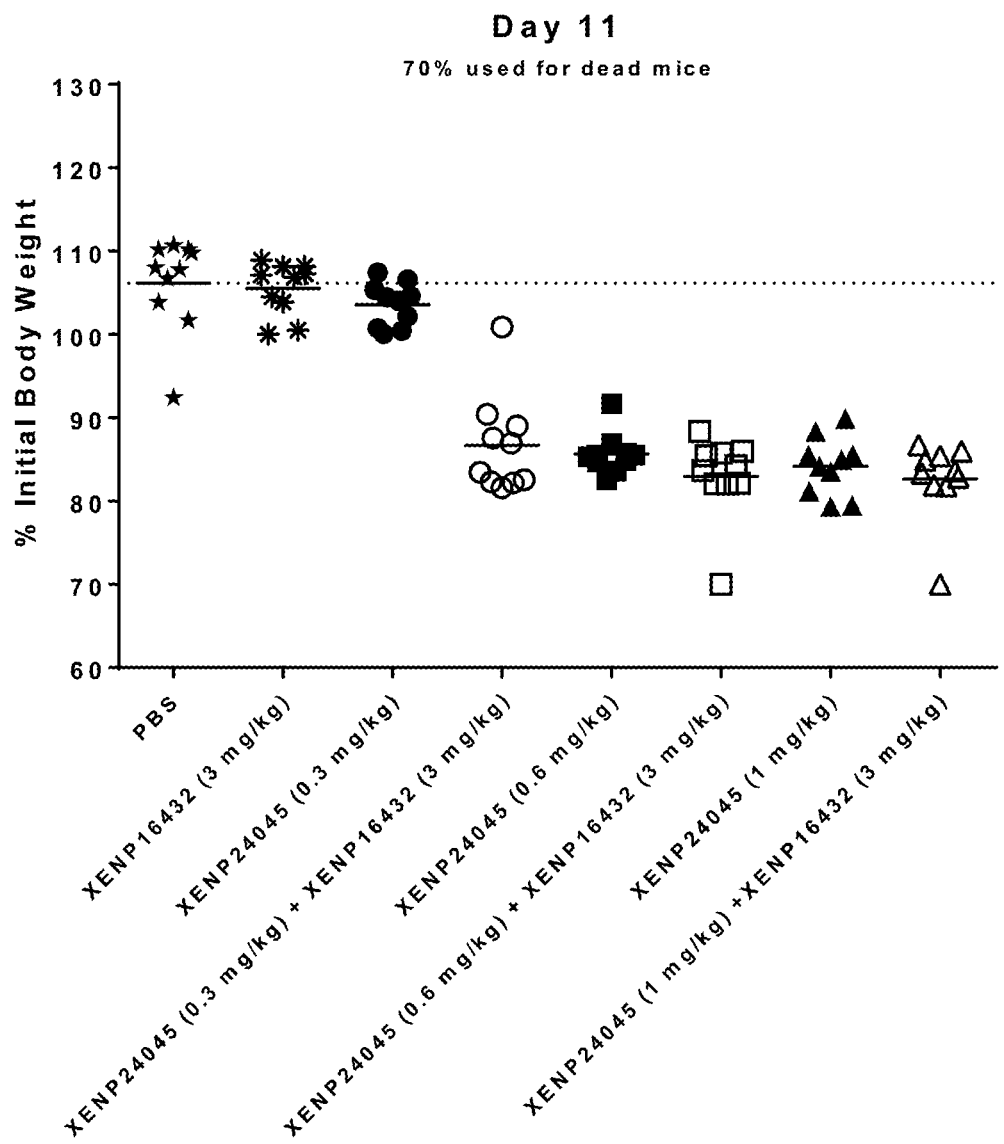

FIG. 180 depicts body weight (as a percentage of initial body weight) of huPBMC-engrafted NSG mice on Day 11 after the first dosing with the indicated test articles at the indicated concentrations.

Figure 181:
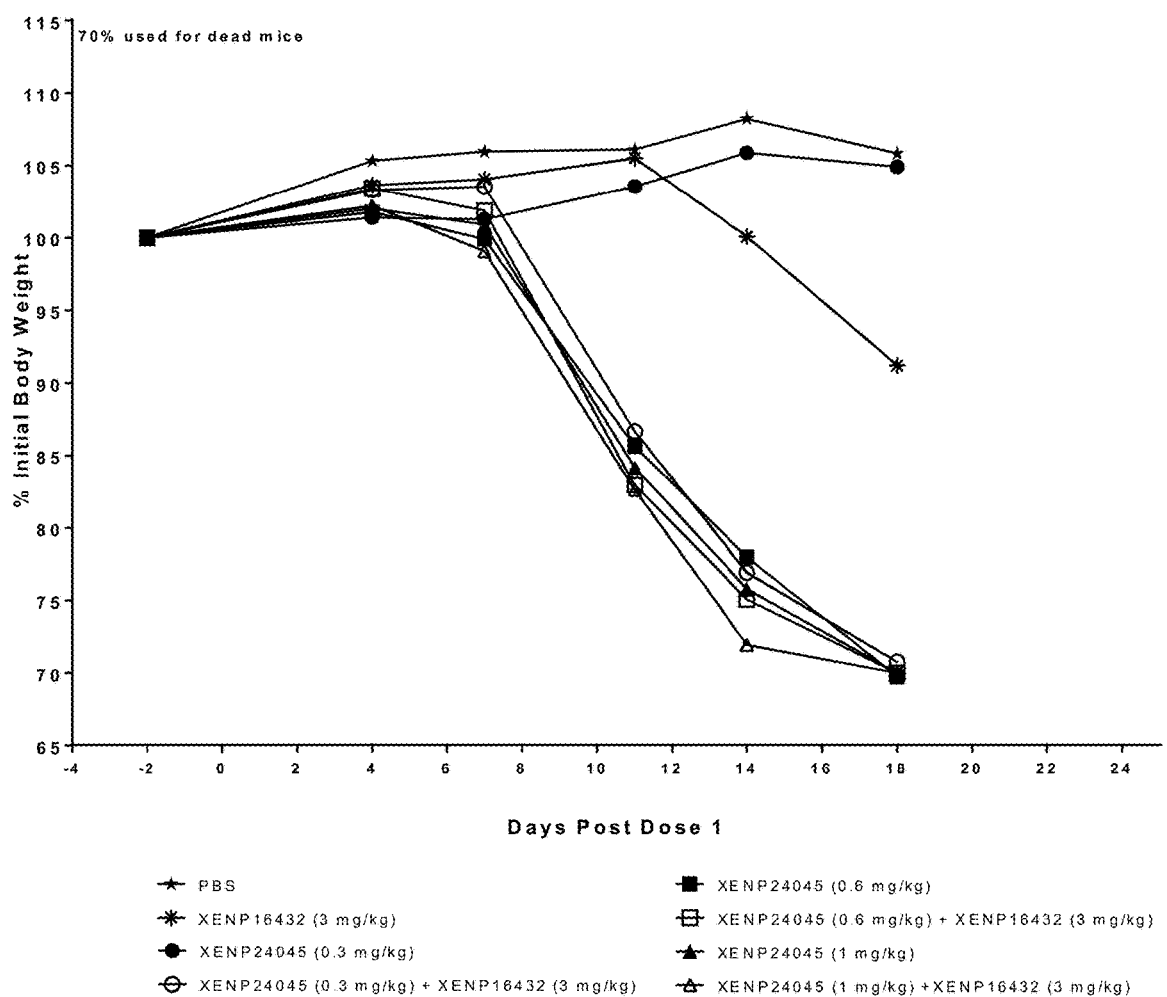

FIG. 181 depicts a time course of body weight (as a percentage of initial body weight) of huPBMC-engrafted NSG mice following the first dosing with the indicated test articles at the indicated concentrations.

Figure 182:
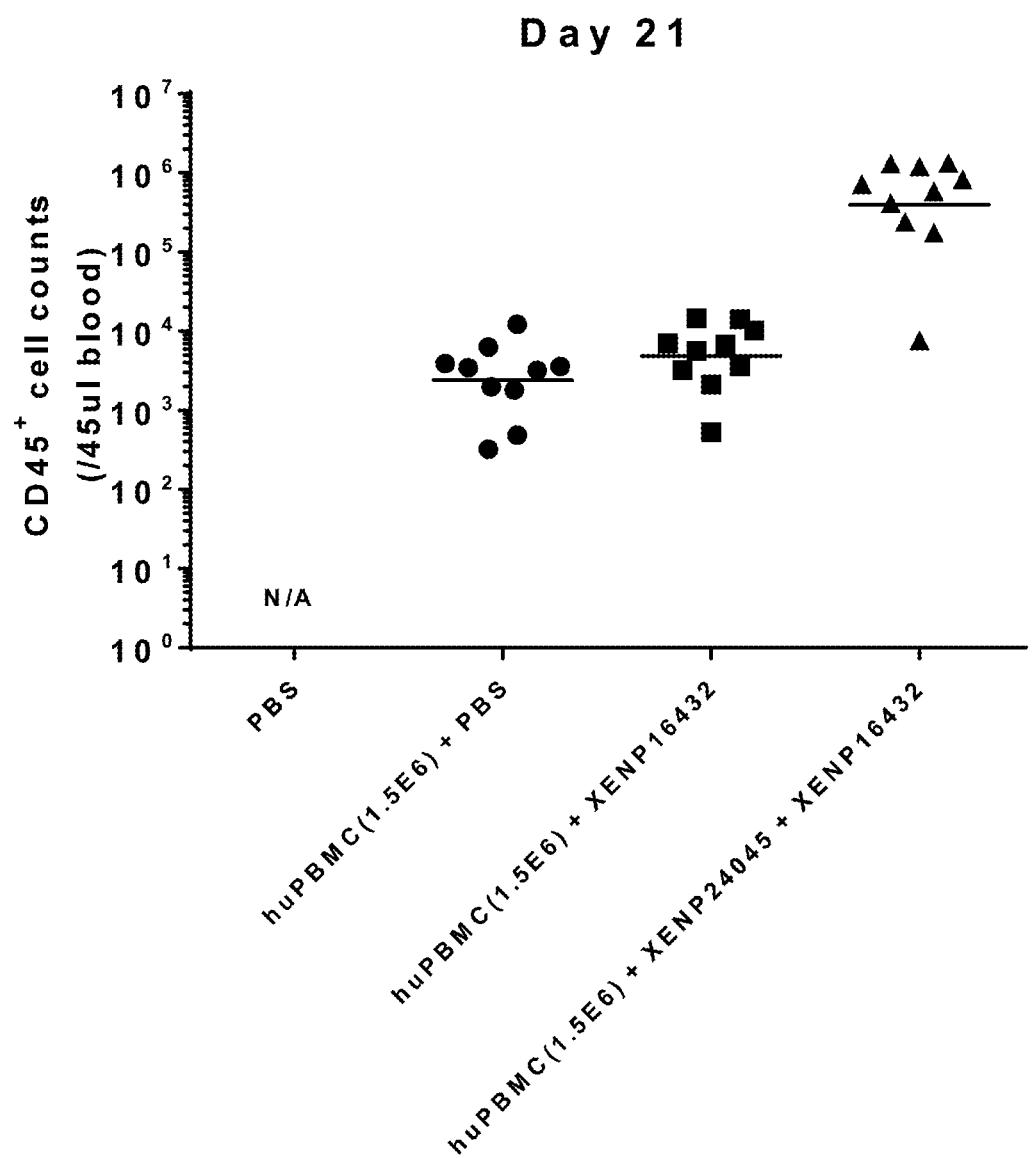

FIG. 182 depicts CD45+ cell counts on Day 21 in pp65-MCF7 and huPBMC-engrafted NSG mice dosed with XENP16432 and/or XENP24045.

Figure 183:
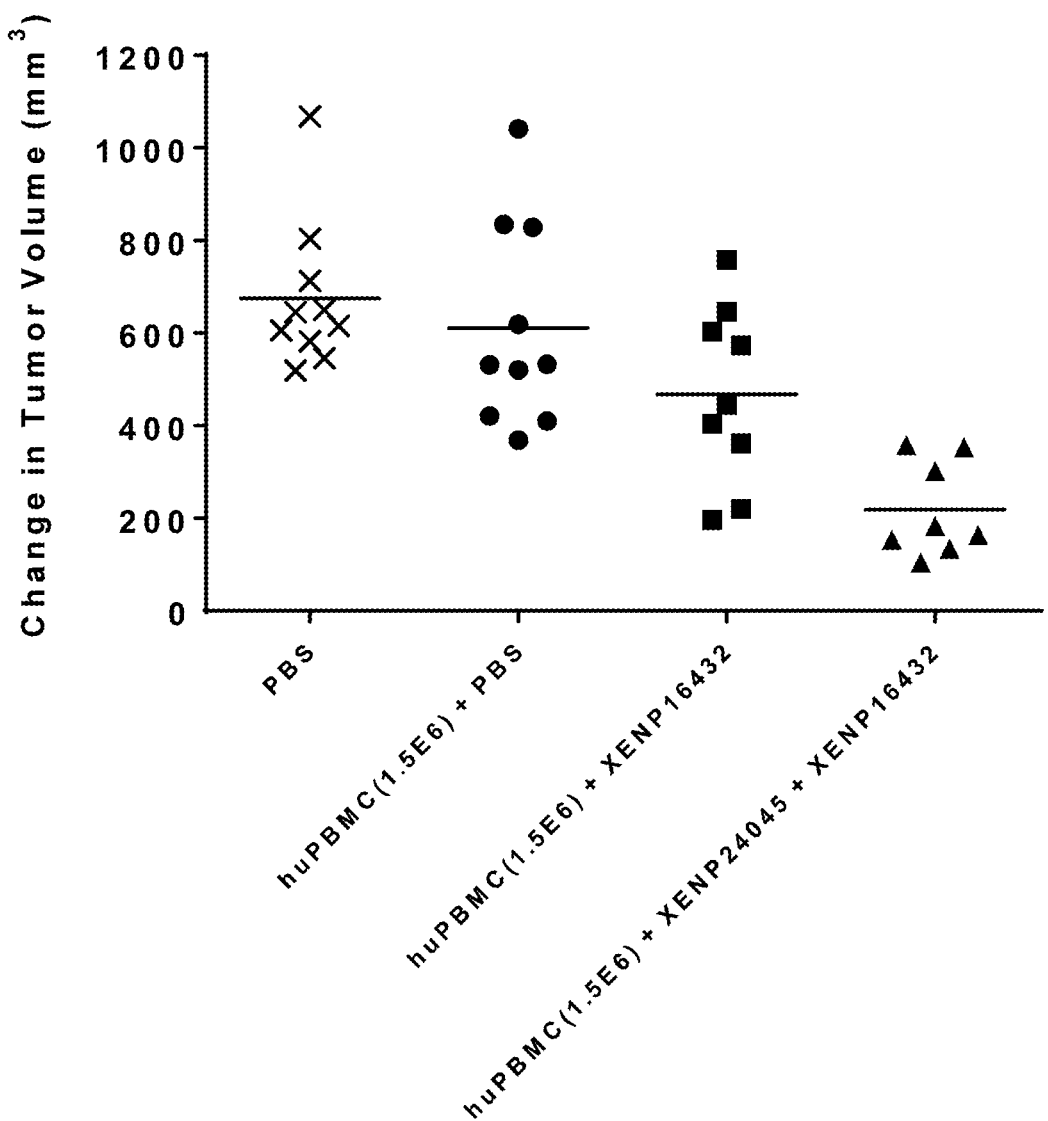

FIG. 183 depicts tumor volume on Day 31 in pp65-MCF7 and huPBMC-engrafted NSG mice dosed with XENP16432 and/or XENP24045.

Figure 184:
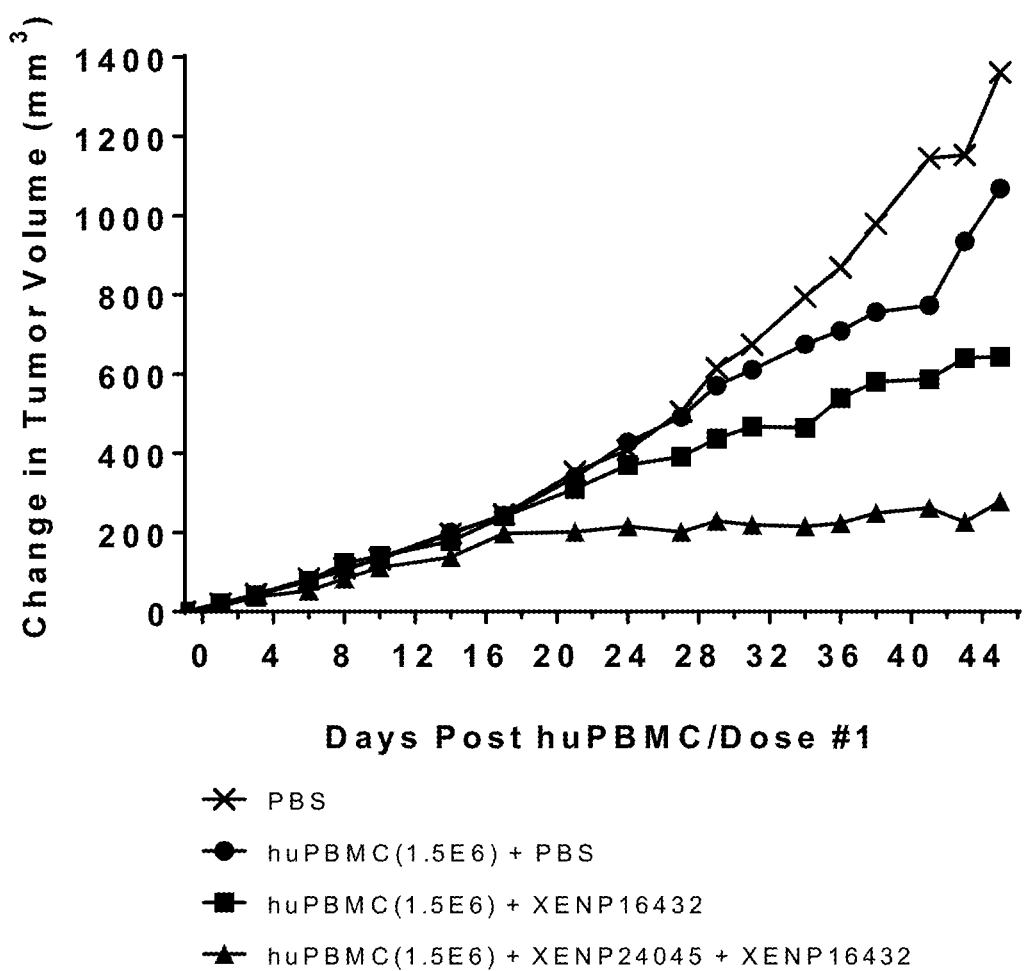

FIG. 184 depicts tumor volume over time (post-huPBMC engraftment) in pp65-MCF7 and huPBMC ($1.5 \times 10^6$)-engrafted NSG mice dosed with XENP16432 and/or XENP24045.

Figure 185:
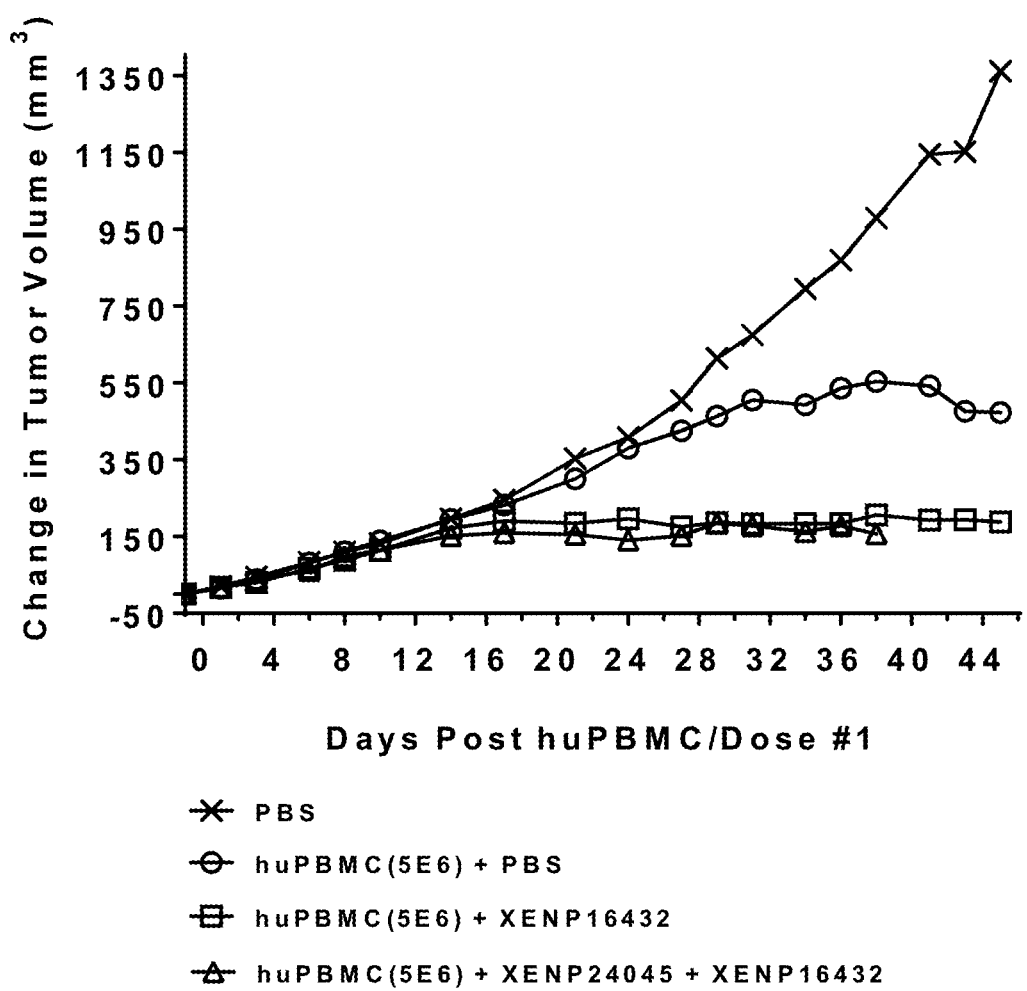

FIG. 185 depicts tumor volume over time (post-huPBMC engraftment) in pp65-MCF7 and huPBMC ($5 \times 10^6$)-engrafted NSG mice dosed with XENP16432 and/or XENP24045.

FIG. 186 depicts the sequences of XENP21993, an scIL-15/Rα-Fc fusion comprising a wild-type IL-15. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

FIG. 187 depicts the sequences of XENP22853, an IL-15/Rα-heteroFc fusion comprising a wild-type IL-15 and Xtend Fc (M428L/N434S) variant. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

FIG. 188 depicts the sequences of XENP24294, an scIL-15/Rα-Fc fusion comprising an IL-15(N4D/N65D) variant and Xtend Fc (M428L/N434S) substitution. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

Figure 189:
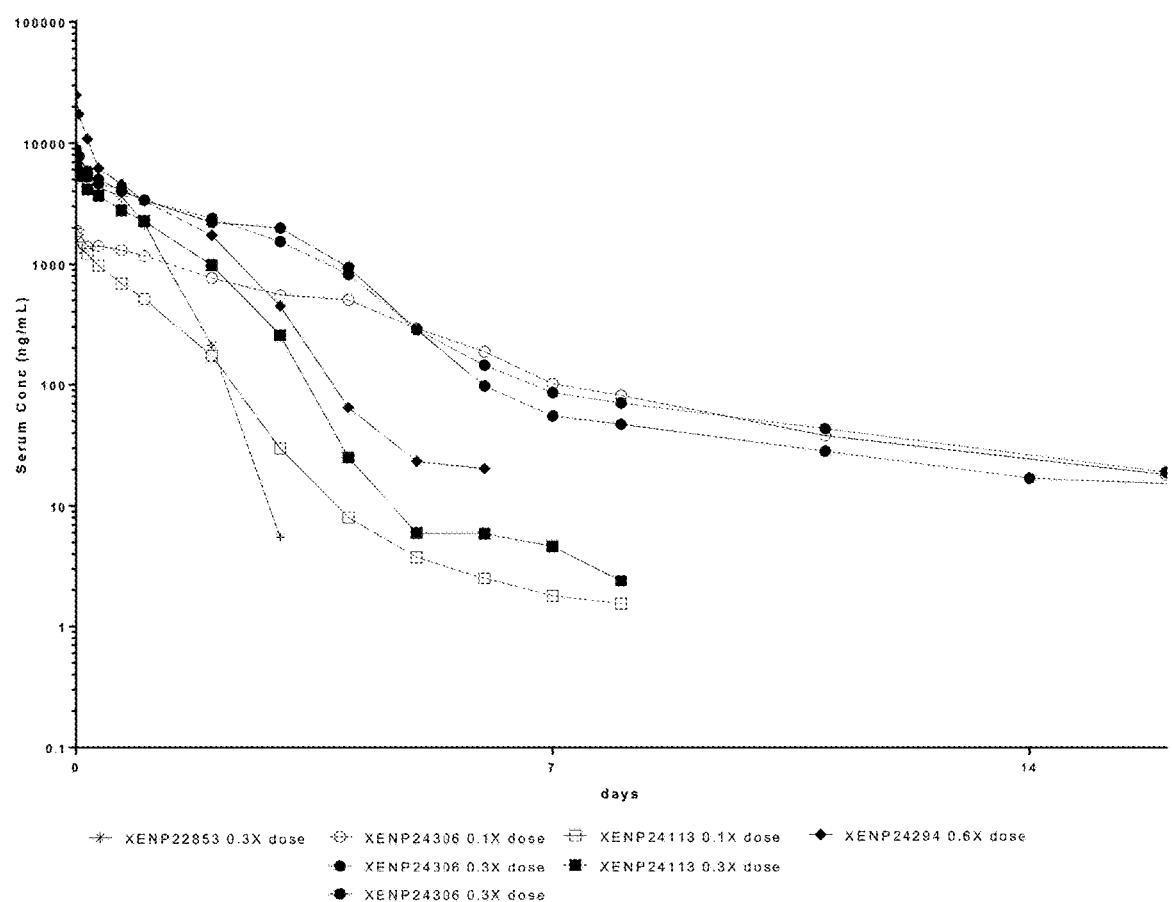

FIG. 189 depicts the serum concentration of the indicated test articles over time in cynomolgus monkeys following a first dose at the indicated relative concentrations.

Figure 190:
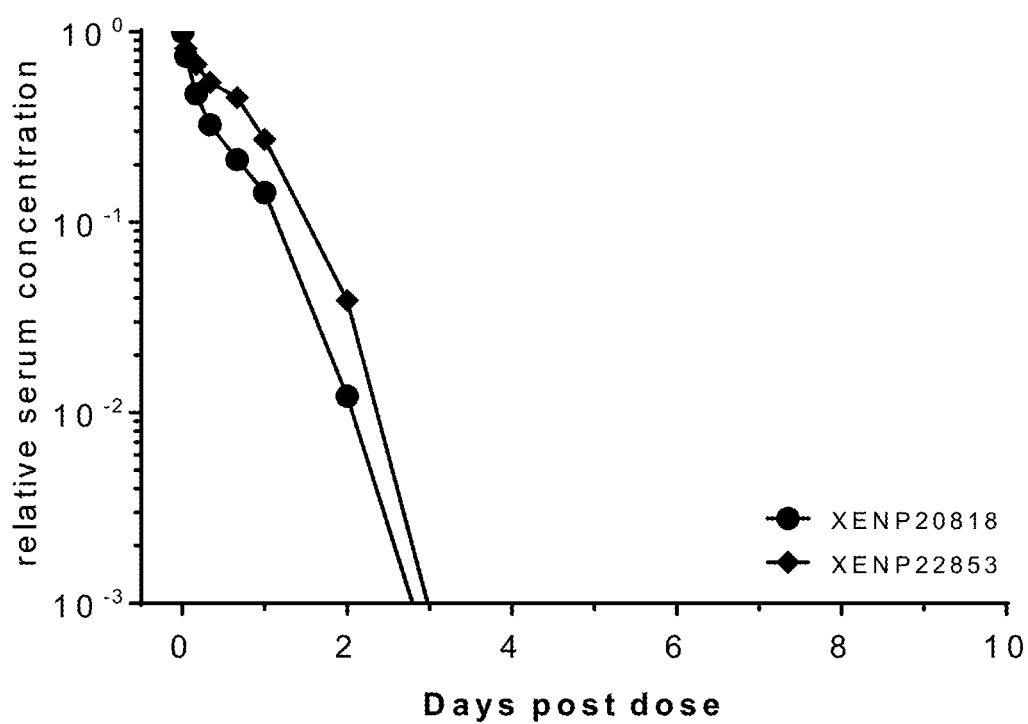
Figure 193A:
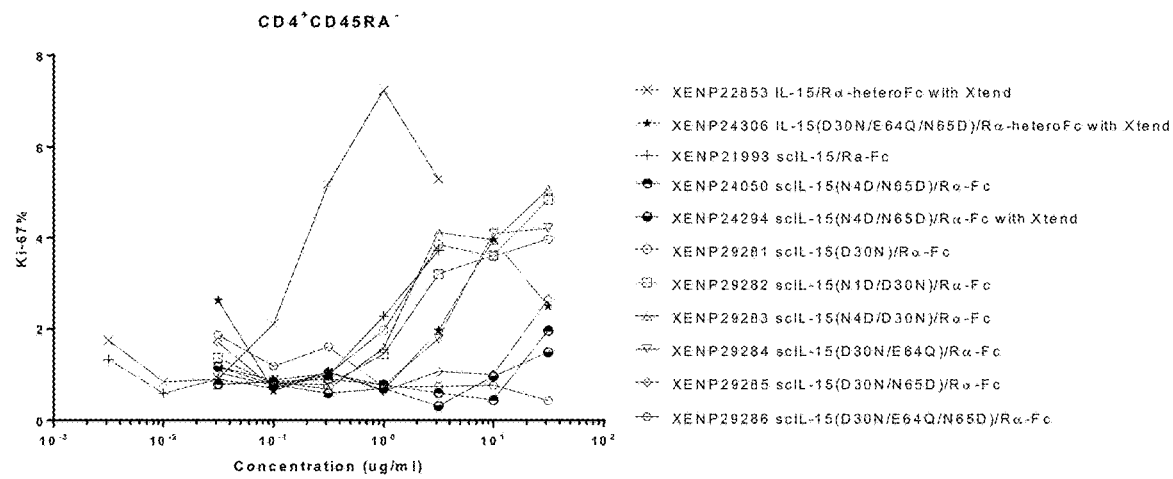
Figure 193B:
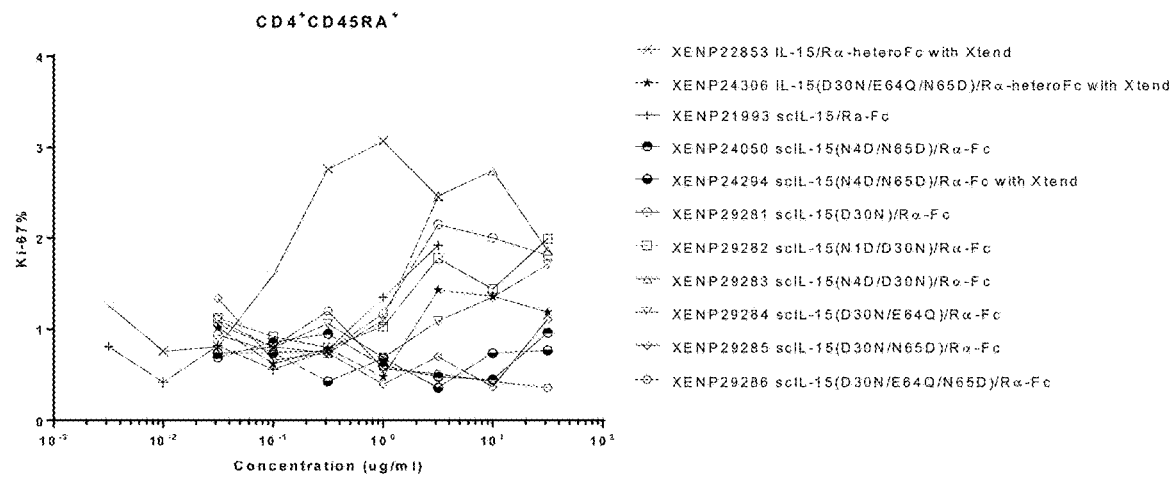
Figure 193C:
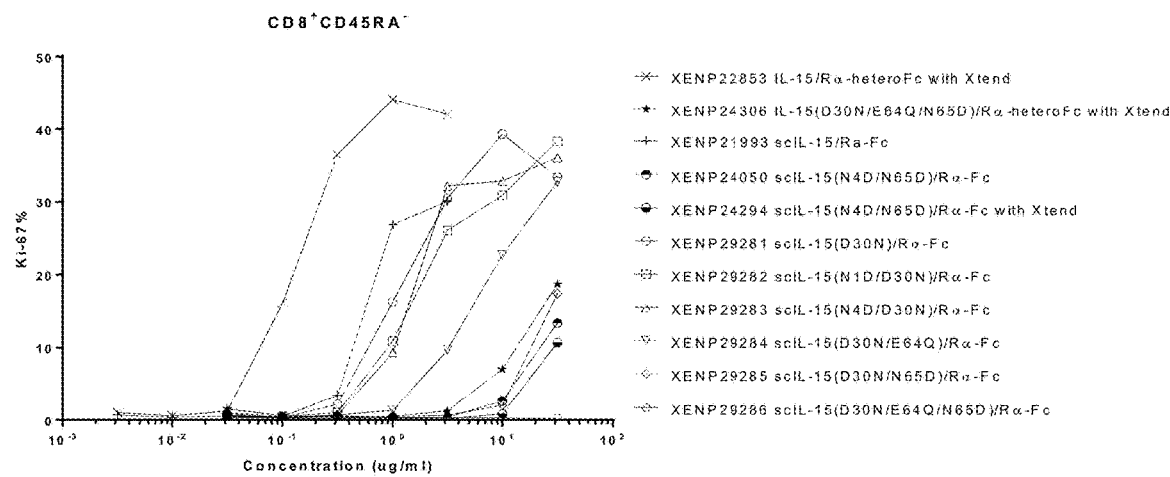
Figure 193D:
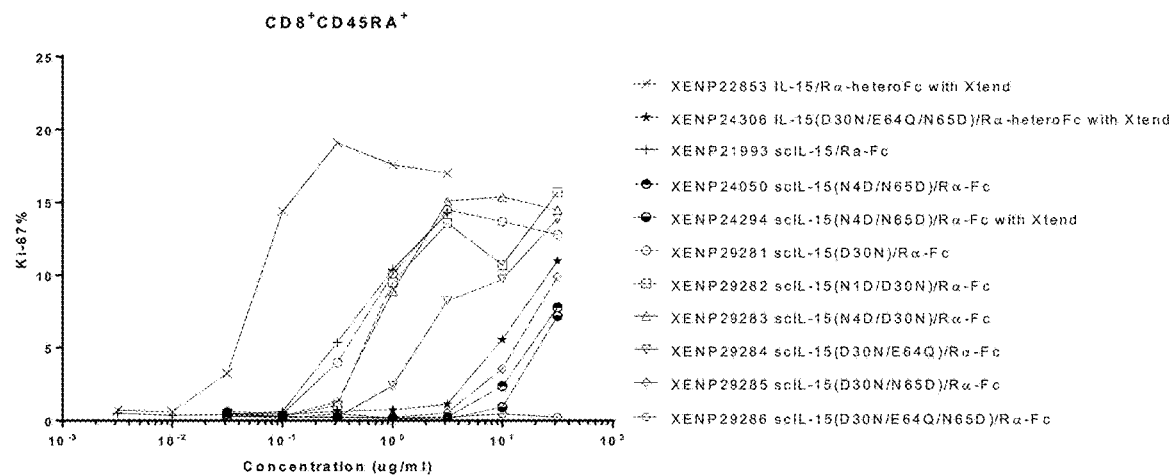
Figure 193E:
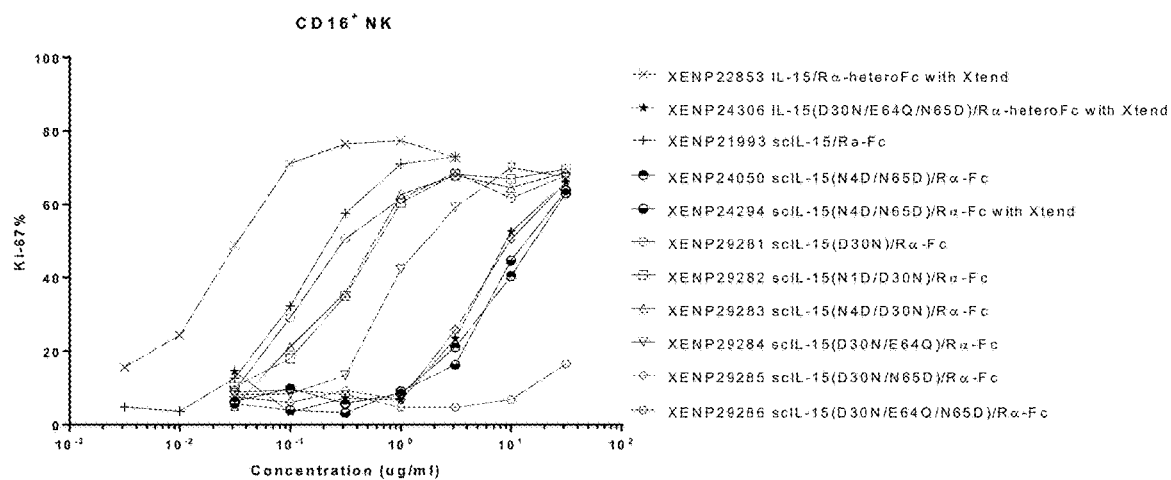
Figure 193F:
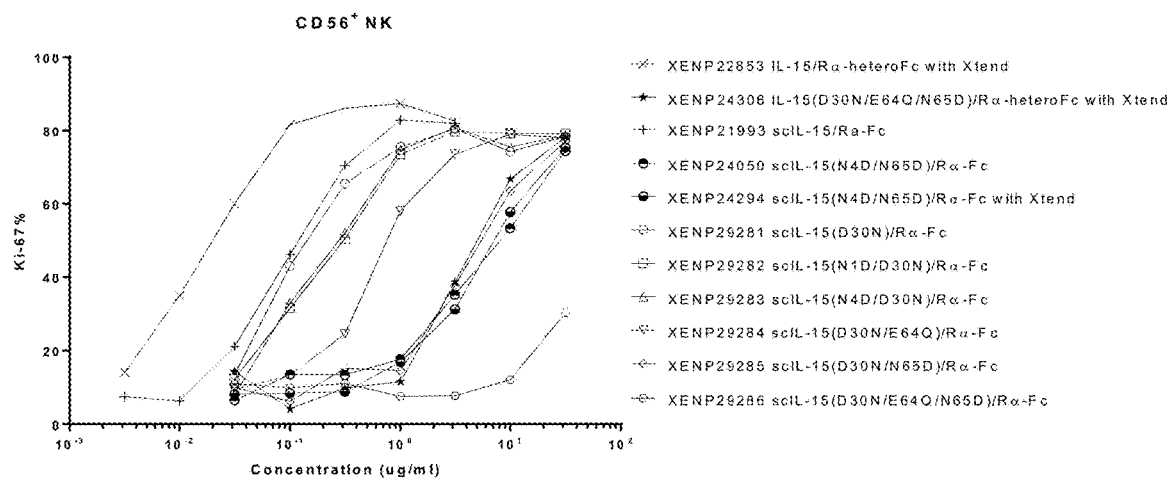
Figure 193G:
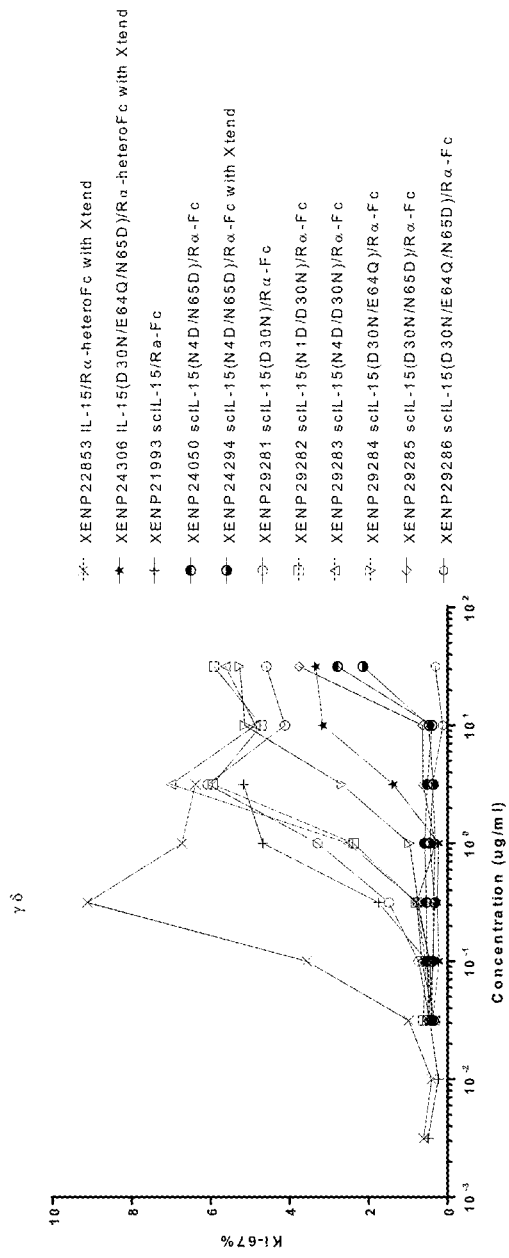
Figures 194A, 194B, 194C, 194D, 194E:
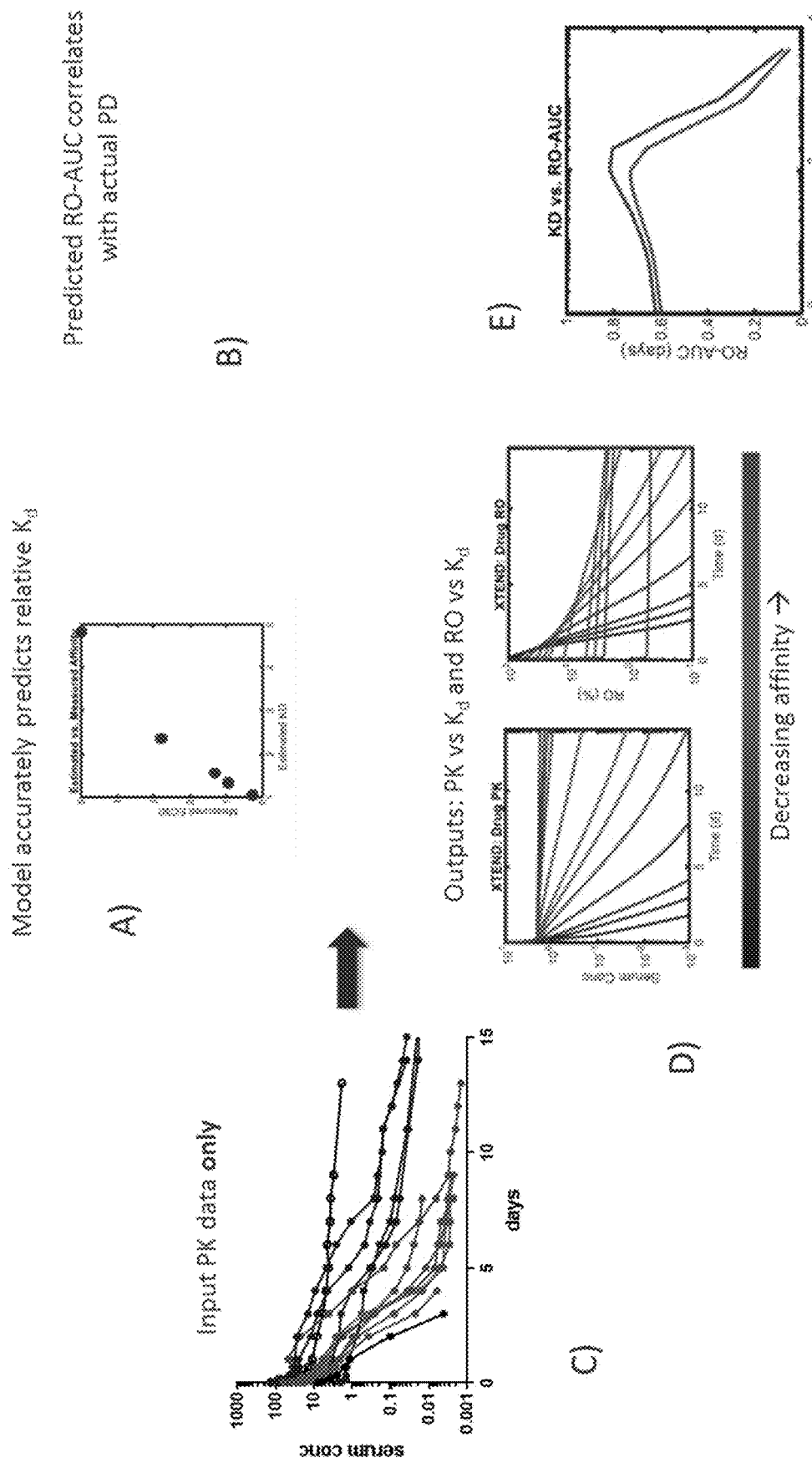

FIG. 190 depicts relative serum concentrations of XENP22853 and corresponding WT non-Xtend XENP20818 over time.

FIG. 191 depicts sequences for illustrative IL-15 variants engineered for reduced potency and comprising a D30N substitution. Including within each of these variant IL-15 sequences are sequences that are 90%, 95%, 98% and 99% identical (as defined herein) to the recited sequences, and/or contain from 1, 2, 3, 4, 5, 6, 7, 8, 9 or 10 additional amino acid substitutions. In a nonlimiting example, the recited sequences may contain additional amino acid modifications such as those contributing to formation of covalent disulfide bonds as described in Example 2.

FIG. 192A-FIG. 192C depict illustrative scIL-15/Rα-Fc fusions having IL-15 variants comprising D30N substitution. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

FIG. 193A, FIG. 193B, FIG. 193C, FIG. 193D, FIG. 193E, FIG. 193F and FIG. 193G depict percentage of A) CD4+CD45RA−, B) CD4+CD45RA+, C) CD8+CD45RA−, D) CD8+CD45RA+, E) CD16+ NK cells, F) CD56+ NK cells, and G) γδ cells expression Ki67 following incubation with the indicated test articles.

FIG. 194A, FIG. 194B, FIG. 194C, FIG. 194D and FIG. 194E show that a mechanistic PK/RO/TMDD model depicts relative PD effects as discussed in Example 18. Remarkably, the predicted RO-AUC values correlate very well with experimentally determined PD-AUC (pharmacodynamic AUC), indicating that RO-AUC is a target value to optimize, allowing a prediction of the optimal Kd value.

Figure 195:
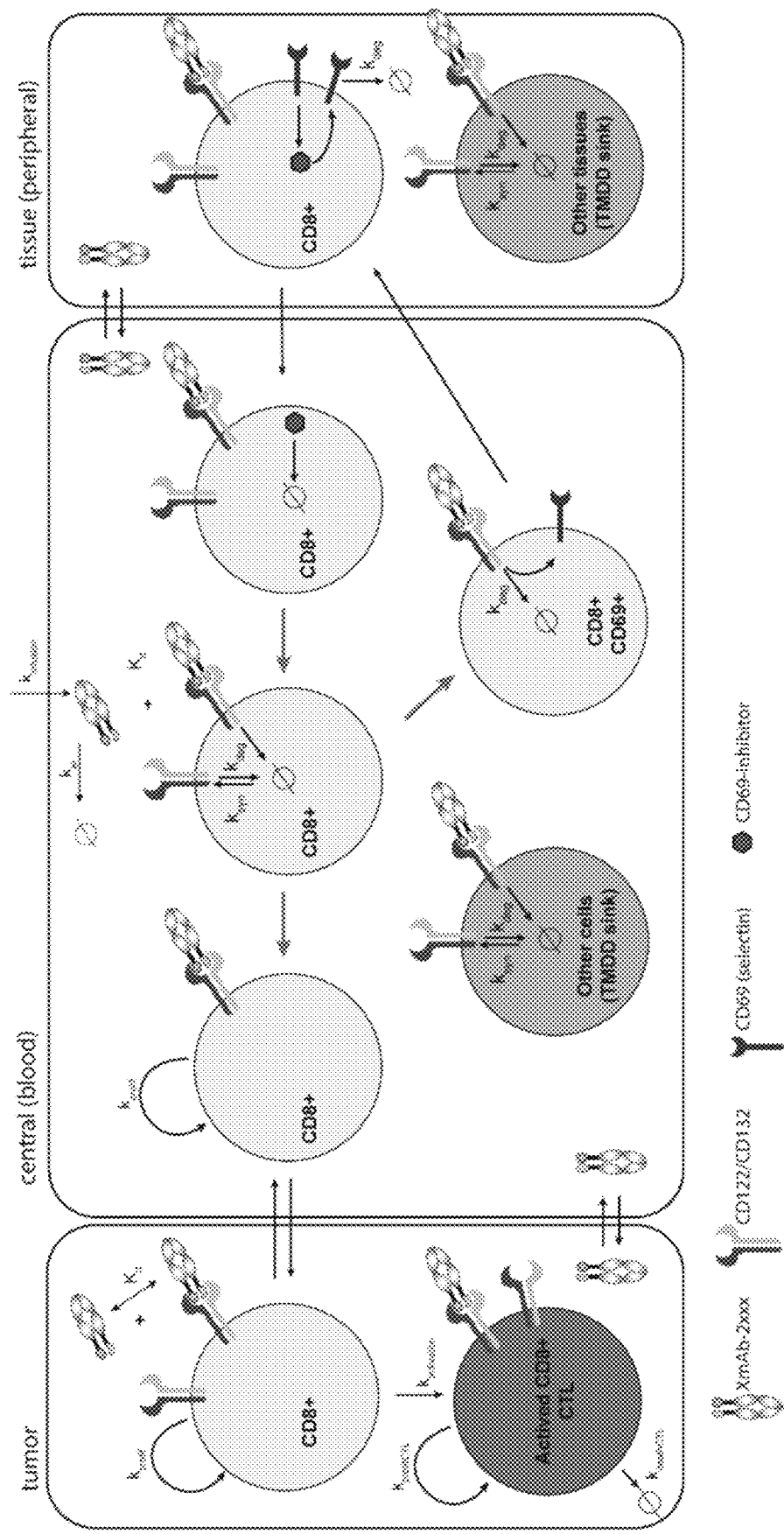

FIG. 195 shows a schematic illustrating the hypothesis that receptor-mediated internalization is a key factor that influences the PK/PD relationships of various IL-15s. $k_{prolif}$ indicates proliferation rate. $kd_{cathCTL}$ indicates rate of cell death. $K_d$ indicates dissociation constant. $k_{el}$ indicates rate of elimination. $k_{infusion}$ indicates rate of infusion into central blood. $k_{syn}$ indicates rate of synthesis of IL-15 receptors. $k_{deg}$ indicates rate of degradation of IL-15 receptors.

Figure 196:
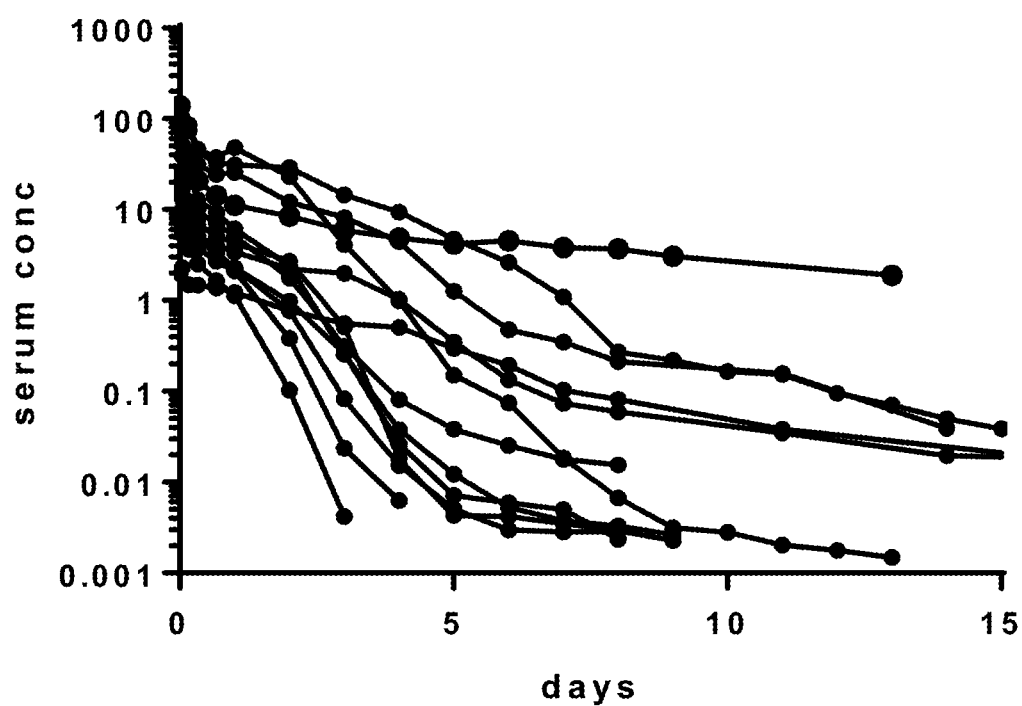

FIG. 196 depicts overlay of PK data from multiple cynomolgus monkey studies which were input into simulations based on the model depicted in FIG. 195.

Figure 197:
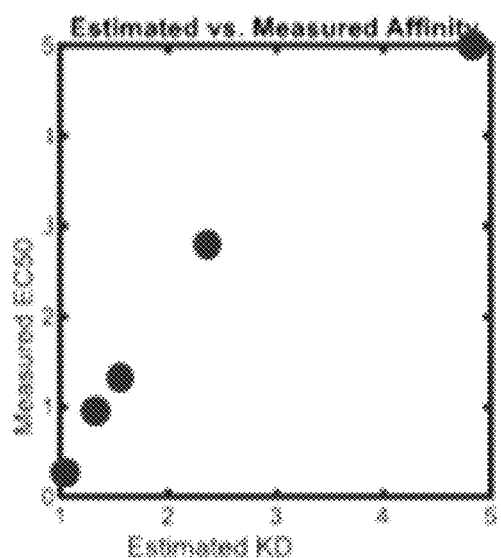

FIG. 197 depicts that estimated KD values based on model depicted in FIG. 1 correlate linearly with experimentally measured EC50 values for binding.

Figure 198:
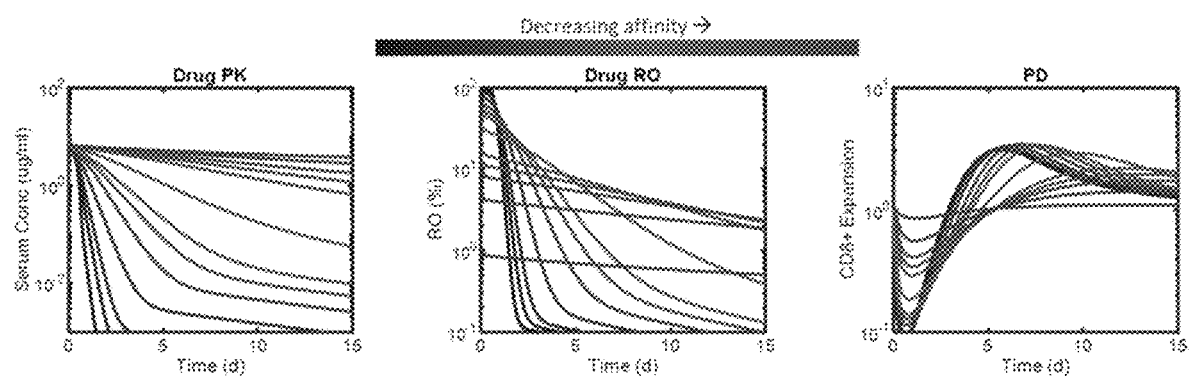

FIG. 198 depicts simulated PK profiles, receptor occupancy (RO) curves, and pharmacodynamic profiles based on the model depicted in FIG. 195. The model demonstrates that reduced potency prolongs exposure, and that an optimal KD exists for maximal pharmacodynamic (i.e., T cell expansion).

FIG. 199A-FIG. 199F depict correlation between A) predicted RO-AUC values with experimentally determined PD-AUC (pharmacodynamic AUC), B) predicted RO-AUC values with experimentally determined PD-Max (peak CD8+ T cell counts), C) predicted RO-AUC values with experimentally determined ALB-min (nadir serum albumin concentration), D) predicted RO-Max (maximum receptor occupancy) values with experimentally determined PD-AUC, E) predicted RO-Max with experimentally determined PD-Max, and F) predicted RO-Max with experimentally determined ALB-Min. Remarkably, the predicted RO-AUC values correlate very well with experimentally determined PD-AUC and PD-max, while the predicted RO-Max values correlate very well with experimentally determined ALB-Min.

Figure 200:
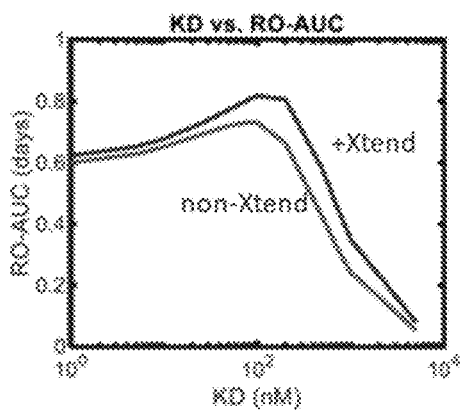

FIG. 200 depicts a simulation scan (based on the model depicted in FIG. 195) over a variety of $K_D$ values was performed for either Xtend or non-Xtend versions of IL-15/Rα-heteroFc fusions, revealing that the predicted optimal $K_D$ is approximately 200 nM, similar to the estimated $K_D$ value of XmAb24306.

Figure 201A:
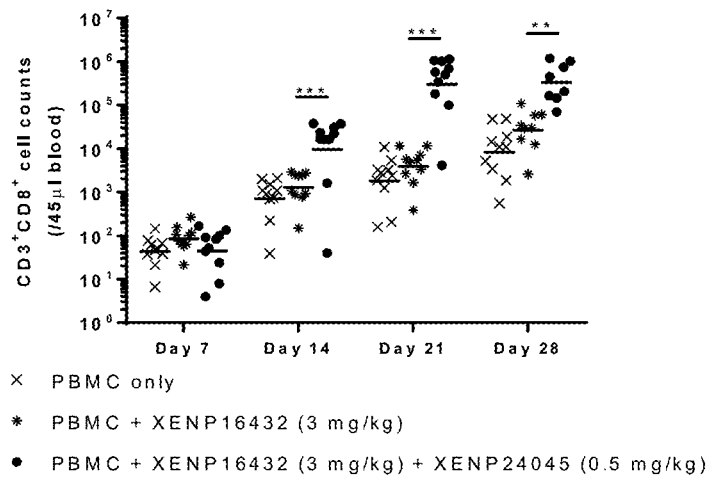
Figure 201B:
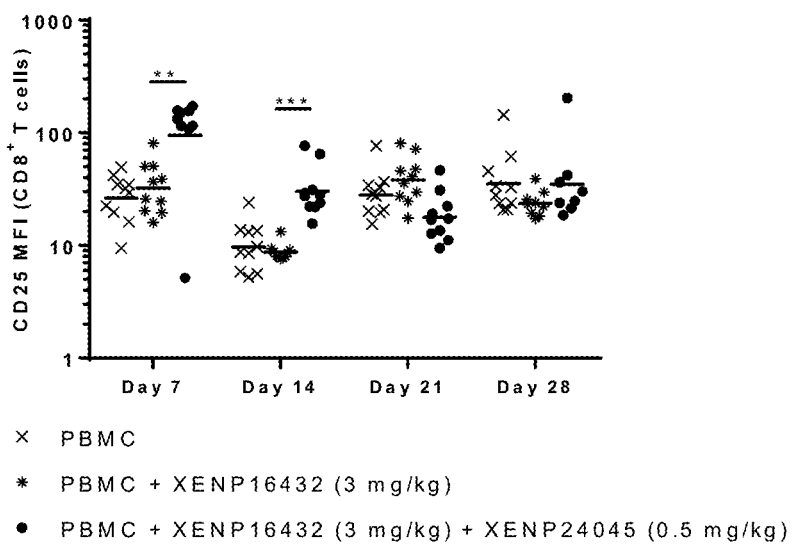

FIG. 201A and FIG. 201B depict A) human CD8+ T cell counts and B) CD25 expression on human CD8+ T cells in pp65-MCF7 and huPBMC-engrafted NSG mice dosed with XENP16432 and/or XENP24045. * indicates p≤0.001 and  indicates p≤0.01 as determined by an unpaired t-test. It was found that treatment with the combination of XENP24045 and anti-PD-1 mAb significantly enhanced CD8+ T cell expansion on later days, and induced earlier activation of CD8+ T cells.

Figure 202A:
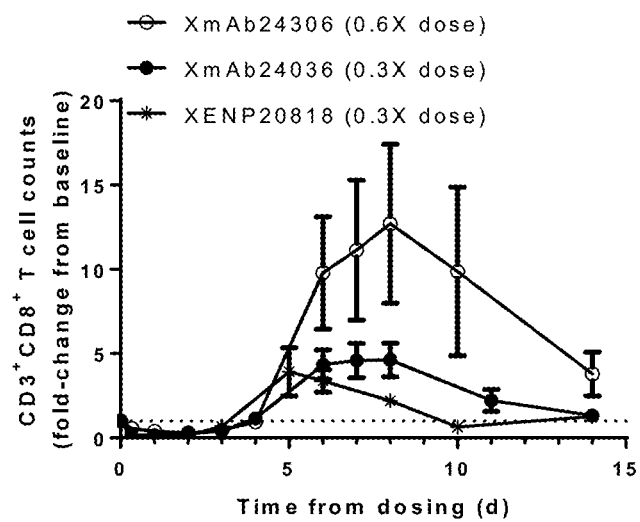
Figure 202B:
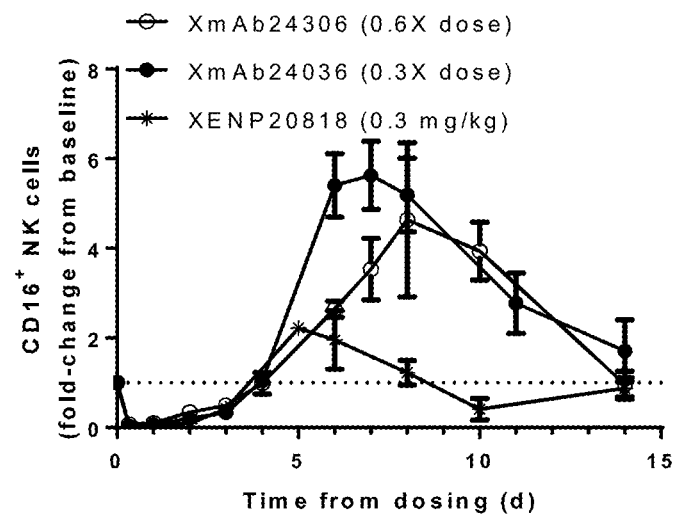
Figure 202C:
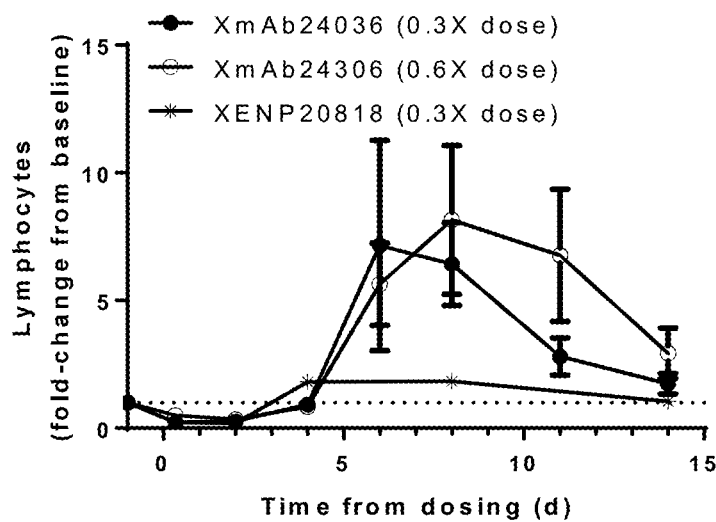

FIG. 202A-FIG. 202C depict expansion of A) CD8+ T cells, B) CD16+ NK cells, and C) lymphocytes in cynomolgus monkeys following dosing with 0.3× dose XENP20818, 0.3× dose XmAb24306, and 0.6× dose XmAb24306. The data shows enhanced pharmacodynamics conferred by reduced-potency XmAb24306.

Figure 203:
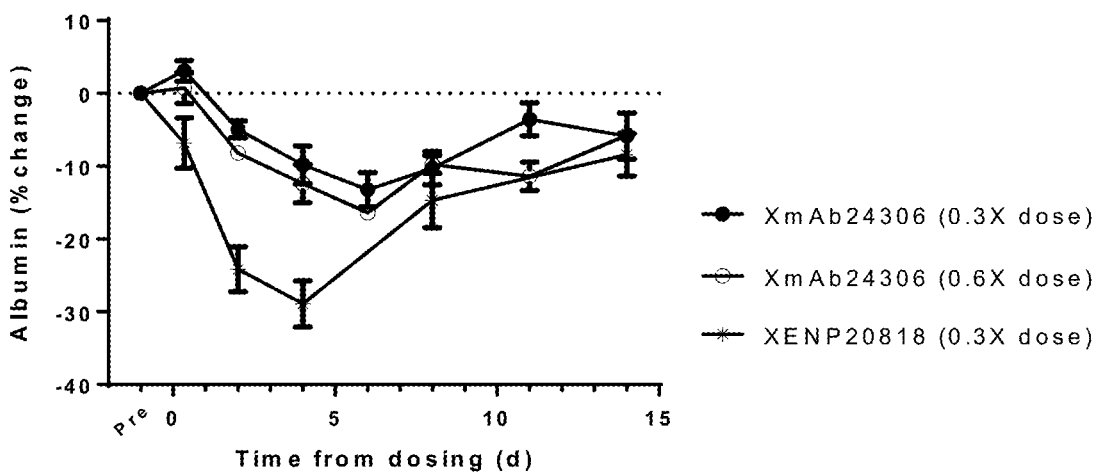
Figures 204A, 204B, 204C, 204D, 204E, 204F:
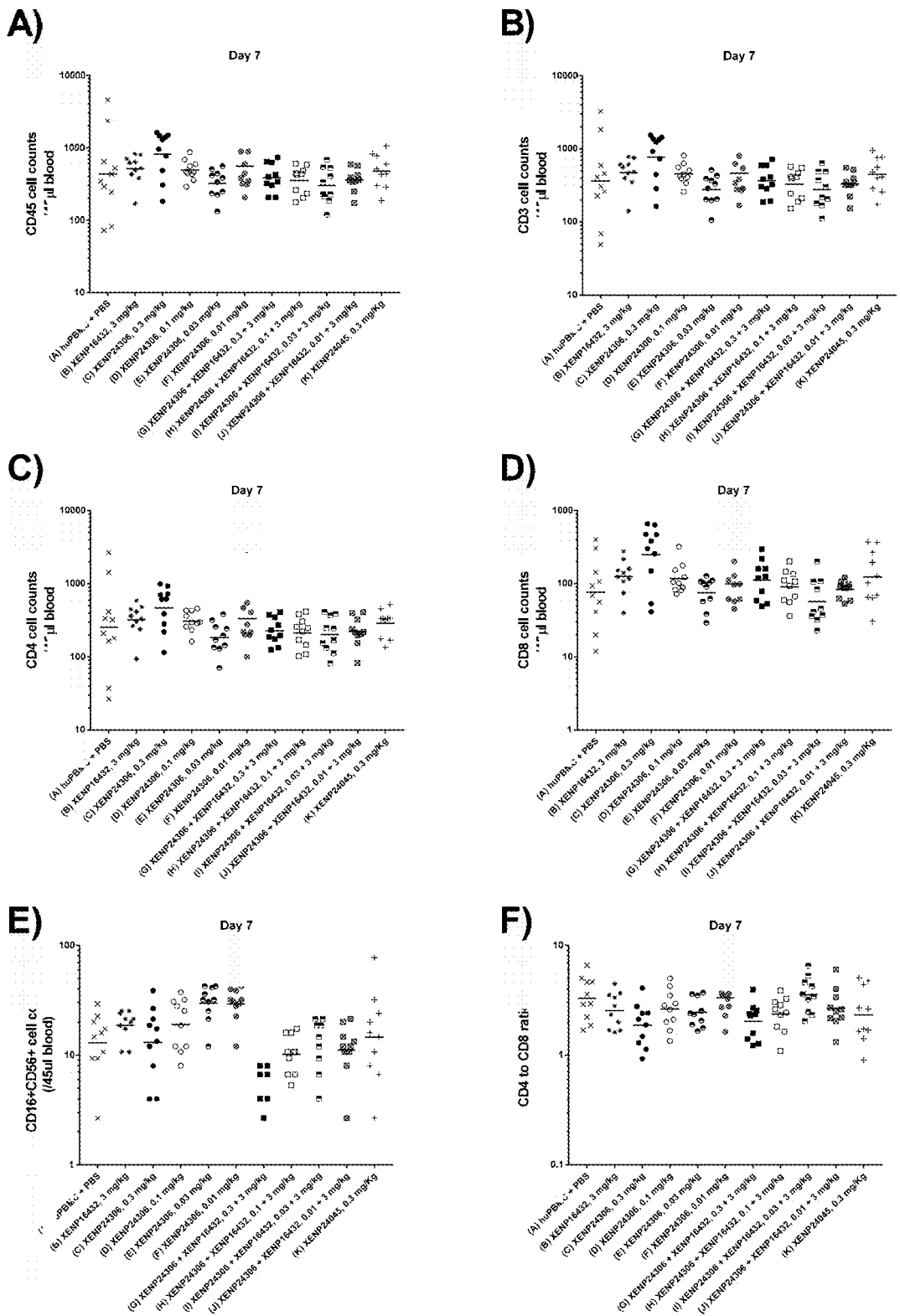
Figures 205A, 205B, 205C, 205D, 205E, 205F:
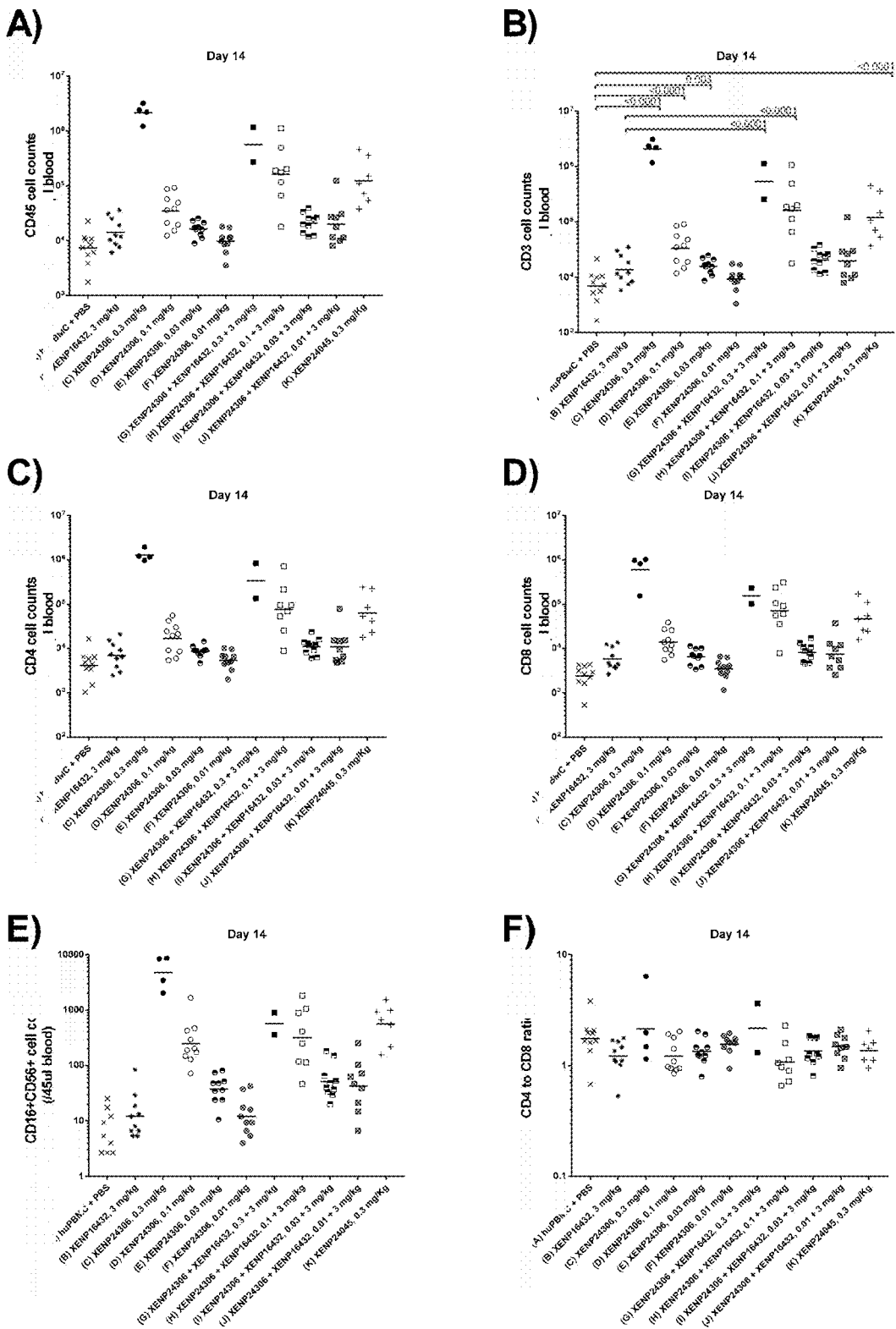
Figures 206A, 206B, 206C, 206D, 206E, 206F:
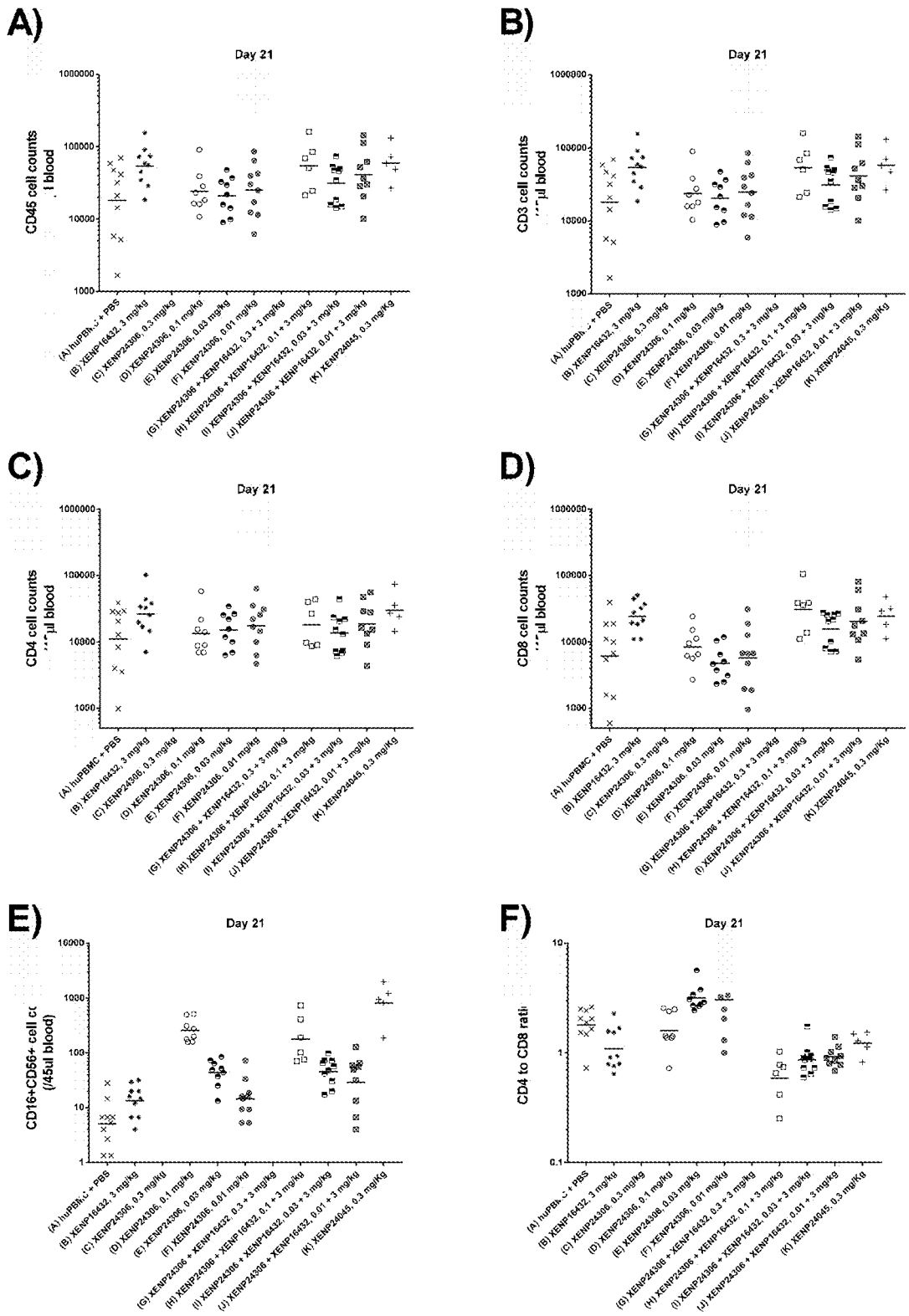
Figures 207A, 207B, 207C, 207D:
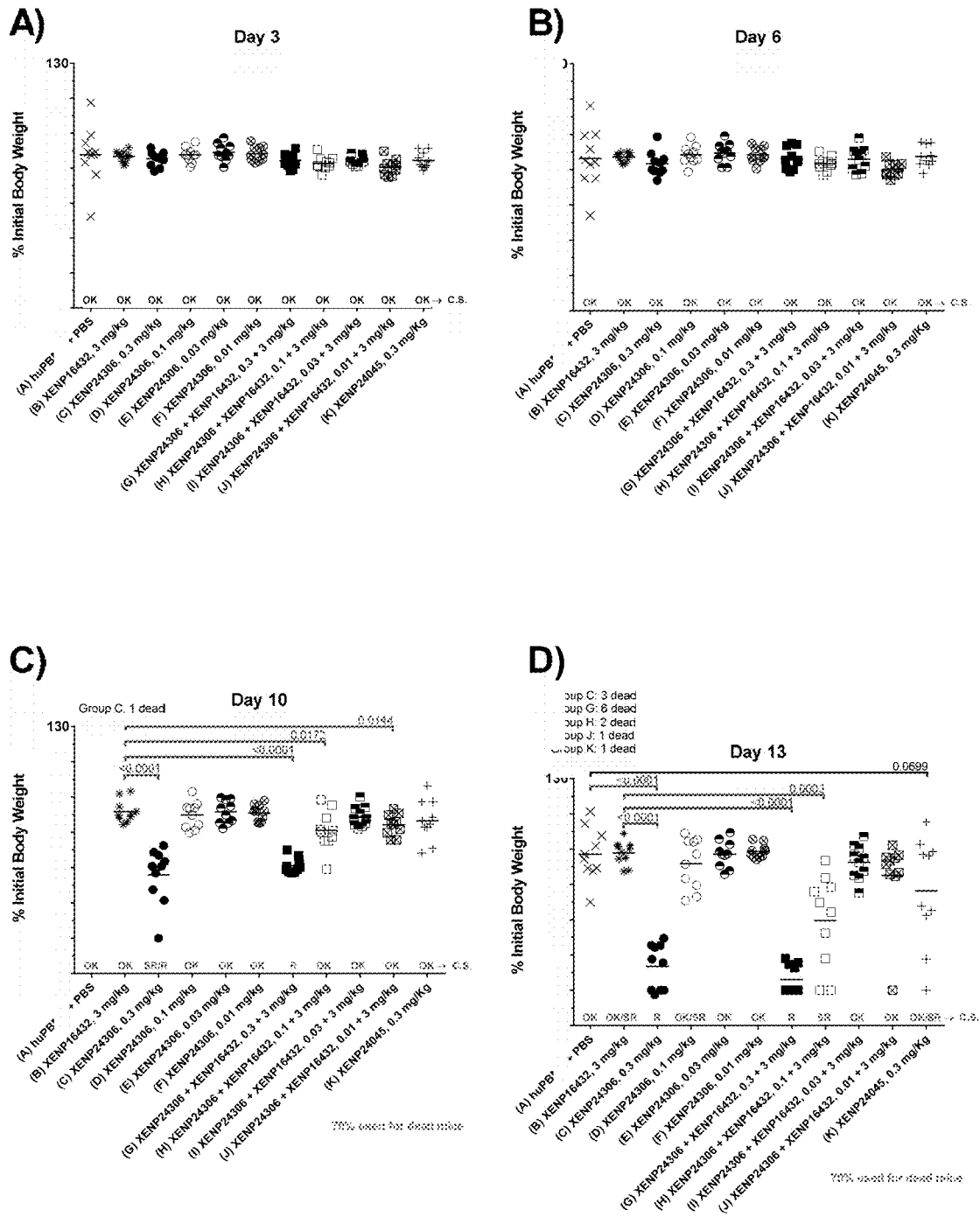
Figures 207E, 207F, 207G, 207H:
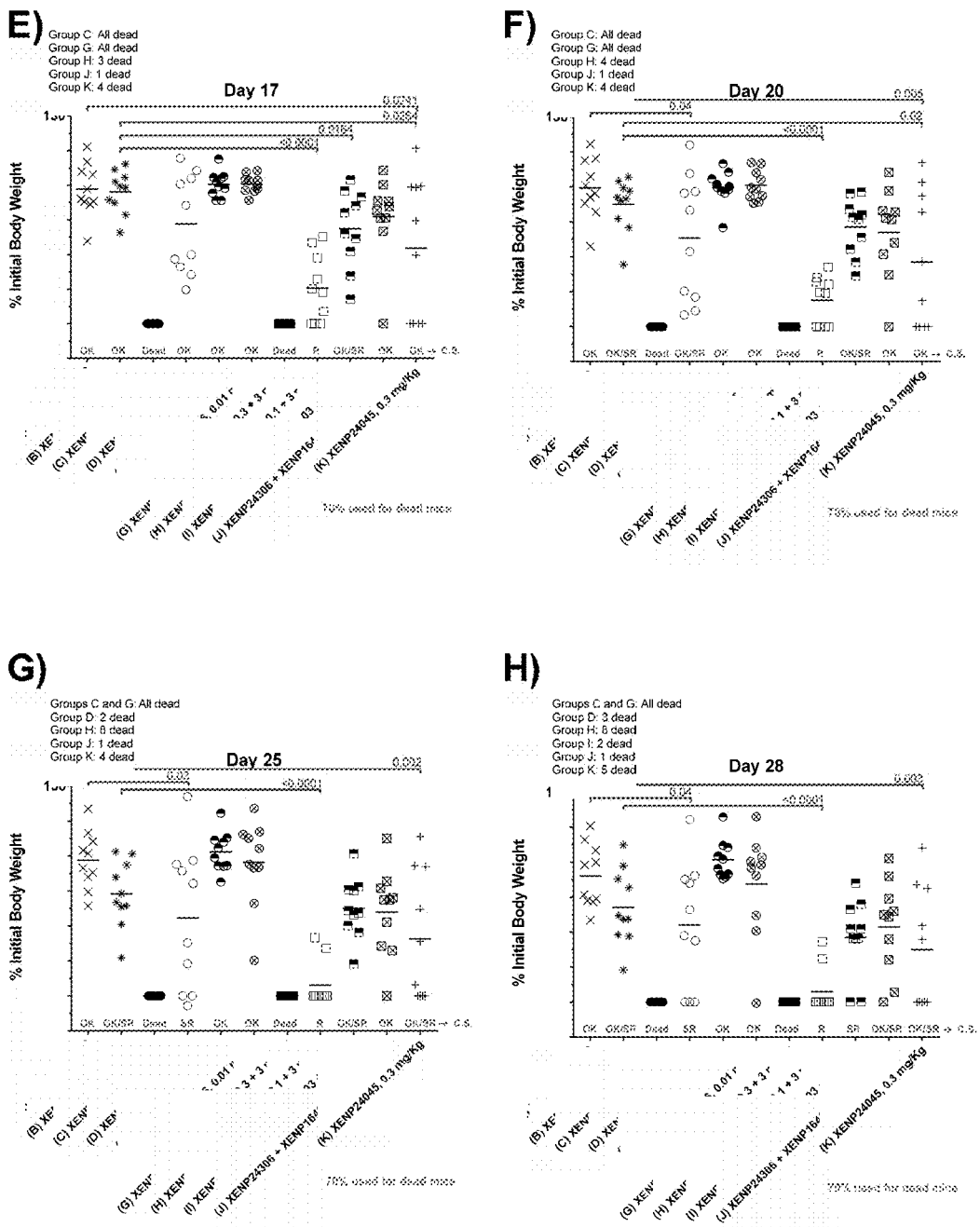
Figure 207I:
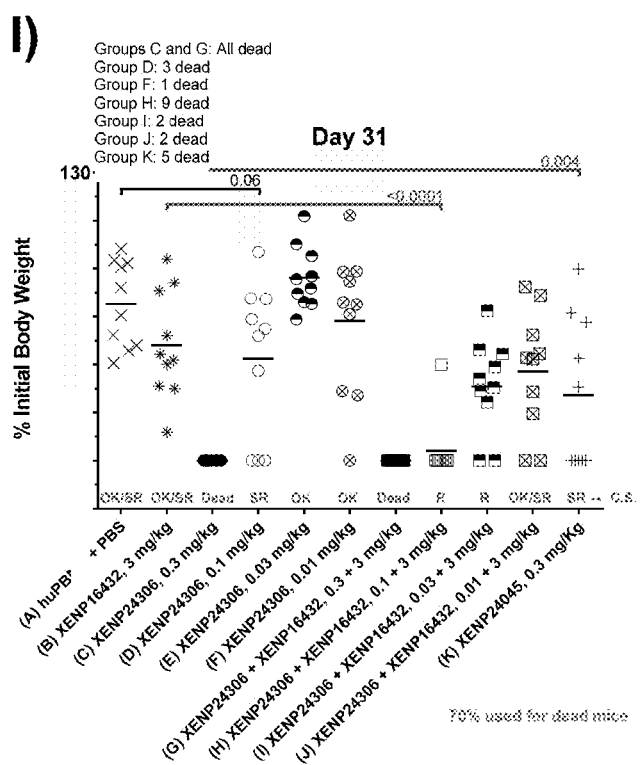

FIG. 203 depicts the percent change in serum albumin (as an indicator of vascular leak) in cynomolgus monkeys following dosing with 0.3× dose XENP20818, 0.3× dose XmAb24306, and 0.6× dose XmAb24306. The data shows enhanced tolerability (as indicated by reduction in albumin drop) conferred by reduced-potency XmAb24306.

FIG. 204A-FIG. 204F depict A) CD45+ cell, B) CD3+ T cell, C) CD4+ T cell, D) CD8+ T cell, E) CD16+CD56+ NK cell counts, and F) CD4 to CD8 ratio in blood of huPBMC-engrafted NSG mice on Day 7 after the first dosing with the indicated test articles at the indicated concentrations.

FIG. 205A-FIG. 205F depict A) CD45+ cell, B) CD3+ T cell, C) CD4+ T cell, D) CD8+ T cell, E) CD16+CD56+ NK cell counts, and F) CD4 to CD8 ratio in blood of huPBMC-engrafted NSG mice on Day 14 after the first dosing with the indicated test articles at the indicated concentrations. The data show that by Day 14, treatment with a combination of 0.3 mg/kg or 0.1 mg/kg XENP24306 and 3 mg/kg XENP16432 significantly enhanced CD3+ T cell expansion beyond treatment with 3 mg/kg XENP16432 alone (statistics were performed on log-transformed data using unpaired t-test).

FIG. 206A-FIG. 206F depict A) CD45+ cell, B) CD3+ T cell, C) CD4+ T cell, D) CD8+ T cell, E) CD16+CD56+ NK cell counts, and F) CD4 to CD8 ratio in blood of huPBMC-engrafted NSG mice on Day 21 after the first dosing with the indicated test articles at the indicated concentrations.

FIG. 207A-207I depict the change in body weight (as an indicator of GVHD) of huPBMC-engrafted NSG mice on A) Day 3, B) Day 6, C) Day 10, D) Day 13, E) Day 17, F) Day 20, G) Day 25, H) Day 28, and I) Day 29 after the first dosing with the indicated test articles at the indicated concentrations. The data show that by Day 10, treatment with a combination of 0.3 mg/kg, 0.1 mg/kg, or 0.01 mg/kg XENP24306 and 3 mg/kg XENP16432 significantly enhanced GVHD beyond treatment with 3 mg/kg XENP16432 alone (statistics were performed using unpaired t-test).

Figure 208:
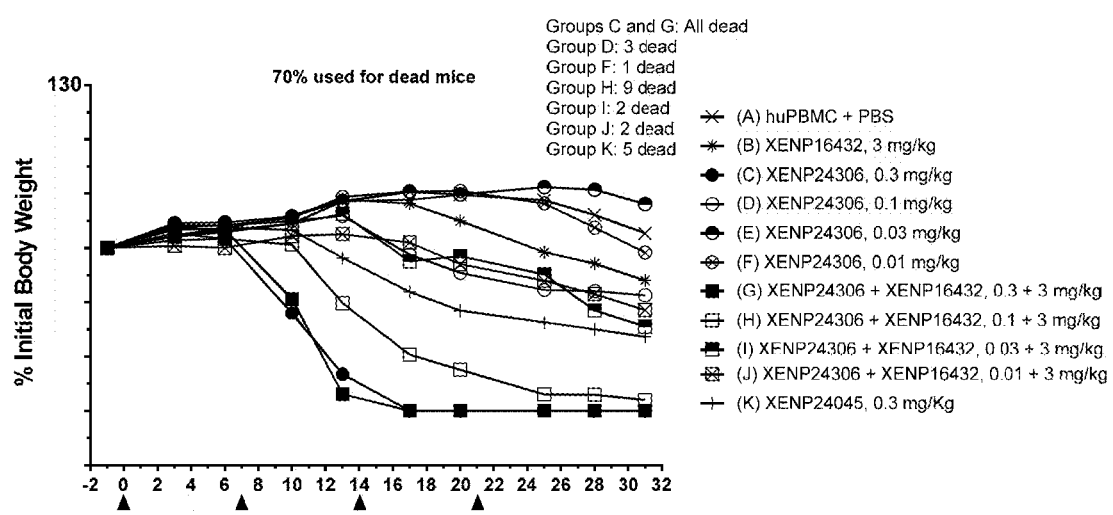

FIG. 208 depicts the change in body weight (as an indicator of GVHD) of huPBMC-engrafted NSG mice over time after dosing with the indicating test articles at the indicated concentrations.

Figure 209A:
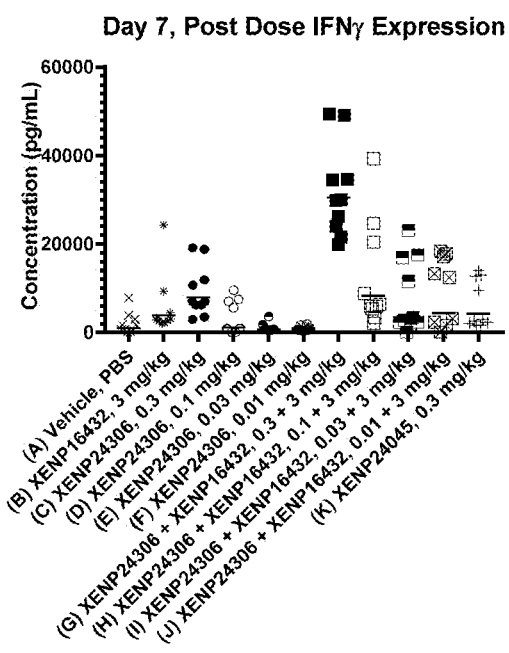
Figure 209B:
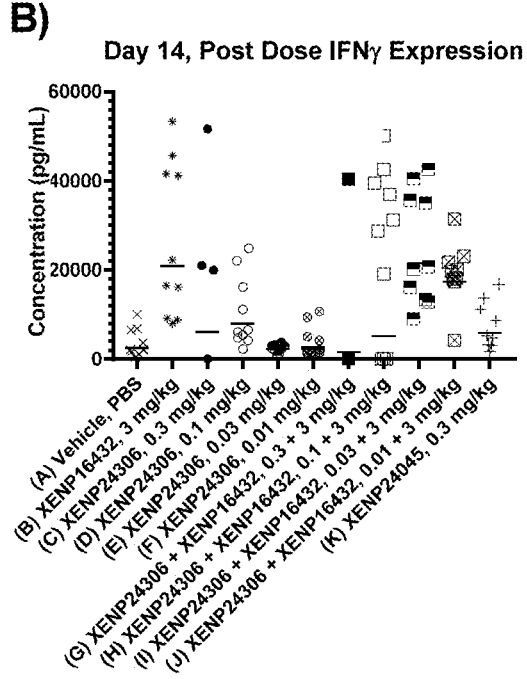
Figure 209C:
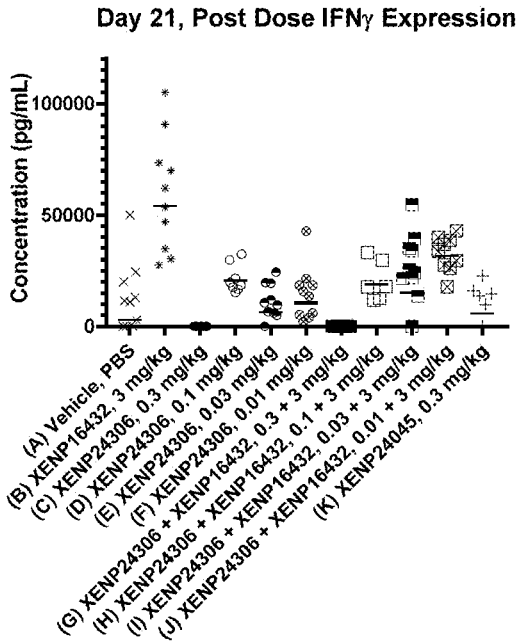

FIG. 209A-FIG. 209C depict serum IFNγ concentration in huPBMC-engrafted NSG mice on A) Day 7, B) Day 14, and C) Day 21 after the first dosing with the indicated test articles at the indicated concentrations.

Figures 210A, 210B, 210C, 210D, 210E, 210F:
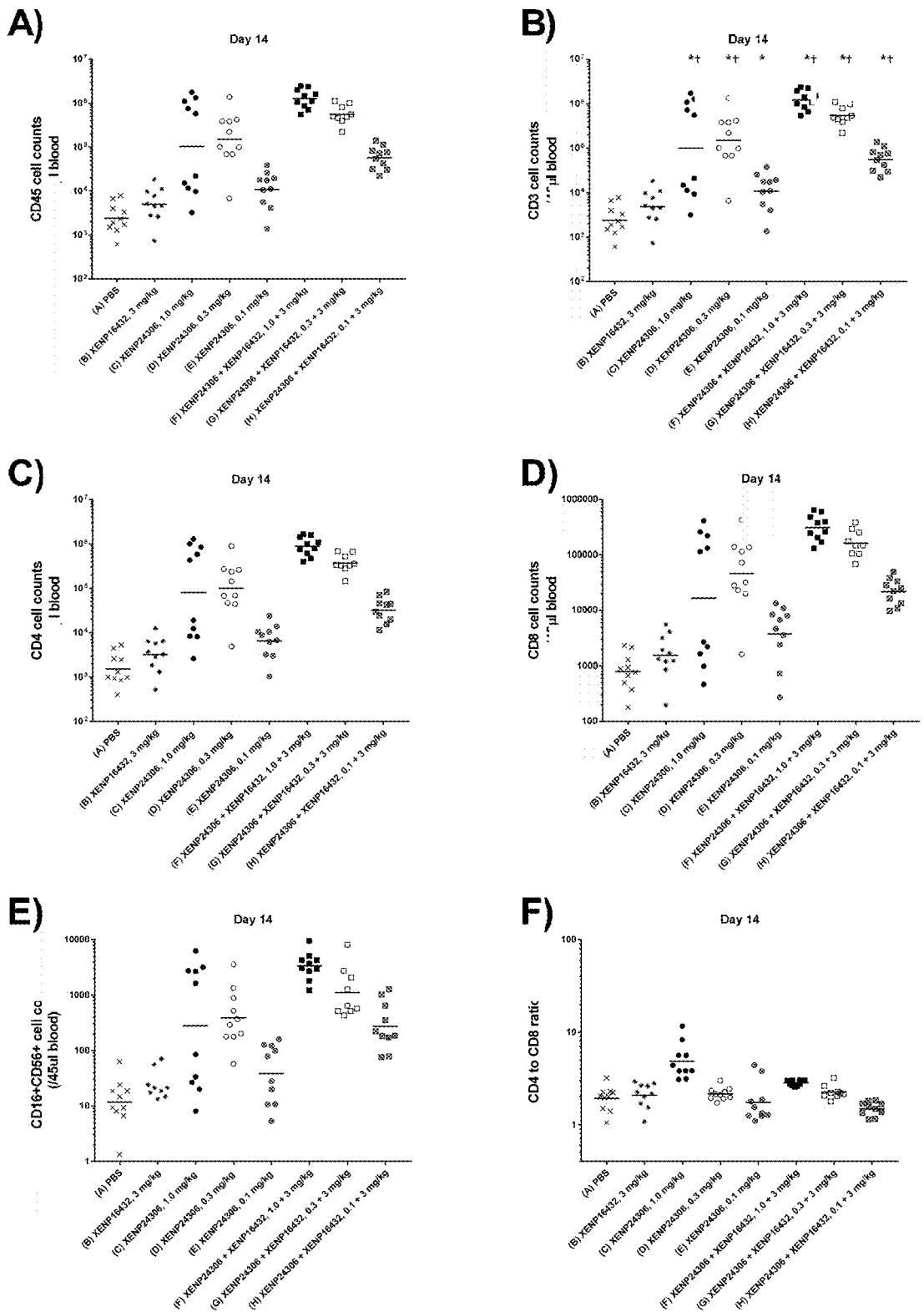
Figures 211A, 211B, 211C, 211D, 211E, 211F:
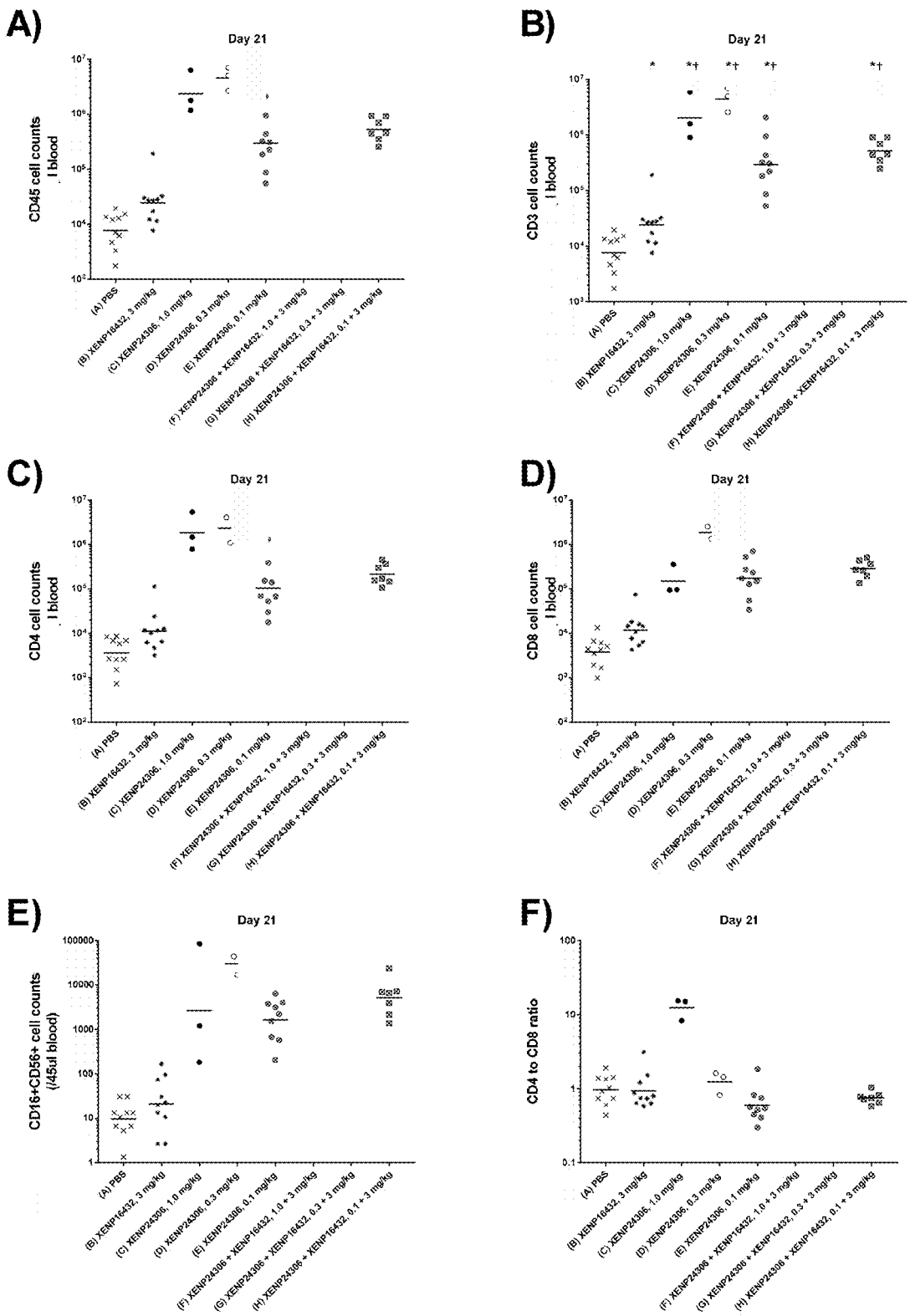
Figures 212A, 212B, 212C, 212D:
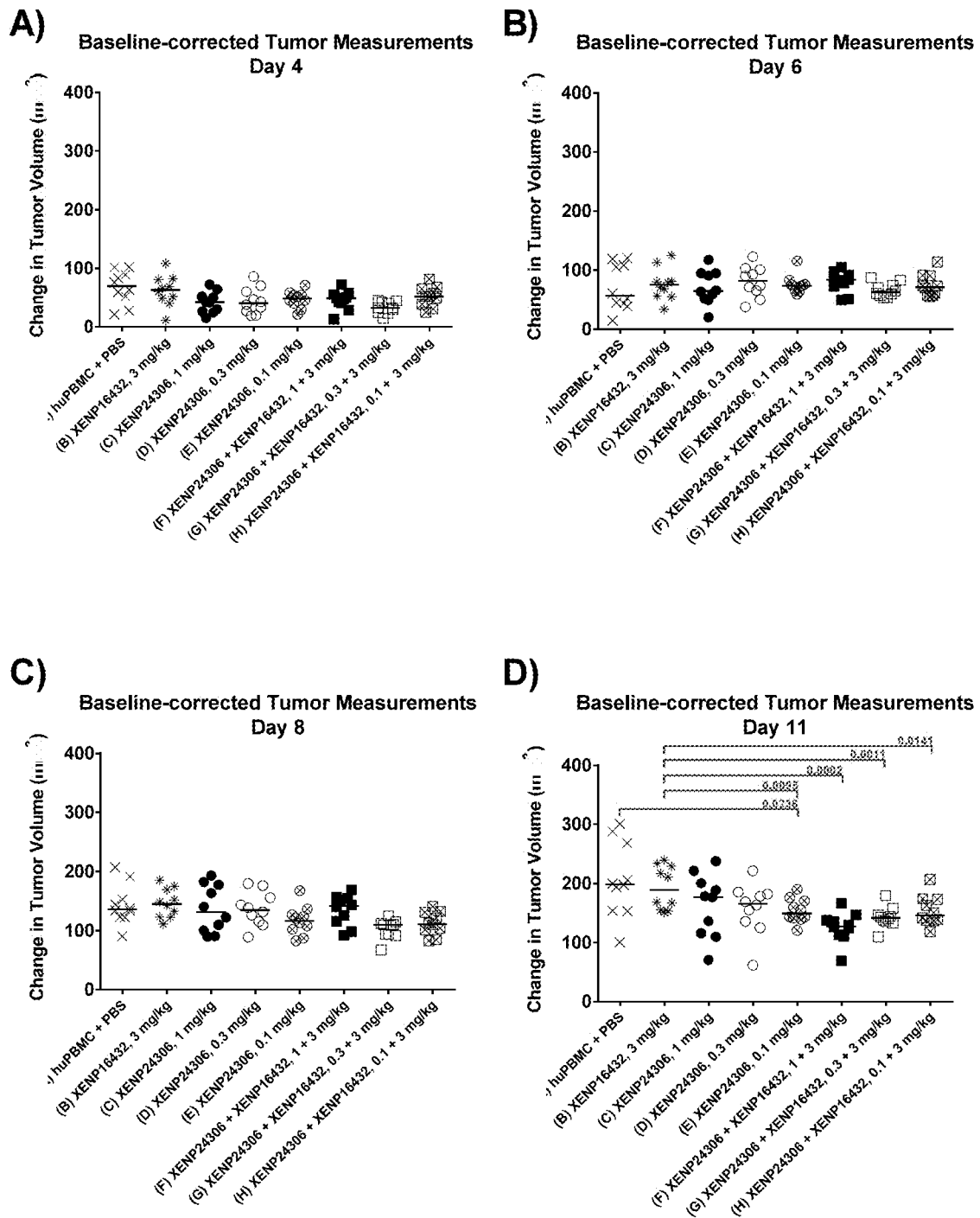
Figures 212E, 212F, 212G, 212H:
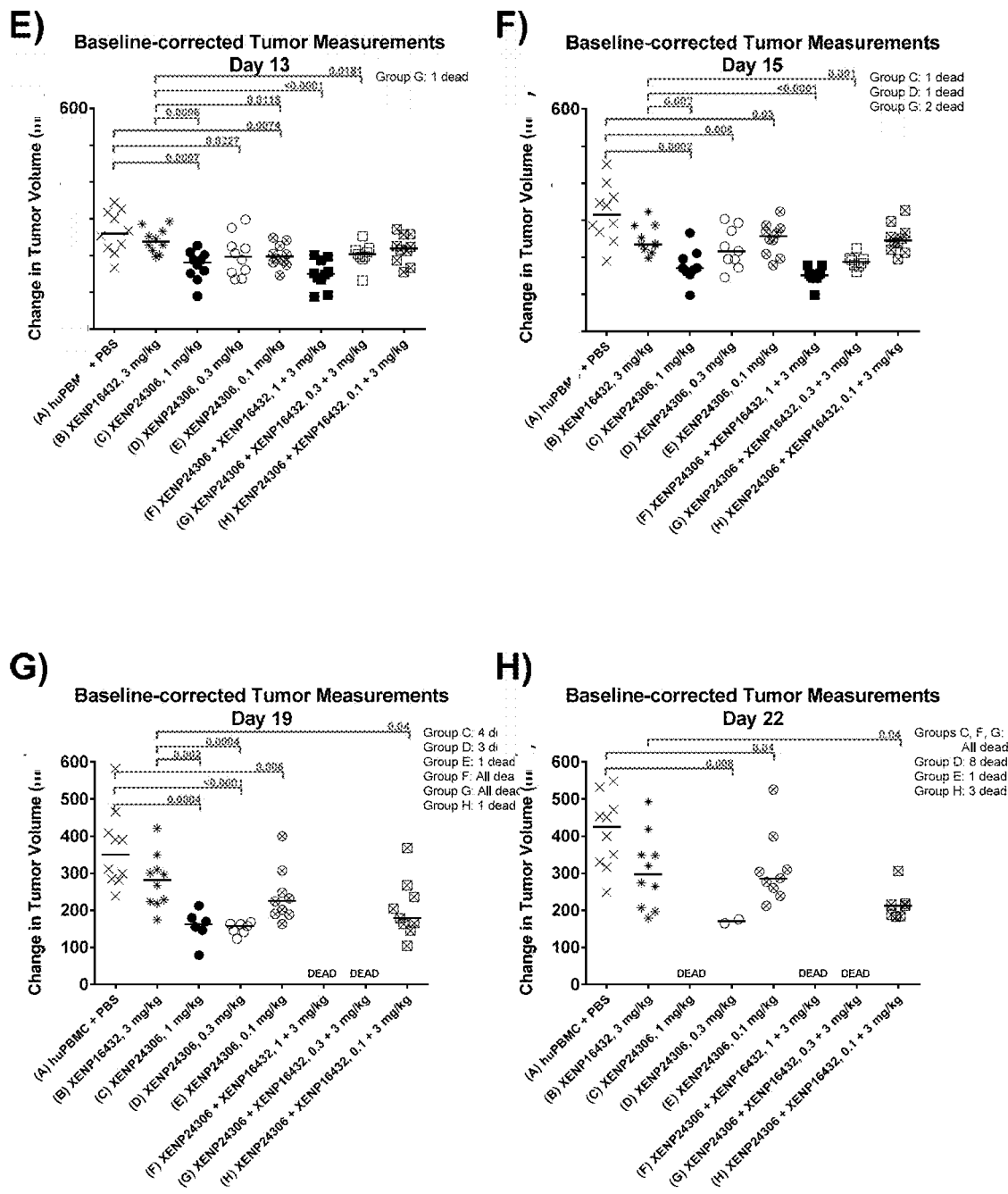
Figure 212I:
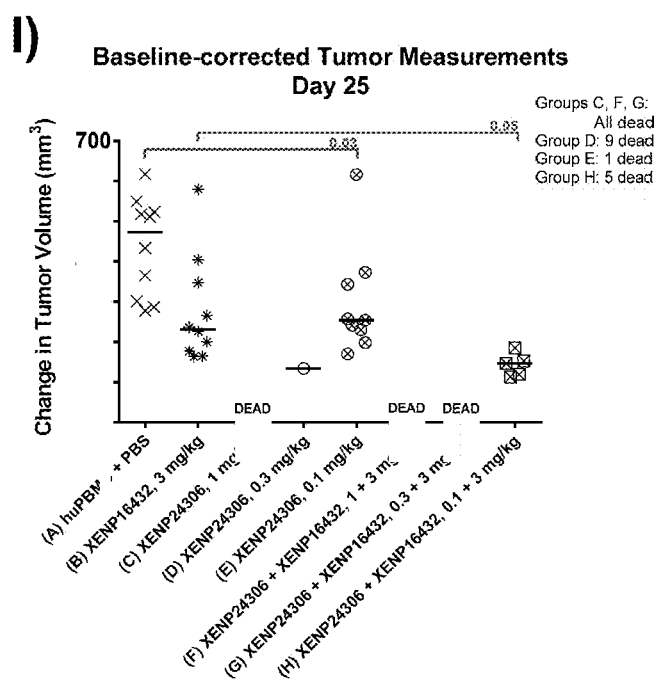

FIG. 210A-FIG. 201F depict A) CD45+ cell, B) CD3+ T cell, C) CD4+ T cell, D) CD8+ T cell, E) CD16+CD56+ NK cell counts, and F) CD4 to CD8 ratio in blood of pp65-MCF-7 and huPBMC-engrafted NSG mice on Day 14 after the first dosing with the indicated test articles at the indicated concentrations. * denotes p<0.05, unpaired t-test, indicated group in comparison to PBS-treated group; † denotes p<0.04, unpaired t-test, indicated group in comparison to XENP16432-treated group. Data were log-transformed prior to statistical analysis. The data show that by Day 14, each of the groups treated with XENP24306 alone or XENP24306 in combination with XENP16432 significantly enhanced lymphocyte expansion beyond PBS-treatment. Notably, by Day 14, each of the groups treated with a combination of XENP24306 and XENP16432, irrespective of XENP24306 concentration, as well as higher concentrations of XENP24306 alone significantly enhanced lymphocyte expansion beyond XENP16432-treatment.

FIG. 211A-FIG. 211F depict A) CD45+ cell, B) CD3+ T cell, C) CD4+ T cell, D) CD8+ T cell, E) CD16+CD56+ NK cell counts, and F) CD4 to CD8 ratio in blood of pp65-MCF-7 and huPBMC-engrafted NSG mice on Day 21 after the first dosing with the indicated test articles at the indicated concentrations. * denotes p<0.05, unpaired t-test, indicated group in comparison to PBS-treated group; † denotes p<0.04, unpaired t-test, indicated group in comparison to XENP16432-treated group. Data were log-transformed prior to statistical analysis.

FIG. 212A-FIG. 212I depict the change in tumor volume (baseline-corrected) in pp65-MCF-7 and huPBMC-engrafted NSG mice on A) Day 4, B) Day 6, C) Day 8, D) Day 11, E) Day 13, F) Day 15, G) Day 19, H) Day 22, and I) Day 25 after the first dosing with the indicated test articles at the indicated concentrations. The data show that by Day 11, treatment with a combination of 1.0 mg/kg, 0.3 mg/kg, or 0.1 mg/kg XENP24306 and 3 mg/kg XENP16432 significantly decreased tumor volume in comparison to treatment with XENP16432 alone (statistics were performed using unpaired t-test on baseline corrected tumor measurements).

Figure 213A:
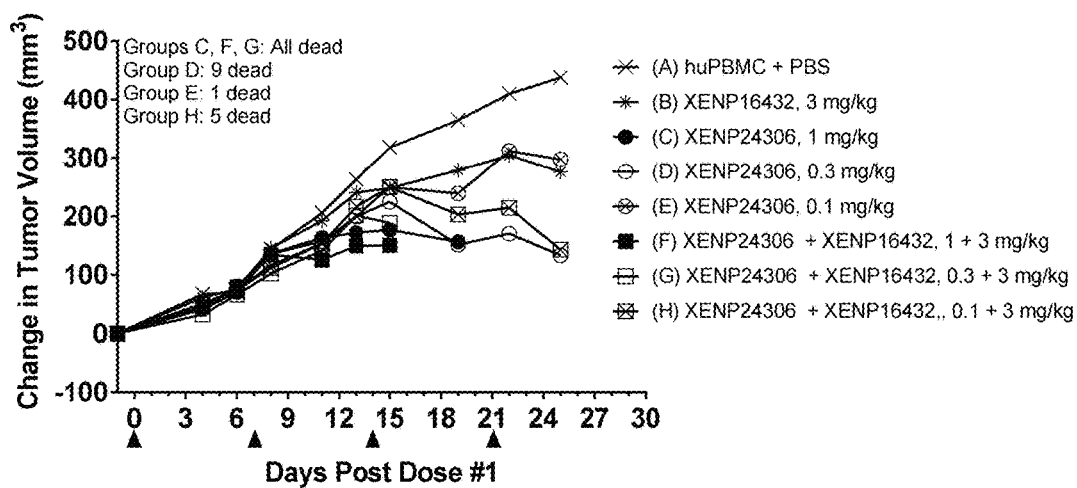
Figure 213B:
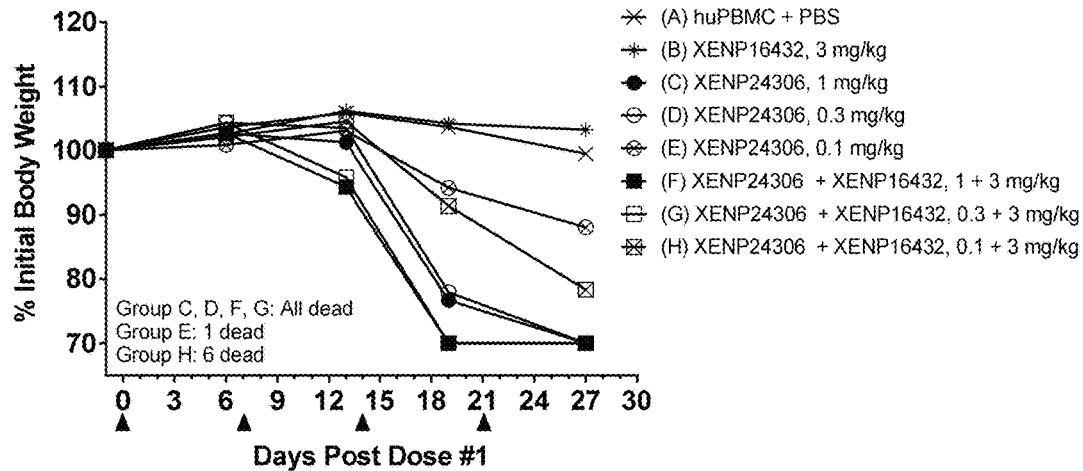

FIG. 213A-FIG. 213B depict the A) change in tumor volume and B) change in body weight (as an indicator of GVHD) of pp65-MCF-7 and huPBMC-engrafted NSG mice over time after dosing with the indicating test articles at the indicated concentrations. The data indicates that although all mice were dead in Groups C, F, and G, this corresponded to GVHD (as indicated by change in body weight).

Figures 214A, 214B, 214C:
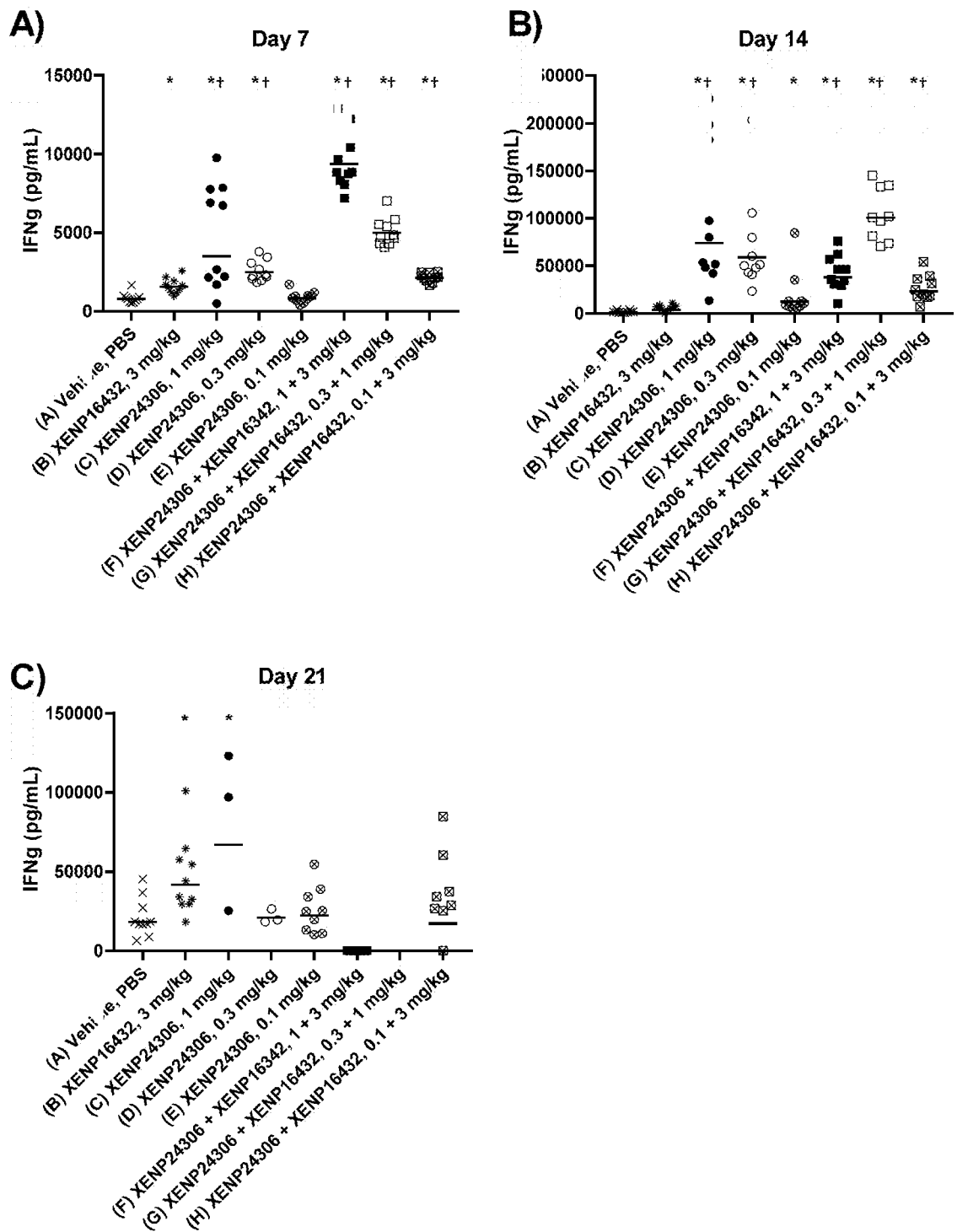

FIG. 214A-FIG. 214C depict serum IFNγ concentration in pp65-MCF-7 and huPBMC-engrafted NSG mice on A) Day 7, B) Day 14, and C) Day 21 after the first dosing with the indicated test articles at the indicated concentrations. * denotes p<0.05, unpaired t-test, indicated group in comparison to PBS-treated group; † denotes p<0.04, unpaired t-test, indicated group in comparison to XENP16432-treated group. Data were log-transformed prior to statistical analysis. The data show that by Day 7, treatment with a combination of 1.0 mg/kg, 0.3 mg/kg, or 0.1 mg/kg XENP24306 and 3 mg/kg XENP16432 significantly enhanced IFNγ secretion in comparison to treatment with XENP16432 alone.

DETAILED DESCRIPTION OF THE INVENTION

I. Definitions

In order that the application may be more completely understood, several definitions are set forth below. Such definitions are meant to encompass grammatical equivalents.

By "ablation" herein is meant a decrease or removal of binding and/or activity. Thus for example, "ablating FcγR binding" means the Fc region amino acid variant has less than 50% starting binding as compared to an Fc region not containing the specific variant, with less than 70-80-90-95-98% loss of binding being preferred, and in general, with the binding being below the level of detectable binding in a Biacore assay. Of particular use in the ablation of FcγR binding are those variants shown in FIG. 5. However, unless otherwise noted, the Fc monomers of the invention retain binding to the FcRn.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity. As is discussed herein, many embodiments of the invention ablate ADCC activity entirely.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g., the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y or 272Y refers to a variant polypeptide, in this case an Fc variant, in which the glutamic acid at position 272 is replaced with tyrosine. For clarity, a protein which has been engineered to change the nucleic acid coding sequence, but not to change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution. Substitutions can include naturally occurring amino acids and, in some cases, synthetic amino acids. Examples include U.S. Pat. No. 6,586,207; WO 98/48032; WO 03/073238; US2004-0214988A1; WO 05/35727A2; WO 05/74524A2; J. W. Chin et al., (2002), Journal of the American Chemical Society 124:9026-9027; J. W. Chin, & P. G. Schultz, (2002), ChemBioChem 11:1135-1137; J. W. Chin, et al., (2002), PICAS United States of America 99:11020-11024; and, L. Wang, & P. G. Schultz, (2002), Chem. 1-10, all entirely incorporated by reference.

By "amino acid insertion" or "insertion" as used herein is meant the addition of an amino acid residue or sequence at a particular position in a parent polypeptide sequence. For example, −233E designates an insertion of glutamic acid after position 233 and before position 234. Additionally, −233ADE or A233ADE designates an insertion of AlaAspGlu after position 233 and before position 234.

By "amino acid deletion" or "deletion" as used herein is meant the removal of an amino acid residue or sequence at a particular position in a parent polypeptide sequence. For example, E233, E233#, E233( ) or E233del designates a deletion of glutamic acid at position 233. Additionally, EDA233- or EDA233# designates a deletion of the sequence GluAspAla that begins at position 233.

By "variant protein," "protein variant", or "variant" as used herein is meant a protein that differs from that of a parent protein by virtue of at least one amino acid modification. Protein variant may refer to the protein itself, a composition comprising the protein, the amino sequence that encodes it, or the DNA or nucleic acid sequence that encodes it. Preferably, the protein variant has at least one amino acid modification compared to the parent protein, e.g., from about one to about seventy amino acid modifications, and preferably from about one to about five amino acid modifications compared to the parent. The medication can be an addition, deletion, or substitution. As described below, in some embodiments the parent polypeptide, for example an Fc parent polypeptide, is a human wild type sequence, such as the Fc region from IgG1, IgG2, IgG3 or IgG4, although human sequences with variants can also serve as "parent polypeptides", for example the IgG1/2 hybrid can be included. The protein variant sequence herein will preferably possess at least about 80% identity with a parent protein sequence, and most preferably at least about 90% identity, more preferably at least about 95-98-99% identity.

Accordingly, by "antibody variant" or "variant antibody" as used herein is meant an antibody that differs from a parent antibody by virtue of at least one amino acid modification, by "IgG variant" or "variant IgG" as used herein is meant an antibody that differs from a parent IgG (again, in many cases, from a human IgG sequence) by virtue of at least one amino acid modification, and by "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The modification can be an addition, deletion, or substitution. The Fc variants of the present invention are defined according to the amino acid modifications that compose them. Thus, for example, N434S or 434S is an Fc variant with the substitution for a serine residue at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, 428L/434S is the same Fc variant as 434S/428L, and so on. For all positions discussed in the present invention that relate to antibodies, or derivatives and fragments thereof, unless otherwise noted, amino acid position numbering is according to the EU index. The EU index or EU index as in Kabat or EU numbering scheme refers to the numbering of the EU antibody (Edelman et al., 1969, Proc Natl Acad Sci USA 63:78-85, hereby entirely incorporated by reference). The modification can be an addition, deletion, or substitution. Substitutions can include naturally occurring amino acids and, in some cases, synthetic amino acids.

As used herein, by "protein" is meant at least two covalently attached amino acids, which includes proteins, polypeptides, oligopeptides and peptides. The peptidyl group may comprise naturally occurring amino acids and peptide bonds, or synthetic peptidomimetic structures, i.e. "analogs", such as peptoids (see Simon et al., PNAS USA 89(20):9367 (1992), entirely incorporated by reference). The amino acids may either be naturally occurring or synthetic (e.g. not an amino acid that is coded for by DNA); as will be appreciated by those in the art. For example, homophenylalanine, citrulline, ornithine and noreleucine are considered synthetic amino acids for the purposes of the invention, and both D- and L-(R or S) configured amino acids may be utilized. The variants of the present invention may comprise modifications that include the use of synthetic amino acids incorporated using, for example, the technologies developed by Schultz and colleagues, including but not limited to methods described by Cropp & Shultz, 2004, Trends Genet. 20(12):625-30, Anderson et al., 2004, Proc Natl Acad Sci USA 101 (2):7566-71, Zhang et al., 2003, 303(5656):371-3, and Chin et al., 2003, Science 301(5635): 964-7, all entirely incorporated by reference. In addition, polypeptides may include synthetic derivatization of one or more side chains or termini, glycosylation, PEGylation, circular permutation, cyclization, linkers to other molecules, fusion to proteins or protein domains, and addition of peptide tags or labels. Wherein a biologically functional molecule comprises two or more proteins, each protein may be referred to as a "monomer" or as a "subunit" or as a "domain"; and the biologically functional molecule may be referred to as a "complex".

By "residue" as used herein is meant a position in a protein and its associated amino acid identity. For example, Asparagine 297 (also referred to as Asn297 or N297) is a residue at position 297 in the human antibody IgG1.

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the IgGs comprise a serine at position 434, the substitution 434S in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "IgG Fc ligand" or "Fc ligand" as used herein is meant a molecule, preferably a polypeptide, from any organism that binds to the Fc region of an IgG antibody to form an Fc/Fc ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136, entirely incorporated by reference). Fc ligands may include undiscovered molecules that bind Fc. Particular IgG Fc ligands are FcRn and Fc gamma receptors.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "FcRn" or "neonatal Fc receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin (β2-microglobulin) and the heavy chain is encoded by the FcRn gene. Unless otherwise noted herein, FcRn or an FcRn protein refers to the complex of FcRn heavy chain with 02-microglobulin. A variety of Fc variants can be used to increase binding to the FcRn, and in some cases, to increase serum half-life. In general, unless otherwise noted, the Fc monomers of the invention retain binding to the FcRn (and, as noted below, can include amino acid variants to increase binding to the FcRn).

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "Fc" or "Fc region" or "Fc domain" as used herein is meant the polypeptide comprising the constant region of an antibody, in some instances, excluding all or a portion of the first constant region immunoglobulin domain (e.g., CH1) or a portion thereof, and in some cases, further excluding all or a portion of the hinge. Thus, an Fc can refer to the last two constant region immunoglobulin domains (e.g., CH2 and CH3) of IgA, IgD, and IgG, the last three constant region immunoglobulin domains of IgE and IgM, and optionally, all or a portion of the flexible hinge N-terminal to these domains. For IgA and IgM, Fc may include the J chain. For IgG, the Fc domain comprises immunoglobulin domains CH2 and CH3 (C72 and C73) and the lower hinge region between CH1 (C71) and CH2 (C72). Although the boundaries of the Fc region may vary, the human IgG heavy chain Fc region is usually defined to include residues E216, C226, or A231 to its carboxyl-terminus, wherein the numbering is according to the EU index as in Kabat. In some embodiments, as is more fully described below, amino acid modifications are made to the Fc region, for example to alter binding to one or more FcγR or to the FcRn.

As will be appreciated by those in the art, the exact numbering and placement of the heavy constant region domains can be different among different numbering systems. A useful comparison of heavy constant region numbering according to EU and Kabat is as below, see Edelman et al., 1969, Proc Natl Acad Sci USA 63:78-85 and Kabat et al., 1991, Sequences of Proteins of Immunological Interest, 5th Ed., United States Public Health Service, National Institutes of Health, Bethesda, entirely incorporated by reference.

TABLE 1

|  | EU Numbering | Kabat Numbering |
|---|---|---|
| CH1 | 118-215 | 114-223 |
| Hinge | 216-230 | 226-243 |
| CH2 | 231-340 | 244-360 |
| CH3 | 341-447 | 361-478 |

By "fusion protein" as used herein is meant covalent joining of at least two proteins. Fusion proteins may comprise artificial sequences, e.g. a domain linker, as described herein. By "Fc fusion protein" or "immunoadhesin" herein is meant a protein comprising an Fc region, generally linked (optionally through a domain linker, as described herein) to one or more different proteins, such as to IL-15 and/or IL-15R, as described herein. In some instances, two Fc fusion proteins can form a homodimeric Fc fusion protein or a heterodimeric Fc fusion protein with the latter being preferred. In some cases, one monomer of the heterodimeric Fc fusion protein comprises an Fc domain alone (e.g., an empty Fc domain) and the other monomer is an Fc fusion, comprising a variant Fc domain and a protein domain, such as a receptor, ligand or other binding partner.

By "position" as used herein is meant a location in the sequence of a protein. Positions may be numbered sequentially, or according to an established format, for example the EU index for antibody numbering.

By "strandedness" in the context of the monomers of the heterodimeric proteins of the invention herein is meant that, similar to the two strands of DNA that "match", heterodimerization variants are incorporated into each monomer so as to preserve, create, and/or enhance the ability to "match" to form heterodimers. For example, if some pI variants are engineered into monomer A (e.g., making the pI higher) then steric variants that are "charge pairs" that can be utilized as well do not interfere with the pI variants, e.g. the charge variants that make a pI higher are put on the same "strand" or "monomer" to preserve both functionalities. Similarly, for "skew" variants that come in pairs of a set as more fully outlined below, the skilled artisan will consider pI in deciding into which strand or monomer that incorporates one set of the pair will go, such that pI separation is maximized using the pI of the skews as well.

By "wild type or WT" herein is meant an amino acid sequence or a nucleotide sequence that is found in nature, including allelic variations. A WT protein has an amino acid sequence or a nucleotide sequence that has not been intentionally modified.

The heterodimeric proteins of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated protein," refers to aa protein which is substantially free of other proteins from a cell culture such as host cell proteins. "Recombinant" means the proteins are generated using recombinant nucleic acid techniques in exogenous host cells.

"Percent (%) amino acid sequence identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. One particular program is the ALIGN-2 program outlined at paragraphs [0279] to [0280] of US Pub. No. 20160244525, hereby incorporated by reference.

The degree of identity between an amino acid sequence of the present invention ("invention sequence") and the parental amino acid sequence is calculated as the number of exact matches in an alignment of the two sequences, divided by the length of the "invention sequence," or the length of the parental sequence, whichever is the shortest. The result is expressed in percent identity.

In some embodiments, two or more amino acid sequences are at least 50%, 60%, 70%, 80%, or 90% identical. In some embodiments, two or more amino acid sequences are at least 95%, 97%, 98%, 99%, or even 100% identical.

By "antigen binding domain" or "ABD" hereins is meant in part of an antigen binding molecule which confers its bindig specificity to an antigen determinant.

As used herein, the term "antigen binding molecule" refers in its broadest sense to any molecule that specifically binds to an antigenic determinant. An antigen binding molecule may be a protein, carbohydrate, lipid, or other chemical compound. Examples of antigen binding molecules are immunoglobulin and derivatives or fragments thereof, e.g., Fab and scFv. Additional examples of antigen binding molecules are receptors and ligands.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

The strength, or affinity, of specific binding can be expressed in terms of dissociation constant ($K_D$) of the interaction, wherein a smaller $K_D$ represents greater affinity and a larger $K_D$ represents lower affinity. Binding properties can be determined by methods well known in the art such as bio-layer interferometry and surface plasmon resonance based methods. One such method entails measuring the rates of antigen-binding site/antigen or receptor/ligand complex association and dissociation, wherein rates depend on the concentration of the complex partners, the affinity of the interaction, and geometric parameters that equally influence the rate in both directions. Thus, both the association rate (ka) and the dissociation rate (kd) can be determined, and the ratio of kd/ka is equal to the dissociation constant $K_D$ (See, e.g., Nature 361:186-187 (1993) and Davies et al. (1990) Annual Rev Biochem 59:439-473).

Specific binding for a particular molecule or an epitope can be exhibited, for example, by an antigen binding molecule having a $K_D$ for an antigen or epitope of at least about 10-4 M, at least about 10-5 M, at least about 10-6 M, at least about 10-7 M, at least about 10-8 M, at least about 10-9 M, alternatively at least about 10-10 M, at least about 10-11 M, at least about 10-12 M, or greater. Typically, an antigen binding molecule that specifically binds an antigen will have a $K_D$ that is 20-, 50-, 100-, 500-, 1000-, 5,000-, 10,000- or more times greater for a control molecule relative to the antigen or epitope.

Also, specific binding for a particular molecule or an epitope can be exhibited, for example, by an antigen binding molecule having a ka or association rate for an antigen or epitope of at least 20-, 50-, 100-, 500-, 1000-, 5,000-, 10,000- or more times greater for the epitope relative to a control.

By "epitope" is herein meant a determinant that interacts with a specific antigen binding domain, for example variable region of an antibody molecule, known as a paratope. Epitopes are groupings of molecules such as amino acids or sugar side chains and usually have specific structural characteristics, as well as specific charge characteristics. A single molecule may have more than one epitope. The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide. Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents. An epitope typically includes at least 3, and more usually, at least 5 or 8-10 amino acids in a unique spatial conformation. Antigen binding molecules that recognize the same epitope can be verified in a simple immunoassay showing the ability of one antigen binding molecule to block the binding of another antigen binding molecule to a target antigen, for example "binning." As outlined below, the invention not only includes the enumerated antigen binding molecules and antigen binding domains herein, but those that compete for binding with the epitopes bound by the enumerated antigen binding molecules or antigen binding domains.

By "fused" or "covalently linked" is herein meant that the components (e.g., IL-15 and an Fc domain) are linked by peptide bonds, either directly or via domain linkers, outlined herein.

As used herein, the term "single-chain" refers to a molecule comprising amino acid monomers linearly linked by peptide bonds.

Before the invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

II. Antibodies

As is discussed below, the term "antibody" is used generally. Antibodies that find use in the present invention can take on a number of formats as described herein, including traditional antibodies as well as antibody derivatives, fragments and mimetics, described herein and depicted in the figures.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to bispecific antibodies that generally are based on the IgG class, which has several subclasses, including, but not limited to IgG1, IgG2, IgG3, and IgG4. In general, IgG1, IgG2 and IgG4 are used more frequently than IgG3. It should be noted that IgG1 has different allotypes with polymorphisms at 356 (D or E) and 358 (L or M). The sequences depicted herein use the 356E/358M allotype, however the other allotype is included herein. That is, any sequence inclusive of an IgG1 Fc domain included herein can have 356D/358L replacing the 356E/358M allotype.

In addition, many of the antibodies herein have at least one of the cysteines at position 220 replaced by a serine; generally this is the on the "scFv monomer" side for most of the sequences depicted herein, although it can also be on the "Fab monomer" side, or both, to reduce disulfide formation. Specifically included within the sequences herein are one or both of these cysteines replaced (C220S).

Thus, "isotype" as used herein is meant any of the subclasses of immunoglobulins defined by the chemical and antigenic characteristics of their constant regions. It should be understood that therapeutic antibodies can also comprise hybrids of isotypes and/or subclasses. For example, as shown in US Publication 2009/0163699, incorporated by reference, the present invention the use of human IgG1/G2 hybrids.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3). A useful comparison of CDR numbering is as below, see Lafranc et al., Dev. Comp. Immunol. 27(1):55-77 (2003):

TABLE 2

|  | Kabat + Chothia | IMGT | Kabat | AbM | Chothia | Contact | Xencor |
|---|---|---|---|---|---|---|---|
| vhCDR1 | 26-35 | 27-38 | 31-35 | 26-35 | 26-32 | 30-35 | 27-35 |
| vhCDR2 | 50-65 | 56-65 | 50-65 | 50-58 | 52-56 | 47-58 | 54-61 |
| vhCDR3 | 95-102 | 105-117 | 95-102 | 95-102 | 95-102 | 93-101 | 103-116 |
| vlCDR1 | 24-34 | 27-38 | 24-34 | 24-34 | 24-34 | 30-36 | 27-38 |
| vlCDR2 | 50-56 | 56-65 | 50-56 | 50-56 | 50-56 | 46-55 | 56-62 |
| vlCDR3 | 89-97 | 105-117 | 89-97 | 89-97 | 89-97 | 89-96 | 97-105 |

Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g, Kabat et al., supra (1991)).

Another type of Ig domain of the heavy chain is the hinge region. By "hinge" or "hinge region" or "antibody hinge region" or "hinge domain" herein is meant the flexible polypeptide comprising the amino acids between the first and second constant domains of an antibody. Structurally, the IgG CH1 domain ends at EU position 215, and the IgG CH2 domain begins at residue EU position 231. Thus for IgG the antibody hinge is herein defined to include positions 216 (E216 in IgG1) to 230 (p230 in IgG1), wherein the numbering is according to the EU index as in Kabat. In some cases, a "hinge fragment" is used, which contains fewer amino acids at either or both of the N- and C-termini of the hinge domain. As noted herein, pI variants can be made in the hinge region as well.

The light chain generally comprises two domains, the variable light domain (containing the light chain CDRs and together with the variable heavy domains forming the Fv region), and a constant light chain region (often referred to as CL or Cκ).

Another region of interest for additional substitutions, outlined below, is the Fc region.

The present invention provides a large number of different CDR sets. In this case, a "full CDR set" comprises the three variable light and three variable heavy CDRs, e.g. a vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning." As outlined below, the invention not only includes the enumerated antigen binding domains and antibodies herein, but those that compete for binding with the epitopes bound by the enumerated antigen binding domains.

Thus, the present invention provides different antibody domains. As described herein and known in the art, the heterodimeric antibodies of the invention comprise different domains within the heavy and light chains, which can be overlapping as well. These domains include, but are not limited to, the Fc domain, the CH1 domain, the CH2 domain, the CH3 domain, the hinge domain, the heavy constant domain (CH1-hinge-Fc domain or CH1-hinge-CH2-CH3), the variable heavy domain, the variable light domain, the light constant domain, Fab domains and scFv domains.

Thus, the "Fe domain" includes the —CH2-CH3 domain, and optionally a hinge domain (—H—CH2-CH3). In the embodiments herein, when a scFv is attached to an Fc domain, it is the C-terminus of the scFv construct that is attached to all or part of the hinge of the Fc domain; for example, it is generally attached to the sequence EPKS (SEQ ID NO: 292) which is the beginning of the hinge. The heavy chain comprises a variable heavy domain and a constant domain, which includes a CH1-optional hinge-Fc domain comprising a CH2-CH3. The light chain comprises a variable light chain and the light constant domain. A scFv comprises a variable heavy chain, an scFv linker, and a variable light domain. In most of the constructs and sequences outlined herein, the C-terminus of the variable heavy chain is attached to the N-terminus of the scFv linker, the C-terminus of which is attached to the N-terminus of a variable light chain (N-vh-linker-vl-C) although that can be switched (N-vl-linker-vh-C).

Some embodiments of the invention comprise at least one scFv domain, which, while not naturally occurring, generally includes a variable heavy domain and a variable light domain, linked together by a scFv linker. As outlined herein, while the scFv domain is generally from N- to C-terminus oriented as vh-scFv linker-vl, this can be reversed for any of the scFv domains (or those constructed using vh and vl sequences from Fabs), to vl-scFv linker-vh, with optional linkers at one or both ends depending on the format.

As shown herein, there are a number of suitable linkers (for use as either domain linkers or scFv linkers) that can be used to covalently attach the recited domains, including traditional peptide bonds, generated by recombinant techniques. In some embodiments, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n (SEQ ID NO: 11), (GSGGS)n (SEQ ID NO: 12), (GGGGS)n (SEQ ID NO: 13), and (GGGS)n (SEQ ID NO: 14), where n is an integer of at least one (and generally from 3 to 4), glycine-alanine polymers, alanine-serine polymers, and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers.

Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g. TCR, FcR, KTR), hinge region-derived sequences, and other natural sequences from other proteins.

In some embodiments, the linker is a "domain linker", used to link any two domains as outlined herein together. For example, there may be a domain linker that attaches the C-terminus of the CH1 domain of the Fab to the N-terminus of the scFv, with another optional domain linker attaching the C-terminus of the scFv to the CH2 domain (although in many embodiments the hinge is used as this domain linker). While any suitable linker can be used, many embodiments utilize a glycine-serine polymer as the domain linker, including for example (GS)n (SEQ ID NO: 15), (GSGGS)n (SEQ ID NO: 16), (GGGGS)n (SEQ ID NO: 17), and (GGGS)n (SEQ ID NO: 18), where n is an integer of at least one (and generally from 3 to 4 to 5) as well as any peptide sequence that allows for recombinant attachment of the two domains with sufficient length and flexibility to allow each domain to retain its biological function. In some cases, and with attention being paid to "strandedness", as outlined below, charged domain linkers, as used in some embodiments of scFv linkers can be used.

In some embodiments, the linker is a scFv linker, used to covalently attach the vh and vl domains as discussed herein. In many cases, the scFv linker is a charged scFv linker.

Accordingly, the present invention further provides charged scFv linkers, to facilitate the separation in pI between a first and a second monomer. That is, by incorporating a charged scFv linker, either positive or negative (or both, in the case of scaffolds that use scFvs on different monomers), this allows the monomer comprising the charged linker to alter the pI without making further changes in the Fc domains. These charged linkers can be substituted into any scFv containing standard linkers. Again, as will be appreciated by those in the art, charged scFv linkers are used on the correct "strand" or monomer, according to the desired changes in pI. For example, as discussed herein, to make triple F format heterodimeric antibody, the original pI of the Fv region for each of the desired antigen binding domains are calculated, and one is chosen to make an scFv, and depending on the pI, either positive or negative linkers are chosen.

Charged domain linkers can also be used to increase the pI separation of the monomers of the invention as well, and thus those included herein can be used in any embodiment herein where a linker is utilized.

In particular, some formats of antibodies, usually referred to as "heterodimeric antibodies", meaning that the protein has at least two associated Fc sequences self-assembled into a heterodimeric Fc domain and at least two Fv regions, whether as Fabs or as scFvs.

III. Chimeric and Humanized Antibodies

In certain embodiments, the checkpoint blockade antibodies of the invention comprise a heavy chain variable region from a particular germline heavy chain immunoglobulin gene and/or a light chain variable region from a particular germline light chain immunoglobulin gene. For example, such antibodies may comprise or consist of a human antibody comprising heavy or light chain variable regions that are "the product of" or "derived from" a particular germline sequence. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody (using the methods outlined herein). A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a humanized antibody typically is at least 90% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody may be at least 95%, 96%, 97%, 98%, or 99%, or even at least 96%, 97%, 98%, or 99% identical in amino acid sequence to the amino acid sequence encoded by the germline immunoglobulin gene. Typically, a humanized antibody derived from a particular human germline sequence will display no more than 10-20 amino acid differences from the amino acid sequence encoded by the human germline immunoglobulin gene (prior to the introduction of any skew, pI and ablation variants herein; that is, the number of variants is generally low, prior to the introduction of the variants of the invention). In certain cases, the humanized antibody may display no more than 5, or even no more than 4, 3, 2, or 1 amino acid difference from the amino acid sequence encoded by the germline immunoglobulin gene (again, prior to the introduction of any skew, pI and ablation variants herein; that is, the number of variants is generally low, prior to the introduction of the variants of the invention).

In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

IV. Heterodimeric Fc Fusion Proteins

The present invention relates to heterodimeric Fc fusion proteins that include IL-15 and IL-15 receptor alpha (IL-15Rα) protein domains in different orientations. The Fc domains can be derived from IgG Fc domains, e.g., IgG1, IgG2, IgG3 or IgG4 Fc domains, with IgG1 Fc domains finding particular use in the invention.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDRs and the framework and made a list thereof (see SEQUENCES OF IMMUNOLOGICAL INTEREST, 5th edition, NIH publication, No. 91-3242, E. A. Kabat et al., entirely incorporated by reference). Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g., Kabat et al., supra (1991)).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-215 according to the EU index as in Kabat. "Hinge" refers to positions 216-230 according to the EU index as in Kabat. "CH2" refers to positions 231-340 according to the EU index as in Kabat, and "CH3" refers to positions 341-447 according to the EU index as in Kabat. As shown in Table 1, the exact numbering and placement of the heavy chain domains can be different among different numbering systems. As shown herein and described below, the pI variants can be in one or more of the CH regions, as well as the hinge region, discussed below.

Another type of Ig domain of the heavy chain is the hinge region. By "hinge" or "hinge region" or "antibody hinge region" or "immunoglobulin hinge region" herein is meant the flexible polypeptide comprising the amino acids between the first and second heavy chain constant domains of an antibody. Structurally, the IgG CH1 domain ends at EU position 215, and the IgG CH2 domain begins at residue EU position 237. Thus for IgG the antibody hinge is herein defined to include positions 216 (E216 in IgG1) to 230 (P230 in IgG1), wherein the numbering is according to the EU index as in Kabat. In some embodiments, for example in the context of an Fc region, the hinge is included, generally referring to positions 216-230. As noted herein, pI variants can be made in the hinge region as well.

Thus, the present invention provides different antibody domains. As described herein and known in the art, the heterodimeric proteins of the invention comprise different domains, which can be overlapping as well. These domains include, but are not limited to, the Fc domain, the CH1 domain, the CH2 domain, the CH3 domain, the hinge domain, and the heavy constant domain (CH1-hinge-Fc domain or CH1-hinge-CH2-CH3).

Thus, the "Fc domain" includes the —CH2-CH3 domain, and optionally a hinge domain. In some embodiments, the Fc domain also includes a portion of the CH1 domain. In some embodiments, when a protein fragment, e.g., IL-15 or IL-15Rα is attached to an Fc domain, it is the C-terminus of the IL-15 or IL-15Rα construct that is attached to all or part of the hinge of the Fc domain; for example, it is generally attached to the sequence EPKSC (SEQ ID NO: 293) which is the beginning of the hinge. In other embodiments herein, when a protein fragment, e.g., IL-15 or IL-15Rα is attached to an Fc domain, it is the N-terminus of the protein fragment that is attached to the C-terminus of the CH3 domain.

In some of the constructs and sequences outlined herein of an Fc domain protein, the C-terminus of the IL-15 or IL-15Rα protein fragment is attached to the N-terminus of a domain linker, the C-terminus of which is attached to the N-terminus of a constant Fc domain (N-IL-15 or IL-15Rα protein fragment-linker-Fc domain-C) although that can be switched (N-Fc domain-linker-IL-15 or IL-15Rα protein fragment-C). In other constructs and sequence outlined herein, C-terminus of a first protein fragment is attached to the N-terminus of a second protein fragment, optionally via a domain linker, the C-terminus of the second protein fragment is attached to the N-terminus of a constant Fc domain, optionally via a domain linker. In yet other constructs and sequences outlined herein, a constant Fc domain that is not attached to a first protein fragment or a second protein fragment is provided. A heterodimer Fc fusion protein can contain two or more of the exemplary monomeric Fc domain proteins described herein. In yet another construct, the N-terminus of a first protein fragment is attached to the C-terminus of a second protein fragment, optionally via a domain linker, the N-terminus of the second protein fragment is attached to the C-terminus of a constant Fc domain, optionally via a domain linker.

In some embodiments, the linker is a "domain linker", used to link any two domains as outlined herein together, some of which are depicted in FIG. 87. While any suitable linker can be used, many embodiments utilize a glycine-serine polymer, including for example (GS)n (SEQ ID NO: 19), (GSGGS)n (SEQ ID NO: 20), (GGGGS)n (SEQ ID NO: 21), and (GGGS)n (SEQ ID NO: 22), where n is an integer of at least one (and generally from 0 to 1 to 2 to 3 to 4 to 5) as well as any peptide sequence that allows for recombinant attachment of the two domains with sufficient length and flexibility to allow each domain to retain its biological function. In some cases, and with attention being paid to "strandedness", as outlined below, the linker is a charged domain linker.

Accordingly, in some embodiments, the present invention provides heterodimeric Fc fusion proteins that rely on the use of two different heavy chain variant Fc sequences, that will self-assemble to form a heterodimeric Fc domain fusion polypeptide.

In one embodiment, heterodimeric Fc fusion proteins contain at least two constant domains which can be engineered to produce heterodimers, such as pI engineering. Other Fc domains that can be used include fragments that contain one or more of the CH1, CH2, CH3, and hinge domains of the invention that have been pI engineered. In particular, the formats depicted in FIGS. 9A-9G, and 39A-39D are heterodimeric Fc fusion proteins, meaning that the protein has two associated Fc sequences self-assembled into a heterodimeric Fc domain and at least one protein fragment (e.g., 1, 2 or more protein fragments). In some cases, a first protein fragment is linked to a first Fc sequence and a second protein fragment is linked to a second Fc sequence. In other cases, a first protein fragment is linked to a first Fc sequence, and the first protein fragment is non-covalently attached to a second protein fragment that is not linked to an Fc sequence. In some cases, the heterodimeric Fc fusion protein contains a first protein fragment linked to a second protein fragment which is linked to a first Fc sequence, and a second Fc sequence that is not linked to either the first or second protein fragments.

The present invention is directed to novel constructs to provide heterodimeric Fc fusion proteins that allow binding to one or more binding partners, ligands or receptors. The heterodimeric Fc fusion constructs are based on the self-assembling nature of the two Fc domains of the heavy chains of antibodies, e.g., two "monomers" that assemble into a "dimer". Heterodimeric Fc fusions are made by altering the amino acid sequence of each monomer as more fully discussed below. Thus, the present invention is generally directed to the creation of heterodimeric Fc fusion proteins which can co-engage binding partner(s) or ligand(s) or receptor(s) in several ways, relying on amino acid variants in the constant regions that are different on each chain to promote heterodimeric formation and/or allow for ease of purification of heterodimers over the homodimers.

There are a number of mechanisms that can be used to generate the heterodimers of the present invention. In addition, as will be appreciated by those in the art, these mechanisms can be combined to ensure high heterodimerization. Thus, amino acid variants that lead to the production of heterodimers are referred to as "heterodimerization variants". As discussed below, heterodimerization variants can include steric variants (e.g. the "knobs and holes" or "skew" variants described below and the "charge pairs" variants described below) as well as "pI variants", which allows purification of homodimers away from heterodimers. As is generally described in WO2014/145806, hereby incorporated by reference in its entirety and specifically as below for the discussion of "heterodimerization variants", useful mechanisms for heterodimerization include "knobs and holes" ("KIH"; sometimes described herein as "skew" variants (see discussion in WO2014/145806), "electrostatic steering" or "charge pairs" as described in WO2014/145806, pI variants as described in WO2014/145806, and general additional Fc variants as outlined in WO2014/145806 and below.

In the present invention, there are several basic mechanisms that can lead to ease of purifying heterodimeric proteins and antibodies; one relies on the use of pI variants, such that each monomer, and subsequently each dimeric species, has a different pI, thus allowing the isoelectric purification of A-A, A-B and B-B dimeric proteins. Alternatively, some formats also allow separation on the basis of size. As is further outlined below, it is also possible to "skew" the formation of heterodimers over homodimers. Thus, a combination of steric heterodimerization variants and pI or charge pair variants find particular use in the invention.

In general, embodiments of particular use in the present invention rely on sets of variants that include skew variants, that encourage heterodimerization formation over homodimerization formation, coupled with pI variants, which increase the pI difference between the two monomers and each dimeric species.

Additionally, as more fully outlined below, depending on the format of the heterodimer Fc fusion protein, pI variants can be either contained within the constant and/or Fc domains of a monomer, or domain linkers can be used. That is, the invention provides pI variants that are on one or both of the monomers, and/or charged domain linkers as well. In addition, additional amino acid engineering for alternative functionalities may also confer pI changes, such as Fc, FcRn and KO variants.

In the present invention that utilizes pI as a separation mechanism to allow the purification of heterodimeric proteins, amino acid variants can be introduced into one or both of the monomer polypeptides; that is, the pI of one of the monomers (referred to herein for simplicity as "monomer A") can be engineered away from monomer B, or both monomer A and B can be changed, with the pI of monomer A increasing and the pI of monomer B decreasing. As discussed, the pI changes of either or both monomers can be done by removing or adding a charged residue (e.g., a neutral amino acid is replaced by a positively or negatively charged amino acid residue, e.g., glutamine to glutamic acid), changing a charged residue from positive or negative to the opposite charge (e.g., aspartic acid to lysine) or changing a charged residue to a neutral residue (e.g., loss of a charge; lysine to serine). A number of these variants are shown in the Figures.

Accordingly, this embodiment of the present invention provides for creating a sufficient change in pI in at least one of the monomers such that heterodimers can be separated from homodimers. As will be appreciated by those in the art, and as discussed further below, this can be done by using a "wild type" heavy chain constant region and a variant region that has been engineered to either increase or decrease its pI (wt A:B+ or wt A:B−), or by increasing one region and decreasing the other region (A+:B− or A−:B+).

Thus, in general, a component of some embodiments of the present invention are amino acid variants in the constant regions that are directed to altering the isoelectric point (pI) of at least one, if not both, of the monomers of a dimeric protein by incorporating amino acid substitutions ("pI variants" or "pI substitutions") into one or both of the monomers. The separation of the heterodimers from the two homodimers can be accomplished if the pIs of the two monomers differ by as little as 0.1 pH unit, with 0.2, 0.3, 0.4 and 0.5 or greater all finding use in the present invention.

As will be appreciated by those in the art, the number of pI variants to be included on each or both monomer(s) to get good separation will depend in part on the starting pI of the components. That is, to determine which monomer to engineer or in which "direction" (e.g., more positive or more negative), the sequences of the Fc domains, and in some cases, the protein domain(s) linked to the Fc domain are calculated and a decision is made from there. As is known in the art, different Fc domains and/or protein domains will have different starting pIs which are exploited in the present invention. In general, as outlined herein, the pIs are engineered to result in a total pI difference of each monomer of at least about 0.1 logs, with 0.2 to 0.5 being preferred as outlined herein.

Furthermore, as will be appreciated by those in the art and outlined herein, in some embodiments, heterodimers can be separated from homodimers on the basis of size. As shown in the Figures, for example, several of the formats allow separation of heterodimers and homodimers on the basis of size.

In the case where pI variants are used to achieve heterodimerization, by using the constant region(s) of Fc domains(s), a more modular approach to designing and purifying heterodimeric Fc fusion proteins is provided. Thus, in some embodiments, heterodimerization variants (including skew and purification heterodimerization variants) must be engineered. In addition, in some embodiments, the possibility of immunogenicity resulting from the pI variants is significantly reduced by importing pI variants from different IgG isotypes such that pI is changed without introducing significant immunogenicity. Thus, an additional problem to be solved is the elucidation of low pI constant domains with high human sequence content, e.g. the minimization or avoidance of non-human residues at any particular position.

A side benefit that can occur with this pI engineering is also the extension of serum half-life and increased FcRn binding. That is, as described in U.S. Ser. No. 13/194,904 (incorporated by reference in its entirety), lowering the pI of antibody constant domains (including those found in antibodies and Fc fusions) can lead to longer serum retention in vivo. These pI variants for increased serum half-life also facilitate pI changes for purification.

In addition, it should be noted that the pI variants of the heterodimerization variants give an additional benefit for the analytics and quality control process of Fc fusion proteins, as the ability to either eliminate, minimize and distinguish when homodimers are present is significant. Similarly, the ability to reliably test the reproducibility of the heterodimeric Fc fusion protein production is important.

A. Heterodimerization Variants

The present invention provides heterodimeric proteins, including heterodimeric Fc fusion proteins in a variety of formats, which utilize heterodimeric variants to allow for heterodimer formation and/or purification away from homodimers. The heterodimeric fusion constructs are based on the self-assembling nature of the two Fc domains, e.g., two "monomers" that assemble into a "dimer".

There are a number of suitable pairs of sets of heterodimerization skew variants. These variants come in "pairs" of "sets". That is, one set of the pair is incorporated into the first monomer and the other set of the pair is incorporated into the second monomer. It should be noted that these sets do not necessarily behave as "knobs in holes" variants, with a one-to-one correspondence between a residue on one monomer and a residue on the other; that is, these pairs of sets form an interface between the two monomers that encourages heterodimer formation and discourages homodimer formation, allowing the percentage of heterodimers that spontaneously form under biological conditions to be over 90%, rather than the expected 50% (25% homodimer A/A: 50% heterodimer A/B:25% homodimer B/B).

B. Steric Variants

In some embodiments, the formation of heterodimers can be facilitated by the addition of steric variants. That is, by changing amino acids in each heavy chain, different heavy chains are more likely to associate to form the heterodimeric structure than to form homodimers with the same Fc amino acid sequences. Suitable steric variants are included in in the FIG. 29 of U.S. Ser. No. 15/141,350, all of which is hereby incorporated by reference in its entirety, as well as in FIG. 84.

One mechanism is generally referred to in the art as "knobs and holes", referring to amino acid engineering that creates steric influences to favor heterodimeric formation and disfavor homodimeric formation, as described in U.S. Ser. No. 61/596,846, Ridgway et al., Protein Engineering 9(7):617 (1996); Atwell et al., J. Mol. Biol. 1997 270:26; U.S. Pat. No. 8,216,805, all of which are hereby incorporated by reference in their entirety. The Figures identify a number of "monomer A-monomer B" pairs that rely on "knobs and holes". In addition, as described in Merchant et al., Nature Biotech. 16:677 (1998), these "knobs and hole" mutations can be combined with disulfide bonds to skew formation to heterodimerization.

An additional mechanism that finds use in the generation of heterodimers is sometimes referred to as "electrostatic steering" as described in Gunasekaran et al., J. Biol. Chem. 285(25):19637 (2010), hereby incorporated by reference in its entirety. This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". These include, but are not limited to, D221E/P228E/L368E paired with D221R/P228R/K409R (e.g., these are "monomer corresponding sets) and C220E/P228E/368E paired with C220R/E224R/P228R/K409R.

Additional monomer A and monomer B variants can be combined with other variants, optionally and independently in any amount, such as pI variants outlined herein or other steric variants that are shown in FIG. 37 of US 2012/0149876, all of which are incorporated expressly by reference herein.

In some embodiments, the steric variants outlined herein can be optionally and independently incorporated with any pI variant (or other variants such as Fc variants, FcRn variants, etc.) into one or both monomers, and can be independently and optionally included or excluded from the proteins of the invention.

A list of suitable skew variants is found in FIGS. 3A-3E. Of particular use in many embodiments are the pairs of sets including, but not limited to, S364K/E357Q:L368D/K370S; L368D/K370S:S364K; L368E/K370S:S364K; T411E/K360E/Q362E:D401K; L368D/K370S:S364K/E357L; K370S:S364K/E357Q; and T366S/L368A/Y407V:T366W (optionally including a bridging disulfide, T366S/L368A/Y407V/Y349C:T366W/S354C). In terms of nomenclature, the pair "S364K/E357Q:L368D/K370S" means that one of the monomers has the double variant set S364K/E357Q and the other has the double variant set L368D/K370S; as above, the "strandedness" of these pairs depends on the starting pI.

C. pI (Isoelectric Point) Variants for Heterodimers

In general, as will be appreciated by those in the art, there are two general categories of pI variants: those that increase the pI of the protein (basic changes) and those that decrease the pI of the protein (acidic changes). As described herein, all combinations of these variants can be used: one monomer may be wild type, or a variant that does not display a significantly different pI from wild-type, and the other can be either more basic or more acidic. Alternatively, each monomer may be changed, one to more basic and one to more acidic.

Preferred combinations of pI variants are shown in FIG. 30 of U.S. Ser. No. 15/141,350, all of which are herein incorporated by reference in its entirety. As outlined herein and shown in the figures, these changes are shown relative to IgG1, but all isotypes can be altered this way, as well as isotype hybrids. In the case where the heavy chain constant domain is from IgG2-4, R133E and R133Q can also be used. pI variants are depicted in FIG. 4.

In one embodiment, a preferred combination of pI variants has one monomer comprising 208D/295E/384D/418E/421D variants (N208D/Q295E/N384D/Q418E/N421D when relative to human IgG1) if one of the Fc monomers includes a CH1 domain. In some instances, the second monomer comprising a positively charged domain linker, including (GKPGS)$_4$ (SEQ ID NO: 294). In some cases, the first monomer includes a CH1 domain, including position 208. Accordingly, in constructs that do not include a CH1 domain (for example for heterodimeric Fc fusion proteins that do not utilize a CH1 domain on one of the domains), a preferred negative pI variant Fc set includes 295E/384D/418E/421D variants (Q295E/N384D/Q418E/N421D when relative to human IgG1).

In some embodiments, mutations are made in the hinge domain of the Fc domain, including positions 216, 217, 218, 219, 220, 221, 222, 223, 224, 225, 226, 227, 228, 229, and 230. Thus, pI mutations and particularly substitutions can be made in one or more of positions 216-230, with 1, 2, 3, 4 or 5 mutations finding use in the present invention. Again, all possible combinations are contemplated, alone or with other pI variants in other domains.

Specific substitutions that find use in lowering the pI of hinge domains include, but are not limited to, a deletion at position 221, a non-native valine or threonine at position 222, a deletion at position 223, a non-native glutamic acid at position 224, a deletion at position 225, a deletion at position 235 and a deletion or a non-native alanine at position 236. In some cases, only pI substitutions are done in the hinge domain, and in others, these substitution(s) are added to other pI variants in other domains in any combination.

In some embodiments, mutations can be made in the CH2 region, including positions 233, 234, 235, 236, 274, 296, 300, 309, 320, 322, 326, 327, 334 and 339. Again, all possible combinations of these 14 positions can be made; e.g., a pI antibody may have 1, 2, 3, 4, 5, 6, 7, 8, 9 or 10 CH2 pI substitutions.

Specific substitutions that find use in lowering the pI of CH2 domains include, but are not limited to, a non-native glutamine or glutamic acid at position 274, a non-native phenylalanine at position 296, a non native phenylalanine at position 300, a non-native valine at position 309, a non-native glutamic acid at position 320, a non-native glutamic acid at position 322, a non-native glutamic acid at position 326, a non-native glycine at position 327, a non-native glutamic acid at position 334, a non native threonine at position 339, and all possible combinations within CH2 and with other domains.

In this embodiment, the mutations can be independently and optionally selected from position 355, 359, 362, 384, 389, 392, 397, 418, 419, 444 and 447. Specific substitutions that find use in lowering the pI of CH3 domains include, but are not limited to, a non native glutamine or glutamic acid at position 355, a non-native serine at position 384, a non-native asparagine or glutamic acid at position 392, a non-native methionine at position 397, a non native glutamic acid at position 419, a non native glutamic acid at position 359, a non native glutamic acid at position 362, a non native glutamic acid at position 389, a non native glutamic acid at position 418, a non native glutamic acid at position 444, and a deletion or non-native aspartic acid at position 447.

D. Isotypic Variants

In addition, many embodiments of the invention rely on the "importation" of pI amino acids at particular positions from one IgG isotype into another, thus reducing or eliminating the possibility of unwanted immunogenicity being introduced into the variants. A number of these are shown in FIG. 21 of US Publ. App. No. 2014/0370013, hereby incorporated by reference. That is, IgG1 is a common isotype for therapeutic antibodies for a variety of reasons, including high effector function. However, the heavy constant region of IgG1 has a higher pI than that of IgG2 (8.10 versus 7.31). By introducing IgG2 residues at particular positions into the IgG1 backbone, the pI of the resulting monomer is lowered (or increased) and additionally exhibits longer serum half-life. For example, IgG1 has a glycine (pI 5.97) at position 137, and IgG2 has a glutamic acid (pI 3.22); importing the glutamic acid will affect the pI of the resulting protein. As is described below, a number of amino acid substitutions are generally required to significantly affect the pI of the variant Fc fusion protein. However, it should be noted as discussed below that even changes in IgG2 molecules allow for increased serum half-life.

In other embodiments, non-isotypic amino acid changes are made, either to reduce the overall charge state of the resulting protein (e.g., by changing a higher pI amino acid to a lower pI amino acid), or to allow accommodations in structure for stability, etc. as is more further described below.

In addition, by pI engineering both the heavy and light constant domains, significant changes in each monomer of the heterodimer can be seen. As discussed herein, having the pIs of the two monomers differ by at least 0.5 can allow separation by ion exchange chromatography or isoelectric focusing, or other methods sensitive to isoelectric point.

E. Calculating pI

The pI of each monomer can depend on the pI of the variant heavy chain constant domain and the pI of the total monomer, including the variant heavy chain constant domain and the fusion partner. Thus, in some embodiments, the change in pI is calculated on the basis of the variant heavy chain constant domain, using the chart in the FIG. 19 of US Publ. App. No. 2014/0370013. As discussed herein, which monomer to engineer is generally decided by the inherent pI of each monomer.

F. pI Variants that Also Confer Better FcRn In Vivo Binding

In the case where the pI variant decreases the pI of the monomer, they can have the added benefit of improving serum retention in vivo.

Although still under examination, Fc regions are believed to have longer half-lives in vivo, because binding to FcRn at pH 6 in an endosome sequesters the Fc (Ghetie and Ward, 1997 Immunol Today. 18(12): 592-598, entirely incorporated by reference). The endosomal compartment then recycles the Fc to the cell surface. Once the compartment opens to the extracellular space, the higher pH, ~7.4, induces the release of Fc back into the blood. In mice, Dall'Acqua et al. showed that Fc mutants with increased FcRn binding at pH 6 and pH 7.4 actually had reduced serum concentrations and the same half-life as wild-type Fc (Dall'Acqua et al. 2002, J. Immunol. 169:5171-5180, entirely incorporated by reference). The increased affinity of Fc for FcRn at pH 7.4 is thought to forbid the release of the Fc back into the blood. Therefore, the Fc mutations that will increase Fc's half-life in vivo will ideally increase FcRn binding at the lower pH while still allowing release of Fc at higher pH. The amino acid histidine changes its charge state in the pH range of 6.0 to 7.4. Therefore, it is not surprising to find His residues at important positions in the Fc/FcRn complex.

G. Additional Fc Variants for Additional Functionality

In addition to pI amino acid variants, there are a number of useful Fc amino acid modification that can be made for a variety of reasons, including, but not limited to, altering binding to one or more FcγRs, altered binding to FcRn, etc.

Accordingly, the proteins of the invention can include amino acid modifications, including the heterodimerization variants outlined herein, which includes the pI variants and steric variants. Each set of variants can be independently and optionally included or excluded from any particular heterodimeric protein.

H. FcγR Variants

Accordingly, there are a number of useful Fc substitutions that can be made to alter binding to one or more of the FcγRs. Substitutions that result in increased binding as well as decreased binding can be useful. For example, it is known that increased binding to FcγRIIIa results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell). Similarly, decreased binding to FcγRIIb (an inhibitory receptor) can be beneficial as well in some circumstances. Amino acid substitutions that find use in the present invention include those listed in U.S. Ser. No. 11/124,620 (particularly FIG. 41), Ser. Nos. 11/174,287, 11/396,495, 11/538,406, all of which are expressly incorporated herein by reference in their entirety and specifically for the variants disclosed therein. Particular variants that find use include, but are not limited to, 236A, 239D, 239E, 332E, 332D, 239D/332E, 267D, 267E, 328F, 267E/328F, 236A/332E, 239D/332E/330Y, 239D, 332E/330L, 243A, 243L, 264A, 264V and 299T.

In addition, amino acid substitutions that increase affinity for FcγRIIc can also be included in the Fc domain variants outlined herein. The substitutions described in, for example, U.S. Ser. No. 11/124,620 and 14/578,305 are useful.

In addition, there are additional Fc substitutions that find use in increased binding to the FcRn and increased serum half-life, as specifically disclosed in U.S. Ser. No. 12/341,769, hereby incorporated by reference in its entirety, including, but not limited to, 434S, 434A, 428L, 308F, 259I, 428L/434S, 259I/308F, 436I/428L, 436I or V/434S, 436V/428L and 259I/308F/428L.

I. Ablation Variants

Similarly, another category of functional variants are "FcγR ablation variants" or "Fc knock out (FcKO or KO)" variants. In these embodiments, for some therapeutic applications, it is desirable to reduce or remove the normal binding of the Fc domain to one or more or all of the Fcγ receptors (e.g., FcγR1, FcγRIIa, FcγRIIb, FcγRIIIa, etc.) to avoid additional mechanisms of action. That is, for example, in many embodiments, particularly in the use of immunomodulatory proteins, it is desirable to ablate FcγRIIIa binding to eliminate or significantly reduce ADCC activity such that one of the Fc domains comprises one or more Fcγ receptor ablation variants. These ablation variants are depicted in FIG. 31 of U.S. Ser. No. 15/141,350, all of which are herein incorporated by reference in its entirety, and each can be independently and optionally included or excluded, with preferred aspects utilizing ablation variants selected from the group consisting of G236R/L328R, E233P/L234V/

L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, according to the EU index. It should be noted that the ablation variants referenced herein ablate FcγR binding but generally not FcRn binding. Useful ablation variants that ablate FcγR binding (sometimes referred to as "knock outs" or "KO" variants) are depicted in FIG. 5.

J. Combination of Heterodimeric and Fc Variants

As will be appreciated by those in the art, all of the recited heterodimerization variants (including skew and/or pI variants) can be optionally and independently combined in any way, as long as they retain their "strandedness" or "monomer partition". In addition, all of these variants can be combined into any of the heterodimerization formats.

In the case of pI variants, while embodiments finding particular use are shown in the Figures, other combinations can be generated, following the basic rule of altering the pI difference between two monomers to facilitate purification.

In addition, any of the heterodimerization variants, skew and pI, may also be independently and optionally combined with Fc ablation variants, Fc variants, FcRn variants, as generally outlined herein.

In addition, a monomeric Fc domain can comprise a set of amino acid substitutions that includes C220S/S267K/L368D/K370S or C220S/S267K/S364K/E357Q.

In addition, the heterodimeric Fc fusion proteins can comprise skew variants (e.g., a set of amino acid substitutions as shown in FIGS. 1A-1C of U.S. Ser. No. 15/141,350, all of which are herein incorporated by reference in its entirety), with particularly useful skew variants being selected from the group consisting of S364K/E357Q: L368D/K370S; L368D/K370S:S364K; L368E/K370S: S364K; T411E/K360E/Q362E:D401K; L368D/K370S: S364K/E357L, K370S:S364K/E357Q, T366S/L368A/Y407V:T366W; and T366S/L368A/Y407V:T366W (optionally including a bridging disulfide, T366S/L368A/Y407V/Y349C:T366W/S354C), optionally ablation variants, optionally charged domain linkers; and optionally pI variants.

In some embodiments, the Fc domain comprises one or more amino acid substitutions selected from the group consisting of: 236R, S239D, S239E, F243L, M252Y, V259I, S267D, S267E, S67K, S298A, V308F, L328F, L328R, 330L, I332D, I332E, M428L, N434A, N434S, 236R/L328R, S239D/I332E, 236R/L328F, V259I/V308F, S267E/L328F, M428L/N43S, Y436I/M428L, N436V/M428L, V436I/N434S, Y436V/N434S, S239D/I332E/330L, M252Y/S54T/T256E, V259I/V308F/M428L, E233P/L234V/L235A/G236del/S239K, E233P/L234V/L235A/G236del/S239K/A327G, E233P/L234V/L235A/G236del/S267K/A327G, E233P/L234V/L235A/G236_, and E233P/L234V/L235A/G236del/S267K according to EU index.

In one embodiment, a particular combination of skew and pI variants that finds use in the present invention is T366S/L368A/Y407V:T366W (optionally including a bridging disulfide, T366S/L368A/Y407V/Y349C:T366W/S354C) with one monomer comprising Q295E/N384D/Q418E/N481D and the other a positively charged domain linker. As will be appreciated in the art, the "knobs in holes" variants do not change pI, and thus can be used on either monomer.

In certain embodiments, the Fc domain comprises amino acid substitutions comprising M428L/N434S. In some embodiments, each Fc domain of the untargeted IL-15/Rα heterodimeric Fc fusion proteins comprises amino acid substitutions comprising M428L/N434S.

Useful embodiments of the Fc domains of the heterodimeric Fc fusion proteins containing IL-15 and IL-15Rα proteins described herein are provided in FIGS. 6A-6E.

V. IL-15 and IL-15Rα Protein Domains

The present invention provides heterodimeric Fc fusion proteins containing IL-15 and IL-15Rα proteins. As shown in the figures, the IL-15 complex can take several forms. As stated above, the IL-15 protein on its own is less stable than when complexed with the IL-15Rα protein. As is known in the art, the IL-15Rα protein contains a "sushi domain", which is the shortest region of the receptor that retains IL-15 binding activity. Thus, while heterodimeric fusion proteins comprising the entire IL-15Rα protein can be made, preferred embodiments herein include complexes that just use the sushi domain, the sequence of which is shown in the figures.

Figure 9A:
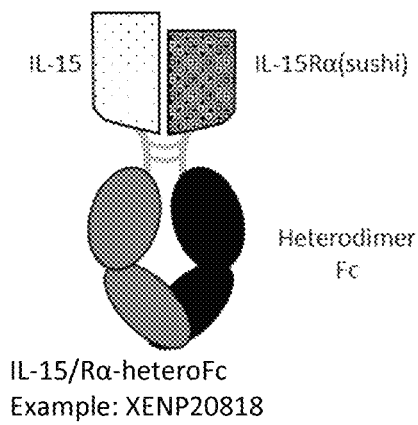
Figure 9B:
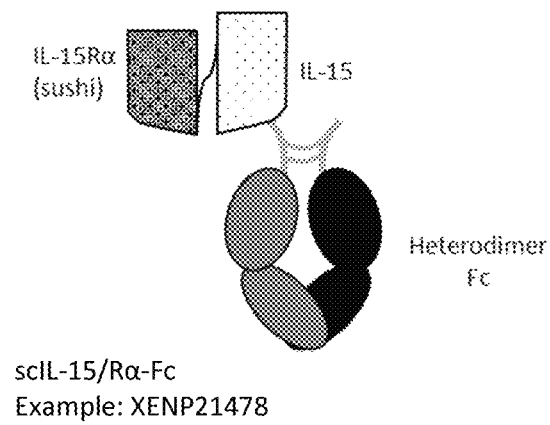

Accordingly, the IL-15 complexes generally comprises the IL-15 protein and the sushi domain of IL-15Rα (unless otherwise noted that the full length sequence is used, "IL-15Rα", "IL-15Rα(sushi)" and "sushi" are used interchangeably throughout). This complex can be used in three different formats. As shown in FIGS. 9A, 9C, 9D, and 9F, the IL-15 protein and the IL-15Rα(sushi) are not covalently attached, but rather are self-assembled through regular ligand-ligand interactions. As is more fully described herein, it can be either the IL-15 domain or the sushi domain that is covalently linked to the Fc domain (generally using an optional domain linker). Alternatively, they can be covalently attached using a domain linker as generally shown in FIGS. 9B, 9E, and 9G. FIG. 9B depicts the sushi domain as the N-terminal domain, although this can be reversed. Finally, each of the IL-15 and sushi domains can be engineered to contain a cysteine amino acid, that forms a disulfide bond to form the complex as is generally shown in FIGS. 39A-39D, again, with either the IL-15 domain or the sushi domain being covalently attached (using an optional domain linker) to the Fc domain.

In some embodiments, the human IL-15 protein has the amino acid sequence set forth in NCBI Ref. Seq. No. NP_000576.1 or SEQ ID NO:1. In some cases, the coding sequence of human IL-15 is set forth in NCBI Ref. Seq. No. NM_000585. An exemplary IL-15 protein of the Fc fusion heterodimeric protein outlined herein can have the amino acid sequence of SEQ ID NO:2 (mature IL-15) or amino acids 49-162 of SEQ ID NO:1. In some embodiments, the IL-15 protein has at least 90%, e.g., 90%, 91%, 92%, 93%, 94%, 95%, 96%, 97%, 98%, 99%, or more sequence identity to SEQ ID NO:2. In some embodiments, the IL-15 protein has the amino acid sequence of SEQ ID NO:2 and one or more amino acid substitutions selected from the group consisting of C42S, L45C, Q48C, V49C, L52C, E53C, E87C, and E89C. The IL-15 protein of the Fc fusion protein can have 1, 2, 3, 4, 5, 6, 7, 8 or 9 amino acid substitutions.

The amino acid substitution(s) may be isosteric substitutions at the IL-15:IL-20 and IL-15:common gamma chain interface. In some embodiments, the human IL-15 protein such as the human mature IL-15 protein has one or more amino acid substitutions selected from the group consisting of N1D, N4D, D8N, D30N, D61N, E64Q, N65D, Q108E, and any combination thereof. In some embodiments, the human IL-15 protein of the Fc fusion protein has the amino acid sequence of SEQ ID NO:2 and amino acid substitutions N4D/N65D. In some cases, the human IL-15 protein of the Fc fusion protein has at least 97% or 98% sequence identity to SEQ ID NO:2 including N4D/N65D substitutions. In some embodiments, the human IL-15 protein of the Fc fusion protein has the amino acid sequence of SEQ ID NO:2 and amino acid substitutions D30N/N65D. In some cases, the human IL-15 protein of the Fc fusion protein has at least 97% or 98% sequence identity to SEQ ID NO:2 including D30N/N65D substitutions. In some embodiments, the human IL-15 protein of the Fc fusion protein has the amino acid sequence of SEQ ID NO:2 and amino acid substitutions D30N/E64Q/N65D. In some cases, the human IL-15 protein of the Fc fusion protein has at least 96% or 97% sequence identity to SEQ ID NO:2 including D30N/E64Q/N65D substitutions.

In some embodiments, the human IL-15 protein, such as a human mature IL-15 protein of the Fc fusion protein is identical to the amino acid sequence of SEQ ID NO:2. In some cases, the human IL-15 protein such as the human mature IL-15 protein has no amino acid substitutions.

In some embodiments, the human mature IL-15 variant protein has one or more amino acid mutations (e.g., substitutions, insertions and/or deletions). In some instances, the mutation introduces a cysteine residue that can form a disulfide bond with human IL-15 receptor alpha (IL-15Rα) protein.

In some embodiments, the human IL-15 receptor alpha (IL-15Rα) protein has the amino acid sequence set forth in NCBI Ref. Seq. No. NP_002180.1 or SEQ ID NO:3. In some cases, the coding sequence of human IL-15Rα is set forth in NCBI Ref. Seq. No. NM_002189.3. An exemplary IL-15Rα protein of the Fc fusion heterodimeric protein outlined herein can comprise or consist of the sushi domain of SEQ ID NO:3 (e.g., amino acids 31-95 of SEQ ID NO:3), or in other words, the amino acid sequence of SEQ ID NO:4. In some embodiments, the IL-15Rα protein has the amino acid sequence of SEQ ID NO:4 and an amino acid insertion selected from the group consisting of D96, P97, A98, D96/P97, D96/C97, D96/P97/A98, D96/P97/C98, and D96/C97/A98, wherein the amino acid position is relative to full-length human IL-15Rα protein or SEQ ID NO:3. For instance, amino acid(s) such as D (e.g., Asp), P (e.g., Pro), A (e.g., Ala), DP (e.g., Asp-Pro), DC (e.g., Asp-Cys), DPA (e.g., Asp-Pro-Ala), DPC (e.g., Asp-Pro-Cys), or DCA (e.g., Asp-Cys-Ala) can be added to the C-terminus of the IL-15Rα protein of SEQ ID NO:4. In some embodiments, the IL-15Rα protein has the amino acid sequence of SEQ ID NO:4 and one or more amino acid substitutions selected from the group consisting of K34C, A37C, G38C, S40C, and L42C, wherein the amino acid position is relative to SEQ ID NO:4. The IL-15Rα (sushi) protein of SEQ ID NO:4 can have 1, 2, 3, 4, 5, 6, 7, 8 or more amino acid mutations (e.g., substitutions, insertions and/or deletions).

SEQ ID NO: 1 is
MRISKPHLRSISIQCYLCLLLNSHFLTEAGI

HVFILGCFSAGLPKTEANWVNVISDLKKIED

LIQSMHIDATLYTESDVHPSCKVTAMKCFLL

ELQVISLESGDASIHDTVENLIILANNSLSS

NGNVTESGCKECEELEEKNIKEFLQSFVHIV

QMFINTS.

SEQ ID NO: 2 is
NWVNVISDLKKIEDLIQSMHIDATLYTESDVH

PSCKVTAMKCFLLELQVISLESGDASIHDTVE

NLIILANNSLSSNGNVTESGCKECEELEEKNI

KEFLQSFVHIVQMFINTS.

SEQ ID NO: 3 is
MAPRRARGCRTLGLPALLLLLLLRPPATRGIT

CPPPMSVEHADIWVKSYSLYSRERYICNSGFK

RKAGTSSLTECVLNKATNVAHWTTPSLKCIRD

PALVHQRPAPPSTVTTAGVTPQPESLSPSGKE

PAASSPSSNNTAATTAAIVPGSQLMPSKSPST

GTTEISSHESSHGTPSQTTAKNWELTASASHQ

PPGVYPQGHSDTTVAISTSTVLLCGLSAVSLL

ACYLKSRQTPPLASVEMEAMEALPVTWGTSSR

DEDLENCSHHL.

SEQ ID NO: 5 is
ITCPPPMSVEHADIWVKSYSLYSRERYICNSG

FKRKAGTSSLTECVLNKATNVAHWTTPSLKCI

R.

In some embodiments, the invention provides proteins comprising a human IL-15 variant with the amino acid variant D30N. In some embodiments, the protein comprises the amino acid sequence of SEQ TD NO:2 and a D30N substitution. In some embodiments, the protein comprises the amino acid sequence of SEQ TD NO:2 and at least a D30N substitution.

In some embodiments, the invention provides proteins comprising a human IL-15 variant with the amino acid variant N1D. In some embodiments, the protein comprises the amino acid sequence of SEQ TD NO:2 and an N1D substitution. In some embodiments, the protein comprises the amino acid sequence of SEQ TD NO:2 and at least an N1D substitution.

In some embodiments, the invention provides proteins comprising a human IL-15 variant with the amino acid variant N4D. In some embodiments, the protein comprises the amino acid sequence of SEQ TD NO:2 and an N4D) substitution. In some embodiments, the protein comprises the amino acid sequence of SEQ TD NO:2 and at least an N4D) substitution.

In some embodiments, the invention provides proteins comprising a human IL-15 variant with the amino acid variant E64Q. In some embodiments, the protein comprises the amino acid sequence of SEQ ID NO:2 and an E64Q substitution. In some embodiments, the protein comprises the amino acid sequence of SEQ ID NO:2 and at least an E64Q substitution.

In some embodiments, the invention provides proteins comprising a human IL-15 variant with the amino acid variant N65D. In some embodiments, the protein comprises the amino acid sequence of SEQ ID NO:2 and an N65D substitution. In some embodiments, the protein comprises the amino acid sequence of SEQ ID NO:2 and at least an N65D substitution.

In some embodiments, the invention provides proteins comprising a human IL-15 variant with amino acid substitutions N1D/D30N. In some embodiments, the protein comprises the amino acid sequence of SEQ ID NO:2 and N1D/D30N substitutions. In some embodiments, the protein comprises the amino acid sequence of SEQ ID NO:2 and at least N1D/D30N substitutions.

In some embodiments, the invention provides proteins comprising a human IL-15 variant with amino acid substitutions N4D/D30N. In some embodiments, the protein comprises the amino acid sequence of SEQ ID NO:2 and N4D/D30N substitutions. In some embodiments, the protein comprises the amino acid sequence of SEQ ID NO:2 and at least N4D/D30N substitutions.

In some embodiments, the invention provides proteins comprising a human IL-15 variant with amino acid substitutions D30N/E64Q. In some embodiments, the protein comprises the amino acid sequence of SEQ ID NO:2 and D30N/E64Q substitutions. In some embodiments, the protein comprises the amino acid sequence of SEQ ID NO:2 and at least D30N/E64Q substitutions.

In some embodiments, the invention provides proteins comprising a human IL-15 variant with amino acid substitutions D30N/N65D. In some embodiments, the protein comprises the amino acid sequence of SEQ ID NO:2 and D30N/N65D substitutions. In some embodiments, the protein comprises the amino acid sequence of SEQ ID NO:2 and at least D30N/N65D substitutions.

In some embodiments, the invention provides proteins comprising a human IL-15 variant with amino acid substitutions D30N/E64Q/N65D. In some embodiments, the protein comprises the amino acid sequence of SEQ ID NO:2 and D30N/E64Q/N65D substitutions. In some embodiments, the protein comprises the amino acid sequence of SEQ ID NO:2 and at least D30N/E64Q/N65D substitutions.

VI. Domain Linkers

In some embodiments, the IL-15 protein and IL-15Rα protein are attached together via a linker. Optionally, the proteins are not attached via a linker. In other embodiments, the IL-15 protein and IL-15Rα protein are noncovalently attached.

In some embodiments, the IL-15 protein is attached to an Fc domain via a linker. In certain embodiments, the IL-15 protein is attached to an Fc domain directly, such as without a linker. In particular embodiments, the IL-15 protein is attached to an Fc domain via a hinge region or a fragment thereof. In some embodiments, the IL-15Rα protein is attached to an Fc domain via a linker. In other embodiments, the IL-15Rα protein is attached to an Fc domain directly, such as without a linker. In particular embodiments, the IL-15Rα protein is attached to an Fc domain via a hinge region or a fragment thereof. In some cases, a linker is not used to attach the IL-15 protein or IL-15Rα protein to an Fc domain.

In some embodiments, the linker is a "domain linker", used to link any two domains as outlined herein together. While any suitable linker can be used, many embodiments utilize a glycine-serine polymer, including for example (GS)n (SEQ ID NO: 23), (GSGGS)n (SEQ ID NO: 24), (GGGGS)n (SEQ ID NO: 25), and (GGGS)n (SEQ ID NO: 26), where n is an integer of at least 0 (and generally from 0 to 1 to 2 to 3 to 4 to 5) as well as any peptide sequence that allows for recombinant attachment of the two domains with sufficient length and flexibility to allow each domain to retain its biological function. In certain cases, useful linkers include $(GGGGS)_0$ ("GGGGS" disclosed as SEQ ID NO: 27) or $(GGGGS)_1$ (SEQ ID NO: 27) or $(GGGGS)_2$ (SEQ ID NO: 28). Useful domain linkers are shown in FIG. 7. In some cases, and with attention being paid to "strandedness", as outlined below, charged domain linkers can be used as discussed herein and shown in FIG. 7 and herein.

VII. Useful Formats of the Invention

As shown in FIGS. 9A-9G and FIGS. 39A-39D there are a number of useful formats of the IL-15/Rα-Fc fusion proteins of the invention. In general, the heterodimeric fusion proteins of the invention have two functional components: an IL-15/IL-15Rα(sushi) component and an Fc component, both of which can take different forms as outlined herein and both of which can be combined with the other component in any configuration.

The first and the second Fc domains can have a set of amino acid substitutions selected from the group consisting of a) S267K/L368D/K370S:S267K/LS364K/E357Q; b) S364K/E357Q:L368D/K370S; c) L368D/K370S:S364K; d) L368E/K370S:S364K; e) T411E/K360E/Q362E:D401K; f) L368D/K370S:S364K/E357L and g) K370S:S364K/E357Q, according to EU numbering. In some embodiments, the first Fc domain has L368D/K370S substitutions and the second Fc domain has S364K/E357Q substitutions. In some embodiments, the first Fc domain has S364K/E357Q substitutions and the second Fc domain has L368D/K370S substitutions.

In some embodiments, the first and/or the second Fc domains have an additional set of amino acid substitutions comprising Q295E/N384D/Q418E/N421D, according to EU numbering.

Optionally, the first and/or the second Fc domains have an additional set of amino acid substitutions consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, according to EU numbering.

Optionally, the first and/or second Fc domains have 428L/434S variants for half life extension. In some cases, the first and/or second Fc domains have M428L/N434S variants for half life extension. In some embodiments, the first Fc domain has M428L/N434S substitutions and the second Fc domain has M428L/N434S substitutions A. IL-15/Rα-heteroFc Format In this embodiment, as shown in FIG. 9A, the heterodimeric fusion protein comprises two monomers (two Fc monomers). The first monomer comprises (from N- to C-terminus) IL-15-optional domain linker-CH2-CH3, where the domain linker sometimes comprises all or part of the hinge. The second monomer comprises the IL-15/Rα(sushi) domain-optional domain linker-CH2-CH3, where the domain linker sometimes comprises all or part of the hinge.

In the IL-15/Rα-heteroFc format, a preferred embodiment utilizes the skew variant pair S364K/E357Q:L368D/K370S. In some instances, the L368D/K370S variant is on the first monomer and the S354K/E357Q variant is on the second monomer.

In the IL-15/Rα-heteroFc format, a preferred embodiment utilizes the IL-15 D30N/N65D variant.

In the IL-15/Rα-heteroFc format, a preferred embodiment utilizes the IL-15 D30N/N65D variant and the skew variant pair S364K/E357Q:L368D/K370S. In the IL-15/Rα-heteroFc format, a preferred embodiment utilizes the IL-15 D30N/N65D variant, the skew variant pair S364K/E357Q: L368D/K370S and the 428L/434S variants on each Fc monomer. In the IL-15/Rα-heteroFc format, a preferred embodiment utilizes the IL-15 D30N/N65D variant, the skew variant pair S364K/E357Q:L368D/K370S and the M428L/N434S variants on each Fc monomer.

In some embodiments, the IL-15/Rα-heteroFc fusion protein comprises a human mature IL-15 D30N/N65D variant, an IL-15Rα(sushi) domain, and Fc monomers comprising the amino acid substitutions depicted in FIG. 6A. In some embodiments, the IL-15/Rα-heteroFc fusion protein comprises a human mature IL-15 D30N/N65D variant; a human IL-15Rα(sushi) domain; an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K; and an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the IL-15/Rα-heteroFc fusion protein comprises a human mature IL-15 D30N/N65D variant; a human IL-15Rα(sushi) domain, an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the IL-15/Rα-heteroFc format, a preferred embodiment utilizes the IL-15 D30N/E64Q/N65D variants.

In the IL-15/Rα-heteroFc format, a preferred embodiment utilizes the IL-15 D30N/E64Q/N65D variants and the skew variant pair S364K/E357Q:L368D/K370S.

In the IL-15/Rα-heteroFc format, a preferred embodiment utilizes the IL-15 D30N/E64Q/N65D variants, the skew variant pair S364K/E357Q:L368D/K370S and the 428L/434S variants on each Fc monomer. In the IL-15/Rα-heteroFc format, a preferred embodiment utilizes the IL-15 D30N/E64Q/N65D variants, the skew variant pair S364K/E357Q:L368D/K370S and the M428L/N434S variants on each Fc monomer. In some embodiments, the IL-15/Rα-heteroFc fusion protein comprises a human mature IL-15 D30N/E64Q/N65D variant, an IL-15Rα(sushi) domain, and Fc monomers comprising the amino acid substitutions depicted in FIG. 6A. In some embodiments, the IL-15/Rα-heteroFc fusion protein comprises a human mature IL-15 D30N/E64Q/N65D variant; a human IL-15Rα(sushi) domain; an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K; and an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the IL-15/Rα-heteroFc fusion protein comprises a human mature IL-15 D30N/E64Q/N65D variant; a human IL-15Rα(sushi) domain, an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the IL-15/Rα-heteroFc format, a preferred embodiment utilizes the IL-15 N4D variant.

In the IL-15/Rα-heteroFc format, a preferred embodiment utilizes the IL-15 N4D variant and the skew variant pair S364K/E357Q:L368D/K370S. In the IL-15/Rα-heteroFc format, a preferred embodiment utilizes the IL-15 N4D variant, the skew variant pair S364K/E357Q:L368D/K370S and the 428L/434S variants on each Fc monomer. In the IL-15/Rα-heteroFc format, a preferred embodiment utilizes the IL-15 N4D variant, the skew variant pair S364K/E357Q:L368D/K370S and the M428L/N434S variants on each Fc monomer. In some embodiments, the IL-15/Rα-heteroFc fusion protein comprises a human mature IL-15 N4D variant, an IL-15Rα(sushi) domain, and Fc monomers comprising the amino acid substitutions depicted in FIG. 6A. In some embodiments, the IL-15/Rα-heteroFc fusion protein comprises a human mature IL-15 N4D variant; a human IL-15Rα(sushi) domain; an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K; and an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the IL-15/Rα-heteroFc fusion protein comprises a human mature IL-15 N4D variant; a human IL-15Rα(sushi) domain, an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the IL-15/Rα-heteroFc format, a preferred embodiment utilizes the IL-15 N65D variant. In the IL-15/Rα-heteroFc format, a preferred embodiment utilizes the IL-15 N65D variant, and the skew variant pair S364K/E357Q:L368D/K370S.

In the IL-15/Rα-heteroFc format, a preferred embodiment utilizes the IL-15 N65D variant, the skew variant pair S364K/E357Q:L368D/K370S and the 428L/434S variants on each Fc monomer. In the IL-15/Rα-heteroFc format, a preferred embodiment utilizes the IL-15 N65D variant, the skew variant pair S364K/E357Q:L368D/K370S and the M428L/N434S variants on each Fc monomer. In some embodiments, the IL-15/Rα-heteroFc fusion protein comprises a human mature IL-15 N65D variant, an IL-15Rα (sushi) domain, and Fc monomers comprising the amino acid substitutions depicted in FIG. 6A. In some embodiments, the IL-15/Rα-heteroFc fusion protein comprises a human mature IL-15 N65D variant; a human IL-15Rα (sushi) domain; an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K; and an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the IL-15/Rα-heteroFc fusion protein comprises a human mature IL-15 N65D variant; a human IL-15Rα(sushi) domain, an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the IL-15/Rα-heteroFc format, a preferred embodiment utilizes the IL-15 N4D/N65D variant.

In the IL-15/Rα-heteroFc format, a preferred embodiment utilizes the IL-15 N4D/N65D variant and the skew variant pair S364K/E357Q:L368D/K370S.

In the IL-15/Rα-heteroFc format, a preferred embodiment utilizes the IL-15 N4D/N65D variant, the skew variant pair S364K/E357Q:L368D/K370S and the 428L/434S variants on each Fc monomer. In the IL-15/Rα-heteroFc format, a preferred embodiment utilizes the IL-15 N4D/N65D variant, the skew variant pair S364K/E357Q:L368D/K370S and the M428L/N434S variants on each Fc monomer. In some embodiments, the IL-15/Rα-heteroFc fusion protein comprises a human mature IL-15 N4D/N65D variant, an IL-15Rα(sushi) domain, and Fc monomers comprising the amino acid substitutions depicted in FIG. 6A. In some embodiments, the IL-15/Rα-heteroFc fusion protein comprises a human mature IL-15 N4D/N65D variant; a human IL-15Rα(sushi) domain; an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K; and an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the IL-15/Rα-heteroFc fusion protein comprises a human mature IL-15 N4D/N65D variant; a human IL-15Rα(sushi) domain, an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the IL-15/Rα-heteroFc format, a preferred embodiment utilizes the IL-15 N1D/N65D variant.

In the IL-15/Rα-heteroFc format, a preferred embodiment utilizes the IL-15 N1D/N65D variant and the skew variant pair S364K/E357Q:L368D/K370S.

In the IL-15/Rα-heteroFc format, a preferred embodiment utilizes the IL-15 N1D/N65D variant, the skew variant pair S364K/E357Q:L368D/K370S and the 428L/434S variants on each Fc monomer. In the IL-15/Rα-heteroFc format, a preferred embodiment utilizes the IL-15 N1D/N65D variant, the skew variant pair S364K/E357Q:L368D/K370S and the M428L/N434S variants on each Fc monomer. In some embodiments, the IL-15/Rα-heteroFc fusion protein comprises a human mature IL-15 N1D/N65D variant, an IL-15Rα(sushi) domain, and Fc monomers comprising the amino acid substitutions depicted in FIG. 6A. In some embodiments, the IL-15/Rα-heteroFc fusion protein comprises a human mature IL-15 N1D/N65D variant; a human IL-15Rα(sushi) domain; an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K; and an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the IL-15/Rα-heteroFc fusion protein comprises a human mature IL-15 N1D/N65D variant; a human IL-15Rα(sushi) domain, an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the IL-15/Rα-heteroFc format, a preferred embodiment utilizes the IL-15 Q108E variant.

In the IL-15/Rα-heteroFc format, a preferred embodiment utilizes the IL-15 Q108E variant and the skew variant pair S364K/E357Q:L368D/K370S.

In the IL-15/Rα-heteroFc format, a preferred embodiment utilizes the IL-15 Q108E variant and the skew variant pair S364K/E357Q:L368D/K370S and the 428L/434S variants on both monomers. In the IL-15/Rα-heteroFc format, a preferred embodiment utilizes the IL-15 Q108E variant and the skew variant pair S364K/E357Q:L368D/K370S and the M428L/N434S variants on both monomers.

In the IL-15/Rα-heteroFc format, a preferred embodiment utilizes the IL-15 Q108E variant, the skew variant pair S364K/E357Q:L368D/K370S and the 428L/434S variants on each Fc monomer. In the IL-15/Rα-heteroFc format, a preferred embodiment utilizes the IL-15 Q108E variant, the skew variant pair S364K/E357Q:L368D/K370S and the M428L/N434S variants on each Fc monomer. In some embodiments, the IL-15/Rα-heteroFc fusion protein comprises a human mature IL-15 Q108E variant, an IL-15Rα(sushi) domain, and Fc monomers comprising the amino acid substitutions depicted in FIG. 6A. In some embodiments, the IL-15/Rα-heteroFc fusion protein comprises a human mature IL-15 Q108E variant; a human IL-15Rα(sushi) domain; an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K; and an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the IL-15/Rα-heteroFc fusion protein comprises a human mature IL-15 Q108E variant; a human IL-15Rα(sushi) domain, an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the IL-15/Rα-heteroFc format, a preferred embodiment utilizes the IL-15 wildtype variant.

In the IL-15/Rα-heteroFc format, a preferred embodiment utilizes the IL-15 wildtype variant and the skew variant pair S364K/E357Q:L368D/K370S.

In the IL-15/Rα-heteroFc format, a preferred embodiment utilizes the IL-15 wildtype variant, the skew variant pair S364K/E357Q:L368D/K370S and the 428L/434S variants on each Fc monomer. In the IL-15/Rα-heteroFc format, a preferred embodiment utilizes the IL-15 wildtype variant, the skew variant pair S364K/E357Q:L368D/K370S and the M428L/N434S variants on each Fc monomer. In some embodiments, the IL-15/Rα-heteroFc fusion protein comprises a human mature IL-15 wildtype variant, an IL-15Rα (sushi) domain, and Fc monomers comprising the amino acid substitutions depicted in FIG. 6A. In some embodiments, the IL-15/Rα-heteroFc fusion protein comprises a human mature IL-15 wildtype variant; a human IL-15Rα (sushi) domain; an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K; and an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the IL-15/Rα-heteroFc fusion protein comprises a human mature IL-15 wildtype variant; a human IL-15Rα(sushi) domain, an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

Figure 94A:
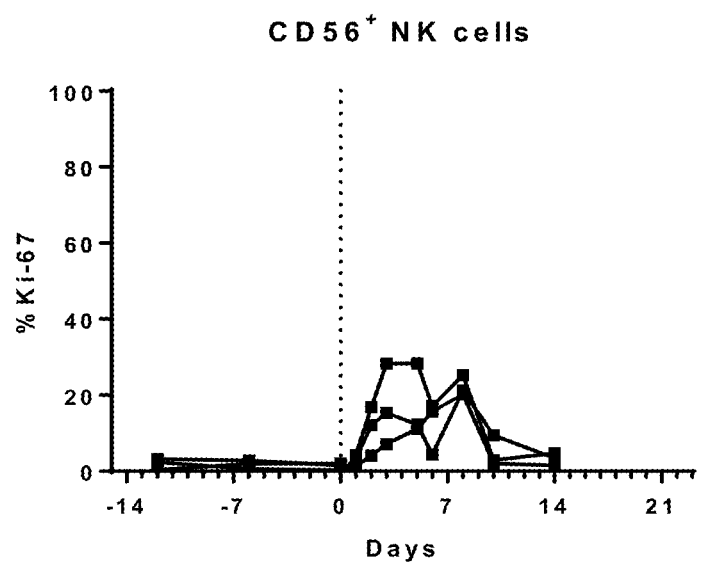
Figure 94B:
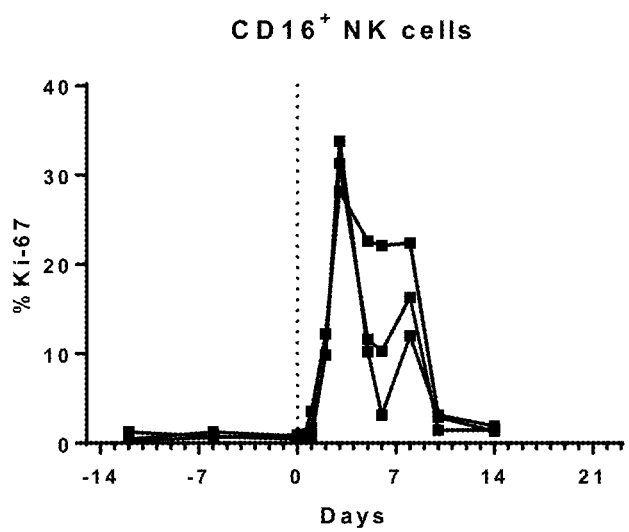
Figure 94C:
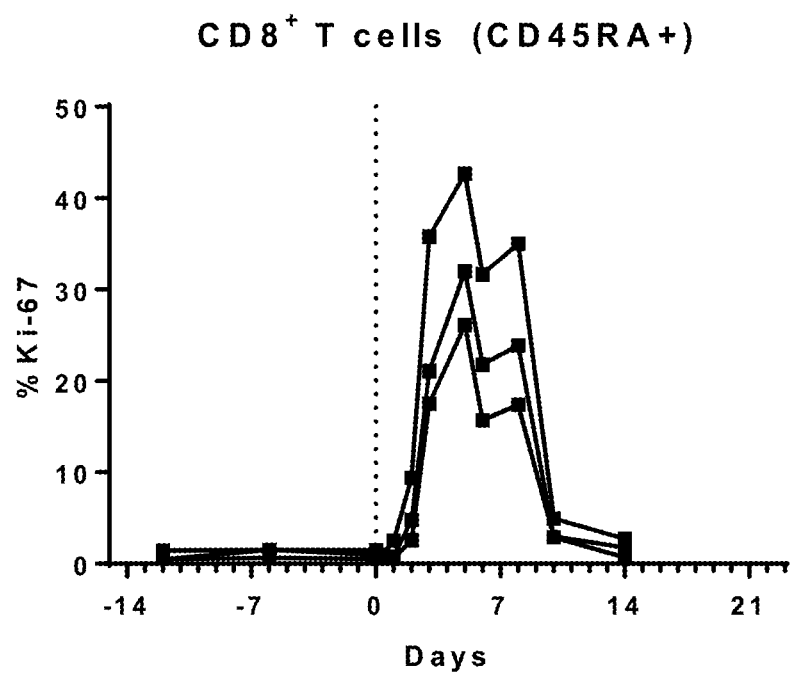
Figure 94D:
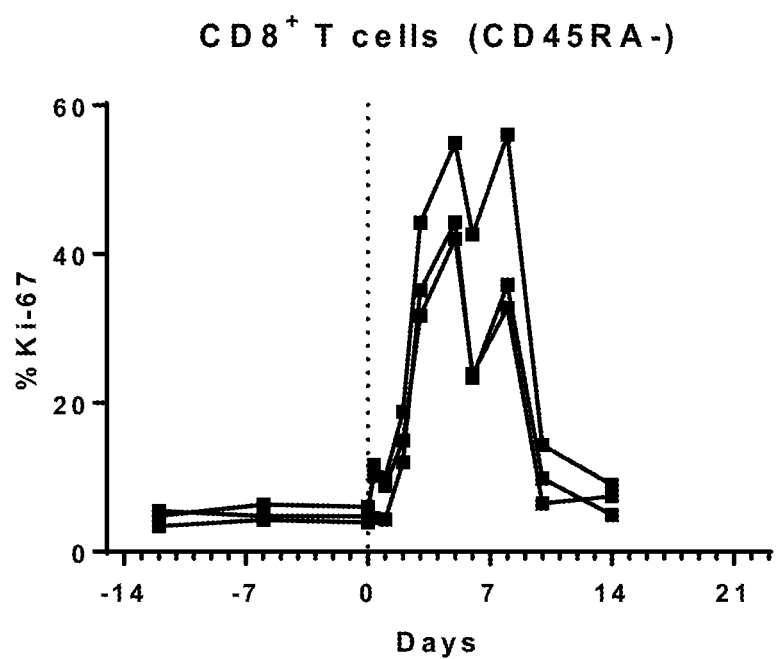
Figure 94E:
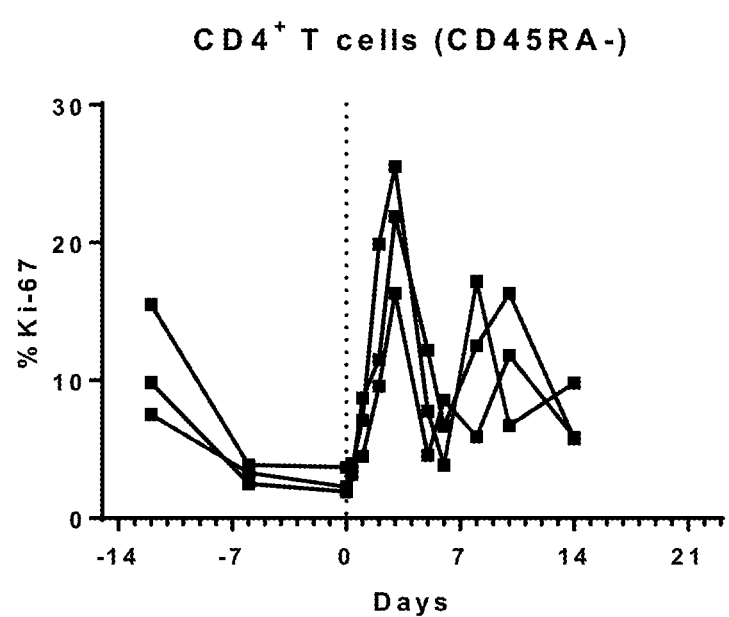

In the IL-15/Rα-heteroFc format, preferred embodiments are shown in WO2018/071919 in FIG. 48A (XENP22822 including chain 1 (17693) and chain 2 (15908)), FIG. 94A (XENP23504 including chain 1 and chain 2), FIG. 104AO (XENP24045 including chain 1 and chain 2), FIG. 104AQ (XENP24306 including chain 1 and chain 2), FIG. 48A (XENP22821 including chain 1 and chain 2), FIG. 94A (XENP23343 including chain 1 and chain 2), FIG. 104AJ (XENP23557 including chain 1 and chain 2), FIG. 104AP (XENP24113 including chain 1 and chain 2), FIG. 104AP (XENP24051 including chain 1 and chain 2), FIG. 104AR (XENP24341 including chain 1 and chain 2), FIG. 104AP (XENP24052 including chain 1 and chain 2), and FIG. 104AP (XENP24301 including chain 1 and chain 2), all of which are herein incorporated by reference in its entirety.

In the TL-15/Rα-heteroFc format, preferred embodiments are shown in FIG. 10 (XENP22822 including chain 1 (15902) and chain 2 (15908)) and (XENP21475 including chain 1 (16479) and chain 2 (16481)).

B. scIL-15-Rα-Fc

In this embodiment, as shown in FIG. 9B, the heterodimeric fusion protein comprises two monomers. The first monomer comprises (from N- to C-terminus) IL-15/Rα (sushi)-domain linker-IL-15-optional domain linker-CH2-CH3, where the domain linker sometimes comprises all or part of the hinge. The second monomer comprises and "empty" Fc, comprising all or part of the hinge-CH2-CH3. This is referred to as "scIL-15/Rα-Fc" with the "sc" standing for "single chain" (e.g. of the IL-15/Rα sushi complex).

In the scIL-15/Rα-Fc format, a preferred embodiment utilizes the IL-15 D30N/N65D variants.

In the scIL-15/Rα-Fc format, a preferred embodiment utilizes the IL-15 D30N/N65D variants and the skew variant pair S364K/E357Q:L368D/K370S.

In the scIL-15/Rα-Fc format, a preferred embodiment utilizes the IL-15 D30N/N65D variants, the skew variant pair S364K/E357Q:L368D/K370S, and on each Fc monomer the 428L/434S variants. In the scIL-15/Rα-Fc format, a preferred embodiment utilizes the IL-15 D30N/N65D variants, the skew variant pair S364K/E357Q:L368D/K370S, and on each Fc monomer the M428L/N434S variants.

In some embodiments, the scIL-15/Rα-Fc fusion protein comprises a single chain comprising a human mature IL-15 D30N/N65D variant and an IL-15Rα(sushi) domain; and Fc monomers comprising the amino acid substitutions depicted in FIG. 6B. In some embodiments, the scIL-15/Rα-Fc fusion protein comprises a single chain comprising a human mature IL-15 D30N/N65D variant and an IL-15Rα(sushi) domain; an scIL-15/Rα-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an empty-Fc monomer comprising the amino acid substitutions C220S, heterodimer pI substitutions S364K/E357Q, and ablation substitutions E233P/L234V/L235A/G236del/S267K. In some embodiments, the scIL-15/Rα-Fc fusion protein comprises a single chain comprising a human mature IL-15 D30N/N65D variant and an IL-15Rα(sushi) domain; an scIL-15/Rα-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an empty-Fc monomer comprising the amino acid substitutions C220S, heterodimer pI substitutions S364K/E357Q, ablation substitutions E233P/L234V/L235A/G236del/S267K, and FcRn substitutions M428L/N434S.

In the scIL-15/Rα-Fc format, a preferred embodiment utilizes the IL-15 D30N/E64Q/N65D variants.

In the scIL-15/Rα-Fc format, a preferred embodiment utilizes the IL-15 D30N/E64Q/N65D variants and the skew variant pair S364K/E357Q:L368D/K370S.

In the scIL-15/Rα-Fc format, a preferred embodiment utilizes the IL-15 D30N/E64Q/N65D variants, the skew variant pair S364K/E357Q:L368D/K370S and the 428L/434S variants on each Fc monomer. In the scIL-15/Rα-Fc format, a preferred embodiment utilizes the IL-15 D30N/E64Q/N65D variants, the skew variant pair S364K/E357Q L368D/K370S and the M428L/N434S variants on each Fc monomer.

In some embodiments, the scIL-15/Rα-Fc fusion protein comprises a single chain comprising a human mature IL-15 D30N/E64Q/N65D variant and an IL-15Rα(sushi) domain; and Fc monomers comprising the amino acid substitutions depicted in FIG. 6B. In some embodiments, the scIL-15/Rα-Fc fusion protein comprises a single chain comprising a human mature IL-15 D30N/E64Q/N65D variant and an IL-15Rα(sushi) domain; an scIL-15/Rα-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an empty-Fc monomer comprising the amino acid substitutions C220S, heterodimer pI substitutions S364K/E357Q, and Ablation substitutions E233P/L234V/L235A/G236del/S267K. In some embodiments, the scIL-15/Rα-Fc fusion protein comprises a single chain comprising a human mature IL-15 D30N/E64Q/N65D variant and an IL-15Rα(sushi) domain; an scIL-15/Rα-Fc monomer comprising an amino acid substitution C220S, heterodimer pI substitutions L368D/

K370S, isosteric pI substitutions Q295E/N384D/Q418E/N421D, ablation substitutions E233P/L234V/L235A/G236del/S267K, and FcRn substitutions M428L/N434S; and an empty-Fc monomer comprising the amino acid substitutions C220S, heterodimer pI substitutions S364K/E357Q, ablation substitutions E233P/L234V/L235A/G236del/S267K, and FcRn substitutions M428L/N434S.

In the scIL-15/Rα-Fc format, a preferred embodiment utilizes the IL-15 N65D variant.

In the scIL-15/Rα-Fc format, a preferred embodiment utilizes the IL-15 N65D variant, and the skew variant pair S364K/E357Q:L368D/K370S In the scIL-15/Rα-Fc format, a preferred embodiment utilizes the IL-15 N65D variant, the skew variant pair S364K/E357Q:L368D/K370S and the 428L/434S variants on each Fc monomer. In the scIL-15/Rα-Fc format, a preferred embodiment utilizes the IL-15 N65D variant, the skew variant pair S364K/E357Q:L368D/K370S and the M428L/N434S variants on each Fc monomer.

In some embodiments, the scIL-15/Rα-Fc fusion protein comprises a single chain comprising a human mature IL-15 N65D variant and an IL-15Rα(sushi) domain; and Fc monomers comprising the amino acid substitutions depicted in FIG. 6B. In some embodiments, the scIL-15/Rα-Fc fusion protein comprises a single chain comprising a human mature IL-15 N65D variant and an IL-15Rα(sushi) domain; an scIL-15/Rα-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an empty-Fc monomer comprising the amino acid substitutions C220S, heterodimer pI substitutions S364K/E357Q, and ablation substitutions E233P/L234V/L235A/G236del/S267K. In some embodiments, the scIL-15/Rα-Fc fusion protein comprises a single chain comprising a human mature IL-15 N65D variant and an IL-15Rα(sushi) domain; an scIL-15/Rα-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an empty-Fc monomer comprising the amino acid substitutions C220S, heterodimer pI substitutions S364K/E357Q, ablation substitutions E233P/L234V/L235A/G236del/S267K, and FcRn substitutions M428L/N434S.

In the scIL-15/Rα-Fc format, a preferred embodiment utilizes the IL-15 N4D/N65D variant.

In the scIL-15/Rα-Fc format, a preferred embodiment utilizes the IL-15 N4D/N65D variant and the skew variant pair S364K/E357Q:L368D/K370S.

In the scIL-15/Rα-Fc format, a preferred embodiment utilizes the IL-15 N4D/N65D variant, the skew variant pair S364K/E357Q:L368D/K370S and the 428L/434S variants on each Fc monomer. In the scIL-15/Rα-Fc format, a preferred embodiment utilizes the IL-15 N4D/N65D variant, the skew variant pair S364K/E357Q:L368D/K370S and the M428L/N434S variants on each Fc monomer.

In some embodiments, the scIL-15/Rα-Fc fusion protein comprises a single chain comprising a human mature IL-15 N4D/N65D variant and an IL-15Rα(sushi) domain; and Fc monomers comprising the amino acid substitutions depicted in FIG. 6B. In some embodiments, the scIL-15/Rα-Fc fusion protein comprises a single chain comprising a human mature IL-15 N4D/N65D variant and an IL-15Rα(sushi) domain; an scIL-15/Rα-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an empty-Fc monomer comprising the amino acid substitutions C220S, heterodimer pI substitutions S364K/E357Q, and ablation substitutions E233P/L234V/L235A/G236del/S267K. In some embodiments, the scIL-15/Rα-Fc fusion protein comprises a single chain comprising a human mature IL-15 N4D/N65D variant and an IL-15Rα(sushi) domain; an scIL-15/Rα-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an empty-Fc monomer comprising the amino acid substitutions C220S, heterodimer pI substitutions S364K/E357Q, ablation substitutions E233P/L234V/L235A/G236del/S267K, and FcRn substitutions M428L/N434S.

In the scIL-15/Rα-Fc format, a preferred embodiment utilizes the IL-15 N1D/N65D variant.

In the scIL-15/Rα-Fc format, a preferred embodiment utilizes the IL-15 N1D/N65D variant and the skew variant pair S364K/E357Q:L368D/K370S.

In the scIL-15/Rα-Fc format, a preferred embodiment utilizes the IL-15 N1D/N65D variant, the skew variant pair S364K/E357Q:L368D/K370S and the 428L/434S variants on each Fc monomer. In the scIL-15/Rα-Fc format, a preferred embodiment utilizes the IL-15 N1D/N65D variant, the skew variant pair S364K/E357Q:L368D/K370S and the M428L/N434S variants on each Fc monomer.

In some embodiments, the scIL-15/Rα-Fc fusion protein comprises a single chain comprising a human mature IL-15 N1D/N65D variant and an IL-15Rα(sushi) domain; and Fc monomers comprising the amino acid substitutions depicted in FIG. 6B. In some embodiments, the scIL-15/Rα-Fc fusion protein comprises a single chain comprising a human mature IL-15 N1D/N65D variant and an IL-15Rα(sushi) domain; an scIL-15/Rα-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an empty-Fc monomer comprising the amino acid substitutions C220S, heterodimer pI substitutions S364K/E357Q, and ablation substitutions E233P/L234V/L235A/G236del/S267K. In some embodiments, the scIL-15/Rα-Fc fusion protein comprises a single chain comprising a human mature IL-15 N1D/N65D variant and an IL-15Rα(sushi) domain; an scIL-15/Rα-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an empty-Fc monomer comprising the amino acid substitutions C220S, heterodimer pI substitutions S364K/E357Q, ablation substitutions E233P/L234V/L235A/G236del/S267K, and FcRn substitutions M428L/N434S.

In the scIL-15/Rα-Fc format, preferred embodiments include XENP21478 including chain 1 (16478) and chain 2 (8924) and is shown in FIG. 11. Other embodiments of this format include XENP21993, XENP21994, XENP21995, XENP23174, XENP23175, XENP24477, and XENP24480 and are shown in WO2018071919 in FIGS. 104G, 104H, 104AG, 104AU, and 104AV and amino acid sequences are found in SEQ ID NOS: 514-518, 519-523, 524-528, 849-853, 1063-1067, and 1078-1082, respectively.

C. ncIL-15/Rα-Fc

Figure 9C:
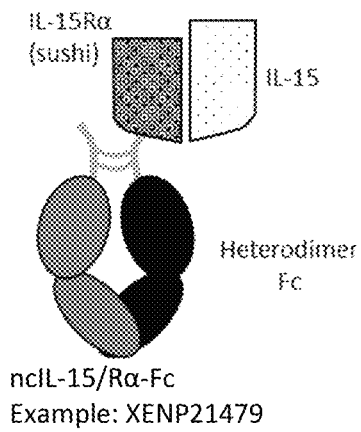

In this embodiment, as shown in FIG. 9C, the heterodimeric fusion protein comprises three monomers. The first monomer comprises (from N- to C-terminus) IL-15/Rα(sushi)-domain linker-CH2-CH3, where the domain linker sometimes comprises all or part of the hinge. The second monomer comprises and "empty" Fc, comprising all or part of the hinge-CH2-CH3. The third monomer is IL-15. This is referred to as "ncIL-15/Rα-Fc" with the "nc" standing for "non-covalent").

In the ncIL-15/Rα-Fc format, a preferred embodiment utilizes the skew variant pair S364K/E357Q:L368D/K370S.

In the ncIL-15/Rα-Fc format, a preferred embodiment utilizes the IL-15 D30N/E64Q/N65D variants.

In the ncIL-15/Rα-Fc format, a preferred embodiment utilizes the IL-15 D30N/E64Q/N65D variants and the skew variant pair S364K/E357Q:L368D/K370S.

In the ncIL-15/Rα-Fc format, a preferred embodiment utilizes the IL-15 D30N/E64Q/N65D variants, the skew variant pair S364K/E357Q:L368D/K370S and the 428L/434S variants on each Fc monomer. In the ncIL-15/Rα-Fc format, a preferred embodiment utilizes the IL-15 D30N/E64Q/N65D variants, the skew variant pair S364K/E357Q L368D/K370S and the M428L/N434S variants on each Fc monomer.

In some embodiments, the ncIL-15/Rα-Fc fusion protein comprises a human mature IL-15 D30N/E64Q/N65D variant, an IL-15Rα(sushi) domain; and Fc monomers comprising the amino acid substitutions depicted in FIG. 6C. In some embodiments, the ncIL-15/Rα-Fc fusion protein comprises a human mature IL-15 D30N/E64Q/N65D variant, an IL-15Rα(sushi) domain; an empty-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an IL-15Rα(sushi)-Fc monomer comprising an amino acid substitution C220S, heterodimer pI substitutions S364K/E357Q, and ablation substitutions E233P/L234V/L235A/G236del/S267K. In some embodiments, the ncIL-15/Rα-Fc fusion protein comprises a single chain comprising a human mature IL-15 D30N/E64Q/N65D variant; an IL-15Rα(sushi) domain; an empty-Fc comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the ncIL-15/Rα-Fc format, a preferred embodiment utilizes the IL-15 N4D variant.

In the ncIL-15/Rα-Fc format, a preferred embodiment utilizes the IL-15 N4D variant, and the skew variant pair S364K/E357Q:L368D/K370S. In the ncIL-15/Rα-Fc format, a preferred embodiment utilizes the IL-15 N4D variant, the skew variant pair S364K/E357Q L368D/K370S and the 428L/434S variants on each Fc monomer. In the ncIL-15/Rα-Fc format, a preferred embodiment utilizes the IL-15 N4D variant, the skew variant pair S364K/E357Q L368D/K370S and the M428L/N434S variants on each Fc monomer.

In some embodiments, the ncIL-15/Rα-Fc fusion protein comprises a human mature IL-15 N4D variant, an IL-15Rα(sushi) domain; and Fc monomers comprising the amino acid substitutions depicted in FIG. 6C. In some embodiments, the ncIL-15/Rα-Fc fusion protein comprises a human mature IL-15 N4D variant, an IL-15Rα(sushi) domain; an empty-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an IL-15Rα(sushi)-Fc monomer comprising an amino acid substitution C220S, heterodimer pI substitutions S364K/E357Q, and ablation substitutions E233P/L234V/L235A/G236del/S267K. In some embodiments, the ncIL-15/Rα-Fc fusion protein comprises a single chain comprising a human mature IL-15 N4D variant; an IL-15Rα(sushi) domain; an empty-Fc comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the ncIL-15/Rα-Fc format, a preferred embodiment utilizes the IL-15 N65D variant.

In the ncIL-15/Rα-Fc format, a preferred embodiment utilizes the IL-15 N65D variant, and the skew variant pair S364K/E357Q:L368D/K370S. In the ncIL-15/Rα-Fc format, a preferred embodiment utilizes the IL-15 N65D variant, the skew variant pair S364K/E357Q:L368D/K370S and the 428L/434S variants on each Fc monomer. In the ncIL-15/Rα-Fc format, a preferred embodiment utilizes the IL-15 N65D variant, the skew variant pair S364K/E357Q L368D/K370S and the M428L/N434S variants on each Fc monomer.

In some embodiments, the ncIL-15/Rα-Fc fusion protein comprises a human mature IL-15 N65D variant, an IL-15Rα(sushi) domain; and Fc monomers comprising the amino acid substitutions depicted in FIG. 6C. In some embodiments, the ncIL-15/Rα-Fc fusion protein comprises a human mature IL-15 N65D variant, an IL-15Rα(sushi) domain; an empty-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an IL-15Rα(sushi)-Fc monomer comprising an amino acid substitution C220S, heterodimer pI substitutions S364K/E357Q, and ablation substitutions E233P/L234V/L235A/G236del/S267K. In some embodiments, the ncIL-15/Rα-Fc fusion protein comprises a single chain comprising a human mature IL-15 N65D variant; an IL-15Rα(sushi) domain; an empty-Fc comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the ncIL-15/Rα-Fc format, a preferred embodiment utilizes the IL-15 N4D/N65D variant.

In the ncIL-15/Rα-Fc format, a preferred embodiment utilizes the IL-15 N4D/N65D variant and the skew variant pair S364K/E357Q:L368D/K370S. In the ncIL-15/Rα-Fc format, a preferred embodiment utilizes the IL-15 N4D/N65D variant, the skew variant pair S364K/E357Q:L368D/K370S and the 428L/434S variants on each Fc monomer. In the ncIL-15/Rα-Fc format, a preferred embodiment utilizes the IL-15 N4D/N65D variant, the skew variant pair S364K/E357Q:L368D/K370S and the M428L/N434S variants on each Fc monomer.

In some embodiments, the ncIL-15/Rα-Fc fusion protein comprises a human mature IL-15 N4D/N65D variant, an IL-15Rα(sushi) domain; and Fc monomers comprising the amino acid substitutions depicted in FIG. 6C. In some embodiments, the ncIL-15/Rα-Fc fusion protein comprises a human mature IL-15 N4D/N65D variant, an IL-15Rα(sushi) domain; an empty-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an IL-15Rα(sushi)-Fc monomer comprising an amino acid substitution C220S, heterodimer pI substitutions S364K/E357Q, and ablation substitutions E233P/L234V/L235A/G236del/S267K. In some embodiments, the ncIL-15/Rα-Fc fusion protein comprises a single chain comprising a human mature IL-15 N4D/N65D variant; an IL-15Rα(sushi) domain; an empty-Fc comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer ablation an amino acid substitution C220S, heterodimer pI substitutions S364K/E357Q, ablation substitutions E233P/L234V/L235A/G236del/S267K, and FcRn substitutions M428L/N434S.

In the ncIL-15/Rα-Fc format, a preferred embodiment utilizes the IL-15 N1D/N65D variant.

In the ncIL-15/Rα-Fc format, a preferred embodiment utilizes the IL-15 N1D/N65D variant and the skew variant pair S364K/E357Q:L368D/K370S. In the ncIL-15/Rα-heteroFc format, a preferred embodiment utilizes the IL-15 N1D/N65D variant, the skew variant pair S364K/E357Q:L368D/K370S and the 428L/434S variants on each Fc monomer. In the ncIL-15/Rα-heteroFc format, a preferred embodiment utilizes the IL-15 N1D/N65D variant, the skew variant pair S364K/E357Q:L368D/K370S and the M428L/N434S variants on each Fc monomer.

In some embodiments, the ncIL-15/Rα-Fc fusion protein comprises a human mature IL-15 N1D/N65D variant, an IL-15Rα(sushi) domain; and Fc monomers comprising the amino acid substitutions depicted in FIG. 6C. In some embodiments, the ncIL-15/Rα-Fc fusion protein comprises a human mature IL-15 N1D/N65D variant, an IL-15Rα(sushi) domain; an empty-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an IL-15Rα(sushi)-Fc monomer comprising an amino acid substitution C220S, heterodimer pI substitutions S364K/E357Q, and ablation substitutions E233P/L234V/L235A/G236del/S267K. In some embodiments, the ncIL-15/Rα-Fc fusion protein comprises a single chain comprising a human mature IL-15 N1D/N65D variant; an IL-15Rα(sushi) domain; an empty-Fc comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the ncIL-15/Rα-Fc format, a preferred embodiment utilizes the IL-15 variant Q108E.

In the nIL-15/Rα-Fc format, a preferred embodiment utilizes the IL-15 variant Q108E and the skew variant pair S364K/E357Q:L368D/K370S.

In the ncIL-15/Rα-Fc format, a preferred embodiment utilizes the IL-15 variant Q108E and the skew variant pair S364K/E357Q:L368D/K370S and the 428L/434S variants on both monomers. In the scIL-15/Rα-Fc format, a preferred embodiment utilizes the IL-15 variant Q108E and the skew variant pair S364K/E357Q:L368D/K370S and the M428L/N434S variants on both monomers.

In some embodiments, the ncIL-15/Rα-Fc fusion protein comprises a human mature IL-15 Q108E variant, an IL-15Rα(sushi) domain; and Fc monomers comprising the amino acid substitutions depicted in FIG. 6C. In some embodiments, the ncIL-15/Rα-Fc fusion protein comprises a human mature IL-15 Q108E variant, an IL-15Rα(sushi) domain; an empty-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an IL-15Rα(sushi)-Fc monomer comprising an amino acid substitution C220S, heterodimer pI substitutions S364K/E357Q, and ablation substitutions E233P/L234V/L235A/G236del/S267K. In some embodiments, the ncIL-15/Rα-Fc fusion protein comprises a single chain comprising a human mature IL-15 Q108E variant; an IL-15Rα(sushi) domain; an empty-Fc comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the ncIL-15/Rα-Fc format, a preferred embodiment utilizes the IL-15 wildtype variant.

In the ncIL-15/Rα-Fc format, a preferred embodiment utilizes the IL-15 wildtype variant and the skew variant pair S364K/E357Q:L368D/K370S. In the ncIL-15/Rα-heteroFc format, a preferred embodiment utilizes the IL-15 wildtype variant, the skew variant pair S364K/E357Q:L368D/K370S and the 428L/434S variants on each Fc monomer. In the ncIL-15/Rα-heteroFc format, a preferred embodiment utilizes the IL-15 wildtype variant, the skew variant pair S364K/E357Q:L368D/K370S and the M428L/N434S variants on each Fc monomer.

In some embodiments, the ncIL-15/Rα-Fc fusion protein comprises a human mature IL-15 wildtype variant, an IL-15Rα(sushi) domain; and Fc monomers comprising the amino acid substitutions depicted in FIG. 6C. In some embodiments, the ncIL-15/Rα-Fc fusion protein comprises a human mature IL-15 wildtype variant, an IL-15Rα(sushi) domain; an empty-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and an IL-15Rα(sushi)-Fc monomer comprising an amino acid substitution C220S, heterodimer pI substitutions S364K/E357Q, and ablation substitutions E233P/L234V/L235A/G236del/S267K. In some embodiments, the ncIL-15/Rα-Fc fusion protein comprises a single chain comprising a human mature IL-15 wildtype variant; an IL-15Rα(sushi) domain; an empty-Fc comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In the ncIL-15/Rα-heteroFc format, preferred embodiments are shown in WO2018071919 in FIG. 104AS (XENP24349 including chain 1 and chain 2) and FIG. 104AT (XENP24383 including chain 1 and chain 2), all of which are herein incorporated by reference in its entirety.

In the ncIL-15/Rα-Fc format, preferred embodiments are shown in FIG. 12A and FIG. 12B such as XENP21479 including chain 1 (16484) and chain 2 (8793) and chain 3 (16481); XENP22366 including chain 1 (16478) and chain 2 (8924) and chain 3 ( ); and XENP22366 including chain 1 (16484) and chain 2 (8793) and chain 3 (15908); and XENP24348.

D. Bivalent ncIL-15/Rα-Fc

Figure 9D:
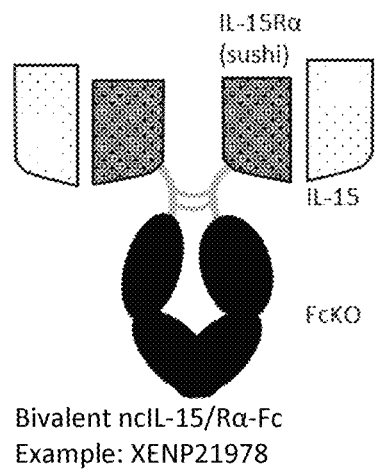
Figure 9E:
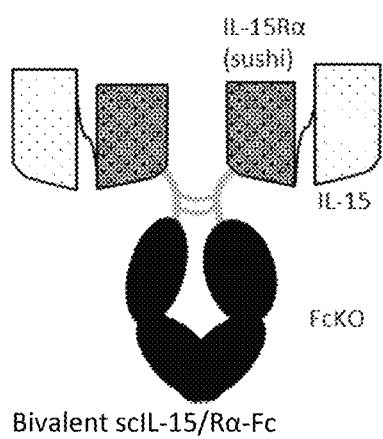

In this embodiment, as shown in FIG. 9D, the homodimeric fusion protein comprises four monomers. The first and second monomers comprise (from N- to C-terminus) IL-15/Rα(sushi)-domain linker-CH2-CH3, where the domain linker sometimes comprises all or part of the hinge. The third and fourth monomers comprise IL-15. This is referred to as "bivalent ncIL-15/Rα-Fc" with the "nc" standing for "non-covalent").

In the bivalent ncIL-15/Rα-Fc format, a preferred embodiment utilizes the skew variant pair S364K/E357Q:L368D/K370S.

In the bivalent ncIL-15/Rα-Fc format, a preferred embodiment utilizes the IL-15 D30N/N65D variants.

In the bivalent ncIL-15/Rα-Fc format, a preferred embodiment utilizes the IL-15 D30N/N65D variants and the skew variant pair S364K/E357Q:L368D/K370S. In the bivalent ncIL-15/Rα-Fc format, a preferred embodiment utilizes the IL-15 D30N/N65D variants, the skew variant pair S364K/E357Q:L368D/K370S and the 428L/434S variants on each Fc monomer. In the bivalent ncIL-15/Rα-Fc format, a preferred embodiment utilizes the IL-15 D30N/N65D variants, the skew variant pair S364K/E357Q:L368D/K370S and the M428L/N434S variants on each Fc monomer.

In some embodiments, the bivalent ncIL-15/Rα-Fc fusion protein comprises a human mature IL-15 D30N/N65D variant, an IL-15Rα(sushi) domain; and two Fc monomers comprising the amino acid substitutions depicted in FIG. 6C. In some embodiments, the bivalent ncIL-15/Rα-Fc fusion protein comprises two human mature IL-15 D30N/N65D variants; a first IL-15Rα(sushi)-Fc monomer comprising a human IL-15Rα(sushi) domain and an Fc monomer comprising an amino acid substitution C220S and ablation substitutions E233P/L234V/L235A/G236del/S267K; and a second IL-15Rα(sushi)-Fc monomer comprising a human IL-15Rα(sushi) domain and an Fc monomer comprising an amino acid substitution C220S and ablation substitutions E233P/L234V/L235A/G236del/S267K. In some embodiments, the bivalent ncIL-15/Rα-Fc fusion protein comprises two human mature IL-15 D30N/N65D variants; a first IL-15Rα(sushi)-Fc monomer comprising a human IL-15Rα(sushi) domain and an Fc monomer comprising an amino acid substitution C220S, ablation substitutions E233P/L234V/L235A/G236del/S267K, and FcRn substitutions M428L/N434S; and a second IL-15Rα(sushi)-Fc monomer comprising a human IL-15Rα(sushi) domain and an Fc monomer comprising an amino acid substitution C220S and ablation substitutions E233P/L234V/L235A/G236del/S267K, and FcRn substitutions M428L/N434S.

In the bivalent ncIL-15/Rα-Fc format, a preferred embodiment utilizes the IL-15 D30N/E64Q/N65D variants.

In the bivalent ncIL-15/Rα-Fc format, a preferred embodiment utilizes the IL-15 D30N/E64Q/N65D variants and the skew variant pair S364K/E357Q:L368D/K370S. In the bivalent ncIL-15/Rα-Fc format, a preferred embodiment utilizes the IL-15 D30N/E64Q/N65D variants, the skew variant pair S364K/E357Q:L368D/K370S and the 428L/434S variants on each Fc monomer. In the bivalent ncIL-15/Rα-Fc format, a preferred embodiment utilizes the IL-15 D30N/E64Q/N65D variants, the skew variant pair S364K/E357Q:L368D/K370S and the M428L/N434S variants on each Fc monomer.

In the bivalent ncIL-15/Rα-Fc format, a preferred embodiment utilizes the IL-15 N65D variant.

In the bivalent ncIL-15/Rα-Fc format, a preferred embodiment utilizes the IL-15 N65D variant, and the skew variant pair S364K/E357Q:L368D/K370S. In the bivalent ncIL-15/Rα-Fc format, a preferred embodiment utilizes the IL-15 N65D variant, the skew variant pair S364K/E357Q:L368D/K370S and the 428L/434S variants on each Fc monomer. In the bivalent ncIL-15/Rα-Fc format, a preferred embodiment utilizes the TL-15 N65D variant, the skew variant pair S364K/E357Q:L368D/K370S and the M428L/N434S variants on each Fc monomer.

In some embodiments, the bivalent ncIL-15/Rα-Fc fusion protein comprises a human mature IL-15 N65D variant, an IL-15Rα(sushi) domain; and two Fc monomers comprising the amino acid substitutions depicted in FIG. 6C. In some embodiments, the bivalent ncIL-15/Rα-Fc fusion protein comprises two human mature IL-15 N65D variants; a first IL-15Rα(sushi)-Fc monomer comprising a human IL-15Rα(sushi) domain and an Fc monomer comprising an amino acid substitution C220S and ablation substitutions E233P/L234V/L235A/G236del/S267K; and a second IL-15Rα(sushi)-Fc monomer comprising a human IL-15Rα(sushi) domain and an Fc monomer comprising an amino acid substitution C220S and ablation substitutions E233P/L234V/L235A/G236del/S267K. In some embodiments, the bivalent ncIL-15/Rα-Fc fusion protein comprises two human mature IL-15 N65D variants; a first IL-15Rα(sushi)-Fc monomer comprising a human IL-15Rα(sushi) domain and an Fc monomer comprising an amino acid substitution C220S, ablation substitutions E233P/L234V/L235A/G236del/S267K, and FcRn substitutions M428L/N434S; and a second IL-15Rα(sushi)-Fc monomer comprising a human IL-15Rα(sushi) domain and an Fc monomer comprising an amino acid substitution C220S and ablation substitutions E233P/L234V/L235A/G236del/S267K, and FcRn substitutions M428L/N434S.

In the bivalent ncIL-15/Rα-Fc format, a preferred embodiment utilizes the IL-15 N4D/N65D variant.

In the bivalent ncIL-15/Rα-Fc format, a preferred embodiment utilizes the IL-15 N4D/N65D variant and the skew variant pair S364K/E357Q:L368D/K370S. In the bivalent ncIL-15/Rα-Fc format, a preferred embodiment utilizes the TL-15 N4D/N65D variant, the skew variant pair S364K/E357Q:L368D/K370S and the 428L/434S variants on each Fc monomer. In the bivalent ncIL-15/Rα-Fc format, a preferred embodiment utilizes the TL-15 N4D/N65D variant, the skew variant pair S364K/E357Q:L368D/K370S and the M428L/N434S variants on each Fc monomer.

In the bivalent ncIL-15/Rα-Fc format, a preferred embodiment utilizes the IL-15 N1D/N65D variant.

In the bivalent ncIL-15/Rα-Fc format, a preferred embodiment utilizes the IL-15 N1D/N65D variant and the skew variant pair S364K/E357Q:L368D/K370S. In the bivalent ncIL-15/Rα-Fc format, a preferred embodiment utilizes the IL-15 N1D/N65D variant, the skew variant pair S364K/E357Q:L368D/K370S and the 428L/434S variants on each Fc monomer. In the bivalent ncIL-15/Rα-Fc format, a preferred embodiment utilizes the IL-15 N1D/N65D variant, the skew variant pair S364K/E357Q:L368D/K370S and the M428L/N434S variants on each Fc monomer.

In some embodiments, the bivalent ncIL-15/Rα-Fc fusion protein comprises a human mature IL-15 N1D/N65D variant, an IL-15Rα(sushi) domain; and two Fc monomers comprising the amino acid substitutions depicted in FIG. 6C. In some embodiments, the bivalent ncIL-15/Rα-Fc fusion protein comprises two human mature IL-15 N1D/N65D variants; a first IL-15Rα(sushi)-Fc monomer comprising a human IL-15Rα(sushi) domain and an Fc monomer comprising an amino acid substitution C220S and ablation substitutions E233P/L234V/L235A/G236del/S267K; and a second IL-15Rα(sushi)-Fc monomer comprising a human IL-15Rα(sushi) domain and an Fc monomer comprising an amino acid substitution C220S and ablation substitutions E233P/L234V/L235A/G236del/S267K. In some embodiments, the bivalent ncIL-15/Rα-Fc fusion protein comprises two human mature IL-15 N1D/N65D variants; a first IL-15Rα(sushi)-Fc monomer comprising a human IL-15Rα (sushi) domain and an Fc monomer comprising an amino acid substitution C220S, ablation substitutions E233P/L234V/L235A/G236del/S267K, and FcRn substitutions M428L/N434S; and a second IL-15Rα(sushi)-Fc monomer comprising a human IL-15Rα(sushi) domain and an Fc monomer comprising an amino acid substitution C220S and ablation substitutions E233P/L234V/L235A/G236del/S267K, and FcRn substitutions M428L/N434S.

In the bivalent ncIL-15/Rα-Fc format, a preferred embodiment utilizes the IL-15 Q108E variant.

In the bivalent ncIL-15/Rα-Fc format, a preferred embodiment utilizes the IL-15 Q108E variant and the skew variant pair S364K/E357Q:L368D/K370S. In the bivalent ncIL-15/Rα-Fc format, a preferred embodiment utilizes the IL-15 Q108E variant and the skew variant pair S364K/E357Q:L368D/K370S and the 428L/434S variants on both monomers. In the bivalent ncIL-15/Rα-Fc format, a preferred embodiment utilizes the IL-15 Q108E variant, the skew variant pair S364K/E357Q:L368D/K370S and the M428L/N434S variants on each Fc monomer.

In some embodiments, the bivalent ncIL-15/Rα-Fc fusion protein comprises a human mature IL-15 Q108E variant, an IL-15Rα(sushi) domain; and two Fc monomers comprising the amino acid substitutions depicted in FIG. 6C. In some embodiments, the bivalent ncIL-15/Rα-Fc fusion protein comprises two human mature IL-15 Q108E variants; a first IL-15Rα(sushi)-Fc monomer comprising a human IL-15Rα (sushi) domain and an Fc monomer comprising an amino acid substitution C220S and ablation substitutions E233P/L234V/L235A/G236del/S267K; and a second IL-15Rα(sushi)-Fc monomer comprising a human IL-15Rα(sushi) domain and an Fc monomer comprising an amino acid substitution C220S and ablation substitutions E233P/L234V/L235A/G236del/S267K. In some embodiments, the bivalent ncIL-15/Rα-Fc fusion protein comprises two human mature IL-Q108E variants; a first IL-15Rα(sushi)-Fc monomer comprising a human IL-15Rα(sushi) domain and an Fc monomer comprising an amino acid substitution C220S, ablation substitutions E233P/L234V/L235A/G236del/S267K, and FcRn substitutions M428L/N434S; and a second IL-15Rα(sushi)-Fc monomer comprising a human IL-15Rα(sushi) domain and an Fc monomer comprising an amino acid substitution C220S and ablation substitutions E233P/L234V/L235A/G236del/S267K, and FcRn substitutions M428L/N434S.

In the bivalent ncIL-15/Rα-Fc format, a preferred embodiment utilizes the IL-15 wildtype variant.

In the bivalent ncIL-15/Rα-Fc format, a preferred embodiment utilizes the IL-15 wildtype variant and the skew variant pair S364K/E357Q:L368D/K370S.

In the bivalent ncIL-15/Rα-Fc format, a preferred embodiment utilizes the IL-15 wildtype variant, the skew variant pair S364K/E357Q:L368D/K370S and the 428L/434S variants on each Fc monomer. In the bivalent ncIL-15/Rα-Fc format, a preferred embodiment utilizes the IL-15 wildtype variant, the skew variant pair S364K/E357Q:L368D/K370S and the M428L/N434S variants on each Fc monomer.

In some embodiments, the bivalent ncIL-15/Rα-Fc fusion protein comprises a human mature IL-15 wildtype variant, an IL-15Rα(sushi) domain; and two Fc monomers comprising the amino acid substitutions depicted in FIG. 6C. In some embodiments, the bivalent ncIL-15/Rα-Fc fusion protein comprises two human mature IL-15 wildtype variants; a first IL-15Rα(sushi)-Fc monomer comprising a human IL-15Rα(sushi) domain and an Fc monomer comprising an amino acid substitution C220S and ablation substitutions E233P/L234V/L235A/G236del/S267K; and a second IL-15Rα(sushi)-Fc monomer comprising a human IL-15Rα (sushi) domain and an Fc monomer comprising an amino acid substitution C220S and ablation substitutions E233P/L234V/L235A/G236del/S267K. In some embodiments, the bivalent ncIL-15/Rα-Fc fusion protein comprises two human mature IL-15 wildtype variants; a first IL-15Rα (sushi)-Fc monomer comprising a human IL-15Rα(sushi) domain and an Fc monomer comprising an amino acid substitution C220S, ablation substitutions E233P/L234V/L235A/G236del/S267K, and FcRn substitutions M428L/N434S; and a second IL-15Rα(sushi)-Fc monomer comprising a human IL-15Rα(ablation) domain and an Fc monomer comprising an amino acid substitution C220S and ablation substitutions E233P/L234V/L235A/G236del/S267K, and FcRn substitutions M428L/N434S.

In the bivalent ncIL-15/Rα-Fc format, a preferred embodiment is shown in WO2018071919 in FIG. 104E (XENP21979 including chain 1 and chain 2) and in the sequence listing as SEQ ID NOS: 480-483, all of which are herein incorporated by reference in its entirety.

In the bivalent ncIL-15/Rα-Fc format, preferred embodiments are shown in FIG. 13 such as XENP21978 including chain 1 (17023) and chain 2 (16484).

E. Bivalent scIL-15/Rα-Fc

In this embodiment, as shown in FIG. 9e, the homodimeric fusion protein comprises two monomers. The first and second monomers comprise (from N- to C-terminus) IL-15/Rα(sushi)-domain linker-IL-15-optional domain linker-CH2-CH3, where the domain linker sometimes comprises all or part of the hinge. This is referred to as "bivalent scIL-15/Rα-Fc" with the "sc" standing for "single chain" (e.g., of the IL-15/Rα sushi complex).

In the bivalent scIL-15/Rα-Fc format, a preferred embodiment utilizes the skew variant pair S364K/E357Q:L368D/K370S.

In the bivalent scIL-15/Rα-Fc format, a preferred embodiment utilizes the IL-15 D30N/N65D variant.

In the bivalent scIL-15/Rα-Fc format, a preferred embodiment utilizes the IL-15 D30N/N65D variant and the skew variant pair S364K/E357Q:L368D/K370S. In the bivalent scIL-15/Rα-Fc format, a preferred embodiment utilizes the IL-15 D30N/N65D variant and the skew variant pair S364K/E357Q:L368D/K370S and the 428L/434S variants on both monomers.

In some embodiments, the bivalent scIL-15/Rα-Fc fusion protein comprises two human mature IL-15 D30N/N65D variants, two IL-15Rα(sushi) domains; and two Fc monomers comprising the amino acid substitutions depicted in FIG. 6D. In some embodiments, the bivalent scIL-15/Rα-Fc fusion protein comprises a first IL-15/Rα(sushi)-Fc monomer comprising a human mature IL-15 D30N/N65D variant linked to a human IL-15Rα(sushi) domain linked to an Fc monomer comprising an amino acid substitution C220S and ablation substitutions E233P/L234V/L235A/G236del/S267K; and a second IL-15/Rα(sushi)-Fc monomer comprising a human mature IL-15 D30N/N65D variant linked to a human IL-15Rα(sushi) domain linked to an Fc monomer comprising an amino acid substitution C220S and ablation substitutions E233P/L234V/L235A/G236del/S267K. In some embodiments, the bivalent scIL-15/Rα-Fc fusion protein comprises a first IL-15/Rα(sushi)-Fc monomer comprising a human mature IL-15 D30N/N65D variant linked to a human IL-15Rα(sushi) domain linked to an Fc monomer comprising an amino acid substitution C220S, ablation substitutions E233P/L234V/L235A/G236del/S267K, and FcRn substitutions M428L/N434S; and a second IL-15/Rα(sushi)-Fc monomer comprising a human mature IL-15 D30N/N65D variant linked to a human IL-15Rα(sushi) domain linked to an Fc monomer comprising an amino acid substitution C220S, ablation substitutions E233P/L234V/L235A/G236del/S267K, and FcRn substitutions M428L/N434S.

In the bivalent scIL-15/Rα-Fc format, a preferred embodiment utilizes the IL-15 D30N/E64Q/N65D variants.

In the bivalent scIL-15/Rα-Fc format, a preferred embodiment utilizes the IL-15 D30N/E64Q/N65D variants and the skew variant pair S364K/E357Q:L368D/K370S.

In the bivalent scIL-15/Rα-Fc format, a preferred embodiment utilizes the IL-15 D30N/E64Q/N65D variants, the skew variant pair S364K/E357Q:L368D/K370S and the 428L/434S variants on each Fc monomer. In the bivalent scIL-15/Rα-Fc format, a preferred embodiment utilizes the IL-15 D30N/E64Q/N65D variants, the skew variant pair S364K/E357Q:L368D/K370S and the M428L/N434S variants on each Fc monomer.

In some embodiments, the bivalent scIL-15/Rα-Fc fusion protein comprises two human mature IL-15 D30N/E64Q/N65D variants, two IL-15Rα(sushi) domains; and two Fc monomers comprising the amino acid substitutions depicted in FIG. 6D. In some embodiments, the bivalent scIL-15/Rα-Fc fusion protein comprises a first IL-15/Rα(sushi)-Fc monomer comprising a human mature IL-15 D30N/E64Q/N65D variant linked to a human IL-15Rα(sushi) domain linked to an Fc monomer comprising an amino acid substitution C220S and ablation substitutions E233P/L234V/L235A/G236del/S267K; and a second IL-15/Rα(sushi)-Fc monomer comprising a human mature IL-15 D30N/E64Q/N65D variant linked to a human IL-15Rα(sushi) domain linked to an Fc monomer comprising an amino acid substitution C220S and ablation substitutions E233P/L234V/L235A/G236del/S267K. In some embodiments, the bivalent scIL-15/Rα-Fc fusion protein comprises a first IL-15/Rα(sushi)-Fc monomer comprising a human mature IL-15 D30N/E64Q/N65D variant linked to a human IL-15Rα (sushi) domain linked to an Fc monomer comprising an amino acid substitution C220S, ablation substitutions E233P/L234V/L235A/G236del/S267K, and FcRn substitutions M428L/N434S; and a second IL-15/Rα(sushi)-Fc monomer comprising a human mature IL-15 D30N/E64Q/N65D variant linked to a human IL-15Rα(sushi) domain linked to an Fc monomer comprising an amino acid substitution C220S, ablation substitutions E233P/L234V/L235A/G236del/S267K, and FcRn substitutions M428L/N434S.

In the bivalent scIL-15/Rα-Fc format, a preferred embodiment utilizes the IL-15 N65D variant.

In the bivalent scIL-15/Rα-Fc format, a preferred embodiment utilizes the IL-15 N65D variant, and the skew variant pair S364K/E357Q:L368D/K370S. In the bivalent scIL-15/Rα-Fc format, a preferred embodiment utilizes the IL-15 N65D variant, the skew variant pair S364K/E357Q:L368D/K370S and the 428L/434S variants on each Fc monomer. In the bivalent scIL-15/Rα-Fc format, a preferred embodiment utilizes the IL-15 N65D variant, the skew variant pair S364K/E357Q:L368D/K370S and the M428L/N434S variants on each Fc monomer.

In some embodiments, the bivalent scIL-15/Rα-Fc fusion protein comprises two human mature IL-15 N65D variants, two IL-15Rα(sushi) domains; and two Fc monomers comprising the amino acid substitutions depicted in FIG. 6D. In some embodiments, the bivalent scIL-15/Rα-Fc fusion protein comprises a first IL-15/Rα(sushi)-Fc monomer comprising a human mature IL-15 N65D variant linked to a human IL-15Rα(sushi) domain linked to an Fc monomer comprising an amino acid substitution C220S and ablation substitutions E233P/L234V/L235A/G236del/S267K; and a second IL-15/Rα(sushi)-Fc monomer comprising a human mature IL-15 N65D variant linked to a human IL-15Rα (sushi) domain linked to an Fc monomer comprising an amino acid substitution C220S and ablation substitutions E233P/L234V/L235A/G236del/S267K. In some embodiments, the bivalent scIL-15/Rα-Fc fusion protein comprises a first IL-15/Rα(sushi)-Fc monomer comprising a human mature IL-15 N65D variant linked to a human IL-15Rα (sushi) domain linked to an Fc monomer comprising an amino acid substitution C220S, ablation substitutions E233P/L234V/L235A/G236del/S267K, and FcRn substitutions M428L/N434S; and a second IL-15/Rα(sushi)-Fc monomer comprising a human mature IL-15 N65D variant linked to a human IL-15Rα(sushi) domain linked to an Fc monomer comprising an amino acid substitution C220S, ablation substitutions E233P/L234V/L235A/G236del/S267K, and FcRn substitutions M428L/N434S.

In the bivalent scIL-15/Rα-Fc format, a preferred embodiment utilizes the IL-15 N4D/N65D variant.

In the bivalent scIL-15/Rα-Fc format, a preferred embodiment utilizes the IL-15 N4D/N65D variant and the skew variant pair S364K/E357Q:L368D/K370S. In the bivalent scIL-15/Rα-Fc format, a preferred embodiment utilizes the IL-15 N4D/N65D variant, the skew variant pair S364K/E357Q:L368D/K370S and the 428L/434S variants on each Fc monomer. In the bivalent scIL-15/Rα-Fc format, a preferred embodiment utilizes the IL-15 N4D/N65D variant, the skew variant pair S364K/E357Q:L368D/K370S and the M428L/N434S variants on each Fc monomer.

In some embodiments, the bivalent scIL-15/Rα-Fc fusion protein comprises two human mature IL-15 N4D/N65D variants, two IL-15Rα(sushi) domains; and two Fc monomers comprising the amino acid substitutions depicted in FIG. 6D. In some embodiments, the bivalent scIL-15/Rα-Fc fusion protein comprises a first IL-15/Rα(sushi)-Fc monomer comprising a human mature IL-15 N4D/N65D variant linked to a human IL-15Rα(sushi) domain linked to an Fc monomer comprising an amino acid substitution C220S and ablation substitutions E233P/L234V/L235A/G236del/S267K; and a second IL-15/Rα(sushi)-Fc monomer comprising a human mature IL-15 N4D/N65D variant linked to a human IL-15Rα(sushi) domain linked to an Fc monomer comprising an amino acid substitution C220S and ablation substitutions E233P/L234V/L235A/G236del/S267K. In some embodiments, the bivalent scIL-15/Rα-Fc fusion protein comprises a first IL-15/Rα(sushi)-Fc monomer comprising a human mature IL-15 N4D/N65D variant linked to a human IL-15Rα(sushi) domain linked to an Fc monomer comprising an amino acid substitution C220S, ablation substitutions E233P/L234V/L235A/G236del/S267K, and FcRn substitutions M428L/N434S; and a second IL-15/Rα(sushi)-Fc monomer comprising a human mature IL-15 N4D/N65D variant linked to a human IL-15Rα(sushi) domain linked to an Fc monomer comprising an amino acid substitution C220S, ablation substitutions E233P/L234V/L235A/G236del/S267K, and FcRn substitutions M428L/N434S.

In the bivalent scIL-15/Rα-Fc format, a preferred embodiment utilizes the IL-15 N1D/N65D variant.

In the bivalent scIL-15/Rα-Fc format, a preferred embodiment utilizes the IL-15 N1D/N65D variant and the skew variant pair S364K/E357Q:L368D/K370S. In the bivalent scIL-15/Rα-Fc format, a preferred embodiment utilizes the IL-15 N1D/N65D variant, the skew variant pair S364K/E357Q:L368D/K370S and the 428L/434S variants on each Fc monomer. In the bivalent scIL-15/Rα-Fc format, a preferred embodiment utilizes the IL-15 N1D/N65D variant, the skew variant pair S364K/E357Q:L368D/K370S and the M428L/N434S variants on each Fc monomer.

In some embodiments, the bivalent scIL-15/Rα-Fc fusion protein comprises two human mature IL-15 N1D/N65D variants, two IL-15Rα(sushi) domains; and two Fc monomers comprising the amino acid substitutions depicted in FIG. 6D. In some embodiments, the bivalent scIL-15/Rα-Fc fusion protein comprises a first IL-15/Rα(sushi)-Fc monomer comprising a human mature IL-15 N1D/N65D variant linked to a human IL-15Rα(sushi) domain linked to an Fc monomer comprising an amino acid substitution C220S and ablation substitutions E233P/L234V/L235A/G236del/S267K; and a second IL-15/Rα(sushi)-Fc monomer comprising a human mature IL-15 N1D/N65D variant linked to a human IL-15Rα(sushi) domain linked to an Fc monomer comprising an amino acid substitution C220S and ablation substitutions E233P/L234V/L235A/G236del/S267K. In some embodiments, the bivalent scIL-15/Rα-Fc fusion protein comprises a first IL-15/Rα(sushi)-Fc monomer comprising a human mature IL-15 N1D/N65D variant linked to a human IL-15Rα(sushi) domain linked to an Fc monomer comprising an amino acid substitution C220S, ablation substitutions E233P/L234V/L235A/G236del/S267K, and FcRn substitutions M428L/N434S; and a second IL-15/Rα(sushi)-Fc monomer comprising a human mature IL-15 N1D/N65D variant linked to a human IL-15Rα(sushi) domain linked to an Fc monomer comprising an amino acid substitution C220S, ablation substitutions E233P/L234V/L235A/G236del/S267K, and FcRn substitutions M428L/N434S.

In the bivalent scIL-15/Rα-Fc format, a preferred embodiment utilizes the IL-15 Q108E variant and the skew variant pair S364K/E357Q:L368D/K370S. In the bivalent scIL-15/Rα-Fc format, a preferred embodiment utilizes the IL-15 Q108E variant and the skew variant pair S364K/E357Q:L368D/K370S and the 428L/434S variants on both monomers.

In some embodiments, the bivalent scIL-15/Rα-Fc fusion protein comprises two human mature IL-15 Q108E variants, two IL-15Rα(sushi) domains; and two Fc monomers comprising the amino acid substitutions depicted in FIG. 6D. In some embodiments, the bivalent scIL-15/Rα-Fc fusion protein comprises a first IL-15/Rα(sushi)-Fc monomer comprising a human mature IL-15 Q108E variant linked to a human IL-15Rα(sushi) domain linked to an Fc monomer comprising an amino acid substitution C220S and ablation substitutions E233P/L234V/L235A/G236del/S267K; and a second IL-15/Rα(sushi)-Fc monomer comprising a human mature IL-15 Q108E variant linked to a human IL-15Rα(sushi) domain linked to an Fc monomer comprising an amino acid substitution C220S and ablation substitutions E233P/L234V/L235A/G236del/S267K. In some embodiments, the bivalent scIL-15/Rα-Fc fusion protein comprises a first IL-15/Rα(sushi)-Fc monomer comprising a human mature IL-15 Q108E variant linked to a human IL-15Rα(sushi) domain linked to an Fc monomer comprising an amino acid substitution C220S, ablation substitutions E233P/L234V/L235A/G236del/S267K, and FcRn substitutions M428L/N434S; and a second IL-15/Rα(sushi)-Fc monomer comprising a human mature IL-15 Q108E variant linked to a human IL-15Rα(sushi) domain linked to an Fc monomer comprising an amino acid substitution C220S, ablation substitutions E233P/L234V/L235A/G236del/S267K, and FcRn substitutions M428L/N434S.

In the bivalent scIL-15/Rα-Fc format, a preferred embodiment utilizes the IL-15 wildtype variant.

In the bivalent scIL-15/Rα-Fc format, a preferred embodiment utilizes the IL-15 wildtype variant and the skew variant pair S364K/E357Q:L368D/K370S. In the bivalent scIL-15/Rα-Fc format, a preferred embodiment utilizes the IL-15 wildtype variant, the skew variant pair S364K/E357Q:L368D/K370S and the 428L/434S variants on each Fc monomer. In the bivalent scIL-15/Rα-Fc format, a preferred embodiment utilizes the IL-15 wildtype variant, the skew variant pair S364K/E357Q:L368D/K370S and the M428L/N434S variants on each Fc monomer.

In some embodiments, the bivalent scIL-15/Rα-Fc fusion protein comprises two human mature IL-15 wildtype variants, two IL-15Rα(sushi) domains; and two Fc monomers comprising the amino acid substitutions depicted in FIG. 6D. In some embodiments, the bivalent scIL-15/Rα-Fc fusion protein comprises a first IL-15/Rα(sushi)-Fc monomer comprising a human mature IL-15 N1D/N65D variant linked to a human IL-15Rα(sushi) domain linked to an Fc monomer comprising an amino acid substitution C220S and ablation substitutions E233P/L234V/L235A/G236del/S267K; and a second IL-15/Rα(sushi)-Fc monomer comprising a human mature IL-15 N1D/N65D variant linked to a human IL-15Rα(sushi) domain linked to an Fc monomer comprising an amino acid substitution C220S and ablation substitutions E233P/L234V/L235A/G236del/S267K. In some embodiments, the bivalent scIL-15/Rα-Fc fusion protein comprises a first IL-15/Rα(sushi)-Fc monomer comprising a human mature IL-15 N1D/N65D variant linked to a human IL-15Rα(sushi) domain linked to an Fc monomer comprising an amino acid substitution C220S, ablation substitutions E233P/L234V/L235A/G236del/S267K, and FcRn substitutions M428L/N434S; and a second IL-15/Rα(sushi)-Fc monomer comprising a human mature IL-15 N1D/N65D variant linked to a human IL-15Rα(sushi) domain linked to an Fc monomer comprising an amino acid substitution C220S, ablation substitutions E233P/L234V/L235A/G236del/S267K, and FcRn substitutions M428L/N434S.

In the bivalent scIL-15/Rα-Fc format, a preferred embodiment is shown in FIG. 14.

F. Fc-ncIL-15/Rα

Figure 9F:
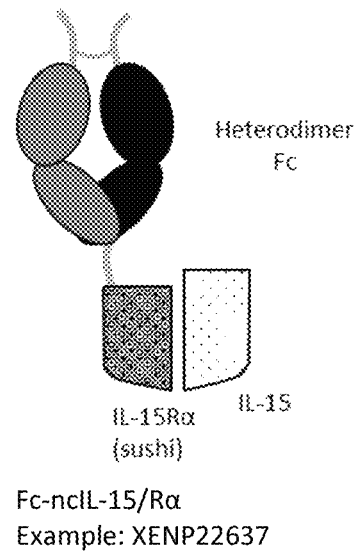
Figure 9G:
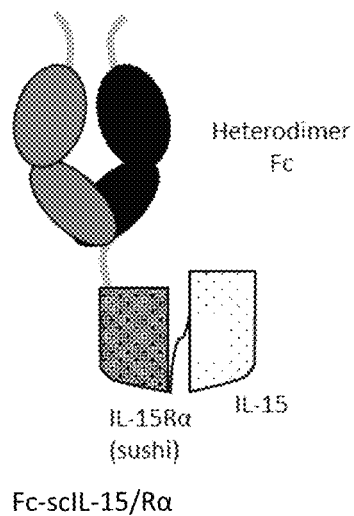

In this embodiment, as shown in FIG. 9F, the heterodimeric fusion protein comprises three monomers. The first monomer comprises (from N- to C-terminus) CH2-CH3-domain linker-IL-15/Rα(sushi), wherein the Fc comprises all of part of the hinge. The second monomer comprises and "empty" Fc, comprising all or part of the hinge-CH2-CH3. The third monomer is IL-15. This is referred to as "ncIL-15/Rα-Fc" with the "nc" standing for "non-covalent").

In the ncIL-15/Rα-Fc (or Fc-ncIL-15/Rα) format, a preferred embodiment utilizes the skew variant pair S364K/E357Q:L368D/K370S.

In the ncIL-15/Rα-Fc format, a preferred embodiment utilizes the IL-15 D30N/N65D variant.

In the ncIL-15/Rα-Fc format, a preferred embodiment utilizes the IL-15 D30N/N65D variant and the skew variant pair S364K/E357Q:L368D/K370S. In the Fc-ncIL-15/Rα format, a preferred embodiment utilizes the IL-15 D30N/N65D variant and the skew variant pair S364K/E357Q:L368D/K370S and the 428L/434S variants on both monomers. In the Fc-ncIL-15/Rα format, a preferred embodiment utilizes the IL-15 D30N/N65D variant and the skew variant pair S364K/E357Q:L368D/K370S and the M428L/N434S variants on both monomers.

In some embodiments, the ncIL-15/Rα-Fc fusion protein comprises human mature IL-15 D30N/N65D variant, IL-15Rα(sushi) domain; and two Fc monomers comprising the amino acid substitutions depicted in FIG. 6E. In some embodiments, the ncIL-15/Rα-Fc fusion protein comprises a human IL-15 D30N/N65D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, and ablation substitutions E233P/L234V/L235A/G236del/S267K; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the ncIL-15/Rα-Fc fusion protein comprises a human IL-15 D30N/N65D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, ablation substitutions E233P/L234V/L235A/G236del/S267K, and FcRn substitutions M428L/N343S; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-ncIL-15/Rα format, a preferred embodiment utilizes the IL-15 D30N/E64Q/N65D variants.

In the Fc-ncIL-15/Rα format, a preferred embodiment utilizes the IL-15 D30N/E64Q/N65D variants and the skew variant pair S364K/E357Q:L368D/K370S. In the Fc-ncIL-15/Rα format, a preferred embodiment utilizes the IL-15 D30N/E64Q/N65D variants, the skew variant pair S364K/E357Q:L368D/K370S and the 428L/434S variants on each Fc monomer. In the Fc-ncIL-15/Rα format, a preferred embodiment utilizes the IL-15 D30N/E64Q/N65D variants, the skew variant pair S364K/E357Q:L368D/K370S and the M428L/N434S variants on each Fc monomer.

In some embodiments, the ncIL-15/Rα-Fc fusion protein comprises human mature IL-15 D30N/E64Q/N65D variant, IL-15Rα(sushi) domain; and two Fc monomers comprising the amino acid substitutions depicted in FIG. 6E. In some embodiments, the ncIL-15/Rα-Fc fusion protein comprises a human IL-15 D30N/E64Q/N65D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, and ablation substitutions E233P/L234V/L235A/G236del/S267K; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the ncIL-15/Rα-Fc fusion protein comprises a human IL-15 D30N/E64Q/N65D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, ablation substitutions E233P/L234V/L235A/G236del/S267K, and FcRn substitutions M428L/N343S; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-ncIL-15/Rα format, a preferred embodiment utilizes the IL-15 N4D variant.

In the Fc-ncIL-15/Rα format, a preferred embodiment utilizes the IL-15 N4D variant, and the skew variant pair S364K/E357Q:L368D/K370S. In the Fc-ncIL-15/Rα format, a preferred embodiment utilizes the IL-15 N4D variant, the skew variant pair S364K/E357Q:L368D/K370S and the 428L/434S variants on each Fc monomer. In the Fc-ncIL-15/Rα format, a preferred embodiment utilizes the IL-15 N4D variant, the skew variant pair S364K/E357Q:L368D/K370S and the M428L/N434S variants on each Fc monomer.

In some embodiments, the ncIL-15/Rα-Fc fusion protein comprises human mature IL-15 N4D variant, IL-15Rα(sushi) domain; and two Fc monomers comprising the amino acid substitutions depicted in FIG. 6E. In some embodiments, the ncIL-15/Rα-Fc fusion protein comprises a human IL-15 N4D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, and ablation substitutions E233P/L234V/L235A/G236del/S267K; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the ncIL-15/Rα-Fc fusion protein comprises a human IL-15 N4D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, ablation substitutions E233P/L234V/L235A/G236del/S267K, and FcRn substitutions M428L/N343S; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-ncIL-15/Rα format, a preferred embodiment utilizes the IL-15 N65D variant.

In the Fc-ncIL-15/Rα format, a preferred embodiment utilizes the IL-15 N65D variant, and the skew variant pair S364K/E357Q:L368D/K370S. In the Fc-ncIL-15/Rα format, a preferred embodiment utilizes the IL-15 N65D variant, the skew variant pair S364K/E357Q:L368D/K370S and the 428L/434S variants on each Fc monomer. In the ncIL-15/Rα-Fc format, a preferred embodiment utilizes the IL-15 N65D variant, the skew variant pair S364K/E357Q L368D/K370S and the M428L/N434S variants on each Fc monomer.

In some embodiments, the ncIL-15/Rα-Fc fusion protein comprises human mature IL-15 N65D variant, IL-15Rα (sushi) domain; and two Fc monomers comprising the amino acid substitutions depicted in FIG. 6E. In some embodiments, the ncIL-15/Rα-Fc fusion protein comprises a human IL-15 N65D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, and ablation substitutions E233P/L234V/L235A/G236del/S267K; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the ncIL-15/Rα-Fc fusion protein comprises a human IL-15 N65D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, ablation substitutions E233P/L234V/L235A/G236del/S267K, and FcRn substitutions M428L/N343S; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-ncIL-15/Rα format, a preferred embodiment utilizes the IL-15 N4D/N65D variant.

In the Fc-ncIL-15/Rα format, a preferred embodiment utilizes the IL-15 N4D/N65D variant and the skew variant pair S364K/E357Q:L368D/K370S. In the Fc-ncIL-15/Rα format, a preferred embodiment utilizes the IL-15 N4D/N65D variant, the skew variant pair S364K/E357Q:L368D/K370S and the 428L/434S variants on each Fc monomer. In the Fc-ncIL-15/Rα format, a preferred embodiment utilizes the IL-15 N4D/N65D variant, the skew variant pair S364K/E357Q:L368D/K370S and the M428L/N434S variants on each Fc monomer.

In some embodiments, the ncIL-15/Rα-Fc fusion protein comprises human mature IL-15 N4D/N65D variant, IL-15Rα(sushi) domain; and two Fc monomers comprising the amino acid substitutions depicted in FIG. 6E. In some embodiments, the ncIL-15/Rα-Fc fusion protein comprises a human IL-15 N4D/N65D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, and ablation substitutions E233P/L234V/L235A/G236del/S267K; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the ncIL-15/Rα-Fc fusion protein comprises a human IL-15 N4D/N65D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, ablation substitutions E233P/L234V/L235A/G236del/S267K, and FcRn substitutions M428L/N343S; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-ncIL-15/Rα format, a preferred embodiment utilizes the IL-15 N1D/N65D variant.

In the Fc-ncIL-15/Rα format, a preferred embodiment utilizes the IL-15 N1D/N65D variant and the skew variant pair S364K/E357Q:L368D/K370S.

In the Fc-ncIL-15/Rα format, a preferred embodiment utilizes the IL-15 N1D/N65D variant, the skew variant pair S364K/E357Q:L368D/K370S and the 428L/434S variants on each Fc monomer. In the Fc-ncIL-15/Rα format, a preferred embodiment utilizes the IL-15 N1D/N65D variant, the skew variant pair S364K/E357Q:L368D/K370S and the M428L/N434S variants on each Fc monomer.

In some embodiments, the ncIL-15/Rα-Fc fusion protein comprises human mature IL-15 N1D/N65D variant, IL-15Rα(sushi) domain; and two Fc monomers comprising the amino acid substitutions depicted in FIG. 6E. In some embodiments, the ncIL-15/Rα-Fc fusion protein comprises a human IL-15 N1D/N65D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, and ablation substitutions E233P/L234V/L235A/G236del/S267K; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the ncIL-15/Rα-Fc fusion protein comprises a human IL-15 N1D/N65D variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, ablation substitutions E233P/L234V/L235A/G236del/S267K, and FcRn substitutions M428L/N343S; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the ncIL-15/Rα-Fc format, a preferred embodiment utilizes the skew variant pair S364K/E357Q:L368D/K370S.

In the Fc-ncIL-15/Rα format, a preferred embodiment utilizes the IL-15 Q108E variant.

In the Fc-ncIL-15/Rα format, a preferred embodiment utilizes the IL-15 Q108E variant and the skew variant pair S364K/E357Q:L368D/K370S. In the Fc-ncIL-15/Rα format, a preferred embodiment utilizes the IL-15 Q108E variant and the skew variant pair S364K/E357Q:L368D/K370S and the 428L/434S variants on both monomers. In the Fc-ncIL-15/Rα format, a preferred embodiment utilizes the IL-15 Q108E variant and the skew variant pair S364K/E357Q:L368D/K370S and the M428L/N434S variants on both monomers.

In some embodiments, the ncIL-15/Rα-Fc fusion protein comprises human mature IL-15 Q108E variant, IL-15Rα (sushi) domain; and two Fc monomers comprising the amino acid substitutions depicted in FIG. 6E. In some embodiments, the ncIL-15/Rα-Fc fusion protein comprises a human IL-15 Q108E variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, and ablation substitutions E233P/L234V/L235A/G236del/S267K; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the ncIL-15/Rα-Fc fusion protein comprises a human IL-15 Q108E variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, ablation substitutions E233P/L234V/L235A/G236del/S267K, and FcRn substitutions M428L/N343S; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-ncIL-15/Rα format, a preferred embodiment utilizes the IL-15 wildtype variant.

In the Fc-ncIL-15/Rα format, a preferred embodiment utilizes the IL-15 wildtype variant and the skew variant pair S364K/E357Q:L368D/K370S. In the Fc-ncIL-15/Rα format, a preferred embodiment utilizes the IL-15 wildtype variant, the skew variant pair S364K/E357Q:L368D/K370S and the 428L/434S variants on each Fc monomer. In the Fc-ncIL-15/Rα format, a preferred embodiment utilizes the IL-15 wildtype variant, the skew variant pair S364K/E357Q:L368D/K370S and the M428L/N434S variants on each Fc monomer.

In some embodiments, the ncIL-15/Rα-Fc fusion protein comprises human mature IL-15 wildtype variant, IL-15Rα (sushi) domain; and two Fc monomers comprising the amino acid substitutions depicted in FIG. 6E. In some embodiments, the ncIL-15/Rα-Fc fusion protein comprises a human IL-15 wildtype variant, a Fc-IL-15/Rα(sushi) monomer comprising a human IL-15Rα(sushi) domain linked to the C-terminus of an Fc monomer comprising an amino acid substitution C220S, heterodimer pI variants L368D/K370S, and ablation substitutions E233P/L234V/L235A/G236del/S267K; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the ncIL-15/Rα-Fc fusion protein comprises a human IL-15 wildtype variant, a Fc-IL-15/Rα(sushi) monomer comprising a human IL-15Rα(sushi) domain linked to to the C-terminus of an Fc monomer comprising an amino acid substitution C220S, heterodimer pI variants L368D/K370S, ablation substitutions E233P/L234V/L235A/G236del/S267K, and FcRn substitutions M428L/N343S; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-ncIL-15/Rα format, preferred embodiments including XENP22638 are shown in WO2018071919 in FIG. 104T and in the sequence listing as SEQ ID NOS: 668-672, all of which are herein incorporated by reference in its entirety.

In the Fc-ncIL-15/Rα format, preferred embodiments include XENP22637 as chain 1 (17603) and chain 2 (8927) and chain 3 (16484) and is shown in FIG. 15.

G. Fc-scIL-15/Rα

In this embodiment, as shown in FIG. 9G, the heterodimeric fusion protein comprises two monomers. The first monomer comprises (from N- to C-terminus) CH2-CH3-optional domain linker-IL-15/Rα(sushi)-domain linker-IL-15, wherein the Fc comprises all of part of the hinge. The second monomer comprises and "empty" Fc, comprising all or part of the hinge-CH2-CH3. This is referred to as "Fc-scIL-15/Rα" or "scIL-15/Rα-Fc" with the "sc" standing for "single chain" (e.g. of the IL-15/Rα sushi complex).

In some embodiments, the Fc-scIL-15/Rα fusion protein comprises human mature IL-15 variant, IL-15Rα(sushi) domain; and two Fc monomers comprising the amino acid substitutions depicted in FIG. 6E. In some embodiments, the Fc-scIL-15/Rα fusion protein comprises a Fc-IL-15/Rα (sushi) monomer comprising a Fc monomer comprising an amino acid substitution C220S, heterodimer pI variants L368D/K370S, and ablation substitutions E233P/L234V/L235A/G236del/S267K, such that the Fc domain is linked to a human IL-15Rα(sushi) domain linked to a human mature IL-15 variant; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the Fc-scIL-15/Rα fusion protein comprises a Fc-IL-15/Rα(sushi) monomer comprising a Fc monomer comprising an amino acid substitution C220S, heterodimer pI variants L368D/K370S, ablation substitutions E233P/L234V/L235A/G236del/S267K, and FcRn substitutions M428L/N343S, such that the Fc domain is linked to a human IL-15Rα(sushi) domain linked to a human mature IL-15 variant; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-scIL-15/Rα format, a preferred embodiment utilizes the skew variant pair S364K/E357Q:L368D/K370S.

In the Fc-scIL-15/Rα format, a preferred embodiment utilizes the IL-15 D30N/N65D variant.

In the Fc-scIL-15/Rα format, a preferred embodiment utilizes the IL-15 D30N/N65D variant and the skew variant pair S364K/E357Q:L368D/K370S. In the Fc-scIL-15/Rα format, a preferred embodiment utilizes the IL-15 D30N/N65D variant and the skew variant pair S364K/E357Q:L368D/K370S and the 428L/434S variants on both monomers. In the Fc-scIL-15/Rα format, a preferred embodiment utilizes the IL-15 D30N/N65D variant and the skew variant pair S364K/E357Q:L368D/K370S and the M428L/N434S variants on both monomers.

In some embodiments, the Fc-scIL-15/Rα fusion protein comprises human mature IL-15 D30N/N65D variant, IL-15Rα(sushi) domain; and two Fc monomers comprising the amino acid substitutions depicted in FIG. 6E. In some embodiments, the Fc-scIL-15/Rα fusion protein comprises a Fc-IL-15/Rα(sushi) monomer comprising a Fc monomer comprising an amino acid substitution C220S, heterodimer pI variants L368D/K370S, and ablation substitutions E233P/L234V/L235A/G236del/S267K, such that the Fc domain is linked to a human IL-15Rα(sushi) domain linked to a human mature IL-15 D30N/N65D variant; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the Fc-scIL-15/Rα fusion protein comprises a Fc-IL-15/Rα (sushi) monomer comprising a Fc monomer comprising an amino acid substitution C220S, heterodimer pI variants L368D/K370S, ablation substitutions E233P/L234V/L235A/G236del/S267K, and FcRn substitutions M428L/N343S, such that the Fc domain is linked to a human IL-15Rα(sushi) domain linked to a human mature IL-15 D30N/N65D variant; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-scIL-15/Rα format, a preferred embodiment utilizes the IL-15 D30N/E64Q/N65D variants.

In the Fc-scIL-15/Rα format, a preferred embodiment utilizes the IL-15 D30N/E64Q/N65D variants and the skew variant pair S364K/E357Q:L368D/K370S. In the Fc-scIL-15/Rα format, a preferred embodiment utilizes the IL-15 D30N/E64Q/N65D variants, the skew variant pair S364K/E357Q:L368D/K370S and the 428L/434S variants on each Fc monomer. In the Fc-scIL-15/Rα format, a preferred embodiment utilizes the IL-15 D30N/E64Q/N65D variants, the skew variant pair S364K/E357Q:L368D/K370S and the M428L/N434S variants on each Fc monomer.

In some embodiments, the Fc-scIL-15/Rα fusion protein comprises human mature IL-15 D30N/E64Q/N65D variant, IL-15Rα(sushi) domain; and two Fc monomers comprising the amino acid substitutions depicted in FIG. 6E. In some embodiments, the Fc-scIL-15/Rα fusion protein comprises a Fc-IL-15/Rα(sushi) monomer comprising a Fc monomer comprising an amino acid substitution C220S, heterodimer pI variants L368D/K370S, and ablation substitutions E233P/L234V/L235A/G236del/S267K, such that the Fc domain is linked to a human IL-15Rα(sushi) domain linked to a human mature IL-15 D30N/E64Q/N65D variant; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the Fc-scIL-15/Rα fusion protein comprises a Fc-IL-15/Rα(sushi) monomer comprising a Fc monomer comprising an amino acid substitution C220S, heterodimer pI variants L368D/K370S, ablation substitutions E233P/L234V/L235A/G236del/S267K, and FcRn substitutions M428L/N343S, such that the Fc domain is linked to a human IL-15Rα(sushi) domain linked to a human mature IL-15 D30N/E64Q/N65D variant; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-scIL-15/Rα format, a preferred embodiment utilizes the IL-15 N65D variant.

In the Fc-scIL-15/Rα format, a preferred embodiment utilizes the IL-15 N65D variant, and the skew variant pair S364K/E357Q:L368D/K370S. In the Fc-scIL-15/Rα format, a preferred embodiment utilizes the IL-15 N65D variant, the skew variant pair S364K/E357Q:L368D/K370S and the 428L/434S variants on each Fc monomer. In the Fc-scIL-15/Rα format, a preferred embodiment utilizes the IL-15 N65D variant, the skew variant pair S364K/E357Q L368D/K370S and the M428L/N434S variants on each Fc monomer.

In some embodiments, the Fc-scIL-15/Rα fusion protein comprises human mature IL-15 N65D variant, IL-15Rα (sushi) domain; and two Fc monomers comprising the amino acid substitutions depicted in FIG. 6E. In some embodiments, the Fc-scIL-15/Rα fusion protein comprises a Fc-IL-15/Rα(sushi) monomer comprising a Fc monomer comprising an amino acid substitution C220S, heterodimer pI variants L368D/K370S, and ablation substitutions E233P/L234V/L235A/G236del/S267K, such that the Fc domain is linked to a human IL-15Rα(sushi) domain linked to a human mature IL-15 N65D variant; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the Fc-scIL-15/Rα fusion protein comprises a Fc-IL-15/Rα (sushi) monomer comprising a Fc monomer comprising an amino acid substitution C220S, heterodimer pI variants L368D/K370S, ablation substitutions E233P/L234V/L235A/G236del/S267K, and FcRn substitutions M428L/N343S, such that the Fc domain is linked to a human IL-15Rα(sushi) domain linked to a human mature IL-15 N65D variant; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-scIL-15/Rα format, a preferred embodiment utilizes the IL-15 N4D/N65D variant.

In the Fc-scIL-15/Rα format, a preferred embodiment utilizes the IL-15 N4D/N65D variant and the skew variant pair S364K/E357Q:L368D/K370S. In the Fc-scIL-15/Rα format, a preferred embodiment utilizes the IL-15 N4D/N65D variant, the skew variant pair S364K/E357Q:L368D/K370S and the 428L/434S variants on each Fc monomer. In Fc-scIL-15/Rα format, a preferred embodiment utilizes the IL-15 N4D/N65D variant, the skew variant pair S364K/E357Q:L368D/K370S and the M428L/N434S variants on each Fc monomer.

In some embodiments, the Fc-scIL-15/Rα fusion protein comprises human mature IL-15 N4D/N65D variant, IL-15Rα(sushi) domain; and two Fc monomers comprising the amino acid substitutions depicted in FIG. 6E. In some embodiments, the Fc-scIL-15/Rα fusion protein comprises a Fc-IL-15/Rα(sushi) monomer comprising a Fc monomer comprising an amino acid substitution C220S, heterodimer pI variants L368D/K370S, and ablation substitutions E233P/L234V/L235A/G236del/S267K, such that the Fc domain is linked to a human IL-15Rα(sushi) domain linked to a human mature IL-15 N4D/N65D variant; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the Fc-scIL-15/Rα fusion protein comprises a Fc-IL-15/Rα (sushi) monomer comprising a Fc monomer comprising an amino acid substitution C220S, heterodimer pI variants L368D/K370S, ablation substitutions E233P/L234V/L235A/G236del/S267K, and FcRn substitutions M428L/N343S, such that the Fc domain is linked to a human IL-15Rα(sushi) domain linked to a human mature IL-15 N4D/N65D variant; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-scIL-15/Rα format, a preferred embodiment utilizes the IL-15 N1D/N65D variant.

In the Fc-scIL-15/Rα format, a preferred embodiment utilizes the IL-15 N1D/N65D variant and the skew variant pair S364K/E357Q:L368D/K370S. In the Fc-scIL-15/Rα format, a preferred embodiment utilizes the IL-15 N1D/N65D variant, the skew variant pair S364K/E357Q:L368D/K370S and the 428L/434S variants on each Fc monomer. In the Fc-scIL-15/Rα format, a preferred embodiment utilizes the IL-15 N1D/N65D variant, the skew variant pair S364K/E357Q:L368D/K370S and the M428L/N434S variants on each Fc monomer.

In some embodiments, the Fc-scIL-15/Rα fusion protein comprises human mature IL-15 N1D/N65D variant, IL-15Rα(sushi) domain; and two Fc monomers comprising the amino acid substitutions depicted in FIG. 6E. In some embodiments, the Fc-scIL-15/Rα fusion protein comprises a Fc-IL-15/Rα(sushi) monomer comprising a Fc monomer comprising an amino acid substitution C220S, heterodimer pI variants L368D/K370S, and ablation substitutions E233P/L234V/L235A/G236del/S267K, such that the Fc domain is linked to a human IL-15Rα(sushi) domain linked to a human mature IL-15 N1D/N65D variant; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the Fc-scIL-15/Rα fusion protein comprises a Fc-IL-15/Rα(sushi) monomer comprising a Fc monomer comprising an amino acid substitution C220S, heterodimer pI variants L368D/K370S, ablation substitutions E233P/L234V/L235A/G236del/S267K, and FcRn substitutions M428L/N343S, such that the Fc domain is linked to a human IL-15Rα(sushi) domain linked to a human mature IL-15 N1D/N65D variant; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-scIL-15/Rα format, a preferred embodiment utilizes the IL-15 variant Q108E.

In the Fc-scIL-15/Rα format, a preferred embodiment utilizes the IL-15 variant Q108E and the skew variant pair S364K/E357Q:L368D/K370S. In the Fc-scIL-15/Rα format, a preferred embodiment utilizes the IL-15 variant Q108E and the skew variant pair S364K/E357Q:L368D/K370S and the 428L/434S variants on both monomers. In the Fc-scIL-15/Rα format, a preferred embodiment utilizes the IL-15 variant Q108E and the skew variant pair S364K/E357Q:L368D/K370S and the M428L/N434S variants on both monomers.

In some embodiments, the Fc-scIL-15/Rα fusion protein comprises human mature IL-15 Q108E variant, IL-15Rα(sushi) domain; and two Fc monomers comprising the amino acid substitutions depicted in FIG. 6E. In some embodiments, the Fc-scIL-15/Rα fusion protein comprises a Fc-IL-15/Rα(sushi) monomer comprising a Fc monomer comprising an amino acid substitution C220S, heterodimer pI variants L368D/K370S, and ablation substitutions E233P/L234V/L235A/G236del/S267K, such that the Fc domain is linked to a human IL-15Rα(sushi) domain linked to a human mature IL-15 Q108E variant; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the Fc-scIL-15/Rα fusion protein comprises a Fc-IL-15/Rα (sushi) monomer comprising a Fc monomer comprising an amino acid substitution C220S, heterodimer pI variants L368D/K370S, ablation substitutions E233P/L234V/L235A/G236del/S267K, and FcRn substitutions M428L/N343S, such that the Fc domain is linked to a human IL-15Rα(sushi) domain linked to a human mature IL-15 Q108E variant; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the Fc-scIL-15/Rα format, a preferred embodiment utilizes the IL-15 wildtype variant.

In the Fc-scIL-15/Rα format, a preferred embodiment utilizes the IL-15 wildtype variant and the skew variant pair S364K/E357Q:L368D/K370S. In the Fc-scIL-15/Rα format, a preferred embodiment utilizes the IL-15 wildtype variant and the skew variant pair S364K/E357Q:L368D/K370S and the 428L/434S variants on both monomers. In the Fc-scIL-15/Rα format, a preferred embodiment utilizes the IL-15 wildtype variant and the skew variant pair S364K/E357Q:L368D/K370S and the M428L/N434S variants on both monomers.

In some embodiments, the Fc-scIL-15/Rα fusion protein comprises human mature IL-15 wildtype variant, IL-15Rα(sushi) domain; and two Fc monomers comprising the amino acid substitutions depicted in FIG. 6E. In some embodiments, the Fc-scIL-15/Rα fusion protein comprises a Fc-IL-15/Rα(sushi) monomer comprising a Fc monomer comprising an amino acid substitution C220S, heterodimer pI variants L368D/K370S, and ablation substitutions E233P/L234V/L235A/G236del/S267K, such that the Fc domain is linked to a human IL-15Rα(sushi) domain linked to a human mature IL-15 wildtype variant; and an empty-Fc monomer comprising an amino acid substitution C220S, heterodimer pI variants S364K/E357Q, isosteric pI substitutions P217R/P228R/N276K, and ablation substitutions E233P/L234V/L235A/G236del/S267K. In some embodiments, the Fc-scIL-15/Rα fusion protein comprises a Fc-IL-15/Rα (sushi) monomer comprising a Fc monomer comprising an amino acid substitution C220S, heterodimer pI variants L368D/K370S, ablation substitutions E233P/L234V/L235A/G236del/S267K, and FcRn substitutions M428L/N343S, such that the Fc domain is linked to a human IL-15Rα(sushi) domain linked to a human mature IL-15 wildtype variant; and an empty-Fc monomer comprising an amino acid substitution C220S, heterodimer pI variants S364K/E357Q, isosteric pI substitutions P217R/P228R/N276K, ablation substitutions E233P/L234V/L235A/G236del/S267K, and FcRn substitutions M428L/N343S.

In the scIL-15/Rα-Fc format, a preferred embodiment is shown in FIG. 16.

VIII. Particular Embodiments of the Invention

Provided herein are compositions comprising untargeted IL-15/IL-15Rα-Fc fusion proteins in different formats and checkpoint blockade antibodies. Also provided are methods comprising administering untargeted IL-15/IL-15Rα-Fc fusion proteins and checkpoint blockade antibodies to a subject, e.g., a human subject.

In some embodiments, the checkpoint blockade antibody of the compositions described herein is selected from the group consisting of an anti-PD-1 antibody. In some embodiments, the anti-PD-1 antibody is selected from the group consisting of nivolumab, pembrolizumab, or pidilizumab.

In some embodiments, the untargeted IL-15/IL-15Rα-Fc fusion protein of the compositions described herein is organized in a format described herein, such as an IL-15/IL-15Rα-hetero Fc format, scIL-15/Rα-Fc format, ncIL-15/Rα-Fc format, bivalent ncIL-15/Rα-Fc format, bivalent scIL-15/Rα-Fc format, Fc-ncIL-15/Rα format, or Fc-scIL-15/Rα format. In some embodiments, the untargeted IL-15/IL-15Rα-Fc fusion protein has an IL-15/IL-15Rα-hetero Fc format.

In some embodiments, the untargeted IL-15/IL-15Rα-Fc fusion protein of the composition has an IL-15/IL-15Rα-hetero Fc format and comprises a human mature IL-15 D30N/E64Q/N65D variant; a human IL-15Rα(sushi) domain; an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K; and an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the IL-15/Rα-heteroFc fusion protein comprises a human mature IL-15 N65D variant; a human IL-15Rα(sushi) domain, an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and an IL-15Rα(sushi)-Fc monomer comprising an amino acid substitution C220S, heterodimer pI substitutions S364K/E357Q, ablation substitutions E233P/L234V/L235A/G236del/S267K, and FcRn substitutions M428L/N434S.

In some embodiments, the composition or method described herein comprises an anti-PD-1 antibody and an untargeted IL-15/IL-15Rα-Fc fusion protein that comprises: (a) first monomer that (from N- to C-terminal) comprises a human mature IL-15 D30N/E64Q/N65D variant linked an IL-15-Fc monomer comprising an amino acid substitution C220S, heterodimer pI0 substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition comprises an anti-PD-1 antibody and an untargeted IL-15/IL-15Rα-Fc fusion protein that comprises: (a) first monomer that (from N- to C-terminal) comprises a human mature IL-15 D30N/E64Q/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition or method described herein comprises nivolumab and an untargeted IL-15/IL-15Rα-Fc fusion protein that comprises: (a) first monomer that (from N- to C-terminal) comprises a human mature IL-15 D30N/E64Q/N65D variant linked an IL-15-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition or method described herein comprises nivolumab and an untargeted IL-15/IL-15Rα-Fc fusion protein that comprises: (a) first monomer that (from N- to C-terminal) comprises a human mature IL-15 D30N/E64Q/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition or method described herein comprises pembrolizumab and an untargeted IL-15/IL-15Rα-Fc fusion protein that comprises: (a) first monomer that (from N- to C-terminal) comprises a human mature IL-15 D30N/E64Q/N65D variant linked an IL-15-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition comprises pembrolizumab and an untargeted IL-15/IL-15Rα-Fc fusion protein that comprises: (a) first monomer that (from N- to C-terminal) comprises a human mature IL-15 D30N/E64Q/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition or method described herein comprises pidilizumab and an untargeted IL-15/IL-15Rα-Fc fusion protein that comprises: (a) first monomer that (from N- to C-terminal) comprises a human mature IL-15 D30N/E64Q/N65D variant linked an IL-15-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition or method described herein comprises pidilizumab and an untargeted IL-15/IL-15Rα-Fc fusion protein that comprises: (a) first monomer that (from N- to C-terminal) comprises a human mature IL-15 D30N/E64Q/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition or method described herein comprises an anti-PD-1 antibody and an untargeted IL-15/IL-15Rα-Fc fusion protein that comprises: (a) first monomer that (from N- to C-terminal) comprises a human mature IL-15 N4D/N65D variant linked an IL-15-Fc monomer comprising an amino acid substitution C220S, heterodimer pI0 substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition comprises an anti-PD-1 antibody and an untargeted IL-15/IL-15Rα-Fc fusion protein that comprises: (a) first monomer that (from N- to C-terminal) comprises a human mature IL-15 N4D/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition or method described herein comprises nivolumab and an untargeted IL-15/IL-15Rα-Fc fusion protein that comprises: (a) first monomer that (from N- to C-terminal) comprises a human mature IL-15 N4D/N65D variant linked an IL-15-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition or method described herein comprises nivolumab and an untargeted IL-15/IL-15Rα-Fc fusion protein that comprises: (a) first monomer that (from N- to C-terminal) comprises a human mature IL-15 N4D/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition or method described herein comprises pembrolizumab and an untargeted IL-15/IL-15Rα-Fc fusion protein that comprises: (a) first monomer that (from N- to C-terminal) comprises a human mature IL-15 N4D/N65D variant linked an IL-15-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition or method described herein comprises pembrolizumab and an untargeted IL-15/IL-15Rα-Fc fusion protein that comprises: (a) first monomer that (from N- to C-terminal) comprises a human mature IL-15 N4D/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition or method described herein comprises pidilizumab and an untargeted IL-15/IL-15Rα-Fc fusion protein that comprises: (a) first monomer that (from N- to C-terminal) comprises a human mature IL-15 N4D/N65D variant linked an IL-15-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition or method described herein comprises pidilizumab and an untargeted IL-15/IL-15Rα-Fc fusion protein that comprises: (a) first monomer that (from N- to C-terminal) comprises a human mature IL-15 N4D/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi)

domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition or method described herein comprises an anti-PD-1 antibody and an untargeted IL-15/IL-15Rα-Fc fusion protein that comprises: (a) first monomer that (from N- to C-terminal) comprises a human mature IL-15 D30N/N65D variant linked an IL-15-Fc monomer comprising an amino acid substitution C220S, heterodimer pI0 substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition or method described herein comprises an anti-PD-1 antibody and an untargeted IL-15/IL-15Rα-Fc fusion protein that comprises: (a) first monomer that (from N- to C-terminal) comprises a human mature IL-15 D30N/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition or method described herein comprises nivolumab and an untargeted IL-15/IL-15Rα-Fc fusion protein that comprises: (a) first monomer that (from N- to C-terminal) comprises a human mature IL-15 D30N/N65D variant linked an IL-15-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition or method described herein comprises nivolumab and an untargeted IL-15/IL-15Rα-Fc fusion protein that comprises: (a) first monomer that (from N- to C-terminal) comprises a human mature IL-15 D30N/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition or method described herein comprises pembrolizumab and an untargeted IL-15/IL-15Rα-Fc fusion protein that comprises: (a) first monomer that (from N- to C-terminal) comprises a human mature IL-15 D30N/N65D variant linked an IL-15-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition or method described herein comprises pembrolizumab and an untargeted IL-15/IL-15Rα-Fc fusion protein that comprises: (a) first monomer that (from N- to C-terminal) comprises a human mature IL-15 D30N/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition or method described herein comprises pidilizumab and an untargeted IL-15/IL-15Rα-Fc fusion protein that comprises: (a) first monomer that (from N- to C-terminal) comprises a human mature IL-15 D30N/N65D variant linked an IL-15-Fc monomer comprising an amino acid substitution C220S, heterodimer pI substitutions L368D/K370S, isosteric pI substitutions Q295E/N384D/Q418E/N421D, and ablation substitutions E233P/L234V/L235A/G236del/S267K; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, and ablation substitutions E233P/L234V/L235A/G236del/S267K. In some embodiments, the composition or method described herein comprises pidilizumab and an untargeted IL-15/IL-15Rα-Fc fusion protein that comprises: (a) first monomer that (from N- to C-terminal) comprises a human mature IL-15 D30N/N65D variant linked an IL-15-Fc monomer comprising an amino acid substitution C220S, heterodimer pI substitutions L368D/K370S, isosteric pI substitutions Q295E/N384D/Q418E/N421D, ablation substitutions E233P/L234V/L235A/G236del/S267K, and FcRn substitutions M428L/N434S; and (b) a second monomer that (from N- to C-terminal) comprises a human IL-15Rα(sushi) domain linked to an IL-15Rα(sushi)-Fc monomer comprising the amino acid substitutions C220S, heterodimer pI substitutions S364K/E357Q, ablation substitutions E233P/L234V/L235A/G236del/S267K, and FcRn substitutions M428L/N434S.

In some embodiments, the composition comprises an anti-PD-1 antibody selected from the group consisting of nivolumab, pembrolizumab, and pedilizumab, and XENP24306 (as will be understand from those in the art, including the sequence identifiers thereof). In some embodiments, the composition comprises nivolumab and XENP24306. In some embodiments, the composition comprises pembrolizumab and XENP24306. In some embodiments, the composition comprises pedilizumab and XENP24306. In some embodiments, the composition comprises an anti-PD-1 antibody selected from the group consisting of nivolumab, pembrolizumab, and pedilizumab, and XENP24045 (as will be understand from those in the art, including the sequence identifiers thereof). In some embodiments, the composition comprises nivolumab and XENP24045. In some embodiments, the composition comprises pembrolizumab and XENP24045. In some embodiments, the composition comprises pedilizumab and XENP24045.

In some embodiments, the combination therapy or treatment comprises an anti-PD-1 antibody selected from the group consisting of nivolumab, pembrolizumab, and pedilizumab, and XENP24306 (as will be understand from those in the art, including the sequence identifiers thereof). In some embodiments, the combination therapy or treatment comprises nivolumab and XENP24306. In some embodiments, the combination therapy or treatment comprises pembrolizumab and XENP24306. In some embodiments, the combination therapy or treatment comprises pedilizumab and XENP24306. In some embodiments, the combination therapy or treatment comprises an anti-PD-1 antibody selected from the group consisting of nivolumab, pembrolizumab, and pedilizumab, and XENP24045 (as will be understand from those in the art, including the sequence identifiers thereof). In some embodiments, the combination therapy or treatment comprises nivolumab and XENP24045. In some embodiments, the combination therapy or treatment comprises pembrolizumab and XENP24045. In some embodiments, the combination therapy or treatment comprises pedilizumab and XENP24045. In some instances, the combination therapy is useful for treating cancer, inducing T cell expansion, and/or results in minimal vascular leakage in a subject. In some embodiments, the combination therapy is administered to a subject and induces T cell expansion in the subject. In some cases, the expanded T cell population, e.g., the TIL population is greater than when the subject is administered either the anti-PD-1 antibody or the untargeted IL-15/IL-15Rα-Fc fusion protein alone. In some embodiments, the combination therapy is administered to a subject and results in a minimal level of vascular leakage compared to adminitration either the anti-PD-1 antibody or the untargeted IL-15/IL-15Rα-Fc fusion protein alone.

In some embodiments, the method of treating cancer comprises an anti-PD-1 antibody selected from the group consisting of nivolumab, pembrolizumab, and pedilizumab, and XENP24306 (as will be understand from those in the art, including the sequence identifiers thereof). In some embodiments, the method of method of treating cancer comprises nivolumab and XENP24306. In some embodiments, the composition comprises pembrolizumab and XENP24306. In some embodiments, the method of treating cancer comprises pedilizumab and XENP24306. In some embodiments, the method of treating cancer that comprises an anti-PD-1 antibody selected from the group consisting of nivolumab, pembrolizumab, and pedilizumab, and XENP24045 (as will be understand from those in the art, including the sequence identifiers thereof). In some embodiments, the method of treating cancer comprises nivolumab and XENP24045. In some embodiments, the method of treating cancer comprises pembrolizumab and XENP24045. In some embodiments, the method of treating cancer comprises pedilizumab and XENP24045.

In some embodiments, the method for expanding T cells in a subject comprises an anti-PD-1 antibody selected from the group consisting of nivolumab, pembrolizumab, and pedilizumab, and XENP24306 (as will be understand from those in the art, including the sequence identifiers thereof). In some embodiments, the method for expanding T cells in a subject comprises nivolumab and XENP24306. In some embodiments, the method for expanding T cells in a subject comprises pembrolizumab and XENP24306. In some embodiments, the method for expanding T cells in a subject comprises pedilizumab and XENP24306. In some embodiments, the method for expanding T cells in a subject comprises an anti-PD-1 antibody selected from the group consisting of nivolumab, pembrolizumab, and pedilizumab, and XENP24045 (as will be understand from those in the art, including the sequence identifiers thereof). In some embodiments, the method for expanding T cells in a subject comprises nivolumab and XENP24045. In some embodiments, the method for expanding T cells in a subject comprises pembrolizumab and XENP24045. In some embodiments, the method for expanding T cells in a subject comprises pedilizumab and XENP24045.

Administration a treatment of an anti-PD-1 antibody and an exemplary IL-15/Rα-Fc fusion variant induces proliferation of T cells including activated T cells in a subject. As shown in Example 22, the combination of an anti-PD-1 antibody (e.g., XENP16432) and IL-15/Rα-Fc fusion variants (e.g., XENP24306) can exhibit extended expansion of lymphocytes in vivo as compared to anti-PD-1 antibody alone. In some embodiments, administration of an anti-PD-1 antibody and an exemplary IL-15/Rα-Fc fusion variant induces IFNγ production. In some cases, the level of IFNγ production increases by administering an anti-PD-1 antibody and an IL-15/Rα-Fc fusion protein. The level of IFNγ is higher upon administering a treatment comprising an anti-PD-1 antibody and an IL-15/Rα-Fc fusion protein, compared to anti-PD-1 antibody or IL-15/Rα-Fc fusion protein alone.

In some embodiments, administration of an anti-PD-1 antibody and an exemplary IL-15/Rα-Fc fusion variant decreases tumor size. In some instances, tumor size is lower upon administering a treatment comprising an anti-PD-1 antibody and an IL-15/Rα-Fc fusion protein, compared to anti-PD-1 antibody or IL-15/Rα-Fc fusion protein alone.

In some embodiments, the composition or method includes an anti-PD-1 antibody and any of the heterodimeric fusion proteins of the present invention. As will be appreciated by those in the art and discussed more fully below, the heterodimeric fusion proteins of the present invention can take on a wide variety of configurations, as are generally depicted in FIGS. 9A-9G and FIGS. 39A-39D. The amino acid sequences of exemplary fusion proteins are provided in FIGS. 12A, 12B, 13, 14, 15, 16, 40A, 40B, 41A, 41B, 42, 43, 48A-48H, 49A-49D, 50A-50B, 51, 52, 53, 99A-99C, 100, 101, and 102, as will be apparent from the sequence identifiers.

In some embodiments, the composition or method includes an anti-PD-1 antibody and any exemplary "IL-15/Rα hetero Fc" and "dsIL-15/Rα hetero Fc" protein. Many of the embodiments outlined herein rely in general on the format comprising a first monomer (first fusion protein) comprising an IL-15 protein domain covalently attached using a first domain linker to the N-terminus of a first Fc domain, and a second monomer (second fusion protein) comprising an IL-15Rα protein domain covalently attached using a second domain linker to the N-terminus of a second Fc domain. Exemplary embodiments of this format ("IL-15/Rα hetero Fc" and "dsIL-15/Rα hetero Fc") include, but are not limited to, XENP20818, XENP20819, XENP21471, XENP21472, XENP21473, XENP21474, XENP21475, XENP21476, XENP21477, XENP22013, XENP22815, XENP22816, XENP22817, XENP22818, XENP22819, XENP22820, XENP22821, XENP22822, XENP22823, XENP22824, XENP22825, XENP22826, XENP22827, XENP22828, XENP22829, XENP22830, XENP22831, XENP22832, XENP22833, XENP22834, XENP22815, XENP22816, XENP22817, XENP22818, XENP22819, XENP22820, XENP22821, XENP23343, XENP23554, XENP23555, XENP23557, XENP23559, XENP23561, XENP24018, XENP24019, XENP24020, XENP24051, XENP24052, XENP23504, XENP24306, XENP24306, XENP23343, XENO24113, XENP24341, and XENP24301 (including the corresponding sequence identifiers).

In some embodiments, the composition or method comprises an anti-PD-1 antibody and an IL-15/Rα heterodimeric Fc fusion protein having a "IL-15/Rα hetero Fc" and "dsIL-15/Rα hetero Fc" format of XENP22357, XENP22358, XENP22359, XENP22360, XENP22362, XENP22363, XENP22364, XENP22365, XENP22366, XENP22684, XENP22361, XENP22816, XENP22819, XENP22820, XENP22821, XENP22822, XENP22829, XENP22834, XENP23554, XENP23557, XENP23561, XENP24018, XENP24019, XENP24045, XENP24051, XENP24052, XENP23343, XENP23504, XENP24113, XENP24301, XENP24306, XENP24341, XENP23472, XENP23473, XENP22815, XENP22817, XENP22818, XENP22823, XENP22824, XENP22825, XENP22826, XENP22827, XENP22828, XENP22830, XENP22831, XENP22832, XENP22833, XENP23555, XENP23559, XENP23560, XENP24017, XENP24020, XENP24043, or XENP24048 (including the corresponding sequence identifiers). Exemplary amino acid sequences of such formats are set forth in FIGS. 41A, 41B, 48A, 48B, 48C, 48D, 48E, 48F, 48G, 48H, 53, 90A, 99B, and 99C, as will be apparent from the sequence identifiers.

In some embodiments, the composition or method includes an anti-PD-1 antibody and an scIL-15/Rα-Fc heterodimeric fusion protein comprising a fusion protein comprising a first protein domain covalently attached to the N-terminus of a second protein domain via a first domain linker that is covalently attached to the N-terminus of a first Fc domain via a second domain linker, and a second Fc domain (e.g., an empty Fc domain). In some cases, the first protein domain is an IL-15Rα protein domain and the second protein domain is an IL-15 protein domain. An exemplary embodiment of this format ("scIL-15/Rα-Fc") includes, but is not limited to, XENP21478 (including the corresponding sequence identifiers).

In some embodiments, the composition or method comprises an anti-PD-1 antibody and an IL-15/Rα heterodimeric Fc fusion protein having a "scIL-15/Rα-Fc" format of XENP24013, XENP24014, XENP24016, XENP24015, XENP24050, XENP24475, XENP24476, XENP24478, XENP24479, XENP24481, and XENP25938 (including the corresponding sequence identifiers). Exemplary amino acid sequences of such formats are set forth in FIGS. 49A, 49B, 49C, 49D, and 100, as will be apparent from the sequence identifiers.

In some embodiments, the composition or method includes an anti-PD-1 antibody and an ncIL-15/Rα-Fc or dsIL-15/Rα-Fc heterodimeric fusion protein comprising a first protein domain covalently attached to the N-terminus a first Fc domain via a domain linker, a second Fc domain (e.g., an empty Fc domain), and a second protein domain that is noncovalently attached to the first protein domain. In some cases, the first protein domain is an IL-15 protein domain and the second protein domain is an IL-15Rα protein domain. An exemplary embodiment of this format ("ncIL-15/Rα-Fc" or "dsIL-15/Rα-Fc") includes, but is not limited to, XENP21479, XENP22357, XENP22354, XENP22355, XENP22356, XENP22357, XENP22358, XENP22359, XENP22360, XENP22361, XENP22362, XENP22363, XENP22364, XENP22365, XENP22366, XENP22637, XENP24348, XENP24349, and XENP24383 (including the corresponding sequence identifiers).

In some embodiments, the IL-15/Rα heterodimeric Fc fusion protein having a "ncIL-15/Rα-Fc" format is XENP21479, XENP22366, XENP24348, XENP24383, XENP24349, XENP24890, and XENP25138 (including the corresponding sequence identifiers). Exemplary amino acid sequences of such formats are set forth in FIGS. 12A, 12B, 50A, 50B, and 101, as will be apparent from the sequence identifiers.

In some embodiments, the composition or method includes an anti-PD-1 antibody and a bivalent ncIL-15/Rα-Fc or bivalent dsIL-15/Rα-Fc fusion protein comprising a first fusion protein comprising a first protein domain covalently attached to the N-terminus of said first Fc domain via a first domain linker, a second fusion protein comprising a second protein domain covalently attached to the N-terminus of said second Fc domain via a second domain linker, a third protein domain noncovalently attached to said first protein domain of said first fusion protein, and a fourth protein domain noncovalently attached to said second protein domain of said second fusion protein. In some cases, the first and second protein domains are IL-15 Rα protein domains, and the third and fourth protein domains are IL-15 protein domains. An exemplary embodiment of this format ("bivalent ncIL-15/Rα-Fc" or "bivalent dsIL-15/Rα-Fc") includes, but is not limited to, XENP21978, XENP22634, XENP24342, and XENP24346 (including the corresponding sequence identifiers).

In some embodiments, the IL-15/Rα heterodimeric Fc fusion protein having a "bivalent ncIL-15/Rα-Fc" format is XENP21978, XENP24342, XENP24346, and XENP24351 (including the corresponding sequence identifiers). Exemplary amino acid sequences of such formats are set forth in FIGS. 13, 52, and 102, as will be apparent from the sequence identifiers.

Another useful format ("bivalent scIL-15/Rα-Fc") is outlined herein in FIG. 14, as will be apparent from the sequence identifiers.

In some embodiments, the composition or method includes an anti-PD-1 antibody and an Fc-ncIL-15/Rα fusion protein or Fc-dsIL-15/Rα fusion protein comprising a first fusion protein comprising a first Fc domain covalently attached to the N-terminus of a first protein domain using a domain linker, a second Fc domain (e.g., an empty Fc domain), and a second protein domain noncovalently attached to said first protein domain. An exemplary embodiment of this format ("Fc-ncIL-15/Rα" or "Fc-dsIL-15/Rα") includes, but is not limited to, XENP22637 and XENP22639, and those depicted in FIG. 15, as will be apparent from the sequence identifiers. In some embodiments, the first protein and the second protein are attached via a linker (FIG. 9G).

In some embodiments, the IL-15/Rα heterodimeric Fc fusion protein having a "Fc-ncIL-15/Rα" format is XENP22637 and XENP22638. Exemplary amino acid sequences of such formats are set forth in FIG. 15, as will be apparent from the sequence identifiers.

In some embodiments, the IL-15/Rα heterodimeric Fc fusion protein having a "Fc-scIL-15/Rα" format is set forth in FIG. 16, as will be apparent from the sequence identifiers.

In some embodiments, the IL-15/Rα heterodimeric Fc fusion protein having a "Fc-dsIL-15/Rα" is XENP22639 and XENP22640 Exemplary amino acid sequences of such formats are set forth in FIG. 42, as will be apparent from the sequence identifiers.

For any of the heterodimer Fc fusion proteins outlined herein, the first domain linker and the second domain linker can be the same or different. In addition, the first Fc domain and the second Fc domain of the heterodimeric protein can have different amino acid sequences.

The Fc domains of the present invention comprise IgG Fc domains, e.g., IgG1, IgG2, IgG3 or IgG4 Fc domains, with IgG1, IgG2, and IgG4 Fc domains finding particular use in some embodiments. In some embodiments, the first and second Fc domains comprising a set of amino acid substitutions selected from the group consisting of: L368D/K370S and S364K; L368D/K370S and S364K/E357L; L368D/K370S and S364K/E357Q; T411E/K360E/Q362E and D401K; L368E/K370S and S364K; K370S and S364K/E357Q; K370S and S364K/E357Q; S267K/L368D/K370S and S267K/S364K/E357Q, according to EU numbering. In some instances, the first and/or the second Fc domains of any of the heterodimeric Fc fusion formats outlined herein can have an additional set of amino acid substitutions comprising Q295E/N384D/Q418E/N421D, according to EU numbering. In some embodiments, the first and/or the second Fc domains have an additional set of amino acid substitutions consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, according to EU numbering.

Additional heterodimerization variants can be independently and optionally included and selected from variants outlined in the figures. These compositions can further comprise ablation variants, pI variants, charged variants, isotypic variants, etc.

Provided herein are compositions comprising anti-PD-1 antibodies and IL-15/Rα-Fc heterodimeric fusion proteins with engineered disulfide bonds at the IL-15/Rα interface (see, e.g., Example 2). Such IL-15/Rα-Fc fusion proteins can induce or promote proliferation of immune cells including NK cells, CD8$^+$ T cells, and CD4$^+$ T cells.

Also provided herein are compositions comprising anti-PD-1 antibodies and IL-15/Rα-Fc fusion proteins engineered for decreased potency (also referred to as"IL-15/Rα-Fc affinity variants"; see, e.g., Example 3). In some cases, the IL-15/Rα-Fc fusion protein variants show improved pharmacokinetics, decreased potency, and prolonged (e.g., increased) half-life.

In some embodiments, compositions comprising anti-PD-1 antibodies and IL-15/Rα-Fc fusion variants engineered for decreased potency are also engineered with an Xtend (FcRn) Fc substitution such that each Fc monomer comprises amino acid substitutions M428L/N434S. Exemplary embodiments of such IL-15/Rα-Xtend Fc variants are depicted in FIGS. 99A-99C, 100, 101, and 102 (see also Table 6). Administration of IL-15/Rα-Xtend Fc variants induces proliferation of T cells including activated T cells in a subject. As shown in Example 4D, IL-15/Rα-Fc affinity variants with domain linker (e.g., XENP24113) can exhibit extended expansion of lymphocytes in vivo as compared to corresponding IL-15/Rα-Fc affinity variants without linker (hinge only; e.g., XENP24341). IL-15/Rα-Fc affinity variants can provide prolonged T cell pharmacology.

The IL-15/Rα-Fc fusion proteins of the present invention can preferentially bind to T cells and NK cells, and in some cases, selectively target activated T cells in a cancer environment in a subject. Notably, IL-15/Rα-Fc fusion variants (e.g., IL-15/Rα-Fc affinity variants) without domain linkers (hinge only; e.g., XENP24341) demonstrated less binding to various lymphocyte populations than corresponding IL-15/Rα-Fc affinity variant with a domain linker (e.g., XENP24113) (see FIG. 117).

IL-15/Rα-Fc fusion proteins described herein can enhance anti-tumor effects of activated T cells (see Examples 5B and 5C). In one embodiments, IL-15/Rα-Fc fusion proteins described herein can induce the proliferation of CD8$^+$ T cells (e.g., activated CD8$^+$ T cells) and CD4$^+$ T cells (e.g., activated CD4$^+$ T cells). In some cases, the IL-15/Rα-Fc fusion proteins can induce proliferation of CD8$^+$ T cells over CD4$^+$ T cells. In certain embodiments, IL-15/Rα-Fc fusion proteins described herein can induce the proliferation of CD8$^+$ T cells (e.g., CD69$^+$/IFNγ$^+$ fractions and/or CD69$^+$/Ki-67$^+$ fractions of CD8$^+$ T cells) and CD4$^+$ T cells (e.g., CD69$^+$/IFNγ$^+$ fractions and/or CD69$^+$/Ki-67$^-$ fractions of CD4$^+$ T cells). The IL-15/Rα-Fc fusion proteins of the invention can promote killing of tumor cells and can selectively expand activated lymphocytes including tumor-infiltrating lymphocytes. Notably, the IL-15/Rα-Fc fusion proteins can preferentially induce proliferation of CD8$^+$ and CD4$^+$ T cells.

In some embodiments, IL-15/Rα-Fc fusion proteins described herein can enhance anti-tumor effects in subjects that are administered such proteins. As illustrated in the Examples described below (see Example 5D), treatment with IL-15/Rα-Fc fusion proteins significantly reduced tumor growth in subjects having tumors compared to treatment without such IL-15/Rα-Fc fusion proteins.

In some embodiments, reduction in potency of IL-15/Rα-Fc fusion proteins with and without Xtend-Fc substitutions described herein can enhance both pharmacodynamics and pharmacokinetics in subjects that are administered such proteins. As illustrated in the Examples described below (see, Example 6), IL-15/Rα-Fc fusion proteins with Xtend (FcRn) substitutions (e.g., M428L/N434S variants on each Fc monomer) of the present invention such as XmAb24306 and XENP23343 exhibited a longer serum half-life in subjects compared to corresponding IL-15/Rα-Fc fusion proteins without Xtend substitutions. In some cases, Xtend substitutions significantly improved exposure as indicated by increased half-life.

It is shown below (see, Example 7) that reduced potency IL-15/Rα-Fc variants such as XENP22821 can expand lymphocyte counts for a greater duration than wild-type IL-15/Rα-Fc fusion proteins described herein such as XENP20818. Notably, XENP23343, the Xtend-analog of XENP22821, further enhanced the duration of lymphocyte expansion beyond XENP22821.

As illustrated in the Examples described below (see, Example 8), IL-15/Rα-Fc fusion proteins such as, but not limited to XmAb24306 (also referred to as XENP24306) can overcome Treg suppression of anti-CD3 induced effector T cell proliferation.

As described herein (see, Example 9), IL-15/Rα-Fc fusion proteins such as, but not limited to XENP24045 can promote leukocyte expansion and exacerbate xenogeneic GVHID over a range of dose levels. Notably, combination therapy of XENP24045 and an anti-PD-1 antibody such as XENP13432 showed synergy (e.g., a synergic effect), particularly at a low dose.

In some embodiments, the IL-15/Rα-Fc fusion protein of the present invention is XENP23557 (see, FIG. 48E). XENP23557 comprises chain 1 (human_IL15_N4D/N65D_

(GGGGS)1_Fc(216)_IgG1_pI(−)_Isosteric_A_C220S/ PVA_/S267K/L368D/K370S (18786)) and chain 2 (human_ IL15Rα(Sushi)_(GGGGS)1_Fc(216)_IgG1_C220S/PVA_/ S267K/S364K/E357Q (15908)).

In some embodiments, the IL-15/Rα-Fc fusion protein of the present invention is XENP24045 (see, FIG. 48E). XENP24045 comprises chain 1 (human_IL15_D30N/E64Q/ N65D_(GGGGS)1_Fc(216)_IgG1_pI(−)_Isosteric_A_ C220S/PVA_/S267K/L368D/K370S) and chain 2 (human_IL15Rα(Sushi)_(GGGGS)1_Fc(216)_IgG1_ C220S/PVA_/S267K/S364K/E357Q).

In some embodiments, the IL-15/Rα-Fc fusion protein of the present invention is XENP24113 (see, FIG. 99B). XENP24113 comprises chain 1 (human_IL15_N4D/N65D_ (GGGGS)1_Fc(216)_IgG1_pI(−)_Isosteric_A_C220S/ PVA_/S267K/L368D/K370S/M428L/N434S) and chain 2 (human_IL15Rα(Sushi)_(GGGGS)1_Fc(216)_IgG1_ C220S/ PVA_/S267K/S364K/E357Q/M428 L/N434S).

In some embodiments, the IL-15/Rα-Fc fusion protein of the present invention is XENP24306 (see, FIG. 99C). XENP24306 comprises chain 1 (human_IL15_D30N/E64Q/ N65D_(GGGGS)1_Fc(216)_IgG1_pI(−)_ Isosteric_A_C220S/PVA_/S267K/L368D/K370S/M428L/ N434S) and chain 2 (human_IL15Rα(Sushi)_(GGGGS) 1_Fc(216)_IgG1_C220S/PVA_/S267K/S364K/E357Q/ M428 L/N434S).

Accordingly, in one aspect the present invention provides a heterodimeric protein comprising a) a first fusion protein comprising a first protein domain and a first Fc domain, wherein the first protein domain is covalently attached to the N-terminus of the first Fc domain using a first domain linker; b) a second fusion protein comprising a second protein domain and a second Fc domain, wherein the second protein domain is covalently attached to the N-terminus of the Fc domain using a second domain linker; wherein the first and the second Fc domains have a set of amino acid substitutions selected from the group consisting of S267K/L368D/ K370S:S267K/LS364K/E357Q; S364K/E357Q:L368D/ K370S; L368D/K370S:S364K; L368E/K370S:S364K; T411E/K360E/Q362E:D401K; L368D/K370S:S364K/ E357L and K370S:S364K/E357Q, according to EU numbering and wherein the first protein domain comprises an IL-15 protein and the second protein domain comprises an IL-15Rα protein. In some embodiments, the first protein domain is covalently attached to the N-terminus of the first Fc domain directly and without using the first domain linker and/or the second protein domain is covalently attached to the N-terminus of the second Fc domain directly and without using the second domain linker. In some embodiments, the invention also provides a checkpoint blockade antibody such as an anti-PD-1 antibody.

In some instances, the heterodimeric protein is selected from the group consisting of XENP20818, XENP20819, XENP21471, XENP21472, XENP21473, XENP21474, XENP21475, XENP21476, XENP21477, XENP22013, XENP22815, XENP22816, XENP22817, XENP22818, XENP22819, XENP22820, XENP22821, XENP22822, XENP22823, XENP22824, XENP22825, XENP22826, XENP22827, XENP22828, XENP22829, XENP22830, XENP22831, XENP22832, XENP22833, XENP22834, XENP23343, XENP23554, XENP23555, XENP23557, XENP23559, XENP24019, and XENP24020 (including the corresponding sequence identifiers).

In a further aspect, the invention provides a heterodimeric protein comprising: a) a fusion protein comprising a first protein domain, a second protein domain, and a first Fc domain, wherein the first protein domain is covalently attached to the N-terminus of the second protein domain using a first domain linker, and wherein the second protein domain is covalently attached to the N-terminus of the first Fc domain using a second domain linker; b) a second Fc domain; wherein the first and the second Fc domains have a set of amino acid substitutions selected from the group consisting of S267K/L368D/K370S:S267K/LS364K/ E357Q; S364K/E357Q:L368D/K370S; L368D/K370S: S364K; L368E/K370S:S364K; T411E/K360E/Q362E: D401K; L368D/K370S:S364K/E357L and K370S:S364K/ E357Q, according to EU numbering and wherein the first protein domain comprises an IL-15Rα protein and the second protein domain comprises an IL-15 protein. In some case, also provided is checkpoint blockade antibody such as an anti-PD-1 antibody.

In some embodiments, the heterodimeric protein can be XENP21478.

In another aspect, the invention provides a heterodimeric protein comprising: a) a fusion protein comprising a first protein domain and a first Fc domain, wherein the first protein domain is covalently attached to the N-terminus of the first Fc domain using a domain linker; b) a second Fc domain; and c) a second protein domain noncovalently attached to the first protein domain; wherein the first and the second Fc domains have a set of amino acid substitutions selected from the group consisting of S267K/L368D/ K370S:S267K/LS364K/E357Q; S364K/E357Q:L368D/ K370S; L368D/K370S:S364K; L368E/K370S:S364K; T411E/K360E/Q362E:D401K; L368D/K370S:S364K/ E357L and K370S:S364K/E357Q, according to EU numbering and wherein the first protein domain comprises an IL-15Rα and the second protein domain comprises an IL-15 protein. In some case, also provided is checkpoint blockade antibody such as an anti-PD-1 antibody.

In some embodiments, the heterodimer protein can be selected from the group consisting of XENP21479, XENP22357, XENP22354, XENP22355, XENP22356, XENP22357, XENP22358, XENP22359, XENP22360, XENP22361, XENP22362, XENP22363, XENP22364, XENP22365, XENP22366, and XENP22637 (including the corresponding sequence identifiers).

In an additional aspect, the invention provides a heterodimeric protein comprising: a) a first fusion protein comprising a first protein domain and a first Fc domain, wherein the first protein domain is covalently attached to the N-terminus of said first Fc domain using a domain linker; b) a second fusion protein comprising a second heavy chain comprising a second protein domain and a first second heavy chain comprising a second Fc domain, wherein the second protein domain is covalently attached to the C-terminus of the second Fc domain using a domain linker; c) a third protein domain noncovalently attached to the first protein domain of the first fusion protein; and d) a fourth protein domain noncovalently attached to the second protein domain of the second fusion protein, wherein the first and the second Fc domains have a set of amino acid substitutions selected from the group consisting of S267K/L368D/K370S:S267K/ LS364K/E357Q; S364K/E357Q:L368D/K370S; L368D/ K370S:S364K; L368E/K370S:S364K; T411E/K360E/ Q362E:D401K; L368D/K370S:S364K/E357L and K370S: S364K/E357Q, according to EU numbering and wherein the first protein domain and the second protein domain comprise an IL-15Rα protein, and wherein the third protein domain and the fourth protein domain comprises an IL-15 protein. In some embodiments, the heterodimer protein can be XENP21978 or XENP22634. In some case, also provided is checkpoint blockade antibody such as an anti-PD-1 antibody.

In an additional aspect, the invention provides a heterodimeric protein comprising: a) a first fusion protein comprising a first Fc domain and a first protein domain, wherein the first Fc domain is covalently attached to the N-terminus of the first protein domain using a domain linker; b) a second Fc domain, and c) a second protein domain noncovalently attached to the first protein domain of the first fusion protein; wherein the first and the second Fc domains have a set of amino acid substitutions selected from the group consisting of S267K/L368D/K370S:S267K/LS364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering and wherein the first protein domain comprises an IL-15Rα protein and the second protein domain comprises an IL-15 protein. In some case, also provided is checkpoint blockade antibody such as an anti-PD-1 antibody.

In any of the embodiments of the present invention, the first and/or the second Fc domains can have an additional set of amino acid substitutions comprising Q295E/N384D/Q418E/N421D, according to EU numbering. In some cases, the first and/or the second Fc domains have an additional set of amino acid substitutions consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, according to EU numbering.

In any of the embodiments of the present invention, the IL-15 protein has a polypeptide sequence selected from the group consisting of full-length human IL-15 and a truncated human IL-15, and the IL-15Rα protein has a polypeptide sequence selected from the group consisting of full-length human IL-15Rα and the sushi domain of human IL-15Rα. In some cases, the IL-15 protein and the IL1-5Rα protein have a set of amino acid substitutions or additions selected from the group consisting of E87C:D96/P97/C98; E87C:D96/C97/A98; V49C:S40C; L52C:S40C; E89C:K34C; Q48C:G38C; E53C:L42C; C42S:A37C; and L45C:A37C, respectively.

In an additional aspect, the present invention provides a checkpoint blockade antibody and a heterodimeric protein selected from the group consisting of XENP20818, XENP20819, XENP21471, XENP21472, XENP21473, XENP21474, XENP21475, XENP21476, XENP21477, XENP21478, XENP21479, XENP21978, XENP22013, XENP22015, XENP22017, XENP22354, XENP22355, XENP22356, XENP22357, XENP22358, XENP22359, XENP22360, XENP22361, XENP22362, XENP22363, XENP22364, XENP22365, XENP22366, XENP22637, and XENP22639 (including the corresponding sequence identifiers). In some aspects, the present invention provides a heterodimeric protein selected from the group consisting of XENP20818, XENP20819, XENP21471, XENP21472, XENP21473, XENP21474, XENP21475, XENP21476, XENP21477, XENP22013, XENP22815, XENP22816, XENP22817, XENP22818, XENP22819, XENP22820, XENP22821, XENP22822, XENP22823, XENP22824, XENP22825, XENP22826, XENP22827, XENP22828, XENP22829, XENP22830, XENP22831, XENP22832, XENP22833, XENP22834, XENP23343, XENP23554, XENP23555, XENP23557, XENP23559, XENP24019, and XENP24020 (including the corresponding sequence identifiers). Nucleic acids, expression vectors and host cells are all provided as well, in addition to methods of making these proteins and treating patients with them.

In some aspects, provided herein is a method of treating cancer in a patient in need thereof and minimizing the level of vascular leakage in said patient. Such a method comprises administering a therapeutically effective amount of a checkpoint blockade antibody, e.g., an anti-PD-1 antibody and a therapeutically effective amount of an IL-15/IL-15Rα heterodimeric Fc fusion protein described herein or a pharmaceutical composition described herein to the patient.

In some embodiments, the method also includes administering a therapeutically effective amount of a checkpoint blockade antibody. In some embodiments, the checkpoint blockade antibody is selected from an anti-PD-1 antibody, an anti-PD-L1 antibody, an anti-TIM3 antibody, an anti-TIGIT antibody, an anti-LAG3 antibody, and an anti-CTLA-4 antibody. In some embodiments, the anti-PD-1 antibody is nivolumab, pembrolizumab, or pidilizumab. In some embodiments, the anti-PD-L1 antibody is atezolizumab, avelumab, or durbalumab.

In some embodiments, the level of vascular leakage ranges from a 20% reduction or less, e.g., a 20% reduction, a 19% reduction, a 18% reduction, a 17% reduction, a 16% reduction, a 20% reduction, a 20% reduction, a 20% reduction, a 20% reduction, a 20% reduction, a 15% reduction, a 14% reduction, a 13% reduction, a 12% reduction, a 11% reduction, a 10% reduction, or less reduction in serum albumin in the patient following administration of an IL-15/IL-15Rα heterodimeric Fc fusion protein and an anti-PD-1 antibody. In some instances, such a reduction in serum albumin occurs at day 1 to day 15 after administration. In some embodiments, the reduction occurs (or is detectable) at day 1, day 2, day 3, day 4, day 5, day 6, day 7, day 8, day 9, day 10, day 11, day 12, day 13, day 14, day 15 or later after administration of an IL-15/IL-15Rα heterodimeric Fc fusion protein and an anti-PD-1 antibody.

In some embodiments, the patient exhibits a 2-fold to 15-fold increase, e.g., a 2-fold, a 3-fold, a 4-fold, a 5-fold, a 6-fold, a 7-fold, an 8-fold, a 9-fold, a 10-fold, a 11-fold, a 12-fold, a 13-fold, a 14-fold, or a 15-fold increase in lymphocytes following administration of an IL-15/IL-15Rα heterodimeric Fc fusion protein and an anti-PD-1 antibody. In some instances, such an increase in lymphocytes occurs at day 1 to day 15 after administration. In some embodiments, the increase in lymphocytes occurs (or is detectable) at day 1, day 2, day 3, day 4, day 5, day 6, day 7, day 8, day 9, day 10, day 11, day 12, day 13, day 14, day 15 or later after administration.

In some embodiments, the patient exhibits a 2-fold to 13-fold increase, e.g., a 2-fold, a 3-fold, a 4-fold, a 5-fold, a 6-fold, a 7-fold, an 8-fold, a 9-fold, a 10-fold, a 11-fold, a 12-fold, or a 13-fold increase in peripheral CD8+ T cells following administration of an IL-15/IL-15Rα heterodimeric Fc fusion protein and an anti-PD-1 antibody. In some instances, such an increase in peripheral CD8+ T cells occurs at day 1 to day 15 after administration. In some embodiments, the increase in peripheral CD8+ T cells occurs (or is detectable) at day 1, day 2, day 3, day 4, day 5, day 6, day 7, day 8, day 9, day 10, day 11, day 12, day 13, day 14, day 15 or later after administration.

In some aspects, provided herein is a method of inducing T cell expansion in a patient in need thereof without increasing the likelihood of inducing hypoalbuminemia comprising administering a therapeutically effective amount of an IL-15/IL-15Rα heterodimeric Fc fusion protein described herein or a pharmaceutical composition described herein to said patient. In some embodiments, the method also includes administering a therapeutically effective amount of a checkpoint blockade antibody. In some embodiments, the checkpoint blockade antibody is selected from an anti-PD-1 antibody, an anti-PD-L1 antibody, an anti-TIM3 antibody, an anti-TIGIT antibody, an anti-LAG3 antibody, and an anti-CTLA-4 antibody. In some embodiments, the anti-PD-1 antibody is nivolumab, pembrolizumab, or pidilizumab.

In some embodiments, the T cell expansion is at least a 2-fold, e.g., a 2-fold, a 3-fold, a 4-fold, a 5-fold, a 6-fold, a 7-fold, a 8-fold, a 9-fold, a 10-fold, a 11-fold, a 12-fold, a 13-fold, a 14-fold, a 15-fold, a 16-fold, a 17-fold, a 18-fold, a 19-fold, a 20-fold, a 21-fold, or more fold increase in T cells. In some embodiments, the T cell expansion ranges from a 2-fold to a 15-fold increase, e.g., a 2-fold, a 3-fold, a 4-fold, a 5-fold, a 6-fold, a 7-fold, an 8-fold, a 9-fold, a 10-fold, a 11-fold, a 12-fold, a 13-fold, a 14-fold, or a 15-fold increase in T cells. In some instances, such an expansion in T cells occurs at day 1 to day 15 after administration of an IL-15/IL-15Rα heterodimeric Fc fusion and a checkpoint blockade antibody, e.g., an anti-PD-1 antibody. In some embodiments, the expansion in T cells occurs (or is detectable) at day 1, day 2, day 3, day 4, day 5, day 6, day 7, day 8, day 9, day 10, day 11, day 12, day 13, day 14, day 15 or later after administration of an IL-15/IL-15Rα heterodimeric Fc fusion and a checkpoint blockade antibody, e.g., an anti-PD-1 antibody.

In some embodiments, the IL-15/IL-15Rα heterodimeric Fc fusion protein described herein in combination with an anti-PD-1 antibody enhances lymphocytes expansion in comparison to a control IL-15 or IL-15Rα containing protein, and also results in a reduction in albumin drop (data depicted in FIG. 203). The reduction in albumin drop indicates a superior therapeutic index for the IL-15/IL-15Rα heterodimeric Fc fusion protein and anti-PD-1 antibody. In some embodiments, the IL-15/IL-15Rα heterodimeric Fc fusion protein in combination with the anti-PD-1 antibody promotes at least a 3-fold (200%) increase in peripheral CD8$^+$ T cells. In some embodiments, the IL-15/IL-15Rα heterodimeric Fc fusion protein in combination with the anti-PD-1 antibody mediated or facilitated the extent of albumin decrease as not to exceed a 15% reduction. In some instances, the IL-15/IL-15Rα heterodimeric Fc fusion protein in combination with the anti-PD-1 antibody caused or induced a decrease in albumin levels that is lower than a control IL-15 or IL-15Rα containing protein. In some embodiments, a patient described herein is administered IL-15/IL-15Rα heterodimeric Fc fusion protein and an anti-PD-1 antibody which promotes an at least 11-fold (1000%) increase of peripheral CD8$^+$ T cells while maintaining albumin levels above a 20% decrease.

The present invention provides in a method of inducing T cell expansion in a patient by administering a checkpoint blockade antibody and an IL-15 protein in complex with an IL-15Rα protein, the improvement comprising administering to the patient an anti-PD-1 antibody and an IL-15 variant protein in complex with an IL-15Rα protein, wherein the IL-15 variant protein has reduced affinity such that the patient has a reduced likelihood of hypoalbuminemia.

In some embodiments of the method described herein, the variant IL-15 has one or more amino acid substitutions selected from the group consisting of N1D, N4D, D8N, D30N, D61N, E64Q, N65D, and Q108E. In some embodiments, the variant IL-15 has an N1D substitution or at least an N1D substitution. In some embodiments, the variant IL-15 has an N4D substitution or at least an N4D substitution. In some embodiments, the variant IL-15 has an N1D substitution or at least an D8N substitution. In some embodiments, the variant IL-15 has an D30N substitution or at least an D30N substitution. In some embodiments, the variant IL-15 has an D61N substitution or at least an D61N substitution. In some embodiments, the variant IL-15 has an E64Q substitution or at least an E64Q substitution. In some embodiments, the variant IL-15 has an N65D substitution or at least an N65D substitution. In some embodiments, the variant IL-15 has an Q108E substitution or at least an Q108E substitution.

In some embodiments of the method described herein, the IL-15 variant protein has an amino acid substitution(s) selected from the group consisting of N4D, N65D, N4D/N65D, D30N/N65D, and D30N/E64Q/N65D. In some embodiments, the variant IL-15 has an N4D substitution. In some embodiments, the variant IL-15 has an N65D substitution. In some embodiments, the variant IL-15 has N4D/N65D substitutions. In some embodiments, the variant IL-15 has D30N/N65D substitutions. In some embodiments, the variant IL-15 has D30N/E64Q/N65D substitutions.

In some embodiments of the method described herein, the IL-15 variant protein in complex with an IL-15Rα protein is any one of the IL-15/IL-15Rα heterodimeric Fc fusion proteins described herein.

Accordingly, in one aspect the present invention provides an IL-15/IL-15Rα heterodimeric Fc fusion protein comprising (a) a first fusion protein comprising a first protein domain and a first Fc domain, wherein the first protein domain is covalently attached to the N-terminus of the first Fc domain using a first domain linker; (b) a second fusion protein comprising a second protein domain and a second Fc domain, wherein the second protein domain is covalently attached to the N-terminus of the Fc domain using a second domain linker; wherein the first and the second Fc domains have a set of amino acid substitutions selected from the group consisting of S267K/L368D/K370S:S267K/LS364K/E357Q; S364K/E357Q:L368D/K370S; L368D/K370S:S364K; L368E/K370S:S364K; T411T/E360E/Q362E:D401K; L368D/K370S:S364K/E357L and K370S:S364K/E357Q, according to EU numbering and wherein the first protein domain comprises an IL-15 protein and the second protein domain comprises an IL-15Rα protein. In some embodiments, the first protein domain is covalently attached to the N-terminus of the first Fc domain directly and without using the first domain linker and/or the second protein domain is covalently attached to the N-terminus of the second Fc domain directly and without using the second domain linker.

In some embodiments, the first and/or the second Fc domains have an additional set of amino acid substitutions comprising Q295E/N384D/Q418E/N421D, according to EU numbering. In some embodiments, wherein the first and/or the second Fc domains have an additional set of amino acid substitutions consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, according to EU numbering. In some embodiments, the first and/or the second Fc domains have an additional amino acid substitution M428L/N434S, according to EU numbering In some embodiments, the IL-15 protein has a polypeptide sequence selected from the group consisting of full-length human IL-15 protein and a truncated human IL-15 protein, and said IL-15Rα protein has a polypeptide sequence selected from the group consisting of full-length human IL-15Rα protein and the sushi domain of human IL-15Rα protein. In certain embodiments, the IL-15 protein has one or more amino acid substitutions selected from the group consisting of N1D, N4D, D8N, D30N, D61N, E64Q, N65D, and Q108E. In particular embodiments, IL-15 protein has an amino acid substitution selected from the group consisting of N4D, N65D, N4D/N65D, and D30N/E64Q/N65D.

In some embodiments, the IL-15 protein and the IL-15Rα protein have a set of amino acid substitutions or additions selected from the group consisting of E87C:D96/P97/C98; E87C D96/C97/A98; V49C:S40C; L52C:S40C; E89C: K34C; Q48C:G38C; E53C:L42C; C42S A37C; and L45C: A37C, respectively.

In some embodiments, the first protein domain is covalently attached to the N-terminus of the first Fc domain directly and without using the first domain linker and/or the second protein domain is covalently attached to the N-terminus of the second Fc domain directly and without using the second domain linker.

In some embodiments, the IL-15/IL-15Rα heterodimeric Fc fusion protein is selected from the group consisting of XENP20818, XENP22013, XENP22014, XENP22015, XENP22017, XENP23343, XENP23504, XENP23557, XENP24045, XENP24113, XENP24301, XENP24306, and XENP24341.

Nucleic acids, expression vectors and host cells are all provided as well, in addition to methods of making these proteins and treating patients with them.

In one aspect, the present invention provides a pharmaceutical composition comprising any one of the IL-15/IL-15Rα Fc fusion heterodimeric proteins described herein and a pharmaceutically acceptable carrier. In another aspect, the present invention provides a pharmaceutical composition comprising an IL-15/IL-15Rα heterodimeric Fc fusion protein selected from the group consisting of XENP20818, XENP22013, XENP22014, XENP22015, XENP22017, XENP23343, XENP23504, XENP23557, XENP24045, XENP24113, XENP24301, XENP24306, and XENP24341; and a pharmaceutically acceptable carrier.

In another aspect, the present invention provides a method of treating cancer in a patient in need thereof comprising administering a therapeutically effective amount of any of the IL-15/IL-15Rα heterodimeric Fc fusion proteins described herein or a pharmaceutical composition thereof to the patient. In some embodiments, the method also comprises administering a therapeutically effective amount of a checkpoint blockade antibody. In certain embodiments, the checkpoint blockade antibody is selected from an anti-PD-1 antibody, an anti-PD-L1 antibody, an anti-TIM3 antibody, an anti-TIGIT antibody, an anti-LAG3 antibody, and an anti-CTLA-4 antibody. In some instances, the anti-PD-1 antibody is nivolumab, pembrolizumab, or pidilizumab. In some instances, the anti-PD-L1 antibody is atezolizumab, avelumab, or durbalumab.

Additional IL-15/IL-15Rα heterodimeric Fc fusion proteins are described in detail, for example, in U.S. Ser. No. 62/408,655, filed Oct. 14, 2016, U.S. Ser. No. 62/416,087, filed Nov. 1, 2016, U.S. Ser. No. 62/443,465, filed Jan. 6, 2017, U.S. Ser. No. 62/477,926, filed Mar. 28, 2017, U.S. patent application Ser. No. 15/785,401, filed on Oct. 16, 2017, and WO2018071919, which are expressly incorporated herein by reference in their entirety, with particular reference to the figures, legends and claims therein.

In one aspect, the present invention provides a method of treating cancer in a patient in need thereof and minimizing the level of vascular leakage in the patient. In some embodiments, the method comprises administering a therapeutically effective amount of an IL-15/IL-15Rα heterodimeric Fc fusion protein described herein or a pharmaceutical composition described herein to the patient.

In some embodiments, the method also comprises administering a therapeutically effective amount of a checkpoint blockade antibody. In some embodiments, the checkpoint blockade antibody is selected from an anti-PD-1 antibody, an anti-PD-L1 antibody, an anti-TIM3 antibody, an anti-TIGIT antibody, an anti-LAG3 antibody, and an anti-CTLA-4 antibody. In some embodiments, the anti-PD-1 antibody is nivolumab, pembrolizumab, or pidilizumab. In some embodiments, the anti-PD-L1 antibody is atezolizumab, avelumab, or durbalumab.

In some embodiments, the level of vascular leakage ranges from a 20% reduction or less in serum albumin in the patient following administration.

In some embodiments, the patient exhibits a 2-fold to 15-fold increase in lymphocytes following administration.

In some embodiments, the patient exhibits a 2-fold to 13-fold increase in peripheral CD8+ T cells following administration.

In one aspect, the present invention provides a method of inducing T cell expansion in a patient in need thereof without increasing the likelihood of inducing hypoalbuminemia comprising administering a therapeutically effective amount of an IL-15/IL-15Rα heterodimeric Fc fusion protein described herein or a pharmaceutical composition described herein to the patient.

In some embodiments, the method also comprises administering a therapeutically effective amount of a checkpoint blockade antibody.

In some embodiments, the checkpoint blockade antibody is selected from an anti-PD-1 antibody, an anti-PD-L1 antibody, an anti-TIM3 antibody, an anti-TIGIT antibody, an anti-LAG3 antibody, and an anti-CTLA-4 antibody. In some embodiments, the anti-PD-1 antibody is nivolumab, pembrolizumab, or pidilizumab. In some embodiments, the anti-PD-L1 antibody is atezolizumab, avelumab, or durbalumab.

In some embodiments, the T cell expansion is at least a 2-fold increase in T cells. In some embodiments, the T cell expansion ranges from a 2-fold to a 15-fold increase in T cells.

In some aspects, the present invention provides in a method of inducing T cell expansion in a patient by administering an IL-15 protein in complex with an IL-15Rα protein, the improvement comprising administering to the patient an IL-15 variant protein in complex with an IL-15Rα protein, wherein the IL-15 variant protein has reduced affinity such that the patient has a reduced likelihood of hypoalbuminemia.

In some embodiments of the method described herein, the variant IL-15 has one or more amino acid substitutions selected from the group consisting of N1D, N4D, D8N, D30N, D61N, E64Q, N65D, and Q108E.

In some embodiments of the method described herein, the IL-15 variant protein has an amino acid substitution(s) selected from the group consisting of N4D, N65D, N4D/N65D, and D30N/E64Q/N65D.

In some embodiments of the method described herein, the IL-15 variant protein in complex with an IL-15Rα protein is any one of the IL-15/IL-15Rα heterodimeric Fc fusion proteins described herein.

IX. Nucleic Acids of the Invention

The invention further provides nucleic acid compositions encoding the heterodimeric Fc fusion protein of the invention (or, in the case of a monomer Fc domain protein, nucleic acids encoding those as well).

As will be appreciated by those in the art, the nucleic acid compositions will depend on the format of the heterodimeric protein. Thus, for example, when the format requires three amino acid sequences, three nucleic acid sequences can be incorporated into one or more expression vectors for expression. Similarly for some formats, only two nucleic acids are needed; again, they can be put into one or two expression vectors.

As is known in the art, the nucleic acids encoding the components of the invention can be incorporated into expression vectors as is known in the art, and depending on the host cells used to produce the heterodimeric Fc fusion proteins of the invention. Generally the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with mammalian cells (e.g., CHO cells), finding use in many embodiments.

In some embodiments, nucleic acids encoding each monomer, as applicable depending on the format, are each contained within a single expression vector, generally under different or the same promoter controls. In embodiments of particular use in the present invention, each of these two or three nucleic acids are contained on a different expression vector.

The heterodimeric Fc fusion protein of the invention are made by culturing host cells comprising the expression vector(s) as is well known in the art. Once produced, traditional fusion protein or antibody purification steps are done, including an ion exchange chromatography step. As discussed herein, having the pIs of the two monomers differ by at least 0.5 can allow separation by ion exchange chromatography or isoelectric focusing, or other methods sensitive to isoelectric point. That is, the inclusion of pI substitutions that alter the isoelectric point (pI) of each monomer so that each monomer has a different pI and the heterodimer also has a distinct pI, thus facilitating isoelectric purification of the heterodimer (e.g., anionic exchange chromatography, cationic exchange chromatography). These substitutions also aid in the determination and monitoring of any contaminating homodimers post-purification (e.g., IEF gels, cIEF, and analytical IEX columns).

X. Biological and Biochemical Functionality of IL-15/IL-15Rα Heterodimeric Immunomodulatory Fc Fusion Proteins Generally the heterodimeric Fc fusion proteins of the invention are administered to patients with cancer, and efficacy is assessed, in a number of ways as described herein. Thus, while standard assays of efficacy can be run, such as cancer load, size of tumor, evaluation of presence or extent of metastasis, etc., immuno-oncology treatments can be assessed on the basis of immune status evaluations as well. This can be done in a number of ways, including both in vitro and in vivo assays. For example, evaluation of changes in immune status (e.g., presence of ICOS+ CD4+ T cells following ipi treatment) along with "old fashioned" measurements such as tumor burden, size, invasiveness, LN involvement, metastasis, etc. can be done. Thus, any or all of the following can be evaluated: the inhibitory effects of PVRIG on CD4+ T cell activation or proliferation, CD8+ T (CTL) cell activation or proliferation, CD8+ T cell-mediated cytotoxic activity and/or CTL mediated cell depletion, NK cell activity and NK mediated cell depletion, the potentiating effects of PVRIG on Treg cell differentiation and proliferation and Treg- or myeloid derived suppressor cell (MDSC)-mediated immunosuppression or immune tolerance, and/or the effects of PVRIG on proinflammatory cytokine production by immune cells, e.g., IL-2, IFN-γ or TNF-α production by T or other immune cells.

In some embodiments, assessment of treatment is done by evaluating immune cell proliferation, using for example, CFSE dilution method, Ki67 intracellular staining of immune effector cells, and $^3$H-thymidine incorporation method.

In some embodiments, assessment of treatment is done by evaluating the increase in gene expression or increased protein levels of activation-associated markers, including one or more of: CD25, CD69, CD137, ICOS, PD1, GITR, OX40, and cell degranulation measured by surface expression of CD107A.

In general, gene expression assays are done as is known in the art.

In general, protein expression measurements are also similarly done as is known in the art.

In some embodiments, assessment of treatment is done by assessing cytotoxic activity measured by target cell viability detection via estimating numerous cell parameters such as enzyme activity (including protease activity), cell membrane permeability, cell adherence, ATP production, co-enzyme production, and nucleotide uptake activity. Specific examples of these assays include, but are not limited to, Trypan Blue or PI staining, $^{51}$Cr or $^{35}$S release method, LDH activity, MTT and/or WST assays, Calcein-AM assay, Luminescent based assay, and others.

In some embodiments, assessment of treatment is done by assessing T cell activity measured by cytokine production, measure either intracellularly in culture supernatant using cytokines including, but not limited to, IFNγ, TNFα, GM-CSF, IL2, IL6, IL4, IL5, IL10, IL13 using well known techniques.

Accordingly, assessment of treatment can be done using assays that evaluate one or more of the following: (i) increases in immune response, (ii) increases in activation of αβ and/or γδ T cells, (iii) increases in cytotoxic T cell activity, (iv) increases in NK and/or NKT cell activity, (v) alleviation of αβ and/or γδ T-cell suppression, (vi) increases in pro-inflammatory cytokine secretion, (vii) increases in IL-2 secretion; (viii) increases in interferon-γ production, (ix) increases in Th1 response, (x) decreases in Th2 response, (xi) decreases or eliminates cell number and/or activity of at least one of regulatory T cells (Tregs).

A. Assays to Measure Efficacy and Potency

In some embodiments, T cell activation is assessed using a Mixed Lymphocyte Reaction (MLR) assay as is known in the art. An increase in activity indicates immunostimulatory activity. Appropriate increases in activity are outlined below.

In one embodiment, the signaling pathway assay measures increases or decreases in immune response as measured for an example by phosphorylation or de-phosphorylation of different factors, or by measuring other post translational modifications. IL-15 mediates IFNγ expression and secretion through phosphorylation of STAT5. Accordingly, in some embodiments, the signaling pathway assay measures increases or decreases in immune response as indicated by phosphorylation of STAT5. An increase in activity indicates immunostimulatory activity. Appropriate increases in activity are outlined below.

In one embodiment, the signaling pathway assay measures increases or decreases in activation of αβ and/or γδ T cells as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in cytotoxic T cell activity as measured for an example by direct killing of target cells like for an example cancer cells or by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in NK and/or NKT cell activity as measured for an example by direct killing of target cells like for an example cancer cells or by cytokine secretion or by changes in expression of activation markers like for an example CD107a, etc. An increase in activity indicates immunostimulatory activity. Appropriate increases in activity are outlined below.

In one embodiment, the signaling pathway assay measures increases or decreases in αβ and/or γδ T-cell suppression, as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in pro-inflammatory cytokine secretion as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in TL-2 secretion as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in interferon-γ production as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in Th1 response as measured for an example by cytokine secretion or by changes in expression of activation markers. An increase in activity indicates immunostimulatory activity. Appropriate increases in activity are outlined below.

In one embodiment, the signaling pathway assay measures increases or decreases in Th2 response as measured for an example by cytokine secretion or by changes in expression of activation markers. An increase in activity indicates immunostimulatory activity. Appropriate increases in activity are outlined below.

In one embodiment, the signaling pathway assay measures increases or decreases cell number and/or activity of at least one of regulatory T cells (Tregs), as measured for example by flow cytometry or by IHC. A decrease in response indicates immunostimulatory activity. Appropriate decreases are the same as for increases, outlined below.

In one embodiment, the signaling pathway assay measures increases or decreases in M2 macrophages cell numbers, as measured for example by flow cytometry or by IHC. A decrease in response indicates immunostimulatory activity. Appropriate decreases are the same as for increases, outlined below.

In one embodiment, the signaling pathway assay measures increases or decreases in M2 macrophage pro-tumorigenic activity, as measured for an example by cytokine secretion or by changes in expression of activation markers. A decrease in response indicates immunostimulatory activity. Appropriate decreases are the same as for increases, outlined below.

In one embodiment, the signaling pathway assay measures increases or decreases in N2 neutrophils increase, as measured for example by flow cytometry or by IHC. A decrease in response indicates immunostimulatory activity. Appropriate decreases are the same as for increases, outlined below.

In one embodiment, the signaling pathway assay measures increases or decreases in N2 neutrophils pro-tumorigenic activity, as measured for an example by cytokine secretion or by changes in expression of activation markers. A decrease in response indicates immunostimulatory activity. Appropriate decreases are the same as for increases, outlined below.

In one embodiment, the signaling pathway assay measures increases or decreases in inhibition of T cell activation, as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in inhibition of CTL activation as measured for an example by direct killing of target cells like for an example cancer cells or by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in αβ and/or γδ T cell exhaustion as measured for an example by changes in expression of activation markers. A decrease in response indicates immunostimulatory activity. Appropriate decreases are the same as for increases, outlined below.

In one embodiment, the signaling pathway assay measures increases or decreases αβ and/or γδ T cell response as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in stimulation of antigen-specific memory responses as measured for an example by cytokine secretion or by proliferation or by changes in expression of activation markers like for an example CD45RA, CCR7 etc. An increase in activity indicates immunostimulatory activity. Appropriate increases in activity are outlined below.

In one embodiment, the signaling pathway assay measures increases or decreases in apoptosis or lysis of cancer cells as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases in stimulation of cytotoxic or cytostatic effect on cancer cells, as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases direct killing of cancer cells as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases Th17 activity as measured for an example by cytokine secretion or by proliferation or by changes in expression of activation markers. An increase in activity indicates immunostimulatory activity. Appropriate increases in activity are outlined below.

In one embodiment, the signaling pathway assay measures increases or decreases in induction of complement dependent cytotoxicity and/or antibody dependent cell-mediated cytotoxicity, as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, T cell activation is measured for an example by direct killing of target cells like for an example cancer cells or by cytokine secretion or by proliferation or by changes in expression of activation markers like for an example CD137, CD107a, PD1, etc. For T-cells, increases in proliferation, cell surface markers of activation (e.g., CD25, CD69, CD137, PD1), cytotoxicity (ability to kill target cells), and cytokine production (e.g., IL-2, IL-4, IL-6, IFNγ, TNF-α, IL-10, IL-17A) would be indicative of immune modulation that would be consistent with enhanced killing of cancer cells.

In one embodiment, NK cell activation is measured for example by direct killing of target cells like for an example cancer cells or by cytokine secretion or by changes in expression of activation markers like for an example CD107a, etc. For NK cells, increases in proliferation, cytotoxicity (ability to kill target cells and increases CD107a, granzyme, and perforin expression), cytokine production (e.g., IFNγ and TNF), and cell surface receptor expression (e.g. CD25) would be indicative of immune modulation that would be consistent with enhanced killing of cancer cells.

In one embodiment, γδ T cell activation is measured for example by cytokine secretion or by proliferation or by changes in expression of activation markers.

In one embodiment, Th1 cell activation is measured for example by cytokine secretion or by changes in expression of activation markers.

Appropriate increases in activity or response (or decreases, as appropriate as outlined above), are increases of 10%, 20%, 30%, 40%, 50%, 60%, 70%, 80%, 90%, 95% or 98 to 99% percent over the signal in either a reference sample or in control samples, for example test samples that do not contain an anti-PVRIG antibody of the invention. Similarly, increases of at least one-, two-, three-, four- or five-fold as compared to reference or control samples show efficacy.

XI. Checkpoint Blockade Antibodies

In some embodiments, the heterodimeric Fc fusion proteins containing IL-15 and IL-15Rα proteins described herein are combined with other therapeutic agents including checkpoint blockade antibodies, such as but not limited to, a PD-1 inhibitor, a TIM3 inhibitor, a CTLA4 inhibitor, a PD-L1 inhibitor, a TIGIT inhibitor, a LAG3 inhibitor, or a combination thereof.

A. Anti-PD1 Antibodies

In some embodiments, an IL-15/Rα-Fc fusion proteins described herein can be administered to a subject with cancer in combination with a checkpoint blockage antibody, e.g., an anti-PD-1 antibody. In some cases, the anti-PD-1 antibody includes XENP13432 (a bivalent anti-PD-1 mAb based on nivolumab with ablated effector function; amino acid sequence of XENP13432 is depicted in FIG. 160).

Exemplary non-limiting anti-PD-1 antibody molecules are disclosed in US 2015/0210769, published on Jul. 30, 2015, entitled "Antibody Molecules to PD-1 and Uses Thereof," incorporated by reference in its entirety.

In one embodiment, the anti-PD-1 antibody molecule includes at least one or two heavy chain variable domain (optionally including a constant region), at least one or two light chain variable domain (optionally including a constant region), or both, comprising the amino acid sequence of BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both, as shown in Table 4 of US 2015/0210769; or a sequence substantially identical thereto.

In yet another embodiment, the anti-PD-1 antibody molecule includes at least one, two, or three complementarity determining regions (CDRs) from a heavy chain variable region and/or a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three CDRs (or collectively all of the CDRs) from a heavy chain variable region comprising an amino acid sequence shown in Table 1 of US 2015/0210769, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-1 antibody molecule includes at least one, two, or three CDRs (or collectively all of the CDRs) from a light chain variable region comprising an amino acid sequence shown in Table 1 of US 2015/0210769, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, three, four, five or six CDRs (or collectively all of the CDRs) from a heavy and light chain variable region comprising an amino acid sequence shown in Table 1 of US 2015/0210769, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-1 antibody molecule includes:
  (a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33, each disclosed in Table 1 of US 2015/0210769;
  (b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each disclosed in Table 1 of US 2015/0210769;
  (c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33, each disclosed in Table 1 of US 2015/0210769; or
  (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each disclosed in Table 1 of US 2015/0210769.

In another embodiment, the anti-PD-1 antibody molecule comprises (i) a heavy chain variable region (VH) comprising a VHCDR1 amino acid sequence chosen from SEQ ID NO: 1, SEQ ID NO: 4, or SEQ ID NO: 224; a VHCDR2 amino acid sequence of SEQ ID NO: 2 or SEQ ID NO: 5; and a VHCDR3 amino acid sequence of SEQ ID NO: 3; and (ii) a light chain variable region (VL) comprising a VLCDR1 amino acid sequence of SEQ ID NO: 10 or SEQ ID NO: 13, a VLCDR2 amino acid sequence of SEQ ID NO: 11 or SEQ ID NO: 14, and a VLCDR3 amino acid sequence of SEQ ID NO: 32 or SEQ ID NO: 33, each disclosed in Table 1 of US 2015/0210769.

In other embodiments, the PD-1 inhibitor is an anti-PD-1 antibody chosen from nivolumab, pembrolizumab, or pidilizumab.

In some embodiments, the anti-PD-1 antibody is nivolumab. Alternative names for nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. In one embodiment, the inhibitor of PD-1 is nivolumab, and having a sequence disclosed herein (or a sequence substantially identical or similar thereto, e.g., a sequence at least 85%, 90%, 95% identical or higher to the sequence specified). In some embodiments, the anti-PD-1 antibody is pembrolizumab. Pembrolizumab (also referred to as lambrolizumab, MK-3475, MK03475, SCH-900475 or KEYTRUDA©; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335.

In one embodiment, the inhibitor of PD-1 is pembrolizumab disclosed in, e.g., U.S. Pat. No. 8,354,509 and WO 2009/114335, and having a sequence disclosed herein (or a sequence substantially identical or similar thereto, e.g., a sequence at least 85%, 90%, 95% identical or higher to the sequence specified).

In some embodiments, the anti-PD-1 antibody is pidilizumab. Pidilizumab (CT-011; Cure Tech) is a humanized IgG1k monoclonal antibody that binds to PD1. Pidilizumab and other humanized anti-PD-1 monoclonal antibodies are disclosed in U.S. Pat. No. 8,747,847 and WO2009/101611.

Other anti-PD1 antibodies include AMP 514 (Amplimmune), among others, e.g., anti-PD1 antibodies disclosed in U.S. Pat. No. 8,609,089, US 2010028330, and/or US 20120114649.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224 (B7-DCIg; Amplimmune; e.g., disclosed in WO2010/027827 and WO2011/066342), is a PD-L2 Fc fusion soluble receptor that blocks the interaction between PD-1 and B7-H1.

In some embodiments, anti-PD-1 antibodies can be used in combination with an IL-15/Rα Fc fusion protein of the invention. There are several anti-PD-1 antibodies including, but not limited to, two currently FDA approved antibodies, pembrolizumab and nivolizumab, as well as those in clinical testing currently, including, but not limited to, tislelizumab, Sym021, REGN2810 (developed by Rengeneron), JNJ-63723283 (developed by J and J), SHR-1210, pidilizumab, AMP-224, MEDI0680, PDR001 and CT-001, as well as others outlined in Liu et al., J. Hemat. & Oncol. (2017) 10:136, the antibodies therein expressly incorporated by reference.

In some embodiments, an IL-15/Rα Fc fusion protein described herein can be used in combination with a PD-1 inhibitor (e.g., an anti-PD-1 antibody). In certain embodiments, an IL-15/Rα Fc fusion protein (e.g., XENP24113, XENP24306, XENP23557, or XENP24045) described herein is administered in combination with an anti-PD-1 antibody.

B. Anti-TIM3 Antibodies

Exemplary non-limiting anti-TIM-3 antibody molecules are disclosed in US 2015/0218274, published on Aug. 6, 2015, entitled "Antibody Molecules to TIM-3 and Uses Thereof," incorporated by reference in its entirety.

In one embodiment, the anti-TIM-3 antibody molecule includes at least one or two heavy chain variable domain (optionally including a constant region), at least one or two light chain variable domain (optionally including a constant region), or both, comprising the amino acid sequence of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences. The anti-TIM-3 antibody molecule, optionally, comprises a leader sequence from a heavy chain, a light chain, or both, as shown in US 2015/0218274; or a sequence substantially identical thereto.

In yet another embodiment, the anti-TIM-3 antibody molecule includes at least one, two, or three complementarity determining regions (CDRs) from a heavy chain variable region and/or a light chain variable region of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In yet another embodiment, the anti-TIM-3 antibody molecule includes at least one, two, or three CDRs (or collectively all of the CDRs) from a heavy chain variable region comprising an amino acid sequence shown in Tables 1-4 of US 2015/0218274, or encoded by a nucleotide sequence shown in Tables 1-4. In one embodiment, one or more of the CDRs (or collectively all of the CDRs) have one, two, three, four, five, six or more changes, e.g., amino acid substitutions or deletions, relative to the amino acid sequence shown in Tables 1-4, or encoded by a nucleotide sequence shown in Table 1-4.

In yet another embodiment, the anti-TIM-3 antibody molecule includes at least one, two, or three CDRs (or collectively all of the CDRs) from a light chain variable region comprising an amino acid sequence shown in Tables 1-4 of US 2015/0218274, or encoded by a nucleotide sequence shown in Tables 1-4. In one embodiment, one or more of the CDRs (or collectively all of the CDRs) have one, two, three, four, five, six or more changes, e.g., amino acid substitutions or deletions, relative to the amino acid sequence shown in Tables 1-4, or encoded by a nucleotide sequence shown in Tables 1-4. In certain embodiments, the anti-TIM-3 antibody molecule includes a substitution in a light chain CDR, e.g., one or more substitutions in a CDR1, CDR2 and/or CDR3 of the light chain.

In another embodiment, the anti-TIM-3 antibody molecule includes at least one, two, three, four, five or six CDRs (or collectively all of the CDRs) from a heavy and light chain variable region comprising an amino acid sequence shown in Tables 1-4 of US 2015/0218274, or encoded by a nucleotide sequence shown in Tables 1-4. In one embodiment, one or more of the CDRs (or collectively all of the CDRs) have one, two, three, four, five, six or more changes, e.g., amino acid substitutions or deletions, relative to the amino acid sequence shown in Tables 1-4, or encoded by a nucleotide sequence shown in Tables 1-4.

In one embodiment, the anti-TIM-3 antibody molecule includes:

(a) a heavy chain variable region (VH) comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274;

(b) a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274;

(c) a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274;

(d) a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274;

(e) a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274; or (f) a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274.

Exemplary anti-TIM-3 antibodies are disclosed in U.S. Pat. No. 8,552,156, WO 2011/155607, EP 2581113 and U.S Publication No.: 2014/044728, and include Sym023 (in clinical development for Symphogen), TSR-22 (in clinical development for Tesaro), LY3321367, in clinical development for Eli Lilly), BGTB-A425 (in clinical development for BeiGene), MBG453 (in clinical development for Novartis) and INCAGN02390 (in clinical development for Incyte).

In some embodiments, anti-TIM-3 antibodies can be used in combination an IL-15/Rα Fc fusion protein of the invention. There are several TIM-3 antibodies in clinical development, including, but not limited to, MBG453 and TSR-022.

In some embodiments, an IL-15/Rα Fc fusion protein described herein can be used in combination with a TIM-3 inhibitor (e.g., an anti-TIM3 antibody). In certain embodiments, an IL-15/Rα Fc fusion protein (e.g., XENP24113, XENP24306, XENP23557, or XENP24045) described herein is administered in combination with an anti-TIM3 antibody.

C. Anti-CTLA4 Antibodies

Exemplary anti-CTLA4 antibodies include tremelimumab (IgG2 monoclonal antibody available from Pfizer, formerly known as ticilimumab, CP-675,206); and ipilimumab (CTLA-4 antibody, also known as MDX-010, CAS No. 477202-00-9). Other exemplary anti-CTLA-4 antibodies are disclosed, e.g., in U.S. Pat. No. 5,811,097.

In one embodiment, the anti-CTLA4 antibody is ipilimumab disclosed in, e.g., U.S. Pat. Nos. 5,811,097, 7,605,238, WO00/32231 and WO97/20574, and having a sequence disclosed herein (or a sequence substantially identical or similar thereto, e.g., a sequence at least 85%, 90%, 95% identical or higher to the sequence specified).

In one embodiment, the anti-CTLA4 antibody is tremelimumab disclosed in, e.g., U.S. Pat. No. 6,682,736 and WO00/37504, and having a sequence disclosed herein (or a sequence substantially identical or similar thereto, e.g., a sequence at least 85%, 90%, 95% identical or higher to the sequence specified).

In some embodiments, anti-CTLA-4 antibodies can be used in combination with an IL-15/Rα Fc fusion protein of the invention. Thus, suitable anti-CTLA-4 antibodies for use in combination therapies as outlined herein include, but are not limited to, one currently FDA approved antibody ipilimumab, and several more in development, including CP-675,206 and AGEN-1884.

In some embodiments, an IL-15/Rα Fc fusion protein described herein can be used in combination with a CTLA-4 inhibitor (e.g., an anti-CTLA-4 antibody). In certain embodiments, an IL-15/Rα Fc fusion protein (e.g., XENP24113, XENP24306, XENP23557, or XENP24045) described herein is administered in combination with an anti-CTLA-4 antibody.

D. Anti-PD-L1 Antibodies

Exemplary non-limiting anti-PD-L1 antibody molecules are disclosed in US 2016/0108123, published on Apr. 21, 2016, entitled "Antibody Molecules to PD-L1 and Uses Thereof," incorporated by reference in its entirety.

In one embodiment, the anti-PD-L1 antibody molecule includes at least one or two heavy chain variable domain (optionally including a constant region), at least one or two light chain variable domain (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 1 of US 2016/0108123, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-L1 antibody molecule includes at least one, two, or three CDRs (or collectively all of the CDRs) from a light chain variable region comprising an amino acid sequence shown in Table 1 of US 2016/0108123, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1 of US 2016/0108123. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-L1 antibody molecule includes:
  (i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 2; and a VHCDR3 amino acid sequence of SEQ ID NO: 3, each disclosed in Table 1 of US 2016/0108123; and
  (ii) a light chain variable region (VL) including a VLCDR1 amino acid sequence of SEQ ID NO: 9, a VLCDR2 amino acid sequence of SEQ ID NO: 10, and a VLCDR3 amino acid sequence of SEQ ID NO: 11, each disclosed in Table 1 of US 2016/0108123.

In another embodiment, the anti-PD-L1 antibody molecule includes:
  (i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 5, and a VHCDR3 amino acid sequence of SEQ ID NO: 3, each disclosed in Table 1 of US 2016/0108123; and
  (ii) a light chain variable region (VL) including a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Table 1 of US 2016/0108123.

In one embodiment, the anti-PD-L1 antibody molecule comprises the VHCDR1 amino acid sequence of SEQ ID NO: 1. In another embodiment, the anti-PD-L1 antibody molecule comprises the VHCDR1 amino acid sequence of SEQ ID NO: 4. In yet another embodiment, the anti-PD-L1 antibody molecule comprises the VHCDR1 amino acid sequence of SEQ ID NO: 195, each disclosed in Table 1 of US 2016/0108123.

In some embodiments, the PD-L1 inhibitor is an antibody molecule. In some embodiments, the anti-PD-L1 inhibitor is chosen from YW243.55.570, MPDL3280A, MEDI-4736, MSB-0010718C, MDX-1105, atezolizumab, durbalumab, avelumab, or BMS936559.

In some embodiments, the anti-PD-L1 antibody is atezolizumab. Atezolizumab (also referred to as MPDL3280A and Atezo®; Roche) is a monoclonal antibody that binds to PD-L1. Atezolizumab and other humanized anti-PD-L1 antibodies are disclosed in U.S. Pat. No. 8,217,149, and having a sequence disclosed herein (or a sequence substantially identical or similar thereto, e.g., a sequence at least 85%, 90%, 95% identical or higher to the sequence specified).

In some embodiments, the anti-PD-L1 antibody is avelumab. Avelumab (also referred to as A09-246-2; Merck Serono) is a monoclonal antibody that binds to PD-L1. Avelumab and other humanized anti-PD-L1 antibodies are disclosed in U.S. Pat. No. 9,324,298 and WO2013/079174, and having a sequence disclosed herein (or a sequence substantially identical or similar thereto, e.g., a sequence at least 85%, 90%, 95% identical or higher to the sequence specified).

In some embodiments, the anti-PD-L1 antibody is durvalumab. Durvalumab (also referred to as MEDI4736; AstraZeneca) is a monoclonal antibody that binds to PD-L1. Durvalumab and other humanized anti-PD-L1 antibodies are disclosed in U.S. Pat. No. 8,779,108, and having a sequence disclosed herein (or a sequence substantially identical or similar thereto, e.g., a sequence at least 85%, 90%, 95% identical or higher to the sequence specified).

In some embodiments, the anti-PD-L1 antibody is BMS-936559. BMS-936559 (also referred to as MDX-1105; BMS) is a monoclonal antibody that binds to PD-L1. BMS-936559 and other humanized anti-PD-L1 antibodies are disclosed in U.S. Pat. No. 7,943,743 and WO2007005874, and having a sequence disclosed herein (or a sequence substantially identical or similar thereto, e.g., a sequence at least 85%, 90%, 95% identical or higher to the sequence specified).

In some embodiments, anti-PD-L1 antibodies can be used in combination with an IL-15/Rα Fc fusion protein of the invention. There are several anti-PD-L1 antibodies including three currently FDA approved antibodies, atezolizumab, avelumab, durvalumab, as well as those in clinical testing currently, including, but not limited to, LY33000054 and CS1001, as well as others outlined in Liu et al., J. Hemat. & Oncol. (2017) 10:136, the antibodies therein expressly incorporated by reference.

In some embodiments, an IL-15/Rα heterodimeric fusion protein described herein can be used in combination with a PD-L1 or PD-L2 inhibitor (e.g., an anti-PD-L1 antibody).

E. Anti-TIGIT Antibodies

In some embodiments, the anti-TIGIT antibody is OMP-313M32. OMP-313M32 (OncoMed Pharmaceuticals) is a monoclonal antibody that binds to TIGIT. OMP-313M32 and other humanized anti-TIGIT antibodies are disclosed in US20160376365 and WO2016191643, and having a sequence disclosed herein (or a sequence substantially identical or similar thereto, e.g., a sequence at least 85%, 90%, 95% identical or higher to the sequence specified).

In some embodiments, the anti-TIGIT antibody is BMS-986207. BMS-986207 (also referred to as ONO-4686; Bristol-Myers Squibb) is a monoclonal antibody that binds to TIGIT. BMS-986207 and other humanized anti-TIGIT antibodies are disclosed in US20160176963 and WO2016106302, and having a sequence disclosed herein (or a sequence substantially identical or similar thereto, e.g., a sequence at least 85%, 90%, 95% identical or higher to the sequence specified).

In some embodiments, the anti-TIGIT antibody is MTIG7192. MTIG7192 (Genentech) is a monoclonal antibody that binds to TIGIT. MTIG7192 and other humanized anti-TIGIT antibodies are disclosed in US2017088613, WO2017053748, and WO2016011264, and having a sequence disclosed herein (or a sequence substantially identical or similar thereto, e.g., a sequence at least 85%, 90%, 95% identical or higher to the sequence specified).

In some embodiments, anti-TIGIT antibodies can be used in combination with an IL-15/Rα Fc fusion protein of the invention. There are several TIGIT antibodies in clinical development, BMS-986207 (in clinical development with BMS), OMP-313M32 (in clinical development with OncoMed), MTIG7192A (in clinical development with Genentech), and AB154 (in clinical development with Arcus Biosciences).

In some embodiments, an IL-15/Rα Fc fusion protein described herein can be used in combination with a TIGIT inhibitor (e.g., an anti-TIGIT antibody). In certain embodiments, an IL-15/Rα Fc fusion protein (e.g., XENP24113, XENP24306, XENP23557, or XENP24045) described herein is administered in combination with an anti-TIGIT antibody.

In some embodiments, anti-TIGIT antibodies can be used in combination with XENP24306, including, but not limited to, BMS-986207 (in clinical development with BMS), OMP-313M32 (in clinical development with OncoMed), MTIG7192A (in clinical development with Genentech), and AB154 (in clinical development with Arcus Biosciences).

F. Anti-LAG3 Antibodies

Exemplary non-limiting anti-LAG-3 antibody molecules are disclosed in US 2015/0259420 published on Sep. 17, 2015, entitled "Antibody Molecules to LAG-3 and Uses Thereof," incorporated by reference in its entirety.

In one embodiment, the anti-LAG-3 antibody molecule includes at least one or two heavy chain variable domain (optionally including a constant region), at least one or two light chain variable domain (optionally including a constant region), or both, comprising the amino acid sequence of any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three complementarity determining regions (CDRs) from a heavy chain variable region and/or a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three CDRs (or collectively all of the CDRs) from a heavy chain variable region comprising an amino acid sequence shown in Table 1 of US 2015/0259420, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-LAG-3 antibody molecule includes at least one, two, or three CDRs (or collectively all of the CDRs) from a light chain variable region comprising an amino acid sequence shown in Table 1 of US 2015/0259420, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-L1 antibody molecule includes a substitution in a light chain CDR, e.g., one or more substitutions in a CDR1, CDR2 and/or CDR3 of the light chain.

In another embodiment, the anti-LAG-3 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1 of US 2015/0259420. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-LAG-3 antibody molecule includes:
 (i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3, each disclosed in Table 1 of US 2015/0259420; and
 (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 12, each disclosed in Table 1 of US 2015/0259420.

In another embodiment, the anti-LAG-3 antibody molecule includes:
 (i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 5, and a VHCDR3 amino acid sequence of SEQ ID NO: 3, each disclosed in Table 1 of US 2015/0259420; and
 (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 15, each disclosed in Table 1 of US 2015/0259420.

In one embodiment, the anti-LAG-3 antibody molecule comprises the VHCDR1 amino acid sequence of SEQ ID NO: 1. In another embodiment, the anti-LAG-3 antibody molecule comprises the VHCDR1 amino acid sequence of SEQ ID NO: 4. In yet another embodiment, the anti-LAG-3 antibody molecule comprises the VHCDR1 amino acid sequence of SEQ ID NO: 286, each disclosed in Table 1 of US 2015/0259420.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

In some embodiments, the anti-LAG3 antibody is LAG525. LAG525 (also referred to as IMP701; Novartis) is a monoclonal antibody that binds to LAG3. LAG525 and other humanized anti-LAG3 antibodies are disclosed in U.S. Pat. No. 9,244,059 and WO2008132601, and having a sequence disclosed herein (or a sequence substantially identical or similar thereto, e.g., a sequence at least 85%, 90%, 95% identical or higher to the sequence specified).

Other exemplary anti-LAG3 antibodies are disclosed, e.g., in US2011150892 and US2018066054.

In some embodiments, anti-LAG-3 antibodies can be used in combination with an IL-15/Rα Fc fusion protein of the invention. There are several anti-LAG-3 antibodies in clinical development including REGN3767, by Regeneron, TSR-033 (Tesaro), BMS-986016 (BMS) and Sym022 (Symphogen).

In some embodiments, an IL-15/Rα Fc fusion protein described herein can be used in combination with a LAG3 inhibitor (e.g., an anti-LAG3 antibody). In certain embodiments, an IL-15/Rα Fc fusion protein (e.g., XENP24113, XENP24306, XENP23557, or XENP24045) described herein is administered in combination with an anti-LAG3 antibody.

In some embodiments, anti-LAG-3 antibodies can be used in combination with XENP24306, including, but not limited to, REGN3767, by Regeneron, TSR-033 (Tesaro), BMS-986016 (BMS) and Sym022 (Symphogen).

XII. Combination Therapy

In some aspects, the IL-15/Rα Fc fusion proteins described herein is administered in combination with another therapeutic agent. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The IL-15/Rα Fc fusion protein (e.g., XENP24113, XENP24306, XENP23557, or XENP24045) described herein and the at least one additional therapeutic agent can be administered simultaneously, in the same or in separate compositions, or sequentially. For sequential administration, the IL-15/Rα Fc fusion proteins (e.g., XENP24113, XENP24306, XENP23557, or XENP24045) described herein can be administered first, and the additional agent can be administered second, or the order of administration can be reversed.

The IL-15/Rα Fc fusion protein (e.g., XENP24113, XENP24306, XENP23557, or XENP24045) described herein and/or other therapeutic agents, procedures or modalities can be administered during periods of active disorder, or during a period of remission or less active disease. The IL-15/Rα Fc fusion protein (e.g., XENP24113, XENP24306, XENP23557, or XENP24045) can be administered before the other treatment, concurrently with the treatment, post-treatment, or during remission of the disorder.

When administered in combination, the IL-15/Rα Fc fusion protein (e.g., XENP24113, XENP24306, XENP23557, or XENP24045) and the additional agent (e.g., second or third agent), or all, can be administered in an amount or dose that is lower or the same than the amount or dosage of each agent used individually, e.g., as a monotherapy. In some embodiments, the administered amount or dosage of IL-15/Rα Fc fusion protein (e.g., XENP24113, XENP24306, XENP23557, or XENP24045), the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the IL-15/Rα Fc fusion protein (e.g., XENP24113, XENP24306, XENP23557, or XENP24045), the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In further aspects, an IL-15/Rα Fc fusion protein (e.g., XENP24113, XENP24306, XENP23557, or XENP24045) described herein may be used in a treatment regimen in combination with chemotherapy, radiation, immunosuppressive agents, such as cyclosporin, azathioprine, methotrexate, mycophenolate, and FK506, antibodies directed against checkpoint inhibitors, or other immunoablative agents such as CAMPATH, other antibody therapies, cytoxan, fludarabine, cyclosporin, FK506, rapamycin, mycophenolic acid, steroids, FR90165, cytokines, and irradiation. peptide vaccine, such as that described in Izumoto et al. 2008 J Neurosurg 108:963-971.

In certain instances, compounds of the present invention are combined with other therapeutic agents, such as other anti-cancer agents, anti-allergic agents, anti-nausea agents (or anti-emetics), pain relievers, cytoprotective agents, and combinations thereof.

In one embodiment, an IL-15/Rα Fc fusion protein (e.g., XENP24113, XENP24306, XENP23557, or XENP24045) described herein can be used in combination with a chemotherapeutic agent. Exemplary chemotherapeutic agents include an anthracycline (e.g., idarubicin, daunorubicin, doxorubicin (e.g., liposomal doxorubicin)), a anthracenedione derivative (e.g., mitoxantrone), a vinca alkaloid (e.g., vinblastine, vincristine, vindesine, vinorelbine), an alkylating agent (e.g., cyclophosphamide, dacarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, cytarabine, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide), a kinase inhibitor such as ibrutinib (e.g., Imbruvica), a corticosteroid (e.g., dexamethasone, prednisone), and CVP (a combination of cyclophosphamide, vincristine, and prednisone), CHOP (a combination of cyclophosphamide, hydroxydaunorubicin, Oncovin® (vincristine), and prednisone) with or without etoposide (e.g., VP-16), a combination of cyclophosphamide and pentostatin, a combination of chlorambucil and prednisone, a combination of fludarabine and cyclophosphamide, or another agent such as mechlorethamine hydrochloride (e.g. Mustargen), doxorubicin (Adriamycin®), methotrexate, oxaliplatin, or cytarabine (ara-C).

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU@), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

XIII. Treatments

Once made, the compositions of the invention find use in a number of oncology applications, by treating cancer, generally by promoting T cell activation (e.g., T cells are no longer suppressed) with the binding of the heterodimeric Fc fusion proteins of the invention.

Accordingly, the heterodimeric compositions of the invention find use in the treatment of these cancers including but not limited to metastatic cancers.

A. Heterodimeric Protein Compositions for In Vivo Administration

Formulations of the antibodies used in accordance with the present invention are prepared for storage by mixing an antibody having the desired degree of purity with optional pharmaceutically acceptable carriers, excipients or stabilizers (as generally outlined in Remington's Pharmaceutical Sciences 16th edition, Osol, A. Ed. [1980]), in the form of lyophilized formulations or aqueous solutions. Acceptable carriers, buffers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

B. Administrative Modalities

The heterodimeric proteins and chemotherapeutic agents of the invention are administered to a subject, in accord with known methods, such as intravenous administration as a bolus or by continuous infusion over a period of time.

C. Treatment Modalities

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (e.g., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the protein or protein portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the heterodimeric proteins used in the present invention depend on the disease or condition to be treated and may be determined by the persons skilled in the art.

An exemplary, non-limiting range for a therapeutically effective amount of an heterodimeric protein used in the present invention is about 0.1-100 mg/kg.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

EXAMPLES

Examples are provided below to illustrate the present invention. These examples are not meant to constrain the present invention to any particular application or theory of operation. For all constant region positions discussed in the present invention, numbering is according to the EU index as in Kabat (Kabat et al., 1991, Sequences of Proteins of Immunological Interest, 5th Ed., United States Public Health Service, National Institutes of Health, Bethesda, entirely incorporated by reference). Those skilled in the art of antibodies will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

General and specific scientific techniques are outlined in US Publications 2015/0307629, 2014/0288275 and WO2014/145806, all of which are expressly incorporated by reference in their entirety and particularly for the techniques outlined therein.

XIV. Example 1: IL-15/IL-15Rα(sushi) Fc Fusion Proteins

In order to address the short half-life of IL-15/IL-15Rα heterodimers, we generated the IL-15/IL-15Rα(sushi) complex as a Fc fusion (hereon referred to as IL-15/Rα-Fc fusion proteins) with the goal of facilitating production and promoting FcRn-mediated recycling of the complex and prolonging half-life.

A. 1A: Engineering IL-15/Rα-Fc Fusion Proteins

Plasmids coding for IL-15 or IL-15Rα sushi domain were constructed by standard gene synthesis, followed by subcloning into a pTT5 expression vector containing Fc fusion partners (e.g., constant regions as depicted in FIGS. 8A-8D). Cartoon schematics of illustrative IL-15/Rα-Fc fusion protein formats are depicted in FIGS. 9A-9G.

The IL-15Rα heterodimeric Fc fusion or "IL-15/Rα-heteroFc" format comprises IL-15 recombinantly fused to one side of a heterodimeric Fc and IL-15Rα sushi domain recombinantly fused to the other side of the heterodimeric Fc (FIG. 9A). The IL-15 and IL-15Rα may have a variable length linker (see FIG. 7) between their respective C-terminus and the N-terminus of the Fc region. Illustrative proteins of this format include XENP20818 and XENP21475, sequences for which are depicted in FIG. 10 (see also Table 2). Sequences for additional proteins of this format including XENP20819, XENP21471, XENP21472, XENP21473, XENP21474, XENP21476, XENP21477 are depicted in WO2018071919 in FIGS. 104A-104D, respectively and as SEQ ID NOS: 418-423, 424-429, 430-435, 436-441, 442-447, 454-459, and 460-465, respectively, herein incorporated by reference.

TABLE 2

| XENP | IL-15-Fc Linker | IL-15Rα (sushi)-Fc Linker |
|---|---|---|
| 20818 | $(GGGGS)_1$ (SEQ ID NO: 27) | $(GGGGS)_1$ (SEQ ID NO: 27) |
| 20819 | $(GGGGS)_1$ (SEQ ID NO: 27) | $(GGGGS)_4$ (SEQ ID NO: 29) |
| 21471 | NONE | $(GGGGS)_1$ (SEQ ID NO: 27) |
| 21472 | $(GGGGS)_1$ (SEQ ID NO: 27) | NONE |

TABLE 2-continued

| XENP | IL-15-Fc Linker | IL-15Rα (sushi)-Fc Linker |
|---|---|---|
| 21473 | (GGGGS)$_1$ (SEQ ID NO: 27) | (GGGGS)$_3$ (SEQ ID NO: 30) |
| 21474 | NONE | (GGGGS)$_4$ (SEQ ID NO: 29) |
| 21475 | NONE | NONE |
| 21476 | (GGGGS)$_2$ (SEQ ID NO: 28) | (GGGGS)$_2$ (SEQ ID NO: 28) |
| 21477 | (GGGGS)$_2$ (SEQ ID NO: 28) | (GGGGS)$_4$ (SEQ ID NO: 29) |

The single-chain IL-15/Rα-Fc fusion or "scIL-15/Rα-Fc" format comprises IL-15Rα sushi domain fused to IL-15 by a variable length linker (termed a "single-chain" IL-15/IL-15Rα complex or "scIL-15/Rα") which is then fused to the N-terminus of a heterodimeric Fc-region, with the other side of the molecule being a "Fc-only" or "empty-Fc" heterodimeric Fc (FIG. 9B). Sequences for illustrative linkers are depicted in FIG. 7. An illustrative protein of this format is XENP21478, sequences for which are depicted in FIG. 11 (also see Table 3). Sequences for additional proteins of this format including XENP21993, XENP21994, XENP21995, XENP23174, XENP24477, and XENP24480 are depicted in WO2018071919 in FIGS. 104G, 104H, 104AG, 104AU, and 104AV, respectively and as SEQ ID NOS: 514-518, 519-523, 524-528, 849-853, 1063-1067, and 1078-1082, respectively, herein incorporated by reference.

TABLE 3

| XENP | Linker between IL-15 and IL-15Rα |
|---|---|
| 21478 | (GGGGS)$_6$ (SEQ ID NO: 31) |
| 21993 | (GGGGS)$_5$ (SEQ ID NO: 32) |
| 21994 | (GGGGS)$_4$ (SEQ ID NO: 29) |
| 21995 | (GGGGS)$_3$ (SEQ ID NO: 30) |
| 23174 | (GKPGS)$_6$ (SEQ ID NO: 33) |
| 23175 | (GKPGS)$_5$ (SEQ ID NO: 34) |
| 24477 | (GGGGS)$_7$ (SEQ ID NO: 35) |
| 24480 | 30AA-linker |

The non-covalent IL-15/Rα-Fc fusion or "ncIL-15/Rα-Fc" format comprises IL-15Rα sushi domain fused to a heterodimeric Fc region, while IL-15 is transfected separately so that a non-covalent IL-15/IL-15Rα complex is formed, with the other side of the molecule being a "Fc-only" or "empty-Fc" heterodimeric Fc (FIG. 9C). Illustrative proteins of this format include XENP21479, XENP22366 and XENP24348, sequences for which are depicted in FIGS. 12A-12B.

The bivalent non-covalent IL-15/Rα-Fc fusion or "bivalent ncIL-15/Rα-Fc" format (FIG. 9D) comprises IL-15Rα (sushi) fused to the N-terminus of a homodimeric Fc region, while IL-15 is transfected separately so that a non-covalent IL-15/Rα complex is formed. An illustrative protein of this format is XENP21978, sequences for which are depicted in FIG. 13. Sequences for additional proteins of this format including XENP21979 are depicted in WO2018071919 in FIG. 104E and as SEQ ID NOS: 480-483, herein incorporated by reference.

The bivalent single-chain IL-15/Rα-Fc fusion or "bivalent scIL-15/Rα-Fc" format (FIG. 9E) comprises IL-15 fused to IL-15Rα(sushi) by a variable length linker (termed a "single-chain" IL-15/IL-15Rα(sushi) complex or "scIL-15/Rα") which is then fused to the N-terminus of a homodimeric Fc-region. Sequences for illustrative linkers are depicted in FIG. 7. Sequences for an illustrative protein of this format are depicted in FIG. 14.

The Fc-non-covalent IL-15/Rα fusion or "Fc-ncIL-15/Rα" format (FIG. 9E) comprises IL-15Rα(sushi) fused to the C-terminus of a heterodimeric Fc region, while IL-15 is transfected separately so that a non-covalent IL-15/Rα complex is formed, with the other side of the molecule being "Fc-only" or "empty Fc". An illustrative protein of this format is XENP22637, sequences for which are depicted in FIG. 15. Sequences for additional proteins of this format including XENP22638 are depicted in WO2018071919 in FIG. 104T and as SEQ ID NOS: 668-672, herein incorporated by reference.

The Fc-single-chain IL-15/Rα fusion or "Fc-scIL-15/Rα" format (FIG. 9G) comprises IL-15 fused to IL-15Rα(sushi) by a variable length linker ("scIL-15/Rα") which is then fused to the C-terminus of a heterodimeric Fc region, with the other side of the molecule being "Fc-only" or "empty Fc". Sequences for illustrative linkers are depicted in FIG. 7. Sequences for an illustrative protein of this format are depicted in FIG. 16.

Proteins were produced by transient transfection in HEK293E cells and were purified by a two-step purification process comprising protein A chromatography (GE Healthcare) and anion exchange chromatography (HiTrapQ 5 mL column with a 5-40% gradient of 50 mM Tris pH 8.5 and 50 mM Tris pH 8.5 with 1 M NaCl).

B. 1B: Characterization of IL-15/Rα-Fc Fusion Proteins for Purity and Homogeneity IL-15/Rα-Fc fusion proteins produced in several of the formats as described above were characterized by size-exclusion chromatography (SEC) and capillary isoelectric focusing (CEF) for purity and homogeneity as generally described below.

The proteins were analyzed using SEC to measure their size (i.e. hydrodynamic volume) and determine the native-like behavior of the purified samples. The analysis was performed on an Agilent 1200 high-performance liquid chromatography (HPLC) system. Samples were injected onto a Superdex™ 200 10/300 GL column (GE Healthcare Life Sciences) at 1.0 mL/min using 1×PBS, pH 7.4 as the mobile phase at 4° C. for 25 minutes with UV detection wavelength at 280 nM. Analysis was performed using Agilent OpenLab Chromatography Data System (CDS) ChemStation Edition AIC version C.01.07. Chromatograms for selected IL-15/Rα-Fc fusion proteins are shown in FIGS. 17B, 18B, and 19B.

The proteins were analyzed electrophoretically via CEF using LabChip GXII Touch HT (PerkinElmer, Waltham, Mass.) using Protein Express Assay LabChip and Protein Express Assay Reagent Kit carried out using the manufacturer's instructions. Samples were run in duplicate, one under reducing (with dithiothreitol) and the other under non-reducing conditions. Gel images for selected IL-15/Rα-Fc fusion proteins are shown in FIGS. 17C, 18C, and 19C.

The symmetry of the peaks and the relatively low populations of other species for each of the fusion proteins indicate that the various formats were robust.

C. 1C: Characterization of IL-15/Rα-Fc Fusion Proteins for Affinity and Stability Affinity screens of IL-15/Rα-Fc fusion proteins were performed using Octet, a BioLayer Interferometry (BLI)-based method. Experimental steps for Octet generally included the following: Immobilization (capture of ligand or test article onto a biosensor); Association (dipping of ligand- or test article-coated biosensors into wells containing serial dilutions of the corresponding test article or ligand); and Dissociation (returning of biosensors to well containing buffer) in order to determine the affinity of the test articles. A reference well containing buffer alone was also included in the method for background correction during data processing. In particular, anti-human Fc (AHC) biosensors were used to capture the test articles and then dipped into multiple concentration of IL-2Rβ (R&D Systems, Minneapolis, Minn.) for KD determination. The affinity results and corresponding sensorgrams are depicted in FIGS. 17D, 18D, and 19D. Each of the three constructs showed high affinity binding (3-8 nM) for IL-1RP.

Stability of IL-15/Rα-Fc fusion proteins were evaluated using Differential Scanning Fluorimetry (DSF). DSF experiments were performed using a Bio-Rad CFX Connect Real-Time PCR Detection System. Proteins were mixed with SYPRO Orange fluorescent dye and diluted to 0.2 mg/mL in PBS. The final concentration of SYPRO Orange was 10×. After an initial 10 minute incubation period at 25° C., proteins were heated from 25 to 95° C. using a heating rate of 1° C./min. A fluorescence measurement was taken every 30 sec. Melting temperatures (Tm) were calculated using the instrument software. The stability results and corresponding melting curves are depicted in FIGS. 17E, 18E, and 19E. Each of the constructs showed favorable overall stability with Tm~68° C.

D. 1D: Activity of IL-15/Rα-Fc Fusion Proteins in Cell Proliferation Assays

IL-15/Rα-Fc fusion proteins in the various formats as described above were tested in a cell proliferation assay. Human PBMCs were treated with the test articles at the indicated concentrations. 4 days after treatment, the PBMCs were stained with anti-CD8-FITC (RPA-T8), anti-CD4-PerCP/Cy5.5 (OKT4), anti-CD27-PE (M-T271), anti-CD56-BV421 (5.1H11), anti-CD16-BV421 (3G8), and anti-CD45RA-BV605 (Hi100) to gate for the following cell types: CD4+ T cells, CD8+ T cells, and NK cells (CD56+/CD16+). Ki67 is a protein strictly associated with cell proliferation, and staining for intracellular Ki67 was performed using anti-Ki67-APC (Ki-67) and Foxp3/Transcription Factor Staining Buffer Set (Thermo Fisher Scientific, Waltham, Mass.). The percentage of Ki67 on the above cell types was measured using FACS (depicted in FIGS. 20A-20C and FIGS. 21A-21C).

The various IL-15/Rα-Fc fusion proteins induced strong proliferation of CD8+ T cells and NK cells. Notably, differences in proliferative activity were dependent on the linker length on the IL-15-Fc side. In particular, constructs having no linker (hinge only), including XENP21471, XENP21474, and XENP21475, demonstrated weaker proliferative activity.

E. 1E: Activity of IL-15/Rα-Fc Fusion Proteins in an SEB-Stimulated PBMC Assay

As described above, IL-15/Rα heterodimers can potently activate T cells. IL-15/Rα-Fc fusion proteins in the various formats as described above were tested in an SEB-stimulated PBMC assay. Staphylococcal Enterotoxin B (SEB) is a superantigen that causes T cell activation and proliferation in a manner similar to that achieved by activation via the T cell receptor (TCR). Stimulating human PBMC with SEB is a common method for assaying T cell activation and proliferation.

Human PBMCs from multiple donors were stimulated with 10 ng/mL of SEB for 72 hours in combination with 20 µg/mL of various IL-15/Rα-Fc fusion proteins or controls (PBS, an isotype control, and a bivalent anti-PD-1 antibody). After treatment, supernatant was collected and assayed for IL-2, data for which is depicted in FIG. 22. The data clearly show that the IL-15/Rα-Fc fusion proteins enhanced IL-2 secretion more than PBS and isotype control. Notably, a number of the IL-15/Rα-Fc fusion proteins have activity equivalent to or better than that of the anti-PD-1 antibody.

F. 1F: IL-15/Rα-Fc Fusion Proteins Enhance Engraftment and Disease Activity in Human PBMC-Engrafted NSG Mice IL-15/Rα-Fc fusion protein XENP20818 was evaluated in a Graft-versus-Host Disease (GVHD) model conducted in female NSG (NOD-SCID-gamma) immunodeficient mice. When the NSG mice were injected with human PBMCs, the human PBMCs developed an autoimmune response against mouse cells. Treatment of NSG mice injected with human PBMCs followed with IL-15/Rα-Fc fusion proteins enhances proliferation of the engrafted T cells.

10 million human PBMCs were engrafted into NSG mice via IV-OSP on Day 0 followed by dosing of XENP20818 (1 mg/kg on Day 1 and then weekly thereafter) and recombinant IL-15 (Biolegend; 0.17 mg/kg on Day 1 and then weekly thereafter). The survival curve is shown in FIG. 23. The data show that mice receiving the IL-15/Rα-Fc fusion protein demonstrated rapid morbidity and mortality (all dead by Day 10) compared with mice receiving recombinant IL-15 (all alive by Day 14). This is likely due to the expected longer half-life of the IL-15/Rα-Fc fusion protein.

In another experiment, 10 million human PBMCs were engrafted in NSG mice via IV-OSP on Day 0 followed by dosing of XENP20818 (1 mg/kg, 0.3 mg/kg, 0.1 mg/kg, or 0.03 mg/kg on Day 1 and then weekly thereafter) or PBS. Control groups in which mice were not engrafted with PBMCs were included to investigate any effect of XENP20818 on wild-type NSG mice. Blood was collected on Day 7 to measure IFNγ, data for which is depicted in FIG. 24, and to measure CD4+ T cell, CD8+ T cell, and CD45+ cell counts, data for which are depicted in FIGS. 25A-25C. The data shows a clear dose response for XENP20818.

XV. Example 2: IL-15/Rα-Fc Heterodimeric Fusion Proteins with Engineered Disulfide Bonds To further improve stability and prolong the half-life of IL-15/Rα-Fc fusion proteins, we engineered disulfide bonds into the IL-15/Rα interface.

A. 2A: Engineering and Characterization of IL-15/Rα Heterodimers with Engineered Disulfide Bonds By examining the crystal structure of the IL-15/Rα complex, as well as by modeling using Molecular Operating Environment (MOE; Chemical Computing Group, Montreal, Quebec, Canada) software, it was predicted that residues at the IL-15/Rα interface may be substituted with cysteine in order to form covalent disulfide bonds, as depicted in FIG. 26.

Plasmids coding for IL-15 or IL-15Rα(sushi) were constructed by standard gene synthesis, followed by subcloning into a pTT5 expression vector. The IL-15Rα(sushi) chain included a C-terminal polyhistidine tag. Residues identified as described above were substituted with cysteines by standard mutagenesis techniques. Additionally, up to three amino acids following the sushi domain in IL-15Rα were added to the C-terminus of IL-15Rα(sushi) as a scaffold for engineering cysteines (illustrative sequences for which are depicted in FIG. 27). Sequences for illustrative IL-15 and IL-15Rα(sushi) variants engineered with cysteines are respectively depicted in FIGS. 28 and 29, and the sequence listing.

Cartoon schematics of IL-15/Rα heterodimers with and without engineered disulfides are depicted in FIGS. 30A-30C.

Sequences for an illustrative ncIL-15/Rα heterodimer XENP21996 is depicted in FIG. 31. Sequences for illustrative dsIL-15/Rα heterodimers XENP22004, XENP22005, XENP22006, XENP22008, and XENP22494 are depicted in FIG. 32. Sequences for an illustrative scIL-15/Rα heterodimer XENP22049 are depicted in FIG. 33.

"Wild-type" IL-15/Rα heterodimers, with additional residues at the C-terminus but without engineered cysteines, were generated as controls. Sequences for additional proteins of this format including XENP22001, XENP22002, and XENP22003 are depicted in WO2018/071919, in FIGS. 104H and 104I, respectively and as SEQ ID NOS: 531-532, 533-534, and 535-536, respectively, herein incorporated by reference.

Proteins were produced by transient transfection in HEK293E cells and purified by Ni-NTA chromatography.

After the proteins were purified, they were characterized by capillary isoelectric focusing (CEF) for purity and homogeneity as generally described in Example 1B, gel images for which are depicted in FIGS. 34-35. The proteins were then screened for stability using DSF as generally described in Example 1C, data for which are depicted in FIGS. 36-38. Finally, the proteins were screened for binding to IL-2Rβ by Octet as generally described in Example 1C, data for which is depicted in FIG. 38.

Many of the disulfide bonds were correctly formed as indicated by denaturing non-reducing CEF, where the larger molecular weight of the covalent complex can be seen when compared to the controls without engineered disulfide bonds (FIGS. 34-35). The disulfide bonded IL-15/Rα heterodimers had increased thermostability of up to +13° C. (FIG. 38). Binding to IL-2Rβ was not affected by the inclusion of engineered disulfide bonds (FIG. 38). Favorite disulfide bonded pairs were XENP22005, XENP22006, XENP22008, and XENP22494 and were constructed as Fc fusion proteins as described below.

B. 2B: Characterization of IL-15/Rα-Fc Fusion Proteins with Engineered Disulfide Bonds Plasmids coding for IL-15 or IL-15Rα sushi domain with the above-described mutations were subcloned into a pTT5 expression vector containing Fc fusion partners (e.g., constant regions as depicted in FIGS. 8A-8D). Cartoon schematics of IL-15/Rα-Fc fusion proteins with engineered disulfide bonds are depicted in FIGS. 39A-39D.

Disulfide-bonded IL-15/Rα heterodimeric Fc fusion or "dsIL-15/Rα-heteroFc" (FIG. 39A) is the same as "IL-15/Rα-heteroFc", but wherein IL-15Rα(sushi) and IL-15 are further covalently linked as a result of engineered cysteines. Illustrative proteins of this format include XENP22013, XENP22014, XENP22015, and XENP22017, sequences for which are depicted in FIGS. 40A-40B.

Disulfide-bonded IL-15/Rα Fc fusion or "dsIL-15/Rα-Fc" (FIG. 39B) is the same as "ncIL-15/Rα-Fc", but wherein IL-15Rα(sushi) and IL-15 are further covalently linked as a result of engineered cysteines. Illustrative proteins of this format include XENP22357, XENP22358, XENP22359, XENP22684, and XENP22361, sequences for which are depicted in FIGS. 41A-41B. Sequences for additional proteins of this format including XENP22360, XENP22362, XENP22363, XENP22364, XENP22365, XENP22366 are depicted in WO2018071919 in FIGS. 104O, 104P, 104Q, and 104R, respectively and as SEQ ID NOS: 612-616, 622-626, 627-631, 632-636, 637-641, and 642-646, respectively, herein incorporated by reference.

Bivalent disulfide-bonded IL-15/Rα-Fc or "bivalent dsIL-15/Rα-Fc" (FIG. 39C) is the same as "bivalent ncIL-15/Rα-Fc", but wherein IL-15Rα(sushi) and IL-15 are further covalently linked as a result of engineered cysteines. Illustrative proteins of this format include XENP22634, XENP22635, and XENP22636, sequences for which are depicted in FIG. 42. Sequences for additional proteins of this format including XENP22687 are WO2018071919 in FIG. 104V and as SEQ ID NOS: 685-688, herein incorporated by reference.

Fc-disulfide-bonded IL-15/Rα fusion or "Fc-dsIL-15/Rα" (FIG. 39D) is the same as "Fc-ncIL-15/Rα", but wherein IL-15Rα(sushi) and IL-15 are further covalently linked as a result of engineered cysteines. An illustrative proteins of this format include XENP22639 and XENP22640, sequences for which are depicted in FIG. 43.

"Wild-type" IL-15/Rα-Fc fusion proteins, with additional residues at the C-terminus but without engineered cysteines, were generated as controls. Sequences for these control IL-15/Rα-Fc fusion proteins including XENP21988, XENP21989, XENP21990, XENP21991, XENP21992, XENP22354, and XENP22355 are depicted in WO2018071919 in FIGS. 104F, 104G, 104L, and 104M and as SEQ ID NOS: 484-489, 490-495, 496-501, 502-507, 508-513, 582-586, and 587-591, respectively, herein incorporated by reference.

Proteins were produced by transient transfection in HEK293E cells and were purified by a two-step purification process comprising protein A chromatography (GE Healthcare) and anion exchange chromatography (HiTrapQ 5 mL column with a 5-40% gradient of 50 mM Tris pH 8.5 and 50 mM Tris pH 8.5 with 1 M NaCl).

After the proteins were purified, they were characterized by capillary isoelectric focusing (CEF) for purity and homogeneity as generally described in Example 1B. As above, many of the disulfide bonds were correctly formed as indicated by denaturing non-reducing CEF, where the larger molecular weight of the covalent complex can be seen when compared to the controls without engineered disulfide bonds (FIG. 44).

The proteins were then tested in a cell proliferation assay. IL-15/Rα-Fc fusion proteins (with or without engineered disulfide bonds) or controls were incubated with PBMCs for 4 days. Following incubation, PBMCs were stained with anti-CD4-PerCP/Cγ5.5 (RPA-T4), anti-CD8-FITC (RPA-T8), anti-CD45RA-BV510 (HI100), anti-CD16-BV421 (3G8), anti-CD56-BV421 (HCD56), anti-CD27-PE (0323), and anti-Ki67-APC (Ki-67) to mark various cell populations and analyzed by FACS as generally described in Example 1D. Proliferation of NK cells, CD4+ T cells, and CD8+ T cells as indicated by Ki67 expression are depicted in FIGS. 45A-45C. Each of the IL-15/Rα-Fc fusion proteins and the IL-15 control induced strong proliferation of NK cells, CD8+ T cells, and CD4+ T cells.

XVI. Example 3: IL-15/Rα-Fc Fusion Proteins Engineered for Lower Potency and Increased PK and Half-Life In order to further improve PK and prolong half-life, we reasoned that decreasing the potency of IL-15 would decrease the antigen sink, and thus, increase the half-life.

A. 3A: Engineering and Production of Variant IL-15/Rα-Fc Fusion Proteins

By examining the crystal structure of the IL-15:IL-2Rβ and IL-15:common gamma chain interfaces, as well as by modeling using MOE software, it was predicted that residues at these interfaces that may be substituted in order to reduce potency. FIG. 46 depicts a structural model of the IL-15:receptor complexes showing locations of the predicted residues that were engineered isosteric substitutions (in order to reduce the risk of immunogenicity). Sequences for illustrative IL-15 variants engineered for reduced potency are depicted in FIGS. 47A-47C.

Plasmids coding for IL-15 or IL-15Rα(sushi) were constructed by standard gene synthesis, followed by subcloning into a pTT5 expression vector containing Fc fusion partners (e.g., constant regions as depicted in FIGS. 8A-8D). Substitutions identified as described above were incorporated by standard mutagenesis techniques.

Sequences for illustrative IL-15/Rα-Fc fusion proteins of the "IL-15/Rα-heteroFc" format engineered for reduced potency are depicted in FIGS. 48A-48H, with additional sequences including XENP22815, XENP22817, XENP22818, XENP22823, XENP22824, XENP22825, XENP22826, XENP22827, XENP22828, XENP22830, XENP22831, XENP22832, XENP22833, XENP23555, XENP23559, XENP23560, XENP24017, XENP24020, XENP24043, and XENP24048 depicted in WO2018071919 in FIGS. 104Z, 104AA, 104AC, 104AD, 104AE, 104AF, 104AJ, 104AK, 104AM, 104AN, and 104AO and as SEQ ID NOs: 729-734, 741-746, 747-752, 777-782, 783-788, 789-794, 795-800, 801-806, 807-812, 819-824, 825-830, 831-836, 837-842, 887-892, 899-904, 905-910, 937-942, 955-960, 961-966, and 979-984, respectively, herein incorporated by reference.

Sequences for illustrative IL-15/Rα-Fc fusion proteins of the "scIL-15/Rα-Fc" format engineered for lower potency are depicted in FIGS. 49A-49D, with additional sequences including XENP24013, XENP24014, and XENP24016 depicted WO2018071919 in FIGS. 104AK and 104AL and as SEQ ID NOS: 914-921, 922-926, and 932-936, respectively, herein incorporated by reference.

Sequences for illustrative IL-15/Rα-Fc fusion proteins of the "ncIL-15/Rα-Fc" format engineered for lower potency are depicted in FIGS. 50A-50B. Sequences for illustrative ncIL-15/Rα heterodimers engineered for lower potency are depicted in FIG. 51, with additional sequences including XENP22791, XENP22792, XENP22793, XENP22794, XENP22795, XENP22796, XENP22803, XENP22804, XENP22805, XENP22806, XENP22807, XENP22808, XENP22809, XENP22810, XENP22811, XENP22812, XENP22813, and XENP22814 depicted in WO2018071919 in FIGS. 104V, 104W, 104X, 104Y, and 104Z and as SEQ ID NOS: 689-690, 691-692, 693-694, 695-696, 697-698, 699-700, 705-706, 707-708, 709-710, 711-712, 713-714, 715-716, 717-718, 719-720, 721-722, 723-724, 725-726, and 727-728, respectively, herein incorporated by reference.

Sequences for an illustrative IL-15/Rα-Fc fusion protein of the "bivalent ncIL-15/Rα-Fc" format engineered for lower potency are depicted in FIG. 52. Sequences for illustrative IL-15/Rα-Fc fusion proteins of the "dsIL-15/Rα-Fc" format engineered for lower potency are depicted in FIG. 53.

Proteins were produced by transient transfection in HEK293E cells and were purified by a two-step purification process comprising protein A chromatography (GE Healthcare) and anion exchange chromatography (HiTrapQ 5 mL column with a 5-40% gradient of 50 mM Tris pH 8.5 and 50 mM Tris pH 8.5 with 1 M NaCl).

B. 3B: In Vitro Activity of Variant IL-15/Rα-heteroFc and scIL-15/Rα-Fc Fusion Proteins Engineered for Decreased Potency The variant IL-15/Rα-Fc fusion proteins were tested in a number of cell proliferation assays.

In a first cell proliferation assay, IL-15/Rα-Fc fusion proteins (with or without engineered substitutions) or control were incubated with PBMCs for 4 days. Following incubation, PBMCs were stained with anti-CD4-Evolve605 (SK-3), anti-CD8-PerCP/Cy5.5 (RPA-T8), anti-CD45RA-APC/Cy7 (HI100), anti-CD16-eFluor450 (CB16), anti-CD56-eFluor450 (TULY56), anti-CD3-FITC (OKT3), and anti-Ki67-APC (Ki-67) to mark various cell populations and analyzed by FACS as generally described in Example 1D. Proliferation of NK cells, CD8+ T cells, and CD4+ T cells as indicated by Ki67 expression are depicted in FIGS. 54A-54C and FIG. 55. Most of the IL-15/Rα-Fc fusion proteins induced proliferation of each cell population; however, activity varied depending on the particular engineered substitutions.

In a second cell proliferation assay, IL-15/Rα-Fc fusion proteins (with or without engineered substitutions) were incubated with PBMCs for 3 days. Following incubation, PBMCs were stained with anti-CD3-FITC (OKT3), anti-CD4-Evolve604 (SK-3), anti-CD8-PerCP/Cy5.5 (RPA-T8), anti-CD16-eFluor450 (CB16), anti-CD56-eFluor450 (TULY56), anti-CD27-PE (0323), anti-CD45RA-APC/Cy7 (HI100) and anti-Ki67-APC (20Raj1) antibodies to mark various cell populations. FIGS. 56A-56C and 57A-57C depict selection of various cell populations following incubation with XENP22821 by FACS. Lymphocytes were first gated on the basis of side scatter (SSC) and forward scatter (FSC) (FIG. 56A). Lymphocytes were then gated based on CD3 expression (FIG. 56B). Cells negative for CD3 expression were further gated based on CD16 expression to identify NK cells (CD16+) (FIG. 56C). CD3+ T cells were further gated based on CD4 and CD8 expression to identify CD4+ T cells, CD8+ T cells, and γδ T cells (CD3+CD4−CD8−) (FIG. 57A). The CD4+ and CD8+ T cells were gated for CD45RA expression as shown respectively in FIGS. 57B-C. Finally, the proliferation of the various cell populations were determined based on percentage Ki67 expression, and the data are shown in FIGS. 59A-59D. NK and CD8+ T cells are more sensitive than CD4+ T cells to IL-15/Rα-Fc fusion proteins, and as above, proliferative activity varied depending on the particular engineered substitutions. FIG. 59D shows the fold change in EC50 of various IL-15/Rα-Fc fusion proteins relative to control XENP20818. FIGS. 58A and 58B further depict the activation of lymphocytes following treatment with IL-15/Rα-Fc fusion proteins by gating for the expression of CD69 and CD25 (T cell activation markers) before and after incubation of PBMCs with XENP22821.

In a third experiment, additional variant IL-15/Rα-Fc fusion proteins were incubated with human PBMCs for 3 days at 37° C. Following incubation, PBMCs were stained with anti-CD3-FITC (OKT3), anti-CD4-SB600 (SK-3), anti-CD8-PerCP/Cy5.5 (RPA-T8), anti-CD45RA– APC/Cy7

(HI100), anti-CD16-eFluor450 (CB16), anti-CD25-PE (M-A251), and anti-Ki67-APC (Ki-67) to mark various cell populations and analyzed by FACS as generally described in Example 1D. Proliferation of CD8+ (CD45RA−) T cells, CD4+ (CD45RA−) T cells, γδ T cells, and NK cells as indicated by Ki67 expression are depicted in FIGS. 60A-60D.

In a fourth experiment, human PBMCs were incubated with the additional IL-15/Rα-Fc variants at the indicated concentrations for 3 days. Following incubation, PBMCs were stained with anti-CD3-FITC (OKT3), anti-CD4 (SB600), anti-CD8-PerCP/Cy5.5 (RPA-T8), anti-CD16-eFluor450 (CB16), anti-CD25-PE (M-A251), anti-CD45RA-APC/Cy7 (H1100), and anti-Ki67-APC (Ki67) and analyzed by FACS as generally described in Example 1D. Percentage of Ki67 on CD8+ T cells, CD4+ T cells and NK cells following treatment are depicted in FIGS. 61A-61C.

In a fifth experiment, variant IL-15/Rα-Fc fusion proteins were incubated with human PBMCs for 3 days at 37° C. Following incubation, cells were stained with anti-CD3-PE (OKT3), anti-CD4-FITC (RPA-T4), anti-CD8α-BV510 (SKi), anti-CD8β-APC (2ST8.5H7), anti-CD16-BV421 (3G8), anti-CD25-PerCP/Cy5.5 (M-A251), anti-CD45RA-APC/Cy7 (HI100), anti-CD56-BV605 (NCAM16.2), and anti-Ki67-PE/Cy7 (Ki-67) and analyzed by FACS as generally described in Example 1D. Percentage of Ki67 on CD8+ T cells, CD4+ T cells, γδ T cells, and NK cells are depicted in FIGS. 62A-62E.

In a sixth experiment, variant IL-15/Rα-Fc fusion proteins were incubated with human PBMCs for 3 days at 37° C. Following incubation, cells were stained with anti-CD3-PE (OKT3), anti-CD4-FITC (RPA-T4), anti-CD8α-BV510 (SKi), anti-CD8β-APC (SIDI8BEE), anti-CD16-BV421 (3G8), anti-CD25-PerCP/Cy5.5 (M-A251), anti-CD45RA-APC/Cy7 (HI100), anti-CD56-BV605 (NCAM16.2), and anti-Ki67-PE/Cy7 (Ki-67) and analyzed by FACS as generally described in Example 1D. Percentage of Ki67 on CD8+ T cells, CD4+ T cells, γδ T cells are depicted in FIGS. 63A-63E.

C. 3C: In Vitro Activity of Variant scIL-15/Rα-Fc Fusion Proteins Engineered for Decreased Potency with Different Linker Lengths Between IL-15 and IL-15Rα

IL-15/Rα-Fc fusion proteins with some of the substitutions described above, further with different lengths linkers between IL-15 and IL-15Rα (as depicted in Table 4) were incubated with human PBMCs at the indicated concentrations for 3 days at 37° C. Following incubation, PBMCs were stained with anti-CD3-PE (OKT3), anti-CD4-FITC (RPA-T4), anti-CD8-APC (RPA-T8), anti-CD16-BV605 (3G8), anti-CD25-PerCP/Cy5.5 (M-A251), anti-CD45RA-APC/Fire750 (HI100) and anti-Ki67-PE/Cy7 (Ki-67) and analyzed by FACS as generally described in Example 1D. Percentage Ki67 on CD8+ T cells, CD4+ T cells, γδ T cells and NK (CD16+) cells are depicted in FIGS. 64A-D. The data show that the ncIL-15/Rα-Fc fusion protein XENP21479 is the most potent inducer of CD8+ T cell, CD4+ T cell, NK (CD16+) cell, and γδ T cell proliferation. Each of the scIL-15/Rα-Fc fusion proteins were less potent than XENP21479 in inducing proliferation, but differences were dependent on both the linker length as well as the particular engineered substitutions.

TABLE 4

| XENP | Format | Linker between IL-15 and IL-15Rα | Mutation |
|---|---|---|---|
| 24013 | scIL-15/Rα-Fc | (GGGGS)$_5$ (SEQ ID NO: 32) | D61N |
| 21014 | scIL-15/Rα-Fc | (GGGGS)$_5$ (SEQ ID NO: 32) | N65D |
| 24015 | scIL-15/Rα-Fc | (GGGGS)$_5$ (SEQ ID NO: 32) | Q108E |
| 24475 | scIL-15/Rα-Fc | (GGGGS)$_6$ (SEQ ID NO: 31) | Q108E |
| 24476 | scIL-15/Rα-Fc | (GGGGS)$_6$ (SEQ ID NO: 31) | N4D/N65D |
| 24478 | scIL-15/Rα-Fc | (GGGGS)$_7$ (SEQ ID NO: 35) | Q108E |
| 24479 | scIL-15/Rα-Fc | (GGGGS)$_7$ (SEQ ID NO: 35) | N4D/N65D |
| 24481 | scIL-15/Rα-Fc | 30AA-linker | Q108E |

D. 3D: In Vitro Activity of Variant IL-15/Rα-Fc Fusion Proteins Engineered for Decreased Potency in Additional Formats Variant IL-15/Rα-Fc fusion proteins in different formats (as depicted in Table 5) were incubated with human PBMCs at the indicated concentrations for 3 days at 37° C. Following incubation, PBMCs were stained with anti-CD3-PE (OKT3), anti-CD4-FITC (RPA-T4), anti-CD8-APC (RPA-T8), anti-CD16-BV605 (3G8), anti-CD25-PerCP/Cy5.5 (M-A251), anti-CD45RA-APC/Fire750 (HI100) and anti-Ki67-PE/Cy7 (Ki-67) and analyzed by FACS as generally described in Example 1D. Percentage Ki67 on CD8+ T cells, CD4+ T cells, γδ T cells and NK (CD16+) cells are respectively depicted in FIGS. 65A-65D. As above, the data show that the ncIL-15/Rα-Fc fusion protein XENP21479 is the most potent inducer of CD8+ T cell, CD4+ T cell, NK (CD16+) cell, and γδ T cell proliferation. Notably, introduction of Q108E substitution into the ncIL-15/Rα-Fc format (XENP24349) drastically reduces its proliferative activity in comparison to wildtype (XENP21479).

TABLE 5

| XENP | Format | Mutation |
|---|---|---|
| 24351 | Bivalent IL-15/Rα-Fc | N4D/N65D |
| 21479 | ncIL-15/Rα-Fc | WT |
| 23472 | dsIL-15/Rα-Fc | N65D |
| 23557 | IL-15/Rα-heteroFc | N4D/N65D |
| 24349 | ncIL-15/Rα-Fc | Q108E |

E. 3E: STAT5 Phosphorylation by Variant IL-15/Rα-Fc Fusion Proteins

Transpresentation of IL-15 and IL-15Rα drives phosphorylation of STAT5 and subsequent proliferation of NK and T cells (CD4+ and CD8+). Accordingly, CD8+ and CD4+ T cells were analyzed for STAT5 phosphorylation following 15 minutes incubation with the indicated IL-15/Rα-Fc test articles. PBMCs were stained with anti-CD4-BV421 (RPA-T4) and anti-CD8-A700 (SKi) for 30-45 minutes at room temperature. Cells were washed and incubated with pre-chilled (−20° C.) 90% methanol for 20-60 minutes. After incubation with methanol, cells were washed again and stained with anti-CD45RA-BV510 (HI100), anti-CD27-BV605 (L128), anti-CD25-PE (M A251), anti-pSTAT5-Alexa647 (pY687), and anti-FoxP3-Alexa488 (259D) to mark various cell populations and STAT5 phosphorylation. FIGS. 66A-66D depict selection of various cell populations following incubation with XENP22821. Lymphocytes were first gated on the basis of SSC and FSC (FIG. 66A). The lymphocytes were then gated based on CD4 and CD8 expression to identify CD4+ and CD8+ T cells (FIG. 66B). The CD4+ and CD8+ T cells were then further gated based on CD45RA and CD27 expression to identify further subpopulations depicted respectively in FIGS. 66C-66D. Finally, the phosphorylation of STAT5 in the various cell populations was determined, and the data are shown in FIGS. 67A-67C. STAT5 phosphorylation on T cells was induced in a dose dependent manner and also varied depending on the particular engineered substitutions. FIG. 67C shows the fold change in EC50 for STAT5 phosphorylation of the variant IL-15/Rα-Fc fusion proteins relative to control.

In another experiment, splenocytes from B6 mice were incubated with the indicated test articles at the indicated concentrations for 15 minutes. Following incubation, splenocytes were stained with anti-CD44-BV605 (IM7). Cells were washed and incubated with pre-chilled (−20° C.) 90% methanol for 20-60 minutes. After methanol incubation, cells were washed again and stained with anti-CD3-BV421 (145-2C11), anti-CD4-PE (GK1.5), anti-CD8-FITC (53-6.7), and anti-pSTAT5-Alexa647 (pY694) for 30-45 minutes at room temperature to mark various cell populations and STAT5 phosphorylation. Alexa647 MFI indicating STAT5 phosphorylation on mouse CD8+CD45RA− and CD4+CD45RA− are depicted in FIGS. 68A-68B.

F. 3F: PK of Variant IL-15/Rα-Fc Fusion Proteins Engineered for Lower Potency

In order to investigate if IL-15/Rα-Fc fusion proteins engineered for reduced potency had improved half-life and PK, we examined these variants in a PK study in C57BL/6 mice. Two cohorts of mice (5 mice per test article per cohort) were dosed with 0.1 mg/kg of the indicated test articles via IV-TV on Day 0. Serum was collected 60 minutes after dosing and then on Days 2, 4, and 7 for Cohort 1 and Days 1, 3, and 8 for Cohort 2. Serum levels of IL-15/Rα-Fc fusion proteins were determined using anti-IL-15 and anti-IL-15Rα antibodies in a sandwich ELISA. The results are depicted in FIG. 69. FIG. 70 depicts the correlation between human NK cell potency and half-life of the test articles. FIG. 71 depicts the correlation between mouse STAT5 signaling potency and half-life of the test articles.

As predicted, variants with reduced potency demonstrated substantially longer half-life. Notably, half-life was improved up to almost 9 days (see XENP22821 and XENP22822), as compared to 0.5 days for the wild-type control XENP20818.

G. 3G: IL-15/Rα-Fc Fusion Proteins with Reduced Potency Enhance Lymphocyte Expansion In a further experiment in C57BL/6 albino mice, animals were dosed with the indicated test articles at the indicated concentrations (5 mice per group). Mice were bled and sacrificed on Day 8 to assess serum concentration of test articles (FIGS. 146A-146D) and CD8+ T cell counts in spleen (FIG. 73).

The data show that variants with reduced potency such as XENP22818 and XENP22829 promote greater lymphocyte expansion. However, too much reduction in potency (such as seen with XENP22821) ablates the enhancement in lymphocyte expansion.

H. 3H: Variant IL-15/Rα-Fc Fusion Proteins Enhance Engraftment and Disease Activity in Human PBMC-Engrafted NSG Mice The variant IL-15/Rα-Fc fusion proteins were evaluated in a GVHD models conducted in female NSG immunodeficient mice as generally described in Example 1F.

In a first study, 10 million human PBMCs were engrafted into NSG mice via IV-OSP on Day 0 followed by dosing of IL-15/Rα-Fc fusion proteins at the indicated concentrations on Day 1. CD45+ proliferation correlates with decreased body weight (as shown in FIG. 74), and so CD45+ cells were measured on Days 4 and 8 as an indicator of disease activity in this study (FIGS. 75A-75B). The data show that each of the IL-15/Rα-Fc fusion proteins enhance proliferation of CD45+ cells in human PBMC-engrafted NSG mice as compared to control (PBS).

In another study, 10 million human PBMCs were engrafted into NSG mice via IV-OSP on Day 0 followed by dosing with IL-15/Rα-Fc fusion proteins at the indicated concentrations on Day 1. IFNγ levels and human NK cell, CD45+ lymphocytes, CD8+ T cell and CD4+ T cell counts were measured at days 4, 7, and 11 (FIGS. 76A-76C, 77A-77C, 78A-78B, 79A-79B, and 80A-80B). The data show that the variant IL-15/Rα-Fc fusion proteins enhance IFNγ secretion and proliferation of human NK cell and T cells in a dose dependent manner. Notably, the observed activity is correlated to the in vitro potency of each variant.

In yet another study, 10 million human PBMCs were engrafted into NSG mice via IV-OSP on Day −8 followed by dosing with the indicated test articles at the indicated concentrations on Day 0. IFNγ levels and human NK cell, CD45+ lymphocytes, CD8+ T cell and CD4+ T cell counts were measured at Days 4, 7, and 11. FIG. 81 depicts IFNγ levels in mice serum on Days 4, 7, and 11. FIGS. 82A-82C respectively depict CD8+ T cell counts on Days 4, 7, and 11. FIGS. 83A-83C respectively depict CD4+ T cell counts on Days 4, 7, and 11. FIGS. 84A-84C respectively depict CD45+ cell counts on Days 4, 7, and 11. Body weight of the mice were also measured on Days 4, 7, and 11 and depicted as percentage of initial body weight in FIGS. 85A-85C.

I. 3I: IL-15/Rα-Fc Fusion Proteins Proliferate Cynomolgus Lymphocytes

For ease of clinical development, it is useful to assess various parameters of the IL-15/Rα-Fc fusion proteins such as pharmacodynamics, pharmacokinetics, and toxicity in cynomolgus monkeys. Accordingly, it was investigated whether IL-15/Rα-Fc fusion proteins were able to proliferate cynomolgus monkey lymphocytes. Cyno PBMCs were incubated with the indicated test articles and the expression of Ki67 on various lymphocyte populations was assessed, data for which are depicted in FIG. 86.

J. 3J: IL-15/Rα-Fc Fusion Proteins are Active in Cynomolgus Monkeys

Cynomolgus monkeys were administered a single intravenous (i.v.) dose of XENP20818 (n=3), XENP22819 (n=1), XENP22821 (n=3), XENP22822 (n=3), XENP22834 (n=3), and XENP23343 (n=3). Lymphocyte counts (FIGS. 87A-87E, 89A-89E, 91A-91E, 93A-93E, 95A-95E, and 97A-97E) and proliferation (FIGS. 88A-88E, 90A-90E, 92A-92E, 94A-94E, 96A-96E, and 98A-98E) were assessed over time. The data show significant changes in CD56+ NK cells (FIG. 91A), CD16+ NK cells (FIG. 91B), γδ T cells (FIG. 91C), CD8+ T cells (CD45RA+) (FIG. 91D), CD8+ T cells (CD45RA−) (FIG. 91E), and CD4+ T cells (FIG. 91F) following treatment with XENP22821 peaking at Day 6 with subsequent recovery and normalizing. Finally, FIGS. 92A-92E show significant expression of Ki67 on CD56+ NK cells (FIG. 92A), CD16+ NK cells (FIG. 92B), CD8+ T cells (CD45RA+) (FIG. 92C), CD8+ T cells (CD45RA−) (FIG. 92D), and CD4+ T cells (FIG. 92E) indicating proliferative activity following treatment with XENP22821. Similar proliferative activity was observed following treatment with XENP20818, XENP22819, XENP22822, and XENP23343, demonstrating that most of the IL-15/Rα-Fc fusion proteins of the invention are active in cynomolgus monkeys.

XVII. Example 4: IL-15/Rα-Fc Fusion Proteins Engineered with Xtend Fc

IL-15/Rα-Fc variants engineered for decreased potency as described above were further engineered with Xtend Fc (hereon referred to as "IL-15/Rα-XtendFc" fusion proteins) to further increase half-life by subcloning plasmids coding for IL-15 and/or IL-15Rα(sushi) into a pTT5 expression vector containing Fc fusion partners with M428L/N434S substitutions (see FIG. 8A-8D, Backbone 11). Sequences for illustrative IL-15/Rα-XtendFc are depicted in FIGS. 99A-99C, 100, 101, and 102 (see also Table 6).

TABLE 6

| XENP | Format | Mutation |
| --- | --- | --- |
| 24306 | IL-15/Rα-heteroFc | D30N/E64Q/N65D |
| 24341 | IL-15/Rα-heteroFc | N1D/N65D |
| 24301 | IL-15/Rα-heteroFc | N4D/N65D |
| 24383 | ncIL-15/Rα-Fc | Q108E |
| 24346 | Bivalent IL-15/Rα-Fc | Q108E |

A. 4A: In Vitro Activity of Additional IL-15/Rα-Fc Variants
1. 4A(a): Proliferation of Human Lymphocytes Human PBMCs were incubated with the IL-15/Rα-XtendFc variants at the indicated concentrations for 3 days. Following incubation, PBMCs were stained with anti-CD3-FITC (OKT3), anti-CD4-PE (RPA-T4), anti-CD8-eFluor450 (SK-1), anti-CD45RA-PE/Cy7 (HI100), anti-CD16-PerCP/Cy5.5 (3G8), anti-CD25-APC/Fire750 (M-A251), and anti-Ki67-APC (Ki-67) to mark various cell populations and analyzed by FACS as generally described in Example 1D. Proliferation of CD8+ T cells, CD4+ T cells and NK cells following treatment as indicated by Ki67 expression are depicted in FIGS. 103A-103C.

In another experiment, human PBMCs were treated with XENP20818 and XENP24306 at the indicated concentrations. 3 days after treatment, the PBMCs were first stained with anti-CD3-PerCP/Cy5.5 (OKT3), anti-CD4-BV786 (RPA-T4), anti-CD813-PE/Cy7 (SIDI8BEE), anti-CD16-BV421 (3G8), anti-CD56-BV605, and anti-CD45RA-APC/Cy7 (HI100). Cells were washed again and stained with anti-FoxP3-AF488 (259D) and anti-Ki67-APC using eBioscience™ Foxp3/Transcription Factor Staining Buffer Set (Thermo Fisher Scientific, Waltham, Mass.). Proliferation of CD8+ T cells, CD4+ T cells, NK cells, and γδ T cells following treatment as indicated by Ki67 expression are depicted in FIGS. 104A-104D.

2. 4A(b): Proliferation of Cynomolgus Lymphocytes as Indicated by Ki67

As the Xtend variants were selected for investigating activity in cynomolgus monkeys, their ability to proliferate cynomolgus T cells was investigated. Cyno PBMCs were incubated with selected test articles at the indicated concentrations for 3 days. Following incubation, PBMCs were stained with anti-CD3-FITC (SP34), anti-CD4-PE/Cy7 (OKT4), anti-CD8-APC (RPA-T8), anti-CD45RA-APC/Fire750 (HI100), anti-CD16-BV605 (3G8), anti-CD25-BV421 (M-A251), and anti-Ki67-PerCP/Cy5.5 (Ki-67) to mark various cell populations and analyzed by FACS as generally described in Example 1D. Proliferation of CD8+ T cells, CD4+ T cells and NK cells following treatment as indicated by Ki67 expression are depicted in FIGS. 105A-105C. Additionally, as consistent with the data depicted in Example 1D, an IL-15/Rα-Fc affinity variant without domain linker (hinge only; i.e., XENP24341) demonstrated less potency in proliferating cynomolgus lymphocytes than corresponding IL-15/Rα-Fc affinity variant with linker (e.g., XENP24113). In another experiment, cyno PBMCs for 3 animals were incubated with XENP20818 and XMAb24306 at the indicated concentrations for 4 days. Following incubation, PBMCs were stained with anti-CD3-FITC (SP34), anti-CD4-PE/Cy7 (OKT4), anti-CD8α-PB (BW135), anti-CD8b-eF660 (SIDI8BEE), anti-CD45RA-APC/H7 (5H9), anti-CD16-BV605 (3G8), anti-CD56-PerCP/Cy5.5 (B159), and anti-Ki67-PerCP/Cy5.5 (Ki-67) to mark various cell populations and analyzed by FACS as generally described in Example 1D. Proliferation of CD8+CD8α+CD45RA− T cells following treatment as indicated by Ki67 expression are depicted in FIG. 106.

B. 4B: In Vivo Activity of IL-15/Rα-XtendFc Variants in a GVHD Model 10 million human PBMCs were engrafted into NSG mice via IV-OSP on Day −7 followed by dosing with the indicated test articles (0.3 mg/kg) on Day 0. Whole blood was collected on Day 4 and 7, and mice were sacrificed on Days 5-8 or 11 for their spleens to measure CD4+ T cell, CD8+ T cell, and CD45+ cell counts using FACS. FIGS. 107A 107C respectively depict CD4+ T cell counts on Days 4 and 7 in whole blood and Day 8 in spleen. FIGS. 108A 108C respectively depict CD8+ T cell counts on Days 4 and 7 in whole blood and Day 8 in spleen. FIGS. 109A 109C respectively depict CD4+ T cell counts on Days 4 and 7 in whole blood and Day 8 in spleen. Body weight of the mice were also measured on Day −8, −2, 1, 5, 8 and 11 as depicted in FIGS. 110A 110F. Each point represents one female NSG mouse.

C. 4C: In Vitro Activity of Variant IL-15/Rα-XtendFc Fusion Proteins in Cynomolgus PBMC The ability of variant IL-15/Rα-XtendFc fusion proteins to proliferate cynomolgus was performed as generally described in Example 31. In particular, cyno PBMCs were incubated with the indicated test articles for 3 days. Following incubation, the cells were stained with anti CD3 FITC (OKT3), anti-CD4-PE (RPA-T4), anti-CD8-Efluor450 (SK-1), anti CD15 PerCP/Cy5.5 (3G8), anti-CD25-APC/Fire750 (M-A251), anti-CD45RA-PE/Cy7 (HI100), and anti-Ki67-APC and assessed by flow cytometry. Data depicting the percentage of various lymphocyte populations expressing Ki67 are depicted in FIGS. 111A-111D.

D. 4D: In Vivo Activity of Variant IL-15/Rα-XtendFc Fusion Proteins in Cynomolgus Monkeys Monkeys (n=3) were administered a single intravenous (i.v.) dose of indicated test articles (Day 1) and blood was collected daily. CD8+ T cell, CD4+ T cell and NK cell counts in blood were assessed over time as depicted respectively in FIGS. 112A-112C. Each point is an average of 3 cynomolgus monkeys. The data show that each of the variants were active in proliferating immune cells indicating that the IL-15/Rα-Fc fusion proteins of the invention could be useful as therapeutics for cancer in humans. Additionally, as consistent with the data depicted in Examples 1D and 4A, an IL-15/Rα-Fc affinity variant with domain linker (i.e., XENP24113) demonstrated extended expansion of cynomolgus lymphocytes as compared to corresponding IL-15/

Rα-Fc affinity variant without linker (hinge only; i.e., XENP24341). Serum concentrations of the test articles were also assessed over time and half-life determined as depicted in FIG. 113A-113H. The data show that XENP24306 displays the most prolonged T cell pharmacology. XENP24113 also shows prolonged T cell pharmacology. Future studies will evaluate XENP24113 at lower doses.

XVIII. Example 5: IL-15/Rα-Fc Fusion Proteins Enhance Anti-Tumor Activity of Activated T Cells A. 5A: IL-15/Rα-Fc Fusion Proteins Preferentially Bind Activated T Cells In the context of immuno-oncology, it is important for the IL-15/Rα-Fc fusion proteins of the invention to selectively target activated T cells in the cancer environment. To investigate this, a binding experiment was performed with fresh and activated PBMCs were used. Activated PBMCs, used as surrogates for activated lymphocytes in the tumor environment, were prepared by stimulating fresh PBMCs with 100 ng/mL plate-bound anti-CD3 (OKT3) and 1 µg/ml anti-IL-2 for 2 days. Fresh and activated PBMCs were incubated with the indicated AF647-labelled test articles for 1 hour on ice. Following incubation, PBMCs were stained with anti-CD3-PE/Cγ7 (OKT3), anti-CD4-FITC (RPA-T4), anti-CD8-PerCP/Cγ5.5 (SKi), anti-CD16-BV421 (3G8), and anti-CD45RA-PE-HI100 to identify various cell populations. Binding of test articles to the various cell populations as indicated by AF647 MFI are depicted in FIGS. 114A-114F (for IL-15/Rα-Fc affinity variants with Xtend and without domain linkers), FIGS. 115A-115F (for IL-15/Rα-Fc affinity variants with Xtend and with domain linkers), and FIGS. 116A-116F (IL-15/Rα-Fc fusion proteins in additional formats with Xtend). The data show that the IL-15/Rα-Fc fusion proteins of the inventions preferentially bound to T cells and NK cells in activated PBMCs suggesting the suitability of their use in immune-oncology. Additionally, as consistent with the data depicted in Examples 1D, 4A, and 4D, an IL-15/Rα-Fc affinity variant without domain linker (hinge only; e.g., XENP24341) demonstrated less binding to various lymphocyte populations than corresponding IL-15/Rα-Fc affinity variant with linker (e.g., XENP24113), as depicted in FIG. 117.

B. 5B: XmAb24306 Enhances Anti-Tumor Effect of Activated T Cells

T cells were purified from human PBMCs (CMV+ HLA-A0201) using EasySep™ Human T Cell Enrichment Kit (STEMCELL Technologies, Vancouver, Canada) according to the manufacturer's instructions. Purified T cells were incubated with CFSE-labeled parental MCF-7 tumor cells (designated in this Example as Group 1) or CFSE-labeled pp65-expressing MCF-7 tumor cells (designated in this Example as Group 2) at a 20:1 E:T ratio and the indicated test articles for 4 days. At Day 3, Brefeldin A (BioLegend, San Diego, Calif.) and anti CD107a PerCP/Cγ5.5 (LAMP-1) were added to the cells. Following incubation, cells were incubated with Zombie Aqua™ Fixable Viability Kit (BioLegend, San Diego, Calif.) for 30 minutes at room temperature. Cells were washed and stained with anti-CD4-APC/eFluor780 (RPA-T4), anti-CD8b-PE/Cγ7 (SIDI8BEE), anti-CD25-PE (M-A251), and anti-CD69-BV605 (FN50) for 1 hour on ice. Cells were washed again and stained with anti-IFNγ-BV421 (4S.B3) and anti-Ki67-APC using eBioscience™ Foxp3/Transcription Factor Staining Buffer Set (Thermo Fisher Scientific, Waltham, Mass.). Cells were analyzed by flow cytometry for various cell populations. Target cells were identified based on CFSE staining, and dead target cells were identified based on Zombie staining. Effector cells (CFSE-) were gated based on CD4 and CD8 expression.

CD25 and CD69 are T cell activation markers. FIGS. 118A and 118B respectively depict CD25 expression (as indicated by PE MFI) on CD8+ T cells in the two groups, and FIGS. 119A and 119B respectively depict CD25 expression on CD4+ T cells. FIGS. 120A and 120B respectively depict CD69 expression (as indicated by BV605 MFI) on CD8+ T cells in the two groups, and FIGS. 121A 121B respectively depict CD69 expression on CD4+ T cells.

Ki67 is a protein strictly associated with protein proliferation. FIGS. 122A-122B respectively depict intracellular IFNγ expression (as indicated by BV421 MFI) in CD8+ T cells in the two groups, and FIGS. 123A-123B respectively depict intracellular IFNγ expression in CD4+ T cells. FIGS. 124A-124C respectively depict Ki-67+/IFNγ–, Ki-67+/IFNγ+, and Ki-67–/IFNγ+ fractions of CD8+ T cells in Group 1. FIGS. 125A-125C respectively depict Ki-67+/IFNγ−, Ki-67+/IFNγ+, and Ki-67−/IFNγ+ fractions of CD4+ T cells in Group 1. FIGS. 126A-126C respectively depict Ki-67+/IFNγ−, Ki-67+/IFNγ+, and Ki-67−/IFNγ+ fractions of CD8+ T cells in Group 2. FIGS. 127A-127C respectively depict Ki-67+/IFNγ−, Ki-67+/IFNγ+, and Ki-67−/IFNγ+ fractions of CD4+ T cells in Group 2.

CD107a is associated with degranulation and a further indicator of cytolytic activity. FIGS. 128A-128B respectively depict CD107a expression (as indicated by PerCP/Cy5.5 MFI) on CD8+ T cells in the two groups, and FIGS. 129A-129B respectively depict CD107a expression on CD4+ T cells.

FIGS. 130A-130B respectively depict the number of remaining target cells (i.e. parental MCF-7 tumor cells or pp65-expressing MCF-7 tumor cells) for the two groups, and FIGS. 131A-131B depict the number of dead target cells.

Overall, the data show that the IL-15/Rα-Fc fusion proteins of the invention not only promote killing of tumor cells, but also that the fusion proteins selectively expand activated lymphocytes, indicating potential for selectivity towards tumor-infiltrating lymphocytes. Notably, the IL-15/Rα-Fc fusion proteins preferentially induce proliferation of CD8+ and CD4+ T cells as indicated by percentage of each population that are Ki67+IFNγ+.

In a similar experiment to confirm the preferential proliferation of activated T cells, purified T cells from human PBMCs (CMV+ HLA-A0201) were incubated with parental or pp65-expressing MCF-7 tumor cells at a 30:1 E:T ratio without or with anti-HLA-A antibody (W6/32) (to reduce/abrogate T cell activation via the TCR). Data depicting percentage of CD8+ T cells that are Ki67+/IFNγ+ are shown in FIG. 132. Data depicting the number of remaining target cells (e.g., parental MCF-7 tumor cells or pp65-expressing MCF-7 tumor cells) are depicted in FIG. 133. Incubation with anti-HLA-A antibody and subsequent reduction in T cell activation resulted in lower percentage of CD8+Ki67+IFNγ+ T cells and less potent killing of target cells, further illustrating the selective expansion of activated lymphocytes.

C. 5C: XENP24113 Enhances Anti-Tumor Effect of Activated T Cells

T cells were purified from human PBMCs (CMV+ HLA-A0201) using EasySep™ Human T Cell Enrichment Kit (STEMCELL Technologies, Vancouver, Canada) according to the manufacturer's instructions. Purified T cells were incubated with CFSE-labeled pp65-expressing MCF-7 tumor cells at a 20:1 E:T ratio and the indicated test articles for 4 days. At Day 3, Brefeldin A (BioLegend, San Diego, Calif.) and anti-CD107a-PerCP/Cy5.5 (LAMP-1) were added to the cells. Following incubation, cells were incubated with Zombie Aqua™ Fixable Viability Kit (BioLegend, San Diego, Calif.) for 30 minutes at room temperature. Cells were washed and stained with anti-CD4-APC/eFluor780 (RPA-T4), anti-CD8b-PE/Cy7 (SIDI8BEE), anti-CD25-PE (M-A251), and anti-CD69-BV605 (FN50) for 1 hour on ice. Cells were washed again and stained with anti-IFNγ-BV421 (4S.B3) and anti-Ki67-APC using eBioscience™ Foxp3/Transcription Factor Staining Buffer Set (Thermo Fisher Scientific, Waltham, Mass.). Cells were analyzed by flow cytometry for various cell populations. Target cells were identified based on CFSE staining, and dead target cells were identified based on Zombie staining. Effector cells (CFSE−) were gated based on CD4 and CD8 expression.

CD25 and CD69 are T cell activation markers. FIGS. 134A-134B respectively depict CD25 expression (as indicated by PE MFI) on CD8$^+$ T cells and CD4$^+$ T cells. FIGS. 135A-135B respectively depict CD69 expression (as indicated by BV605 MFI) on CD8$^+$ T cells and CD4$^+$ T cells. Ki67 is a protein strictly associated with protein proliferation. FIGS. 136A-B respectively depict Ki67 expression (as indicated by APC MFI) in CD8$^+$ T cells and CD4$^+$ T cells. FIGS. 137A-137B respectively depict Ki-67$^+$/IFNγ$^+$ fractions of CD8$^+$ T cells and CD4$^+$ T cells. FIGS. 138A-138B respectively depict CD69$^+$/IFNγ fractions of CD8$^+$ T cells and CD4$^+$ T cells. FIGS. 139A-139B respectively depict CD69$^+$/Ki-67$^+$ fractions of CD8$^+$ T cells and CD4$^+$ T cells. FIG. 140 depicts the number of remaining target cells (e.g., pp65-expressing MCF-7 tumor cells), and FIG. 141 depicts the number of dead target cells.

Consistent with Example 5B, each of the IL-15/Rα-Fc fusion proteins preferentially induce proliferation of CD8$^+$ T cells over CD4$^+$ T cells as indicated by Ki67 expression. Notably, increase in both CD69$^+$KI67$^+$ and CD69$^+$IFNγ$^+$ fractions correlated with pp65-MCF7 target killing. Therefore, XENP24113 which has greater potency than XmAb24306 in proliferating activated T cells is also more potent in target killing.

D. 5D: IL-15/Rα-Fc Enhances Anti-Tumor Effect in Mice

In the study depicted in Example 4B, some of the lower potency variants including XmAb24306 failed to enhance GVHD. While Xtend substitutions (M428L/N434S) enhance PK in human and cynomolgus monkey, the substitutions actually decrease exposure in mice. Accordingly for the studies depicted in this Example, XENP24045, the non-Xtend analog of XmAb24306, was assessed for its anti-tumor effect in mice.

NOD SCID gamma (NSG) mice (10 per group) were engrafted intradermally with 3×10$^6$ pp65-expressing MCF-7 cells in the rear flank on Day −14. On Day 0, mice were engrafted intraperitoneally with 5×10$^6$ human PBMCs from an HLA matched CMV$^+$ donor that screened positive for T cell pp65 reactivity (or PBS for control mice). Mice were treated weekly with the indicated test articles or PBS (for control mice) for 4 weeks (4 total doses). Tumor volumes were monitored by caliper measurements, data for which are shown (days post 1st dose) in FIGS. 142A-142B. Blood was drawn on Day 7, 12, 19, and 26 and analyzed by flow cytometry to count various lymphocyte populations as depicted in FIGS. 143A-143D. In this model, XENP24045 significantly reduced tumor growth compared to PBMC only.

XIX. Example 6: Reduction in Potency of IL-15/Rα-Fc Fusion Proteins with and without Xtend-Fc Enhances Both Pharmacodynamics and Pharmacokinetics in Cynomolgus Monkeys As depicted in Example 3J, a number of the reduced potency IL-15/Rα-Fc variants, as well as XENP23343, which is the Xtend-analog of XENP22821, were active in cynomolgus monkeys.

Serum concentration of the test articles over time and half-lives are depicted in FIG. 144. The data show that potency is inversely correlated with exposure in cynomolgus monkeys, with inactive IL-15/Rα-Fc fusion variant XENP22834 having the longest half-life. This is consistent with data in mice as depicted in Example 3F. Notably, increasing dose has minimal impact on PK as indicated by Cmax normalized serum concentration for XENP22821 at 1× and 3× dose (depicted in FIG. 145). Additionally, Xtend substitutions significantly improve exposure as indicated by half-life of XENP23343.

Additionally, the lymphocytes counts in cynomolgus monkeys following treatment with XENP20818, XENP22821 and XENP23343 as depicted in FIGS. 87A-87E, 91A-91E, and 97A-97E were re-plotted as overlays of their mean fold change in FIGS. 146A-146E to emphasize the improvement in pharmacodynamics. The data clearly show that the reduced potency IL-15/Rα-Fc variant XENP22821 expands lymphocyte counts for a greater duration than wild-type IL-15/Rα-Fc fusion XENP20818. Notably, XENP23343, the Xtend-analog of XENP22821, further enhanced the duration of lymphocyte expansion beyond XENP22821.

In a further study, cynomolgus monkeys were administered a single intravenous (i.v.) dose of 0.3× dose XENP22821 (n=3) or 0.6× dose XmAb24306, and various parameters were assessed over time. The data show that XmAb24306 displays similar PK/PD at lower 0.6× dose (in comparison to 3× dose as depicted in Example 4D; overlay of lymphocyte expansion from the two studies depicted in FIGS. 147A-147B) with favorable tolerability. Notably, despite similar dose to XENP22821 (at 0.3× dose), XmAb24306 (at 0.6× dose) displays superior PK/PD to more potent XENP22821, with peripheral Ki-67 positivity through day 10 (FIGS. 149-151) and lymph node Ki-67 positivity through day 15 (end of study; FIG. 148). Additionally, XmAb24306 preferentially expands CD8+ T cells over CD4+ T cells, including Tregs (see, FIGS. 153-154). FIGS. 155A-155C depicts overlays of the CD8+ T cell, CD4+ T cell, CD16+ NK cell counts from this study (following dosing with XmAb24306) and the study depicted in Example 3J (following dosing with XENP20818, WT IL-15/Rα-Fc) to further illustrate the enhanced pharmacodynamics conferred by potency reduction.

XX. Example 7: Reduction in Potency does not Affect the Immune Mechanism of IL-15/Rα-Fc Fusion Proteins The reduced potency of XmAb24306 requires a greater concentration to achieve the same level of T cell expansion at higher potency IL-15/Rα-Fc fusion proteins such as WT XENP20818. However, there were concerns that the reduction in potency and/or the greater concentration would alter the immune mechanism associated with IL-15/Rα-Fc treatment. Accordingly, we investigated the profile of immune-related genes in PBMCs, isolated CD8+ T cells, and isolated NK cells following incubation with either XENP20818 (WT IL-15/Rα-Fc fusion) and XmAb24306 at their respective EC50.

CD8+ T cells were enriched using the EasySep™ Human CD8+ T Cell Enrichment Kit (STEMCELL Technologies, Vancouver, Canada) according to the manufacturer's instructions. NK cells were enriched with EasySep™ Human CD56 Positive Selection Kit II (STEMCELL Technologies, Vancouver, Canada) according to the manufacturer's instructions. 2 million fresh PBMCs, CD8+ T cells or NK cells were incubated with XENP20818, XmAb24306, recombinant IL-15 or recombinant IL-2 for 24 or 48 hours. Following incubation, RNA were extracted using RNeasy Plus Mini Kit (Qiagen, Hilden, Germany). 100 ng RNA per sample were assayed by nCounter® PanCancer Immune Profiling Panel (NanoString Technologies, Seattle, Wash.). Fold change in gene expression following treatment with XENP20818 and XmAb24306 were plotted for the various conditions as depicted in FIGS. 156A-156C and FIGS. 157A-157C. The data show that in each case, gene expression profile correlated well between XENP20818 and XmAb24306 suggesting that there should be no change in immune mechanism after dosing lower potency IL-15/Rα-heteroFc fusion at a higher concentration. In comparison, correlation in fold change in gene expression following 48 hour treatment with XmAb24306 vs. IL-15 is depicted in FIG. 158A. The lower correlation is presumed to be due to recombinant IL-15 also binding to cells with IL-15Rα receptor. Further in comparison, correlation in fold change in gene expression following 48 hour treatment with XmAb24306 vs. IL-2 is depicted in FIG. 158B. The lower correlation is presumed to be due to recombinant IL-2 binding to a different receptor (i.e., IL-2Rα).

XXI. Example 8: IL-15/Rα-Fc Fusion Proteins and Tregs

In addition to proliferating effector T cells, IL-15 can also bind receptors on Tregs and enhance their proliferation; however, Tregs suppress the immune response and are therefore thought to be unfavorable for oncology treatment. In the study depicted in Example 6, we found that the IL-15/Rα-Fc fusion proteins of the invention selectively expanded CD8+ T cells over Tregs. Here we also investigated the effect of the IL-15/Rα-Fc fusion proteins of the invention on Treg suppression of effector T cells.

It has been previously reported that rapamycin promotes proliferation of CD4+CD25+FOXP3+ Tregs in vitro, and resulting expanded Tregs suppress CD4+ and CD8+ T cell proliferation (see, for example, Battaglia et al. (2006) Rapamycin promotes expansion of functional CD4+CD25+ FOXP3+ regulatory T cells of both healthy subjects and type 1 diabetic patients. J Immunol. 177(12) 8338-8347; and Strauss et al. (2007) Selective survival of naturally occurring human CD4+CD25+Foxp3+ regulatory T cells cultured with rapamycin. J Immunol. 178(1) 320-329). Accordingly, CD4+ T cells were enriched from human PBMCs by negative selection using EasySep™ Human CD4+ T Cell Enrichment Kit (STEMCELL Technologies, Vancouver, Canada). Treg were expanded using Dynabeads™ Human Treg Expander (Thermo Fisher Scientific, Waltham, Mass.) in RPMI1640+10% fetal bovine serum+0.1 µg/ml rapamycin+ 500 U/ml TL-2 for 1-4 days. Tregs were transferred to T75 flasks coated with 0.5 µg/ml anti-CD3 (OKT3, Biolegend, San Diego, Calif.) and cultured with RPMI1640+10% fetal bovine serum+0.1 µg/ml rapamycin+100 U/ml IL-2+0.5 µg/ml anti-CD28 mAb. Experiments were performed at least 8 days after initial enrichment of CD4+ T cells from PBMCs.

$1\times10^5$ CFSE-labeled PBMCs (autologous) was co-cultured with 2-fold dilutions of Tag-it Violet labeled Tregs on plate-bound anti-CD3 (100 ng/ml; OKT3) with 10 µg/ml XmAb24306 for 3 days at 37° C. Proliferation of CD8+ and CD4+ responder cells was measured by CFSE or Tag-it Violet dilution, and staining with Zombie Aqua™ Fixable Viability Kit (BioLegend, San Diego, Calif.) was used to exclude dead cells, data for which are depicted in FIGS. 159A-159B. The data show that XmAb24306 overcomes Treg suppression of anti-CD3 induced effector T cell proliferation.

XXII. Example 9: IL-15/Rα-Fc Fusion Proteins in Combination with Checkpoint Blockade Antibodies Next, we investigated whether the IL-15/Rα-Fc fusion proteins of the invention were suitable for stacking with checkpoint blockade. As with Example 5B, the non-Xtend analog of XmAb24306 was used. Checkpoint blockade antibody used was XENP16432 (a bivalent anti-PD-1 mAb based on nivolumab with ablated effector function; sequence depicted in FIG. 160). 10 million human PBMCs were engrafted into NSG mice via IV-OSP on Day -1 followed by dosing with the indicated test articles at the indicated concentrations on Days 0, 7, 14, and 21. Whole blood was collected on Days 6 and 10 to measure CD4+ T cell, CD8+ T cell, CD45+ cell, and NK cell counts using FACS as well as serum concentrations of IFNγ, and body weights were measured twice a week. Cell counts on Days 6 and 10 are depicted in FIGS. 161A-161B, 162A-162B, 163A-163B, and 164A-164B, serum IFNγ concentration on Day 7 are depicted in FIG. 165, and change in body weight by Days 7, 11, 14, and 18 are depicted in FIGS. 166A-166D. Each point represents one female NSG mouse. The data show that XENP24045 promotes leukocyte expansion and exacerbates xenogeneic GVHD at all dose levels. Notably, XENP24045 shows strong synergy with PD-1 blockade (XENP16432), particularly at lower 0.3 mg/kg XENP24045 dose.

XXIII. Example 10: WT IL-15/Rα-Fc Proliferative Effect on Various Lymphocyte Populations Percentage of various lymphocyte populations expressing Ki67 following incubation with WT IL-15/Rα-Fc (XENP20818) was investigated as generally described elsewhere in the Examples described herein, data for which are depicted in FIG. 167.

XXIV. Example 11: XENP24306 Demonstrates Decreased Potency in Stimulating STAT5 Phosphorylation on CD8$^+$CD25$^+$ T Cells STAT5 phosphorylation on CD8+CD45RA+ T cells following incubation with XENP24306, WT IL-15/Rα-Fc (XENP20818), and other potency variants was investigated as generally described elsewhere in the Examples, data for which are depicted in FIGS. 168 and 169.

XXV. Example 12: Potency Reduction Demonstrates Similar Signaling Kinetics when Adjusted for Dose Human PBMCs were stimulated with EC50 dose of XENP20818 or XENP24306 and assayed every day for 6 days. Cells were washed of the test articles after day 3. Data depicting percentage CD8$^+$CD45RA$^-$ T cells expressing Ki67, as well as BCL-2 and CD25 expression on CD8$^+$CD45RA$^-$ T cells are depicted respectively in FIGS. 170, 171, and 172. The data show that potency reduction demonstrates similar signaling kinetics in comparison to WT when adjusted for dose.

XXVI. Example 13: XENP24045 Preferentially Induces STAT5 Phosphorylation on Activated T Cells STAT5 phosphorylation on CD8$^+$ T cells in fresh versus stimulated human PBMCs following incubation with XENP24045 (the non-Xtend analog of XENP24306) and WT IL-15/Rα-Fc was investigated as generally described elsewhere in the Examples described herein, data for which are depicted in FIG. 173. The data show that both XENP20818 and XENP24045 preferentially induced STAT5 phosphorylation on CD8$^+$ T cells in stimulated PBMCs indicating a preference for activated T cells.

XXVII. Example 14: XENP24306 Preferentially Expands Activated T Cells

2×10$^5$ CFSE-labelled human PBMCs were incubated with indicated dose of XENP24306 for 4 days on indicated dose of plate bound anti-CD3 (OKT3). Proliferation of T cells was measured by CFSE dilution and Zombie dye was used to exclude dead cells. Data depicting percentage proliferating CD8$^+$CD45RA$^-$ T cells are depicted in FIG. 174 and show that increased activation of T cells (by greater concentrations of αCD3) enabled greater proliferation of CD8$^+$ T cells by XENP24306.

XXVIII. Example 15: XENP24045 and XENP23557 Potentiate T Cell Proliferation and IFNγ Production in huPBMC-Engrafted NSG Mice (GVHD Model), and Combines with Checkpoint Blockade XENP24045 (the non-Xtend analog of XENP24306) and XENP23557 (the non-Xtend analog of XENP24113) were investigated, alone or in combination with an anti-PD-1 mAb, in another GVHD study. NSG mice were engrafted with 5×10$^6$ human PBMCs via IV-OSP on Day −1, and dosed with indicated concentrations of indicated test articles on Days 0, 7, 14, and 21. FIG. 175 depicts serum IFNγ concentrations on Day 10, FIG. 176 depicts CD45$^+$ cell counts on Day 17, and FIG. 177 depicts body weight (as percentage of initial body weight) on Day 25

The data show that XENP24045 and XENP23557 potentiate T cell proliferation and IFNγ production, as well as enhance GVHD. Notably, the data shows a clear dose response for both as T cell proliferation and IFNγ production was further enhanced, and GVHD further exacerbated as indicated by change in body weight, at 0.3 mg/kg dose in comparison to 0.1 mg/kg for XENP24045 and 0.1 mg/kg vs 0.03 mg/kg for XENP23557. Additionally, the data show that IL-15/Rα-Fc fusions stack well with checkpoint blockade as indicated by enhanced T cell proliferation and IFNγ section and enhanced GVHD.

XXIX. Example 16: XENP24045 Potentiates T Cell Proliferation and IFN? Production in huPBMC-Engrafted NSG Mice (GVHD Model), and Combines with Checkpoint Blockade In another GVHD study investigating XENP24045 (the non-Xtend analog of XENP24306), alone or in combination with an anti-PD-1 mAb, NSG mice were engrafted with 10×106 human PBMCs via IV-OSP on Day −1, and dosed with indicated concentrations of indicated test articles on Days 0, 7, 14, and 21.

FIG. 178 depicts serum IFNγ concentrations on Day 7, FIG. 179 depicts counts of various lymphocyte populations on Day 10, and FIGS. 180-181 respectively depict body weight (as percentage of initial body weight) on Day 11 and over the duration of the study. Consistent with Example 15, the data show that XENP24045 potentiates T cell proliferation and IFNγ production. Additionally, the data show again that XENP24045 stacks well with checkpoint blockade as indicated by enhanced T cell proliferation and IFNγ section and enhanced GVHD.

XXX. Example 17: IL-15-Fc Fusions Enhances Anti-Tumor Activity of PD-1 Blockade in Mouse Tumor Model NSG mice (10 per group) were intradermally inoculated with 3×106 pp65-transduced MCF-7 cells on Day −14. Mice were then intraperitoneally injected with 1.5×106 or 5×106 pp65-reactive human PBMCs (or PBS for control) and treated with test articles (PBS, 3.0 mg/kg XENP16432, or 0.5 mg/kg XENP24045 in combination with 3 mg/kg XENP16432) on Day 0, and further treated with the indicated test articles on Days 7, 14, and 21. CD45+ cell counts on Day 21 post-huPBMC engraftment in mice engrafted with 1.5×106 huPBMCs are depicted in FIG. 182. Tumor volume on Day 31 post-huPBMC engraftment in mice engrafted with 1.5×106 huPBMCs, as well as over the duration of the study, are depicted in FIGS. 183 and 184. Tumor volume in mice engrafted with 5×106 huPBMCs over the duration of the study are depicted in FIG. 185. The data show that IL-15-Fc fusion XENP24045 enhances the anti-tumor activity of anti-PD-1 blockade in mice engrafted with 1.5×106 huPBMCs. Notably as shown in FIG. 185, in mice engrafted with 5×106 huPBMCs, combining XENP24045 with XENP16432 did not enhance anti-tumor activity over treating with XENP16432 alone. This suggests: a) that combining IL-15-Fc fusions with checkpoint blockade can provide substantial benefit in treatment of tumors having low numbers of tumor infiltrating lymphocytes (TTLs); and b) that in patients with suboptimal response to checkpoint blockade immunotherapy alone, addition of cytokine immunotherapy such as the IL-15-Fc fusions of the invention could enhance anti-tumor response.

XXXI. Example 18: Investigating the Pharmacokinetics of IL-15-Fc Potency Variants in Cynomolgus Monkeys In another study to investigate the pharmacokinetics of IL-15-Fc potency variants with Xtend, cynomolgus monkeys were administered a first single intravenous (i.v.) dose of XENP22853 (WT IL-15/Rα-heteroFc with Xtend), XENP24306 (IL-15(D30N/E64Q/N65D)/Rα-heteroFc with Xtend), XENP24113 (IL-15(N4D/N65D)/Rα-heteroFc with Xtend), and XENP24294 (scIL-15(N4D/N65D)/Rα-Fc with Xtend) at varying concentrations.

FIG. 189 depicts the serum concentration of the test articles over time following the first dose. FIG. 190 depicts relative serum concentrations of XENP22853 and corresponding WT non-Xtend XENP20818 (from an earlier study in cynomolgus monkeys) over time. Consistent with the data depicted in Example 6, the data show that Xtend substitution alone (as in XENP22853) provide some improvement to the pharmacokinetics of IL-15-Fc fusions. Notably, incorporating potency variants in addition to Xtend substitution (as in XENP24306 and XENP24113) greatly improves the pharmacokinetics of IL-15-Fc fusions. Unexpectedly, XENP24113 demonstrated substantially inferior pharmacokinetics in comparison to XENP24306. Similarly, scIL-15/Rα-Fc fusion XENP24294 (which has the same IL-15(N4D/N65D) potency variant as XENP24113) also demonstrated substantially inferior pharmacokinetics in comparison to XENP24306. While a decrease in pharmacokinetics for XENP24113 (and XENP24294) was expected on the basis of the IL-15-Fc fusions having IL-15(N4D/N65D) variant demonstrating greater in vitro potency than IL-15-Fc fusions having the IL-15(D30N/E64Q/N65D) variant (as depicted in Example 3B and FIG. 61), the decrease in pharmacokinetics was unexpectedly disproportionate to the increase in potency.

Monkey studies indicated half-lives of several days for potency-reduced IL-15/Rα-heteroFc fusions, which are significantly longer than the <1 hr half-life of IL-15. Moreover, a marked inverse correlation of pharmacodynamics and clearance was observed, with reduced potency variants allowing higher, more tolerated doses and enhanced lymphocyte proliferation due to more sustained exposure. Based on these observations, we hypothesized that receptor-mediated internalization is a key factor that influences the PK/PD relationships of various IL-15s (as schematically depicted in FIG. 195).

Figures 199A, 199B, 199C, 199D, 199E, 199F:
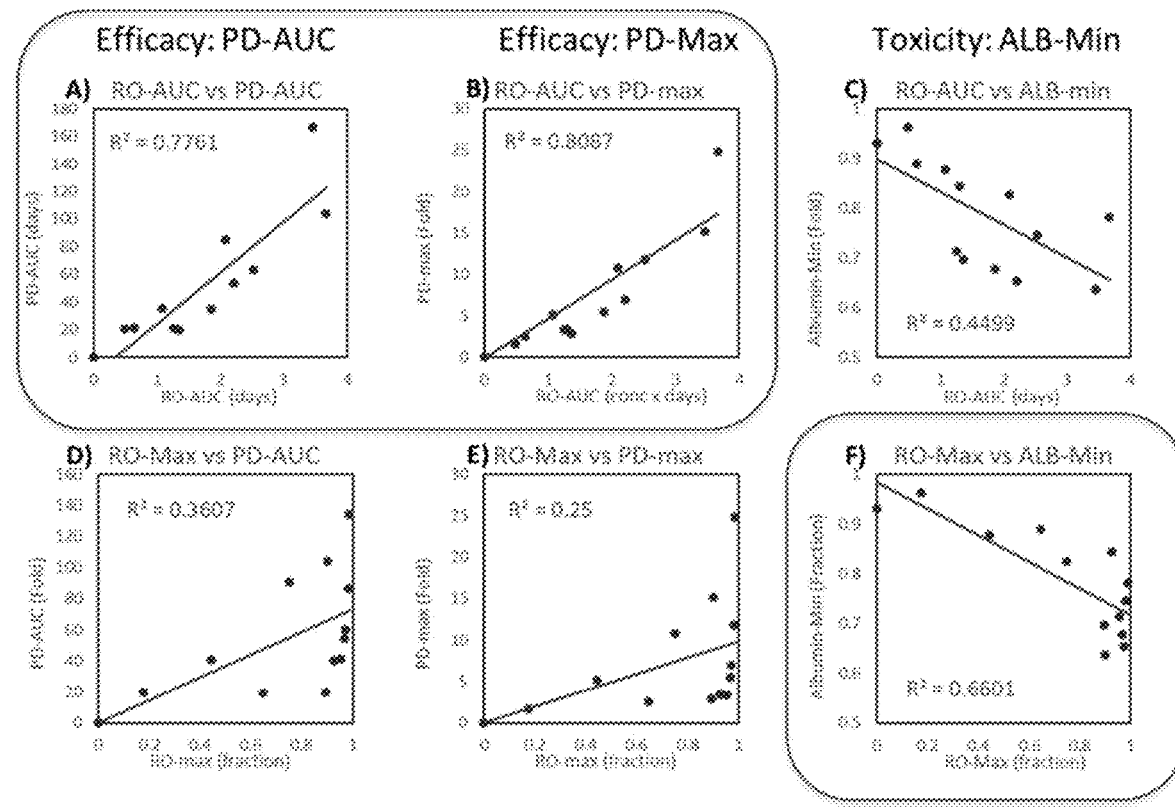

To investigate this further, we developed a mechanism-based PK/PD model to predict optimal drug-receptor affinities, balancing potency vs. target-mediated clearance. Some results are shown in FIG. 194. PK data from multiple cynomolgus monkey studies (FIG. 196) were input into these simulations, and multiple additional parameters were allowed to vary (floated) in a global fit of the PK data. Remarkably, the simulations converged on estimated $K_D$ values that correlate linearly with experimentally measured EC50 values for binding (FIG. 197). Utilizing the estimated $K_D$ values, simulated PK profiles, receptor occupancy (RO) curves, and pharmacodynamic profiles were generated (as depicted in FIG. 198), which enabled a determination of predicted area under the curve for RO (RO-AUC) as well as maximum receptor occupancy (RO-Max). We plotted predicted RO-AUC values against experimentally determined PD-AUC (pharmacodynamic AUC: the area under the curve for the fold increase of $CD8^+$ T cells over time) (FIG. 199A), predicted RO-AUC values against experimentally determined PD-Max (peak $CD8^+$ T cell increase (fold versus baseline)) (FIG. 199B), predicted RO-AUC values against experimentally determined ALB-min (nadir of the % reduction of albumin relative to baseline levels) (FIG. 199C), predicted RO-Max (maximum receptor occupancy) values against experimentally determined PD-AUC (FIG. 199D), predicted RO-Max against experimentally determined PD-Max (FIG. 199E), and predicted RO-Max against experimentally determined ALB-Min (FIG. 199F). Remarkably, the predicted RO-AUC values correlate very well with experimentally determined PD-AUC (pharmacodynamic AUC) as depicted in FIG. 199A, as well as PD-Max as depicted in FIG. 198B, indicating that RO-AUC is a target value to minimize.

Finally, a simulation scan over a variety of $K_D$ values was performed for either Xtend or non-Xtend versions of IL-15/Rα-heteroFc fusions (as depicted in FIG. 200), revealing that the predicted optimal $K_D$ is approximately 200 nM, similar to the estimated $K_D$ value of XmAb24306.

XXXII. Example 19: Potency-Reduced IL-15/Rα-heteroFc Fusion Combines Productively with Anti-PD-1 to Expand Peripheral T Cells In the mouse tumor model described in Example 17, treatment with the combination of XENP24045 and anti-PD-1 mAb significantly enhanced anti-tumor activity in comparison to treatment with anti-PD-1 mAb alone (p≤0.05 on Days 21, 27, 38, 41, and 43; and p≤0.01 on Days 24, 29, 31, 34, and 36 according to unpaired t-test). We further investigated the expansion of peripheral T cells. Data depicting the expansion of human $CD8^+$ T cell (as indicated by counts on Days 7, 14, 21 and 28 of the study) are shown in FIG. 201A and FIG. 201B. Notably on Days 14, 21, and 28, $CD8^+$ T cell counts were significantly enhanced by treatment with the combination of XENP24045 and anti-PD-1 mAb in comparison to treatment with anti-PD-1 mAb alone. Further as shown in FIG. 201B, treatment with the combination of XENP24045 and anti-PD-1 mAb enhanced activation of $CD8^+$ T cells (as indicated by expression of CD25 by CD8 T cells) much earlier than treatment with anti-PD-1 mAb alone.

XXXIII. Example 20: Potency-Reduced IL-15/Rα-heteroFc Fusion not Only Enhances Pharmacodynamics, but Also Improves Tolerability Based on data collected from various cynomolgus studies, we found that engineering reduced-potency in IL-15/Rα-heteroFc fusions enhances pharmacodynamics over IL-15/Rα-heteroFc fusions comprising WT IL-15 (data overlayed in FIG. 202A-FIG. 202C showing expansion of $CD8^+$ T cells, $CD16^+$ NK cells, and lymphocyte by dosing with 0.3× dose XENP20818, 0.3× dose XmAb24306, and 0.6× dose XmAb24306), with up to 1000% increase in lymphocytes. Vascular leak syndrome is a hallmark toxic side-effect associated with treatment with cytokines such as IL-2. One indication of vascular leak is hypoalbuminemia, a drop in serum albumin concentration. Accordingly, we investigated albumin drop in cynomolgus monkeys dosed as described above, and remarkably found that XmAb24306 not only enhances lymphocytes expansion in comparison to XENP20818, but also results in a reduction in albumin drop (data depicted in FIG. 203), indicating a superior therapeutic index for XmAb24306. For example, while both XmAb24306 and XENP20818 promoted at least a 3-fold (200%) increase in peripheral $CD8^+$ T cells (when dosed at the same level), the extent of albumin decrease mediated by XmAb24306 did not exceed 15% whereas XENP20818 caused albumin decreases of at least 25%. Moreover, a 2-fold higher (0.6×) dose of XmAb24306 promoted at least an 11-fold (1000%) increase of peripheral $CD8^+$ T cells while maintaining albumin levels above a 20% decrease. Additionally, in the modeling described in Example 18, it appears that the predicted RO-Max values correlated very well with experimentally determined ALB-Min (see FIG. 199F), indicating that RO-Max is a target value to optimize to fine-tune the tolerability of IL-15 and other cytokines.

XXXIV. Example 21: Engineering Further Reduced Potency IL-15 Variants Comprising Modifications at the IL-15:CD132 Interface As shown in Example 3B and FIG. 55, wild-type scIL-15/Rα-Fc fusion XENP21478 was less potent than wildtype IL-15/Rα-heteroFc XENP20818 in inducing proliferation of NK cells and CD8+ T cells. Accordingly, we reasoned that reduced potency IL-15 variants suitable for use in IL-15/Rα-heteroFc fusions may be too weak and unsuitable for use in other IL-15 fusion formats such as scIL-15/Rα-Fc fusions. Accordingly, we were interested in the IL-15(N4D/N65D) variant for use in such other formats as Il-15/Rα-heteroFc fusions having IL-15(N4D/N65D) variant demonstrated greater in vitro potency than IL-15/Rα-heteroFc fusions having the IL-15(D30N/E64Q/N65D) variant.

However, as shown above, IL-15-Fc fusions having the IL-15(N4D/N65D) variant demonstrated inferior pharmacokinetics in comparison to IL-15-Fc fusions having the IL-15 (D30N/E64Q/N65D) variant. We noted that IL-15(N4D/N65D) has both its substitutions at the IL-15 interface responsible for binding to CD122, while IL-15(D30N/E64Q/N65D) has two substitutions (E64Q and N65D) at IL-15:CD122 interface; and one substitution (D30N) at the IL-15 interface responsible for binding to CD132. Accordingly, we reasoned that the modification at the IL-15:CD132 interface may contribute to the superior pharmacokinetics observed for XENP24306.

In view of the foregoing, we generated an additional library of IL-15 potency variants incorporating the D30N substitution. Sequences for illustrative such IL-15 variants are depicted in FIG. 191 and illustrative scIL-15/Rα-Fc fusions comprising these variants (sequences for which are depicted in FIG. 192) were produced and investigated in a cell proliferation assay.

Human PBMCs were incubated with the indicated test articles at the indicated concentrations for 3 days. Following incubation, the PBMCs were stained with anti-CD3-PE (OKT3), anti-CD4-FITC (RPA-T4), anti-CD8-eF660 (SIDI8BEE), anti-CD16-BV421 (3G8), anti-CD45RA-APC/Fire750 (HI100), anti-CD56-BV605 (5.1H11), and anti-Ki67-PE/Cy7 (Ki-67) and analyzed by flow cytometry. FIG. 193A-FIG. 193G depicts the percentage of various lymphocyte populations expressing Ki67 indicative of proliferation.

As expected, the data show that scIL-15/Rα-Fc fusions comprising IL-15(D30N/E64Q/N65D) variant had no activity or drastically reduced activity in proliferation of various lymphocyte populations, in comparison both to an IL-15/Rα-heteroFc comprising the same IL-15 variant as well as to scIL-15/Rα-Fc fusions comprising the IL-15(N4D/N65D) variant. However, many of the scIL-15/Rα-Fc fusions having IL=15 variants comprising D30N substitution showed activity similar to that of WT scIL-15/Rα-Fc XENP21993. Notably, we identified a particular IL-15 (D30N/N65D) variant which not only comprises the IL-15:CD132 interface modification, but also potency similar to that of the IL-15(N4D/N65D) variant (in the context of scIL-15/Rα-Fc fusion).

XXXV. Example 22: Additional Studies

A. 22A: XENP24306 Potentiates T Cell Proliferation and IFNγ Production in Human PBMC-Engrafted NSG Mice (GVHD Model), and Combines Productively with Checkpoint Blockade Various concentrations of XENP24306 were investigated, alone or in combination with anti-PD-1 mAb XENP16432, in a GVHD study. NSG mice were engrafted with 10×10$^6$ human PBMCs via IV-OSP on Day −1 and dosed with indicated concentrations of indicated concentrations of indicated test articles on Days 0, 7, 14, and 21. Blood was drawn on Days 3, 7, 14, and 21 to investigate lymphocyte expansion (data depicted in FIGS. 204-206) and IFNγ concentration (data depicted in FIG. 209); and body weights were assessed twice per week as an indicator of GVHD (data depicted in FIGS. 207-208).

The data show that by Day 10, treatment with a combination of 0.3 mg/kg, 0.1 mg/kg, or 0.01 mg/kg XENP24306 and 3 mg/kg XENP16432 significantly enhanced GVHD beyond treatment with 3 mg/kg XENP16432 alone (statistics were performed using unpaired t-test). By Day 14, treatment with a combination of 0.3 mg/kg or 0.1 mg/kg XENP24306 and 3 mg/kg XENP16432 significantly enhanced CD3+ T cell expansion beyond treatment with 3 mg/kg XENP16432 alone (statistics were performed on log-transformed data using unpaired t-test).

B. 22B: XENP24306 Enhances Anti-Tumor Activity of PD-1 Blockade in Mouse Tumor Model Various concentrations of XENP24306 were investigated, alone or in combination, with anti-PD-1 mAb XENP16432, in a mouse tumor model. NSG mice were intradermally inoculated with 3×10$^6$ pp65-transduced MCF-7 on Day −15. On Day 0, mice were then intraperitoneally injected with 1.5×10$^6$ human PBMCs, and further treated with the indicated test articles on Days 0, 7, 14, and 21. Blood was drawn on Days 7, 14, and 21 to investigate lymphocyte expansion (data depicted in FIGS. 210-211) and IFNγ concentration (data depicted in FIG. 214). Tumor volume was measured by caliper measurements three times per week (data depicted in FIGS. 212 and 213A), and weights were assessed twice per week as an indicator of GVHD (data depicted in FIG. 213B).

The data show that by Day 11, treatment with a combination of 1.0 mg/kg, 0.3 mg/kg, or 0.1 mg/kg XENP24306 and 3 mg/kg XENP16432 significantly decreased tumor volume in comparison to treatment with XENP16432 alone (statistics were performed using unpaired t-test on baseline corrected tumor measurements). By Day 7, treatment with a combination of 1.0 mg/kg, 0.3 mg/kg, or 0.1 mg/kg XENP24306 and 3 mg/kg XENP16432 significantly enhanced IFNγ secretion in comparison to treatment with XENP16432 alone. By Day 14, each of the groups treated with XENP24306 alone or XENP24306 in combination with XENP16432 significantly enhanced lymphocyte expansion beyond PBS-treatment. Notably, by Day 14, each of the groups treated with a combination of XENP24306 and XENP16432, irrespective of XENP24306 concentration, as well as higher concentrations of XENP24306 alone significantly enhanced lymphocyte expansion beyond XENP16432-treatment.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

MANY MODIFICATIONS AND VARIATIONS OF THIS APPLICATION CAN BE MADE WITHOUT DEPARTING FROM ITS SPIRIT AND SCOPE, AS WILL BE APPARENT TO THOSE SKILLED IN THE ART. THE SPECIFIC EMBODIMENTS AND EXAMPLES DESCRIBED HEREIN ARE OFFERED BY WAY OF EXAMPLE ONLY, AND THE APPLICATION IS TO BE LIMITED ONLY BY THE TERMS OF THE APPENDED CLAIMS, ALONG WITH THE FULL SCOPE OF EQUIVALENTS TO WHICH THE CLAIMS ARE ENTITLED.

What is claimed is:

1. A method of inducing T cell expansion in a patient comprising administering:
a therapeutically effective amount of an IL-15/IL-15Rα heterodimeric Fc fusion protein comprising:
a) a first monomer comprising, from N- to C-terminal:
  i) an IL-15 receptor alpha (IL-15Rα) sushi domain;
  ii) a first domain linker; and
  iii) a first variant Fc domain comprising CH2-CH3; and
b) a second monomer comprising from N- to C-terminal:
  i) a variant IL-15 domain comprising the amino acid sequence of SEQ ID NO:2 and any one of the amino acid substitutions selected from the group consisting of N4D/N65D, D30N/N65D, and D30N/E64Q/N65D;
  ii) a second domain linker; and
  iii) a second variant Fc domain comprising CH2-CH3;
wherein the first and second variant Fc domains are variants of a human IgG1 Fc domain and have a set of amino acid substitutions selected from the group consisting of S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering; and
a therapeutically effective amount of an anti-PD-L1 antibody.

2. The method according to claim 1, wherein the variant IL-15 domain comprises the amino acid sequence of SEQ ID NO: 2 and the amino acid substitutions D30N/E64Q/N65D.

3. The method according to claim 1, wherein the IL-15Rα sushi domain comprises the amino acid sequence of SEQ ID NO:4.

4. The method according to claim 1, wherein the first and second variant Fc domains have S364K/E357Q: L368D/K370S substitutions.

5. The method according to claim 1, wherein the first variant Fc domain has S364K/E357Q substitutions and the second variant Fc domain has L368D/K370S substitutions.

6. The method according to claim 1, wherein the first and second variant Fc domains each comprise M428L/N434S substitutions.

7. The method according to claim 1, wherein the first and second variant Fc domains each comprise E233P/L234V/L235A/G236del/S267K substitutions.

8. The method according to claim 1, wherein the IL-15/IL-15Rα heterodimeric Fc fusion protein and the anti-PD-L1 antibody are administered concomitantly or sequentially.

9. The method according to claim 1, wherein the anti-PD-L1 antibody is atezolizumab, avelumab, or durbalumab.

10. The method according to claim 1, wherein the IL-15/IL-15Rα heterodimeric Fc fusion protein comprises the amino acid sequences of i) SEQ ID NOs 253 and 254 or ii) SEQ ID NOs: 204 and 205.

11. The method according to claim 10, wherein the IL-15/IL-15Rα heterodimeric Fc fusion protein comprises the amino acid sequences of SEQ ID NOs: 253 and 254, and the anti-PD-L1 antibody is atezolizumab.

12. The method according to claim 10, wherein the IL-15/IL-15Rα heterodimeric Fc fusion protein comprises the amino acid sequences of SEQ ID NOs: 253 and 254, and the anti-PD-L1 antibody is avelumab.

13. The method according to claim 10, wherein the IL-15/IL-15Rα heterodimeric Fc fusion protein comprises the amino acid sequences of SEQ ID NOs: 253 and 254, and the anti-PD-L1 antibody is durbalumab.

14. The method according to claim 10, wherein the IL-15/IL-15Rα heterodimeric Fc fusion protein comprises the amino acid sequences of SEQ ID NOs: 204 and 205, and the anti-PD-L1 antibody is atezolizumab.

15. The method according to claim 10, wherein the IL-15/IL-15Rα heterodimeric Fc fusion protein comprises the amino acid sequence of SEQ ID NOs: 204 and 205, and the anti-PD-L1 antibody is avelumab.

16. The method according to claim 10, wherein the IL-15/IL-15Rα heterodimeric Fc fusion protein comprises the amino acid sequence of SEQ ID NOs: 204 and 205, and the anti-PD-L1 antibody is durbalumab.

17. The method according to claim 1, wherein the level of vascular leakage ranges from a 20% reduction or less in serum albumin in the patient following administration.

18. The method according to claim 1, wherein the T cell expansion is at least a 2-fold increase in T cells.

19. The method according to claim 1, wherein the T cell expansion ranges from a 2-fold to a 15-fold increase in T cells.

20. The method according to claim 1, wherein the T cells comprise tumor infiltrating lymphocytes.

* * * * *